US007052833B1

(12) United States Patent
Reed-Gitomer et al.

(10) Patent No.: US 7,052,833 B1
(45) Date of Patent: May 30, 2006

(54) ABSORPTIVE HYPERCALCIURIA LOCUS ON HUMAN CHROMOSOME 1

(75) Inventors: Berenice Y. Reed-Gitomer, Dallas, TX (US); Charles Y. C. Pak, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 913 days.

(21) Appl. No.: 09/339,352

(22) Filed: Jun. 23, 1999

Related U.S. Application Data

(60) Provisional application No. 60/090,348, filed on Jun. 23, 1998.

(51) Int. Cl.
*C12Q 1/68* (2006.01)

(52) U.S. Cl. ................................ 435/6; 435/7; 435/7.2; 435/5; 435/23; 435/69.1; 435/230; 435/252.3; 435/320.1; 435/810; 530/300; 530/350; 530/395; 530/312; 424/12; 424/142.1; 424/8; 436/501; 436/87; 536/23.1; 514/8; 514/654

(58) Field of Classification Search ..................... 435/7, 435/23, 230, 5, 6, 810, 320.1, 69.1, 252.3, 435/7.2; 424/12, 142.1, 8; 514/8, 654; 530/300, 530/395, 312; 536/23.1; 500/350; 436/501, 436/87
See application file for complete search history.

(56) References Cited

U.S. PATENT DOCUMENTS 4,683,202 A 7/1987 Mullis ......................... 435/91

OTHER PUBLICATIONS

Rhodes S. Direct Submission. Submitted Jan. 6, 1999.*

Grafham D. Direct Submission. Submitted Oct. 27, 1997.*

Abbondanzo et al., "Prognostic significance of immunocytochemically determined ps2 in axillary node–negative breast carcinoma," *Breast Cancer Res. Treat.*, 16:182 (#151), 1990.

Abrams, "Clinical studies of mineral metabolism in children using stable isotopes," *J. Ped. Gastroenter. Nutr.*, 19:151–163, 1994.

Allred et al., "Comprehensive evaluation of prognostic factors by immunocytochemistry on extremely small samples (50 MG) of "pulverized" breast carcinomals," *Breast Cancer Res. Treat.*, 16:182 (#149), 1990.

Bataille et al., "Diet, vitamin D and vertebral mineral density in hypercalciuric calcium stone–formers," *Kidney Intern*, 39:1193–1205, 1991.

Breslau et al., "Use of ketoconazole to probe the pathogenic importance of 1,25–dihydoxyvitamin D in absorptive hypercalciuria," *J. Clin. Endocrinol Metab.*, 75:1446–1452, 1992.

Brown et al., "Prognostic significance and clinical–pathological correlations of cell–cycle kinetics measured by KI–7 immunocytochemistry in axillary node–negative carcinoma of the breast," *Breast Cancer Res. Treat.*, 16:192 (#191), 1990.

Buck et al., "Cytosolic adenylyl cyclase defines a unique signalling molecule in mammals," *Proc. Natl. Acad. Sci. USA*, 96: 79–84.

Collins et al., "A metric map of humans: 23,500 loci in 850 bands," *Proc. Natl. Acad. Sci. USA*, 93:14771–14775, 1996.

DeMay et al., "Sequences in the human parathyroid hormone gene that bind the 1,25–dihydroxyvitamin $D_3$ receptor and mediate transcriptional repression in response to 1,25–dihydroxyvitamin $D_3$," *Proc. Natl. Acad. Sci.*, 89: 8097–8101, 1992.

Fujita and Swaroop, "Alu–Vector PCR with Biotinylated Primers to Isolate YAC Ends Ready for Sequencing," *Bio-Techniques* 18: 796–799, 1995.

Heller et al., "Sustained reduction in urinary calcium during long–term treatment with slow release neutral potassium phosphate in absorptive hypercalciuria," *J. Urol.*, 159:1451–1456, 1988.

Hess et al., "Relative Hypoparathyroidism and Calcitriol Up–Regulation in Hypercalciuric Calcium Renal Stone Formers—Impact of Nutrion," *Am. J. Nephrol.* 13:18–26, 1993.

Horrigan and Westbrook, "Construction and Use of YAC Contigs in Disease Regions," *Gene Isolation and Mapping Protocols.*, Human Press, ed. J. Boultwood, 123–125, 1997.

Krieger et al., "Increased sensitivity to $1,25(OH)_2D_3$ in bone from gentic hypercalciuric rats," *J. Physiol.* 271:C130–C135, 1996.

Krizman, "Gene Isolation by Exon Trapping," *Gene Isolation and Mapping Protocols*, Human Press, ed. J. Boultwood, 167–182, 1997.

Kruglyak et al.,"Parametric and non–parametric linkage analysis: a unified multilocus approach," *Am. J. Hum. Genet.*, 58:1347–1363, 1996.

Lathrop et al., "Multilocus Linkage Analysis in Humans: Detection Linkage and Estimation of Recombination," *Am. J. Hum. Genet 37:482–498*, 1985.

Ledbetter et al., Rapid Isolation of DNA Probes within Specific Chromosome Regions by Interspersed Repetitive Sequence Polymerase Chain Reaction*Genomics* 6: 475–481, 1990.

Levy et al., "Ambulatory evaluation of nephrolithiasis: an update of a 1980 protocol," *Am. J. Med.*, 98:50–59, 1995.

(Continued)

*Primary Examiner*—Jon Weber
*Assistant Examiner*—Hope Robinson
(74) *Attorney, Agent, or Firm*—Fulbright & Jaworksi LLP

(57) ABSTRACT

Disclosed is a region on human chromosome 1 that provides a genetic basis for absorptive hypercalciuria. The genes, proteins, and other biological materials provided are envisioned for use in diagnostic and therapeutic methods related to absorptive hypercalciuria and osteoporosis with hypercalciuria.

14 Claims, 2 Drawing Sheets

OTHER PUBLICATIONS

Li et al., "Increased intestinal vitamin D receptor in genetic hypercalciuric rats: a cause of intestinal calcium hyperabsorption," *J. Clin. Invest.*, 91:661–667, 1993.

Lloyd et al., "A common molecular basis for three inherited kidney stone diseases," *Nature*, 379:445–449, 1996.

Pacifici et al., "Increased Monocyte Interleukin–1 Activity and Decreased Vertebral Bone Density in Patients with Fasting Idiopathic Hypercalciuria," *J. Clin. Endo. Metab.*, 71:138–145, 1990.

Pak and Galosy, "Fasting urinary calcium and adenosine 3', 5,–monophosphate: a discriminant analysis for the identification of renal and absorptive hypercalciurias," *J. Clin. Endocrinol. Metab.*, 48: 260–265, 1979.

Pak et al., "A simple test for the diagnosis of absorptive, resorptive and renal hypercalciurias," *N. Engl. J. Med.*, 292:497–500, 1975.

Pak et al., "Ambulatory evaluation of nephrolithiasis: classification clinical presentation, and diagnostic criteria," *Am. J. Med.*, 69:19–30, 1980.

Pak et al., "Familial absorptive hypercalciuria in a large kindred," *J. Urology*, 126:717–719, 1981.

Pak et al., "The hypercalciurias: causes, parathyroid functions and diagnostics criteria," *J. Clin. Invest.*, 54:387–400, 1974.

Pietchmann et al., "Reduced vertebral bone density in hypercalciuric nephrolithiasis," *J. Bone Min. Res.*, 7:1383–1388, 1992.

Preminger et al., "Differentiation of unclassified hypercalciuria utilizing a sodium cellulose phosphate trial," *In Urolithiasis*, Walker, Sutton, Cameron, Pak, Robertson (eds.), Plenum Press New York and London, 325–328, 1989.

Reed et al., "Linkage analysis in absorptive hypercalciuria: lack of linkage to the vitamin D receptor or $1{,}25(OH)_2D_3$ hydroxylase loci," *In Urolithiasis*, Pak, Resnick, Preminger (eds), Millet Press, Dallas, TX, 540–542, 1996.

Reed et al., "Mapping a Gene Defect in Absorptive Hypercalciuria to Chromosome 1q23.3–q24*," *Journal of Clinical Endocrinology & Metabolism* 84:3907–3913, 1999.

Ruml et al., "Medical Therapy; Calcium Oxalate Urolithiasis," *Urol. Clinics of N. Am.* 24:117–132, 1997.

Tenenhouse, "Cellular and molecular mechanisms of renal phosphate transport," *J. Bone Min. Res.*, 12:159–163, 1997.

Weisinger et al.,"Possible role of cytokines on the bone mineral loss in idiopathic hypercalciuria," *Kidney Int.* 49:224–250, 1996.

Zerwekh et al., "Evidence for normal vitamin D receptor messager ribonucleic acid and genotype in absorptive hypercalciuria," *J. Clim. Endocrinol. Metab.*, 80:2960–2965, 1995.

Zerwekh et al., "Vitamin D receptor quantitation in human mononuclear cells in health and disease," *Mol. Cell Endocrinol.*, 96:1–6, 1993.

Imamura et al., "4q33–qter deletion and adsorptive hypercalciuria: report of two unrelated girls," *American J. of Med. Gene.*, 78:52–54, 1998.

Lemann, Jr. and Gray, "Idiopathic hypercalciuria," *J. of Urology*, 141:715–718, 1989.

Pearce et al., "A familial syndrome of hypocalcemia with hypercalciuria due to mutation in the calcium–sensing receptor," *The New England J of Med.*, 335:1115–1122, 1996.

Thakker, "Renal chloride channel, CLCN%, mutations and hypercalciuric nephrolithiasis disorders," *Nova Acta Leopolidina NF*, 302:23–33, 1997.

Reed et al., "Identification and characterization of a gene with base substitutions associated with the absorptive hypercalciuria phenotype and low spinal bone density," *Journal of Clinical Endocrinology and Metabolism*, 87(4):1476–1485, 2002.

Pearce, "Human DNA sequence from PAC 313L4 on chromosome 1q24," Accession No. Z99943, OCt. 8, 1997.

GenBank Accession No. AA707634, Jan. 12, 1999, NCI–C-GAP.

* cited by examiner

ABSORPTIVE HYPERCALCIURIA LOCUS ON HUMAN CHROMOSOME 1

This application is a continuation of U.S. Provisional Application, Ser. No. 60/090,348, filed Jun. 23, 1998. The government owns rights in the present invention pursuant to grant numbers PO1-DK20543 and MO1-RR00633 from the National Institute of Health.

BACKGROUND OF THE INVENTION

1. Field of the Invention

The present invention relates generally to the field of hypercalciuria. More particularly, it concerns the determination and identification of a genetic basis for absorptive hypercalciuria and osteoporosis with hypercalciuria. This determination allows the development of diagnostics and therapeutics.

2. Description of Related Art

Nephrolithiasis is a common debilitating clinical disorder associated with an estimated lifetime risk of stone formation of 20% for males and of 5% for females in the western population. In the United States, the annual incidence of nephrolithiasis is 7 to 21 per 10,000, with up to 10% of patients undergoing active stone passage requiring hospitalization to control complications.

Absorptive hypercalciuria (AH) causes stone formation in about 50% of the reported cases. AH is invariably associated with intestinal hyperabsorption of calcium in the presence of normal serum calcium concentration and a normal or suppressed level of parathyroid hormone. Osteoporosis or bone loss, particularly of trabecular bone (Barkin et al., 1985), is a frequent complication. The mechanism by which hypercalciuria leads to osteoporosis is not fully understood.

Both clinical and experimental data indicate that AH is heterogeneous in origin. Serum calcitriol concentration is high in some, but not all, patients with AH (Kaplan et al., 1977, Broadus et al., 1984, Breslau et al., 1992). The reduced calcitriol synthesis with ketoconazole restores normal intestinal calcium absorption in some patients, but not in all of them (Breslau et al., 1992). While spinal bone density is often low, some patients enjoy normal density. Also some patients with AH exhibit exaggerated renal synthesis of 1,25$(OH)_2$D (Insogna et al., 1985).

One mechanism that has been proposed for the basis of AH involves an increase in the number of vitamin D receptors in the intestine. Li et al. demonstrated such an increase in the intestine of a normocalcemic, normal calcitriolemic rat model for AH (Li et al., 1993). An elevated level of vitamin D receptors was also observed in the activated blood lymphocytes of some AH patients who had normal levels of circulating 1,25 $(OH)_2$D (Zerwekh et al., 1993). While evidence of genetic linkage between AH and the vitamin D receptor or the 1, α-hydroxylase gene loci has been pursued, none has been produced to suggest any linkage. Other reports implicate vitamin D-independent factors. A ketoconazole study showed some patients to be ketoconazole-resistant because their intestinal hyperabsorption of calcium and hypercalciuria were unaffected by treatment (Breslau et al., 1992). Bianchi et al. suggested that an activation of the plasma membrane of Ca/ATPase may be etiologically important in AH, based on the finding of accelerated activity of this enzyme in red blood cells (Bianchi et al., 1988).

While environmental-nutritional factors have been implicated in the pathogenesis of AH (Hess et al., 1993), strong evidence suggests involvement of a genetic process in AH; a familial pattern is present in 45% or reported stone cases, and an autosomal dominant inheritance pattern has been disclosed (Coe et al., 1979, Pak et al., 1981). Stone formation may be influenced by multiple risk factors, both environmental and intrinsic. However, the intrinsic factors, that is, a molecular and genetic basis of AH, have not yet been characterized. The evaluation of large stone-forming kindreds by Coe et al. (1979) and by the group (Pak et al., 1981) indicated that AH was inherited in an autosomal dominant manner. However, no molecular genetic basis for the intestinal hyperabsorption of calcium in AH has been identified. It has been speculated that AH could result from stimulation of renal 1,25$(OH)_2$D synthesis, (Insogna et al., 1985; Broadus et al., 1984) increased vitamin D receptor sensitivity, (Breslau et al., 1992; Li et al., 1993; Zerwekh et al., 1993) or activation of the plasma membrane Ca/ATPase (Bianchi et al., 1988). The prior studies failed to show an abnormal vitamin D receptor genotype (Zerwekh et al., 1995) or a positive linkage between AH and gene loci expected to be involved vitamin D metabolism (Reed et al., 1996). In Dent's disease and related conditions that have a clinical presentation that includes hypercalciuria and nephrolithiasis, a mutation in the chloride transporter gene, CLCN5, has been reported (Lloyd et al., 1996). However, AH, unlike Dent's Disease, does not have an X-linked mode of inheritance.

There has been a clear need to identify, if any, a genetic basis for AH. Such information would yield a better understanding of the condition, providing important implications in the diagnosis and therapy of AH. Furthermore, identification of a genetic basis for AH may furnish a definitive diagnostic test to identify at risk, but asymptomatic, individuals. Detection of such individuals then allows for dietary and therapeutic intervention to prevent the onset of stone disease or osteoporosis.

AH is frequently accompanied by bone loss or "osteoporosis". Osteoporosis is defined as a group of disorders that is characterized by aberrant bone remodeling; the net rate of bone resorption is greater, rather than in dynamic equilibrium with, the rate of bone formation. The condition can occur as either a primary disorder or as a disorder associated with a various disease, such as hypercalciuria. Examples of osteoporosis with hypercalciuria include ideopathic osteoporosis with hypercalciuria and postmenopausal osteoporosis with hypercalciuria. Ideopathic ostoeporosis is often times seen in young women or men demonstrating increased calcium absorption for unknown reasons. Postmenopausal osteoporosis is seen in postmenopausal women and is associated with decreased estrogen levels and increased calcium absorption. L2–L4 bone density was 10% below normal levels overall and had declined by more than 25% in approximately one-fourth of patients who had AH (Pietchmann et al., 1992). Histomorphometric studies confirmed an abnormal bone picture, characterized by an increased osteoclastic resorption surface (Bordier et al., 1977), decreased osteoblastic activity (Malluche et al., 1980), or both (Steiniche et al., 1989) in idiopathic hypercalciuria. In the animal model of AH, bone calcium loss was associated with an increase in Vitamin D receptor (Krieger et al., 1996). However, the exact role of bone in the pathogenesis of AH remains unclear. Some have implicated cytokine involvement in the etiology of bone loss associated with AH (Pacifici et al., 1990; Weisinger et al., 1996). Increased production of IL-1 by monocytes of hypercalciuric patients has been observed (Pacifici et al., 1990), and a recent study reported that hypercalciuric patients with stones had increased levels of basal secretion of IL-1α by circulating monocytes and enhanced levels of TNFα and L-6 production by activated monocytes (Weisinger et al., 1996). It was suggested that IL-1 could stimulate prostaglandin production, which would account for previous reports of high $PGE_2$ in hypercalciuric stone-formers (Buck et al., 1981). Weisinger subsequently implied that prostaglandin-dependent synthesis of calcitriol could cause hyperabsorption of calcium and hypercalciuria, but no concrete evidence of this has been produced.

An understanding of a molecular/genetic basis of AH would facilitate the development of new therapeutic strategies for the treatment of AH. Current diagnosis is based on stone risk profile, markers for bone turnover, and bone densitometry and also involves blood tests and urinalysis. The results of many of these tests are influenced significantly by diet and thus require patient compliance with defined diet. A straightforward genetic test would eliminate the complications of extended testing and increase the certainty of the diagnosis. Unfortunately such a test is not presently available.

SUMMARY OF THE INVENTION

The present invention relates to the inventors' discovery that there exists an area on human chromosome 1 that is genetically linked to absorptive hypercalciuria (AH), and thus to some forms of osteoporosis as well. The invention further relates to the development of a familial screening method based on the identification of this region on human chromosome 1. The invention also contemplates further refining the locus to identify a gene involved in AH and to use this information for familial and nonfamilial detection and therapeutic intervention of AH and osteoporosis with hypercalciuria.

The discoveries of this invention eliminate the complications associated with screening methods currently available. Extensive blood tests and urinalysis that require compliance with a defined diet are no longer necessary to implement the present invention, which involves a simple, straightforward genetic test that can be implemented in diagnosing AH and osteoporosis with hypercalciuria.

Described in this invention is a method for screening for an increased risk of hypercalciuria by obtaining a sample nucleic acid from a subject; and analyzing the sample nucleic acid to detect the presence or absence of a genetic mutation in genomic region associated with an increased risk of developing hypercalciuria. The hypercalciuria is further defined as absorptive hypercalciuria or as osteoporosis with hypercalciuria. In certain embodiments, the osteoporosis with hypercalciuria is further defined as ideopathic osteoporosis with hypercalciuria or postmenopausal osteoporosis with hypercalciuria.

In one embodiment, this invention contemplates the identification of a region associated with an increased risk of AH on human chromosome 1. In further embodiments, the region is defined as containing 1q23 and 1q24. Further refinement of this region identifies a loci between markers D1S2681 and D1S2815. This region is further defined as having a lod score of greater than 3.0 but less than 30.0. Moreover, markers D1S2681 and D1S2815 further define a 4.3 megabase region when analyzed against two kindreds. The genomic region associated with an increased risk of AH may have a sequence contained in at least one genetic sequence selected from the group consisting of the the genetic sequences set forth in GenBank Accession # Z97876 (SEQ ID NO. 7, SEQ ID NO. 8 and SEQ ID NO. 9), GenBank Accession # Z99943 (SEQ ID NO. 10), and GenBank Accession # AL031733 (SEQ ID NO. 11).

The genomic region associated with an increased risk of AH contains a large number of genes encoding a large number of proteins. Within this large genomic regions may be families of genes, related to each other structurally or functionally. Isoforms of related proteins or groupings of subunits of a larger multimeric protein structure are often times found localized to the same genomic region. Therefore, the genetic lesions actually associated with an increased risk of AH may localize to more than one gene in this area. It is expected that there are several unique mutations associated with an increased risk of AH in different individuals.

In one aspect of the invention, a putative AH-genetically associated gene and the encoded AH-genetically associated protein has been identified. This putative gene is shown as SEQ ID NO:1 and the encoded protein is shown as SEQ ID NO:2. Methodologies for identification and characterization of this putative gene and encoded protein, mapping of specific mutations associated with this putative gene, diagnostic uses of this putative gene and encoded proteins, as well as therapies and screens for modulators of this putative gene and encoded protein are also described.

Identification of a region and a marker associated with an increased risk of absorptive hypercalciuria leads to another embodiment of the present invention for the detection of family members who may be individuals at risk for AH. In certain embodiments, linkage analysis is the screening tool using markers linked to AH. In other embodiments, the detection involves screening for a mutation in the region associated with AH. These embodiments contemplate the use of PCR, hybridization techniques using a probe complementary to a portion of the region associated with an increased risk of AH, and other techniques involving the detection or characterization of nucleic acids.

The nucleic acid to be analyzed can be either RNA or DNA. The nucleic acid can be analyzed from a blood sample, from a urine sample, or from any other tissue containing DNA or RNA corresponding to the AH loci.

The present invention discloses all loci directly related to the genetic basis for AH. This includes the nucleic acid sequences of all genes and open reading frames associated with the genetic basis for AH.

The present invention provides DNA segments, vectors and the like comprising at least a first isolated gene, DNA segment or coding sequence region that encodes a protein, polypeptide, domain, peptide or any fusion protein thereof associated with the genetic basis of AH, and particularly, that encode a human protein, domain, fragment or derivative associated with the genetic basis of AH. Moreover, all nucleic acids isolated from the AH loci are also considered in the present invention, including primers, probes, oligonucleotides, any moiety from 15 base pairs (bps) or greater, or any other distinct and discrete segment of nucleic acid that is substantially similar to the sequence of the region containing the AH locus.

As used herein in the context of the instant compositions, the AH locus providing a genetic basis for AH will be understood to include wild-type, polymorphic and mutant sequences of this region. Wild-type sequences are defined as the first identified sequence, polymorphic sequences are defined as naturally occurring variants of the wild-type sequence that have no effect on the expression or function of proteins or domains thereof associated with the genetic basis of AH, and mutant sequences are defined as changes in the wild-type sequence, either naturally occurring or introduced by the hand of man, that have an effect on either the expression, stability, cellular location, post-translation modification, and/or the function of the proteins or domains thereof that are associated with the genetic basis of AH.

Thus, the invention also includes the provision of DNA segments, vectors, genes and coding sequence regions that encode proteins, polypeptides, domains, peptides or any fusion protein thereof that are associated with the genetic basis of AH (hereinafter "AH-genetically-associated" region), where the protein element comprises at least one mutation in comparison to the wild-type sequence. The mutation may be deliberately introduced by the hand of man, for example, in order to test the function of the changed amino acid. Additionally, the mutation may be a naturally occurring polymorphic change, either isolated from normal cells or introduced by the hand of man.

A mutation may also be in a purified protein obtained directly from an aberrant cell, or may be a recombinant protein that has been changed to introduce a mutation that mirrors one identified in a patient. A mutation may result in a gene or protein related to the genetic basis of AH, or may result in increased, decreased or undetectable levels of such a gene or protein being produced. Where diagnostic or prognostic genes, proteins and antibodies that are associated with the genetic basis of AH are concerned the mutant gene, DNA segment, antibody or even peptide will preferably have specificity for the mutant sequence in preference to the wild-type sequence, allowing effective differentiation between the two, as may be used in diagnostic or prognostic tests for AH or osteoporosis with hypercalciuria.

It will be understood that while the normal, native, wild-type proteins associated with the genetic basis of AH are defined in terms of these properties and domains, the overall features will generally be the same for AH polymorphic and mutant proteins and domains as well. The polymorphic and mutant AH-genetically-associated genes and proteins can be understood with reference to the wild-type sequences and the exemplary mutants included herein.

The genes and DNA segments of the present invention preferably encode wild-type or polymorphic proteins, polypeptides, domains, peptides or fusion constructs thereof that are associated with the genetic basis of AH where the sequence includes a contiguous amino acid sequence from the region containing the AH locus or a biologically functional equivalent thereof. The present invention also provides genes and DNA segments that encode mutant proteins, polypeptides, domains, peptides or fusion constructs thereof that are related to the genetic basis of AH where the sequence includes a contiguous amino acid sequence from a region containing the AH locus, or a biologically functional equivalent thereof. As used herein, the term "contiguous amino acid sequence" will be understood to include a contiguous amino acid sequence of at least about 4, about 6, about 9, about 10, about 12, about 15 or about 20 amino acids or any number of amino acids greater than 20.

The DNA segments and coding regions may encode wild-type, polymorphic or mutant AH-genetically-associated peptides, e.g., of from about 15 to about 30 or about 50 amino acids in length or any number of amino acids greater than 20. The peptides may be lacking in any defined AH-genetically-associated protein activity, and may, for example, be used in generating antibodies or in other embodiments. The peptides or domains may also be deliberately engineered to include a mutation, e.g., in order to prepare antibodies that are specific for a mutated AH-genetically-associated gene, particularly where the mutation represents one identified in a patient AH or osteoporosis with hypercalciuria.

The present invention also provides DNA segments and coding regions that may encode an AH-genetically-associated peptide from about 6 to about 30 amino acids in length, the peptide having an amino acid sequence that corresponds to a wild-type AH-genetically associated sequence of an AH-genetically-associated protein sequence region that is susceptible to mutations that are indicative of a malignant phenotype. Where diagnostic or prognostic AH-genetically-associated genes, proteins and antibodies are concerned the gene, DNA segment, antibody or even peptide will preferably allow effective differentiation between the mutant AH-genetically-associated sequence and the wild-type AH-genetically-associated sequence as may be used in diagnostic or prognostic tests for AH or osteoporosis with hypercalciuria, as described in more detail herein below.

The genes, DNA segments, vectors and coding sequence regions may also encode wild-type, polymorphic or mutant AH-genetically-associated polypeptides and peptides with certain, but necessary all, AH-genetically-associated functional properties. As such genes and coding sequences encoding isolated wild-type, polymorphic or mutant AH-genetically-associated domains are provided.

The AH-genetically-associated domains may also be mutant domains, which include naturally occurring polymorphisms, mutations found in AH-genetically-associated proteins in patients and, also, mutations deliberately engineered into a domain to test their function in assays. The mutant domains are also useful in antibody generation and in various in vitro and cellular assays. Engineering increased binding to AH-genetically-associated domains is also contemplated.

DNA segments, isolated genes or coding regions may also be manipulated to encode AH-genetically-associated fusion proteins or constructs in which at least one AH-genetically-associated protein sequence is operatively attached or linked to at least one distinct, selected amino acid sequence. This includes the combination of AH-genetically-associated sequences with selected antigenic amino acid sequences; selected non-antigenic carrier amino acid sequences; selected adjuvant sequences; amino acid sequences with specific binding affinity for a selected molecule; and amino acid sequences that form an active DNA binding or transactivation domain are particularly contemplated. Certain fusion proteins may be linked together via a protease-sensitive peptide linker, allowing subsequent easy separation.

The DNA segments intended for use in expression will be operatively positioned under the control of, i.e., downstream from, a promoter that directs expression of AH-genetically-associated gene or genes in a desired host cell, such as *E. coli*, or in certain preferred embodiments in a mammalian or human cell. The promoter may be a recombinant promoter or a promoter naturally associated with an AH-genetically-associated gene. Recombinant vectors thus form another aspect of the present invention.

The use of isolated AH-genetically-associated genes positioned, in reverse orientation, under the control of a promoter that directs the expression of an antisense product in a cell is also contemplated.

The nucleic acid segments provided by the invention are thus further characterized as including:

(a) a nucleic acid segment comprising a sequence region that consists of at least about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 35, about 40, about 45, about 50, about 55, about 60, about 65, about 70, about 75, about 80, about 85, about 90, about 100, about 110, about 120, about 130, about 140, about 150, about 160, about 170, about 180, about 190, about 200, about 225, about 250, about 275, about 300, about 325, about 350, about 375, about 400, about 450, about 475, about 500, about 550, about 600, about 650, about 700, about 750, about 800, about 850, about 900, about 950, or about 1000 contiguous nucleotides that have the same sequence as, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 35, about 40, about 45, about 50, about 55, about 60, about 65, about 70, about 75, about 80, about 85, about 90, about 100, about 110, about 120, about 130, about 140, about 150, about 160, about 170, about 180, about 190, about 200, about 225, about 250, about 275, about 300, about 325, about 350, about 375, about 400, about 450, about 475, about 500, about 550, about 600, about 650, about 700, about 750, about 800, about 850, about 900, about 950, or are complementary to, or any other number of contiguous nucleotides of an AH-genetically-associated nucleic acid sequence; or (b) a nucleic acid segment from about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 35, about 40, about 45, about 50, about 55, about 60, about 65, about 70, about 75, about 80, about 85, about 90, about 100, about 110, about 120, about 130, about 140, about 150, about 160, about 170, about 180, about 190, about 200, about 225, about 250, about 275, about 300, about 325, about 350, about 375, about 400, about 450, about 475, about 500, about 550, about 600, about 650, about 700, about 750, about 800, about 850, about 900, about 950, to about 1000, or any other number greater than about 1000 to 20,000 nucleotides in length that specifically hybridizes to the nucleic acid segment of an AH-genetically-associated sequence, or the complements thereof, under standard stringency, or preferably, under high stringency hybridization conditions.

Standard and high stringency hybridization conditions are well known to those of skill in the art. An exemplary, but not limiting, standard hybridization is incubated at 42° C. in 50% formamide solution containing dextran sulfate for 48 hours and subjected to a final wash in 0.5× SSC, 0.1% SDS at 65° C. In addition to hybridization to Southern or northern blots, hybridization of primers for use in PCR is another preferred method for identification of sequences contemplated for use in the present invention.

Where the "complement" of any of the above nucleic acid segments are provided, such a complement may be functionally considered as an antisense nucleic acid, which includes nucleic acid segments positioned, in reverse orientation, under the control of a promoter that directs the expression of an antisense product. Antisense products may be used to inhibit the transcription or translation of any AH-genetically-associated genes, in in vitro systems in order to more precisely define the cellular consequence of inhibition, or even in vivo in situations where inhibition of one or more of any AH-genetically-associated genes would be believed to be result in a beneficial effect, such as an anti-AH effect.

Mutants of each of the foregoing sequences and their encoded proteins, polypeptides, and peptides are also contemplated. The mutants may be used in the detection of physiologically relevant mutations or in further testing an functional analyses.

Segments of AH-genetically-associated nucleic acid sequences, or the complements thereof, or the mutants thereof, may variously be any length, for example, about 10, 11, 12, 13, 14, 15, 16, 17, 18, 19, 20, 25, 30, 35, 40, 45, 50, 60, 70, 80, 90, 100, 200, 300, 400, 500, 600, 700, 800, 900 or 1000 or so nucleotides in length, up to and including the full length sequences, or even longer, as may be achieved by duplication of certain domains.

Any segment may be combined into a DNA segment or vector of, for example, up to about 50,000, about 40,000, about 30,000, or about 20,000 basepairs in length. Segments of up to about 20,000, 19,000, 18,000, 17,000, 16,000, 15,000, 14,000, 13,000, 12,000, 11,000, 10,000, 9,000, 8,000, 7,000, 6,000, or about 5,000 basepairs in length will generally be preferred, and segments of up to about 5,000, 4,000 and 3,000 basepairs in length are also provided.

The nucleic acids of the present invention may also be DNA segments or RNA segments. Nucleic acid detection kits are also provided.

The present invention further provides recombinant host cells comprising at least one DNA segment or vector that comprises an isolated gene that encodes an AH-genetically-associated protein, polypeptide, domain, peptide or any fusion protein or mutant thereof. The invention also contemplates recombinant host cells comprising at least one DNA segment or vector that comprises an isolated region of DNA that affects the transcription of a gene associated with the genetic basis for AH. Prokaryotic recombinant host cells, such as *E. coli*, are provided, as are eukaryotic host cells, including kidney cells and cells involved with bone remodeling provided with the AH-genetically-associated gene constructs of the invention.

The recombinant host cells may further comprise an operative AH-genetically-associated protein or active fragment or domain thereof. Such recombinant host cells may be provided with the AH-genetically-associated sequence in vitro, for example, to test its interactions, or may naturally express AH-genetically-associated sequences, including cells provided with an AH-genetically-associated sequence in vivo and in vitro, either for treatment or for study.

The recombinant host cells of the present invention preferably have one or more DNA segments introduced into the cell by means of a recombinant vector, and preferably express the DNA segment to produce the encoded AH-genetically-associated protein or peptide.

Methods of using AH-genetically-associated DNA segments are provided that comprise expressing a AH-genetically-associated DNA segment in a recombinant host cell and collecting the AH-genetically-associated protein, peptide, domain or mutant expressed by said cell. As represented by the steps of:

(a) preparing a recombinant vector in which an AH-genetically-associated-encoding DNA segment is positioned under the control of a promoter;

(b) introducing said recombinant vector into a recombinant host cell;

(c) culturing the recombinant host cell under conditions effective to allow expression of an AH-genetically-associated protein, peptide, domain or mutant; and (d) collecting said expressed AH-genetically-associated protein, peptide, domain or mutant.

Methods for detecting AH-genetically-associated genes in cells or samples are also provided and generally comprise contacting sample nucleic acids from a sample suspected of containing an AH-genetically-associated sequence with a nucleic acid segment that encodes an AH-genetically-associated protein or peptide under conditions effective to allow hybridization of substantially complementary nucleic acids, and detecting the hybridized complementary nucleic acids thus formed.

Other methods for detecting AH-genetically-associated genes in cells or samples include amplification and PCR, RNA mismatch cleavage assays and RNase protection assays. Several variations and improvements to these assays are described in the specification and are incorporated herein by reference.

The methods may be diagnostic of AH or osteoporosis with hypercalciuria by detecting AH-genetically-associated mutants as opposed to wild-type sequences. The use of both AH-genetically-associated wild-type and mutant sequences as probes or primers in such methods will naturally be included. A wild-type sequence probe or primer will be expected to bind to the native, non-mutant sequences, but not to a mutant, and vice versa. The use of a mutant-specific probe that corresponds to a mutant identified in a family member with AH may be preferred in screening other family members. In any event, irrespective of the AH-genetically-associated nucleic acid segment employed, these studies will still only allow hybridization of substantially complementary nucleic acids, thus facilitating the detection only of wild-type or only mutant hybridized nucleic acid complexes.

In further embodiments, the present invention AH-genetically-associated proteins, polypeptides, domains, peptides, mutants and any fusion proteins thereof, including AH-genetically-associated compounds purified from natural sources, such as from mammalian and human cells, and AH-genetically-associated amino acid sequences prepared by recombinant means. Recombinant AH-genetically-associated proteins and peptides may be defined as being prepared by expressing an AH-genetically-associated protein or peptide in a recombinant host cell and purifying the AH-genetically-associated protein or peptide away from total recombinant host cell components.

The AH-genetically-associated protein compositions, whether natural or recombinant, will generally be obtained free from total cell components, and will comprise at least one type of isolated AH-genetically-associated protein or peptide, purified relative to the natural level in a given cell.

AH-genetically-associated fusion proteins or constructs comprising AH-genetically-associated sequences operatively attached to distinct, selected amino acid sequences, such as selected antigenic amino acid sequences, amino acid sequences with selected binding affinity, and DNA binding or transactivation amino acid sequences, are also encompassed within the invention. Fusion proteins with selectably-cleavable bonds are also provided.

The AH-genetically-associated proteinaceous compositions will include the same types of mutants as described above for the nucleic acids. The use of specific mutated AH-genetically-associated peptides to prepare mutant-specific antibodies is particularly contemplated. In terms of diagnostic AH-genetically-associated peptides and antibodies, these compositions will generally be more useful in regard to point mutants, whereas nucleic acid probes may be more suitable for detecting deletion, duplication, translocation and insertional mutations in addition to point mutants.

The AH-genetically-associated proteins, polypeptides, domains, peptides and fusion proteins, as well as AH-genetically-associated DNA segments, vectors, isolated genes and coding sequences may also be formulated with a pharmaceutically acceptable diluent or vehicle to form an AH-genetically-associated-pharmaceutical composition in accordance with this invention.

Further compositions of the present invention are antibodies, including monoclonal antibodies and antibody conjugates, that have immunospecificity for an AH-genetically-associated protein or peptide. The antibodies may be operatively attached to a detectable label. The antibodies and antibody conjugates may be specific for mutant AH-genetically-associated proteins or peptides and allow differential binding from wild-type AH-genetically-associated proteins. Antibody detection kits are also provided.

Certain methods for detecting AH-genetically-associated protein sequences in a sample comprise contacting a sample suspected of such sequences with a first antibody that binds to an AH-genetically-associated protein or peptide, or a mutant thereof, under conditions effective to allow the formation of immune complexes, and detecting the immune complexes thus formed. In addition to their diagnostic use, these methods are also suitable for purifying AH-genetically-associated protein sequences, identifying AH-genetically-associated protein expression, in identifying engineered mutants and in titering AH-genetically-associated proteins and/or AH-genetically-associated antibodies.

The invention further provides diagnostic methods, particularly useful in connection with AH, but also of potential usefulness in connection with osteoporosis with hypercalciuria.

Diagnostically, the present invention provides methods for identifying a patient having or at risk for AH or osteoporosis with hypercalciuria, comprising determining the type or amount of AH-genetically-associated protein present within a biological sample from the patient, wherein the presence of an AH-genetically-associated mutant or an altered amount of wild-type AH-genetically-associated protein, in comparison to a sample from a normal subject, is indicative of a patient having or at risk for AH or osteoporosis with hypercalciuria.

The "type" of AH-genetically-associated protein may be determined, allowing mutant genes and proteins to be distinguished from wild-types. The use of mutant- and wild-type-specific nucleic acid probes is particularly contemplated. In the beginning, the use of wild-type-specific nucleic acid probes will be preferred. The identification of a particularly diagnostic mutant sequence will then lead to the increased use of that mutant sequence, either in the population or in defined families. The use of mutant- and wild-type-specific antibodies is also contemplated, as may be prepared using mutant- and wild-type-specific AH-genetically-associated peptides.

Where the "amount" of AH-genetically-associated protein is determined, a differential amount of the natural AH-genetically-associated protein may be indicative of the propensity to AH or osteoporosis with hypercalciuria. Changes from the naturally observed range in the population will be easily detected and will have implications for disease risk and development.

The type or amount of AH-genetically-associated protein may be determined by means of a molecular biological assay to determine the type or amount of a nucleic acid that encodes an AH-genetically-associated protein. Such molecular biological assays will often comprise a direct or indirect step that allows a determination of the sequence of at least a portion of the AH-genetically-associated-encoding nucleic acid, which sequence can be compared to a wild-type AH-genetically-associated sequence.

It is contemplated that AH-genetically-associated sequences diagnostic or prognostic for AH or osteoporosis with hypercalciuria may comprise at least one point mutation, deletion, translocation, insertion, duplication or other aberrant change. Diagnostic RFLPs are thus also contemplated. RNase protection assays may also be employed in certain embodiments.

Diagnostic methods may be based upon the steps of:

(a) obtaining a blood or urine sample from a subject or patient;

(b) contacting sample nucleic acids from the sample with an isolated AH-genetically-associated nucleic acid segment under conditions effective to allow hybridization of substantially complementary nucleic acids; and (c) detecting, and optionally further characterizing, the hybridized complementary nucleic acids thus formed.

The methods may involve in situ detection of sample nucleic acids located within the cells of the sample. The sample nucleic acids may also be separated from the cell prior to contact. The sample nucleic acids may be DNA or RNA.

The methods may involve the use of isolated AH-genetically-associated nucleic acid segments that comprises a radio, enzymatic or fluorescent detectable label, wherein the hybridized complementary nucleic acids are detected by detecting the label.

PCR® will often be preferred, as exemplified by the steps of:

(a) contacting the sample nucleic acids with a pair of nucleic acid primers that hybridize to distant sequences from a mutant, polymorphic or wild-type AH-genetically-associated nucleic acid sequence, the primers capable of amplifying a mutant, polymorphic or wild-AH-genetically-associated nucleic acid segment when used in conjunction with a polymerase chain reaction;

(b) conducting a polymerase chain reaction to create amplification products; and (c) detecting and characterizing the amplification products thus formed.

Diagnostic immunoassay methods are also provided, wherein the type or amount of AH-genetically-associated protein is determined by means of an immunoassay to determine the type or amount of an AH-genetically-associated protein. Such methods may comprise the steps of:

(a) obtaining a blood or urine sample from a subject or patient;

(b) contacting the sample with a first antibody that binds to an AH-genetically-associated protein or peptide, or mutant, under conditions effective to allow the formation of specific immune complexes; and (c) detecting the specific immune complexes thus formed.

The first antibody may be linked to a detectable label, wherein the immune complexes are directly detected by detecting the presence of the label. The immune complexes may also be indirectly detected by means of a second antibody linked to a detectable label, the second antibody having binding affinity for the first antibody.

Methods utilizing the nucleic acid region that provides the genetic basis for AH are also contemplated by the present invention. Such methods include, but are not limited to: detecting mutations in the AH nucleic acid region; characterizing any and all mutations within the region in an effort to elucidate the molecular mechanisms underlying AH and osteoporosis with hypercalciuria; identifying modulators, both in wild-type and mutant forms, that may interact with the AH nucleic acid region to alter expression of the region, to affect the integrity of the region, or to affect the stability of the region.

The invention also encompasses a method of treating individuals who have been identified as exhibiting the genetic profile of those at risk for AH or osteoporosis with hypercalciuria. In certain embodiments, the osteoporosis with hypercalciuria is further defined as ideopathic osteoporosis with hypercalciuria or postmenopausal osteoporosis with hypercalciuria.

The AH or osteoporosis with hypercalciuria treatment methods of the present invention may be combined with any standard strategy, such as dietary modification, hormone therapy, and pharmacological treatments. Examples of appropriate treatment regimes known to those of skill in the art are described in the examples. These include conservative dietary and fluid regimens to be incorporated into the daily routine of patients with kidney stones and therapeutic measures directed towards reducing urinary calcium excretion and decreasing intestinal calcium bioavalability. The treatment of asymptomatic diagnosed individuals is directed towards prevention of the first stone-forming episode. The administration of a biologically effective amount of an AH-genetically-associated protein, peptide or recombinant vector composition is also contemplated.

Furthermore, the invention considers the use of the AH nucleic acid region to encode a polypeptide, in part or whole, in order to study further the molecular basis AH and investigate diagnostic and therapeutic strategies. The identification, isolation, characterization of any modulators, either in their wild-type or mutant form, of the polypeptide are also part of the present invention. In addition, the genetic basis for the modulators is also encompassed within the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Pedigree for kindred AH-01. (FIG. 1B) Pedigree for kindred AH-$O_2$. (FIG. 1C) Pedigree of kindred AH-03.

(FIG. 2A) Filled portion of the vertical bar indicates the interval likely to harbor the AH gene based on haplotypes. Individuals are designated as in FIG. 1. Recombinants localize the defective gene to a 4.3 cM region between D1S2681 and D1S2815, shown as the filled region of the locus bar. (FIG. 2B) Multipoint analysis: The position of marker D1S426 was arbitrarily set at 0 cM and the positions of the other loci were fixed according to composite map distance from the linkage data base. Multipoint non-parametric LOD scores on the x-axis are plotted against chromosomal-1 loci on the y-axis.

DESCRIPTION OF ILLUSTRATIVE EMBODIMENTS

Figure 1:
FIG. 1A, FIG. 1B, and FIG. 1C. Pedigrees of 3 kindreds studied. A filled symbol indicates affected individual, an open symbol represents non-evaluated individual, a "U" in a symbol represents unaffected status, a "?" in a symbol represents unknown status and an "S" below the patient identifier number indicates the presence of a kidney stone. Probands are indicated by an arrow. A slash through the symbol indicates the individual is deceased.

The present invention concerns the detection, diagnosis, prognosis, and treatment of absorptive hypercalciuria. The present invention describes the first genetic basis for AH. The genetic region linked to AH is disclosed. Also disclosed is a method of screening for and detecting an increased risk for hypercalciuria premised on the genetic basis for the condition. Identification of at risk individuals can result in the diagnosis and therapeutic treatment of such patients in an effort to reduce the risk of stone formation or osteoporosis.

I. ABSORPTIVE HYPERCALCIURIA GENES AND DNA SEGMENTS

Important aspects of the present invention concern isolated DNA segments and recombinant vectors encoding wild-type, polymorphic or mutant proteins whose nucleic acid sequences are genetically associated with absorptive hypercalciuria. This invention also includes the creation and use of recombinant host cells through the application of DNA technology, that express wild-type, polymorphic or mutant AH-genetically-associated proteins, using sequences located on human chromosome 1 that are genetically associated with AH.

The present invention concerns DNA segments, isolatable from mammalian and human cells, that are free from total genomic DNA and that are capable of expressing a protein or polypeptide that is encoded for by a nucleic acid sequence that is genetically associated with AH.

As used herein, the term "DNA segment" refers to a DNA molecule that has been isolated free of total genomic DNA of a particular species. Therefore, a DNA segment encoding a region genetically associated with AH refers to a DNA segment that contains wild-type, polymorphic or mutant AH-genetically-associated coding sequences yet is isolated away from, or purified free from, total mammalian or human genomic DNA. Included within the term "DNA segment" are DNA segments and smaller fragments of such segments, and also recombinant vectors, including, for example, plasmids, cosmids, phage, viruses, and the like.

Similarly, a DNA segment comprising an isolated or purified wild-type, polymorphic or mutant AH-genetically-associated gene refers to a DNA segment including wild-type, polymorphic or mutant AH-genetically-associated protein coding sequences and, in certain aspects, wild-type, polymorphic or mutant AH-genetically associated regulatory sequences, including promoters, enhancers, and 3' regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences and smaller engineered gene segments that express, or may be adapted to express, proteins, polypeptides, domains, peptides, fusion proteins and mutants.

"Isolated substantially away from other coding sequences" means that the gene of interest, in this case the wild-type, polymorphic or mutant AH-genetically-associated gene forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode a wild-type, polymorphic or mutant AH-genetically-associated protein or peptide that includes within its amino acid sequence a contiguous amino acid sequence in accordance with the nucleic acid sequence corresponding to wild-type, polymorphic or mutant human AH-genetically-associated proteins. Moreover, in other particular embodiments, the invention concerns isolated DNA segments and recombinant vectors that encode an AH-genetically-associated protein or peptide that includes within its amino acid sequence the substantially full length protein sequence encoded for by the nucleic acid sequence of a region genetically associated with AH.

In a preferred embodiment, a putative AH-genetically associated gene and the encoded AH-genetically associated protein has been identified. This putative gene is shown as SEQ ID NO:1 and the encoded protein is shown as SEQ ID NO:2. These sequences are given as examples of an AH-genetically associated gene and protein. Elsewhere in this application, SEQ ID NO:1 and SEQ ID NO:2 are refered to as an AH-genetically associated gene and protein, respectively.

The term "a sequence essentially as set forth in SEQ ID NO:2" means that the sequence substantially corresponds to a portion of SEQ ID NO:2 and has relatively few amino acids that are not identical to, or a biologically functional equivalent of, the amino acids of SEQ ID NO:2.

The term "biologically functional equivalent" is well understood in the art and is further defined in detail herein. Accordingly, sequences that have between about 60% and about 65%; or more preferably, between about 66% and about 70%; or more preferably, between about 71% and about 75%; or more preferably, between about 76% and about 80%; or more preferably, between about 81% and about 85%; or more preferably, between about 86% and about 90%; or even more preferably, between about 91% and about 95%; or, between about 96% and about 99% of amino acids that are identical or functionally equivalent to the amino acids of SEQ ID NO:2 will be sequences that are "essentially as set forth in SEQ ID NO:2", provided the biological activity of the protein is maintained. Similarly, sequences that have between about 60% and about 65%; or more preferably, between about 66% and about 70%; or more preferably, between about 71% and about 75%; or more preferably, between about 76% and about 80%; or more preferably, between about 81% and about 85%; or more preferably, between about 86% and about 90%; or even more preferably, between about 91% and about 95%; or, between about 96% and about 99% of nucleic acids that are identical or functionally equivalent to the nucleic acids of SEQ ID NO:1 will be sequences that are "essentially as set forth in SEQ ID NO:1", provided the biological activity of the sequence is maintained.

The term "functionally equivalent codon" is used herein to refer to codons that encode the same amino acid, such as the six codons for arginine or serine, and also refers to codons that encode biologically equivalent amino acids (see Table 1, below).

TABLE 1

CODON TABLE

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have between about 70% and about 79%; or more preferably, between about 80% and about 89%; or even more preferably, between about 90% and about 99%; of nucleotides that are identical to the nucleotides of SEQ ID NO:1, will be sequences that are "essentially as set forth in SEQ ID NO:1".

Sequences that are essentially the same as those set forth in SEQ ID NO:1 may also be functionally defined as sequences that are capable of hybridizing to a nucleic acid segment containing the complement of SEQ ID NO:1 under relatively stringent conditions. Suitable relatively stringent hybridization conditions will be well known to those of skill in the art, as disclosed herein.

Naturally, the present invention also encompasses DNA segments that are complementary, or essentially complementary, to the sequence set forth in SEQ ID 1. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 under relatively stringent conditions such as those described herein.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

For example, nucleic acid fragments may be prepared that include a short contiguous stretch identical to or complementary to the nucleic acid sequence genetically associated with AH, such as about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 35, about 40, about 45, about 50, about 55, about 60, about 65, about 70, about 75, about 80, about 85, about 90, about 100, about 110, about 120, about 130, about 140, about 150, about 160, about 170, about 180, about 190, about 200, about 225, about 250, about 275, about 300, about 325, about 350, about 375, about 400, about 450, about 475, about 500, about 550, about 600, about 650, about 700, about 750, about 800, about 850, about 900, about 950, to about 1000, or any other number greater than about 1000 to 20,000 nucleotides in length, or about 10,000, or about 5,000 base pairs in length, with segments of about 3,000 being preferred in certain cases. DNA segments with total lengths of about 1,000, about 500, about 200, about 100 and about 50 base pairs in length (including all intermediate lengths) are also contemplated to be useful.

It will be readily understood that "intermediate lengths", in these contexts, means any length between the quoted ranges, such as 10, 11, 12, 13, 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002, 15,000, 20,000 and the like.

The various probes and primers designed around the disclosed nucleotide sequences of the present invention may be of any length. By assigning numeric values to a sequence, for example, the first residue is 1, the second residue is 2, etc., an algorithm defining all primers can be proposed:

$$n \text{ to } n+y$$

where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

It will also be understood that this invention is not limited to the particular nucleic acid and amino acid sequences of the region on human chromosome 1 that is genetically associated with AH. This includes the AH-genetically associated gene sequence of SEQ ID NO:1 and the AH-genetically associated protein sequence of SEQ ID NO:2. Recombinant vectors and isolated DNA segments may therefore variously include these coding regions themselves, coding regions bearing selected alterations or modifications in the basic coding region, or they may encode larger polypeptides that nevertheless include such coding regions or may encode biologically functional equivalent proteins or peptides that have variant amino acids sequences.

The DNA segments of the present invention encompass biologically functional equivalent AH-genetically-associated proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine DNA binding activity at the molecular level.

One may also prepare fusion proteins and peptides, e.g., where AH-genetically-associated protein coding regions are aligned within the same expression unit with other proteins or peptides having desired functions, such as for purification or immunodetection purposes (e.g., proteins that may be purified by affinity chromatography and enzyme label coding regions, respectively).

Encompassed by the invention are DNA segments encoding relatively small peptides, such as, for example, peptides of from about 15 to about 50 amino acids in length, and more preferably, of from about 15 to about 30 amino acids in length; and also larger polypeptides up to and including proteins corresponding to the full-length sequences set forth in SEQ ID NO:2.

B. Recombinant Vectors, Host Cells and Expression

Recombinant vectors form important further aspects of the present invention. The term "expression vector or construct" means any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a RNA into a gene product. In other embodiments, expression only includes transcription of the nucleic acid, for example, to generate antisense constructs.

Particularly useful vectors are contemplated to be those vectors in which the coding portion of the DNA segment, whether encoding a full length protein or smaller peptide, is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned", "under control" or "under transcriptional control" means that the promoter is in the correct location and orientation in relation to the nucleic acid to control RNA polymerase initiation and expression of the gene.

The promoter may be in the form of the promoter that is naturally associated with a wild-type, polymorphic or mutant AH-genetically-associated gene as may be obtained by isolating the 5' non-coding sequences located upstream of the coding segment or exon, for example, using recombinant cloning and/or PCR technology, in connection with the compositions disclosed herein (PCR technology is disclosed in U.S. Pat. No. 4,683,202 and U.S. Pat. No. 4,682,195, each incorporated herein by reference).

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a wild-type, polymorphic or mutant AH-genetically-associated gene in its natural environment. Such promoters may include promoters normally associated with other genes, and/or promoters isolated from any other bacterial, viral, eukaryotic, or mammalian cell.

Similarly, the promoter or other regulatory sequences of the AH-genetically-associated region may be used to control the expression of a heterologous gene, such as a reporter gene for use in expression assays. Such genes may include genes normally associated with other bacterial, viral, eukaryotic, or mammalian cells.

Naturally, it will be important to employ a promoter that effectively directs the expression of the DNA segment in the cell type, organism, or even animal, chosen for expression or to employ a cell type, organism, or even animal that can be used with the regulatory region of a gene in the AH locus. The use of promoter and cell type combinations for protein expression is generally known to those of skill in the art of molecular biology, for example, see Sambrook et al. (1989), incorporated herein by reference. The promoters employed may be constitutive, or inducible, and can be used under the appropriate conditions to direct high level expression of the introduced DNA segment, such as is advantageous in the large-scale production of recombinant proteins or peptides.

At least one module in a promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. Preferred promoters include those derived from HSV, including the HNF1$\alpha$ promoter. Another preferred embodiment is the tetracycline controlled promoter.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose. Tables 2 and 3 below list several elements/promoters which may be employed, in the context of the present invention, to regulate the expression of wild-type, polymorphic or AH-genetically-associated gene. This list is not intended to be exhaustive of all the possible elements involved in the promotion of transgene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a transgene. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 2

PROMOTER TABLE

| PROMOTER |
|---|
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| α-Globin |
| β-Globin |
| c-fos |
| c-HA-ras |
| Insulin |
| Neural Cell Adhesion Molecule (NCAM) |
| $\alpha_1$-Antitrypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |

TABLE 2-continued

PROMOTER TABLE

| PROMOTER |
|---|
| Hepatitis B Virus |
| Human Immunodeficiency Virus |
| Cytomegalovirus |
| Gibbon Ape Leukemia Virus |

TABLE 3

ENHANCER TABLE

| Element | Inducer |
|---|---|
| MT II | Phorbol Ester (TPA)<br>Heavy metals |
| MMTV (mouse mammary tumor virus) | Glucocorticoids |
| β-Interferon | poly(rI)X<br>poly(rc) |
| Adenovirus 5 E2 | ElA |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |

Turning to the expression of the wild-type, polymorphic or mutant AH-genetically-associated proteins of the present invention, once a suitable clone or clones have been obtained such as SEQ ID NO:1, whether they be cDNA based or genomic, one may proceed to prepare an expression system. The engineering of DNA segment(s) for expression in a prokaryotic or eukaryotic system may be performed by techniques generally known to those of skill in recombinant expression. It is believed that virtually any expression system may be employed in the expression of the proteins of the present invention.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired.

In expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

It is proposed that wild-type, polymorphic or mutant AH-genetically-associated genes may be co-expressed with other genes believed to be involved in bone loss or the hyperabsorption of calcium, such as 1-α hydroxylase, Vitamin D Receptor, calmodulin, IL-1α or β, IL-1α receptor or IL-1β receptor, or parathyroid hormone-related proteins, wherein the proteins may be co-expressed in the same cell or wherein wild-type, polymorphic or mutant AH-genetically-associated genes may be provided to a cell that already has the other genes involved in bone loss or the hyperabsorption of calcium. Co-expression may be achieved by co-transfecting the cell with two distinct recombinant vectors, each bearing a copy of either the respective DNA. Alternatively, a single recombinant vector may be constructed to include the coding regions for both of the proteins, which could then be expressed in cells transfected with the single vector. In either event, the term "co-expression" herein refers to the expression of both the wild-type, polymorphic or mutant AH-genetically-associated genes and the genes encoding proteins involved in bone loss or in hyperabsorption of calcium in the same recombinant cell.

As used herein, the terms "engineered" and "recombinant" cells are intended to refer to a cell into which an exogenous DNA segment or gene, such as a cDNA or gene encoding an AH-genetically-associated protein has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic gene, and also include genes positioned adjacent to a promoter not naturally associated with the particular introduced gene.

To express a recombinant AH-genetically-associated protein, whether mutant or wild-type, in accordance with the present invention one would prepare an expression vector that comprises a wild-type, polymorphic or mutant AH-genetically-associated nucleic acid under the control of one or more promoters. To bring a coding sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No. 31537) as well as *E. coli* W3110 (F—, lambda-, prototrophic, ATCC No. 273325); bacilli such as *Bacillus subtilis*; and other enterobacteriaceae such as *Salmonella typhimurium, Serratia marcescens*, and various *Pseudomonas* species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as *E. coli* LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

The following details concerning recombinant protein production in bacterial cells, such as *E. coli*, are provided by way of exemplary information on recombinant protein production in general, the adaptation of which to a particular recombinant expression system will be known to those of skill in the art.

Bacterial cells, for example, *E. coli*, containing the expression vector are grown in any of a number of suitable media, for example, Luria Broth (LB). The expression of the recombinant protein may be induced, e.g., by adding isopropyl-β-D-thiogalactoside (IPTG) to the media or by switching incubation to a higher temperature. After culturing the bacteria for a further period, generally of between 2 and 24 hours, the cells are collected by centrifugation and washed to remove residual media.

The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed.

If the recombinant protein is expressed in the inclusion bodies, as is the case in many instances, these can be washed in any of several solutions to remove some of the contaminating host proteins, then solubilized in solutions containing high concentrations of urea (e.g. 8M) or chaotropic agents such as guanidine hydrochloride in the presence of reducing agents, such as β-mercaptoethanol or DTT (dithiothreitol).

Under some circumstances, it may be advantageous to incubate the protein for several hours under conditions suitable for the protein to undergo a refolding process into a conformation which more closely resembles that of the native protein. Such conditions generally include low protein concentrations, less than 500 mg/ml, low levels of reducing agent, concentrations of urea less than 2 M and often the presence of reagents such as a mixture of reduced and oxidized glutathione which facilitate the interchange of disulfide bonds within the protein molecule.

The refolding process can be monitored, for example, by SDS-PAGE, or with antibodies specific for the native molecule (which can be obtained from animals vaccinated with the native molecule or smaller quantities of recombinant protein). Following refolding, the protein can then be purified further and separated from the refolding mixture by chromatography on any of several supports including ion exchange resins, gel permeation resins or on a variety of affinity columns.

For expression in *Saccharomyces*, the plasmid YRp7, for example, is commonly used. This plasmid already contains the trpl gene which provides a selection marker for a mutant strain of yeast lacking the ability to grow in tryptophan, for example ATCC No. 44076 or PEP4-1. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more wild-type, polymorphic or mutant AH-genetically-associated coding sequences.

In a useful insect system, Autograph californica nuclear polyhedrosis virus (AcNPV) is used as a vector to express foreign genes. The virus grows in *Spodoptera frugiperda* cells. The wild-type, polymorphic or mutant AH-genetically-associated coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051, Smith, incorporated herein by reference).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein.

Different host cells have characteristic and specific mechanisms for the post-translational processing and modification of proteins. Appropriate cells lines or host systems can be chosen to ensure the correct modification and processing of the foreign protein expressed.

Expression vectors for use in mammalian such cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adenovirus, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired wild-type, polymorphic or mutant AH-genetically-associated gene sequence, provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing wild-type, polymorphic or mutant AH-genetically-associated proteins in infected hosts.

Specific initiation signals may also be required for efficient translation of wild-type, polymorphic or mutant AH-genetically-associated coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators.

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant wild-type, polymorphic or mutant AH-genetically-associated proteins, stable expression is preferred. For example, cell lines that stably express constructs encoding wild-type, polymorphic or mutant AH-genetically-associated proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited, to the herpes simplex virus thymidine kinase, hypoxanthine-guanine phosphoribosyltransferase and adenine phosphoribosyltransferase genes, in tk-, hgprt- or aprt-cells, respectively. Also, antimetabolite resistance can be used as the basis of selection for dhfr, that confers resistance to methotrexate; gpt, that confers resistance to mycophenolic acid; neo, that confers resistance to the aminoglycoside G-418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

It is contemplated that the wild-type, polymorphic or mutant AH-genetically-associated proteins of the invention may be "overexpressed", i.e., expressed in increased levels relative to its natural expression in cells. Such overexpression may be assessed by a variety of methods, including radio-labelling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural cells is indicative of overexpression, as is a relative abundance of the specific protein in relation to the other proteins produced by the host cell and, e.g., visible on a gel.

C. Nucleic Acid Detection

In addition to their use in directing the expression of the wild-type, polymorphic or mutant AH-genetically-associated proteins, the nucleic acid sequences disclosed herein also have a variety of other uses. For example, they also have utility as probes or primers in nucleic acid hybridization embodiments.

1. Hybridization

The use of a hybridization probe of between 17 and 100 nucleotides or longer in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production.

Accordingly, the nucleotide sequences of the invention may be used for their ability to selectively form duplex molecules with complementary stretches of genes or RNAs or to provide primers for amplification of DNA or RNA from tissues. Depending on the application envisioned, one will desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, for example, substitution of nucleotides by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

2. Amplification and PCR

Nucleic acid used as a template for amplification is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids corresponding to wild-type, polymorphic or mutant AH-genetically-associated protein are contacted with the isolated nucleic acid under conditions that permit selective hybridization. The term "primer", as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology).

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and 4,800,159, and each incorporated herein by reference in entirety.

Briefly, to perform PCR, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labelling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR Gingeras et al., PCT Application WO 88/10315, incorporated herein by reference. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase 1), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990 incorporated by reference).

Methods based on ligation of two (or more) oligonucleotides in the presence of nucleic acid having the sequence of the resulting "di-oligonucleotide", thereby amplifying the di-oligonucleotide, may also be used in the amplification step of the present invention.

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light.

Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

All the essential materials and reagents required for detecting wild-type, polymorphic or mutant AH-genetically-associated protein markers in a biological sample may be assembled together in a kit. This generally will comprise preselected primers for specific markers. Also included may be enzymes suitable for amplifying nucleic acids including various polymerases (RT, Taq, etc.), deoxynucleotides and buffers to provide the necessary reaction mixture for amplification.

Such kits generally will comprise, in suitable means, distinct containers for each individual reagent and enzyme as well as for each marker primer pair. Preferred pairs of primers for amplifying nucleic acids are selected to amplify the sequences on human chromosome 1 that are genetically associated with AH such as the AH-genetically associated gene sequences specified in SEQ ID NO:1.

In another embodiment, such kits will comprise hybridization probes specific for wild-type, polymorphic or mutant AH-genetically-associated protein chosen from a group including nucleic acids corresponding to the sequences specified in SEQ ID NO:1. Such kits generally will comprise, in suitable means, distinct containers for each individual reagent and enzyme as well as for each marker hybridization probe.

3. Other Assays

Other methods for genetic screening to accurately detect mutations in genomic DNA, cDNA or RNA samples may be employed, depending on the specific situation.

Historically, a number of different methods have been used to detect point mutations, including denaturing gradient gel electrophoresis ("DGGE"), restriction enzyme polymorphism analysis, chemical and enzymatic cleavage methods, and others. The more common procedures currently in use include direct sequencing of target regions amplified by PCR™ (see above) and single-strand conformation polymorphism analysis ("SSCP").

Another method of screening for point mutations is based on RNase cleavage of base pair mismatches in RNA/DNA and RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single and multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. After the RNase cleavage reaction, the RNase is inactivated by proteolytic digestion and organic extraction, and the cleavage products are denatured by heating and analyzed by electrophoresis on denaturing polyacrylamide gels. For the detection of mismatches, the single-stranded products of the RNase A treatment, electrophoretically separated according to size, are compared to similarly treated control duplexes. Samples containing smaller fragments (cleavage products) not seen in the control duplex are scored as +.

Currently available RNase mismatch cleavage assays, including those performed according to U.S. Pat. No. 4,946,773, require the use of radiolabeled RNA probes. Myers and Maniatis in U.S. Pat. No. 4,946,773 describe the detection of base pair mismatches using RNase A. Other investigators have described the use of *E. Coli* enzyme, RNase I, in mismatch assays. Because it has broader cleavage specificity than RNase A, RNase I would be a desirable enzyme to employ in the detection of base pair mismatches if components can be found to decrease the extent of non-specific cleavage and increase the frequency of cleavage of mismatches. The use of RNase I for mismatch detection is described in literature from Promega Biotech. Promega markets a kit containing RNase I that is shown in their literature to cleave three out of four known mismatches, provided the enzyme level is sufficiently high.

The RNase protection assay was first used to detect and map the ends of specific mRNA targets in solution. The assay relies on being able to easily generate high specific activity radiolabeled RNA probes complementary to the mRNA of interest by in vitro transcription. Originally, the templates for in vitro transcription were recombinant plasmids containing bacteriophage promoters. The probes are mixed with total cellular RNA samples to permit hybridization to their complementary targets, then the mixture is treated with RNase to degrade excess unhybridized probe. Also, as originally intended, the RNase used is specific for single-stranded RNA, so that hybridized double-stranded probe is protected from degradation. After inactivation and removal of the RNase, the protected probe (which is proportional in amount to the amount of target mRNA that was present) is recovered and analyzed on a polyacrylamide gel.

The RNase Protection assay was adapted for detection of single base mutations. In this type of RNase A mismatch cleavage assay, radiolabeled RNA probes transcribed in vitro from wild-type sequences, are hybridized to complementary target regions derived from test samples. The test target generally comprises DNA (either genomic DNA or DNA amplified by cloning in plasmids or by PCR™), although RNA targets (endogenous mRNA) have occasionally been used. If single nucleotide (or greater) sequence differences occur between the hybridized probe and target, the resulting disruption in Watson-Crick hydrogen bonding at that position ("mismatch") can be recognized and cleaved in some cases by single-strand specific ribonuclease. To date, RNase A has been used almost exclusively for cleavage of single-base mismatches, although RNase I has recently been shown as useful also for mismatch cleavage. There are recent descriptions of using the MutS protein and other DNA-repair enzymes for detection of single-base mismatches.

D. Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

II. AH-GENETICALLY-ASSOCIATED PROTEINS AND PEPTIDES

The present invention therefore provides purified, and in preferred embodiments, substantially purified, AH-genetically-associated proteins and peptides. The term "purified AH-genetically-associated protein or peptide" as used herein, is intended to refer to a wild-type, polymorphic or mutant AH-genetically-associated proteinaceous composition, isolatable from mammalian cells or recombinant host cells, wherein the wild-type, polymorphic or mutant AH-genetically-associated protein or peptide is purified to any degree relative to its naturally-obtainable state, i.e., relative to its purity within a cellular extract. A purified wild-type, polymorphic or AH-genetically-associated protein or peptide therefore also refers to a wild-type, polymorphic or AH-genetically-associated protein or peptide free from the environment in which it naturally occurs. An AH-genetically associated protein or peptide is given as SEQ ID NO:2.

Wild-type, polymorphic or mutant AH-genetically-associated proteins may be full length proteins. Wild-type, polymorphic or mutant AH-genetically-associated proteins, polypeptides and peptides may also be less then full length proteins, such as individual domains, regions or even epitopic peptides. Where less than full length wild-type, polymorphic or mutant AH-genetically-associated proteins are concerned the most preferred will be those containing predicted immunogenic sites and those containing the functional domains identified herein.

Generally, "purified" will refer to a wild-type, polymorphic or AH-genetically-associated protein or peptide composition that has been subjected to fractionation to remove various non-wild-type, polymorphic or mutant AH-genetically-associated protein or peptide components, and which composition substantially retains its wild-type, polymorphic or mutant activity.

Where the term "substantially purified" is used, this will refer to a composition in which the wild-type, polymorphic or mutant AH-genetically-associated protein or peptide forms the major component of the composition, such as constituting about 50% of the proteins in the composition or more. In preferred embodiments, a substantially purified protein will constitute more than 60%, 70%, 80%, 90%, 95%, 99% or even more of the proteins in the composition.

A polypeptide or protein that is "purified to homogeneity," as applied to the present invention, means that the polypeptide or protein has a level of purity where the polypeptide or protein is substantially free from other proteins and biological components. For example, a purified polypeptide or protein will often be sufficiently free of other protein components so that degradative sequencing may be performed successfully.

Various methods for quantifying the degree of purification of wild-type, polymorphic or mutant AH-genetically-associated proteins or peptides will be known to those of skill in the art in light of the present disclosure. These include, for example, determining the specific activity of a fraction, or assessing the number of polypeptides within a fraction by gel electrophoresis. Assessing the number of polypeptides within a fraction by SDS/PAGE analysis will often be preferred in the context of the present invention as this is straightforward.

To purify a wild-type, polymorphic or mutant AH-genetically-associated protein or peptide a natural or recombinant composition comprising at least some wild-type, polymorphic or mutant AH-genetically-associated proteins or peptides will be subjected to fractionation to remove various non-wild-type, polymorphic or AH-genetically-associated components from the composition. Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques.

Another purification method involves a fusion protein using a specific binding partner. Such purification methods are routine in the art. As the present invention provides DNA sequences for AH-genetically-associated proteins, any fusion protein purification method can now be practiced. This is currently exemplified by the generation of a AH-genetically-associated-glutathione S-transferase fusion protein, expression in *E. coli*, and isolation to homogeneity using affinity chromatography on glutathione-agarose.

The exemplary purification method disclosed herein represents one method to prepare a substantially purified wild-type, polymorphic or mutant AH-genetically-associated protein or peptide. This method is preferred as it results in the substantial purification of the wild-type, polymorphic or mutant AH-genetically-associated protein or peptide in yields sufficient for further characterization and use. However, given the DNA and proteins provided by the present invention, any purification method can now be employed.

Although preferred for use in certain embodiments, there is no general requirement that the wild-type, polymorphic or mutant AH-genetically-associated protein or peptide always be provided in their most purified state. Indeed, it is contemplated that less substantially purified wild-type, polymorphic or mutant AH-genetically-associated proteins or peptides, which are nonetheless enriched in wild-type, polymorphic or mutant AH-genetically-associated protein compositions, relative to the natural state, will have utility in certain embodiments. These include, for example antibody generation where subsequent screening assays using purified wild-type, polymorphic or AH-genetically-associated proteins are conducted.

Methods exhibiting a lower degree of relative purification may have advantages in total recovery of protein product, or in maintaining the activity of an expressed protein. Inactive products also have utility in certain embodiments, such as, e.g., in antibody generation.

III. ANTIBODIES TO AH-GENETICALLY-ASSOCIATED PROTEINS

A. Epitopic Core Sequences

Peptides corresponding to one or more antigenic determinants, or "epitopic core regions", of wild-type, polymorphic or mutant AH-genetically-associated proteins of the present invention can also be prepared. Such peptides should generally be at least five or six amino acid residues in length, will preferably be about 10, 15, 20, 25 or about 30 amino acid residues in length, and may contain up to about 35–50 residues or so.

Synthetic peptides will generally be about 35 residues long, which is the approximate upper length limit of automated peptide synthesis machines, such as those available from Applied Biosystems (Foster City, Calif.). Longer peptides may also be prepared, e.g., by recombinant means.

U.S. Pat. No. 4,554,101, (Hopp) incorporated herein by reference, teaches the identification and preparation of epitopes from primary amino acid sequences on the basis of hydrophilicity. Through the methods disclosed in Hopp, one of skill in the art would be able to identify epitopes from within an amino acid sequence such as the wild-type, polymorphic or mutant AH-genetically-associated sequences disclosed herein.

Numerous scientific publications have also been devoted to the prediction of secondary structure, and to the identification of epitopes, from analyses of amino acid sequences (Chou & Fasman, 1974a,b; 1978a,b, 1979). Any of these may be used, if desired, to supplement the teachings of Hopp in U.S. Pat. No. 4,554,101.

Moreover, computer programs are currently available to assist with predicting antigenic portions and epitopic core regions of proteins. Examples include those programs based upon the Jameson-Wolf analysis (Jameson & Wolf, 1998; Wolf et al., 1988), the program PepPlot® (Brutlag et al., 1990; Weinberger et al., 1985), and other new programs for protein tertiary structure prediction (Fetrow & Bryant, 1993). Further commercially available software capable of carrying out such analyses is termed MacVector (IBI, New Haven, Conn.).

In further embodiments, major antigenic determinants of a polypeptide may be identified by an empirical approach in which portions of the gene encoding the polypeptide are expressed in a recombinant host, and the resulting proteins tested for their ability to elicit an immune response. For example, PCR can be used to prepare a range of peptides lacking successively longer fragments of the C-terminus of the protein. The immunoactivity of each of these peptides is determined to identify those fragments or domains of the polypeptide that are immunodominant. Further studies in which only a small number of amino acids are removed at each iteration then allows the location of the antigenic determinants of the polypeptide to be more precisely determined.

Another method for determining the major antigenic determinants of a polypeptide is the SPOTs™ system (Genosys Biotechnologies, Inc., The Woodlands, Tex.). In this method, overlapping peptides are synthesized on a cellulose membrane, which following synthesis and deprotection, is screened using a polyclonal or monoclonal antibody. The antigenic determinants of the peptides which are initially identified can be further localized by performing subsequent syntheses of smaller peptides with larger overlaps, and by eventually replacing individual amino acids at each position along the immunoreactive peptide.

Once one or more such analyses are completed, polypeptides are prepared that contain at least the essential features of one or more antigenic determinants. The peptides are then employed in the generation of antisera against the polypeptide. Minigenes or gene fusions encoding these determinants can also be constructed and inserted into expression vectors by standard methods, for example, using PCR cloning methodology.

The use of such small peptides for vaccination typically requires conjugation of the peptide to an immunogenic carrier protein, such as hepatitis B surface antigen, keyhole limpet hemocyanin or bovine serum albumin. Methods for performing this conjugation are well known in the art.

B. Antibody Generation

In certain embodiments, the present invention provides antibodies that bind with high specificity to wild-type, polymorphic or mutant AH-genetically-associated proteins provided herein. Thus, antibodies that bind to the protein products of the isolated nucleic acid sequences of SEQ ID NO:1 are provided. Antibodies specific for the wild-type and polymorphic proteins and peptides and those specific for any one of a number of mutants are provided. As detailed above, in addition to antibodies generated against the full length proteins, antibodies may also be generated in response to smaller constructs comprising epitopic core regions, including wild-type, polymorphic and mutant epitopes.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

However, "humanized" antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's tumor are likewise known and such custom-tailored antibodies are also contemplated.

The term "antibody" is used to refer to any antibody-like molecule that has an antigen binding region, and includes antibody fragments such as Fab', Fab, $F(ab')_2$, single domain antibodies (DABs), Fv, scFv (single chain Fv), and the like. The techniques for preparing and using various antibody-based constructs and fragments are well known in the art.

Means for preparing and characterizing antibodies are well known in the art (See, e.g., Antibodies: A Laboratory Manual, Cold Spring Harbor Laboratory, 1988; incorporated herein by reference).

The methods for generating monoclonal antibodies (MAbs) generally begin along the same lines as those for preparing polyclonal antibodies. Briefly, a polyclonal antibody is prepared by immunizing an animal with an immunogenic wild-type, polymorphic or mutant AH-genetically-associated protein composition in accordance with the present invention and collecting antisera from that immunized animal.

A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, toxins or synthetic compositions.

Adjuvants that may be used include IL-1, IL-2, IL-4, IL-7, IL-12, g-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion. MHC antigens may even be used.

Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or down-regulate suppressor cell activity. Such BRMs include, but are not limited to, Cimetidine (CIM; 1200 mg/d) (Smith/Kline, PA); or low-dose Cyclophosphamide (CYP; 300 $mg/m^2$) (Johnson/Mead, NJ) and Cytokines such as γ-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified wild-type, polymorphic or mutant AH-genetically-associated protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways.

A sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration.

The individual cell lines could also be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Alternatively, monoclonal antibody fragments encompassed by the present invention can be synthesized using an automated peptide synthesizer, or by expression of full-length gene or of gene fragments in *E. coli.*

C. Antibody Conjugates

The present invention further provides antibodies against wild-type, polymorphic or mutant AH-genetically-associated proteins, generally of the monoclonal type, that are linked to one or more other agents to form an antibody conjugate. Any antibody of sufficient selectivity, specificity and affinity may be employed as the basis for an antibody conjugate. Such properties may be evaluated using conventional immunological screening methodology known to those of skill in the art.

Certain examples of antibody conjugates are those conjugates in which the antibody is linked to a detectable label. "Detectable labels" are compounds or elements that can be detected due to their specific functional properties, or chemical characteristics, the use of which allows the antibody to which they are attached to be detected, and further quantified if desired. Another such example is the formation of a conjugate comprising an antibody linked to a cytotoxic or anti-cellular agent, as may be termed "immunotoxins". In the context of the present invention, immunotoxins are generally less preferred.

Antibody conjugates are thus preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging". Again, antibody-directed imaging is less preferred for use with this invention.

Many appropriate imaging agents are known in the art, as are methods for their attachment to antibodies (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the antibody (U.S. Pat. No. 4,472,509). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred.

Ions useful in other contexts, such as X-ray imaging, include but are not limited to lanthanum (III), gold (III), lead (II), and especially bismuth (III).

In the case of radioactive isotopes for therapeutic and/or diagnostic application, one might mention $^{211}$astatine, $^{14}$carbon, $^{51}$chromium, $^{36}$chlorine, $^{57}$cobalt, $^{58}$cobalt, $^{67}$copper, $^{152}$Eu, $^{67}$gallium, $^{3}$hydrogen, $^{123}$iodine, $^{125}$iodine, $^{131}$iodine, $^{111}$indium, $^{59}$iron, $^{32}$phosphorus, $^{186}$rhenium, $^{188}$rhenium, $^{75}$selenium, $^{35}$sulphur, $^{99m}$technicium and $^{90}$yttrium. $^{125}$I is often being preferred for use in certain embodiments, and $^{99m}$technicium and $^{111}$indium are also often preferred due to their low energy and suitability for long range detection.

Radioactively labeled monoclonal antibodies of the present invention may be produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with $^{99m}$technicium by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as $SNCl_2$, a buffer solution such as sodium-potassium phthalate solution, and the antibody.

Intermediary functional groups which are often used to bind radioisotopes which exist as metallic ions to antibody are diethylenetriaminepentaacetic acid (DTPA) and ethylene diaminetetracetic acid (EDTA).

Fluorescent labels include rhodamine, fluorescein isothiocyanate and renographin.

The much preferred antibody conjugates of the present invention are those intended primarily for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

D. Immunodetection Methods

In still further embodiments, the present invention concerns immunodetection methods for binding, purifying, removing, quantifying or otherwise generally detecting biological components such as wild-type, polymorphic or mutant AH-genetically-associated protein components. The wild-type, polymorphic or mutant AH-genetically-associated proteins or peptides of the present invention may be employed to detect and purify AH-genetically-associated polypeptides, and antibodies prepared in accordance with the present invention, may be employed to detect wild-type, polymorphic or mutant AH-genetically-associated proteins or peptides. As described throughout the present application, the use of wild-type, polymorphic and mutant specific antibodies is contemplated. The steps of various useful immunodetection methods have been described in the scientific literature, such as, e.g., Nakamura et al. (1987), incorporated herein by reference.

In general, the immunobinding methods include obtaining a sample suspected of containing a wild-type, polymorphic or mutant AH-genetically-associated protein or peptide, and contacting the sample with a first anti-wild-type, polymorphic or mutant AH-genetically-associated protein antibody in accordance with the present invention, as the case may be, under conditions effective to allow the formation of immunocomplexes.

These methods include methods for purifying wild-type, polymorphic or mutant AH-genetically-associated protein, as may be employed in purifiying wild-type, polymorphic or mutant AH-genetically-associated protein from patients' samples or for purifying recombinantly expressed wild-type, polymorphic or mutant AH-genetically-associated protein. In these instances, the antibody removes the antigenic wildtype, polymorphic or mutant AH-genetically-associated protein component from a sample. The antibody will preferably be linked to a solid support, such as in the form of a column matrix, and the sample suspected of containing the wild-type, polymorphic or mutant AH-genetically-associated protein antigenic component will be applied to the immobilized antibody. The unwanted components will be washed from the column, leaving the antigen immunocomplexed to the immobilized antibody, which wild-type, polymorphic or mutant AH-genetically-associated protein antigen is then collected by removing the wild-type, polymorphic or mutant AH-genetically-associated protein from the column.

The immunobinding methods also include methods for detecting or quantifying the amount of a wild-type, polymorphic or mutant AH-genetically-associated protein reactive component in a sample, which methods require the detection or quantification of any immune complexes formed during the binding process. Here, one would obtain a sample suspected of containing a wild-type, polymorphic or mutant AH-genetically-associated protein or peptide, and contact the sample with an antibody against wild-type, polymorphic or mutant AH-genetically-associated protein, and then detect or quantify the amount of immune complexes formed under the specific conditions.

In terms of antigen detection, the biological sample analyzed may be any sample that is suspected of containing a wild-type, polymorphic or mutant AH-genetically-associated protein-specific antigen, such as a blood or urinary sample or specimen, a bone or kidney tissue section or specimen, a homogenized bone or kidney tissue extract, a bone or kidney cell, separated or purified forms of any of the above wild-type, polymorphic or mutant AH-genetically-associated protein-containing compositions, or even any biological fluid that comes into contact with bone or kidney tissue, including blood and serum.

Contacting the chosen biological sample with the antibody under conditions effective and for a period of time sufficient to allow the formation of immune complexes (primary immune complexes) is generally a matter of simply adding the antibody composition to the sample and incubating the mixture for a period of time lone enough for the antibodies to form immune complexes with, i.e., to bind to, any wild-type, polymorphic or mutant AH-genetically-associated protein antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological or enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The wild-type, polymorphic or mutant AH-genetically-associated protein antibody employed in the detection may itself be linked to a detectable label, wherein one would then simply detect this label, thereby allowing the amount of the primary immune complexes in the composition to be determined.

Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

The immunodetection methods of the present invention have evident utility in the diagnosis or prognosis of conditions such stone formation and osteoporosis. Here, a biological or clinical sample suspected of containing a wild-type, polymorphic or mutant AH-genetically-associated protein or peptide is used. However, these embodiments also have applications to non-clinical samples, such as in the titering of antigen or antibody samples, in the selection of hybridomas, and the like.

In the clinical diagnosis or monitoring of patients with stone formation or osteoporosis, the detection of an AH-genetically-associated protein mutant, or an alteration in the levels of AH-genetically-associated protein, in comparison to the levels in a corresponding biological sample from a normal subject may be indicative of a patient with a genetic basis for AH.

However, as is known to those of skill in the art, such a clinical diagnosis would not necessarily be made on the basis of this method in isolation. Those of skill in the art are very familiar with differentiating between significant differences in types or amounts of biomarkers, which represent a positive identification, and low level or background changes of biomarkers. Indeed, background expression levels are often used to form a "cut-off" above which increased detection will be scored as significant or positive.

1. ELISAs

As detailed above, immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and Western blotting, dot blotting, FACS analyses, and the like may also be used.

In one exemplary ELISA, the anti-wild-type, polymorphic or mutant AH-genetically-associated protein antibodies of the invention are immobilized onto a selected surface exhibiting protein affinity, such as a well in a polystyrene microtiter plate. Then, a test composition suspected of containing the wild-type, polymorphic or mutant AH-genetically-associated protein antigen, such as a clinical sample, is added to the wells. After binding and washing to remove non-specifically bound immune complexes, the bound wild-type, polymorphic or mutant AH-genetically-associated protein antigen may be detected. Detection is generally achieved by the addition of another anti-wild-type, polymorphic or mutant AH-genetically-associated protein antibody that is linked to a detectable label. This type of ELISA is a simple "sandwich ELISA". Detection may also be achieved by the addition of a second anti-wild-type, polymorphic or mutant AH-genetically-associated protein antibody, followed by the addition of a third antibody that has binding affinity for the second antibody, with the third antibody being linked to a detectable label.

In another exemplary ELISA, the samples suspected of containing the wild-type, polymorphic or mutant AH-genetically-associated protein antigen are immobilized onto the well surface and then contacted with the anti-wild-type, polymorphic or mutant AH-genetically-associated protein antibodies of the invention. After binding and washing to remove non-specifically bound immune complexes, the bound anti-wild-type, polymorphic or mutant AH-genetically-associated protein antibodies are detected. Where the initial anti-wild-type, polymorphic or mutant AH-genetically-associated protein antibodies are linked to a detectable label, the immune complexes may be detected directly. Again, the immune complexes may be detected using a second antibody that has binding affinity for the first anti-wild-type, polymorphic or mutant AH-genetically-associated protein antibody, with the second antibody being linked to a detectable label.

Another ELISA in which the wild-type, polymorphic or mutant AH-genetically-associated proteins or peptides are immobilized, involves the use of antibody competition in the detection. In this ELISA, labeled antibodies against wild-type, polymorphic or mutant AH-genetically-associated protein are added to the wells, allowed to bind, and detected by means of their label. The amount of wild-type, polymorphic or mutant AH-genetically-associated protein antigen in an unknown sample is then determined by mixing the sample with the labeled antibodies against wild-type, polymorphic or mutant AH-genetically-associated protein before or during incubation with coated wells. The presence of wild-type, polymorphic or mutant AH-genetically-associated protein in the sample acts to reduce the amount of antibody against wild-type, polymorphic or mutant AH-genetically-associated protein available for binding to the well and thus reduces the ultimate signal. This is also appropriate for detecting antibodies against wild-type, polymorphic or mutant AH-genetically-associated protein in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immune complexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

2. Immunohistochemistry

The antibodies of the present invention may also be used in conjunction with both fresh-frozen and formalin-fixed, paraffin-embedded tissue blocks prepared for study by immunohistochemistry (IHC). For example, each tissue block consists of 50 mg of residual "pulverized" diabetic tissue. The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" diabetic tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25–50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

E. Immunodetection Kits

In still further embodiments, the present invention concerns immunodetection kits for use with the immunodetection methods described above. As the wild-type, polymorphic or mutant AH-genetically-associated protein antibodies are generally used to detect wild-type, polymorphic or mutant AH-genetically-associated proteins or peptides, the antibodies will preferably be included in the kit. However, kits including both such components may be provided. The immunodetection kits will thus comprise, in suitable container means, a first antibody that binds to a wild-type, polymorphic or mutant AH-genetically-associated protein or peptide, and optionally, an immunodetection reagent and further optionally, a wild-type, polymorphic or mutant AH-genetically-associated protein or peptide.

In preferred embodiments, monoclonal antibodies will be used. In certain embodiments, the first antibody that binds to the wild-type, polymorphic or mutant AH-genetically-associated protein or peptide may be pre-bound to a solid support, such as a column matrix or well of a microtitre plate.

The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present invention.

The kits may further comprise a suitably aliquoted composition of the wild-type, polymorphic or mutant AH-genetically-associated protein or polypeptide, whether labeled or unlabeled, as may be used to prepare a standard curve for a detection assay.

The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, and preferably, suitably aliquoted. Where wild-type, polymorphic or mutant AH-genetically-associated protein or a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

IV. BIOLOGICAL FUNCTIONAL EQUIVALENTS

As modifications and changes may be made in the structure of wild-type, polymorphic or mutant AH-genetically-associated genes and proteins of the present invention, and still obtain molecules having like or otherwise desirable characteristics, such biologically functional equivalents are also encompassed within the present invention.

For example, certain amino acids may be substituted for other amino acids in a protein structure without appreciable loss of interactive binding capacity with structures such as, for example, antigen-binding regions of antibodies, binding sites on substrate molecules or receptors, DNA binding sites, or such like. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. It is thus contemplated by the inventors that various changes may be made in the sequence of wild-type, polymorphic or mutant AH-genetically-associated proteins or peptides, or underlying DNA, without appreciable loss of their biological utility or activity.

Equally, the same considerations may be employed to create a protein or peptide with countervailing, e.g., antagonistic properties. This is relevant to the present invention in which AH-genetically-associated mutants or analogues may be generated. For example, a AH-genetically-associated mutant may be generated and tested functionally to identify those residues important for its activity. AH-genetically-associated mutants may also be synthesized to reflect a AH-genetically-associated mutant that occurs in the human population and that is linked to the development of hypercalciuria and osteoporosis. Such mutant proteins are particularly contemplated for use in generating mutant-specific antibodies and such mutant DNA segments may be used as mutant-specific probes and primers.

In terms of functional equivalents, it is well understood by the skilled artisan that, inherent in the definition of a "biologically functional equivalent protein or peptide or gene", is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted.

In particular, where shorter length peptides, it is contemplated that fewer amino acids should be made within the given peptide. Longer domains may have an intermediate number of changes. The full length protein will have the most tolerance for a larger number of changes. Of course, a plurality of distinct proteins/peptides with different substitutions may easily be made and used in accordance with the invention.

It is also well understood that where certain residues are shown to be particularly important to the biological or structural properties of a protein or peptide, e.g., residues in binding regions or active sites, such residues may not generally be exchanged. Changes in domains should be carefully considered and subsequently tested to ensure maintenance of biological function, where maintenance of biological function is desired. In this manner, functional equivalents are defined herein as those peptides which maintain a substantial amount of their native biological activity.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent protein or peptide thereby created is intended for use in immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented herein for use in such embodiments, as well as for other uses, such as in the design of probes and primers and the like.

In addition to the wild-type, polymorphic or mutant AH-genetically-associated peptidyl compounds described herein, the inventors also contemplate that other sterically similar compounds may be formulated to mimic the key portions of the peptide structure. Such compounds, which may be termed peptidomimetics, may be used in the same manner as the peptides of the invention and hence are also functional equivalents.

Certain mimetics that mimic elements of protein secondary structure are described in Johnson et al. (1993). The underlying rationale behind the use of peptide mimetics is that the peptide backbone of proteins exists chiefly to orientate amino acid side chains in such a way as to facilitate molecular interactions, such as those of antibody and antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

The generation of further structural equivalents or mimetics may be achieved by the techniques of modeling and chemical design known to those of skill in the art. The art of receptor modeling is now well known, and by such methods a chemical that binds to wild-type, polymorphic or mutant AH-genetically-associated protein or to a wild-type, polymorphic or mutant AH-genetically-associated protein complex can be designed and then synthesized. It will be understood that all such sterically designed constructs fall within the scope of the present invention.

V. PURIFICATION AND ASSAYS OF PROTEINS THAT INTERACT WITH EITHER AH LOCI OR THE AH-GENTICALLY-ASSOCIATED PROTEINS

Certain aspects of this invention concern methods for conveniently evaluating candidate substances to identify compounds capable of interacting with a wild-type, polymorphic or mutant AH-genetically-associated protein, or even transcription of a wild-type, polymorphic or mutant AH-genetically-associated protein.

Successful candidate substances may function in the absence of mutations in AH-genetically-associated protein, in which case the candidate compound may be termed a “positive stimulator” of AH-genetically-associated protein. Alternatively, such compounds may stimulate transcription in the presence of mutated AH-genetically-associated protein, overcoming the effects of the mutation, i.e., function to oppose AH-genetically-associated protein-mutant mediated AH, and thus may be termed an "AH-genetically-associated protein mutant agonist". Compounds may even be discovered which combine both of these actions. Compounds of any such class will likely be useful therapeutic agents for use in treating AH or osteoporosis.

AH-genetically-associated proteins may function by binding to DNA. One method by which to identify a candidate substance capable of stimulating AH-genetically-associated protein is based upon specific protein:protein binding. Accordingly, to conduct such an assay, one may prepare a protein with a domain and determine the ability of a candidate substance to increase the activity of the AH-genetically-associated protein to bind DNA.

Another method by which to identify a candidate substance capable of stimulating AH-genetically-associated proteins is based upon specific protein:DNA binding. Accordingly, to conduct such an assay, one would prepare an AH-genetically-associated protein and determine the ability of a candidate substance to increase the binding to a specific DNA segment, i.e., to increase the amount or the binding affinity of a specific protein:DNA complex.

Binding assays can be parallel assays, one of which contains the binding components alone and one of which contains the added candidate substance composition. One would perform each assay under conditions, and for a period of time, effective to allow the formation of protein:protein complexes or protein:DNA complexes, and one would then separate the bound complexes from any unbound protein and/or DNA and measure the amount of the complexes. An increase in the amount of any bound complex formed in the presence of the candidate substance would be indicative of a candidate substance capable of promoting AH-genetically-associated protein binding to DNA.

In such binding assays, the amount of the bound complex may be measured, after the removal of unbound species, by detecting a label, such as a radioactive or enzymatic label, which has been incorporated into the original wild-type, polymorphic or mutant AH-genetically-associated protein or even in a DNA segment. Alternatively, one could detect the protein portion of the complex by means of an antibody directed against the protein, such as those disclosed herein.

Preferred binding assays are those in which AH-genetically-associated protein is bound to a solid support and contacted with the another component to allow complex formation. Unbound protein components are then separated from the bound complexes by washing and the amount of the remaining bound complex is quantitated by detecting the label or with antibodies. Such binding assays form the basis of filter-binding and microtiter plate-type assays and can be performed in a semi-automated manner to enable analysis of a large number of candidate substances in a short period of time. Electrophoretic methods of DNA binding, such as gel-shift assays, could also be employed to separate unbound protein or DNA from bound protein:DNA complexes.

Virtually any candidate substance may be analyzed by these methods, including compounds which may interact with wild-type, polymorphic, mutant AH-genetically-associated protein, and also substances such as enzymes which may act by physically altering one of the structures present. Of course, any compound isolated from natural sources such as plants, animals or even marine, forest or soil samples, may be assayed, as may any synthetic chemical or recombinant protein.

Another potential method for stimulating AH-genetically-associated activity is to prepare a wild-type, polymorphic, mutant AH-genetically-associated protein composition and to modify the protein composition in a manner effective to increase its binding activity. The binding assays would be performed in parallel, similar to those described above, allowing the native and modified wild-type, polymorphic, mutant AH-genetically-associated protein binding to be compared. In addition to site specific mutagenesis, phosphatase and kinase enzymes may be tested, as may other agents, including proteases and chemical agents, could be employed to modify the binding properties of wild-type, polymorphic, mutant AH-genetically-associated proteins.

Cellular assays also are available for screening candidate substances to identify those capable of stimulating wild-type, polymorphic, mutant AH-genetically-associated protein and/or capable of stimulating the transcription and gene expression of AH-genetically-associated genes. A reporter gene under the control of the transcriptional regulating region of an AH-genetically-associated gene can be used. A reporter gene is a gene that confers on its recombinant host cell a readily detectable phenotype that emerges only under specific conditions.

Reporter genes are genes which encode a polypeptide not otherwise produced by the host cell which is detectable by analysis of the cell culture, e.g., by fluorometric, radioisotopic or spectrophotometric analysis of the cell culture. Exemplary enzymes include luciferases, transferases, esterases, phosphatases, proteases (tissue plasminogen activator or urokinase), and other enzymes capable of being detected by their physical presence or functional activity. A reporter gene often used is chloramphenicol acetyltransferase (CAT) which may be employed with a radiolabeled substrate, or luciferase, which is measured fluorometrically.

Another class of reporter genes which confer detectable characteristics on a host cell are those which encode polypeptides, generally enzymes, which render their transformants resistant against toxins, e.g., the neo gene which protects host cells against toxic levels of the antibiotic G418, and genes encoding dihydrofolate reductase, which confers resistance to methotrexate. Other genes of potential for use in screening assays are those capable of transforming hosts to express unique cell surface antigens, e.g., viral env proteins such as HIV gp120 or herpes gD, which are readily detectable by immunoassays.

The transcriptional promotion process which, in its entirety, leads to enhanced transcription is termed "activation." The mechanism by which a successful candidate substance acts is not material since the objective is to promote wild-type, polymorphic, mutant AH-genetically-associated gene expression.

To create an appropriate vector or plasmid for use in such assays one would ligate the AH-genetically-associated protein promoter and any necessary response elements to a DNA segment encoding the reporter gene by conventional methods. The relevant promoter sequences may be obtained by in vitro synthesis or recovered from genomic DNA and should be ligated upstream of the start codon of the reporter gene. An AT-rich TATA box region should also be employed and should be located between the sequence and the reporter gene start codon. The region 3' to the coding sequence for the reporter gene will ideally contain a transcription termination and polyadenylation site. The promoter and reporter gene may be inserted into a replicable vector and transfected into a cloning host such as *E. coli*, the host cultured and the replicated vector recovered in order to prepare sufficient quantities of the construction for later transfection into a suitable eukaryotic host.

Host cells for use in the screening assays of the present invention will generally be mammalian cells, and are preferably cell lines which may be used in connection with transient transfection studies. Cell lines should be relatively easy to grow in large scale culture. Also, they should contain as little native background as possible considering the nature of the reporter polypeptide. Examples include the Hep G2, VERO, HeLa, human embryonic kidney, 293, CHO, W138, BHK, COS-7, and MDCK cell lines, with monkey CV-1 cells being particularly preferred.

The screening assay typically is conducted by growing recombinant host cells in the presence and absence of candidate substances and determining the amount or the activity of the reporter gene. Cells containing varying proportions of candidate substances would then be evaluated for signal activation in comparison to the suppressed levels. Candidates that demonstrate dose related enhancement of reporter gene transcription or expression are then selected for further evaluation as clinical therapeutic agents.

VI. DIAGNOSTICS

As with the therapeutic methods of the present invention, the diagnostic methods are based upon the weight of evidence of the importance of AH-genetically-associated genes and other genes identified.

The diagnostic methods of the present invention generally involve detecting the presence of a particular marker or gene genetically associated with AH from a blood or urine sample from a patient with heightened susceptibility either to develop nephrolithiasis/urolithiasis or to develop osteoporosis. Once more information is known about the molecular mechanism of such markers or genes, a diagnostic method may involve determining either the type or the amount of a wild-type, polymorphic or mutant AH-genetically-associated protein present within a biological sample from a patient suspected of having AH or osteoporosis with hypercalciuria. Irrespective of the actual role of AH-genetically-associated proteins, it will be understood that the detection of either the genetic basis for AH or a mutant protein encoded by an AH gene on human chromosome 1 is likely to be diagnostic of an increased risk of AH and osteoporosis with hypercalciuria and that the detection of altered amounts of AH-genetically-associated proteins, either at the mRNA or protein level, is also likely to have diagnostic implications, particularly where there is a reasonably significant difference in amounts.

The type or amount of a wild-type or mutant AH-genetically-associated protein present within a biological sample, such as a blood, urine, or tissue sample, may be determined by means of a molecular biological assay to determine the level of a nucleic acid that encodes such a AH-genetically-associated protein, or by means of an immunoassay to determine the level of the polypeptide itself.

Any of the foregoing nucleic acid detection methods or immunodetection methods may be employed as a diagnostic methods in the context of the present invention.

VII. THERAPEUTICS

AH leads to elevated urinary calcium excretion. The elevated calcium salts in the urine leads to precipitate formation and eventual stone development. The underlying mechanism pertaining to the elevated calcium absorption is not understood as is the relationship of AH to osteoporosis. Osteoporosis is defined as a group of disorders that is characterized by aberrant bone remodeling; the net rate of bone resorption is greater, rather than in dynamic equilibrium with, the rate of bone formation. The condition can occur as either a primary disorder or as a disorder associated with a various disease, such as hypercalciuria. Examples of osteoporosis with hypercalciuria include ideopathic osteoporosis with hypercalciuria and postmenopausal osteoporosis with hypercalciuria. Ideopathic ostoeporosis is often times seen in young women or men demonstrating increased calcium absorption for unknown reasons. Postmenopausal osteoporosis is seen in postmenopausal women and is associated with decreased estrogen levels and increased calcium absorption.

In some families, as described later in significant detail, the risk of developing AH is associated with the presence of particular loci located on human chromosome 1. In addition to dietary adjustments and hormone therapy, more permanent therapeutic methods are also contemplated by the present invention. Depending on the underlying molecular mechanism of AH, certain therapies can be implemented to correct the AH defect.

1. Gene Therapy

If a mutant form of an AH gene is involved in the susceptibility of a patient of developing AH, a general approach of the present invention is to provide a cell with a wild-type or polymorphic AH-genetically-associated protein, thereby permitting the proper regulatory activity of the proteins to take effect. While it is conceivable that the protein may be delivered directly, a preferred embodiment involves providing a nucleic acid encoding a AH-genetically-associated protein to the cell. Following this provision, the polypeptide is synthesized by the transcriptional and translational machinery of the cell, as well as any that may be provided by the expression construct. In providing antisense, ribozymes and other inhibitors, the preferred mode is also to provide a nucleic acid encoding the construct to the cell. All such approaches are herein encompassed within the term “gene therapy”.

In various embodiments of the invention, DNA is delivered to a cell as an expression construct. Several non-viral methods for the transfer of expression constructs into cultured mammalian cells also are contemplated by the present invention. These include calcium phosphate precipitation, DEAE-dextran, electroporation, direct microinjection, DNA-loaded liposomes and lipofectamine-DNA complexes, cell sonication, gene bombardment using high velocity microprojectiles, and receptor-mediated transfection. Some of these techniques may be successfully adapted for in vivo or ex vivo use, as discussed below.

In another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro, but it may be applied to in vivo use as well.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them. Several devices for accelerating small particles have been developed. One such device relies on a high voltage discharge to generate an electrical current, which in turn provides the motive force. The microprojectiles used have consisted of biologically inert substances such as tungsten or gold beads.

In a further embodiment of the invention, the expression construct may be entrapped in a liposome, as discussed below. Also contemplated are lipofectamine-DNA complexes. Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. In certain embodiments of the invention, the liposome may be complexed with a hemagglutinating virus (HVJ). This has been shown to facilitate fusion with the cell membrane and promote cell entry of liposome-encapsulated DNA. In other embodiments, the liposome may be complexed or employed in conjunction with nuclear non-histone chromosomal proteins (HMG-1). In yet further embodiments, the liposome may be complexed or employed in conjunction with both HVJ and HMG-1. In other embodiments, the delivery vehicle may comprise a ligand and a liposome. Where a bacterial promoter is employed in the DNA construct, it also will be desirable to include within the liposome an appropriate bacterial polymerase.

The ability of certain viruses to enter cells via receptor-mediated endocytosis and to integrate into host cell genome and express viral genes stably and efficiently have made them attractive candidates for the transfer of foreign genes into mammalian cells. Preferred gene therapy vectors of the present invention will generally be viral vectors.

Retroviruses have promise as gene delivery vectors due to their ability to integrate their genes into the host genome, transferring a large amount of foreign genetic material, infecting a broad spectrum of species and cell types and of being packaged in special cell-lines (Miller, 1992).

Other viruses, such as adenovirus, herpes simplex viruses (HSV), cytomegalovirus (CMV), and adeno-associated virus (AAV), such as those described by U.S. Pat. No. 5,139,941, incorporated herein by reference, may also be engineered to serve as vectors for gene transfer. Although some viruses that can accept foreign genetic material are limited in the number of nucleotides they can accommodate and in the range of cells they infect, these viruses have been demonstrated to successfully effect gene expression. However, adenoviruses do not integrate their genetic material into the host genome and therefore do not require host replication for gene expression, making them ideally suited for rapid, efficient, heterologous gene expression. Techniques for preparing replication-defective infective viruses are well known in the art.

In certain further embodiments, the gene therapy vector will be HSV. A factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations. HSV also is relatively easy to manipulate and can be grown to high titers. Thus, delivery is less of a problem, both in terms of volumes needed to attain sufficient MOI and in a lessened need for repeat dosings.

Of course, in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

Gene delivery using second generation retroviral vectors has been reported. Kasahara et al. (1994) prepared an engineered variant of the Moloney murine leukemia virus, that normally infects only mouse cells, and modified an envelope protein so that the virus specifically bound to, and infected, human cells bearing the erythropoietin (EPO) receptor. This was achieved by inserting a portion of the EPO sequence into an envelope protein to create a chimeric protein with a new binding specificity.

2. Antisense

In an alternative embodiment, the AH-genetically-associated protein nucleic acids employed may actually encode antisense constructs that hybridize, under intracellular conditions, to AH-genetically-associated protein nucleic acids. The term "antisense construct" is intended to refer to nucleic acids, preferably oligonucleotides, that are complementary to the base sequences of a target DNA or RNA. Antisense oligonucleotides, when introduced into a target cell, specifically bind to their target nucleic acid and interfere with transcription, RNA processing, transport, translation and/or stability.

Antisense constructs may be designed to bind to the promoter and other control regions, exons, introns or even exon-intron boundaries of a gene. Antisense RNA constructs, or DNA encoding such antisense RNA's, may be employed to inhibit gene transcription or translation or both within a host cell, either in vitro or in vivo, such as within a host animal, including a human subject. Nucleic acid sequences which comprise "complementary nucleotides" are those which are capable of base-pairing according to the standard Watson-Crick complementarity rules. That is, that the larger purines will base pair with the smaller pyrimidines to form combinations of guanine paired with cytosine (G:C) and adenine paired with either thymine (A:T), in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

As used herein, the terms "complementary" means nucleic acid sequences that are substantially complementary over their entire length and have very few base mismatches. For example, nucleic acid sequences of fifteen bases in length may be termed complementary when they have a complementary nucleotide at thirteen or fourteen positions with only a single mismatch. Naturally, nucleic acid sequences which are "completely complementary" will be nucleic acid sequences which are entirely complementary throughout their entire length and have no base mismatches.

Other sequences with lower degrees of homology also are contemplated. For example, an antisense construct which has limited regions of high homology, but also contains a non-homologous region (e.g., a ribozyme) could be designed. These molecules, though having less than 50% homology, would bind to target sequences under appropriate conditions.

While all or part of the AH-genetically-associated protein gene sequence may be employed in the context of antisense construction, short oligonucleotides are easier to make and increase in vivo accessibility. However, both binding affinity and sequence specificity of an antisense oligonucleotide to its complementary target increases with increasing length. One can readily determine whether a given antisense nucleic acid is effective at targeting of the corresponding host cell gene simply by testing the constructs in vitro to determine whether the function of the endogenous gene is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression.

VIII. PHARMACEUTICAL COMPOSITIONS

A. Pharmaceutically Acceptable Carriers

Aqueous compositions of the present invention comprise an effective amount of the AH-genetically-associated protein, peptide, epitopic core region, inhibitor, or such like, dissolved or dispersed in a pharmaceutically acceptable carrier or aqueous medium. Aqueous compositions of gene therapy vectors expressing any of the foregoing are also contemplated. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, subcutaneous, intralesional, or even intraperitoneal routes. The preparation of an aqueous composition that contains an AH-genetically-associated agent as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An AH-genetically-associated protein, peptide, agonist or antagonist of the present invention can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In terms of using peptide therapeutics as active ingredients, the technology of U.S. Pat. Nos. 4,608,251; 4,601,903; 4,599,231; 4,599,230; 4,596,792; and 4,578,770, each incorporated herein by reference, may be used.

The preparation of more, or highly, concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

The active AH-genetically-associated protein-derived peptides or agents may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including cremes.

One may also use nasal solutions or sprays, aerosols or inhalants in the present invention. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5.

In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Additional formulations which are suitable for other modes of administration include vaginal suppositories and pessaries. A rectal pessary or suppository may also be used.

Suppositories are solid dosage forms of various weights and shapes, usually medicated, for insertion into the rectum, vagina or the urethra. After insertion, suppositories soften, melt or dissolve in the cavity fluids.

In general, for suppositories, traditional binders and carriers may include, for example, polyalkylene glycols or triglycerides; such suppositories may be formed from mixtures containing the active ingredient in the range of 0.5% to 10%, preferably 1%–2%.

Vaginal suppositories or pessaries are usually globular or oviform and weighing about 5 g each. Vaginal medications are available in a variety of physical forms, e.g., creams, gels or liquids, which depart from the classical concept of suppositories. Vaginal tablets, however, do meet the definition, and represent convenience both of administration and manufacture.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25–60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

B. Liposomes and Nanocapsules

In certain embodiments, the use of liposomes and/or nanoparticles is contemplated for the introduction of wild-type, polymorphic or mutant AH-genetically-associated protein peptides or agents, or gene therapy vectors, including both wild-type and antisense vectors, into host cells. The formation and use of liposomes is generally known to those of skill in the art, and is also described below.

Nanocapsules can generally entrap compounds in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

The following information may also be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

C. Kits

Therapeutic kits of the present invention are kits comprising a wild-type, polymorphic or mutant AH-genetically-associated protein, peptide, inhibitor, gene, vector or other AH-genetically-associated protein effector. Such kits will generally contain, in suitable container means, a pharmaceutically acceptable formulation of an AH-genetically-associated protein, peptide, domain, inhibitor, or a gene or vector expressing any of the foregoing in a pharmaceutically acceptable formulation, optionally comprising other anti-AH or osteoporosis agents. The kit may have a single container means, or it may have distinct container means for each compound.

When the components of the kit are provided in one or more liquid solutions, the liquid solution is an aqueous solution, with a sterile aqueous solution being particularly preferred. The AH-genetically-associated protein compositions may also be formulated into a syringeable composition. In which case, the container means may itself be a syringe, pipette, or other such like apparatus, from which the formulation may be applied to an infected area of the body, injected into an animal, or even applied to and mixed with the other components of the kit.

However, the components of the kit may be provided as dried powder(s). When reagents or components are provided as a dry powder, the powder can be reconstituted by the addition of a suitable solvent. It is envisioned that the solvent may also be provided in another container means.

The container means will generally include at least one vial, test tube, flask, bottle, syringe or other container means, into which the AH-genetically-associated protein or gene or inhibitory formulation are placed, preferably, suitably allocated. Where a second AH therapeutic is provided, the kit will also generally contain a second vial or other container into which this agent may be placed. The kits may also comprise a second/third container means for containing a sterile, pharmaceutically acceptable buffer or other diluent.

The kits of the present invention will also typically include a means for containing the vials in close confinement for commercial sale, such as, e.g., injection or blow-molded plastic containers into which the desired vials are retained.

Irrespective of the number or type of containers, the kits of the invention may also comprise, or be packaged with, an instrument for assisting with the injection/administration or placement of the ultimate AH-genetically-associated protein or gene composition within the body of an animal. Such an instrument may be a syringe, pipette, forceps, or any such medically approved delivery vehicle.

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Clinical Evaluation of Absorptive Hypercalciuria (AH)

This example demonstrates the clinical evaluation of three kindreds with severe AH. Examination of multiple clinical parameters was used for phenotypic assignment.

Methods

Kindred Description and Evaluation

All participants gave informed consent to a protocol approved by the Institutional Review Board. Three kindreds with severe AH participated in this study. The probands were identified from patients in the kidney stone clinic. In the first kindred, AH-01 (FIG. 1A), 22 family members and 4 unrelated spouses were evaluated. In the second kindred, AH-02 (FIG. 1B), 5 individuals were evaluated and in the third kindred, AH-03 (FIG. 1C), 4 family members were evaluated. All kindreds were North American Caucasians of Western European descent. The number of subjects evaluated and the scope of investigation depended on the willingness and cooperation of the subjects. Either an inpatient or outpatient evaluation was done on consenting study participants. Some individuals agreed to undergo only a partial outpatient evaluation.

Inpatient Evaluation

Patients were evaluated according to established protocols (Breslau et al., 1992; Pak et al., 1974). Individuals were admitted to the General Clinical Research Center for 4 days where they were maintained on a constant metabolic diet containing 100 mmol sodium, 10 mmol calcium and 25.8 mmol phosphorous per day for 3 days (Days 1–3) after being on an instructed diet of similar composition for 1 week prior to admission. Fasting blood samples on days 1–4 were analyzed for calcium and alkaline phosphatase (Smith-Kline Beecham, Dallas, Tex.). Fasting venous blood samples on days 1 and 4 were analyzed for serum iPTH by immunoradiometric assay (Nichols Institute, San Juan Capistrano, Calif.) and 1,25$(OH)_2$D (by radioreceptor assay). Calcium and creatinine were measured in three successive 24-h urine collections (Days 1 to 3). On Day 4, a 2 h fasting urine collection was obtained for measurement of calcium and creatinine, and a 4 h urine collection was obtained for the same tests after an oral ingestion of a synthetic meal containing 1 g of calcium (Pak et al., 1980; Pak et al., 1975). The calciuric response after the calcium load gave an indirect measure of intestinal calcium absorption (Pak et al., 1980; Pak et al., 1975). Fractional calcium absorption (α) was determined either from the fecal recovery of $^{47}$Ca after ingestion of a synthetic test meal containing trace radiocalcium, (Pak et al., 1974) or by using a double stable isotope technique (Abrams, 1994). The two tests yielded equivalent results. Bone mineral density of L2–L4 vertebrae, femoral neck and radial shaft was measured using dual energy x-ray absorptiometry (Hologic QDR-2000, Waltham Mass.). A heparinized venous blood was obtained for lymphocyte isolation and immortalization and an EDTA treated venous blood for genomic DNA isolation (Neitzel, 1989).

Outpatient Evaluation

Subjects underwent an outpatient evaluation (Pak et al., 1989) following one week on an instructed diet designed to mimic the inpatient metabolic diet in sodium, calcium and phosphorous content. This evaluation included: fasting venous serum for calcium, creatinine, iPTH and 1,25(OH)$_2$D, heparinized venous blood for lymphocyte isolation and immortalization, EDTA treated venous blood for genomic DNA isolation, a 24-h urine collection for calcium and creatinine, a 2 h fasting urine collection was obtained for measurement of calcium and creatinine, and a 4 h urine collection was obtained for the same tests after an oral ingestion of a synthetic meal containing 1 g of calcium (Pak et al., 1980; Pak et al., 1975). Each participant completed a standardized questionnaire that included kidney stone and dietary history.

Phenotype Assignment

Phenotype assignment in kindreds AH-01 and AH-02 was based on 4 criteria: (1) evidence of hyperabsorption of calcium, either a calciuric response to an oral calcium load >0.20 mg Ca/dl glomerular filtrate (GF) or α>61%, (2) elevated fasting urinary calcium (>0.11 mg Ca/dl GF), (3) hypercalciuria (>200 mg Ca/day on a calcium restricted diet) and (4) a low or normal serum PTH (<65 pg/ml) (Levy et al., 1995). Individuals who satisfied at least three of the four criteria were assigned affected phenotype. Those with intestinal hyperabsorption of calcium (criterion 1) who met only one additional criterion were classified as unknown phenotype. If an unrelated spouse had either an AH phenotype or was not evaluated, their progeny, who would otherwise have an affected or unknown phenotype, were assigned unknown phenotype. All others were classified as unaffected.

In kindred AH-03, affected phenotype assignment was based on the satisfaction of criteria 3 and 4 alone, since fasting urinary calcium, calciuric response to an oral calcium load and were done only on the proband. An unknown status was assigned when only criterion 3 was met.

All affected members from all 3 kindreds had normocalcemia. Bone density was not utilized in the definition of AH phenotype since only a limited number of subjects were available for this measurement.

Results

Probands

The proband of the kindred AH-01 (FIG. 1A, III-14) was a 37 year old white male who underwent an outpatient evaluation. He had a history of recurrent kidney stone formation, elevated 24 h urine calcium, fasting urinary calcium and calcium load response and a low serum iPTH. The proband of the kindred AH-02 (FIG. 1B, III-2) was a 47 year old white female who underwent an inpatient evaluation. She had elevated 24 h urine calcium, fasting urinary calcium, calcium load response and • and a normal iPTH. The proband of the kindred AH-03 (FIG. 1C, III-4) was a 32 year old white male who underwent an inpatient evaluation. He had a history of recurrent kidney stone formation, elevated 24 h urine calcium, calcium load response and α and a high normal fasting urinary calcium and a normal iPTH. All three probands had no history of bowel disease, primary hyperparathyroidism, primary hyperoxaluria, renal tubular acidosis, gout or cystinuria. They all satisfied the diagnostic criteria of AH (Levy et al., 1995; Breslau et al., 1992).

Families

Kindred AH-01 (FIG. 1A). Twenty-six blood samples, including the proband, were collected for genotype analysis. Twenty-four members of the family underwent clinical evaluation using the outpatient protocol. Bone density measurements were obtained on eight family members and three unrelated spouses. Biochemical and physiological characteristics of family members with affected phenotype are presented in Table 4.

The 12 affected family members including the proband had biochemical features of severe AH, (Levy et al., 1980; Breslau et al., 1992) with markedly elevated 24 h urinary Ca, fasting hypercalciuria, notably exaggerated calciuric response to oral Ca load, and low normal serum PTH. Serum calcium and 1,25-(OH)$_2$D were normal. Bone density was low (Table 4).

There were 7 stone-formers in the family (FIG. 1A) and 1 stone-forming spouse (III-2). Stones that were analyzed were calcium oxalate and/or calcium phosphate in composition. Six of the 7 stone-formers had the affected phenotype (FIG. 1A), while the remaining stone-former (IV-I) was of uncertain phenotype. Based on clinical evaluation, 5 additional non-stone-forming family members and one spouse had the AH phenotype (FIG. 1A). Individuals III-18 and III-19 were monozygotic twins and were treated as a single entity for purposes of linkage analysis.

Kindred AH-02 (FIG. 1B). Five individuals underwent phenotypic evaluation and genotype analysis. Three members of the kindred had inpatient evaluations with the determination of a, while the remaining two had outpatient evaluations. Bone density measurements were obtained on three family members. The three affected family members, including the proband (FIG. 1B), had evidence of severe AH, with fasting hypercalciuria and low bone density (Table 4). One member was assigned unknown phenotype (III-1). There was a family history of stone formation on the maternal side of the family (I-3 and II-4).

Kindred AH-03 (FIG. 1C). Four members of the kindred underwent phenotypic evaluation and genotype analysis. The proband had an inpatient evaluation while the three family members had a partial outpatient evaluation that excluded the determination of fasting urinary calcium and the calciuric response to a calcium load. Bone density measurements were obtained in three family members. The three affected individuals, including the proband (II-1, III-2 and III-4, FIG. 1C), had biochemical features compatible with severe AH (Table 4). They had marked hypercalciuria, and low bone density. One member (III-5) was assigned an unknown phenotype. Of the subjects evaluated, only the proband had nephrolithiasis although a paternal cousin (III-7) also reported a history of nephrolithiasis.

TABLE 4

Mean Biochemical and Physiological Characteristics of Affected Individuals From Study Kindreds

| Parameter | Family AH-01 | Family AH-02 | Family AH-03 | Normal Range |
|---|---|---|---|---|
| Serum | | | | |
| IPTH, ng/L | 15 ± 8[a] (10) | 38 ± 10 (3) | 31 ± 2 (3) | 10–65 |
| Alkaline Phosphatase (IU/L) | 61 ± 13 (10) | 62 ± 30 (2) | 76 ± 23 (3) | 30–140 |
| 1,25 $(OH)_2D$, pmol/L | 115 ± 26 (10) | 82 ± 24 (3) | 84 ± 7 (3) | 48–132 |
| Ca, mmol/L | 2.3 ± 0.05 (10) | 2.1 ± 0.1 (3) | 2.4 ± 0.03 (3) | |
| Urine | | | | |
| 24 hour Ca, nmol/day | 7.3 ± 2.2 (11) | 6.1 ± 1.0 (3) | 7.0 ± 0.9 (3) | <5.0 |
| Fasting Ca, mg/dL GF | 0.037 ± 0.015 (10) | 0.0370 ± 0.015 (3) | 0.022 (1) | <0.027 |
| Post Ca load, mg/dL GF | 0.097 ± 0.030 (9) | 0.070 ± 0.010 (3) | 0.065 (1) | <0.050 |
| Intestinal Ca Absorption | | | | |
| α, % | ND | 67.9 ± 7.7 (3) | 68.8 (1) | 40–60 |
| Bone Density L2–L4 | | | | |
| BMD ($g/cm^2$) | 1.02 ± 0.09 (9) | 0.748 ± 0.07 (3) | 0.88 ± 0.04 (2) | |
| T Score | −0.82 ± 0.81 | −3.10 ± 0.68 | −2.10 ± 0.35 | |
| Z Score | −041 ± 0.78 | −1.90 ± 0.91 | −1.95 ± 0.13 | |
| Femur (Neck) | | | | |
| BMD | 0.83 ± 0.14 (9) | 0.53 ± 0.03 (3) | 0.84 ± 0.11 (2) | |
| T Score | −0.46 ± 1.22 | −2.84 ± 0.26 | −0.69 ± 0.82 | |
| Z Score | −0.14 ± 0.76 | −1.79 ± 1.23 | −0.48 ± 0.78 | |
| Radius | | | | |
| BMD | 0.61 ± 0.09 (8) | 0.57 ± 0.08 (3) | 0.76 ± 0.03 (2) | |
| T Score | −2.91 ± 1.56 | −1.97 ± 1.29 | −1.08 ± 0.53 | |
| Z Score | −2.41 ± 1.42 | −0.62 ± 0.99 | −0.79 ± 0.52 | |

[a]All values are presented mean ± SD with number of samples given in ( ). ND, not determined.

Example 2

Determination of the Chromosomal Locus that is Linked to Intestinal Calcium Hyperabsorption in Three Kindreds with Severe AH.

The presence of a family history of nephrolithiasis, in about half of the affected individuals studied, indicates that an inherited genetic defect is one likely cause of AH. While it is known that intestinal calcium absorption is regulated by a number of factors, the molecular biological basis for the increased calcium absorption in AH is unknown. This example demonstrates the identification of the chromosomal locus of the gene defect linked to the AH phenotype in three families with a severe form of AH.

Methods

DNA Analysis

Genomic DNA was prepared from peripheral blood lymphocytes (Qiagen, Valencia, Calif.) DNA genotyping was performed using fluorescently labeled primers available from Perkin-Elmer Applied Biosystems (ABI), or Research Genetics, on an ABI Model 377 automated DNA sequencer with GENESCAN 2.0 software. A total of 178 randomly spaced markers (10–30 cM spacing) were analyzed in the initial low density screening. Regions where a two-point lod score was >0.3 were screened using high density markers. Fifty-five additional markers were used in this secondary screening. All PCR™ amplification reactions were performed in a Perkin Elmer thermal cycler, Model 9600 following suppliers protocols. Samples were analyzed on 4% polyacrylamide gels. Data analysis was performed using GENOTYPER software (ABI).

Linkage Analysis

Two point lod scores were calculated using the computer program Linkage 5.1 (Lathrop et al., 1985). The AH trait was assumed to be dominant with a penetrance of 80% and a disease frequency of 0.02. Non-parametric multipoint linkage analysis was performed using GENEHUNTER software (Whitehead Institute for Biomedical Research) (Kruglyak et al., 1996). Analyses were run on a 180 MHz Pentium Pro computer using max bits=20. All affected individuals were included in the analysis. Allele frequencies and map distances were taken from the literature (Collins et al., 1996; CEPH genotype database, Ceph-Genethon internet site http//www.cephb.fr.).

Results

Linkage Analysis

Kindred AH-01 was first tested for linkage at potential candidate gene loci, which included genes coding for the vitamin D receptor, 1-α hydroxylase, plasma membrane calcium ATPase (PMCal), calbindin 28K, PTHrp, NPT1, NPT2, osteocalcin, IL-1α, IL-1α and IL-1 receptor. No evidence for linkage was found at any of these loci. Candidate genes located on the X chromosome, such as CLCN5 and calbindin 9K, were eliminated, since male-to-male transmission was present in kindreds AH-01 and AH-03 ruling out a sex-linked gene defect (FIG. 1A and FIG. 1C). After elimination of these candidate gene loci, a genome wide screen was undertaken. Strong evidence of linkage was found only on the q-arm of chromosome 1 after analyzing 178 markers randomly distributed at 10–30 cM intervals within the genome. An additional 55 high density markers were analyzed in regions where a lod score of >0.3 was obtained.

The maximum two point lod scores calculated for chromosomes 2 to 22 are shown in Table 5. None exceeded 1.3. However, on chromosome 1, a positive two point lod score of 2.7 was obtained for kindred AH-01 between marker D1S196 and the AH phenotype at $\theta=0$ (Table 6). Values are given separately for each of the individiual families, AH-01, AH-02 and AH-03, and also as the combined score for all three families. Combination of the three kindreds gave a two point lod score of 3.3 (Table 6).

TABLE 5

Maximum 2 point lod scores calculated for each chromosome between microsatellite markers and AH phenotype.

| Chromosome | Marker | Z max | $\theta$ max |
|---|---|---|---|
| 2 | D2S396 | 0.8 | 0.2 |
| 3 | D3S1565 | 0.8 | 0.2 |
| 4 | D4S391 | 0.8 | 0.2 |
| 5 | D5S422 | 0.4 | 0.2 |
| 6 | D6S422 | 0.4 | 0.2 |
| 7 | D7S515 | 0.1 | 0 |
| 8 | D8S260 | 0.92 | 0.1 |
| 9 | D9S161 | 0.01 | 0.4 |
| 10 | D10S537 | 0.7 | 0.2 |
| 11 | D11S935 | −0.1 | 0.4 |
| 12 | D12S80 | 0.9 | 0.1 |
| 13 | D13S158 | −0.1 | 0.4 |
| 14 | D14S280 | 0.1 | 0.4 |
| 15 | D15S131 | 1.3 | 0.1 |
| 16 | D16S401 | −0.1 | 0.4 |
| 17 | D17S799 | −0.2 | 0.4 |
| 18 | D18S559 | 0.3 | 0.4 |
| 19 | D19S418 | 0.3 | 0.3 |
| 20 | D20S117 | 0.1 | 0.4 |
| 21 | D21S263 | −0.1 | 0.4 |
| 22 | D22S280 | 0.02 | 0.4 |

Using data from all 3 kindreds, high density mapping was performed using 13 additional markers, and multipoint linkage analysis was conducted over the region spanning the D1S196 locus. Several markers were either non-informative or partially informative and were not included in the multipoint analysis. Multipoint non-parametric analysis of the data yielded a non-parametric lod (NPL) score of 12.7 (p=0.000006) between markers D1S318 and D1S431 (FIG. 2B). This locus corresponded to a region contained in 1q23.3-q24, based on current mapping location for these markers (Collins et al., 1996). Since the phenotype workup of the third kindred was not as complete as for the other two kindreds, a multipoint analysis using only the first two kindreds was done. An NPL score of 15.2 (p=0.000007) was obtained for kindreds AH-01 and AH-02.

Haplotypes were constructed and analyzed for informative recombinations using the markers D1S426, D1S2681, D1S318, D1S196, D1S431 D1S2750, D1S2799, D1S2815, D1S218, D1S416 and D1S466 (FIG. 2A). Key recombinational events in individuals III-18 and IV-7 from kindred AH-01 delineated the AH gene locus between markers D1S2681 (centromere) and D1S2815 (telomere). This locus corresponded to a physical map distance of approximately 4.3 cM based on the current Linkage Data Base (LDB) composite map (Collins et al., 1996. Six additional individuals (II-2, III-3, III-15, IV-1, IV-2 and IV-8) from kindred AH-01 carried the affected genotype based on haplotype analysis. Five of these individuals, including one stone-former, had previously been classified as uncertain phenotype, while the sixth individual had not undergone a clinical evaluation. All phenotypically affected individuals carried the disease genotype.

Discussion

The inventors have identified a single locus on chromosome 1q23.3-q24 linked to an AH phenotype in three unrelated kindreds with AH. Members of all three kindreds who were classified as phenotypically affected met the diagnostic criteria for AH (Pak et al., 1980; Levy et al., 1995. The common genotypes at the chromosome 1q23.3-q24 locus were identified in all of the related members with stones.

TABLE 6

Critical 2 point lod scores between microsatellite markers and AH phenotype.

| | Recombination Fraction, $\theta$ | | | | | | | |
|---|---|---|---|---|---|---|---|---|
| Marker | 0 | 0.01 | 0.05 | 0.1 | 0.2 | 0.3 | Z max | $\theta$ max |
| AH-01 | | | | | | | | |
| D1S426 | −0.7 | −0.7 | −0.5 | −0.2 | 0.03 | 0.08 | 0.08 | 0.28 |
| D1S2681 | 0.4 | 0.4 | 0.5 | 0.6 | 0.6 | 0.5 | 0.7 | 0.17 |
| D1S196 | 2.7 | 2.7 | 2.5 | 2.3 | 1.8 | 1.2 | 2.7 | 0 |
| D1S2815 | 0.6 | 1.0 | 1.3 | 1.4 | 1.2 | 0.8 | 1.4 | 0.09 |
| AH-02 | | | | | | | | |
| D1S426 | 0.3 | 0.3 | 0.2 | 0.2 | 0.1 | 0.06 | 0.3 | 0 |
| D1S2681 | 0.3 | 0.3 | 0.2 | 0.2 | 0.1 | 0.1 | 0.3 | 0 |
| D1S196 | 0.3 | 0.3 | 0.2 | 0.2 | 0.1 | 0.1 | 0.3 | 0 |
| D1S2815 | $8 \times 10^{-4}$ | $8 \times 10^{-4}$ | $7 \times 10^{-4}$ | $5 \times 10^{-4}$ | $3 \times 10^{-4}$ | $1 \times 10^{-4}$ | $8 \times 10^{-4}$ | 0 |
| AH-03 | | | | | | | | |
| D1S426 | −1.1 | −0.9 | −0.6 | −0.4 | −0.2 | −0.07 | −0.02 | 0.4 |
| D1S2681 | 0.3 | 0.3 | 0.3 | 0.2 | 0.1 | 0.1 | 0.3 | 0 |
| D1S196 | 0.3 | 0.3 | 0.3 | 0.2 | 0.1 | 0.1 | 0.3 | 0 |
| D1S2815 | 0.3 | 0.3 | 0.3 | 0.2 | 0.1 | 0.1 | 0.3 | 0 |
| Combined | | | | | | | | |
| D1S426 | −1.2 | −1.1 | −0.7 | −0.4 | 0 | 0.1 | 0.1 | 0.3 |
| D1S2681 | −0.3 | −0.2 | 0.2 | 0.4 | 0.6 | 0.5 | 0.6 | 0.2 |
| D1S196 | 3.3 | 3.2 | 3.0 | 2.7 | 2.0 | 1.3 | 3.3 | 0 |
| D1S2815 | 0.9 | 1.2 | 1.5 | 1.6 | 1.3 | 0.9 | 1.6 | 0.08 |

The clinical presentations of AH in all three kindreds were compatible with a severe form of AH. Thus, their characteristic features were a moderate to marked hypercalciuria, low bone density and fasting hypercalciuria. However, there is some evidence that the molecular abnormality disclosed here may be more generalized. Fasting hypercalciuria is not an uncommon finding in AH and may be present in a substantial number of patients, especially in those with marked intestinal hyperabsorption of calcium and parathyroid suppression (Preminger et al., 1989; Breslau et al., 1992; *Pak and Galosy,* 1979; Heller et al., 1998. In addition, low spinal bone density (Bataille et al., 1991; Barkin et al., 1985) was present in AH patients with normal fasting urinary calcium (Pietchmann et al., 1992) as well as the subgroup with fasting hypercalciuria.

Despite a rich family history of kidney stone formation in patients with AH, controversy persists concerning the mode of inheritance of this disease (Coe et al., 1979; Pak et al., 1981; Resnick et al., 1968). The inventors therefore used a non-parametric model-independent method of analysis (Genehunter) (Kruglyak et al., 1996) as well as a parametric method of analysis that assumed an autosomal dominant mode of inheritance (Coe et al., 1979; Pak et al., 1981). The results of the genome wide screening, using both methods of analysis, indicated that only one region of the genome met the criteria for linkage. Thus, the inventors conclude that AH is inherited in an autosomal dominant mode due to a gene mutation in the chromosome 1q23.3-q24 locus, at least in the three kindreds evaluated. Based on the most recent chromosome 1 map, no genes of known function have been identified in this candidate region. This lack of a known calcium-regulatory gene at this chromosomal locus leads to the intriguing possibility that an, as yet, unreported gene may be involved in the regulation of intestinal calcium absorption and possibly bone loss.

Prior pathogenetic mechanisms for AH have implicated an abnormality in either vitamin D metabolism or the vitamin D receptor Breslau et al., 1992; Insogna et al., 1985; Zerwekh et al., 1993; Krieger et al., 1996. However, both the vitamin D receptor and 1-α hydroxylase gene, which catalyzes the formation of $1,25(OH)_2D$, have been eliminated as candidates in the three families based on the linkage data. Several other candidate genes, including PMCA1, PMCA4, the 28K and 9K calbindins and the Na/Pi cotransporter genes, NPT1 and NPT2 (Tieder et al., 1985; *Tenehouse,* 1997) have been implicated in the regulation of either the cellular transport of calcium or the renal excretion of calcium. However, all of these genes were also eliminated from being involved in the etiology of AH in the families studied, since their reported chromosomal loci did not correspond to chromosome 1q23.3-q24.

Some family members without stones also had the common genotype at chromosome 1q23.3-q24. The incomplete penetrance of stone formation is likely due to the influence of environmental factors or possibly to other disease modifying genes. The inventors chose not to use stone formation as part of the phenotype in order to prevent other factors from complicating the analysis.

Identification of the specific gene and mutations contained therein will be necessary in order to determine both the relationship of this gene defect to the clinical features associated with AH and the prevalence of this gene defect in the AH patient population.

Example 3

Methods for Isolation and Characterization of a Gene Linked to AH

The initial identification of YACs (yeast artificial chromosomes) derived from the chromosomal region containing the disease gene is done by querying the CEPH/Genethon database. There are 8 YACs available spanning the D1S196 region and these have been ordered into a contiguous region ("contig"). YACs are available from Genome Systems, Inc., or Research Genetics. An example of a detailed protocol for preparation of YAC DNA in liquid form for PCR analysis or agarose plugs known to those of skill in the art is described by Horrigan and Westbrook (1997). The suspected overlaps in the YACs are confirmed by fingerprinting and endclone rescue. Human specific sequences are identified by interspersed repeated sequence PCR (IRS-PCR) (Ledbetter et al., 1990). Generation of IRS-PCR fingerprints is performed as follows: a 50 μl PCR reaction will be set up to contain 5–10 ng YAC DNA, 10× XL buffer II, 1.5 mM $Mg(OAc)_2$, 200 mM dNTPs, ng IRS primer (e.g. ALU3' GAT CGC GCC ACT GCA CTC C, SEQ ID NO:3, and ALU 5 GGA TTA CAG GCG TGA GCC AC, SEQ ID NO:4) total for all primers and 2.5 U rTth XL polymerase (Perkin Elmer); typical cycling conditions are 94° C. for 3 minutes then 25 cycles of 94° C. for 40 seconds, 60° C. for 1 minute, 72° C. for 5 minute a final 10 minute elongation at 72° C. is performed. Products are then analyzed by separation on a 1.5% agarose gel stained with ethidium bromide (EtBr). If overlap of YACs is not apparent, the ends of the YAC clone will be isolated by IRS-vector PCR (Fujita and Swaroop, 1995). At this stage the YAC may be converted into a series of smaller overlapping cosmid clones for maintenance. DNA derived by IRS-PCR can be used directly as a hybridization probe to select clones on high density filters containing a human genomic DNA library. Briefly DNA products will be purified on Qiax spin columns and labelled by random priming. Probes will be combined and prehybridized with 50 μg/ml Cot-1 DNA and 100 mg/ml sonicated human placental DNA in 500 ml of 0.12 M $Na_2HPO_4$ for 4 hours at 68° C. Filters containing the target clones are prehybridized in 0.5 M $Na_2HPO_4$, 7% SDS, 1 mM EDTA, 50 mg/ml denatured sonicated salmon sperm DNA for 4 hours at 68° C. Filters will be hybridized with $5\times10^6$ cpm/ml probe for 18–24 hours at 68° C. Filters will be washed at 68° C. for 30 minutes in 40 mM $Na_2HPO_4$, 5% SDS, 1 mM EDTA and then twice for 30 minutes in 40 mM $Na_2HPO_4$, 1% SDS, 1 mM EDTA. X-ray fill will be exposed to the filters for 1–2 days at −70° C. with intensifying screens. Genes contained within the YACs will be identified by exon trapping; both internal and 3' exons will be isolated as described in detail by Krizman (1997). Internal exon sequences will be used for coding region searches of databases for identification of similarities with other known proteins in an attempt to identify the type of gene product. 3' terminal sequences can be used for direct screening of cDNAs. pSPL3 is a vector of choice for internal exon trapping and replication will be performed in Cos 7 cells as previously described (Krizman 1997). Once the entire sequence of a cDNA or gene has been determined, sequencing primers are prepared for analysis of the gene in patient samples of DNA. Comparison of the patient and wildtype DNA sequences will allow identification of any mutations present in AH DNA. More rapid screening of patient cDNA or genomic DNA can be achieved by RNA mismatch cleavage analysis. Depending on the nature of the mutation, a prediction can be made regarding the effect of the mutation on the protein structure. Coincidence of mutation and phenotype will be confirmed by analyzing DNA from all affected and non-affected family members. Expression studies will be performed to confirm the effect of the mutation on protein function.

Example 4

Detection of a Mutation in the AH Loci to Identify Individuals at Risk for AH An example of a typical technique for screening for mutations is based on PCR amplification of the identified region or regions of the AH gene containing the mutated sequence, if the mutation involves either an insertion or a deletion. For instance, a typical protocol would involve preparing genomic DNA from 1 ml whole blood sample from a patient using a Qiagen micro-DNA preparation kit (Qiagen, Valencia, Calif.). DNA genotyping will be performed using fluorescently-labeled primers designed to flank known region(s) containing the mutated sequence with an ABI Model 377 automated DNA sequencer with GENESCAN 2.0 software. All PCR amplification reactions will be performed in a 9600 Perkin Elmer thermal cycler. Typical conditions for such mutliplex PCR will be as follows: 60 ng of genomic DNA will be amplified by mutiplex PCR in a total volume of 15 μl, containing PCR buffer (Perkin Elmer), 2.5 mM $MgCl_2$, 0.25 units of AmpliTaq Gold DNA polymerase (Perkin Elmer), 250 nM dNTPs and 330 nM primers. The following cycling conditions will be used: 95° C. for 10 min followed by 10 cycles (95° C. for 15 s, 55° C. for 15 s, 72° C. for 30 s) followed by 35 cycles of (89° C. for 15 s, 55° C. for 15 s, 72° C. for 30 s) and a final elongation step of 72° C. for 10 min.). Analysis of the resulting PCR products will be performed by separation on a denaturing polyacrylamide gel. Mutant DNA will be identified based on size through comparison to both wildtype and known samples of mutant DNA.

If the mutation does not involve either a deletion or insertion but is instead a base substitution, the preferred diagnostic testing will involve RNase cleavage mismatch analysis. cDNA will be analyzed if the mutation resides within the coding region. The illegitimate transcription technique (Chelly et al., 1989) will be used to prepare specific mRNA for cDNA analysis. Briefly, mRNA will be prepared from 0.5–1.0×$10^7$ lymphocytes using a Pharmacia micro quick prep mRNA extraction kit (Pharmacia, Piscataway N.J.). cDNA will be prepared using mouse mammary leukemia virus (MMLV) and Superscript first strand cDNA synthesis kit (BRL) according to supplier's directions. Genomic DNA may also be analyzed by this technique. Both wild type and unknown DNA samples will be amplified using specific primers flanking the region of the mutation. These primers will contain the T7 or SP6 phage promoter consensus sequences respectively at their 5' ends followed by 15–18 bases of the target-specific sense or anti-sense flanking DNA sequences. Sense and anti-sense PCR products will be transcribed using T7 or SP6 polymerase. Complementary wild-type and patient transcripts will be hybridized. The resulting RNA duplexes will be digested with either RNase 1, RNase TI and/or RNase A. Resulting products will be analyzed by separation on 2% agarose gel. Reagents and detailed protocols for this methodology are available in kit form (Ambion, Austin Tex.). This technique is capable of detecting both homozygous and heterozygous mutations.

Example 5

Description of a Putative Gene and Specific Mutations Linked to Absorptive Hypercalciuria Example 2 describes genetic linkage between the clinical phenotype associated with absorptive hypercalciuria (AH) and the chromosome 1q24 locus. This example describes specific mutations of a putative gene located in this region and the relationship between this putative gene and AH. The frequency of mutations in this gene in patients with another disease, idiopathic osteoporosis, is also described, indicating a potential link between this gene and bone loss. The putative gene described here and the techniques described for elucidating the nature of this putative gene's role in AH are given as an example. Should the putative gene described in this example eventually be shown not to be the AH gene, similar methodologies as described throughout this specification and proceeding examples will be used to identify the true AH gene.

Figure 2:
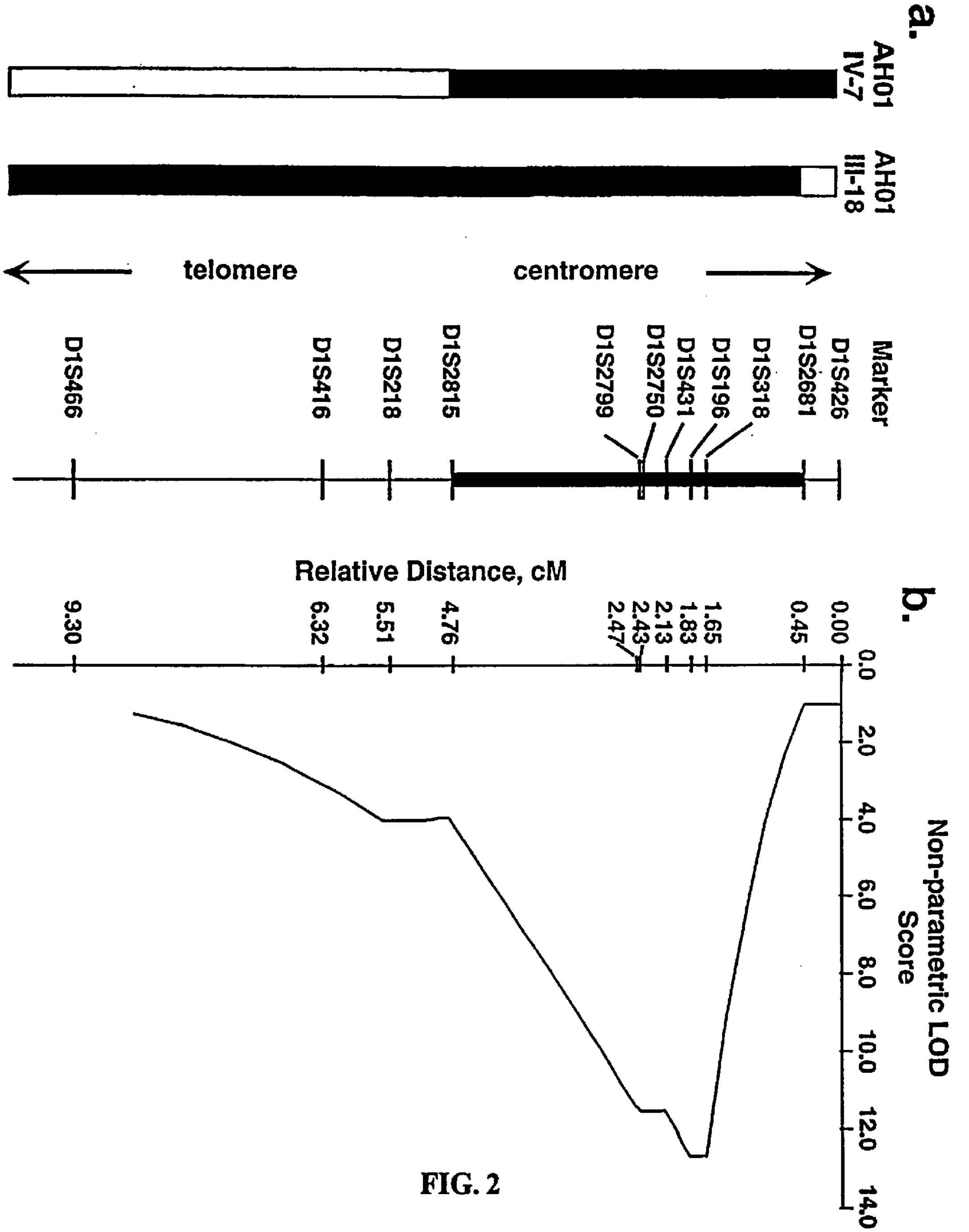
FIG. 2A and FIG. 2B. Localization of the gene for AH.

Linkage studies and haplotype analysis localized a gene defect associated with AH to a 4.3 cM region of chromosome 1q between the markers D1S2681 centromere and D1S2815 (FIG. 2). As the highest lod scores were obtained between markers D1S196 and D1S431, this locus was initially chosen as the most likely location of the AH gene. Published sequence data from the Human Genome Project (www.sanger.ac.uk) identified the region of interest as chromosome 1 contig196. A large portion of this region is contained in 3 clones, namely dJ455J7 (GenBank Accession # AL031733) (SEQ ID NO. 11) containing D1S196, and dJ313L4 (GenBank Accession # Z99943)(SEQ ID NO 10) and dJ295C6 (GenBank Accession # Z97876)(SEQ ID, NO. 7, SEQ ID NO. 8 and SEQ ID NO. 9), both of which contain marker D1S431. Sequence data for these clones is available through GenBank (www.nih.gov). All clones contain numerous est's (expressed sequence tags) and therefore potential genes. No obvious candidate genes of known function are currently mapped to this region.

A 2567 base pair cDNA (GenBank Accession # AL035122) encoding a hypothetical protein of unknown function (GenBank Accession # CAA22684) has been mapped to the genomic region contained in dJ313L4 (GenBank Accession # Z99943) (SEQ ID NO. 10), and dJ295C6 (GenBank Accession #Z97876) (SEQ ID NO. 7, SEQ ID NO. 8 and SEQ ID NO. 9). The nucleotide sequence of this cDNA is given as SEQ ID NO: 1, and the deduced amino acid sequence given as SEQ ID NO:2. BLAST alignment of the SEQ ID NO:1 and genomic sequence of dJ313L4 reveals a gene of at least 38,844 base pairs encompassing at least 16 exons (Bases 85943 to 124787 of dJ313L4, GenBank Accession # Z99943). The complete length of the gene is longer as the sequence for exon 1 is most likely incomplete and identification of the promoter sequences responsible for transcriptional control of this putative AH gene are yet to be determined.

Evidence for Association of the Putative Gene With the AH Defect

A probe was prepared by PCR amplification of genomic DNA using primers spanning the intron/exon boundaries for what is defined as exon 5 (Primer 1 CATCTAGGTTGCCTTACCCGAAGT, SEQ ID NO:5, primer 2 TGATTAGGAGCACAGCCTCAGTGC, SEQ ID NO:6) with the following amplification conditions: 10 minutes at 95° C., followed by 35 cycles of 94° C. for 10 seconds, 63° C. for 30 seconds and 72° C. for 45 seconds and one final 10 minute incubation at 72° C. The probe was labeled with biotin and used to screen a human multiple tissue mRNA blot (Human RNA Master Blot, Catalog # 7770-1, Clonetech Laboratories, Palo Alto, Calif.), using conditions as described by the supplier. The results demonstrate high level expression of the putative AH gene in adult human colon, small intestine, kidney and liver. As the invariant features of AH are intestinal hyperabsorption of calcium and excessive urinary calcium excretion, intestine and kidney are target tissues for expression of a defective gene.

Sequence analysis of all exons and intron/exon boundaries of the putative gene in the probands from 2 of the kindred's revealed the same point mutation in what is defined as exon 5. The mutation was a C to A transversion mutation at position 823 of SEQ ID NO:1 and patients were heterozygous for the mutation. This is the expected finding as AH has a dominant mode of inheritance. This mutation occurs in the 5' nontranslated region of the of the putative open reading frame, 127 bases 5' to the intiator methionine. This particular mutation is not going to result in an amino acid change, but rather could affect translatability or stability/half-life of the messenger RNA. This could lead to either an increased amount or decreased amount of the encoded protein, resulting in the AH phenotype.

The mutation destroys an Alu 1 restriction endonulease recognition site (AGCT to AGAT), thus providing a rapid RFLP screening method involving PCR amplification of the genomic DNA from a individual followed by Alu 1 restriction of the resulting PCR product. Cleavage of the PCR fragment by Alu 1 represents a wild type allele with mutant alleles being resistant to Alu 1 cleavage. Preliminary analysis of the frequency of this mutation in normal, AH and idiopathic osteoporotic populations revealed evidence of a significantly higher occurrence of this mutation in both the AH and idiopathic osteoporotic populations (Table 7).

TABLE 7

Exon 5 Alu 1 RFLP, Occurrence in Control and Patient Populations.

| | Control | AH | Idiopathic Osteoporotic |
|---|---|---|---|
| n | 93 | 103 | 30 |
| mutations | 1 | 10* | 4 |

*p = 0.02 (Fisher Exact Test)

Screening of all other exons will be undertaken using RNA mismatch cleavage analysis as described in the specification. For instance, analysis of AH patients using this method has identified a second mutation in what is defined as exon 4 of the putative gene. This second mutation is a T to C transition mutation at position 483 of SEQ ID NO:1 and patients were heterozygous for the mutation. Again, this is the expected finding as AH has a dominant mode of inheritance. This second mutation is not found in a number of normal control patients. In addition, analysis of 91 AH patients using this method identified 13 patients with two distinct mutations in what is defined as exon 2 of the putative gene. Sequence analysis of these patients will confirm the nature of the mutation. With each new mutation a population of normal individuals will be screened to confirm that it is not simply a polymorphism.

BLAST analysis of both the cDNA sequence, SEQ ID NO:1, and amino acid sequence, SEQ ID NO:2, revealed little homology with known sequences. However modeling studies of SEQ ID NO:2 predict a structure with 3 transmembrane domains. This is suggestive of a transport function. As the transport of calcium is enhanced in AH, this suggested structure would indicate a possible membrane ion transport protein. Due to the small size of the encoded protein (372 amino acids) it is likely that the gene may encode a subunit of a larger multimeric protein. Recombinant expression of the putative gene in tissue culture cells followed by ion transport experiments will be conducted in an attempt to determine the function of the protein. Recombinant expression of the gene product will also enhance purification of the protein, generation of antibodies specific for the protein, the development of assay systems to allow biochemical studies of the proteins function, and development of screening assays for candidate compounds that modulate the proteins functions. Gene knockout in transgenic mice will be undertaken in an attempt to define the function of the gene in all organ systems and also the effect of lack of expression during embryonic development.

Example 6

Characterization of Other AH-Related Modulators

To investigate the mechanisms involved in the transcriptional control of the AH gene, expression studies of the 5' flanking region of AH gene are performed. As many of the genes involved in the regulation of intestinal calcium absorption are regulated by vitamin D, this may include investigation of consensus vitamin D response elements in the AH locus.

A fragment of the AH-gene promoter region of interest is first inserted by standard cloning techniques into a reporter vector such as herpes simplex virus thymidine kinase promoter-containing vector pUTKAT3, which contains the chloramphenicol acetyl transferase (CAT) reporter gene (DeMay 1992). Transfection of the plasmid into GH4C1 cells is achieved using lipofection (GIBCO). 24 h before transfection the GH4C1 cells are fed with charcoal-stripped fetal calf serum (10% vol/vol in Dulbeccos modified Eagles medium (DMEM). In order to investigate the effect of vitamin D/vitamin D receptor-mediated transcriptional activity the cells are treated with $10^{-8}$ M 1,25 $(OH)_2$ $D_3$. Following a 24–48 h incubation period, CAT activity is assessed by thin layer chromatography (TLC). More specific analysis of interactions between various components of the vitamin D transcriptional modulation pathway is performed by transient co-transfection assays with the retinoid X receptor or other transcription factors. Additionally, gel-retardation assays are performed to directly investigate any interaction between various regulatory proteins and the AH-gene promoter.

Identification of proteins interacting directly with the AH protein is best achieved by co-precipitation of a complex containing AH protein from human cells using a specific antibody directed against the AH-protein. This could be followed by purification of the modulator by standard protein chemistry techniques.

Example 7

Treatment of a Symptomatic or Asymptomatic Diagnosed Individual

Dietary and fluid regimens: Conservative dietary and fluid regimens should be incorporated into the daily routine of all patients with kidney stones. Fluid intake should typically be sufficient to produce 2–3 liters of urine/day. Additional fluid may be required in the summer or during exercise to compensate for fluid loss due to perspiration. Adequate hydration alone has been shown to decrease stone formation by as much as 60% (Hosking, 1983). Dietary modification should include restriction of sodium intake as high sodium intake results in increased urinary excretion of calcium and consequent increase in the saturation of stone-forming salts in urine. Intake of animal protein should be limited as this leads to an increase in bone resorption and a decrease in renal calcium resorption. Protein should be restricted to less than 8 ounces per day. There should also be a modest restriction of daily calcium intake in patients consuming a high calcium diet. However, patients with hypercalciuria with bone loss should not restrict calcium as this may lead to a negative calcium balance and potential worsening of bone problems. Certain food high in oxalate should also be restricted such as nuts, chocolate, brewed tea and green leafy vegetables. Daily consumption of citrus fruits or juices is beneficial due to their citrate, which directly binds calcium and also serves to increase urinary pH.

Therapeutic Measures: Therapeutic measures are directed towards reducing urinary calcium excretion and decreasing intestinal calcium bioavailability. Thiazides are the first drug of choice: trichlormethiazide, 4 mg daily in a normal sized adult, hydrochlorothiazide, 25 mg twice daily or bendroflumethiazide, 2.5 mg twice daily. Hypokalemia and hypocitraturia are frequent complications of thiazide therapy and can be avoided by administration of potassium citrate, 15 to 20 mEq twice daily. Long term efficacy of thiazide therapy may be limited. It is recommended that in patients where hypocalciuric response is lost, a brief drug holiday of 6 months be instituted where sodium cellulose phosphate (SCP) therapy of 10–15 g/day in divided doses with meals is administered in place of thiazides. After completion of the SCP course thiazide responsiveness usually resumes. A new treatment, a slow-release, neutral potassium phosphate salt (UroPhos-K), has been shown to significantly reduce urinary calcium excretion with the added advantage of having sustained effectiveness. Efficacy is currently being assessed in a multi-institutional, double-blinded trial. In the future this may present a more beneficial treatment alternative. Detailed description of recommended medical therapy has been described by our group (Ruml et al., 1997).

Medications: Certain medications are contraindicated; these include carbonic anhydrase inhibitors such as acetazolamide or methozolamide, ascorbic acid supplementation in patients with elevated urinary oxalate level, and trimethterene or trimethaterene-containing diuretics (Dyazide, Maxzide).

Treatment of asymptomatic diagnosed individuals: The emphasis of treatment is directed towards prevention of the first stone-forming episode. In all such individuals conservative dietary and fluid regiments should be followed as detailed in the previous section. Periodic urine analysis for evaluation of stone-forming salts and risk factors is recommended in addition. The frequency of these assessments should be determined by the individual's physician based on the evaluation of a baseline stone-risk profile. Potential worsening of risk factors can thus be assessed and, if necessary, therapeutic intervention can be introduced to prevent stone formation.

All of the methods and compositions disclosed and claimed herein can be made and executed without undue experimentation in light of the present disclosure. While the compositions and methods of this invention have been described in terms of preferred embodiments, it will be apparent to those of skill in the art that variations may be applied to the methods and/or compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abbondanzo et al., *Breast Cancer Res. Treat.,* 16: 182 (#151), 1990.

Abrams, "Clinical studies of mineral metabolism in children using stable isotopes," *J. Ped. Gastroenter. Nutr.,* 19:151–163, 1994.

Allred et al., *Breast Cancer Res. Treat.,* 16:182(#149), 1990.

Barkin, Wilson, Manuel, Bayley et al., "Bone mineral content in idiopathic calcium nephrolithiasis," *Miner Electrol. Metab.,* 11: 19–24, 1985.

Bataille, Achard, Fournier et al., "Diet, vitamin D and vertebral mineral density in hypercalciuric calcium stone-formers," *Kidney Intern,* 39:1193–1205, 1991.

Bianchi, Vezzoli, Cusi et al., "Abnormal red-cell calcium pump in patients with idiopathic hypercalciuria," *N. Engl. J. Med.,* 319:897–901, 1988.

Bordier et al., *Am. J. Med* 63:398–409, 1977.

Breslau, Preminger, Adams, Otey, Pak "Use of ketoconazole to probe the pathogenic importance of 1,25-dihydroxyvitamin D in absorptive hypercalciuria," *J. Clin. Endocrinol Metab.,* 75:1446–1452, 1992.

Broadus, Insogna, Lang et al., "Evidence for disordered control of 1,25-dihydroxyvitamin D production in absorptive hypercalciuria," *N. Engl. J. Med.,* 311:73–80, 1984.

Brown et al., *Breast Cancer Res. Treat.,* 16: 192(#191), 1990.

Brutlag et al., *CABIOS,* 6:237–245, 1990.

Buck et al., *Br. J. Urol.* 53:485–491, 1981.

Campbell, in *Monoclonal Antibody Technology, Laboratory Techniques in Biochemistry and Molecular Biology*, Vol. 13, eds. Burden and Von Knippenberg, Amsterdam, Elseview, 75–83, 1984.

Chelly et al., *Proc. Natl. Acad. Sci.* 86:2617–2621, 1989.

Chou and Fasman, "Conformational Parameters for Amino Acids in Helical, β-Sheet, and Random Coil Regions Calculated from Proteins," *Biochemistry,* 13(2):211–222, 1974b.

Chou and Fasman, "Empirical Predictions of Protein Conformation," *Ann. Rev. Biochem.,* 47:251–276, 1978b.

Chou and Fasman, "Prediction of b-Turns," *Biophys. J.,* 26:367–384, 1979.

Chou and Fasman, "Prediction of Protein Conformation," *Biochemistry,* 13(2):222–245, 1974a.

Chou and Fasman, "Prediction of the Secondary Structure of Proteins from Their Amino Acid Sequence," *Adv. Enzymol. Relat. Areas Mol. Biol.,* 47:45–148, 1978a.

Coe, Parks, Moore, "Familial idiopathic hypercalciuria," *New Engl. J. Med.,* 300:337–340, 1979.

Collins, Frezal, Teague, Morton, "A metric map of humans: 23,500 loci in 850 bands," *Proc. Natl. Acad. Sci. USA,* 93:1471–1475, 1996.

DeMay et al., *Proc. Natl. Acad. Sci.,* 89: 8097–8101, 1992.

Fetrow and Bryant, "New Programs for Potein Tertiary Structure Prediction," *Biotech.,* 11:479–483, 1993.

Frohman, In PCR Protocols: *A Guide to Methods and Applications,* 1990.

Fujita R. and Swaroop A., *BioTechniques* 18: 796–799, 1995.

Gefter et al., *Somatic Cell Genet.* 3:231–236, 1977.

Goding, in *Monoclonal Antibodies: Principles and Practice,* 2d ed., Orlando, Fla., Academic Press, 60–61, 65–66, 71–74, 1986.

Heller, Reza-Albarran, Breslau, Pak, "Sustained reduction in urinary calcium during long-term treatment with slow release neutral potassium phosphate in absorptive hypercalciuria," *J. Urol.,* 159:1451–1456, 1988.

Hess et al., *Am. J. Nephrol.* 13:18–26, 1993.

Horrigan and Westbrook, in *Gene Isolation and Mapping Protocols*. Human Press, ed. J. Boultwood, 123–125, 1997.

Hosking, *J. Urol.* 130:1115, 1983.

Inouye et al., *Nucleic Acids Res.,* 13:3101–3109, 1985.

Insogna, Broadus, Dreyer et al., "Elevated production rate of 1,25-dihydroxyvitamin D in patients with absorptive hypercalciuria," *J. Clin. Endocrinol Metab.,* 61:490–495, 1985.

Jameson and Wolf, "The Antigenic Index: A Novel Algorithm for Predicting Antigenic Determinants," *Comput. Appl. Biosci.,* 4(1):181–186, 1988.

Johnson et al., "Peptide Turn Mimetics," in *Biotechnology and Pharmacy*, Pezzuto et al., eds., Chapman and Hall, New York, 1993.

Kaplan et al., *J. Clin. Invest.* 59:756–760, 1977.

Kasahara et al., *Science,* 266:1373–1376, 1994.

Kohler and Milstein, *Eur. J. Immunol.,* 6:511–519, 1976.

Kohler and Milstein, *Nature,* 256:495–497, 1975.

Krieger et al., *Am. J. Physiol.* 271:C130–C135, 1996.

Krizman, in *Gene Isolation and Mapping Protocols*, Human Press, ed. J. Boultwood, 167–182, 1997.

Kruglyak, Daly, Reeve-Daly, Lander, "Parametric and non-parametric linkage analysis: a unified multilocus approach," *Am. J. Hum. Genet.,* 58:1347–1363, 1996.

Kyte and Doolittle, "A simple method for displaying the hydropathic character of a protein," *J. Mol. Biol.,* 157(1):105–132, 1982.

Lathrop, Lalouel, Julier, Ott, "Multilocus linkage analysis in humans: detection of linkage and estimation of recombination," *Am. J. Hum. Genet.,* 37: 482–498, 1985.

Ledbetter et al., *Genomics* 6: 475–481, 1990.

Levy, Adams-Huet, Pak, "Ambulatory evaluation of nephrolithiasis: an update of a 1980 protocol," *Am. J. Med.,* 98:50–59, 1995.

Li, Tembe, Horowitz, Bushinsky, Favus, "Increased intestinal vitamin D receptor in genetic hypercalciuric rats: a cause of intestinal calcium hyperabsorption," *J. Clin. Invest.,* 91:661–667, 1993.

Lloyd, Pearce, Fisher et al., "A common molecular basis for three inherited kidney stone diseases," *Nature,* 379:445–449, 1996.

Malluche et al., *J. Clin Endocrin. Metab.* 50:654–658, 1980.

Miller, *Curr. Top. Microbiol. Immunol.,* 158:1, 1992.

Nakamura et al., In: *Enzyme Immunoassays: Heterogeneous and Homogeneous Systems*, Chapter 27.

Neitzel, "A routine method for the establishment of permanent growing lymphoblastoid cell lines," *Hum. Genet.,* 73:320–326, 1989.

Pacifici et al., *J. Clin. Endo. Metab.,* 71:138, 1990.

Pak and Galosy, "Fasting urinary calcium and adenosine 3', 5,-monophosphate: a discriminant analysis for the identification of renal and absorptive hypercalciurias," *J. Clin. Endocrinol. Metab.,* 48: 260–265, 1979.

Pak, Britton, Peterson et al., "Ambulatory evaluation of nephrolithiasis: classification clinical presentation, and diagnostic criteria," *Am. J. Med.,* 69:19–30, 1980.

Pak, Kaplan, Bone et al., "A simple test for the diagnosis of absorptive, resorptive and renal hypercalciurias," *N. Engl. J. Med.,* 292:497–500, 1975.

Pak, Mc Guire, Peterson et al., "Familial absorptive hypercalciuria in a large kindred," *J. Urology,* 126:717–721, 1981.

Pak, Ohata, Lawrence, Snyder, "The hypercalciurias: causes, parathyroid functions and diagnostic criteria," *J. Clin. Invest.,* 54:387–400, 1974.

Pietchmann, Breslau, Pak, "Reduced vertebral bone density in hypercalciuric nephrolithiasis," *J. Bone Min. Res.,* 7:1383–1388, 1992.

Preminger, Peterson, Pak, "Differentiation of unclassified hypercalciuria utilizing a sodium cellulose phosphate trial," *In Urolithiasis*, Walker, Sutton, Cameron, Pak, Robertson (eds.), Plenum Press New York and London, 325–328, 1989.

Reed, Heller, Lemke et al., "Linkage analysis in absorptive hypercalciuria: lack of linkage to the vitamin D receptor or 1,25$(OH)_2D_3$ hydroxylase loci," *In Urolithiasis*, Pak, Resnick, Preminger (eds), Millet Press, Dallas, Tex., 540–542, 1996.

Resnick, Prigden, Goodman, "Genetic predisposition to formation of calcium oxalate renal calculi," *N. Engl. J. Med.,* 278:1313–1318, 1968.

Ruml et al., *Urol. Clinics of N. Am.* 24:117–132, 1997.

Sambrook, Fritsch, Maniatis, *Molecular Cloning: A Laboratory Manual,* 2nd Ed., Cold Spring Harbor Press, Cold Spring Harbor, N.Y., 1989.

Steiniche et al., *APMIS* 97:309–316, 1989.

Tenenhouse, "Cellular and molecular mechanisms of renal phosphate transport," *J. Bone Min. Res.,* 12:159–164, 1997.

Tieder, Modat, Samuel, et al., "Heriditary hypophosphatemic rickets with hypercalciuria," *N. Eng. J. Med.,* 312:611–617, 1985.

Weinberger et al., *Science,* 228:740–742, 1985.

Weisinger et al. *Kidney Int.* 49:244–250, 1996.

Wolf et al., "An Integrated Family of Amino Acid Sequence Analysis Programs," *Comput. Appl. Biosci.,* 4(1):187–191, 1988.

Wong et al., "Appearance of β-lactamase activity in animal cells upon liposome mediated gene transfer," *Gene,* 10:87–94, 1980.

Zerwekh, Hughes, Reed et al., "Evidence for normal vitamin D receptor messenger ribonucleic acid and genotype in absorptive hypercalciuria," *J. Clin. Endocrinol. Metab.,* 80:2960–2965, 1995.

Zerwekh, Yu, Breslau, Manologas, Pak, "Vitamin D receptor quantitation in human mononuclear cells in health and disease," *Mol. Cell Endocrinol.,* 96:1–6, 1993.

---

What is claimed is:

1. A method for screening for an increased risk of hypercalciuria comprising:

(a) obtaining a sample nucleic acid from a subject; and (b) analyzing the sample nucleic acid to detect the presence or absence of a genetic mutation in a genomic region associated with an increased risk of developing hypercalciuria, wherein said genomic region is comprised in chromosome 1q23.3-1q24.

2. The method of claim 1, wherein the hypercalciuria is further defined as absorptive hypercalciuria.

3. The method of claim 1, wherein the hypercalciuria is further defined as osteoporosis with hypercalciuria.

4. The method of claim 3, wherein the osteoporosis with hypercalciuria is further defined as postmenopausal osteoporosis with hypercalciuria.

5. The method of claim 3, wherein the osteoporosis with hypercalciuria is further defined as ideopathic osteoporosis with hypercalciuria.

6. The method of claim 1, wherein the nucleic acid is DNA.

7. The method of claim 1, wherein the subject is a human.

8. The method of claim 1, wherein the genomic region is located between markers D1S2681 and D1S2815.

9. The method of claim 1, wherein the genomic region has a sequence contained in SEQ ID NO:1.

10. The method of claim 1, wherein the genomic region has a sequence contained in at least one genetic sequence selected from the group consisting of the genetic sequences set forth in GenBank Accession # Z97876 (SEQ ID NO: 7, SEQ ID NO: 8 and SEQ ID NO: 9), GenBank Accession #

Z99943 (SEQ ID NO: 10), and GenBank Accession # AL031733 (SEQ ID NO: 7).

11. The method of claim 1, wherein the genomic region has a lod score of greater than 3.0 but less than 30.0.

12. The method of claim 1, wherein analyzing the sample nucleic acid is done with a PCR procedure, diagnostic RFLP analysis, RNase protection assay, or RNase mismatch cleavage assay.

13. The method of claim 12, wherein analyzing the sample nucleic acid is done with a PCR procedure.

14. The method of claim 13, wherein the screening for an increased risk of hypercalciuria comprises:

(a): obtaining a sample nucleic acid from a subject; and (b) analyzing the sample nucleic acid to detect the presence or absence of a genetic mutation in genomic region associated with an increased risk of developing hypercalciuria.

* * * * *

UNITED STATES PATENT AND TRADEMARK OFFICE

CERTIFICATE OF CORRECTION

PATENT NO. : 7,052,833 B1 
APPLICATION NO. : 09/339352
DATED : May 30, 2006
INVENTOR(S) : Reed-Gitomer et al.

It is certified that error appears in the above-identified patent and that said Letters Patent is hereby corrected as shown below:

In claim 5, column 398, line 54, delete "ideopathic" and insert --idiopathic-- therefor.

Signed and Sealed this

Third Day of October, 2006

JON W. DUDAS
*Director of the United States Patent and Trademark Office*

SEQUENCE LISTING

```
<160> NUMBER OF SEQ ID NOS: 18

<210> SEQ ID NO 1
<211> LENGTH: 2567
<212> TYPE: DNA
<213> ORGANISM: Human

<400> SEQUENCE: 1

gaataacctg ttcaagtatt ccattaagct aacagagaag ttaaacatgg ttactctcca      60
```

-continued

```
tagtgataag gaaagtgaag aagtctgtca cctcacaagt ggtgtcagac tgaaaaacct    120
gtcacctcca acgtcattaa aagaaatctc tctgatccag ctggatagca tgagactttc    180
ccaccaaatg ctggtgagat gtgctgccat cattggcctg accttcacca ctgagttgtt    240
gtttgagatt ctcccctgtt ggaatatgaa gatgatgatc aagaccctgg caaccctagt    300
ggaatctaac atttttttatt gtttccggaa tggcaaggag cttcaaaagg ccctgaaaca    360
gaatgatccc tcatttgagg tgcactatcg ttccttgtct ctgaagccca gtgaagggat    420
ggatcacggt gaagaggaac agcttcgtga actggagaat gaggtgatcg agtgccacag    480
gattcgattc tgtaacccta tgatgcagaa aacagcctac gagctgtggc tcaaggacca    540
gagaaaagcc atgcacttga aatgtgcccg ctttttagaa gaagatgccc acagatgtga    600
ccactgccga ggcagggact tcattcccta tcatcacttc acagtgaata ttcggctcaa    660
cgctttagac atggatgcca ttaaaaagat ggctatgtct catggattta aaagatgcat    720
gagactggga gatactgcct caccttatta tattcttcaa gtctgatctt accttggtgt    780
gcacacgtgc taagatttgc ctaatgatgt tgggaggtga agctgaagtg atgagagttg    840
tgcagggact tacttcctca tccacctccc aaaatgaccc tggcaaagga agtgggggtg    900
attcataatt catttaaaaa ctgaagacca acttctcaca gatgtgggga tgctgttcaa    960
ggcatacatg tatttgaatg aaggacagaa gttgctaaaa actctcaaga aggacaaatc   1020
ttggagccag acatttgagt ctgccacctt ttacagcctc aaaggtgagg tctgtttcaa   1080
tatgggccag atagtgcttg ccaagaaaat gctgaggaag gcactgaagc tcctcaaccg   1140
aatctttcct tacaacttaa tctccttgtt tctccatatc catgtcgaga aaaacagaca   1200
ctttcattat gtgaatcggc aggcccaaga gagcccacct ccagggaaga agaggctggc   1260
acaactttac cggcaaactg tctgcctttc cttgctgtgg cgcatctata gctacagtta   1320
tctttttcac tgcaagtatt atgcccacct ggcagttatg atgcaaatga atactgcact   1380
ggaaactcaa aattgtttcc agatcattaa ggcttaccta gactattcgc tataccacca   1440
cctggctggc tacaaaggtg tgtggttcaa atatgaagtc atggccatgg agcacatctt   1500
caacctcccc ctgaaaggcg agggcattga aatcgtggca tacgtggctg agacactggt   1560
cttcaacaag ctcataatgg gacacctgga tttggccatt gagttaggct cccgagccct   1620
tcagatgtgg gcactgctcc agaatcccaa ccgacattat cagtccctct gcagacttag   1680
cagatgtctc cttctgaaca gcagataccc gcaattgatc caggtgctgg ggcggctgtg   1740
ggagctttct gtaacacagg aacacatctt cagcaaggca tttttctatt ttgtctgctt   1800
ggacatcctg ctttattctg gttttgttta tagaacattt gaagaatgtt tggaattcat   1860
acaccaatac gaaaacaaca gaatcctcaa gttccacagt ggactcctcc tgggacttta   1920
ttcctctgta gctatctggg agtgtgaagc aggggtaggc aggagactac acacttccag   1980
agacccaggt atgccagact tcaggaatgg gacaactttt acaaattttc caatagagct   2040
aaaaatcttt tgccaagaag aaccatgaca cttacttact atgacggaat atctaggtac   2100
atggaggggc aagttcttca ccttcaaaaa caaatcaaag aacagtcaga gaatgcccaa   2160
gccagtgggg aggagctact caagaacttg gagaatctgg tggctcaaaa taccactggc   2220
cctgtctttt gcccaaggct ctaccacctg atggcttacg tctgtatatt aatgggagat   2280
gggcagaaat gtggcctctt cctgaacaca gccttgcggc tctctgaaac acaggggaat   2340
atactggaga aatgctggct gaacatgaac aaagaatcat ggtactcaac ctctgagtta   2400
aaagaagacc aatggcttca gacgatcttg agtctcccat catgggaaaa aattgtagca   2460
```

-continued

```
ggcagggtaa acattcagga tcttcaaaaa aacaaattcc tgatgagagc taataccgtg   2520

gacaatcatt tctaacatgt caaagaaaaa agattttaat aagcact                 2567


<210> SEQ ID NO 2
<211> LENGTH: 372
<212> TYPE: PRT
<213> ORGANISM: Human

<400> SEQUENCE: 2

Met Leu Phe Lys Ala Tyr Met Tyr Leu Asn Glu Gly Gln Lys Leu Leu
  1               5                  10                  15

Lys Thr Leu Lys Lys Asp Lys Ser Trp Ser Gln Thr Phe Glu Ser Ala
             20                  25                  30

Thr Phe Tyr Ser Leu Lys Gly Glu Val Cys Phe Asn Met Gly Gln Ile
         35                  40                  45

Val Leu Ala Lys Lys Met Leu Arg Lys Ala Leu Lys Leu Leu Asn Arg
     50                  55                  60

Ile Phe Pro Tyr Asn Leu Ile Ser Leu Phe Leu His Ile His Val Glu
 65                  70                  75                  80

Lys Asn Arg His Phe His Tyr Val Asn Arg Gln Ala Gln Glu Ser Pro
                 85                  90                  95

Pro Pro Gly Lys Lys Arg Leu Ala Gln Leu Tyr Arg Gln Thr Val Cys
            100                 105                 110

Leu Ser Leu Leu Trp Arg Ile Tyr Ser Tyr Ser Tyr Leu Phe His Cys
        115                 120                 125

Lys Tyr Tyr Ala His Leu Ala Val Met Met Gln Met Asn Thr Ala Leu
    130                 135                 140

Glu Thr Gln Asn Cys Phe Gln Ile Ile Lys Ala Tyr Leu Asp Tyr Ser
145                 150                 155                 160

Leu Tyr His His Leu Ala Gly Tyr Lys Gly Val Trp Phe Lys Tyr Glu
                165                 170                 175

Val Met Ala Met Glu His Ile Phe Asn Leu Pro Leu Lys Gly Glu Gly
            180                 185                 190

Ile Glu Ile Val Ala Tyr Val Ala Glu Thr Leu Val Phe Asn Lys Leu
        195                 200                 205

Ile Met Gly His Leu Asp Leu Ala Ile Glu Leu Gly Ser Arg Ala Leu
    210                 215                 220

Gln Met Trp Ala Leu Leu Gln Asn Pro Asn Arg His Tyr Gln Ser Leu
225                 230                 235                 240

Cys Arg Leu Ser Arg Cys Leu Leu Leu Asn Ser Arg Tyr Pro Gln Leu
                245                 250                 255

Ile Gln Val Leu Gly Arg Leu Trp Glu Leu Ser Val Thr Gln Glu His
            260                 265                 270

Ile Phe Ser Lys Ala Phe Phe Tyr Phe Val Cys Leu Asp Ile Leu Leu
        275                 280                 285

Tyr Ser Gly Phe Val Tyr Arg Thr Phe Glu Glu Cys Leu Glu Phe Ile
    290                 295                 300

His Gln Tyr Glu Asn Asn Arg Ile Leu Lys Phe His Ser Gly Leu Leu
305                 310                 315                 320

Leu Gly Leu Tyr Ser Ser Val Ala Ile Trp Glu Cys Glu Ala Gly Val
                325                 330                 335

Gly Arg Arg Leu His Thr Ser Arg Asp Pro Gly Met Pro Asp Phe Arg
            340                 345                 350
```

-continued

```
Asn Gly Thr Thr Phe Thr Asn Phe Pro Ile Glu Leu Lys Ile Phe Cys
        355                 360                 365

Gln Glu Glu Pro
    370


<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3

gatcgcgcca ctgcactcc                                                 19


<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 4

ggattacagg cgtgagccac                                                20


<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 5

catctaggtt gccttacccg aagt                                           24


<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 6

tgattaggag cacagcctca gtgc                                           24


<210> SEQ ID NO 7
<211> LENGTH: 39960
<212> TYPE: DNA
<213> ORGANISM: Homo sapiens

<400> SEQUENCE: 7

gatcattctg tttcagggcc ttttgaagct ccttgccatt ccggaaacaa taaaaaatgt     60

tagattccac tagggttgcc agggtcttga tcatcatctt catattccaa caggggagaa    120

tctcaaacaa caactcagtg gtgaaggtca ggccaatgat ggcagcacat ctcaccagca    180

tttggtggga aagtctcatg ctatccagct ggatcagaga gatttctgca ggtagaaggc    240

cacacagtag aaaactagtt atttatcttt atctaatatg ctgtatttaa tatagagcag    300

gtggacaacc atcctgctct acagttcttg ttgcaagaaa ctcagccaag ctaagtcaaa    360

agaagtattt gtttagtacc taatttgtgg atagcacttg tgctgggagt actaaagatg    420
```

-continued

```
caggcttatg gcctagaaag acacacagca caatgacctg acaaaattaa gatctatttc    480
atggtgttct gattttgtgc taaagtgtga caagtgtgtg tgaggagagg agaggacatt    540
gtaatcacta ttgtcagaag gagcaggccc tgccattcct gtgctttgtt gacttcctca    600
gctggtcctt ttgtatcttc ttctctgcct cccctttctc ctagaaactc ctggtttctc    660
tctatctgcc ctagaaattt atgtattctc atgacataca ttatcatctc tgtgtcatga    720
ccaagtgtca gagagttcac agctcctatc ccaacttttc atctaagctt gaatatcggt    780
agctcatgtg actttctgga cattttgacc aggatgtcct tctgttaggg acaaaattag    840
aatttctcaa cttgcccaaa aaacacagta gaaactaagc tagtccatcc tcttttttt     900
tttttgagat ggagtctcac tcttgttgcc caagctggag tgcaatggct gatctcggct    960
cactgcaacc tccgcctcct gggttcaaga gattctcctg cctcagcctc ttgagtagct   1020
gggattatag gcacccacca ccatgcccgg ctaatttttt gtgtttgtag gagagatggg   1080
atttcaccat gttgaccagg ctggtctcga actcctgacc tcaggtgatc cacctgcctc   1140
ggcctcccaa agtgctggga ttacaggtgt gagctactgc cttcttacat tagtagacac   1200
agctaacgaa acataaatgg cactcttttg aagactgagg accttgagat gtccctaggc   1260
cacctttcta aacattgaaa gttgcttatg gatggcatga attggagctg agttcatact   1320
aaaacattcc ttgaaagtca tttttcttta aaagaataat aatacatctt tctttctttc   1380
tttctttctt ttttgagaca gagtttttct cttgttgccc aggctggagt gcaatggcgt   1440
gatctcggct cactgcaacc tccgcctcct gggttcaagc aattctcctg cctcagtctc   1500
ctcagtagct gggattacat gcatgcgcca ccatgcccgg ctaatttttt tttgtatttt   1560
tagtagagac ggggtttctc catgttggtc aggctggtct ctagaacttc tgacctcaag   1620
tgatccaccc gacttggcct cccaaaatgc tgggattaca ggagtaagcc actgtgcctg   1680
gccaataata tgtctttcat ataaactcgt ttgtcatttc tttctcataa aagtggatga   1740
caggaagtat ctcagtatta gattttctcc ctcattattt ggtttctgtt taattgaaaa   1800
tgtacaatat ttcattcttt tatgcagatc ccagaatata cacaggggga aagatggctc   1860
ttaggagcaa agccaagcct accctgagcc ttctcactgc ttcaggcagt acagagcaaa   1920
cagacaaaca accaatgttg ctgtttttct ttttcctttt aaaaacagac atcctagaga   1980
aagccaaagt ggagtttagg gactagaaaa taaataccag gtcagatttt cttttctttt   2040
ttttttgag atggagtctc actctgtcac ccaggctgga gtgcagtggc tcactgcaac    2100
ctccgcctcc caggttcaag caattctcct gcctcagctt cccgagtagc tgggattaca   2160
ggtgtgtgcc tggctaattt ttttgtattt ttagtagata cggggtttca ccatattggc   2220
caggctggtc tcaaactcct gaccttgtga tccgcccgcc tcggcctccc aaagtgctgg   2280
gattacaggc gtgagccact gcgcccggcc agattttctt accttttaat gacgttggag   2340
gtgacaggtt tttcagtctg acaccacttg tgaggtgaca gacttcttca ctttccttat   2400
cactatggag agtaaccatg tttaacttct ctgttagctt aatggaatac tctacagggg   2460
tataaaaggg aagaaaagtt gagtcattat cctgtcttat aaggtctgat tttccaatga   2520
actttgagat ggatctcata tgaggaagac tgggcagaga tgtatattgg ctcaccaaat   2580
attctggaaa cctttttttt gttttgtttt gttttgtttt ttgttttttt gaggtggagt   2640
ctctcactgt cgcccaggct ggagtgcagt ggcgtgatct ttgctcactg caacctccgc   2700
ctcccaggtt caagcgattc ctgcctcagc ctcccaagta gctgggatta cagccgccca   2760
```

-continued ctaccatgcc tggctaattt ctgtagagat gaggtttcac catgttggcc aggctgttct 2820
caaactcctg acctcaagtg atctgcctgc ctcggcctcc caaagtgctg ggattacagg 2880
tatgagccac actgcaccag gccgctggaa accttattct aagtaaaact gattcatgaa 2940
aatctagatg tactcaaaaa tgttttgtct ccctctgcca accctgccca accaaaagaa 3000
ttggcactat tgatgtcttc cataggatat aaggctttac aaacgtttga ttcacagtca 3060
gattatcaga atgtattata tatgtattat gtatatacat aatgtatatc agaatgtatt 3120
attatatata tacataaaca tatatttgta tgtatacatt tacataccca cactcagtta 3180
caaacacatt ctgtgaggca ctgtactcta attaggacat agctactatc agagatattt 3240
taaatggtga agtttgaata gtaaatgtgc ctagtaattt ggtttcctag tactccaaaa 3300
tgcattattt ttctatccct tcagccattc atgtagtcct tggtagcggc aagactgtgc 3360
taggtgaggt ggaaatagga aggtgaataa aaccaagttc cttatttcct ggagctctaa 3420
gtcatgtaca ctaagagctg gactgccagg cagtagatga gtgccatgtg attgggcaca 3480
tacagtaagc accagagttc acatcaatac aggacatatt tattaaggac tttctgtgca 3540
tcatatccag tgaaggctat caatgtgaat aacacatgct tccagccctc aagaggctta 3600
aaaatctgtg gagacagata cataagtaac taattataac atcaggatgg gtgacttaag 3660
agctaaagag caaagagtaa catgttgtgg gaacagaaaa taacaattaa atcagacttg 3720
gtggattcag aaaggcttga taggggagga agtactttga tccttgaagg atgaagagat 3780
attctaagcg gcaagtggag gagaggccaa cgcgaaggca caggaacctc agagtactta 3840
gcgagttagg ggaatggagc ggcccagcgt gactaaagtg cagggcctgg agtgctcagg 3900
tgctatgtgg gagacgtgtt tggagagcta gtttgggagc agagcatgga gggcattaaa 3960
caccataata tgaagactgg actttataga caagagggaa aggtcacaga tttctgaaga 4020
ggagatagta gtaatccaac tagtcgtatt taggaaggta ccactggaag cagcatatgg 4080
aaaaggcgag agactaggac agggaagact atgtaaggag ctataacaat ggaatgtcaa 4140
gaagtgagga tggatagaac caggcaagtg gttcagcaag gagaaagcaa atactaaaga 4200
tatggaggaa atggggccta agcaagacag tgatagaagt gacagagaca cgaagtacag 4260
aaggaggggt ggttgagcgg gaggataatg catgaagttt tagatttatt aagtttaagg 4320
gaatctgtgg aatagttcaa tgggcaattg gaaatatggg tgtggaatta agggtgaggt 4380
tagggttcga cacacacgaa ggctgagaaa tagatgagta aatgaaaaca actggggaga 4440
gagttgtttc caattctggc aagctagcaa gaggaaaggg ttaaggatag aacttgaaga 4500
atgtcccagg aggagtagac ccaggtagag agccaaggat tatctgagga ctggtcagag 4560
aggggaacag gaggagtgtg gggtcaggaa agccaaggga ggatagcata ccaaaaaggg 4620
ggccgtgtgt gtgtgtgtgt gtgtgtgtgt gtgtgtgtgt gtgtgtgtgt tgggagtagg 4680
agagtggggc tcaaggatat gacgtggtcc atgctatttt atgcttattt ccccttccag 4740
gacctagcat tgagacaacc attctttcca tcactcaacc agtattaact gattgcctct 4800
aggtgctagg aattttccta ggattgggga ttcaggagag cacaaaactc catgcctcat 4860
gaagctcaca ttctagtggg aaacaaacat taaacaatag ataaatacat taaaaggata 4920
atctcgtaat tcaattatgt gaaagaaata aaagggtgat agacagaatg tactccctac 4980
tcaggttcgc ctgttgtcag cctttgccct atttactata tcctaggttc cttctatgtg 5040
tacatatttt tctgaagcat ttgaatataa gtcacataca tcacacccta tactcccaaa 5100
tactttactc tgtattttct aaaaatattg acactctttt gtttgtttgt ttgttttgtt 5160

-continued

```
tttttgagac agggtctcac tcctgttgcc caggctggag tggagagttg tgatcatagc   5220
ttgctgcagc ctcaacctcc ctggctcaag caatcctccc acctcagcct cccaggtagc   5280
tgggactaca ggcgtgcgac accacacccg ggtaattttt gtatttttag tagagatggg   5340
gttttgtcat gttgcccagg aaggtctcaa actcctgggc tcaagcaatc cgcccgcctc   5400
agagtcccaa agtactggga ttataggtgt gggccactgc acctggccaa cactctctca   5460
tataactaga atatagttat caccttcaag aaacttaaca ttggtcgggc acagtggctc   5520
acgcctgtaa tcccagcatt ttgggaggcc gaggtgggtg gatcacaagt tcaggagttc   5580
aagaccagcc tggccaaggt ggtgaaaccc cgtctctact aaaaatgcaa aaaaaattag   5640
tcaggcatgg tggcagttgc ctgtaatccc agatactcgg gaggctgagg cagagaattg   5700
cttgaaccca ggaggcggag gctgcagtga gccaagatcg tgccactgca ctccagcctg   5760
ggcgacagag tgtctcaaaa aaaaaaaaaa agaaatttaa cattgataca atactttagt   5820
ctactgtcca tatcccaatt ttgtgaattg atcaaataat atcctttaac attctctttt   5880
cttccagtat aggatccagt ccaggattat gtatcatatt tatttttta attgaagtga   5940
aattcaccta acatgcaatt aattatttta aagtatacaa ttcagcggcc tgtagtgcat   6000
tcacaatatt atgtaaccag aatctctcct taatttcagt tttttaaaat taagacacaa   6060
aagacactga agggttttaa atagagaaga cacctgattg tgttttaaaa agctcataac   6120
agggccaggt gcagtggctc acacctgtaa acccagcatt ttgggagccc gaggcgggca   6180
gatcacttga ggtcaggagt tcaagaccag cctggccaac atggcaaaac cctgtctcta   6240
ctaaaaatat gaaaattagc tgggcggtag tggtgcatgc ctgtaatcct tgctacatgg   6300
gaggctgagg caggagaact gcttgagcgc aggagacgga gattgcagtg agccgagatc   6360
gttccactgc accccagcct gggcgacaga gtgagactct gtctcaaaaa aaaaagctca   6420
taacggatac tacataaaca tttattgaac aagtaaacaa agtaaacaaa tgtataaaat   6480
ttagaaatag tatttactct gcagtattta tatttacata tcgctttcct ttaatccatt   6540
ggcatcttaa tattattata atggaattat ttagtctaaa aataataatc atagcagtca   6600
ttatctattt aatgatccac tatcatcttt aaaactaatt tggccagaga aagtcttctc   6660
catttttca tcacaatcat ccagaaagaa aaaaaaaatt gatctttcct taaaaagcaa   6720
gctaatgttt cttgttcctt aaaaaaaaaa aaggtagagc tttgccctgt tctctcagac   6780
aaccatctgt ctcatttctc ctacagatgt gcccttgggg gccacatggt cctgtagtca   6840
tgctattgaa caagaagtga gaggcaacag atgcagcaca gactgaaaca tggataggga   6900
catctgagca tcattcattc acccaggagg caggggtttt taggaagcaa gaggaatctt   6960
ttttatgaaa tttccctcat tgtcaccttt aggtggtgat tttctatcct gctacataga   7020
gacagcagca ccataagtcc tttattgcac cgtattcacc tcatcatgac actgatctca   7080
cacctatatt cttgtcttta aatttagtcg cagaggaata cgttttgacc ctctaggttt   7140
agtaatatta atacacgtcg tgcttatagc tgttaaatca tcgtattact taatttgagt   7200
cacaaaaaaa tgaagaggct tccaattcca ggaagagaga gttggtatgt ttttccctat   7260
tcctcctgct aaatatagtt aaaacccta gacgttatgt gtaaaacaaa cagaagatga   7320
cattgaaggt ggaaagaagt cagaccagct agggacctta ggacccaagg aaaaacgtgg   7380
cagtgggtcc catggcaggg ctttcttttt gcctcacatg ttcaagactt agagcttaag   7440
aatctagcaa ctcagaaaca ccaagggagt ggaaacaaaa aaagtcccaa ttaaagcctg   7500
```

-continued ctctatctag ccttaattct ctgctttcca acttgtaatc tctggccccc accctttttcc 7560 ctgcaataaa attattttcc taaaaattcc aactggcctc cttcatgcca tcacttcaga 7620
tttcatccct gtatatatct gtgtagcacg ggatctttgt tgataactca cttcgtacta 7680
gcaattttac ctctggcaaa aaaggaaagg ctttttgaag ataacatcaa agcggccctt 7740
cagttctggg ccttaagatt tgtcaatgtt ctttcatttc tactatagtt actttttttt 7800
tttttttttt ttttttttga gacagagtct cactctgttg cccaggctgg agtgcagtgg 7860
tgcaatctca gctcacttca acctccacct cccaggctca agagatactc ctgcctcagc 7920
ctcccgagta gctgggatta caagcaccca ccaccacacc tggctaattt ttgtattttt 7980
agtacagatg gggtttcacc atgttggcca ggctggtctt gaactcctga cctcaagtga 8040
tctgcctgcc tcgggctccg aaagtgctga gatttaggcg tgagccaccg cgcccggcca 8100
tagttagaca atctttagcc gagtccagtg agtcccaggc aatgttaagt tcgcttacaa 8160
tctggaatat cggatccaat aattcctggc tccccagaac cttctgactc tacaggaagc 8220
agcctgtgga atagctcatt tttgctacct tctctgaatg aagacttaag ttaggcagaa 8280
cagagtaaga aagaaccatc accgcaggac ttactgaaca ggttattcca ggtcctattt 8340
gtcttttcct cagactccgt ttgttggaaa acgagtacct catgatgttc caggttttta 8400
agcaattctt cacagtaaaa tggaatccca cagcttccct cccccaggta cctgtagtga 8460
aaacaaggca atctgtttac attgaagata catctttttag gaaggaaaaa tatgtaagtc 8520
ttctcaatca cttgaaaata atttcttgtc attcttcatt tgtttctgtt tgttttcagt 8580
tttgaggcat tgctttgttt tctttttatt tcactcatgt gtgtacacaa taagtgtgca 8640
cacacttgat ttatagtttt taaaacagac attggaagga taagccaaaa actaatcaaa 8700
atggttacct ataggataag ggagggaagc aagactaagg atgtaccttt ttggctttgg 8760
aaagatatac atgttctata taatttaaac agagagaggg ggagagagag agagagaccg 8820
acagaaagaa tgagtgccaa attggtgcct ggagttatct taaatgagcc tttgttcaag 8880
acatcttcct tccagaagca gggcaacctc attgcagata ctaagatggg ctgtaaacag 8940
ccagctaaag aaaaaacatt ctctatgttg ttaaggtgac tgctgtcagg acgccaggag 9000
agccaggctc ggtggctcac gcctgtaatc ccagcacttt gggaggccga ggagggcgga 9060
gcatctgagc tcaggatttc aagaccagcc tgaccaatat ggagaaacct catctctact 9120
aaaaatacaa aattagctgg gcgtagtggg gcatgcctgc aatcccagct actcgggagg 9180
ctgaggcaga agaatcgctt gaacccggga ggtggaggtt gcggtgagcc gagatcgtgc 9240
cattgcactc cagcctgggc aatgagagcg aaactaggtc taaaaaacaa aaaacaaaca 9300
aacaaacaaa caaacaaaaa acaaagaaaa ccccaggaga ggaatcactg aaaagctcag 9360
agagcactca ccagtgagtc agctttccac atctgccata gacagagaac accaatacca 9420
gaccacacca ttgccagcca ggtaagacct tgcttagtgg caggtcatgg tctttaacgc 9480
ttaccagttt gcctttcctg tcacttgccc ataacaatgc tcttagtcac tgcaggttaa 9540
agtgagtata cccatacccc ccatgatgaa agggaaatag agcttttcac taagcaaagt 9600
ttaagaaggc gtaacaggga ggcaacatgg aaaaggtgag caacatccat cctaccaagc 9660
attatgaatg gctccttcaa aaggtggacc agaccaagca tggtggctca cacctgtaat 9720
cccagcattt tgggaggctg agatgggagg attgcttgag cccaggagtt catgatcagc 9780
ctgggcaaca ctgtgagacc ccatctctac agaaataaaa aatttaccgg aggtgcacac 9840
ctgtagttct ggtactcaga aagctgaggc aggaggatgg cttgagccca ggaggtcaag 9900

-continued

```
gctgcagtga gccatgatgg caccactaca cttcagcctg ggtgacagag taagaccctg   9960
tctcaaaaga aaacagaaaa aaagaaaaga aaaatttttt aaaaggtggg gccaggaaag  10020
atactgaaat aggcacatca agacacatac taagaaatct gatgaagtct agaccgaggg  10080
aatgtatgca gatgtcgaga gttcagaata gaaagaggtt acttacgagt ccagttcttt  10140
ggagatgcag ctcacattga ggtcaagaca gatcttgttg gagatgtcgt taggctgtac  10200
tgcaccaatg acaatgtagg tggtgttcct gttctttatt acggccctgg cagctgcaca  10260
gggaatgtta acgaagggac acagggacat aatgatgaag ataggaagag tccggataag  10320
cttctccata aatctccagg aggtcgaatc cacaaactgg gcctcatcaa tgataaaaat  10380
aatcctttcc tctttcacta tctggacaag atgcagaaag agaaagagaa acaccatagg  10440
acgtcaggtt tttttacaca tgtatgggta tgcatatgta tccattgagc ttcctggttt  10500
gcttatgatg cagcgaaaga actaagttca atcttttctt tccagtaact ttgcattcat  10560
ttatattcca ttaacttaga atttgtggct atttggacag agctggctgg aatggactct  10620
tacttggtca aagctttgtg taaagatagt gcaaatttgg agaatagatg gagttttagg  10680
ggtacccaca aaagctaact gaagtgccca ttacataaaa ataactggtt tgttaattat  10740
gagtcatttt aatctattga acaatacagt tgtcctgggg aaatctactt gacatttatt  10800
caaccagcat atattcagca catgcttact gagcaccccc tgggctaggt gctgaacaaa  10860
actagtcctc gccctgctgg cagccgatgc tattctagct tgaaatgtgg tatgtgttgc  10920
acttaaaaaa cagatcacag gtcccttttc tcatatagac taccctcccc taagtagtct  10980
gaattattta ttcactcatt aagcatttat tgtgcatcta tcagggtcag gtgctgttct  11040
aggtactggg aatacagtct caaacaaaat acggagccta cattttagcg tcaaccactt  11100
acgtagcagg ctctgcctta ccactgtgta aggtgtcaca atgcagaaaa ccggctcccc  11160
agttctcact gctccagact gctaatggct gctttttgtt tccctctgag aagagattga  11220
gttaacccat tctttctctt tgtgcttgac agtcattata aagtgttata acctgccttg  11280
ttcacacata cctaagtcta ctcctgcagc cccgttctgt caccaaatac ttagcccttt  11340
gactagccct gagaacagtt taattaatga ggaggtaagc actacattgt tttgagtttg  11400
actggtatct ttaaaaagat ggggcagata gaaatttaag ttttaatctt gggatagcct  11460
tgttaatgaa ttattcataa attgaagaga ataaagcagg aacaaaaaat catgaattca  11520
ataataaaac attggcctgg tttcttctaa tctaaaatga ggattgggtt ctttttaaag  11580
tgaaaaaaag ccaacactta cattatactt actatgttcc aagtactgcg ggatgctctt  11640
tacataatta actcacttaa tcctcacaac atccatataa agtggtacta ttgaatctat  11700
ttgctgagaa aatttgggca cagagaagtt aagtaacttg cccagggtca cacagatagt  11760
taatggtcca aagacttgtc agtacataat caaacacagc tttggtagca gtttccaaac  11820
aagattctgc ttcagcacca actgaaaagt tttaaaacaa aagcaaacaa ctaaacaggt  11880
tcctaggccc aatccacatc ctactttttt aatctttaga gttagaactc acaaatccat  11940
atttttaaag gagcttcttg taaatacttg tgatgcaaac agtctaagcc ctgacactta  12000
gaaactactg atattgtctt gcctatgacc tgaagtacaa aagaagaaag ctgtattata  12060
aatataatac aatgccacca acttatatcg atcatttatt atgtacaatt atgaggcaca  12120
tttctcatca atagtgatat ggaaatgtta agagactctc tgttcttaag aagctcacag  12180
gccaggtgtg gtggctcaca cctgtaatcc cagcactttg ggaggctgag atgggcggat  12240
```

-continued

```
cacaaggtca ggagtttgag aacagcctgg ccaacatact gaaaccccat ttctactaaa  12300
aatacaaaaa ttagctaggt gtggtggtgc gtgcctgtag tcccagctag tcgggaggct  12360
gaggcaggag aatcgcttga acctgggagg tggaggtctc agtgagccga gaccgcacca  12420
ttgcactcca gcctgggcga cagagcgaga ctctgtctca aaaaaaaaaa aaaaaaaaaa  12480
aaaagaggct cacgatttcc tgagggagag agaaacagat atataagtaa tgaatggcaa  12540
tatgccataa tagtatagag tgtatagtat aactagaaat gtgttcacag ccttacagaa  12600
gcctggtgga agaagaatta gtcatgtcta gtgatctggg gaagttctca ccaaagaggt  12660
gacattgaaa gatgagcacc atttctctag gttaaaaaaa atcttttggc ttttatctta  12720
ttaccactgg gacttatttc gagagtataa agtatgggtt ggtgtgattt gcatatactc  12780
tgagaattat atgaaggatg aattgaagca gagaggtgtg aagcacagag ttttttggaa  12840
agctatggaa atagtccagg aaaaaatgat aagagcctga actatggcaa taggaaggga  12900
ggacaaggag attccagaga ctgaggtaaa aatagtagga cttggcagtg agtaaatgcg  12960
ggaatgtggg caaaaaagaa ggcaaggata actttaaatg atacagaatg gcataatttg  13020
ctactaatga aatcaaggat caggatcagg atgaggaaga aagggcacta tagtaaaaaa  13080
atgaatttgg cattagacac tcaactcagc gtgagtcact acatccaagt ggaatatata  13140
caaggctctt aggaatatgg ttttggtgtt tataagagag gtggggactg aaatataaat  13200
ttggtgatca atatatagca gacagtcgtg atattactgg gagagagcta acacttgttg  13260
agtgtttctt atgaaagaga cactgttcta agtgtttcta catataatct agtcatttaa  13320
acttacatcc cagtgagcta cgtactatta ttttcctcca tttgatagat gataaagcag  13380
aaacatagag agggtaagtc actgcttgag gttgctcagg tagcaagtga taggcctggg  13440
ggttcaaacc tcagtggtct gacgacagag cctgcatatg taaccacttt ggtacattat  13500
atctcaacaa aggatgaaaa aatgagtgct gagagaggcc agactcctag gagtaatgtt  13560
aagggactct tttcaaggca tctaaattct aaacagacct tttgcttgag gtttggaagg  13620
atggaggaga atgaagcact ttaggacaaa gccttcacat ccttcaaaag cctcttgcca  13680
atgtggtctg aactcctcaa accacctggc tttgtggtga tttgcccagt tttcttcccc  13740
ctacttcttg acccacagat gctcttacca gcttcaagat cttcataaac aatatttcca  13800
attgtttttg ctttttcaag gtgctcatcc tggaaatctc ccgagaaata gggaactgta  13860
caaagaatta tgagaatatt gagtatggga aaatagcaaa gggaactact ggctatgcaa  13920
ctttgggcaa aacacttaac tattctgtgt cttaaaatcc tcatgtgtta gataagtggt  13980
cccaaccttt ttggcaccag ggactagttt tgtggaaaac aatttttttca tgaactgcgg  14040
cagaggggat gattttagga tgattcaggt gcattacatt tattgtgcac tttgcttcta  14100
ttattacatt gtaatatata atgaaataat tatacaactc accataatgt agatagaatc  14160
agtgggagcc ctgagcttgt ttccttgcaa ctagatggtc ccatctgagg gtgatggaag  14220
ccagtgacag atcatcaggc attagattct cataaggagc atgcaaccta ggtcccttgc  14280
atgcacagtt cacaataggg ttcaggctcc tatgagaatc taatgctgct gctgatctga  14340
caagaggagg agcttaggtg gtaatgtgag caatggggag tggctataaa tagagatgaa  14400
gcttcacttg ctcacccact ggttgcctcc tgctgtgtgg tctggtttct aacaggccat  14460
gaactagtac caggggttga ggacccctgt gttagataat tcaggaaaag acagggcaca  14520
gtctgcactg gcatcacttg taggaacaga gtgactttgt gtcccagagt agctagtata  14580
gctatgatag aaaggtaaga aaaaaattag tcagcagatg gccatttgga ttttcttgag  14640
```

-continued

```
tatgatattt caagatacct ctaatatgtc aagaatgttg atgcacatcc agagaggatt  14700
gggagccatt tactcaccat ctggatactg cagatataca gaccaaagag atgctaagtc  14760
acaatgcacc agagaggagt tgctgtgcct gcccatggct atttgtgcag aagtataata  14820
ctagctagtt acctgaacat ggaaaatgtc attaagaaga cagtagaact tttcatccaa  14880
cagtgtcatg actttatttc gaaggttggt ctgtcgttct ttataatgtt tacaagtgtc  14940
taggcctagg acattggcca tgaacatctg gatggtatag aaagtttgat ggaagctgat  15000
cttattcaat gaaatggcaa taatcctgtt tgtgagaaaa tcaagaaaca gaagagagtt  15060
tttaaatata tatttttgaa aataatagag gttgaaggaa agctctgtct tctcatattc  15120
agctataatg atggagattt tccaagctat ctcgcaatgg ttctttattg ctgcttctga  15180
tatactccct cttctcctgt tcctaagccc tgattaattt aacctagcta attctctcct  15240
ttctagtcct actgccaccc tatactacca caatagcaag ccactacccc catccaggtc  15300
atgaccctct gactgggagc tcccattgcc taacggcatg aacccaggcc tcctttatgt  15360
gacacacaag actttccaaa gcctcattct atcctttctt gccactctct gcctagcaat  15420
ctacccttca ccaacagcaa gcaggtgaga gttccctgca cacccagagc tatttctcct  15480
ctccatgcct ttgcttatgc tgtctcctca gcccagagtg ctatggcttc tcattgcccc  15540
tcatttgagg ttcatctcaa gtctcagctc aggtgtagcc tcctggaaac tgtcatcaat  15600
gtcctaaggt tgactacata ccctttcttc tctgaacttc cacaattctc tattgcatga  15660
ctctatcgtt gccctcacta tattcaactt ttaatgctat ctgatatggt ttggctctgt  15720
gtcctcaccc aaatctcatc ccgtattgca acccccgagt gtcaggggag agacctgttg  15780
ggaagtgatt ggatcatgag ggcggttccc cccatgctgt tctcatgata gtgagggagt  15840
tctcatgaga tttgatggtt taaaagtttg gcacttcctc ccttgctcgc tctctcctgc  15900
caccatgtaa gacatgcctt gcttcccctt tgccttctgt catgattata attttcctga  15960
ggcctcccta gccatgtgga actgtgagtc aatgaaacct cttttcttta taaattaccc  16020
agtctcaggt agttctttat agcagcgtga aaacgactaa cacattatct ctctcctcct  16080
cttctgtgag agctccttga gggcagagag cagactttat tgatattcag ggctttggca  16140
cttgttgaca catgtcccca caattcatat gttaaattct tagcctctag ggcctcaaag  16200
tgtgacctta tttgaaaaga gagtcgttgc agatacaatt agttaagatg agatcatgct  16260
agagtagggt aggcctctaa tccaataaaa ctgatgccct tataaaaagg agaaatttgg  16320
acacaaacaa cacacaggga gaatgccatg tgacatgaag gcagagatta gggtgacgct  16380
tctacaagcc atctttggaa caccaaagat ggccagcaac caccagaagc tagcaggtgg  16440
gcatgaaaca gattcttcct catggtccag agaagaaaag atgccttgat ctcagactcc  16500
taccccctgag aactatgaga caaatttctg ttgtaagcca tccatttgta gtactttttt  16560
acagaggccc cggctagtga atacagcact tagtagttcc tgaacatagt aggaattcaa  16620
ttaatgattg aatacatgaa taaacaaatg tcttctgact gttgtgaatt atcccttcag  16680
caatgataaa gatattttaa aactggcctt tctcaggcct aactttaatg tgggatagag  16740
atacagctaa gaatattata agattaacaa gcattttccc ctcacactgt ttaggttagg  16800
tggggaaggg atatgagtca ccatcattat tgtcctggtc atcaccactg ttattgaata  16860
ccatactatc tacttccatg aggaagtaga atggattgtc ccaaagatag ccctcataat  16920
attccttata tgaaaataaa taaacaacat gagacaagta tattagatct gtcttccagg  16980
```

-continued gaaaaatcca aagacctctt attctctatc tccagtctta ggactaaatg gtttgaacta 17040
gtgattccct gttgagggaa gagacagacc ctctcatatt gttttatact cagaaaagga 17100
aagaaaagtg aaattaaagg cagatagccc ggcgcctagg aaccagaccc gaaaccaggc 17160
ctgggcctgc ctgacctaag ctcggtagtt aaaattcgac ccctgaccta gcaactgttg 17220
ttatctatag attccagaca ttgtatggaa gggcattgta tggaaggaca ttgtgaaatc 17280
tctcgttctg ttctgtttca ctgtgaccac cggtgctcac agcccctgtc acgtaccccc 17340
tggcttactc aatcgatcac gaccctctca tgcggacccc cttagagttg tgagccctta 17400
aaagggacag aagttgagca tcagacgagc tcggattttg agacgctagc ctgccgattc 17460
tcccagctga ttaaagccac tcccttcact atctcggtgt ctgaggggtt ttgtctgcgg 17520
ctcatcctgc tacatttctt ggttccctga ccgggaagca aggtgattaa cagatggtcg 17580
aggcagctcc ttaggcggct ttagcctgcc ctgtggaaca tccctgctgg ggactccaac 17640
cagccagagt gacgcggatc ctgagagctc tcctgggtag gcatttgccc cggtgggaca 17700
cctcgccaga gcagtgtgtg gcaggccccc gtggaggatc aacagagtgg ctgaacaccg 17760
ggaaggaatt ggcacttgga gtccggacaa ctaaaacttg gtaagactag tctttggaac 17820
ttgcccactc catttgagtg gaagcatggc ctgatcaccc acggcgtgcc tttatcagca 17880
cttggttttg gttttgactt ggtttgaatt acttgacagg actggtcttg ggaacttgcc 17940
cactccattc ccactccatt tgagtggaag catggcctga tctgatcacc cacggtgtgc 18000
ctgttccggc actttggttt ttgtttttga cttgacttag attgcttgat actttggttt 18060
tggttttgac ctggcttgga tttctgaata ctctgatttt ggttttgatt ttggtttagt 18120
gtaaactgca aaagtgtgtg cgtgcccttt ttacccgttc tttgttttgt ggtgtgcatg 18180
tggtgtgaga gtggtgtttt gtctcgaaga aacatgggtc aggcacaaat aagcccaccc 18240
tactagaaac tatgttgaaa aatttcaaga aaggatttaa gggagattac ggtgttacta 18300
tgacactaga aaaacttaga actttgtgta aaatagactg gccaacatta gaggtgggtt 18360
ggccatcaga aggaagccta gacaggtccc ttgtttcaaa tgtatggcac aaggtaacct 18420
gtaagccaag gcacacagac cagtttctgt acgtagacaa ttacagctgg ttttagaccc 18480
ccttcgcccc cacagtagtt aagagaggca gaaagagagg aagaaacaga ggcaaaagga 18540
aagtcaaaga gagagagagg gagagagaga gacagaaagt caaagagaga aagaaaaata 18600
gagagaaata tccaagtagt taagaaaaaa atagtgtacc ctattccctt taaaagccaa 18660
ggtaaattta aaacctaaaa ttgataatta aaggtattct ccgtaaccct gtaacactct 18720
aataccactt tgttgttagt gtaaacaagg gcgtatcccg aaagcactga ggccttccta 18780
tcaaaaatcc ttaacccagt aacccacgga tggcccagat gcattcaatc tgtagcagca 18840
gctgctttgc taacaggaaa aaaaaaaaaa aagagctgtg ggaaggcaaa atttatgtaa 18900
aaagagtgtt atatggtaaa ttcttgtctt gaaataaatt aactgttgtt taaagaaaga 18960
aatatttgta ataagtcaga aagttgagac atgtcaaaga attatctgcg aaagtcatag 19020
aaaacgatgt tataaaaaat ttatgcaaaa aatattgtat aatttgaaag taataaggcc 19080
tcctgagtac tattgaagaa acagtttatg tgcaaggtgc ataagaaaag taaaatatac 19140
ttttggtaaa aagattagaa ggaggcataa gaatgtggat ttttacctac attaaaaggt 19200
taaaaaaatt attgttttga aagtttaagc aagttttaaa atgttaattg taaaaaaaaa 19260
ttctgtgtgt aaactaatta gctaaagata aaaaggtatc atccagtttt tctgtgaact 19320
ggacattaaa gtaaaaatgc aacaggtttt tcttgaagca ccaacctgct ctttaacaaa 19380

-continued

```
aattataaaa ggttaaaaag agtctgtaaa aacttacctt atggtcaaac atgaaaaatt  19440
ggataaatat gtctatgagg ttttattaaa attaagttta acattaataa cacactaata  19500
taaaggtaaa atttagctta tctggtataa aaatcataca agaagtatta ttaaatataa  19560
aatggtgttt agctttcttt ggtctaaaaa ctaataaaaa taggtcctaa aggaaacatt  19620
cattttacta gaggatcata gaagttaaag acttaaaaca aactttggca attaagacag  19680
cataccaaga tgcaaatgcc tggttgaaat ggatcaaata ttccatctgc acattaaaca  19740
aaagcagttg ttatgcttgt gcacatggca ggccagaggc cctcattgtc cccttccac  19800
taaagtggtc ctccagtcca ccaggcgtgg gctgcatggt agctcttttc caggattcta  19860
cagcctggag taataagtca tgccaaactc tctctgctat ccctgtgggt cagcccccga  19920
gggccatcca gcctccgtct cccaacacta agttcacttc atgtctctca ccacagagag  19980
gaaacttagg attccttgga gacctgaagt gatgcaatga gcttaagaat tttcaagagc  20040
ttatcaatca gtcagccctt gttcatcccc aagcggatgt gtggtggtat tgtggtggac  20100
ctttactggg cactctgccg aataactgga gtggcactta tactttagtc cagttggcta  20160
tccctttcac cctggcattt catcaacaag agggaggaaa aataagacat cgtaaagcga  20220
gagaagcccc cttataggtc tttcgactct cacgtccatt tagacgcaat tggagtccca  20280
cgaggaatac cagatcaatt taaagcttga aatcaaatag ctacaaaatt taagtcaata  20340
ttttagtgag tgatgttaat aaaaatgtaa attagataaa ttatatctat tacaaacaac  20400
agcaacaagc ttttcatgag ttgaaagaaa aactcaggtc ggccccagcc ctggggctac  20460
ctgacctgac gaaagtgcac actctatgtg ccaaaaaaaa aaaaaaaaaa aaagggccat  20520
ctataccaat tctaagttaa tttagactaa acaaggtctt actcatagca aaggataatt  20580
gaaatcccaa acttacaagg ttttcaacaa aagtaaagtt tgctaaaagt taacagtgta  20640
acatgtatta tagtaacttc taatcttgtg gccttagaca gtctagtcca cagatataaa  20700
gaaagttcac ttaaaaaaaa aaaaaaaaga atggttatct tcaaaaaaaa aaaatggcag  20760
ttggagtttt aacccagact gtagggctct ggccaaggcc agtggcctat ctctcaaaac  20820
aactagatgg ggtttccaaa ggctggcccc catatctaag ggccctggca gcaacggccc  20880
tgttagcaca agaagcagat aagctaactc ttaggcaaaa cctaaacata aagtcccccc  20940
catgctgtgg tgactttaat cagtaccaaa ggacatcatt agctaatgaa tgctagacta  21000
actagatacc aaagcttgct ctgtgaaaat ccccacataa ccattgaagt ttgcaacacc  21060
ctaaaccccg ccaccttgct cctggtatca gagagcccag ttaaacataa ctgtgtagaa  21120
gtgttggact cagtttattc tagtgggccc aacctccaaa accatcctta aacatcagta  21180
aactgggagc tgtacgtgga tgggagcagc ttcaccaacc tctgcaaagt gactcagaaa  21240
aagccctgct ccagtcacac ccggaagctg actggtccac gcacggccga agcatgagaa  21300
aactcatcac gggactcatt ttccttaaaa tttggacttg tacagtaagg acttcaactg  21360
accttcctca gactgagaac tgttcccagt atatacatca agtcactgag gtaggacaaa  21420
agattgctac agtcctatta tttcatggtt attataagtg tacgaggact ctaaaagaaa  21480
cttgtttgta taatgctatt ctatccaagg tatgtagcct aggaaataac caacctgatg  21540
tgtgttatga cccattttaa gcctccaatg atcacagttt tttaaaataa attaaggact  21600
ggtccttttc taggtgacac aagtaaagta atagctaaga cagaagaaag agggatcccc  21660
aagcatgtaa cactaaaatt taatgcttgt gccactatca atagcaatcg gcatagaata  21720
```

-continued

```
agatgcggtt ctttaaactg aaaaaaaaaa aagttacaca gcaggaaata agtatatctg  21780
ccacgaatta agctcatgtg caaatgtgtg taattactgg tcttgtgtca tctaggctac  21840
ttagaaaaag gatgaaaaag accctgttta gctccaaaaa ggagaaggca gcccctcctg  21900
tacgagtgga agctgcaacc ccttgaaatt agtaattaca aatcccttaa acccaaggta  21960
gaaaaaaaga agtacacgta tctctgggcg tcgataaaaa aggactagat cctagagtaa  22020
ataccttagt aaaagaggag gttcgtaaac tctctccgga accagtattt cagactttct  22080
atgattaact aaatgtgcca gtaccagaga ctccaggaaa aaccagaaat ttgtttttgc  22140
aattagccga gcatgtagcc cagtctctaa atgtcacctc atgttacgtt tgtggagaaa  22200
ctgtaataag agatcaatgg cataagaagc ccgagaatta gtgcctacag acccagttcc  22260
tgatgaattc ccggcccaaa agaatcaccc tgatcatttc taggttctaa aagtctcaat  22320
tattagacaa tattgcatag ctgaaaaaag gaaagaattc actcatcctg taggatgact  22380
tagttgccta ggacaaaaac tgtataatgg taccacaaaa acagttacat ggtggagttc  22440
aaaccacaca gataaaaatc cattcagtaa atttccaaag ttgcagaccg tttaagccca  22500
cccagaattc caccgggact agacagcccc ccactaggct atactggata cgtggacata  22560
gaacctacgc taagctgcct gaccagtgga caggtagttg tgttattggc actattaaac  22620
catctttctt cctactgccc atacaaatag gcgaactcct gggcttccct gtctatgctt  22680
tccgcgaaaa gcgaaacata gccatagata attaaaaaga tgatgaatga ccacctaaaa  22740
aattatacaa tactataggc ctgccactta gacacaagat ggctcatggg tataccagac  22800
ccccatttac atgctcaact gaatcatacg gttgcaagct gttttagaaa tcatcactaa  22860
taaaaccagt caagccttga ctattctggc ccggcaagaa actcagataa gaaatgctat  22920
ctatcaaaat agattggctc tcgactactt ctagcagctg aaagagaggt ctataaaaat  22980
ttaaccttac taattactgt ctacacatag ataatcaaag gcaagtagtt aaagacgtag  23040
ttaaagacat agttaaaaac atgacaaaac tggcacatat gcccgtacga gtgtagcacg  23100
gattcgaccc tgaagccatg tttagaaggt ggttcccagc actaggagga tttaaaactc  23160
ttatatagga gttataatag taatagaaac ctgcttactg ctcccttgct tgctgcctgt  23220
acttcttcaa atgataaaaa gcttcattgc taccttagtt caccaaaatg cctcaacaca  23280
agtgtactat atgaatcact atcaatctat tgcacaagaa ggcataagtg gcaaaaataa  23340
gagtgagaac tcccactaat aaaaagtgag agtctcaaac gggggaaatg agggaagaga  23400
gagaccctct catattgttt tatattgttt tatactcaga aaaggacaga gaagcgaaac  23460
taaaggcagg tagcccggcg cctaagaacc agacccgaaa ccaggcctgg gcctgcctga  23520
cctaagcctg gtagttaaaa ttcgacccct gacctagcaa ctgttgttat ctatagattc  23580
cacacattgt atggaaggac attgtgaaat ctctcgttct gttctgtttc actgtgacca  23640
ccagtgctca cagcccctgt cacgtacccc ctggcttact caatcgatca cgaccctctc  23700
atgcagaccc ccttagagtt gtgagccctt aaaagggcag aagttgagca ccttgacgag  23760
ctcggatttt gagacgctag cctgccgatt ctcccagctg attaaagcca ctcccttcac  23820
tatctcggtg tctgaggggt tttgtctgca gctggtcctg ctacactgtc agctagctgg  23880
ataaacttaa gtgtttgttc tgcagaccaa atctagcctt gatctcaaca tctatgccaa  23940
ttgttctcga tctgtctgaa tattgggatt acttaggaaa ctttaaataa ccaagccctt  24000
cctggcatta aatcaggata tccatgggtc agcccagttt ctctttttct tagctctatg  24060
tgtttattgt tagttatcta tttagcacaa gggtcatggc atccaataat tgtaggttat  24120
```

-continued agataattta cataaggcaa gttataggaa ggagaggagc atcaaaataa atcaggattc 24180
tatgggttca cacagaacaa tcattccaag acactcacct gtgattctta ccttgggcca 24240
ggtactcaat tttcataagt atctggcttt ttccatatcc tggtaatccc tcatacatta 24300
agacttggct gctgttagat atcaaaaatt tcttcatagt atacatgaag tagttgatct 24360
ctttattacg tcctgttatt tttagtttta aaaaagagca aactcaatca acgtaaaata 24420
gtctagagat ataaaaagtc acatagaaac cctccttcta aaaatatcct tgggccaggc 24480
gctgtggctc actcctgtaa tcccagcact ttgggaggcc gaggtgggcg gatctgctga 24540
ggtcaggagt tcgtgaccag cctggccaac atgatgaaac cctgcctcta ctgaaaatac 24600
aaaaaaaaaa aaaaaaaaaa attagccaga cttggtggcg ggtgcctgta gtcccagcta 24660
ctcaggaggc tgaggtaaga gaattgcttg aacccaggag gcggaggttg cagcgagccg 24720
ggatcctgcc attgcactcc agcctgggcg acaagcaaaa ctccatctaa aaaaaaaaaa 24780
aaaaacttgg aatttccatg gcattgttca cagactttct tcaagcctta tgcactttca 24840
aaattgttta aatcttcctg ggagcttttt agctaaccat gtggttttgc agtttcattt 24900
gattagaagc tgtgagagaa agtattctta taatcctcat tataatgttt aattatagtg 24960
tagaaaactg agatttgctt agattacaca accaggaatt aagccaaggc tatctaaccc 25020
taaagcttgt tttttttgt tttttgtttt ttgtttttat tcaacacact agaagtaata 25080
tgtagactat tacattagga aataaattta ttaaagttag ttttcctaca ttaaacaatt 25140
atggataaaa tatttttatt tctgattctg tgataaagga aatttgccct ctgtaaatga 25200
agattatact taattcaggg ctacaaaaag cattaccagg gataaaattc aatttgcctt 25260
cagaaatcat gtacagatta tttctatcat aagagcaact taaattctta gtgaaaatag 25320
attataggtt ttttctgatt ataaaactaa catatgcttg ctgtagaaaa tatggaaaac 25380
ttggaaaaga aaaaaataaa aatcaccttg ggttacaacc cttatttttc ttgtgtgttt 25440
ttaaatactg taacagccct gggtgaaatc tgaaaccctg ctgtaaggag ctgtaagaat 25500
tgtaatttct aagcagtgag caatttctgt caaaaaagtt ggagactcat tgagagctaa 25560
ctattccttc tgtgctgggc agatgaatgt ggaggcccat tttgttattc actgatagaa 25620
caaataaata tccaggtatt atctaatgtc tttgttgaag gaccattaat tcaagtgtag 25680
acatttaata aaaagaagct aagtgctttg cttggtaata tacatttctg agtatggctt 25740
agtgagaact acttagcaga ctgtattgct tcttttgggt gaaatattcc ctttctgaaa 25800
atgcatttga acctcaattt cgtgagatgt tttgtgtttt tctttggcct gaatgaagct 25860
cacataggaa cttagaagat gaggcttcaa aggctgcata gctgcacacc aacatggcac 25920
atgtatacat atgtaacaaa cctgcacgtt gtgcattgtg taccctagaa cttaaagtat 25980
aataataaaa aataaataaa taaaaaataa taaagtttcc aggctgggag cggtggctca 26040
cgcctgtaat cccagcactt tgggaggccg aggcgggtgg atcccctgag gtcaggagtt 26100
cgagaccagc ctcaacatgg agaaaccccg tctctattaa aaatacaaaa ttagccgggc 26160
gtggtggtgc atgcctgtaa tcccagctac tcaggaggct gaggcaggag aattgcttga 26220
acctgggagg cggaggttac agtaagccga gatggcgcca ttgcactcca gcctgggcaa 26280
caagagcaaa actccatctc aaaaaaaata aagtttccta aggaagctta aaaaaaaaaa 26340
aagcctgcat agctgactct tccagctccc tgtgttctat tcatacagaa cacctactgg 26400
tagaacctta tggagtatct ttagctggat tctaaaatga gattgtctcc ttaacttgaa 26460

-continued atgcatgcac cttgtttcta tctaagcaaa gcctcaatat cggggactgt tgtatgcagt 26520
ttttacccta aaaagccact atttatttat tatagttttg ttgtcaacca tgctgttgca 26580
atttcattta tagcagccct tgtaaaagaa gggcatttcc catgctgcta gcctctgaca 26640
atctgtgttt ggttatagct tgaaggaaag gtatgtggac ctgatcttta tgtcatactg 26700
gtggaatcag tgcaaaaggg caactagatc agactgagaa atatacacat aggctgcacg 26760
cagtggctca cgtctgtaat cccagcactt tgggaggcca aggcgggcag atcacgagat 26820
caggagttca agaccagcct ggccaatatg gtgaaacccc gtctctacta aaaatacaaa 26880
aattagctgg gtgtggtggt gtgcacctgt aatcccagct acttgggaag ctgaggcaga 26940
agaatcgctt gaacccggga cgcagaggtt gtagtgagct gagatcgcgc cactgcactc 27000
cagcctgggc gacagagtga gactctgtct caaaagaaaa aaaaaagaaa tatccacata 27060
atgtgttcta atgtgactgt catgttgggt ctgcaatctt gtagaaagaa ggttaggatt 27120
ctgttgctgt cagttagtaa aataagtata tcctaggatg aaaagtaagg cctctgagga 27180
gggtgagagt gggtattcct tctctctagc ttcaggagtt ttggaatctg gacttaaatg 27240
aagtgattgg cttgaagacc ctgaaaacta cctgaaagca gtgaaagtga ggcatttctg 27300
ctggcccaag tgtttttttg cagttctgga actgttgccc tccttcaggc tctgctgaca 27360
ccaagattgt ggcccaatat ttctccaaag tgtgagacag agcctcctct taattgcctt 27420
gacacagtta ggaccaagat ttaacttatg ataagacttt tggggatgtt cgtgtctgac 27480
agaaggaaat tacaagtgct actagaagtg gctgccttca gaatccacag gtcaatcttc 27540
tttgggtctc ttctcttata ggtatatccc ttcctcattt taggtctact cccctgtcta 27600
atctcgagtt atctttctta caataaggtc cctatcacca ggaatcacaa aaatatcaat 27660
tccaaatgga ttgtagactt aaatataaaa ggtaaaaaca aaatttctga aaaaaatgct 27720
agaaaaatat ctccatgatt tttgggtaag gaaaggtatc tcaaatagta tacagaagca 27780
ctaactataa aagacaggta aatttgatta cattaaagtt aagaattctg tttattaaat 27840
gcataattga gagtaaaaag gcaaacacag agtgggaaaa gtgatataca gtagaaacaa 27900
atgacaaagg acccatctct agaatgtgta aataattcca aaagataatc aaaatataac 27960
ccagttgaaa aataggtgaa aaattgtaca ggtactttaa aaaaatgtct gggctgggca 28020
cagtggctca cgcctgtaat cccagcactt tgggaggctg gggcaagtgg atcacttgaa 28080
gttaggagat caagaccagt ctggccaaca tggtgaaacc ctgcctccac taaaatataa 28140
aaattagctg ggcatggtgg cggacacctg taatcccagc tactcaggag gctgagtcct 28200
gagaatcact tgaacccagg aggtagaggt tgtagtgagc caagattgct cctttgtact 28260
ccagcctggg caacagagtg agactctgtc tcaaaataaa taaataaata aataaatcca 28320
aatggccaat aaacttatga agaaggagct caaccacatc agggaaatac aaatggaaac 28380
cataataaga taccactata cacccaacag aattattgaa aggataaaga ttgataaaac 28440
taagttgttg ccaaagatga agaacaactg gaactctctt aacattctca gtcagaatat 28500
aaataaatac aaccattttg gaaaactatt tggcaccctt tgtcccaaca atttcagtcc 28560
tacgttttac tcctaccttg tactcaacag aaatgcatac atgcattcac caaaagactt 28620
gtgtaagaat gtttatggca atattattca taagaaccaa aaactggaaa taacccaaat 28680
gttgcacagc aacagaatgg gtaaattgtt gtatatttat aaaaatggaa tactacatag 28740
taatgacata gaataaatta cagctacacc caacaatatg gatgaattat ataacatacc 28800
attgagtaag agaaagtata tataagccgt atataattat acaatgtatg attccatctg 28860

-continued

```
tatcaatttt ttaaacaggc ataagtaatc gagggtgtta gaagactttg gggaaaggaa  28920
gaaggaaaga gtaatcctgg tgtattgcta tttttctatt tcttaacctg gatgatgatt  28980
atattttcat tttgtgataa ttcattaagc tgcacagtta tcattgatgt acttttctgc  29040
atgttttgtt ttagttcaat aaagaagttt aaaatcaagg cctactacct acccagcaaa  29100
gggtaatcct cctttctgtt gcagatgagg cacgccatac caaacatgct gaagagaaga  29160
acaaaagaac agatgctaga ttcaaaacag ggacatattg agagcaagag tgattagttc  29220
ttagttccca gaaagtttcc ttctcaattg ctaacaagag tctatcccct gactcacggg  29280
tcgcaaacgc caaaagaagg agaaacgaga aggtctgact tggtagtgga gaatccaaag  29340
aactcaggta gcatctgttt ccatagcatc tggcacattg ttcaataaat gctgttgagt  29400
ctgcactggt agagaaaccc ctttctgggg agatcagaca cctgatatac gacccagtag  29460
atttcaatgt ggtgcagagt cacacatcct gcaaagattc caccaattgc tcaaacaata  29520
atagcgcgcc ttttattgga gcacatgcta tgtgtctggc gcagttccaa gtgctttaca  29580
tgcatcattt tctttaatcc tgacaaaaac actgttaaga agtactactt ggctgggcgc  29640
agtgactcac gcctgtaatc ccagcccttt gggaggccga ggtgggcaga tcacgaggtc  29700
aggagatcga gaccatcctg gctaacacgg tgaaaccccg tctctaccaa aaatacaaaa  29760
agaaattagc caggcatggt ggcggttgcc tgtagtccca gctactcagg gggctgaggc  29820
aggagaatgg tgtgaacccg ggaggggag cttgcagtga gccgagatcg caccactgca  29880
ctccagcgtg ggcagcagag ccagactcca tctcaaaaag aaaaaaaagg actactggcc  29940
aggcacggtg gctcatgctt gtaatcccag cattttggga ggccgaggca ggtggatcat  30000
ctgaggtcag gagtttgaga ccagcctgac caacatggtg aaaacctgtc tctactaaaa  30060
atacaaaaat tagctgggcg tggtggcttg cgcctgccat cccagctact ctggaggctg  30120
aggcaggaga atcgcttgaa cccaagagac agaggttgca gtgagccaag atcacgccat  30180
tgcattccat cctgggcaac aaaagcaaag ctccatctca aaaaaaaaaa aaaaaaagta  30240
ctactcttat gttcattttg ccagtgagga aattcaggca caaagagttt aattgcccaa  30300
gaccccatag caggtggtaa cacaggatac tgacagtatc caaacatagg ccagggtgca  30360
tatgtttgct cactccataa cactatctct tgaagaagcc ttttagtcaa aatggattat  30420
gcccttctct gaactacaat actactttgt tatgcctctc ttatagcata tatcaaaggt  30480
tcccatgtaa catacagcta agtttgtgta tgttggtctt ccccacttga ttgtgagttt  30540
tctgggcagg aactaggccc tgttcatact gtgtgtgtat ttctccactt ttatctgcag  30600
aggtggtaca gaaaaatcat gaagagtaca ggctttggga tcagatagtc ctgggtttgc  30660
atagtaaact gattgcatta atggccccag tacctgtatc tgtgcccttt gctgtgtaac  30720
ttggcagagt cctctcattc tggactcagc cttgtgaatg cttttgtcaa tggactatct  30780
gcaaacataa gacataggaa gaggcttgaa aaatgctttt gcattgggcc tgctctcttg  30840
ctcctccagt attgccagga caaacatgct ggatggaaga tgagacacat agagccagat  30900
tgccctagtt atcccaactg aggccgccag gttggccaac agtctgttga accccaggca  30960
cgtgaataag ccaagacaag atcaaccaaa tccagccaag atcaattgaa ccccacattt  31020
gtgagaaaaa taaatgttta tttttgcaca ccactgaagt tttgtgattg cccgtaaggt  31080
cacattattg tgactgaatc ttgactccat tgctcactat agatatggcc atagacaagt  31140
catttaacat ctctgagcct cagtttttga atttataaaa tggaaattat aatagtttct  31200
```

-continued

```
atctcgtatg gtcaatatta agactggatt atatattttg aggtaaagta cctgatgttt  31260
aataagtact cactaaaaat tattattcat tcatgtattc aaactgcact ttattgatgg  31320
cctatgtatg ccaagcacag tgctaagcct caggaatact gaagggaata ataaagacac  31380
cttgacccaa ctgcagccct ggttctgtta tctgactctt gaagacctcg attccagctt  31440
gctaatctaa tgaataacaa ctttctgctc tctgtgccat tcatttattc atcattattg  31500
aggacctact gtataccaag cactggggat ataagaataa agaaataatt agtatcttca  31560
aagagttcac agtgtaacaa gtgaaaactg taggaagtga ataattgtga tatagggcaa  31620
ggagtgttct aatagaagca tatgctatag gaggaaaaaa ggaagaggaa gaaggaagac  31680
aaagggggaa agagcttaac tgtctagctg ggatggggaa ttcatagagg aatgtctatg  31740
aatccctcga gctgggtttc aaaaattgac tgcggttttc ccaatagacc aggattaggt  31800
gggtgctgat gaggacaatc tacttaaaca acccagagga gggggaacag gaggagatga  31860
ggttggaaag gcaggtggta ccttgtatgt cactgcaaag attttgaaca tcaccatgaa  31920
aatgactgaa agccattgaa ggattttaag cttcaaagtg acacccataa atctatgctg  31980
agcttttggg gaatgtattt cactaaagac ttagaggaga aataatatct tatactcttt  32040
taaccctaac aatgcctcgg catacagttg acataattag taaataatat taaatggttg  32100
gtgattgggc ccatttgggt gcaaatagat actcaaatga gaggattttt tgtttggttt  32160
gtacaacctt tgaagaatta ccctcatatt ctcagatctg aggagagaat gggattttcc  32220
accatgccat agtgtcagtc agatggagga aagattaagg attttgaagt ctgggccttg  32280
gtctggggaa agcatagatt tcaacttttt gaactggctc caaatcttaa atgggtgact  32340
gctttgctat cataattctc ccgcttcttt actaaaatat acttcaaaat taatgctcca  32400
cactcacact ttctcagtac ggccccaata ctgatacaat ggtccagaat ctgcaacacc  32460
tttcataact ttctttggaa gctctttaaa aaagtacgct ggtaggttgc tcccattgta  32520
ggtgacagag tcgcaggtca caattcctgg gtagtacatc atcatcctgg cagctaagtt  32580
gactttttga ccaatgacta tagcaagaaa gagaaagtca aagatcaggg aaataacagg  32640
cattgaactg aatgtaatct gaaacattgt ccccaaatag catttttacc ctttactccc  32700
tttgctgttc atgagtgaca cagaagccta gtctcaagac ccatattcag ccaatggcta  32760
ttcacaaaat gtgcagggag ttagttagcc attagcaaag tttctgcctc acttgggagg  32820
tcaagagaat gacctgctca gggatggaag gggcttgagt atggagcagg ctctgtaagt  32880
gggatggcca cagcactgaa ggctctcaga gaaggtgtca gttggtcttc tgccacaagg  32940
tggacaagca catgcttggg cctggggtac tgatctccat atgagacata aaattgtgtc  33000
tgcatgctcc tatgaataaa ccttcatttg gcgatttctc gatttagtaa atgggctaga  33060
agaggcgtgc atggaggatt gaagcacagg ctctgaaggc agactgtgca gggttgaaca  33120
ccagctctac ccctaactat gtgcaaacta cttgggacaa ttactttaaa taactcctca  33180
tgcctccatt ctctaaccta taaaataggg atgataatag taactctctg agagggtggt  33240
ttatgaagat taattagtta atacacgttt atcactttca acagcagctg gctgcttgta  33300
agccttcaat taatattact acaaatgagg tagcaaatgt gtcactttaa cataaacttg  33360
aatacttctg aacaaggtac tctttttgaa aactatttat tgtggagaaa tttgaccata  33420
aaataaaata taatgaattt ccatataccc atcaccccat cccaacaagc cattagccca  33480
tggctaatcc tgccccatcc tcacccccat acactcccca ccctgtgtac ttttgaagaa  33540
catctcagac attgtatcat ttcagacata actatcgtgg tattttacat atattcagta  33600
```

-continued

```
ttttagatgc attattgctg aaaatcttaa accctgatag gatggaaaag ggaagtaata  33660
gagttgtgaa atctggagat aagatttact tattactact ctcttttgag agtgtcatta  33720
tttttcagta atatcaacat tcataatttt taaggagttc tagcttattc caggaattaa  33780
gagaagtaac tatttaatgt taacaggaaa gtattacagg agcccctcat tccatcaaca  33840
tatagcctcc cactgctccc ctctcatgac tacatatttc tctactcata catagcccca  33900
gaaatgcaca ctctgcaagc attgagggct ccatggcttg gctccatctg gaagactcta  33960
aagtttctga gggcagggct catgtctcac tcatttttgt gcttcctccc gcaaagccca  34020
gtggcaaggt gctgtgtttg cagaaagaaa gctggagatg agctgaccca gcacacctgt  34080
gtactcgtgt ctcacagtgt gtccaacgat cccacagaag acaatcccac tggcaacacc  34140
gatggataca gttctggtgc aggggagaca agatttgtgg ggaaagaaat aaagataatg  34200
agcgtagaga aagtgggaag ggtgggaaat aatgtctggg ttgggaaagg gtgggaaagg  34260
attttctcta cccgttggaa ttagtttatg gcatttctac atggcccgga gatgcgaagg  34320
aggaacaaca gtttgagaca caggactaag ttcttaatta attcttcttt ctttcctgtt  34380
ccctgcatgc cctccctact tatgcctcaa aagggtcagg gaccgctggg tgggaccagg  34440
gtcaatactc actggatttt gtggacttga gagcagaagt caaatatatc catagcacat  34500
tccagagcat gagtgagctc gtcaggtacc ttttccccag ggaagccaaa gacacagagg  34560
aaagagcagc cctgtgaggg agagagacag caaccacagc tgatggacag tgtgctttaa  34620
actggactgg ccagaaggct caacagagag ccggcggcaa tttttggctt ctgaatcaga  34680
ttttatcatg atttctctca cagtatttta tttttagtac acttcaaaca cttctactgc  34740
atcatcaaca ggagggcttg agccttgaga agggcttgtt ttgctccaga tatagtgaat  34800
agggctgagc tatctgtgtg catgcttcgg cctactctct cctgtggcca aggtccatgc  34860
tgcaaagtgc tcagtttaag tctatgaagc agcagcacag agcagtggaa aaggcaccag  34920
ctctggaatc agaaagtctc tgtcctcaag ccacttctca agtgtggaaa cttagataag  34980
tctattacaa tctaggaact tccgtttatc tctctgaaaa tggatatact gtagacctgc  35040
tgagatgttt ttggctacta aaagaattaa tgtgttatat atattcaaaa agtcatccta  35100
aactataaag tactttgcag atactgttat tcttagggat aaaggcttag gctgtaagta  35160
ggttttctta tcataaagct aactgttcca tgcaatgatt caactctaaa acttggcatt  35220
tgtagtatta gtcacttaaa aaatgacctc agtcaggtgc tgttgtctgt aagaaaaggg  35280
cattgtgaat aaagggtgat gggttgaaat tttgagtttt tgacatgtta catcctgata  35340
aaatgcaaag aacactaaaa tacctcaatt tcttcaaccc tctccaaaag aatttgatca  35400
actgttagat cttaaaaagg actgggatct gccttgacat gaagggggaa acactgcttc  35460
taggtacgtg caaagagggc aaccccttg ggggaagcag ggagcttttg cctgcaaatt  35520
tatgtagcgg cctggcaaga gcttttgatt ccccctagca atggaatgac agctctcatt  35580
tattgcacac tgactctaag ataggcatta caccaagtgc ctcacacata ttacattatt  35640
taaaactttc cacaatcatt tgagacaaat actatcccca ttcaaagagg aataaaccaa  35700
ggctcagaga agttcaatga cttgctaagt ctcacagctg ggaatctttg gagccatgtc  35760
tgcaagacac gaaagactgt tctcttagat tctacactct tttcttatga tacccatggg  35820
tcagtattga agaaggtact ggagacacca ggctggaagt aatccctttc cagaactccc  35880
atagcacaga gttagttcgt ctcatataga atgcatgctt cctgcctggt tgtgtcaata  35940
```

-continued

```
tatgtgttac tcatctctgc tgcccagccc tagcttttcg tcttctatga aatgctcagt  36000
aaatgcttgt tgaattagtg agtgagtgga tgtggggcag taattaagtg ctctgctttt  36060
aatacacaaa aggaattgag atgggaaatc aattctcaca tatgcatctg tggtcatttg  36120
ttcatcacat cacttttctc tgaattgatt aagaacagag tgaagaccag gtgcagtggc  36180
tcatgcctgt aatcccagca ctttgggagg ccgaggcagg tggatcactt gaggtcagga  36240
attcgagacc cacctggcca acatggcgaa acctcatctc tactaaaaat acaaaaatta  36300
gccaggtgtg gtggcgcatg cctgtaatcc cagctactca ggaggctgag tcaagagaat  36360
cgcttgaacc cgggaggcgg aggtttcagt gagccgagat catgccactg cattccagcc  36420
tgggcaatag agcaagattc cgtctcaaaa aaaaaaaaaa aaaaaagaac agagcgaaaa  36480
cacctgggag ccagaggcag tcccctccct gccatggatg aaaataaaag gggaactgga  36540
ggtgttgaca tggcaagtgg gctttcttgg aaacaagctt ctggggtaag atggttacta  36600
aagactcctg acctgaaacc cctgggtaat acatcatgca ctgagctgga gacttatgtg  36660
tagtgagagg tagcccagcg tagtgagagg tagcccagca tagtgagctc agacggggat  36720
ggcagactgc ctgggtttga atcccagcct ccccccttact agcttgatga tcataagcaa  36780
aacgtaatct cgccttgtcc tggtatccta atctgtgttt cagcatcctc atctatataa  36840
tgaggataat gacaagagca acctactgct cagagtggtc atgaggatga aatgagtcaa  36900
tagagatcag gtcctgagaa cagtgcctgg cacatagtaa gtgccatatc caccatagaa  36960
gttataatta taaacaaaga ctggccttct aggttaaatt tctttttttg tttagttgag  37020
acggagtctc acgctatagc ccaggctgga gcgcagtggt gcgatctcgg ctcactgcaa  37080
cctccgcctc tcaggttcaa gccattgtcc tgcctcagcc tcctgagtag ctgagattac  37140
aggcacgtgc caccgcaccc agctaatttt tgcattttta gtagagacag ggtttcacta  37200
tgttggccag tctggtcttg aactcctgac ctcaagtgat ccgcccacct ctgcctccca  37260
aagagctggg attacaggcg tgagccacca cgcccagcct ctaggttaaa tttcctgtgt  37320
ctattctcac caatgtgctt gtccatgaat gctaacctaa aactattggt aggttcccat  37380
cccatagttc acacttacct tgtcaaacat gaagacttta ttgatttggc cttggaagat  37440
cttcaggaca gaagtgatgt gcatataggc atcctggatg gctgggccta tctcttctgc  37500
tttgtcttgg tcttcaaaca tcaggttcac aaacacaatc gtcactgggc gaagctcaga  37560
taaatagccc tgaagctgtt tgttatcaat ctgcaaagta gagagcagct ttctgtaggt  37620
gtccttggca gtggatccct cccccaacac cgccccccacc tcatacccga aatcatctag  37680
ggaatgtcta cctcagaatg ggtgaggtac aacatgacag agccagcatg cctgaagtgg  37740
agcagatgga aatataatca aaatccctct cttccagtgg ggacttatgc atgtgctaat  37800
ttttggccag caaccactcc attaccccaa ctgctggctt cctcatgcca atatgagcca  37860
ttgcaataag ggaaataact actgttcttt ttggctctcc tatttttaaa aaaatttaaa  37920
attttttaat ttttgtaggt ctatagtaga tgtatatatt tttgtgttac atgagatatt  37980
ttgatacagg catgcaatgc gtaataatca catcagggta aatggattat tcatcccctc  38040
aagcatttat cctttgtgtt acaaacaatc caattatact cttttagtta tttttaaaat  38100
gtatggttgt attagtccgt tctcccactg ttataaagaa ctacctgata ctgggtaatt  38160
tacaaggaaa agaggtttaa ttgactcaca gttccatggg ctgtacagga agcatggctg  38220
gggaggactc aaacttataa tatggcagaa gacgaaggag aagcaggcac ttcttatatg  38280
gccagaggag agcaggggga gtgctacaca cttttaaaca atcagatccc atgagaactc  38340
```

-continued

```
attcactatc acgagaacag caagggtata atccacccct atgatccaat cacctcctac  38400
cagtcccctc caccaacatt ggggattata attcaacatg agatttggga ggggatacaa  38460
atccaaacca tatcaatgat taaattattt tttactatag ttaccctgtt gtactagcaa  38520
atactaggtc tttctcattc tttctctttt tttgtactca ttgaccaccc ccaattcctc  38580
ctcatccccc actacccttc ccagcctttg gtaaccatcc ttatattctc tacccccatg  38640
agttcaatca ttttaatttt tttttttttt tttttttgag acggagtctc gctctgttgc  38700
tcaggctgga gtgcagtggc gcgatctcgg ctcactgcaa cctctgcctc ctgggttcaa  38760
gcgattctcc tgcctcagct tccagagtag ctgggattgc aggcatgcac caccatgcct  38820
ggctaatttt tgtattttta gtagagacgg ggtttcactg tgttagtcag actggtctcg  38880
aactcctgac ctcatgatct gcctgccttg gcctcccaaa gtgctgggat tacaggcatg  38940
agccaccatg cccagcccaa tagttttaat ttttagctcc cacaaataag tgagaacatg  39000
tggtttctct ttctatacct ggtttatttc acttaatata atgacctcca cttccatcca  39060
cgttgttgca aatgacagat ctcatttttt ttatggctga atagtacttc gttgtgtata  39120
tgtaccacat tttctttatc catttctctg ttgatggaca cttaagctgc ttccaagtct  39180
tgactactgt gaatagcact gcagtaaaca tgggagtgta ggtatctctt caatatattg  39240
atttcttttc ttttgagtat gtatctagga gtagaatttc tagattgtat ggtagctcta  39300
tttttagctt tttgaggaac tttcaaactg ttctccaagg tggctgtgct aatttacttt  39360
ctcattaaca gtgtacaagg attccctttt ttccacatcc tgtccagcgt ttgttattgc  39420
ctgtcttttg gataaaagtc attttaactg gggtaagatg ataatcttat tgtagttttg  39480
attttcattt atctgatgat tggtgatgtt gtgcaccttt tcacatattt ttcacatact  39540
tgtttgccat ttgtatgtct tcctttgaga aatgtctatt tcgatctttt ttttttgaga  39600
cggagtctca ctctgtcacc tgggctggag tgcagtggca catctcatct cactgcaacc  39660
tccgcctcct gggttcaagt gattctgttg cctcagcccc tgagtagctg ggattacagg  39720
cgcccaccac tacgcccagc taattttttg tatttttagt agagacgggg tttcaccatg  39780
ttggccaggc tggtcttgaa ctcctgatct cgtgacttgc ccacctcggc ctcccaaagt  39840
gctgggatta cagctgtgag ccactgcgcc tggccttatt cagacctttt acccattttt  39900
taatcagatt attagatttt tttctataga gctgttacag cttcttatat agggatgtga  39960
```

<210> SEQ ID NO 8
<211> LENGTH: 43560
<212> TYPE: DNA
<213> ORGANISM: Homo sapiens

<400> SEQUENCE: 8

```
aggacctctt caaggagaac tacaaaccac tgctcaacga agtaaaagag gacacaaaca     60
aatggaagaa cattccatgc tcatggatag gaaaaatcaa tatcatgaaa atggccatac    120
tgctcaaggt aatttataga ttccatgcca tccccatcaa gctaccaatg actttcttca    180
cagaattgga aaaatctact ttaaagttca tatggaacca aaaaagagcc tgcattgtca    240
agataatcct aagcaaaaag aacaaagctg gaggcatcat gctacctgac ttcaaactat    300
actacaaggc tacagtaacc aaaacagcat ggtactggta ccaaaacaga aatatagacc    360
aatggaatgg aacagatccc tcagaaataa taccacacat ctacaaccat ctgatctttg    420
acaaacctga aaaagacaag aaatagggaa aggattccct atttaataaa tggtgctggg    480
```

-continued

```
aaaactggct agccatatgt agaaagctga aactggatcc cttccttcca ccttatacaa    540
aaattaattc aagatggatt aaagacttaa atgttagacc taaaaccata aaaaccctag    600
aagaaaccta ggcaatacca ttcagtacat aggcatgggc aaggacttca tgactgaaac    660
accaaaagca atggcaacaa aaaccaaaat tgacaaacag gatccaatta aactaaagag    720
cttctgaaca gcaaaagaaa tcatcagagt gaacaggcat cctacagaat gggagaaaat    780
ttttacaatc tacccatctg acaaagggct aatatccaga atctacaaag aacttaaaca    840
aatttgcaag aaaaaaatca aacaacccca tcaaaaagtg ggcaaaggat atgaacagac    900
acttctcaaa agaagacatt tatgcagcca acagacagat gaaaaaatgt tcatcatcac    960
tggccatcag agacatgcaa atcaaaacca caatgagata ccatctcaca ccagttagaa   1020
tggcaatcat taaaaagtca ggaaacaaca ggtgctggag aggatgtgga gaaataggaa   1080
cacttttaca ctgttggtgg gactgtaaac tagttcaacc attgtggaag acagtgtggc   1140
gattcctcaa ggatctagaa ctagaaatat catttgaccc agccatccca ttactgggta   1200
tgtacccaaa ggattataaa tcatgctgct ataaagacac atgcacatgt atgtttattg   1260
tggcactatt cacaatagca aagacctgga accaacccaa atgtccatca gtggtagact   1320
ggattaagaa aatgtggcat gtatacacag tggaatatta tgcacccata aaaaggatga   1380
gttcacgtcc tttgtaggga catggatgaa gttggaaacc atcattctga gcaaactatc   1440
acaaggatag aaaaccaaac accacatgtt ctcactcata ggtgggaatt gaacaatgag   1500
aacacttaga cacagggtgg ggaacatcac acaccagggc ctgtcgtggg ctggggggaa   1560
gggggaggga tagcattagg agatatacct aatgtaaaag atgagttaat gggtgcagca   1620
taccaacatg ggacatgtat acataacgta acaaacctgc acattgtgca catgtaccct   1680
agaacttaaa agtataataa aaataaataa ataaatataa aaataaaaga ttaaaaaaac   1740
tcatcaatga aactaatttt ttatctgata aaataattct aaaaaaaaaa aacacttgat   1800
gttatcccat ctgtccattt ttgctttggt tgcctgtgct tgtggggtat tactcaagaa   1860
atctttgccc actccaatgt ccttgagagt ctccccaatg ttttcttgta gtagtttcat   1920
ggtttgatgt ctcaaagtcc attttgactt gatttttgta tatagcaaga gataggagtc   1980
tagtttcatt catctgcata tggatatcca gttttcccag cacaatttat tgaagggatt   2040
gtcttttcct ttatattctt ggctcttttg tcaaaaatta gttcactgta gatgtatgag   2100
tttatttctt gtttctctat tctgttccac tggtctatgt gtctgttttc atgccagtac   2160
tatgctattt gggttgctat agctgtggta taatttgaag tcagataata tgattcctcc   2220
tgatttattc tttttgcttc agatagcttt ggctactctg ggtcttttgt ggttccatgt   2280
aaattttaga attttttttt tctatttctg tgaagaatgt cattggtatt ttgttaggta   2340
ttgcattgaa tctgtagatt gctttgggta gtatgaacat tcttccaatc tataagcatg   2400
gaatatcttt catttttttt ttgtggcctc ttcaacttct tgtgtcaaca ttttatagtt   2460
ttcacggtag agatctttca cttctttggt taattactag gtactttatt ttatttttag   2520
ctattgttaa caggattact ttcttgattt ctttttcaga ttgttccctg ttagcatata   2580
gaaatgctga tttttgggcc gggcgcggtg gctcacgcct gtaatcccag cactttggga   2640
ggccgaggcg ggcggatcac gaggtcagga gatcgagacc atcctggcta acacggtgaa   2700
acctcgtctc tattaaaaac acaaaaaatt agcggggcgt ggtggcgggc gcctgtggtc   2760
ccagctactc aggaggctga ggcaggagaa tagagtgaac ccgggaggcg gagcgtgcag   2820
tgagccgaga cagcgcaact gcagtccagc ctgggcgaaa gagggagact ccgtctcaaa   2880
```

-continued

```
aaaaaaaaaa aagaaaaaga aagaaaaaga aatgctgatt tttgtatgat gattttgtat   2940
actgtgacct tgttgaattt gtgtatcagt tctaatggtt ttttggtgga gtctttaggt   3000
ttttccaaat ataataagat catctgaaaa caaggataat ttgacttctt cctttccaat   3060
ttgtatgcca tttctttctt tctcttgtct gattacatag gacttccagt attatgttga   3120
aaaacagtgg taaagtgggc atccttgtgt tctagatctt agaggaaggg cttttagttt   3180
ctccctattc attatgatac tagtggtcgg tctattctat atggcttttc ttatgttgag   3240
gtatgttcct tctatacaca gttttttggg aatttttatc atgaagggat gttgaatttt   3300
atcaactgct ttttcagcat caactgaaat gataatatgg tttttgtcct tcattctgta   3360
gataagacat atcacagtgt ttgatttgca tatgtccaac caccccttgca tccctgggat   3420
aaatcccact tgatcatgat ggatgatctt tttaatatgt tgttgaaccc agtttgctag   3480
tattttgctg aggattttta catcaatatt catcagagat actggcctgt agctttcttt   3540
ttttgatgta cttttgtctg gttttggtat cagggtaata ctggccttgt agaatgagtt   3600
tggaagtatt ccctcctctt ctatgtttca gagtagtttg agtacggttg gtattagttc   3660
ttcaagtctt tggtagaatt cagcagtgaa tacttcgggt cccagatctt gttacttgtt   3720
atttatctgt tcaggtttta gatttcttca gggtccaata ttggtaggat gtatgtgtat   3780
aggagtttat acatttcttc tagattttcc aatttattgg catataattg ctcatagtag   3840
ccaccaatga tcctttgaat ttctgtatta tcagttgtaa tgtctcctct ttcatttctg   3900
attttattta tttgggtctt ttctcttctg ttcttagtta acatggctga aagtttctaa   3960
attctttctc tgtgttatct tgaatttctt tgagtttcct caaacagctt ttttgaatta   4020
cctgtctgaa aggtcacata tctctgtctc tccaccctgg tgccttattt agttcctttg   4080
gtgaggtcat gttttcctgg atggtcttga tacttgtgga agttcgtcag tgtctggaca   4140
ttgaagagtt aggtatttat tgtagtcttt gacatttagg actgtttgta cctgccctcc   4200
ttgggaaggc tttccatata ttcaaaaaaa cttgggtgtt gtgatctaag ccatatctat   4260
attacagagc accgcaagtg cagtaatgct atggttcttg cagacttata gaggtaccac   4320
ctttgtggtc ttaaataaga tccagaagaa ttctctggat taccaagcag agacttttgt   4380
tctcttccct tactttctcc caaacaaatg gagtctctat ttctctgtgc tgagctgctt   4440
ggagctgggg gtggggtcac acaagcaccc ttgtggctac catcactgag actgcactgg   4500
gtcagacctg aagctagcac agcactggat attgcccaag gcccactgtg actactacca   4560
ggctaccacc tatttttgtt caaggctcta gcactctaca atcagcaggt gcaaagccag   4620
ccaggtttgt gtctttccct tcagggtgat gagttcctcc aggccccagg caggtccaca   4680
gatgccatct gggagtttgg ctctcttatt tttatagtta gggataagaa tagcatgcta   4740
tgtaattcaa acttccattt tcattaggta tcttctggaa tgttttcaca ttctgtccta   4800
ctctacgttc aaacaaaatg aaatcagtat tattatcccc attttaccga ttagataact   4860
gatgtatgga gaagtaacac agctttccca aggtcacata aggacacaat aaactagaat   4920
ccaaatctcc agactcctca tccaacattt atttatttat ttagttagtt agttattttt   4980
tgagacagag tctcgctctg tcacccaggc tggagtgcag tggcgcaatc tcggctcact   5040
gcaacctccg cctcctgggt tcaagcgatt ctcctgtctc agcctcctga gtagctggga   5100
ttacaggtgt gtgccaccgc gcctggctaa tttttgtatt tttagtagag acaaggtttc   5160
accatgttgg tcaggctggt cttgaactcc tgacctggtg atccacccac ctcggcctcc   5220
```

-continued

```
caaagtgctg ggattacagg cgtgagccat cacgcttggc tcatctaaca tttaatctgc   5280
cacactctcc tgcctctctg gggtggtggt atatttcatt tagttcccct cttctctcca   5340
acacaacagg cacagggaaa ataaaggaga gtgttgggtc gggcgcagtg gctcacatct   5400
gtaatcccag cactttggga ggctgaggcg ggaagatcac gaggtcagga gatcgagacc   5460
atcctggcta acacggtgaa accctgtctc tactaaaaat acaaaaacgt agccgggcgt   5520
ggtggcgggc gcctgtagtc ccagctactc aggaggctga ggcaggagaa tggcatgaac   5580
ccgggaggcg gagcttgcag tgagccaaga ttgcgccact gcactccagc ctgggcgaca   5640
gaatgagact ctgtctcaaa aaaaaaaaaa aaagaaagaa aggagagtgt tcccaaatta   5700
tccctgccaa tcatcatccc tgaattttgt taattaaata catagcaaat caatggggga   5760
aaatcactgc actttctccc cgaaatagca cagaagtgtc agattcttca acgacaatgt   5820
gaaacacatt ttctagatta aagaaggaat tggtataggg aataatgcag ccatgcttcc   5880
taattgccta gaaggtcctg gtttcatgta attttattct ttttataaaa gagatttaat   5940
aatttctaat taaccaatgt gctaattttt ttcttttctt tttttttttt ttagagacag   6000
ggtcttgctc tgtccccaag gctggagtgc agtggagcaa tctcggctca ctgcaagctc   6060
cgtctccttg ctcaagtgat cctctcacct cagcctccct agtagctggg gctacaggca   6120
cgtgccacca cacccaacta atttttgtat ttttgtggag atgaggtttt gccatgttgt   6180
ccaggctggt cttgaactcc tgggctcaag tgatccacct gtctgggctt cccaaagtgc   6240
tgggattaca ggcatgagcc tggccttgat ttttcaaata aaatcattca caaataaata   6300
aaaaacttct gtcagactat gtattctgag ttttggcttg gaaaagagga ctacggtatc   6360
tttaaggact tctcttcttt gggttcaggg tctggttttg gtaaagttgt aaaaggttgt   6420
ctttggtctt attttcaacc ctcttagctg tacctcttca ccaggtaaac atttttccta   6480
cctggaattt tcccagtgac tcacagagtc catcttatat tccattgcta aagaccttgt   6540
tttcaactgg ttgcaattaa agaagcataa tgtattatat ctcttgagaa tggctgcggg   6600
agaatggggt gacttttttta agcttcaaaa gccatgaaga gtcaagcaat gcaggcacta   6660
ggggtaatgt ttttacaatg ggctgaaggt ggcagggtgc attctgatac ctctccaatt   6720
cactctatga aggcagctac ccactggaca ggcctttgtt acaaagattt cctccaggac   6780
acaacagcat tttgatggga ctaagtatta aagcaggcat atattaggag ggtggatagc   6840
ctgtgcaaaa attgtagaag tcagatagac cagggtccaa atcctagcta tatcttttac   6900
ttgacaacct caggaaaggc tgtagtgttc tctgggtctc agttttctca tgcatataaa   6960
atgaggataa aaatatctac caaggactgt aaagaataaa tacatgaact agcagagtga   7020
ctggcatatg gtgagtgata agagatagtt ataattcaca tggaataata aatttgagag   7080
aaccaagatt aagagaataa aaagagaaaa tattggaggg tggaggtagc tcagagtatt   7140
ctaattacct gcattgttaa atctcaaaac ttaagagcta atgcaaatga cttggagaaa   7200
tagtgtacca atgttcatcc acttgaagtc tttctgctat gtggcatata gaaagggtgc   7260
ccgcatgttc ttatatgctt gcaacagctc ccatttgcgc aattatataa ggcaacgcag   7320
tcctatttta tgcctgttgt catattataa ttatgaataa tgatctcttt gaaagtattg   7380
agatttgaac aatgaatttc acagtcacct acatatagag aatgtctttt taggctcagt   7440
gtggtggctc atgcccataa tcccagcact gtgggagggt gaggcgggca gatttcttga   7500
ggtcaggaat ttgagatcag tcaggccaac atggtgaagc tccatctcta ctaaaaatac   7560
aaaaagttag ctgggtgtgg tggcgcatgt gggaggctga ggcaggagaa ttgcttgaac   7620
```

-continued

```
ccgggaggcg gaggttgcag tgagccaaga tcatgctgct gcacttcagc ctgggtgaca   7680
gagtgagact ctgtctcaaa aaaaaaaaaa aaaaaaaaaa aggaagtctt tttattttaa   7740
tggaacattt tactatttac tagtagctgc tgtttttttt ttcttaaatc ttaaaattcc   7800
agctgtccag atccctgaca tccccaaagc cagtaaattc aattttgaaa atacctgctt   7860
caaaatgctt tccatcacat acttttgtag ggacatctcc agttcaggat caggcttcag   7920
cgtgcatgca agcctcagga ggtctaagaa ggcagaagga gggtgcaggc tcagagaggg   7980
aagtttggct ctgcagtgct agtgagagga ggctcccagt ccctattctc ttgggcagtg   8040
ggccttcttg tccttacagt tgtcaggaga ctctgggaca cctaggggct gaaagggcca   8100
ggggaaatcc aaagaggagc tcttagaggt taaaggtttc ccaaaattca gtcacatgta   8160
gctcaaaacc ttgttcaaac tgacatgacg ctttgggact tagggagatt ttcacttctg   8220
aacttggttt agaactattg ccacaggaga tgggaacaaa caaatgaggg aatgacaaga   8280
gaggagcatg gtgacagaat gaaggggatg gtagagttga aagggcagca ggaataacat   8340
taagaagact ggtttctgat ctcaggcttg ataccgcttc actgtgtgac cctggagaag   8400
tcactttgct gccctggttg cctcctattt cctcacctgg gaaaagagta gttgagcttc   8460
atgatctctg tggttccctt cactataaag attgatagtt ttatgctcta ggatagactg   8520
ataagagatg gtaggaatga gtttgaggga gtcaaaaaat aagggagaca gaaatggcaa   8580
agggttttca gcagggaaga aaatgataat gtgaaaaaaa atgtgtgtgt gtgtgtgtgt   8640
ttaatttggc tggtcctgat ttgtagcctt tataataaaa ccataactgt aagtgtagca   8700
ctttgctgag ttctgtgagt catttcagtg aattactgaa cctgagggca ttaaggagat   8760
ccccagattt gtaggtagtt ggtcagaagt gccggtggtc tggggatccc agagcttgca   8820
gctagtgtct gaagtttgta gaggattcaa ccaatgaaat cctgcactaa ctccaggtgg   8880
ttataacatc agaattgcac tgcaggccga gcacggtggc tcacacctgt aatcccagca   8940
ctttgggagg ccaaggcagg cggatcatga ggtcaagaga tggagaccat cctggccaac   9000
atgggaaacc ctgtctctac taaaaataca aaaattagct gggtgtggtg gcacgcctct   9060
gtattcccag ctactcagga ggctgaggca ggagaatcgc ttgaacccgg gaggcagagg   9120
ttgcagtgag cccatatcgc gccagtgcac tccaacctgg tggcagagtg agactccatc   9180
tcaaaaaaaa aaaaaaaaag gaattgcatt gcagtattat ggtgctcaaa gtaaggcctg   9240
aagaaaccct ttatagaagg taccattaag acccaggaga tggcattagt aaagctcaag   9300
gagtgggtaa tgtcatgagg ctttctcctt catctctgga gcttctgagg ttcttggcct   9360
ttcctgatca atgtttgtac agtctcccca ctccccaccc cactgcctat tgtggctttg   9420
taaaagtaca gtcttctatt tgtaacatct aaaatactcc agacctgtac ataaatgatg   9480
agaaagaatg attcaaagat gtttctgatg tttctcactt ggatggagtt ttcagggaag   9540
ggtaagtagc taaagttcag atacgttaat attagatgcc tatttgacat ccagtggaag   9600
tcgcccatag gtagggtatt ttgtttgttt tttatgaatt caggacaaaa atctgtccta   9660
gaattcagga caaaagactg aagcgaattc tggctgttag gtctgagact cgggtgatgt   9720
aagcaacttg caggaccttg agagtgagtg tctgcttaag ttttgtgata cagtcttctc   9780
acttgcctca tcttactcat atggaagtta agcacgaata aatggttcac taagaagtga   9840
gtagagaaga ctagaaggtc aaagacagat acctgaagtc accaacattt aagacatgga   9900
aaggaaacta agcaaagagg actgaaaata ggtgatttga gacgtaaagg caaaactaga   9960
```

-continued

```
aaagaataat acttttgaac tcaaggaaaa aggagaaggt agtgtccaag aaaagagcat  10020
aagctatggt caaccatcta ggatgaggcc tgagaagagg tcacctggtt tggcaaatta  10080
atggtccttg gtggccttga cataaacagt ctcagtagac agcaggggac tagcgtagaa  10140
gctaggtgtc agcggtgcaa gactgaagag caggtgagca cagacatcaa ggtgcttgca  10200
atcaatattt attggatgaa taaataaata aggggacatg agagcaggta taaatacatt  10260
tacagattac ttttcctaga agtttattgg tgaaggttag gaggggaaag cagcacggaa  10320
agaagcttta ctttttcttt tatcctaggg gatacttatt aatgtttgat ggatgaggga  10380
aaggagtcag tgcctaggga gaggtggatg gtgtggggag tgtcatactt agaattgctg  10440
tcccggagaa tgggaagtag gtcccctttg tgtgctggta aggaccagga gctgtgttga  10500
ggagcccacc caccagtaat gaagctgtcg gcattgatat aagaccctac tgaccactgg  10560
tagaggcaaa ggcatttttc catggtgggt acttactttt gtgctcacca gaaggataat  10620
aatgcatgaa ggtcgtacac tttgtgaaaa attcatcaaa attaaaattg gggggtggtt  10680
ttaagaagtt aacctaaata aaagcaaatg agaagttttc agttattctg agaactgttt  10740
aatcctttga agtgtaattt cttagcagaa agagagtatg cttttgactg aacagtgatt  10800
ggcacactta aacaccaaga ctatttgatt tgtaaaattg aaattttaaa ttgaaaatct  10860
aaaaaatctt tccaattaca gtgttcactc acatctcaat gtttggtata tgtacagaga  10920
gggtcattcc aagggggact aatcttatac ttttctgccc ttagaacttt ttcctgcttt  10980
ttttccttca taacatttta attcaaataa aacctggtta aactgcacac catttcttcc  11040
ttataagtgt taaaggacgg gggctgatgg ccaaaaagga attaggagca tcaccagtca  11100
taagacatca agatcatgag acacatgtga tgacacactg aggatggcac gatctcattt  11160
ttgtggtatt cttggttaaa aaaaaaaaaa agcataaact tggtccaata aagagaaaac  11220
atcaggcctg taatcctagc actttgggag gctgaggtgg gcagattgct tgagctcagg  11280
agttcgagac cagcctgggt aacaatggtg aaatcctgtc tctaccaaaa atacaaaaaa  11340
aaaaaaaaat tagccaggtg tagtggcaca tgtctgtggt cccagttact caggaggctg  11400
tggtgggaga atcgcttgag actgggagtt agaggttgaa gtgagctgag atcatgccac  11460
ctcactcccc actgggtgac agagtaagat tccatctcaa aaaaaaatat atatatatgt  11520
atatatatat agagagagag agagatatgt tgttggagat gcagaagaga tgagagaaag  11580
catcaggcag tgctaaccag agatgtgtgt gacaacatcg gctggcaact ctcttgtgtc  11640
acggtcactg caagacaacg gaaccactga agtgctgttg cagactgcag gagactacat  11700
caaaaatatc aacaaggccg ggcgccaggg gctcacgcct gtaatcccag cactttggga  11760
ggccgaggcg ggcggatcag gaggacagga gatcgagacc atcccggcta aaacggtgaa  11820
accccgtctc tactaaaaat acaaaaaatt agccgggcgt actggcgggc gcctgtagtc  11880
ccagctactt gggaggctga ggcaggggaa tggcgtaaac ccgggaggcg gagcttgcag  11940
tgagccgaga tcgcgccact gcactccaag cctggggcga cagagagaga ctctgtctca  12000
aaaaaaaaaa aaaaaaaaaa aaaaaaatca acaaaatgca atgtgagatc atgcatacag  12060
tcctggaaca ttccactaag tggaccacag tgggaaaact ggtgacattc aaataaggtc  12120
tttaactagt gcatagtatt gtaccaatgt taatttcctg gttttgacta ttgcagtctt  12180
gttatgaaag atgttaacat taggggaagg taggtgaggg atatatggaa actctgtatt  12240
attttttcaa cttttctgta agtctaacat gaattcaaag ttaaaacaat ttttaaaggt  12300
atcaagaatg attgaagaga ggctgggcgt ggtggcttac acctataatc ccagcacttt  12360
```

-continued

```
gggaggctga ggtgggtgga tcacgaagtc aggagttcaa gaccagcctg gccaagatgg  12420
tgaaaccccg tctctactaa aaatacaaaa aattagctgg gcgtggtagc gggcacctgt  12480
aattccagcg actcggaagg ttgaggcagg gaattgcttg aacccgggag gcggaggttg  12540
cagtgagccg agatcacgcc attgcactct agcctggtca acagagcgag actccgtttt  12600
ttttttttta aaaaaagaat gattgaagag catgggaatg ggctattgct ataagccagc  12660
taggccatgc aggctggata tgtcttgctg gaagagtgag gagtgggtgg tggtggtgag  12720
ggttgtaggc tgatgcatga gtgtgggagt gcctcctatc ttgaccagca tctgcacgga  12780
ttctctgtct tttctttctt tctgccgcgt agtcccattc ctttggctca tctagcagca  12840
cacctttctt ccactttcat accctcaaag cacagctttt ttaattgtcc atatcccagg  12900
gacagttctg cttatagtca atctgcaact taaccacaat gttttctact aggcagagcc  12960
acaggaagag aagtctctct tctatcactg aacttcgccg cacttgctca actccaacct  13020
ttaccttcag tgatccctca tcctgggtta ggagggtgtt gggtaaagaa agtgagggtc  13080
aatgacagcc tttaaaacta ttcccctctg ctcctggatg aaccggcaga cccttctggt  13140
tccttaagca aggtcgctag cccctcaaaa ggcctcaatc cccaaattcc atatcctcag  13200
ttacccataa agaagcctaa tcatttcctc ctcaagctca ccagcctggg ctcctcccag  13260
aggagctgcc ctggactaaa gcctctgtag cctaacccag actgacccca tcccaatctc  13320
cagcccagga gctttatgaa accagcgtgc ccagtgactc ttctggcagg gggcctctgt  13380
tacaggctgg cagaactttc tgtaagtagc agcatcacac ccaccttaac tgctctctga  13440
tctggaacac tctcaatttc aatcatgctc cggtcacaga gctgccagca gtttggtgac  13500
agaataacat cattcatctg agccatgttc tgggcaaggc gcacatcgtc cactgcctga  13560
ccaatcacca gaaagtggct gtgtgtttca tctccaaaga ccaacatgct gatgtggcca  13620
gcagccagtc ctggcaagaa ggcaaggaat aggtttgcac aagaagttct ggattatttc  13680
ccagcagcac aggtttttgg aaaaaccata atcttggtgg gactatacta tctcagagca  13740
aaatctcact tctaaaactt tacataggaa ttatggcata cctcttttgg gctcgggcct  13800
tccaaagctc cccttcttcc aaagctagaa agttctacca ctaaattttg cctgtctgta  13860
acattatctc actacatggt cctaccagtc cccaaagtta tttttacctt ttcttcaatt  13920
atgtatactt aagggcaaca gggaatacct ttaataattc ttattttggg agaatttgca  13980
ttttagcaga gattgaagct gtaactaaaa ataatccctt agggttgaat tttagacaac  14040
aaagggtggg ggaaaggaag tatgcatttg acagttacac atcccatccc aacaaccatt  14100
tctctcattg cttttaagtt ggtaaatgaa agttttggaa cctaagtgac agaagaagat  14160
attgtataat atgacatgta cacaaaatat atgtataaat gaactgtaag tgacacacat  14220
ttctttcaaa tgactgtaat acaatcaatg tttatttttt atcttcgctc tctgctatac  14280
tgatttgtca gggctgactc ccccctgatt ctacatacag tttgttttct atctgaaaca  14340
cactgatgtt tggacttact ctaaaaaaag gtgctgggac ccacctcact aacagccaat  14400
cagcatgcaa gagggggctg ggttcccatc attctcaaga aggataacac atcagactcc  14460
ttgggtacta acttagaaaa aatattcagt attataataa ctttgatttt tttttcaaca  14520
aaatatttaa cttatttggg cttttttttt tgagatggag tttcacgctt gttgcccagg  14580
ctggagtgca atggcgccat ctcggctcac tgcaacctcc gcctcctggg ttcaagcaat  14640
tctcctgcct cagcctccca agtagctgag attacaggca cccgccatca cgcctggcta  14700
```

-continued

```
atttttgtat tttagtagag acggggtttc accatgttgg tcaggctggt ctcaaactcc  14760
tgacctcagg tgatccaccc accttggcct cccaaagtgc tgggattaca ggtgtgagcc  14820
actgcacctg gccttatttg gaaattttta acaacatcaa aagcgggcct aggttaaaga  14880
aggctgagaa acagttaatt gtataactgc tgatgatcct atcaggtatg acatgtgaga  14940
attctaagtt ttgcaaagtt tagttaggcg gaagctaaca ccaacagcac caaccataac  15000
tctgttactc attacttata cctctcagaa tctcattttt catctatgaa atggatacaa  15060
tgatgcctgt atctcaggac tgtcatatag tgtgcgtaat gtttgcacgt gcatagtgtg  15120
taatgtctgc aatgtaataa ggaaatatgt gtgactatta ctatattata tgtataactt  15180
taagaagcct tgtgtaaagc tggagctgtg ttgcaggctg acctgttaag cttttcctac  15240
acctcattct tatgaggtag ggggtgacca gtctcatgtc gttgctgaaa ctatgtaatg  15300
gcaagctagt ctctattttg ttttatactg cacaaccttg acaagcagca agatggaata  15360
ataataacag cagtagcagt cataaagact attttattgg gtggttccta tgcattaact  15420
accataccaa ctaatttact ttttgtaata gcttattagg tagatattat gattaaccca  15480
aattctctca actggtatgt gaggaagcca aaattcacat tctgattgtc ctgatgccaa  15540
agttcagggc atcatggggc tgagccacca tgttctacta cttctctttg ggagagagag  15600
atgccccagg agtcaagacc ctatcccagc tgccgtagga tttattcctt ctcaaatgct  15660
tacctatctt gactcggatg tctaggcctt cttcccactc ctgggtctca aacaatccat  15720
ggatctccag gctacattta attaccactg tgataatgtt tttcagctgc tttcgctcca  15780
ccctccacag ggctagcagt gcatcacctt cagagagaga catgccgcgg gcttttgacc  15840
tgccctgggg atcaatctat tttgtatgag atctgtatag aaacttactc atcaagcatt  15900
cctcagccta tctcctggcc actcccttct ctaggatgcc tcctttgtcc ccaacacaga  15960
agcacaggca cctcagcact cctttcttac cccttctatc ttagtaagcc cccatacctg  16020
caaatttcag gatgtctcct ccaaaaatca acacttctga gaaaaaaaaa aaaaattaaa  16080
tcaaaccctg attccttaaa ggtagtaaaa aaacatcatt ctttcttagt ggaatagaaa  16140
ctaggtcaaa agaacagtga ttcagagaat aggcttatac taaagatctc atcccagaca  16200
agccacttaa cccatttgag tctgtttcct caagtggaga atgagtacgt ggaaccagtt  16260
tacatctatg ctccatttct gtgaatgggg aaagacagga gaaaggcagc tagggtttct  16320
gatgaggtat gaagacagct gccctcctcc cacgataatg gaatgctttt aattaattta  16380
ttgatcaata tatgttatag gctggggctt gtgtaagcat gggtgggtgg atgaatgaca  16440
ggactccaca aaaactagga gtcagggaat gggaaaatca caaccatagt cacttgcatt  16500
tttggttatt accaactttg tattttgttt atttagacgg tatggcataa atggccattc  16560
tctcttttag ttacgcatca tcatggattg gttaagcacc tgttgtgcca agtcagatgc  16620
agaaaggaat caaccatagt tcctgctttt atgaagcatt aaattttgtc tagtgggtaa  16680
catcaagata ttactaagga actcagagtc tgataaaaca ctaggccagg agttcaccat  16740
aacagagtaa accgttgtct tcatgaatag tttgaattaa caatgcaaac aagatggcag  16800
gcagaggttg acaaggggac taaagttttc agttcactct aagtgcttca gcatccatca  16860
ttaggagaca aattattgag aagctaatta taaatcattt atctactcat acaacaatct  16920
cttaatgact atctttgggt tttatagatg ctggctttta aaaatacttg gataggccag  16980
gcatggtggc ttacgcctat aatcccagca ctttgggagg ctgaggtggg aggatcacct  17040
gaggtcagga gttagagacc agcctggcca acatggtaaa accctatctc tactgaaaaa  17100
```

-continued

```
aatacaaaat tgctgggcat ggtggcgcac gcctgtaacc ccagctacgt gtgtggctga  17160
ggcaggagaa tcgcttgaac ctgggaggca gaggctgcag tgagctgaga tcgtgccact  17220
gcactccagc ctgggagaca gagtgagact ctgactcaaa aaaaaaaatt aataaataaa  17280
aatagccggg caccctggct ctcacctgta atcccagcac tttgggggc tgaggcaggt  17340
ggatcacttg aggtcaggag tttgagacca gcctggccaa catggtgaga ccccatctct  17400
actaaaaata caacaattag acaggtgtgg gggcgggcgc ctgtaatcct agctactcgg  17460
gaggctgaga catgagaatt gcttgaaccc aggaggcgaa ggttgcagtg agccaagatt  17520
gtgccactgc actccagcct gggcgacaga gcaagactct gtctctaaat aaataaataa  17580
aaataaatat aaatacttgg atatataact aaaagtatta ctactacagt tcttttaaaa  17640
gcagtgtata attcagccct ctaacacaaa acatcccttc cctcaaatag tctgtattag  17700
tgaggtttga ttatatttat ttcttcagtt atactatatc atatttcaaa aaagactggt  17760
tttatacaca tttcatgggg aagaggagga gtgctaagca attgtactct atcaggttat  17820
aattgacaac tacggaaaaa acaatgaatt gaaatattct caagccagaa acctatggga  17880
acacttactc tccactattg cacttatgtg gtagttgagg atctccacca actgctcagc  17940
ccctctgtcc atgtacatgg cactgctgaa cttctcagtc attgcagtaa aacctggaat  18000
aaatgtgcag ctggtttcct tggctgcttg gggaatcaa acagagccag aagaggacta  18060
ccctggaagg cagcgggcct cagctttttt tttttttttt ttttttgag acagagtctt  18120
gctttgtagc ccaggctgga gggcaatggt gtgatctcag ctcactgcaa cctccgcctc  18180
ccgggttcaa gcaattctcc tgcctcagcc ttccgagcag ctgggactat aagcgtgcgc  18240
caccatgcca ggctcgtttt tgtattttta gtacagatgg ggtttcacca tgttagccag  18300
gatggtctcg aactcctgac cttgtgatcc gccctcctcg gcctccaaaa gtgttgggat  18360
tgcaggcgtg agccaccgaa cccggtggcc tcagctttta aaaacaggca gagtttcttc  18420
ttaaggatct ttgtggctgg tcaagtgtca gacatgcagc ctcctctagc tattatttta  18480
ggggtcagga aaaggctcca gatatttctt tcttccaaat tctcaactgt acagtgataa  18540
ctgcaacttc tttaactggg aataaaattt tcattccgtg gtaacaaaaa cacacacatt  18600
tcaaacactt ctgaagaggt ggcaagttta ttagtaagat gtaaacatca tctagggaga  18660
tcatttcctg aggtcaattt tgactgggat gtgtatgggg cttggggctg gagaggatga  18720
gtcagtgaag ttggggcaga gatactggag caaagaatgg gacttgagca tgttaaagat  18780
atgcctatga ctggcagtcc tgagtaaggg aggatgagag agagccaggg ccacaagcta  18840
tttcctccct cttgtgttct cagtggagca catctgctgt gacagcccaa gggctccaga  18900
atggcctccc tactctgcaa tcaagctctg catgtgaatt cccacgcgag cctgttgctc  18960
atccacatta aacaaacatc ccttttgcac ttgcctgaaa tatcaacaaa catcaggact  19020
ccgtcaaaat aatccataaa gggtcgctct ggggagaaat gtccatagac aatgaggtct  19080
ggtaaatgag ctgctattct gactatgggc cagtcctgga attcttcttt tggagtgttc  19140
atgttcaaga caaatgttca ggattttatg gtgacaggaa gcagtctcca aataggtctt  19200
ctaaaaagaa aattgaaata gaggaaatct gatatattca tttgctcatt ttcctattgc  19260
tctttctcca tttgttttgt tctaacctgc ggcctgctta tagtggtgaa aatgccagag  19320
ttgttgagcc acacttcaaa agggccaatt tctatacaga ggaagaaccc tcccaccctg  19380
aacagctgtt gcataagtga gctccattac aaagaggctg ggtgaaaga gggtagctga  19440
```

-continued

```
acggctcaac tcatttgcag gaaggggtag gccctcgcag ggcaagtcca gttgtagtgg  19500
gctgttaagc tctattcact caggccagac ttctttttct tctgtcctca tgtttccttt  19560
taccctctct ctaccttggt cttttacttt tttctctctt taaaaaaaaa aaaagtgtag  19620
atgtgattcg tgtgtgtgag tgtatttata tgtaagtgag tattagagtt ttgtatatag  19680
gcaagagatt aagactataa aggtataatg ttaaataaat ggaagaaaag agttcagaaa  19740
tgtgtgtgtg tgtgtgtgtg tgtggcagct ggaaagatgg aagaccttaa gctgtaaatg  19800
gaaggaaatg ctgaaatttc aatttgttgc ccagttagtt ctgagaaaac taggatttcc  19860
taaggccttc ctgtagctgc tggggcagat taaatgctca tgcctaaatg ttgtaaaaat  19920
catgctctac cagcctgaac agtaaaagca aacacccttt actttttcag agcaatccaa  19980
gttactggaa taggttatac agaaaatata agaggatttg ttttttaag aaaaggaact  20040
gttatttttg gtttaattct gaccagcaga gaggaacttg ttagtaggtc atattgggat  20100
atattagagt attagaggaa aaaattgaga cagtcgctta tatcccttag atttaagggg  20160
aagtatttaa aaaataactc agggaaaaat atttgtacat ttaacagaca aactttaaaa  20220
tgtatatagt atacatttaa aaatgtattt agtattctaa aaaatgagtg ctaaatgtta  20280
catattggat aacctttaaa aggaaaagtc ctggcaaact caaatgttaa gaagtgaaca  20340
aaagaaagaa acatataact aaggtttaaa aaaaaaaagg gtagcattaa aaatgcagca  20400
aaagaccaca gcatgtgcca ggaacagtca atagataaaa ttaaatcaaa taaataactt  20460
cagatagtaa atttggtgct atatgaactt ttaagaaggg tgtgagatgc tagatgcagt  20520
ggtttgtgcc tataatccca gcactttggg aggcctacac aggagtattg cttgagcccg  20580
agttcgagac cagcttgggc aacatagtga aatcccatct ctacaaaaaa aaaaaaaaaa  20640
aattgctggg tgtggtggca tgcacctgta gtcccagcta ttcaggaggc tgaggtggga  20700
ggatggcttg agcccaggag gtcaaggctg caaggagctg agatcgtgtc actgcactct  20760
atcctaggtg acagagtgag actccatctc taaaataata ataatgataa taaaaagaaa  20820
ggtacaagaa aattgaatgt cgagaatgaa agacttacaa aaaatgctaa agttaagaaa  20880
acctagaggg atttttaaag gctttgttga aaacaaggta attaataaaa gaggaataag  20940
gatgaagctt aagtatggtg taccatacac cttttctttt gtttctacct tctccaccat  21000
ggaggattga aaagtataac aagcattgct aagaaagaat tgaaatccaa gataagtagt  21060
gctaaagcac acagtcattt taaataaatt ctagctagtc ccagacaaca tatatctaca  21120
gatactgaaa gaactgacag gtgtaatgtc agtaatctca aaaaaccatg gagaacaaga  21180
gatgggctgg aataccatag atgggcacat tctcttttga atttcaaaag atgaggctac  21240
tcatggatcc cagaaaacac agaccagtaa acataatgta tttgttgaga taatacaggt  21300
tatgtttcat tatcaaataa ctttgaaatc tcaatggctt gaaataacaa aggcttattt  21360
cttgttcatt tcttgctcac actacatgtc ccttgtgggt tgtatggggt tctcctctgt  21420
ttttgccttc actttgggac ccaaactgga atattctggt tgtcaaggta gtgggaaaga  21480
ggatgtagtg gagtatactc attctactcc cagaagtgac gtatttcact tttactcatg  21540
gcattgacca aagcaaatta catgaccatg cctagtttca agtagacagg gaagtgcact  21600
cctaccatgt gcacaatagg aaagagagtt ggaatatttg ggagcagcct caatggttat  21660
ttagattagc aagaggtgat taaaaggagt caaatggatt cagagccaag agcaagccaa  21720
cattatttcc tattttggaa gagttattaa acttttaaat caagagactg ctatagacaa  21780
tgtatatatt gactttaagg catttggcca aatttctcat atccttgtga gtaaaatata  21840
```

-continued

```
caaaattata ggaataaaga aaatataatt ggctggttag caatcacacc taatggaaat  21900
tgattagtat tctggtgtca actcagaggt aagcctccat gggcacgata gaagactttg  21960
ataaagatat aattgaaagt acggccatta tggaaaataa tatgcaggtt cctaaaaaat  22020
taaaaataga actaccatat gatctaacaa tcccacatct gggtatatac ccaaaggaat  22080
tgaaatcagt atccctgcac tcccatgttt atttcagcac tattcacaat agccaagata  22140
tggaaccaac ctaattgttc atcaacatat gaatggataa agaaaacatt ggataatgta  22200
tacaatggag tactattcag ccgtaaaaca gaaggaaatt ctttcttgta tgatagtgtg  22260
gatgaacctg gagggcctta tgttaagtga aataagccgg ccacagaaag acaaaaatat  22320
tgaacgatct cacttatata tggaatctaa aaaagtcaaa atcatagaag cagagtagaa  22380
tggtgatgcc tgaggctggg gttgggtggg tggaatgaga tgttggtggc tgaaggatac  22440
aaagtttcaa ttagacccaa tgaaaaagtc ctggagatct aacctagagc aaggtgaata  22500
cagttaataa agtattatat acttcaaaat ggctaagaga gtagatctta actgttctca  22560
ccacacaaaa atgttaagta tgtgagatga tacgttaatt accttgattt aattatttca  22620
taatgtatac atatattaaa acatcacatt gtacaccata aatatgtaca ctttttgtca  22680
tttttgcctt aataaagctg agggaaaata aaatttgaaa atatagtgag agaactaatg  22740
cactgatgac agagctagga ttttaataca tcttaatcaa ccaaaataat gaaatttcaa  22800
aagaataagt gcaaagtgct gtgtttagag tttttaacaa aatcaaatgc ataagcacga  22860
ggtgctaaaa aactagattt actgcaaatt agtgctatct tttaaaaaac ttttattgaa  22920
gcataacata catgtaggaa aatgtacaaa tcataagtgt atagcttgaa ttactctaag  22980
gtgagcaaat ccgtgtaata cccattcata gcaagaagga aaacattacc agctttccag  23040
aagtttttct catgccacct tcaagtcact acccttctct tttccctgaa ggtaaccttt  23100
cttatttcta acaacataga tcacctttgc cagttttcaa actttatata aatgaaatca  23160
tactacatat tttgtgtttg tgatattcat ccatgttgtt gtatatcaat aattgttcat  23220
tttcaatgct atatagtatt ccatcacctg atggaatata ccacaaaaca tttatccact  23280
atactattga cctgtgggtt gttcccactt ttagaccatt atgaataatg gtgctaagaa  23340
cattcttatt catgtgtttt ggtgaaaaga tgtatgcatt tctcctgggt atatacacag  23400
gagtggaatt gctgggtcat agggtataca catgttaaac tttagtacag gcttgtccaa  23460
gctatgtcct gtgggccaca tgcggtccag gatggctttg aatgcagccc aacacaaatt  23520
tgtaaacttt cttaaaacat tatgagattt ttttgtgatt tttttttctt agctcatcag  23580
ctatcattat tgttagtatt attttatgtg tggcccaaga tgattcttcc tcttccaatt  23640
gtgccccagg gaagccgaaa gattggatac ccctgcttga gtagatcttg ctaaacagct  23700
ttccaaagtg atggtaccaa cttacactcc ctcaggcaag gtatgacagt tcagttgcta  23760
catatctcag ccaacactta ttttgtcagg cttttcaact tttagtcatc ttgctaggta  23820
agtggtggtg aggagacagg ccatttctct tactgtctct tgtctctgaa gagaaagagg  23880
aagtaaaagc tgaaaaacac aggaatgaag tcagtggcaa gaccagccgg cgccactgat  23940
gaccaggtct gaggttaaaa gattaacccc cattctaacc acatgtgcta tctacagatc  24000
tcaatctatt atgacccttt cacgtggaac ccctcacagc tctaagccct taaaagggcc  24060
aggaactgtt tctttgggga cctcagttct tgagatgcaa gtctgccaat gctcccagcc  24120
gaataaagcc tcttccttct ttaacccggg tgtctaaggg gttttgtctg tggctcgtcc  24180
```

-continued

```
tgctacaatg gtatctgtgg ttttgtgttt ccttgttggt actaaggaga ttaagcacct  24240
tttcatatgt taactagcta tttggatgca atgcaatttt aagatacata aaagtgttca  24300
aatctaatcc agaggactga agttcattga cctctttaaa attcattgac tctggaatgt  24360
gaggaatgat ggcagagact ggaaataagt cagaaaatta tgacattttg gttaaaattg  24420
tagttgtctt caaatatttg ggctgaactg tgaaagttgt ggggtaagtg gtggacgtgg  24480
gctaagtggg ggacatgggt gtgtatgcaa ggtgtaatgt gggaccctgc aatcaaagaa  24540
caacttccct accttctcct tgaggtagaa atttggtttg ggttagcaag attaaagttc  24600
atgggaagta tgcagtggga aaggaaagtt ggtgtgtttt tcttcagtgg agggagctag  24660
ttatcaaaga ataagtgact gtaaacagta tgttccgtag gcatgggtgc tctgaagtgg  24720
cttccacaga tgtgctgagt agccagagaa ctaagatagg actgagcaga actgagcagg  24780
gcgtagctct attcttccct ctcctgcccc cagttcactg gctcaacttt gacttcttta  24840
gctaccaagc ttgtaagatt gaaagactga gctaatgaaa acagaggatg ctcagttaaa  24900
tctgaatttt aaataaacaa ttttttagta taaatatatt ccaaacattg cattctttct  24960
agcagcccta ctatcagccc cttcaatctt ggcaatacca cactctcctc acatgcatag  25020
tatagactgt tttgctaaag ttgttaacac tggatggaaa gtgggttagg tttattcttt  25080
gttgctcagg atcaactagg atcaatgact ggcaatcacc gaaggacaaa tataaacaat  25140
gtaagaatga gtgttcaaac tgggcagttt taggaagtgt tgaatagcta tctacctgtg  25200
agggtagagg tataaaaagt aaagtagagg ttcctcttca aagactttcc tccccgtcta  25260
attaggaata aatagtaact tatcttaaaa gcaaaattta ttcaaagacc tgtgctaaca  25320
ttcttaaata tctgctagcc ataataaaga aatcaatgta ctttatgttc ttggctccca  25380
caatgtagcc taaatatttg ccctggcatg cttatactgg tccaagcaac cattaggtca  25440
tagcctgttc ctcttcctta tttaaaagta tttttacttt tctcagcatt ccacaagtta  25500
cttcctcctt cttttgttct cctctacctt tgcctctttt aaaagttcta agttgctagc  25560
cgatcgggac aaatacagaa tgtgaggtcc tgttccggcc aatgggcagt agggtgaacg  25620
tgtcaggtta taaatgaccc cgtctccttt gttcagtgta ctctcgtggc aaaactgctg  25680
gcgagtatac cctctctgca ggaagtaaaa atgcccttac taaataaatt tatgttcaag  25740
tgctatttct ttatggcatt ggagaacaag cgtttcaaac agaggtgatt ttagtcagtg  25800
tagagatgaa ttagatgatt gttaagattc tattgtttta attaaggtga tgtgaatgaa  25860
cttggacaga tttttctgtt tatgatgacc aaacaaggaa agtacatgca ttttgagatt  25920
aagatggcat atgtagatgt gaaactaaaa gaagaaaatg ataggtttaa aaggcaggga  25980
gatctaaaat aaatatctgg gagtttctta tgaacaccca taaaagacaa tagaaatttt  26040
ctatttttga agatatagtt ttctgcttta agttctgcaa catcacaaaa tgattagtga  26100
tagctgtatt tacctttcta caggcacata ccacattgta attataattt attatgacct  26160
ttttatgtga agcattctat tgtaggagtt attaagaaat tattttaggc agatagagag  26220
gaaaaggggt ccttgggaaa ttttcatttt ttaaagcatc tccagaaaat ttcttgtaaa  26280
gccttggctc ttagagccag gccggcaacc tttgataagc aaatgaaggc cattagaaac  26340
agggcccacc caacatggcg attccggagg ccttctttcc cttgccccac atgttcctgg  26400
caacatggcc acctccacat actcccacgt gtgtagaaca tcatggcacc ctgcatttgc  26460
atattaaaag gctagggtga gagggctagc tttttcaagg gctttgtgaa tgacatgcct  26520
ggtcaaacca atcccctgaa ccctatgcaa atcagacact gcctcctcca gcgtctgtaa  26580
```

-continued

```
tatataccta gctgacgtcc accccactgg gggttccctc tctcggcttt ggagcccccc  26640
tccctctgtc tctgtatggg ggagcttctt ccctctttcc tcttccttct tgcctattaa  26700
actctccgat ccttaaaatc actccacatg tgtctgtgtc gttttatcta aaccgggatg  26760
aggactaaga accttggtgt tcctccactc atcggagccg tatcaattct acataggttg  26820
cctcatttaa tcatccaaac agcgctatga agtagacctg atttctatag atatgaaaac  26880
tgaagcacag aggtattaac ttgctctggg ttataaagct ggaatatcca ggtctgtggg  26940
acttgaaagt ccctgttgtt tctactatat catgctatat cccatttgta tacgctttat  27000
agcactttgg ggatgtatat gacctagaca aaagatgtag gtttaattta agagcacttt  27060
caatgcatgt tgatggtacc cttatcaact gttcagccaa ttctatcaca tcaagaatac  27120
agcatgaaca gcatgggtac tgacaaagcg cggaagcacc ttggaatgag aaatgaggat  27180
acctgagtca aaaggcaagc aggcgaatga ggcccgaaag ataaaccaag aaggattcct  27240
gaatgcggag tgtgagtaaa gaaaactcag tagtacccaa aaatgaaaag agaaattagg  27300
gttcgattat attcatcagt ttctctaaat ctctcctcta gaatttccta atagatttta  27360
tattcaactt ttcacctaca tgtaaagtca ggtttcacga gtccaaagag ggagatactc  27420
tgaacttaaa ggcacagtgt tacctgtcat gaaagcttgc ttgcctactc tagccatggt  27480
aatttttctt ctgagctatt gtggctctta atgtctacac ttaagtggct tatttcccat  27540
acaaatatcc ttgattatct tttgaattgc ttctattttg tcttcatctg aattgtaagc  27600
tccccgtttg gaaccatctt ctacatatct ttgtttactc cacagcacct tgccagagcc  27660
cccttcaaga ggtaggcact tggtagttgt tgactgataa aaaggaggat atcacgtgag  27720
aaactgcaga aaagaggcaa ataaagaaag taagctagaa agacagagca tccaggttga  27780
gaaggtgagg caatatttaa gccttcaagc ttctaagctc atgtaaggga ctgacacaga  27840
ggtatacaca aacttgaacc ctgacttcta gccccaggct tcccactcct ctgcaatagc  27900
tgtcttcttt cctgacggtc gccctcatct tcagctctgc aatcaatctt tctgctgaga  27960
ctcttacttc cacatacctc cacttcatcc agggctgagg aaaagccaga cctcagttag  28020
ggactaggtc ttttaagact gcagaagaca ggagaggagg ccgggtgaca ttattctgaa  28080
gacagctgaa gcgccatgtc tgtctatagc tgacccataa aatgacagtt ttgtctaaaa  28140
gccgttttcc aggccacacc ctcatcagta gctcattgtt ccacgggcac cgaccatgtt  28200
tctgattggg tggcactgcc gtcccctccc ccaccaacct gagtggccta ctactgtaca  28260
aggaaggact ggctgtttca ggttctctta tccgcacatt tgaggcaagg gtcaggggag  28320
actgacatga ccccagagta gtttacacaa ttcttccctt ggccatgtgg aggatggttg  28380
aaattaggca atagttggta ggtgatcatc agaagtatct ccagagcaag caaacaccta  28440
attttagtca atagtggtta cagcttgtac caggactatg aaatttacca gttataataa  28500
attcaatact taccttcaga tatatttgtg aggtaaattt ttgtttgaag aattatatac  28560
ctgccctttc tgactggtca agtgcacgct tttaatcaaa tttatcccaa agataacttg  28620
aaatccaatg ggcactggat ttgagttttc tttatctgat gtgacactgg aaaaatgtat  28680
tttaagaggc tggtgtgttt tctaacagct taaatcatgt gttgattttc taaatgttct  28740
tatgtatatc atcacaacca caattatcat ttaggggcac agcttttaaa attggaattt  28800
aaaaagtctt atttaaaaag ctgtacatgt tctcctataa agccccgctc tgtaattgtt  28860
tactgtgtac ttccaaatgt tgtaaaacac agttgtctta gggaggaaaa caagaggtc  28920
```

-continued atttaattat gttcattgag tgaattttct ggtgtgagtt gtggaaacca gtcttataat 28980
tagaatcata cctcatttaa ttaaacaatc cccttaggga gagctattct taataaatgc 29040
cagtgttttc tatttctgct tcattatata aacaggctcc agtagagacc tttgttttac 29100
agaaaggaac cttagctttg aggtccatcc tcattaacat tcaacctttc gctatgattt 29160
tataagttaa aaaagaaaat atttactatg aggaaacagc agcactgaca taccttggat 29220
caaagtttcc ttaaaagaga tgccatacca caaaaaaaga ctaaagaatt tatctcttat 29280
tgagcattct ccaccccacc tactactcct ctaccccaag cagcttcttt tctgctataa 29340
agttattagt tcagaaaccg tgcaaatagg ttaacacagt atatcctttt tgtagtaaaa 29400
ttaaaacttc ctttaaagta cttaaagaaa agtactttct gggtctacct tcaattaata 29460
agattaccat tttctgaact ttcttcttgt tgcccaggct ggagtgcaat ggcgtgatct 29520
cagctcactg caacctccac ctccctggtt caagtgattc tcctgtctca gcctcccaag 29580
tagctcggat tacaggcatg tgccaccata cccagctaat ttttttgtat ttagtagaga 29640
tgcggtttca ccatgttagt cagtcttgtc gcgaactcct gacctcaggt gatccacctg 29700
cctcggcctc tcaaagtgct gggatttcag gcatgcacca ccgcgcctgg cccgtttcct 29760
gaactttcca tatcttcaat atttactgtg gaccaggcac tgtgttaaaa ccttatctca 29820
atctttagaa caatcctatg aagtcagtac tatgattatc ctcattttgc tcttgaaaat 29880
attaaaggtc agagacagag gttaacaaag tctcacagtt aatgtgtggc agagttgagt 29940
tgaaacccag ggctgtcaga cttggcattg agaaagaaaa cttacatagt gaagctatca 30000
ataaagacct gtcaaaaagc tgtgataaag aattcaactc aactatacta atcgatttgc 30060
accactgtgg aaattatttt tacggagttc agtaactgca ttgatagtaa ggacttctaa 30120
tatattctta ctaagtcttt gagaatagtt gtgaaactga taactaggct atgtgttcca 30180
agtggcaatg agagtttttg acaggataca tattgttact ttttgagatg ggagttttgc 30240
tcttgtcgcc caggctggag tgcaaaggcg cgatctcagc tcactgcaac ctccgcctcc 30300
tgggttgaag tgattctcct gcctcagcct ctggagtagc tgggattaca ggcgtgcgcc 30360
accacaccca gctaattttt gtattattag tagagacggg gttttaccat gttggccagg 30420
ctggtctcga actcctgccc tcaggtgatt cacctgcctt ggcctcccaa agtgctcgga 30480
ttacaggcgt gagccaccgc acctggccaa gatttaattt ttaagattaa aaaattggat 30540
agattaagag ttttggggca gaaaagaaaa gaagcatgtg atggttgttt gtcaatgaaa 30600
cttctgagaa acaagaaagg aggactgcct atgattgtat ctaaatgcta caacaaattt 30660
gactgacaag aggggcttag gagaccccgc acagaagagg ttttaatgaa aaggaagtga 30720
aacaccaagc tcacataaat ttttaataaa cttttttgtg tctatgtcat atttcataat 30780
gtttttccta aatgcttaac ctaggaaaca catgtgtgca cacccatgcc aaacacacaa 30840
atgaatttaa cagtgtggtt tatgaaatga aagcaataat agtttgactc ttcagaacct 30900
cttcattgtg gcctatgtca agctctctaa tcttttctcc tcaatggtag gccatggtta 30960
agggacagat gataaagtac aaggttttca attgctaact gccaaatttt cataggttat 31020
agtattactc aaaaagttgt tttgtctcat ttcttcaaat tttgaaataa cttgctttgc 31080
tgactcatct gactatattt ttaatgagga ctggctttat tagcactttt agaaaaaaag 31140
ctctgcactc cacactgaaa gtcaaatcaa atagatagtt aattatttgt agcgtggagt 31200
aatgtatgct cagtctctcc tcacaacgga gccaaaggtc acaaacattt acagaaaacc 31260
tacttatgtc ccaggtactc tgctaggtac tttcctaact tgtctaaagt cacagcatag 31320

-continued

```
gctgggtatg gtggctcatg cctgtattcc agcactttga caggacgagg cgggcagatc  31380
acctgagccc aggagttcga gaccagcctg ggcaacatga caaaacccta cctctacaaa  31440
aatacaaaaa ttagctgggt gtggtggtgt gtgcctgtag tcccagctgc tcgggaggct  31500
gaggcaggag gatcacttga gcccaggagg tagggtttgc agtgagccga gattgtgcca  31560
ctgcactcca gcctgggcca cagagcgaga ccctgtctca aaaaaaaaaa aaaaaaaaaa  31620
gtcacaacag ataagtcata gagctgggat tcaaattcag gtctgtctga atatagagta  31680
ttttctgcta cattatcagt tactgagggt aattgaaaaa tttaacactt atcatggacc  31740
aggcactatg ttaaaacatt atctcattaa tctttacaat gatcctattt aaaaatctgt  31800
agctgtaaaa gaattttata caacatttat acaaaaatca tcaagattct tcatggcaag  31860
ttaaaatgtt tttaaatagt ttgaggtcat cttgatagtc attccactac ccatttctca  31920
gtctcttcag caaaatttcc tttcacttat agctagctac ctgaccatcc tacactaaat  31980
aagcagataa tttaatcttc caacttcttg aatttgtgtg ttcttttatg tacatatgtt  32040
ggctgactgg aacagaagga ggcagggggt atatacgagc aagtatggtt tattacggac  32100
aaatggtaga aaaatgttac taatatccat agataagttc cttaagtcat gtagagagac  32160
tgttattaaa agtttgctgc atttttctat tgaatcaaga actagctacc agttacagtg  32220
ccttctaaac acacagttag ctttgcttta tcaataacca aataataaac taggtcccaa  32280
tggttttgtc cacatctaga ttgttcaggt gatcaggaac tcttttattt gtgtgcttta  32340
gcttttagtt cttggttata tctataaaga aaacagaaag aaaaataatc atcaataata  32400
atagacaaat ttatggtaag gagagaatgg gaagcatact ccatttcttc tttcttggtg  32460
gtcaagtagc tatacagttg taaacagaat cttcccggag ggcttacagg tagaaacagg  32520
cagaaaggaa aggattcaaa gagttcattt gcatctggat tttgtttcag ataataagag  32580
cacaactgcc aaaaactttt tttttttttt tttgagatgg agtctcactc tgtcgcccag  32640
gctggagtgt agtggtgtga tctcggctcg ctgcaagctc tgcctcccgg gttcacgcca  32700
ttctcctgcc tcagcccccc gagtagctgg gactacaggc gcccgccacc acttctggct  32760
aattttttgt atttttagta gagatggtgt ttcaccgtgt tagccaggat ggtctcgatc  32820
tcctgacctt gtggtctgcc tgcctcggcc tcccaaagtg ctgggattac aggagtgagc  32880
caccatgccc ggcctgccaa aaacttttaa cagcttagct gacatatagt ttcctgtgca  32940
aaagtattat tttaataaaa atattctcat tctggaattc tacaagaacg tgacaaactt  33000
gtgaacatat gtataaaatt tagtaaaatg tggtcaccta gaattttaaa atttatactc  33060
gcaaagcacc tttcctaaga ataagatcaa caggtaaagt aaaatatact aaagtaatca  33120
ctaaagtaaa atatacttct aaccactaag gtaaaatata cttctgtgat gcaggcaggc  33180
tattgggtta acagcctgta aacacttaag ttcacaaacg ctaaggacca tttcctcaat  33240
tctcaatcca aagaagtaac cacagagcca tagtctttcc ttcccttcta ccataccttg  33300
ggcttcattt actattcctc ctagcttata atggaatgga gagtagtata aaagcataag  33360
aaggaactta ttccatgaag ccaaccatac ctcctaggtt tctcaaaaga tcctgatttc  33420
aaatatttga tcataatgtc attatcataa atcactgaca atattaacta ctgagtaaat  33480
agtttaaaaa tttccagtgc tcatggaaca ctttccaatg aaagcaaaga cctcactcta  33540
cgtatcattt ccaatactac ataacaatac acttaagttc caatttatta tatacaattg  33600
aaagtgataa aaggtttaca taagaaatta ataaatcata aactgtatat gttgtcttaa  33660
```

-continued

```
taaaagagat tatgtgagat ggttaaccat ctaaatgatg cacagttaaa tctaaaaact  33720
aggtaacata ctgcttaact gattttagtc agttaactag ttaactggtt aacttatttg  33780
taaaccccta gacttttcta gaaatgttaa atttctactt tagatacttc ttgtcttagc  33840
attatatatg aatcttttaa aaaaattagt gccatctcca gcctgggcaa cagagcgaga  33900
ccccgtctca aaaaaaaaaa aaattagtgc catctaagta gcttttgcaa cagttttaaa  33960
aatatctctg gtaggcttac ctccaaatac gaaaaagctg agaggctcct gctgccccca  34020
caaagaaatt aacagcaaac agactccaat tttttggaat aattacaagt gagtatcttg  34080
accaaataaa ccctgttgaa acaaaatgtt actttaaaaa gaatacatac tgcttcaata  34140
acttcagtga atacttaata ttgagtaaag taattacaac aataatgtag gatgagggac  34200
aaagaaatgc tatactctga attttcaatg tttctgtaac ttagtgtcac agaaaatact  34260
caattcttac atgaaagagg aatctttaaa gtgactatta actgtaattt tcttcccact  34320
tataaaaata tgttcatggc aaaaacctga aaagcaaaag cccattcaga tacttattct  34380
ttctgtgact cctccatcca taacttaata acttcctaga cataatactg ttaattcctt  34440
tgtgtgtggg tgtatttcaa acactaagcc actaaataaa ctgatataaa agaaaacaaa  34500
aatcatttat gttctacaag aaacacagaa gatatttatt taatttacct gtagccatca  34560
aaacagcaga ttgagctgtg ctaagttttt ctgcaggtct ggccatatca gccaatccag  34620
cacacaccaa cccctacaca ttaacgcata gaaagaaaaa aagtatcaca aatgtggagt  34680
aatagtttta actttaaatc aagcacaaga catttttgag atttccgtaa gttagcagct  34740
ataattttag tgtccattca ttaagaaaat gtagattaca acaaaaaaaa agcacaatga  34800
attaaaaaac tgctttttga actaatttta ttttgttagg tacactaagc agtctcacat  34860
atctgaaagt cagtagtaca tatatagata agatgtatat gtatgcatta cacgtacata  34920
tatattttgg gttttttttg gtctacctat ttcacatatg aatttatata ctctttatat  34980
atgtcaggaa ccactaacca ctagcatgga agatacctaa aagctgttaa ggtcatttgt  35040
atagattctt cctttgatgt tttctgccaa tgttatcatt tttaaattaa attaaatttt  35100
agatttgggg tatatgtgca ggtttgttac atgggtatat tgtgtgatgc tgaggtttgg  35160
gcttctaatg aattattttt taaaagtata aatatcagaa aaacttataa ttttagtttt  35220
ttggttagat catttttttt tttttagaca gtctcactct gtcacccagg ttagagagca  35280
atggtgcgat ctaggctcac tgcaacctcc acctcccagt ttcaagcaat tctcatgcct  35340
cagcccccaa gtagctggaa ttacaggcgt gtgccaatat gcctggctaa tttttgtatt  35400
tttaatagag acggggtttc accatgttgg ccaggctggt ctcaaactcc tgaccgcagg  35460
tgatccgccc gcctcaacct cccaaagtgc tgggattaca ggtgtgagcc accatgcccg  35520
gccttggctg ttacgccatt tttctttaac atcagcatat acatggccat ttctcttctg  35580
tgtttttaac actgtctcta ttgcactcat gcgtttttgc tcccaccaga tgagctgtat  35640
ttttaccaag tcactatgtt tgtccccaat ctatttatgc cagttttact tgttaatgta  35700
atttacatga tttaataaat tgtttttttt taaaaaaact aagctggaaa ttatatagga  35760
tgcactgtag tgtaatttat ccaggataga aaatgtggag ctcagaaatc catacacaaa  35820
taaaagattt agctttaaaa aagactgatt gtcaatgaat atatatttat atcctttagg  35880
ttaaaataaa atatttaagg tacataggtt tttgttttta ggattatcca ctttgacctt  35940
tatgattagt tatgtggttt caactaaagt ggttacaaag gactctacta cagttatatg  36000
tttgaaggca tatggtctga gagtcttcat gttatagaac atatgtggct tgcagaagca  36060
```

-continued actgttatgt gtcatgtata gaattctaca gattaattat caaatactct gggatagtaa 36120
aacacagtaa gaggtatata aggtaagtat ctaatagaag aagtctcccc accagagaac 36180
aaaacacaga agtttctatt gctatgctgt catctggaga ctatgtatga tttcaacatg 36240
tacttaaaat agatgttctt aaagagacag atagtcaaga aggcatttat gagtatataa 36300
tgctgtcaat atctcacaac agtaatgaac cagttcaaat aaaccccaaa gctattgata 36360
aaatcaataa actcctaaac tgtggtaaat ttgagatcaa agaggcccct aaatttattg 36420
tgaatagatg aaatcactca aactctttta atgattgaat acttcagcaa tcaattccac 36480
tataaagata tattattact atgtaatttt aagtgtaggt agggagagaa gaaggaaatg 36540
gtaatgtaac ttccattagt atagggggtt ttaggatctt ttctcaatat gtagatatga 36600
aaaaaaaaac ctgctcccta gatctctgta aaatacagct cccgaatgac ttatattcta 36660
atcttgtcac tttatagttg aagagacaaa atgacaaaga gactaaactt gcccaaggcc 36720
ataagattga gtcatagcca attccaactc taacattctc aaccacttga atttacaact 36780
gagtttctga attgttctaa ccattttaaa agtacattta agagaattac aacagcccat 36840
cactcaacaa caacaaaaaa caccttgatt aaattaaaaa acaggcaaag gacttgaata 36900
aatatttctc caaagaatat acacaactga ccaataagta caataagtat atgttcagca 36960
tgactaatca ttagggaagt gcaaataaaa acaaagatat ctaacaccca ttaggtgcct 37020
atcataaaaa caaaaacaaa aatgctcccc catcaaaagt aacaagtgtt ggtgaggatg 37080
tggagaaatt agaacactta tgaattgctg gtagaaatgt aaaataatgt agttgctgag 37140
gaaaacaaaa aatattaagc agaattatca tatgatctag caattcaact tctgggtgta 37200
tactaagaag aattaaaagt attgacttaa acagattctt gtacatcaat gttcatggta 37260
gcattattca caacagcaaa aatgtggaag caaaccaatt gtccaatcaa catatagaag 37320
aataaacaaa atgtggtaaa tacatacaat ggaatgctat tcagcattaa aaagaaagga 37380
aagtgacaca tgtgacaacg ttaatgtacc ttgtggacat tatgctaggg gaaataagcc 37440
aactacaaaa agacaaatac attttgattc catttacatg aggtacttag agtagtgaaa 37500
ttcatagaga cagaaggtag aatggtggtt gccagggact gggagaagga gaatggggaa 37560
ttatgggtac agagacttgc ttttacaaga taaaaagggt tctggagatt ggttaacaat 37620
gatgtaaatg tacttaacgc tactgaactg tacactttga aaatggttca gatagtaagt 37680
tttatatgta ttttaccaca ttaaaaaaaa aaaagcctac agaccagtgg ttttcaaact 37740
ttagagggca ttagagaatc atccgaagag gttatgaaaa cagagctcac tggactccac 37800
atctagagtt tcagatttag taggtctgtg atggggccta acaagttctc aaatgatgcc 37860
actgcaggtc cagagagatg acactttgag aagcacagtt atagacccaa actggccctt 37920
tcaacataaa atcaatgatt tgctacaaac agccaccaca attgtttctt ttcagctaag 37980
taagaacttt aagaaagaaa actttgggga agagtaaaag cactgggctt ggagtcagaa 38040
gtcctaggtt ctctcattta ccaaatgcta atatttatat tcgaataaat ccatctactt 38100
tttgagagta actttcctca cctatatttt ggtgatagta ccttcagttc tcatactaaa 38160
ttaataataa aagttaactt gggggttcta actagcttaa tgttttactt agtaataaca 38220
ttttagaatg aaatttcatg tccatgtggt gcacaattgt aagttttttg ataacaagta 38280
tgttcccaga aggcctctta tctaaagagt tcagaaaaac taaagtagat agttgcttta 38340
tgtagaaaac gatatgtctg agaatatttg ccatgaaatc atctagaggc ataccaagaa 38400

-continued

```
tactctaaag tatatccttc ataaaagtta cttcaaatta gtaaattcct attaaggaat  38460
ttgtctttca gtagcttccg taaaaactca agacttaccc atttcataat tggagcccag  38520
aagaaaactg ttctgggacc tgaaaaaaaa aagaaaagaa aaattcagga ataaaccaaa  38580
tatattatac acgtctttta acagctgtca ccaaatttta aaaaccaaag gatttatcaa  38640
cctattttta accactttta ctatgctttt tgcatacttt gtatttcagt taacatttag  38700
agaggcacca cagtatcaca gtacagttga cccttgaata acacaggttt gaactgatag  38760
gttcaactgt atgcaaattt ttttcagtaa atatactgcc atataaaaat attttaggga  38820
accttgattc taatgtactt tcatactagt tttacactca agtaacactc tcatcccaaa  38880
tgaaaatgaa cccagtgata acaccccatt tttgtgcatt ttggctgaat tactataaca  38940
aatagttggg taatcttaac attaagcagc aaaatttgaa aaatgtaaaa atggcagttg  39000
cttccctcca atttttgctt agtatgcagg ttttgaaaag tatcaccaga tagtgcaaac  39060
tacttgcctt tagccttaag tgatggtaat gctacacatt ctgtcttcca caatttaaca  39120
tagtccttga tatttttgtc cctctcgaat tcacagtatt cttacagcaa aattcattaa  39180
ttcaatgtca ttttaaaatc taccacagta cattttacat attttactcc agttatttgt  39240
aaatctatgt acctatcaag attatgactt tctcgaagct agtggctcaa tactattcat  39300
acttgtaccc ctattaccta atagaatgta gaataataaa taaaaaggaa agttagccag  39360
tagagttgga agcagtttat actaacattt attaccctaa tatatatgta tgtgtatata  39420
taatatacag atatacatat acacatatat atatatatat atatatatat atatatacat  39480
atacatatac acacacatat atatatacac atacaaacaa cgtttttttt ttttggtttt  39540
ttttttggtt ttttttgttt ttttttgaga cagagtctca ctctgttgcc caggctggag  39600
tgcaatggca caatctcggc tcactgcaac ctccacctcc cgggttcaag tgattctctt  39660
gccttagcct cccaagtagc tgggattaca ggcgcctgcc accacacccg gctaattttt  39720
ttgtatcttt aatagagaca gggtttcacc atgttggcca ggctggtctc aaactcctga  39780
ccttgtgatc tgcccgcctc agcctcccaa aatgctggga ttacaggcgt gagccaccgt  39840
gcccggccac aaataacttt taaagtactt taaaatcata agttgttttt atcagcctga  39900
tacttaaata ttgataagtc tgtcttatgc ttttaatagt tttaaaatat gtttgctgat  39960
tttctaattt aatcctaaag tcctacagca atctaagttt cattttctca ttcttcagag  40020
aagctgggta tcattagaat aattcttcaa acactagaaa gaagatcacg gcacaaaccc  40080
tgtggttcct tgtgggacta ctcagcccat tataatgtta aactttattt tctcacatac  40140
atctggtatc taaccatttt tacattttct tgtgtacgtt cgaattttcc gtattttaag  40200
ttgtagaata aatctaaaaa cagtgctgaa acagctggtg agagaattta aactatcaag  40260
gagttctaaa ttttgatgtt cttacaactg agtgaaaaac ctatctatat tcagtttctg  40320
ttatccagtt ctctaagcag tattgttctg ggcacagcca ccacacacat agaactctag  40380
ccacatcttt ttctctctac aagatagaaa ataatttagt ttcttctttg gttaaggttg  40440
gaattgaaga catttttacg aagggaaaaa ggggaatata aaagaaaaca tgaagccact  40500
gagtttcaga atatataatc ctaatttaac taaatattag ccaagtcagc ggttctcaac  40560
caggagtgtc cccccagggg catttttagt tgccccaact gtggtgcccc aactgctgca  40620
gatgctgctg ctgctgccgc tgctgctgcc gtctagtggg tagaggcctg ggatgctgtt  40680
aaacatcctc caatgcgcag gacagccgct cccagaaagt agagggttaa gaaatcctgg  40740
cctagggcga ctgataagct aggcaaacat tcaactagtt tcatgctatt tttatggctct  40800
```

-continued tcagttcatg ctgtcccttc tcaatatcct gcttagtctt tacctaactc ctatccatca 40860
gaaactcatc tcaggttgca tctcctcaag gaagccttaa aaaacaaaca aaaaaactcc 40920
aggttaggct aaattgctcc ttctcttaac taccaaagca gcctgtatat tcttctatca 40980
ttttctgtta aaatgattat ttatgcatct gtcacattaa cccgaagaca aggtcctttt 41040
cttaatcttc cttgacaaat aataggtatg tgccaacaga actgaattgg atccaccatg 41100
ttcaggatag atgctaatca aagatattca aactttctgt ctgacccaga tttgcctcga 41160
cactgcttca tcctcaaggc tggaatttgc tgttttctca tctctaggga catcaggttc 41220
cctttatgcc aaggatatat tagatttcac tcattagtta ctctactctt agaccacagc 41280
tctcttcccc tgagtctgat gccataatgc attaatccta taagtcagtc ttctcaaact 41340
ctctggaaat ttagggtgag attctgggat tcctatcatt acacctggtt catttttctt 41400
tgtcatacac agtgtctctg gctcatacac agtatcaatt actaagttta gtttttatcc 41460
tcgcatggag tttcgcttca tcaatcaaga gtcagtccat gtattgtttt agtctctggc 41520
tgaatgggtg ttcattttta ctctgaactc ttcagcagac ttctcttgtt ctatttgaaa 41580
gctgaagttt ctgtcacccc aaaattgttt tctgagtaaa gcctctagat tctggtttca 41640
agcttaaatg gctgacaggc ttaaatggtt gatcctttgg ggttaatagt cgatcttttc 41700
agtaggtttg cctggtaact aatttactaa actgcctaga gctaggtaat agttttacaa 41760
tattaacaac agcccttccc caccaaacca aacaactgaa aaaacttcaa acatcaaatt 41820
atggttgcta gaacctggac caagagaggt attttagtga gtgaataatt ttaaactatg 41880
aaaacaagct ctaattttag tttaacaact gctatgtact aaacagaaaa atagcagtag 41940
ccaatacata aggccttcta aattgctaat ttttctgaga tactaaaaga tgtggacaag 42000
tgacaaaaaa atcagtttaa tatctataac tgcaaacagt gttttcttaa ctgttaaaaa 42060
aaaaggtcgg ccgggcgcgg tggctcatgc ctgtaatccc agcactttgt gaggccgaga 42120
tgggcggatc acgaggtcag aagatcgaga ccatcctggc taacacggtg aaaccctgtc 42180
tctactaaaa atacaaaaaa ttagctgcgc gtggtggcag gcggctgtag tcccagctac 42240
tcgggaggct gaggcaggag aatggcgtga agccgggagg tggagcttgc agtgagccga 42300
gatcgcacca ctgcactcca gaaaaaaaaa aaaaaaagtc acacaatggg ttaacaaaat 42360
tttaaagaaa acttaaccct ttcattgtag ctaattaaca ttcaattaac atttcttagc 42420
ttttttttcc tgtaagagta aataatatgt caaataaagc tagacaggta aatttagaca 42480
tatataaaac agatacagag gctgtcttcc agaaaacagc aattgatcaa cagtggatat 42540
ggtagcgaaa aaacattcca acttacttca acatttctaa acataaagtt ttgacaaaac 42600
aaagcattta gaaataggta tcactcaaat agtgacaata caatgtcaca tgtgtcattc 42660
tagacctgga aaacacaggc ttatgttctg tacaatgaca cagctattct cataggagag 42720
cataaaaata gataattatg acacgtgaag tgattataat accttaatat tagaataagc 42780
agaagtataa actaacagat acctggctaa catccattat gataaatgaa ataacttgat 42840
taggtggaaa atttgaactg ctgaaaatat actgaagaaa aatctcctca taagacatta 42900
atttatagcc caagatgaaa gaaattgtcc acatcaaaca tactatatat tcttttagaa 42960
aaagaattaa tacattttca tcttgtttct ttgaacagta ctactggatg ttgaagaagg 43020
cctccaatgc tgacaattta gaaacattaa acaagtattt aaaatgtcta tacatttagg 43080
ccgggcgtgg tggctcatgc ctgtaatccc agccgtttgg gaggcggagg tgggcggatc 43140

-continued accagaggtg gggagtttga gactagcctg accaacatgg agaaacccca tctctactaa 43200
aaatacaaaa ttagccgggc gtggtggtgc atgcctgtaa tcccagctac ttgggaaggt 43260
tgaggcaggg gaatcgctag aacccaggag gcagaggttg cagtgagccg agattgcacc 43320
attgcactcc agcctgggca ataagagcga aactccgtct cgaaaaaaga aaaaaaaaag 43380
tctacacatt ttaaactatg aactatgttc aagaatgaaa aatactgact ataagttatt 43440
ttgtgtttta ttgccttatt tttaaagtga aactcatgtt tttaaattct aacttttcat 43500
agaatttgag aaattctaca agtgaatatc ataagcaaat aataacagac ataaattttc 43560

<210> SEQ ID NO 9
<211> LENGTH: 18738
<212> TYPE: DNA
<213> ORGANISM: Homo sapiens

<400> SEQUENCE: 9
aaataaacaa atttagttgc cttgaacttc aatgaaccta ttaataaact gacataaact 60
tacttcctaa tttccttatt tgagagaaat tactgttaat aaaatattat atgaatccta 120
cccagaaagt aggccaccta tcgtatatat gattccctcc ctaagtaaag actaactttt 180
tggaacagaa taggtaattt ttactctcaa gcacatatac acacttacaa atactggatt 240
gaggtattca ctatatccct ctgtgaaaaa taaagtttct tactgaatgc taagaggtca 300
taaaatcact acatttccct acctcttccc atccctttca tgccactcct ttatggtttg 360
ttacttttta acacccctct taattcctta cattacacaa gttcacctgt ttgctatcat 420
gtgacaaact agatacaaat ccttagaata tgtaaaggtt aatctttgac atggatactg 480
acggccaaaa aatcattcat ttttatttgt gccaaagcta gttctgattt aacactaaga 540
acatgactaa gctaccattt tagagccata taattttaat attttccaca atgccttgga 600
aatagctatc actaaaatag tacccaaaac atcatgggta gataatgttt ttaaaaatgt 660
tgactgaaaa tacactttgg tttgaaattc cagagtaaag aacaggtaaa gagactaaaa 720
tagctaagat gcattgtagg gatgatacgt tttaaattta cttatttctt caggtacaaa 780
gaatcagtta cttttagatt tagaaagact gttgaaatca tctactgtag gcactcataa 840
atcaggcaaa tgaggcccag taaacaaatt acttgtttaa aataaataat ccaacaagga 900
taaaaaacta gatccctaaa tcctaatcta acaataatta tatgactttc cccaatgaaa 960
tctgagtttc ctgaaggttc tgaatgtaag aaaagtccta agagaatacc aaattataga 1020
ttattagctg gaaaagactt taaggaaagt ccaagctccc tcatttttat aaatgaaaaa 1080
gatgaggcac ttacaagtta agtaatttgt cttacactca ggagagttct ggatagagca 1140
acgactagaa cacagtttct ttgatcctag tcctctttct actgtaccat acagcacttt 1200
aaacatattt cattctctgt tataagcaaa attaatattt ttacatgacc tggaaatgat 1260
aaactattta tagcttaggg ctttcttctc ctttagcaca tctgcataaa cagttctaat 1320
ttcttaaagt tagtttaaaa gcaggatagc acacaaaaaa tatgttaagt gttgaacaac 1380
tgcatcaagg atgataatct gctctgttgc ccaggctgga ttgagtgcag tggcacgatc 1440
ttggctcact gcaacctcca tcttctgggt tcaagcaatt ctcctgcctc accctccaga 1500
gtagctggga ttacaggtgt gcaccaccat gcccagctaa atttcgtatt tttagtagag 1560
acagggtatc accatgttgg ccaggctggt ctcgaactcc tgatttcagg tgatccacac 1620
gcctcggcct cccaaagtgc tgggattaca ggtgtgagct accgcgccca gctgatattc 1680
ctttttatga attcttctga gaatacaaac tctgtgtggg tgggtttcgt tattttatcc 1740

-continued

```
actgctttat cctgagtgcc agaacagtgt ctaatataca ataggccctc aataaatatt   1800
gaataattca accttcttgg tagctgattg tttgaagata ttctattttt caccaatatt   1860
ttacaattgt atttgaaatt ctaatcttac atctatttta gttatctctt aactttaaat   1920
aagttattac tttaaaaaat aatatatgta tatttagtgt atttaaactt aatatattaa   1980
atatacactt aagaatatat atggacatat attaatatct tagactggca ttaagattct   2040
tcactgacaa tctgtggcaa caaaataagt tctaacagag atgctaaaga actgtgtaat   2100
tcaaactatg taggtacgta cactcattat ttgatccata ttagatttta tttacatata   2160
atagaacaat atatatttgc actaagttgt atttaaccat ctattgtaac atcaattctc   2220
ttagcattga atataaaatt tttatgatac agatatttcc ttataaacac tgataacatt   2280
ggttcattta gtttattttt atttaaaaag aaatatcctc taggtcttta aaattaaaca   2340
agctaattat ctaggaaaaa tgcaaatatt attcttattt agactttaaa gtaacttttc   2400
ccatgagtct tcagagggaa cccatgtaat gttaagaatg atattctcag caccagcaca   2460
ttaagcactg caacaagttt cacagaacta tttttcaaa agctcttcca tgtaagccaa    2520
aatgtaattc agtaaaagga gagctataat gcgttaaaat gatatggttc agatagctgt   2580
ttttgggact aacttcacca aaggatagtt tttagactct ttagagctgt ggtcttccag   2640
ctcctcttga acatatgccc tatcagtaaa aaacaatttg agtatacatc ctgtttataa   2700
atcatttata tatttataaa ttatatagaa ttactgcaat aatatatttt tgtattacag   2760
aatgtataca caatgaaaaa tttaagtgga tgaaataaca gtaaacgtta ctggaagttc   2820
tataattttc ttcctacatt ccagtgtttc attgtgtgca ccccttggga tgacttaccc   2880
cattttggaa ctcacaaata caaataaatg acactcctcc actgataatt tttttgtttt   2940
ccttaactaa gcttttaaga aaacattggg ccgggtgtgg ttgctcacac ctgtaatccc   3000
agcactttgg gaggccaagg caggtggatc acctgaggtc aggagtttga gaccagcctg   3060
gccaacatgg ggaaacccca tctctactaa aaacacaaaa attagctgag catggtggca   3120
catgcctgta atcccagcta ctcaggaggc tgaggcagga gaatcgcttg aacccaggag   3180
gccaaggttg cagtgagccc agatcacacc actgcactcc aacctaggga acagagcaag   3240
actctgtctc aaaaaaaaaa aaaaaaaaag aaaagaaaag aaaagaaaaa ataacactgg   3300
gcaacataac ttcaagatta tttctttgac aaacactgga gtacagctat gcaactggct   3360
agggtggagt cacatatttt tatagtcagg tgggggataa tgcggggact gacatccttt   3420
tttgtgagtt gaggaacttg accaggacac acatttggct agaactctat tccttctcta   3480
cagtggcaga tcatgacatg ccagcaaaaa cacataggca aatggataat gagagcctca   3540
aaattctggc tcacaggtca gagatgcaat actgtaacta aaatatgtat ctatacataa   3600
aaacacatta gttttttttt ttttttttga gacagaacct cgctctgttg ccaggctgga   3660
gtgcaatggc acgatcttgg ctaactgcaa cctccacctc ctggtttcaa gtgattctcc   3720
cgcctcagcc tcccaagtag ctgagattac tggcacccgc cactacaccc ggctaatttt   3780
tgtattttag tagagatagg gtttcatcat gttggtcagg ctggtctcaa actcctgacc   3840
tcaggtgatc cacccacctc agcctcccaa agtgctggga ttacaggtgt gagccaccgt   3900
gcctggctaa aaacacattc ttgttacctg tcgagacata cagtgtcagt gataaaatta   3960
aatctcaaaa atctagaatc agcaatgtat gatttccaac tgttaatatt gtagcatttc   4020
atatcattta ataaactcct tgtaggtgaa tctagaaaaa tgtttcaatg acaattcaat   4080
```

-continued

```
aacaaatact gttaggcaaa atagtatgca aaatccttga atattcactc tggataaact   4140
cttaagacaa taatcagtgt ttccttagat tttattcaat actcatcagt caacgtattt   4200
ttcaagctcc tccatttcta cactggtgtg cctccaactt gtcgatcata aataattctg   4260
ctgtaataga tatccttact ctgtatgttg ctcaaatttt agaactgaca gttattgaga   4320
gtctaagtgc aaacgctgtg ctacatgttt tagagacatt agatcatctg attttcacaa   4380
caatcctgaa atgattacaa ttactcccat tttatagatg agataactaa ggcaggaatt   4440
tagggtcaag gtcacacagc caagactgaa acgtaggtct atttcccttc aaagcctagc   4500
tccttttact acactgaaaa aggggggttaa aataactgaa cgaatccaag gattttcagg   4560
tgaaatgcac atcctgcaag tgaaaggtaa tccctcttca ttctgaaagc tgagtagtat   4620
tttaagcagt aattacaggt ggctaaaaac taaaggcttg gaaaggatca aggtaagact   4680
accctccaat tttgtattat tttaagtagt ttaaaattac tcttactctg tcatgccctt   4740
atcctacagc taaaacacaa agcttatgaa ggtcagggtt gacttcacat tcagttgact   4800
ctgtaaagcc cagattatta caaaaagcat agctcaaccc tccttcccga aaatctttgc   4860
cacaaaacac agcataattc caaaaaaatt gaatgttaaa agaactaaaa ggcaaataaa   4920
caaaaacttt ttaaatcagt aacaaactgt ccttaatgat cagttttata atgggttcaa   4980
tgttgcagta aataatatta agggttagag tataatccag atgttcaatt cattccatta   5040
tcaaactgga aatcagattt agtaaccagt tcagactcca gagagctggt tcataatcag   5100
ataatggggg aactagacaa ctttcctaat gataccaact acagaataca gattttaact   5160
atgtaggaga ataaaagcca cttttcgggt agcacttcag tctttcaatt tacaacacat   5220
tttctagttt gccaagtctt aggcttgaaa cagacctcag aatatatctg atgttagccc   5280
ctagcaaata agtattatta caactcactt tatagaagag gtaacagaat tctagatctt   5340
taataaaggg attggaatct ttcagtttct tacagttttt tttttcaacc acaagaacac   5400
agttttccag taggcaaaga gagatgtaac gtttactgag catttacaaa gagtcaagca   5460
catatgttat ctgtcattct catagaccgc gtattacaca aacagagatc taggcttttg   5520
ctcaaggtca caactataag tggtagaaga gaatgatatc caggtctgtc cacacaaaaa   5580
gctctgggta gagcttgttc aacaatttca taaataagga tagacttaaa aaaacacact   5640
ggacctatgg gatgagaaat gacactgact caagcctgga tgaagtaaag catgcagttt   5700
gggggagggc tcagtctgca ggcctctgcc agcagcagct gaagaaagtg acctttactc   5760
caaaccctac agtgcgacaa accacccatc cagctctgcc tagagtgggt taatatgcca   5820
caattcgaaa agagaaagag aatgagtgtt tcatggtggc cccagacagt ttggtggccg   5880
cagaagttga gaaggctcaa atctggagat caggtttggg ttggagtcgt gcgtaaggga   5940
gcggatgtca cataggtggg gaagggagct gacttgagat acgttggctt aggaagagat   6000
gttgcaggag agagggtgaa atgcacaggc taggagagta gacggcttca cttgaaggga   6060
agggattggg gctgtggatg cctctagagg cagttgtcag agggcctcta aaaggtccat   6120
tttagaggaa gcgagaagga aggtctcgat aaggagccat tcagggtcca ttacctgctg   6180
gatggttgta caacggcctc aatttctcgg gcagcatcag ctccacttta tcgaggagcc   6240
ggtggtaggt ggcccgcagg cctcgggcac cggcggccga catcgccgcc gagggatcgt   6300
tggcagccgg gtgggagcgt ggctgtgttc tcgtccctgg ctgacaacga aggggagcta   6360
gtcacttttc ctgccacgac gactcgcgtc cgcctctcgc ctggagtacc cttcccgcgg   6420
ctttccctgc ccgctgtgaa ccgaaaagct gcggcccgcg ccccgcgaag gttgaggggg   6480
```

-continued cggaggctgc cgactgccag cccccggtcc gcctccggcc cccggcagga gagagggagg 6540
agccatggca acaggtgcca aaataatcac ctcaccaagt ctgcgctgcg ccctgctggc 6600
agcgcgcttg cgcaggccga gctgcccgcc atgattggcc cgccccgagg cgcgggcggg 6660
gtcgagcgga aacctcctcc ttctccccat gccctcgagg ccatgttgga gaagggaaag 6720
tgaagctgcg ctggttctac tgccctttca ctttgattaa gcaggcccgt agttaaaatg 6780
ggtttttggg ccttcagtgc ctaaagatga tgccgcacaa ttctcttgct tcttttcact 6840
ggagactcgt gagcgagaga ctacagaatt gagtagcttc tctctctact cgtcttttat 6900
ccctagcgac ttaaggatct ggttagagtg gcccgaatgc attcttccag ggtgagggca 6960
gccgcagcac acaccagcct cagtccccag ggtggtcgtc atctcgcgag aaagggttgg 7020
cggggagggt atccaggacg aggagaggga ggagtcgcca tcgcctccgc ctccgcctcc 7080
tcctgttgga ggggggctga gggaggagac tgttgctgat ctttggatgt tctggttagt 7140
ctaagaagga gagtatgagg cgagctccgg cccgggtgcg gccgggcttc aggggcccag 7200
gcgccgctgc tgccaccgcc atctaacgct gcgccctgga ggcccggcgc gcggatggtg 7260
ccggtgcggc tcgggtgttg aaacgggtgt cccctccccc tcctccccctc ccccacgcgg 7320
tggtctcccc tcccacccgg ctcaggcaga gccatgtctc ggggtggctc ctacccacac 7380
ctgttgtggg acgtgaggaa aaggtccctc gggctggagg acccgtcccg gctgcggagt 7440
cgatacctgg gtgagcgggg gccccggggc ggaggcgctg aggtcgccgc ctagagtggg 7500
ggagggggca cgctgccggg tctgttggag gtgggacggc gtctcggtgg gggcgcccgg 7560
agactctggg gtgttgggtg gggccttggt tgccgaattc cgtgccggtg cctcccccag 7620
tcaagccccc tgtgcatgct gccagccgcc gcccttgctg ggtttttctc ggagggccgg 7680
gccgtgggca gaaggtactg gcttgtaaag gtgttggggt cgctgatggg ttgggactcg 7740
ggagacttgc ggaacctcca ggagctgccg cgtttagagc aaaagttagc tcttttgctc 7800
ttttccagcg cgctttcccc gctcagccga agaacctaag ttgttgccca ccctctcctt 7860
caatctccag agggtttagg tgtcggctgc gacgcgttga ccaccctcag ggacttcacg 7920
ctccagacag aatccgtgta aactgttttt gcggcgctga gccaaaacct aaaagtgata 7980
gctgagctct ccccaccccc gcgcgctctc ccagttccac tctgctcttc agttcgtttt 8040
gaccgcttaa aggtggtgta gggtttcacg ttcctcttcc cacccctgga aaacacactt 8100
ggcatttaca gtttcgtagt taagctttct aaaaacaacc ttcagtactt gggggaacag 8160
tattccactt ttttcgtttt gcataacatt ttttttttga ggattctagg tcacgcccga 8220
gtcaactaaa aagtttggtt tcttaaaaat ggacgtactt agtaaaggtc ttttttgttt 8280
cttcctgtat actcttcatt actctttctt tctatttgga gatacggcaa acaacatcat 8340
aaaatttttt tctttccagt tttgccactt gctagttaaa aagtgtttgt tgctctcatt 8400
tgtttttgat ttcaagtaaa gagaagaaaa tgaaatctca ttacaaccaa cagttctggt 8460
ttgtaaatta tttaagaaaa gttagcatgc aattttttaa ttctttttag tgtctcaagt 8520
aaaatacgaa tacattttgt ttataaaaac tcaataaaaa tgaagcaaaa atccctttga 8580
tccctcccat tcaatttcac tccgccaccc ttagaaataa tattttctgt tttctgaata 8640
ttcttccaga cctttttgtt tgcattctta caagtacata tgtacatgta caaatgctgg 8700
ggtgtgtgtg tgtttgtgtg tgtatgagag agacacctga gtgcatggtg tcatattgta 8760
aacattgttt tcacttctcc acattttgga gatctttcca tggcagtaaa aatagattga 8820

-continued

```
ttctgtcttt taaattatta catagtaggt aacattatga agtaccatag ggtactcaac    8880
ctttcttctt taagtagacg ttcgccctta cagcatttta atgaacatca ttctacaagc    8940
ttctgtgcat ttgttgtagg ataagtacct agagtggtga ttaatcattt taaaattgaa    9000
catagctgga gtctggtttt taaaactatt taccaaaaaa agtgtgcagt atttctttta    9060
gaatttattt gcggagaaag aacttaattt tagcttaata aaacaaacgt taacattgtt    9120
ttgcatggat acatttataa tttggtcctt tatctcagtt ggacagttta agtacttgta    9180
tatagttcta tattttagtg ttttcttttg gttcagttac ttcagctata tctacaaacg    9240
agttaattaa aatataacaa aaccatatac ctgcttttcc ccctcctact ccaactccct    9300
aatggaaatg gaatttgtgt attgggtcta ggggaattga agggttcact gactatatta    9360
gaaagcctga attacagttt ttcaaatgtg tatgtataca tacagggagt tctttatctt    9420
aaataatatt ttagatatga taatatatac tcttaaaata ggacattttt ggaatgactt    9480
cctttaaaag tggttttcta agtacttgaa aatacttttt gaaagtatcg aaacttgaaa    9540
atgtttgcaa agaactaatt tattggcctt tacccttagt agacctttac actgttattc    9600
agctcttcta tactacagtg ctaatcctgg ctttgcattc aggaagcagc aaaatccaca    9660
ttggtaatgt ttgaattagt gatggttttt tttaaaaaat gactttccct cccagtttta    9720
ttggggtata attgacaatt aaaaattgtt atatttaagg tgtaggactt gataacttca    9780
tatacaatca agttaattaa catatccatc atgtcacata attaccatct ttttttgtgt    9840
gtggcgataa aatgacttta tcattattat taattttatt tttattatta gataaaatga    9900
ctttttaaag tacagtactc ttggccgggc gcggtggctt acgcctggaa tcccagcact    9960
ttgggaggcc aaggtgggtg atcacttgag gtcaggagtt tgagaccggc ctggccaaca   10020
tggtgaaacc ctggtcttta ctaaaaatac aaaaattagc cgggagtggt ggcgtacgcc   10080
tgtagtctca gctccttggg aggctgaggc aggagaatag cttgaacttg ggaagtggag   10140
gttgcagtga gccaagattg tgccactgca ctccagcctg ggcgacagag ggaaactctg   10200
cgtcataaat aaataaataa ataaataaag tatggtacac ttataaagcc ttcctttaa    10260
aagtcaaatt ccaagttagg attttcctaa ggaaatagat tcctttttta aaagacttca   10320
atatttaaac attacgattg tctatctaca gggttgtaga tttaagtatt tttctgatac   10380
attttcatta tttgtatttc tacagatttt ttagcagtga attactgcta aatagtaaaa   10440
ttgggataga acaaatagat aaatttttct tgtagccttt acatttccag ttatttcacc   10500
atagcatgtg ccctttcaat gttaatattc aagctttgta attgatttta cttaaactga   10560
ttaattatct cctttcttcc catcaaagaa aattatactt cagaaaactt cctattatgt   10620
tgtgggaatg aagatgaata atttcccaga tgttatttat gattaaaaga tatgtttact   10680
tagagctccc aaatccacaa gattcacctg ggccaacaga gtgttgtttt agactagcat   10740
ggatttagag gataggccag ggattttaat ctttgtgagc cctatctaaa tttcaatgta   10800
ggattctttt ttttggtggg aggcgggggg cagggtgagg cagggttttg ctctgtctcc   10860
caggctggtg tgcagtggca ccctcatggc tcactgcagc ctccacgtcc tgggctcaag   10920
gccatcctcc cacctcagcc tcctggaatt tttttttttt ttaaagaata attatcaaag   10980
tcagagatac ctgtaggttt aaatgtttaa atgtaatagt ttctcaaatt actgtatact   11040
aggtgtagag tagtgctttt ggaaatcagt gatttattag ccacacagat tttattatcc   11100
catatatata cggttttgta aagataaaca ttgttaataa aataaactta tttcaataca   11160
ttgcttgttt ctactcatat ttctttcctt ttggacagac actcctacaa ctttctaacc   11220
```

-continued cttctaaatt aaaagatagt aattgataaa aaagtaattt taaggtactt ctcaagggag 11280
ttatttatta taatgtataa aatgtgtaaa ttatgattag gcagccagtg acaatttttt 11340
agtggagatt gaatctcatc tttttgtaag gagtttatga agtcagtgtc ctttgaatat 11400
cattagagtc agtatgtact gaaatggata attttgcgtg tcgattactc tttagtgcat 11460
cttgaataca tctgcattct agattaccag gttcttcata atatgttgcc aagttacagt 11520
gtatttatta tatgaagatt agtaacttct gacttttgcc tcttttttta gccattgggg 11580
aaaagttagt gaaatatttg tattttgttt ctttagtctt gaaatttcag tgaaagctga 11640
aaaatgtatg attttagtat tgaaaaatga cggtcaattg tgacaaacgt aagatatact 11700
gataattcct taaggcagga caccaaaggc atataagtaa tcataacaac catagacact 11760
atgatagctc tactgtgggt ttcattgctt cctaaaatag gatgaatcaa gttataagtg 11820
cttagaaggt ttagaagctt ctggtagcat ggagcttatg ttacaagtat gctttaggtc 11880
agtgttttta aaatgtttta aaaatgatcc atgataaaag tacatttatg tggcaacctg 11940
tgatatacac aacgaaaata aaggattctc taggtgtata tataaacctt actagatggg 12000
atgcattctg tttttttca tattgttaca actgttggtg ttgaactggt agagtacgca 12060
ctaatgagtc tcagcttgag gtttggaaaa ttgttctaga tggtgtgtag ttcttgtaat 12120
ttaatgttgc ttcaggttta aggtgggcag gcttccccaa gtacttgaag gagattaaaa 12180
aaattttttt ttaaacactg ctgatggctc cacagggaaa atgtaaatag tgaaacttca 12240
tgtacatctt ggacaaaata actagggtcg aacactttta aatagatatc tattgtggga 12300
ttgctgactt gtatggtaag tatgtttaac tttataaaaa acttccagac tgtcttccaa 12360
agtaattcta ccatactgca ttcccaccag cagtatatga gagttccaat tgctccacat 12420
tctcatcagc atttggtgta gtgagtcttc ctaattgtag ccttcatggt aggcgtgtag 12480
aaatatatca ttgttttaat ttgcatttct cttttttgt ttttgagacg gagtttcgct 12540
cttgtcgccc aggctggagt gcaatggcat gatcttggct taccgcaacc tctgcctgct 12600
gggttcaaga gattctcctg cctcagcctg ccaagtagct gggatatggg catgcgccac 12660
catgcccagc taatgttgta tttttagtag acatggggtt ttgccatgtt ggtcaggctg 12720
gtctcgaact cctgacctca ggtgattgac ctgcttcggc ctcccaaagt gctgggatta 12780
caagcatgag ccgctgcgcc tggcctttaa tttgcatttc tctagtggtt aatgatgttg 12840
agtatctttt gtggcttttg tttttgtcat ccatatagtc tggttaaatg ttcaggttta 12900
cctttttaat attgtaagaa ttctataatt ctttatataa cagtccttaa tcagatatgt 12960
actttacaaa tattttctgt cagtttatgt ctttttctta acaggttctt ttatagttca 13020
tactttttat gtcctatcta agaatcttta cctaatccaa ggtaacaaag atttttactt 13080
tttttttcct ggagatttta tctttttacc tcttacattt aggtctgtga acaatttcga 13140
gttaagtttt acatatgttg taagagtcaa gtttcatttc tttgcatatt aatgtgcaat 13200
tgatctaaca gtgtgtggaa agactacttt tttccctttg ttgaaaatca attgaccata 13260
aatgtttaag tcaatttcct agccacattc cattgatcta gcttcatgtc tttataccga 13320
ggattgaaat cagctagtgt gatactttaa acttggtctt ttttttgaga cagagtcttg 13380
ctctgtcacc caggctggag tgcagtggct cgatcttggc tcactacaag ctccgcctcc 13440
tgggttcaca ccattctcct gcctcagcct cccgagtagc tgggactaca ggcacccgcc 13500
accacgcccg gctaattttt ttgtattttt ttagtagaga tggggtttca ccgcgttagc 13560

-continued caggatggtc tcgatctcct gaccttgtga tctgcccgcc ttggcctacc aaagtgctgg 13620
gattacaggc gtgagccacc gcgcctggcc gaaatttggt ctttttttaaa aaaatttata 13680 gttatcctgg ctattctgaa ccctttctat ttccataaaa attttagaac tagcttgtca 13740
atttctacaa aaagacttgg gattttgtgt tgaatctata tattatttca gggagaactg 13800
acatgtttac aatatgaatc ttctcatctg tggttctggt ttgtctccgt gtattaagca 13860
ttctttgatt ctctcagcag tgatttgtat tttttggtgt taggtttatc cttaaatatt 13920
tcatatttgt aatgctattt tagatgatat ttttatttat ttttactttt tatttgtaca 13980
aatttatggg tacatatgca gttttgttac atgcatagat tatgctgcag tcaagtgagg 14040
gcttttaagg tatccatcac ctgaataacg ttctttgtcc tcattaacga atttctcatc 14100
atcctcccac ctcctcattc ttccactcca ttatgtatca ttccactctg catctgtgtg 14160
aacacgtttg tttagaacac acttatgagt cagaacatca tacttgtctt tgtgtgcctg 14220
gtttgtttaa cctaagataa tgacctctag ttccatccac gttgctgtat atgtcatgat 14280
ttcattcatt ttttttttga gatggagtct cactctgtcg cccaggctgt agtgcagtgg 14340
tgagatctcg gcttactgca agttccgcct ccgaggttca cgccattctc ctgcctcagc 14400
ctcccaagta gttgggacta caggtgcccg ccaccacacc tgactaactt ttttttttgta 14460 ttttcagtag agacagggtt tcacagtgtt agccaggatg gcctcgatcc cccgaccttg 14520
tgatctgccc gcctcggcct cccaaagtgc tgggatcaca ggggtgagcc accacgccca 14580
gcctgatttc attctttgtt atggctgaat agtattccat tgtgtatata taccacattt 14640
tctttacctg ttcatccatt gatggacact taggttgatt ccatatcttt gctgttgtga 14700
atagtgctgc agtaaacata ctggtgcaca tatcttttag atatattaat ttcttttctt 14760
tttgtaaaaa tctagtagtg ggattgctag atggaaagat agttctattt ttaattcttg 14820
gagaaatctc catactgttt tccatagagg ctgtactaat ttacattccc accaatggta 14880
tataagagtt cccttttttt cacatgataa ccaacattgt ctgtcttttt aataaaagac 14940
attctgacta ggataaggtg atatctcatt gtgaatttga tttgcatttc tcttatgact 15000
ggtaatgttg agcatttttt catatacctg ttgggtgtat gcttttgaaa aatgtctatt 15060
catgtgtttt gcctactttt taataggatt gttagatttt tttggttgtt gaatcgtttg 15120
agttccttgt gtagtctgga tattagtccc ctgttggatg aataatttgc agatattttc 15180
tgtcattcaa caggattggt tgtctcttca atctgttatt tcttttgcca tgcagaagct 15240
ttttagttta attgagtccc atttgtctgt tttctagtat ctttatagtt ttgggtctta 15300
cacttaagtc tttaatccac cttgagttga tttttatgta ttagtgagag ataagagttc 15360
aattgcattc ttctgcatat ggatatctaa ttttctcagc accattgatt gaagagggtt 15420
tcgtttccac agtgtatgtt cttgtcggct ttgtcaaaca tcagttggct gcaagtatgc 15480
ggctttattt ctgggttctc tatgctgttc cattgacctg tgtgtcttat ttttatacca 15540
gtaacctgct gttctggtta gtatagtctt gtaatataat ttgaagttag ataatgtgat 15600
gcctctagct ttattctttt tgctcagcat tgctttggct attggggctt ctttttggtt 15660
ccatatgaat tttaggattg ttttttctaa ttttgcaaaa aattaacttg gtattttgat 15720
agggattgta tagaatatgt aggctgcttt gtacagtatg gtcattttaa tgatattctt 15780
ctgaatatcc agtgatcatg ggatgttttt ccatttgtgt catgtataat ttcttttagc 15840
tgtgttttgt agttctcctt gtagggattt tacctctggt taaatatatt cctagtttgt 15900
gtgtgtgtgt atgtgtgtgt ttataatttc ttttttcttt ttttcttttt tgagacggag 15960

-continued

```
tctcactctg tcacccaggc tggagtgcag tggcacaatc tcggcttact acaacctccg  16020
gctcccaggt tcaagcactt ctcctgcctg agcctccaga gtagctggga ctacaagtgc  16080
gcaccactat gcccagctaa tttttgtgtg tgtgtgtatt tttagtagag acagggtttc  16140
accatgttgg ccaggatggt ctcgatctct tgaccttgtg atccacccac cttggcctcc  16200
caaagtgctg ggattacagg cgtgagccac cacacccggc cttttttttt ttgttatttg  16260
tagctattgt aaatgggatt gtgttcttga tttggttttc attttgaatc attattggtg  16320
tgtagaaaca ctactaattt ttgtatgttg attttgtatc ttgcaagttt actgaattca  16380
tttaccaaat ctaagggttt tttttttttt ttttttgaga cagaatttca ttctgttgcc  16440
caggctggag tgcaatggca caatctcagc tcactgcaag ctctgcctcc cgggttcaag  16500
tgattctcct gcctcagcct cccgagtagc tgggattaca ggcatgtgcc accacacccg  16560
gctaattttt gtagttttag tagagacagg gtttcaccat gttggccagc tggtcttgaa  16620
ctactgacct caggtgatct ggccacctca gcctcccaaa gtgctgggat tacaggcatg  16680
agctaccgcg cctggcaaat ctaagagttt ttgtggggag tctttaggtt tttctagata  16740
taagatcata tcatcaggaa acagggataa tttgactcct tcctttataa ttttgatgcc  16800
ttttgtttca ttctcttgcc tgattgctct ggttaggact tccaatacta tattgaagag  16860
tggtgaaagt aggcatcctt gttttcttcc agttcttaaa ggaatgcttt catcttttcc  16920
ctattcagta tgatgttagt tacaggttta tcatatatgg cctttattat tttgaggtat  16980
gatctttctg tgcctagttt actaagggtt tttcttatga agggatgttg aattttatta  17040
aattcttttt tcgcgtctat taagatgatc atatggtttt tgcccttcat tctgttgata  17100
tgatgtatca catttattga tttgcatatg ttgacctatc cttgcattcc tggtataaaa  17160
cccacttgat catggtgtat tatctttttg atttggtgtt ggatttggtt tgctagtatt  17220
ttgttgagga tttttgcatt tgtgttcatt aatctgtagt tttcttttta ttctgtatcc  17280
tttgttttgt gtccttcttt ggttttgtta tcagggcgat aatggcctta tagaataagt  17340
tagggagagg cctgtccttg attttttgga atagtttcag gagtattgat attacttctt  17400
ctttgtacat ttggtagaat tcggctgtga agccatctgg tactgggctt ttctttgttg  17460
ggagattgta aaaattactg attaattctt gctgctcatt attggtctat tcagattttc  17520
tgtttctttc tggttcattc ttggtaggtt gtgtttttct gggaatgtat ctatttcctg  17580
taggttttct agtttatgag tatatagttc attatagtct gtgatgatct ttgtacttct  17640
gtggaatcag ttgtaatgtc tcctttttca tttctgattt tatttggctc ttctcccttc  17700
ttttcttggt tagtctggaa agtggtttat caattttttt tatctctttg aggaaccagc  17760
ttttcatttc attgaccttt tgtgggtttt ttttttcagt ccatatttca tttagttctg  17820
ctctgatctt tatttctttt cttctgctag ttttgggttt ggttttttct tggttttctg  17880
gttcctcgag gtgcgttctt agattattaa cttgtaatct ttctcctttt tgatgtagga  17940
atttattgct gtgttcttct tagcactgct tttgctgtat cccacaggtt ttggtatgtt  18000
gtgtttacat tttcatttgt ttcaaaaaca tttttttaaa tttctgtctt aatttcttca  18060
ttgaccctat tgtcattcag gagcatgttg tttaattgtt gtgtatttgt aaggtttgta  18120
aattttctct tggtattgat ttctagtttt attctgctgt tgtctgagaa ggcacttgat  18180
gtgatttcag ttttaaaaaa tttgttgaga ctttgttttg tggcttaaca tatggtctgt  18240
cttggagaat gttccatatg ctgatgaaaa tattgtatat tctgcagttg ttggatagaa  18300
```

-continued

```
tgttttgtaa atgtctgtta agttcatttg gtctaaagtc cagtttaagt ccagtgtttc  18360

tttgctgatt ctttgtctag atgatctgtc taatgctgta agtggggtgt tgaattttca  18420

cactattgtg ttgcagtgta tctctttctt taggtctagt aatacttgtt ttatgactct  18480

tagtactcca gtgtcgggtg caaatatgta tttagaattg ttatatattc ttgctgaatt  18540

ggtctcttta atattatata acgactttct tagtcctttt tttttttttt taactgtttt  18600

tagatggttt tttctcttgc catttttagg attcactctt cactttgact tcagacagtc  18660

tgattataat gttgccatgg tggagacctt tttacactgt atttgtctgg tgattgctga  18720

gcctctcata tctggatc                                                 18738
```

<210> SEQ ID NO 10
<211> LENGTH: 34200
<212> TYPE: DNA
<213> ORGANISM: Homo sapiens

<400> SEQUENCE: 10

```
gatcactaga gtaatagccc catacaactt ggacgtaact cttcagtaat gaagatgaat     60

gttgatatgt aaaaatcagc agctgatgtt attggttcaa cttagaaaat tattgaatct    120

aaaattcttg ccaaatcacc tcttttctgg tcatggatac tgcacataag agtttatctt    180

ttacaggata gcttctaaag ttttatcaag acagttactc agcaaacatt cactgagcac    240

cttttaagtg cttaacactt aaaaggtggg aggttaggtc tcactgtgtt gcccaggctg    300

ctctggaact gaaactcctg ggctccagtg attcctctgc cttttcctcg caagcagctg    360

gggctacagg tgtgtgccac tgtgtagggt cagaagcaca ttggtaaaga tgtactgtgg    420

gagcttgaag gagggtcatt atctcagact gtagttcagg ctactggagg aagggagttt    480

aaactgggta ggcatggggg aggggcagaa gtacatacag agttatgaat gaacctgttg    540

gtagttcagt atagtgggag gttggagtgt atataagggg aatggtggga gttgaggcag    600

gagagcctgc caagggcacc agcttacaaa gggccttgtc tgccacactt aatccaatga    660

ggatttctct gtctattgag atgtgaagga tgggttagag tggggtgagg ctgaagccag    720

agaaggcaga ggactattgt aataatcccg gggaggatga tgaagatctg aattcaagca    780

ttgggctatg aagagaggac acatgttgat gcgccactta gaaagtacgt ttgatagagc    840

ttggaaacat tgatgcaggc ttgaaagagg aggtggataa aatgatcata ggttttgggc    900

ttgggaagct gggcatattt ttggcctttt cacagatggg gaaataggag tcttggggga    960

agaagatgat ggagatactt ttgaatatgt tgagtttgag atgcgggtaa gacatccaaa   1020

tggagatggg cagaaaacaa ttggatagac agttctggag gtgaggagaa agttctggtt   1080

ggaaatggag atttagagag ttatgtggct aatagttaaa gcttggattg tttggatgag   1140

ggcatccagg gaaaatgcac tgaagaacat agcagagagc caaagacgga gttttggggt   1200

atatgaaacc tgacaaagag tctctgtgag taagagaaaa accaggtgag tttggtattt   1260

cagcattgtc agatgaagag agataaaatg tgataagaat tcactgaatt tggtaattga   1320

aatgagcaca tagtatatga ggactaaatc tcagtaattt gtaccatcca tgtcagtaaa   1380

tggaacctcc atacatctaa ttgtgcaggc cagaaaccta gggtccatcc ctgattcttc   1440

cctgtccttc acatccaatc agttctccca tctttaaaat gcatctggaa ttgatgtttt   1500

ttctacctcc actcctagcc ttttagtcaa agtcaccacc atttcttgcc tatattactg   1560

tgatagcctc ccagctgctc ttcctctttt tccccctctg gagtcttgct ctgtctcgcc   1620

caggctggaa tgcagtggca caatctcggc ttactgcaac ctccatctcc cagattcaag   1680
```

-continued

```
tgattcttct tgtgcctcag catcccaagt agctgggact acaggcatgc accaccatgc   1740
ctggctaatt tttgattttt ctatttattt ttaaatttat tttatttatt tattttttgg   1800
gggatggagt ctcgcactgt tgcccaggct ggagtgcagt agcgtgatct cggctcacca   1860
caacctccac ctccctggtt caagcgattc tcctgcctta gcctcccgag tagctgggac   1920
tacaggcgca tgccaccatg cccagctaat ttttgtattt tttagtagaa actgggtttc   1980
actatgttgg ccaggctggt ctcgaactcc tgacctggtg atccacccgc cttggcctcc   2040
caaagtgctg ggattacagg cgtgagccac cacatctggc tgattttttt atttttagta   2100
gagacagggt ttcaccatgt ttgccaggtc tggaactcct gacctcaagt gaccggcctg   2160
cctcagcctc ccaaagtgct gggattacag gcatgagcca ccacgcccag tactcatctt   2220
ggttcgtttt aatccattct tcacaaaact gcaagaatga ttttgttaaa atgcaaatca   2280
gatcatgttg ccttcttttt taaaatcctt aatggcttcc cattgcactt ggaatgaaat   2340
ctaaacttcc catggcctga aaagctcttt gtgatctggt ttctgcttac ctctatgacc   2400
tcaacttgta ccacccacca cccctttctc actatattca agccacactg ccatctttct   2460
gctctgtgac actcattccc acctcctagc ctttgaacta gctgttctga tgttgcccag   2520
ggctggctcc tttccatcac agaggctcta agtttcacat ctttagagag gcctctctga   2580
ccaccttatt ctagggtact tacctgttac tatttgctgg tttgccgttt acttccttat   2640
tgtaatttct atatggtttt tcttctcttt tttttcctcc atcagaatct gggacagaca   2700
aatcatctgt cttgtttata gaagtattcc tagtgcttaa cacagtggat atggtagatg   2760
ctaaaaatat ttgttaaatg gcagtgaggc ataggcatgt cttgacaaca gtttgttagg   2820
agtttgcaat atgtagttat gatttagcat ggtatagtag gtcctcaata tgtgtttatg   2880
caagaagaat atttttccaa agtgtgattt catgcactgc ttatttctca ttatcagttc   2940
ccttggcctt ttacttattt actagtcagg atagtaaaat agaaacttag tcttataaaa   3000
tatgtatatt ttttactcca actccaggat atccactagg cttagatgct gccaaaagaa   3060
aaagataaat gttaagtgaa agacagctat gtgcaaaaga acataaaatg caagtttgtg   3120
ttttcattaa gtctaattta tttacttatt caacgtaaat gaacacctac tgggcacaag   3180
gcactgttta tgtatgggat gcagcaggga gcctagatgc tagtgagaag tgacagacag   3240
gaaacatcta ctcaaataaa taataccaaa ggacagatta aattcccaac aatcacaact   3300
tttaagaaaa tatgattgat ctaatatgaa aatttgcagc aaatttttga aaaatggaac   3360
atcttatttg tattataaaa tatttttaaa acttataagg gatatgttat agggtttctt   3420
taaagattgg tctttcccac tgagttttaa aaacatgatt taattgggaa aaacatagct   3480
tttcagaaat attgctgttt cccctctatc cagtagatgc tggtctacct actaaatatt   3540
tctcaccatc cactttgcat ccacactgga gctaatatag tacagccaca gtcatgtctc   3600
tactggatga ttagagcctt ctaactggag cctgactgtt tttgagttat atcttttatc   3660
tgagaatttg aattatttgt gtaagacata catctcatgt gtacctcaac cttggaaaga   3720
tttttaatct tgctctctaa gaccacagat gtcattttaa aagggagagt aaaatggtaa   3780
gctttggcat ataatttatt atagattagt ctttagcccc atcgaagacg gtataattat   3840
tagaagaact agaagcatct cctgaggtct caagtgtcat atggctctga gacttgaccc   3900
ctaaggctgg tgatattaag ccttcatgta tcttgaatga tattcctttt ttccttttcc   3960
actcttactt tgctaagtcg tttgacatta gcagtgccct agagtccaga caaaagtctt   4020
```

-continued

```
tggaattttt gctgccgtaa gaaagcagag gtcagttggc tccgttcacc atagtgcata   4080
aattgagaaa ttgtggttgt ctcctgggat ctttatatct ttgcctttaa accccctttgt   4140
ttattcatta tcttttttct ttcttttcct tttttttttt tttgagacag agtctcgttt   4200
tgtcgcccag gctggaatgc agtggtgcaa cctcggctca cagcaacctc tgtctcccag   4260
gttcagtgat tctcctgcct cagcctccca agtaactggg attacaggca taagccacca   4320
cgcccaacta attttttttt tttttttttt tctgaggcag agtttcactc ctgttgccca   4380
ggctggagtg cagtcgcgcc atctcggctc attgcagcct cttcctccca cgttcaagcg   4440
attcttctgc ctcagcctgc cgagtagctg ggattacagg tgcctgccac cacgcctggc   4500
taattttttt gtatttttag tagtgatgga attttgccat gtcgggcagg ctggtctcca   4560
actcctgacc tcaggtgatc cacccaaagt gctgggatta caggcgtgag ccaccgtgcc   4620
ctgcccaaat ttttttttctt tttttcttt ctttctttct tttttttttt ttttttgtat   4680
ttttagtaga gatggggttt caccatattg gccaggctgg tctcgaactc ctgacctcag   4740
gtgatccacc cgcctcggcc tcccaaaatg ctaggattat aggcatgagc caccgtgccc   4800
aacctattca ttgtcttttt caatgcatgt ggctactgta attttttatt cacttaacaa   4860
tttttcttg atcccattag gcctttatcc aagatgattt cattgataaa tcctccttca   4920
gtaggtttct tcttctaaac tcagagtctc tagaaactgt gataccttat gatacctctg   4980
atcttattgt tagaacatag agcttgagta attttgtagc aacagtgata cactgaatcc   5040
agtacttagg tttaattgat tggagttaga aatgcagtat gtctttgcct atcctgtgta   5100
ttgcagataa gattgcccca tagaatgaaa tctatgactt aagttttgtt aggagcatgc   5160
tgcaaccaac tgaacagacc ttgatgaact tgcaatgaac attttttcat actgggaccc   5220
tgatattcta ctttaggatc tggggagttt attacgtgca ttttaaaaga tgctgttatc   5280
ggccgggcat ggtgactcat gcctgtaatc ccagcacttt gagaggctga ggcgggtgga   5340
ttgcctgagc taaggagtac aagaccagcc tggacaacat gataaaaccc ccatctttac   5400
tgaaaataaa aaaaaaatta gctgggggtg gtggcgcaca cctataatcc cagccacttg   5460
ggaggctgag gcatgagaat cgcttgagcc tgggaggcag aggttgcagt gagctgagat   5520
cgtgtcatcg cactccagcc tgggtgatag agtgagacac cctgtctcaa aagaaaaaaa   5580
aaaaaagatg ctgttattaa aattaagaaa tgtgttcttt tctctccaaa cattaagttt   5640
acaatgtgga gttatataca tttaacataa tcatgtgctt cttccagata acacttggta   5700
aacttgaaaa gatgaaaagt tataaggtgt tatattgtca gcttagcttc aatgagaacc   5760
tagtgaccct gtggccagac agtgtctaat agttattctc tagtcaagtc caggttatca   5820
ttgctatata ctttcttcca aagggtgttg ctgagaatta ggaagcatag atagaggact   5880
caggttccta agagaaatgt ggtaaaatgc aaatatttga aatctcctag atgtctgaaa   5940
agagaagaga aagagagtga gtgagcagtt agggagatgt tttaacttct ccctctccct   6000
tttctgtttc ttagccctta gaagttaggg catagaacta ggttcatgtt atatcttctg   6060
ctctgctctc atttattgag tgcttactat gtgccacgcc tttgctaaac gatttactta   6120
tatactcctc acagctctgt gcaataatta tttttattaa ttttatagat aagaagagta   6180
agtttcagag agattgtgta acttaagggt cttaagatca cacagctaat acatggtaga   6240
gttgagactc aatttccaaa gcacatgttt gcaaccaccc tgctgtatta tagaattttt   6300
tcttcaaagt ctctaaacat tttggggaag attctggaat gtcttaagtg tttacagagt   6360
ggctttttag ctgtcctggg gcatccagat ttcttctttg ggtgatgttt tgtgccaaga   6420
```

-continued

```
tccctcatgc cttgatgctg ctgactctgt taaagaggaa taaagctgcc gtgttgaagc   6480
catcctcacc aatcatgcag aatctgtttg tgccacccaa tactctaaat gctcctcagg   6540
gatttttaat gatgttcttt tttttttctt tttctttctt tcttttcttt tttgaggcag   6600
agtctcttga tatggcccag gctggagtgc agtggcacga tctccactca gcgcagtctc   6660
cacctccctg gttcaagtga ttctcccacc tcagccttcc taatagctgg gattacaggt   6720
gcctgccacc acacctggct aatttttgtg tttttagtag agacagggtt tcaccatgtt   6780
ggccaggctg gtcttgaact cctgacttca ggtgatccgc ctgccacagc ctcccaaaga   6840
gttgggatta caggtatgag ccaccatgtc agctgatgtg gttcttgtag gttcttctca   6900
ctcatacctc tcccgctatc aagagcacaa gcatgaatcc attatactga gtgataccat   6960
actgggctca gaatggttcc ttgcccctca ttacacatta catgtggaag aagccactaa   7020
gccttgactt tcttcctttg agatgagttc ttctctggag gctgtgcagg tccttttgcc   7080
attagactcc tggcatgctt gccttacaga atgtccaaac aggcccaggc atccaaacca   7140
aagtctcctc ccttgtacct cttcttggct cctctgcccc attgacagag gttctgtagc   7200
catgttgtct gccacaagtt ggaggtctag cacttgtctg ttaactcttg ggaactttga   7260
gtcttgatca ttttcagcta ttaggaattt aattcttttt ttttcttcag tgactgcaaa   7320
tttagaagaa ctgcagtgag gcttgctgaa ccttgcacac taatgaaatt ggtgaatgga   7380
ttaataatga acagaggtga tgctaatttg taatcaggtt gaataatatg gatttaagac   7440
cagaaaatgg gccgggtgcc gtggctcgcg cctgtaatcc cagcactttg ggaggctgag   7500
gtggacggat catttgaggt caggagtttg aagccagcct ggccaacatg atgaaacccc   7560
atctctacta ataatggaaa aaattagttg gatatggtgg cacacacctg ttatcccagc   7620
tattcgggaa ggctgaggca cgagaatcgc ttgaacctgg gggacagagg ttgcagtaag   7680
ccgagattgt gctactgcac ttttacctgg gcgacagagt aaaactgtgt cttttttttt   7740
tttttttttt tgagacggag tcttgctctg tcgcccaggc tggagtgcag tggcgcgatc   7800
tcggctcact gcaagctttg cttcccaggt tcatgccatt ctcctgcctc agcctccaaa   7860
gtagctggga ctacaggcag ccgccaccac acccggctaa tttttttgtat tttttcagta   7920
gagacggtgt ttcaccatgt tagccaggat ggtctcgatt tcctgacctc gtgattccct   7980
cgccttggcc tcccaaactg ctgggattac aggcgtgagc caccgcaccc agcctaaaac   8040
tgtgtctcaa aaaaaaaaaa gggggatcag aaaatgctaa ggaggcagga ggatcacttg   8100
aggccaggag ttcaagactg gctggggcaa aatagcaaga ccccatctct acaaagtaaa   8160
aataaaccaa aaaacaagtt ataggtccac agttttttta tctgtaactg caaagccaca   8220
aatactttga aaattaagtt ttttcctaag tttgatacaa attctttggc tgcaaaattc   8280
aacctgaagt agtaagatac tgtttacaac tgtgatccta tttggtatga ctaattgtat   8340
ttttcaccgc agagatatta atgtgtttga ttgtgggatg ctgccctgta ctctctaggg   8400
actactacat aatatatagt ataggtattg tattaatttt ttaaaatctg aaaaattcta   8460
tattctgaaa tacacctggc cttaagactt ttcgattagc ttgttggctt gtacaatatc   8520
ttatctcaga aatttccttc tactcttgta agtactaaga actacaaaat attgcctggg   8580
caacatggca aaactgcatc tttgggaaga ttgcttagga gtggaggctg aagtaagcca   8640
tgtttatgcc actgcactcc agcctggaca acagagggag accctgtccc aaaaacaaaa   8700
acaaacaaaa aaaatacaaa atacagttta gttatttatt ttttcatttt tagaaatgtg   8760
```

-continued

```
gtctcactat gatgatcagg ctggagtgca gtggctggca attcacaagt atggtcaaag   8820
ttccctgtag cctcaaactt ttgggctcag gtgatcctcc tgtctcagtc tccaagtacc   8880
tgggactaca ggtgtgtgcc accaaacccc agctcttttt agttcttttt ttgagatgag   8940
tctagctctg ttgcccaggt tagagtgcaa tggtgcgacc tcagctcatc acaacctctg   9000
cttcctgggt tcaagcaatt ctcttgccac agcctcctga gtagctggga ttacaggcat   9060
gcactgccat acctggctaa tttttgtaga gatggggttt cgccatgttg accaggctgg   9120
tctcgagctc ctgacctcag gtgacccgcc tgccttggcc tcccaaagtc attttagttc   9180
tttaaatgtt ttggtccaca aagctagtgt gctttccact taagagcttt cattgaaact   9240
cctttagaaa tttatgctac tttggactca gcctgtcttt tattcaagga attctaaatc   9300
tgtgaactgg cacacgtttg ggaattgatt gaagggtcct gactttctgt ttttatgatt   9360
cacattagac tttttgttca cttgacctag aacttttctg tttatataga tcaagtaaga   9420
atttagtagg tttcctatct atttcacttg taggaatacc gtgaccagct gatcaatgcc   9480
atagatctgt gagagtcaga cttccagctg tgccttgact ctgctgtcca tcatggtaat   9540
catgcctacc ttgcttttag cagttcagtg ctgccatttg gcccctgtca tcccatgatc   9600
caattattcc cactgcattt acgtgtccca atttagtgac agcagttccc actgtaagtt   9660
ctaggctata gataagagtg tcacaaagtt cttttaaaat gctgggactc ccctcacaga   9720
tctacttttc acagtcatgt ggtgaaaggt gtgtcctctg gctgggcctg gtggtttatg   9780
cctgtaatcc cagcactttg ggaagctgag atgggtggat tgcttgaggt caggagttca   9840
agaccaggct ggtcaacatg gcaaaacccc atctctacta aaaatacaaa aattagctgg   9900
gcgtgatgat gcgtgcctgt aatcccagct actcaggagg ctgaggcaca agaatcgctt   9960
gaatccagga ggtgaggttg cagtgagctg agattgtgcc actgcactcc accctgggtg  10020
acagagtgag actctgtcaa aaaaaaaaaa aattagccag gcttagtggc gtgagcctgt  10080
agtcctaggt acctgaaagg ctgaggcagg aagattgttt gagcccaaga gttcaaggct  10140
gcagtgagct atgattgagc cactgcactc tagcctgcaa cagagcaaga ccctgtttaa  10200
aaaaaaaaaa agatatgtcc tctggacact cacaggtgag taagtagatc ttaaaagata  10260
aatgcactgt aggccgggtg cggtggctca cgcctgtaat cccagcactt tgggaggcca  10320
aggcggacgg atcatgaggt caggagatca agaccatcct ggcttacatg gtgaaacccc  10380
gtctctacta aaaatacaaa aaattagcca ggcatggtgg tgggcacctg tagtcccagc  10440
tactcgggag gctgaggcag gagaatggcg tgaacccagg aggcagagct tgcaacgagc  10500
caagattgcg ccactgcact ccagcctggg tgacagagcg agactccatc tcaaaaaaaa  10560
aaaaagataa acccactgta acactccagt ctccctaggc ctttgaatgc cttcctccat  10620
agtaagccga ggcaggcctg gcatttcaag ttcatttact gagggccaca ttttggtcca  10680
tgtttcagcc agcaaaccaa actgttagag ccctttctaa caccctgagt tgcgtaacat  10740
taaatgcaga atctctgatt agtgggccca tatcagtaaa tttggcctaa cccaacttga  10800
cgttccctcc accatgatcc cataccctta atatccattc ccacacatat tccccagatt  10860
tctgtttata taaattagaa aaatcaaata gttttttttag agtatgtgca ccttcatggt  10920
tcacattttg tacctcacct ttaggagcct cctgagactt aagtctagtt atagatctag  10980
aagcaaagag aggcgttggg ggtaggtcct gaggagaatc agcagtgtct tgcaatgcag  11040
ctgcctcagg ggaggccatt aaagtttcct caggcacagc aggtttaatt gcctcagatg  11100
tgggtggatg gctgcttcca ctggcaaaaa agactcataa gaatttaggg attcaatgtt  11160
```

-continued

```
tccagctcca taagggagtt cccacatttc tccattccaa tattcaggat ccctttcctt  11220
cccaatcaat gccctcactt tagtagcaga caccctgcag acgttgggaa ttcagtttgt  11280
gctgtagttg agtcatttgc agaataagat tctggatttg attttcagca atttcagctc  11340
tatggctaac agagataagg atatctttca gacataaagt tttctgttca gatatgtagt  11400
gctcaagctg ggaatttgaa tccctgagct catccatttc ttttctcact ttgtccattg  11460
tcattaggag taaccaacaa atctcattat actcattagt ttgacaaaaa tgtttaaagg  11520
tatagtatat gtggtcaccc agaaccttat tcttatacgt gtttgattaa aagtacccaa  11580
tggtgacatt ttgcatatct ccattgccac atcataccca tacttttact actggaaata  11640
gtcattagtg tcctttaatc cagttagaga gccaagtcct gaaaccctag aatcaattca  11700
gagaactcat ccttaagatt ctgctccttt agagccactc ttaaaaccaa aattagggtt  11760
ctccagagaa acagaaccag caagatgtgc atgtgtgtgt gtgtgcactc tctttttctt  11820
tatataaata tagatagata acctatctat atcttgctgg catagataga tagataggaa  11880
ttcgctcata tgattgtgga ggcttggtaa gtccaaaatc tgcagggtag gctggcaggc  11940
tggagaccta gggaaaagtt gcaattcaag tccaaaggcg gtctgctggc agaattcctt  12000
ctttttcagg gatggtcagt ctttgttatt gttaagacct ttaactgatt ggataaggca  12060
cacctacatt ataatggagg gtaatctgct ttactcagag tcccccaatt gtaatattaa  12120
tcttatcaga aaacagcttc acagaaataa ctaatgaatt ttaaaagata agccatagtg  12180
gagatctcaa attgtggttt cccatgattg taaacaattc tattctttgt tgtctctatt  12240
ttagcacttt ctctttacat ctcaacttgg tgctatctga cttcctcctc ctctcactat  12300
ttgacacttt gataaaggcc atctgatatt accaaatcaa ctaacctgtt tcagcctttt  12360
ctttccagac ctttttgctt tccttaacat ggttgaccac tttgatctca tttcctttgc  12420
ctttgtgaca ttactcctgg ttctcatctc tcttccctgt cttcttcaag tcttcatcct  12480
ctgcctgtgg ccccaatgtt gattttcctt aggcaggttc tgctctcagc cctttgctag  12540
tctcactgca tgcttgtctt tggtaatttc gtccattttt gtctgtttgt tgacagtgaa  12600
tatgtggcag ctataggcat tcaatacgta tttgttgaat aaatggtgac tcccaaatat  12660
atccccagtg ctctgaactg cagaatctta ccaactgacc attacataca actggacata  12720
cccatttgaa tgtccagagg cacctcaaac tctgtatgct cagaactcaa ctctatatat  12780
ctctcctcct caaactgtgc ttcctccggc atgccactcg ctattgttat tgcttgctgc  12840
tgtcctattt gtctttccct caagtcagcc aagccaaaaa tttggtcttc atcctagaat  12900
ccttcccttt cctcacctca cctccctgga tttaatcaga tctctgccag tgtttacctt  12960
ttatttctga acccactccc tcctttccat tgtcccagga caaatgccag tcattttaag  13020
ttcatgttac tgcaagaggc ttgagactcc tagatcgtct ctctaatggt agtcatcttc  13080
ccttcaggtc tgccctccca actgttgcca gagggatctc tctcttgggc aaatttaatt  13140
gtaccactct tctgttaaga tcctccatct ctccccatta tctctgggat gtacttaggt  13200
ctgccatccc cttccttgta ctttattgat tttttgcaac atttctgcat aatactgctg  13260
ttttatgtct ccttgaattc gtgtatgata ttttcactct tctgattacc cttgtccctt  13320
atttacctgg ctaactccta tttagctttc tcatctcaga tgtaatctca aggccaagca  13380
ctttgcctct aagcttcctc tatctcttta tctaaaatta tgtttttata tgattgtctc  13440
cccaaataca ggaactgtgt gtcttatata ctttgggtct ccaatgctta acataatgcc  13500
```

-continued

```
tggaacatag taaatgttta gtatatatta gatgaactgt tgaactgtac tcaagtggaa  13560
attacaaaca tcagagcaga gagggtgaaa ataaggaagc agaacctccc agaacttaag  13620
atcttaagag cagggtagta atcagtcctc aactttgtac tgtagacact ggatttgata  13680
gtgatgtggc tcagggccag gatgaggctg gggagggaac tgggccaaga tcaggaaggg  13740
gttgaggggt ggtgttcaat aagatcgtaa cgtcagttta acttacagtg aactttataa  13800
acgctggggg gctagtatat tttagcagat cgggttgtta gtacattctc tccctgtgct  13860
gagatagatt gttctcacaa gattgcccag ggaatatggg ataagcccag tagatgttta  13920
ttgaatgacc tcaatggctc tggccatcaa gctatcatag cctaaaacac ccctttcttc  13980
acagtaggaa tataactgac aggtgcattg gattagttac attacctctt cactgggcag  14040
tgatgcagtg tgctgacaat gacactttag atatgaggat atggcctaga aacattgatt  14100
ggcctttttc tggatcttaa agagatttcc tggatggaga gcctgtcatt tagagtagat  14160
tatctctaca gagaaccaat atcatccatt gagtactgag atttcttgtg tttttttgtt  14220
tgtttgtttg tttgtttgtt ttgagacaga gtcttgctct cgctcaggct ggagtgcagt  14280
ggcgcaatct cggctcgctg caagctccgc ctcctgggtt cacgccattc tcctgcctca  14340
gcctcttgag ttgctgggac tacaggcgcc tgccactgtg cccggctaat tttttgtatt  14400
tttttagaga cgaggttcca ccgtgttagc taggatggtc tcaatctcct gacctcgtga  14460
tccgcccgcc tcggcctccc aaagtgctag gattatagga gtgagccacc gcgcctggcc  14520
aagatttctt gttttaaaat tcattacctt tttttgattt aactaaataa tcaggtctct  14580
accagatttc aagatattta gtacgctaat gttgaattga aagaaccttg gacttgagtc  14640
agtgcacaaa aatgaacatg aagaccacaa atactcatgt ctgctaacaa catagtgata  14700
caaataagat gtccgtgtaa ctactaaccc cattatttac tgatctccat tgctgtactt  14760
tgtatttttc ctactattta tagctggaaa tatattgata tggtttggct ctgtgtcccc  14820
acccaaatat cattttgaat tgtaatcccc agtgttggag gtgggaactg gtgggaggtg  14880
attggatctt gggggtgggg atttctcatg aatgatttag caccatactc ttggtgctgt  14940
tctcttgaca gtgagtgagt gagtgagtta ttgcgagatc tggttgttta aaagtatgta  15000
gcacatcctc ctctctctct tgctcctgct cttgccatgt aagacatgcc tgctccccat  15060
tcaccttctg ccatgattgt aagtttcctg aggcctcccc agaagccgag caaatgccag  15120
catcatgctt cctgtgtagc ctgcagaacc acgagccaat taaacctctt ttcttaataa  15180
attacccagt ctcaggtatt tctttatagt aatgtgagaa tggaccaata catatatttt  15240
ggtttttcgg agtttttttg agagagggtc tcactgtcac ccgggctgga gtacagtggc  15300
tcaatcttgg ctcactgcaa cctccacctc caggttcaag cgattctccc acctcagtct  15360
cgcgagtagc tgggaccaca ggtgcacacc accatgccca gctaagcttt gtgtttttttg  15420
gtagagacag ggtttcacca tgttagtcaa cctggtcttg agctcctgac ctcaggttat  15480
ctgcctgcct tagcctacca aagtgctggg attataggtg tgaaccactg cacccagcca  15540
aagggactaa tacatacaca tacatatata catatataca tatatatata tatatatata  15600
tatatacaca tatatatatt tatgtttatt ctttcttggc gttcctgctg cagtatgaat  15660
ctctgccaag gcccagaaaa gtgactggga catagaatga attcaggtgt ttgttgaatg  15720
aatttattgg tggtgtgcag agtgttacca tgctttgttg gtttgttaat tgaaagtttt  15780
taagtagaag agcttttgaa ttttgaaaga ataattaaag ctttcaaaaa ttctaagatg  15840
taatttacct tatacagatg tagaaattga gctctcaagt tctctgtatg tgctgccttc  15900
```

-continued

```
ccataaacat taaacattgc catgacaccc agagaagccc cagggagcct ggtaagcagc  15960
catatacctg ggaatatag ctagagaact tttgttttct gcctcactct caaaagtgtc  16020
tggatttgcc ccctcatttg tcatatccct gttaactaca gtcactactc taaacatcta  16080
ctttggctct ctttccttac ccctcttatc tgctcagaac ctccttacca gaaaatgtag  16140
caactccaca atcttttccc acccttcaag caccatatcc ttttatagtt tcactacgac  16200
agtttctgga gctcatcaag tcttcccatc cctccctgct tttgttttgt attcgttact  16260
tcctggctgc ttccctctcc cgctccaact tggagtccat agttcattgt tataatcatt  16320
cctttgtaaa ggctcctact tccccagccc ttctgtgcca tcattgcact tacctggcaa  16380
tccctcaacc ctgggaaaac cctaccatct ctttttacat ccttaagcat ttgttgcttt  16440
aattattgcc ctctttagat cattcttact acaatacaaa catgagctag aatttctaat  16500
cttaaaaacc ttctcttggt tctatagtcc tctttagcta catttctggg ccgtaactct  16560
tagcaaattt ttacaaaaat ggactatact cctttctttg tatgtacacc ctcccttccc  16620
actttcttct gtccagccat cccacagctg cctctgccac tccattgaaa cttctcctat  16680
caggatcacc agaggactcc aggttgacaa accatattag ttcttcccta tagccacctt  16740
atatgacttc tcagtccctc ctctcttctc ttggctttac ttacaccaca ttctctggtt  16800
ttcttcccct ctcacagtct gctccctttc cgccaccttt tcagggtctt ttctccctcc  16860
ctgaccttta tagtttgatg tctgtatgac ttcggcttgg ctctcatctt cctctacatt  16920
attttcctat gtaatagcat cttctcctgt agtttaaaat actgcctgta tgctggtaac  16980
ttccaaaatt tatatacaat tcagacctct ctgaacatca gacctgcata tccggttacc  17040
tgcttaactc catttagagg tctcaaggtc tcattgacat tgcaaactta acatttccaa  17100
aatggcaggt tgctttctat tccttctctc cagttaaatc tatccagttg ctcaagctag  17160
aaacccagga gttattctcc attcatccct tctcttcact cccatgtcca atctaatagc  17220
aagaagtcct gtatgtcatc cctttctctc accatctcct tgcctctagt ctaggtcatg  17280
gctgcagtac acagcaccag aattactgca gtcacttctt tggtttttgt tttgagacag  17340
tcttgctctg tcacccagac tcaagtgcag tagtgtaatc acggcttact gcagccttga  17400
actcttgggc tcaagcaatc ctgctgcctc agcctcctaa gtagctggga ctgtaggcat  17460
gtgccaccac gcctggctaa tttttttttt tttttttttt agagatgggg gtttcgctat  17520
gttgtccagg ctggtcttga cctcttgggc tcaagtgatc ctcctgcctc agcctcccaa  17580
agtgctggga ttacaggcat gagtcaccac gtctagcctg cagtcacttt tttttttttt  17640
ttttcctgac aaggtctcac ttgtcaccca ggcgtgctgt ggcatgatct cagctcactg  17700
caacctccgc ctcccagatt ccagcaattc ttgtgcctca gcctcctgag tagctggaat  17760
tacaggcaca cgccaccacg cctggctaat ttttgtattt ttagtagagc tggatttcac  17820
catgttgacc aggctagtct tgaattcctg acctcaagtg atctgctcgc ctcagcctcc  17880
caaagtgttg ggattacagg catgagccac tgtgcctggc ctgcagtcac ttcttaactg  17940
ctttcccaat ttcagtccgt attcccctcc actccatttt ctacatagca gcaagaacta  18000
ttttacatca ggtgctgtca ttttgttgtt taaaaccctt tagtcttggc tgggcactgt  18060
ggctcatgcc gataatccca gcactttggg aggtcaaggc aggaggatca cttgagctca  18120
gcagttcaag accggcctgg gcaacatggt gaaaccctgt ctctacaaaa aatataaaag  18180
ttagctgggc ctgatggctc acacctgtag tcccagctac tcaggaggct gaagtgggaa  18240
```

-continued

```
gattgcttgc acctgggagg ttgagggtga agtgagccat gatcatgcca ctgcactcca  18300
gcctgggtga caaagtgaga ccctgccccc agaaaaaaac ccttgttggg aggtcaaggc  18360
aagtgtatca cctgaggtca ggagtttgag accagcctgg ccaacatggc aaaaccccgt  18420
ctctactaaa aatagaaaaa ttagccaggc gtggtggccc tcacctgtag tcccagctac  18480
tcgggaggtt gaggcaggag aatcacttta acctgggagg cggaggttgc agtgagcaga  18540
gatcatgcca ctgcacttca gcctgggtga cagagcaaga caaaaaaaag aaaaaaaaat  18600
ctttgatctt atcaaattgt tcttgttttc cataatatca aaaacccggc atataaatat  18660
ataacaagta taagagtgta tcgcctaact atattatggg cagatacctt aatagtatct  18720
ttcaaataaa aaagatactt gccaactttt aaaataaata tatatggagt gcctgaggga  18780
atttcttaag gagtccatag tctatcatca gtctaccata atcagaatag gaactatagt  18840
ttattttgga atggattgtg aagattttct ctcactctgt gggttgtctg tttactctgc  18900
tgactgttcc ttttgccaca caaaagctct ttagtttaag tcccagctat ttatctttgt  18960
ttttgttgca tttgcttttg ggtcttggtc atgaagtctt tgcgtaagct aatgtctaga  19020
agggtttttc caatgttctc ttctagaatt tttatagttt caggtcttag atttaagtcc  19080
ttgatctatc ttgagttgat ttttgtataa ggtgagagat gaggatccag tttcattctc  19140
ctacatgtgg ctagccaatt atcccagcac cagttgttga atagggtgtc ctttccccac  19200
ttgatgtttt tgtttgcttt gtcaatgatc agtaggctgt aagtatttgg gtttattttt  19260
gggttctcta ttttgttcct ttggtctatg tgcctatttt tattacagta ccaggctgct  19320
ttgatgactg tggccttata gtatggtttg aaatcaggta atgtgatgtc tccagattgt  19380
atgcaggctc ttttttggtt ccatatgaat tttaggattg ttttttctag ttctgtgaaa  19440
actgatggtg gtattttgat gggaattgcg ttgaatttgt agattacttt tggcagtatc  19500
atcattttca cttttttttt ttcttcgaga cagagtctcg ctctgtcgcc aggctggatt  19560
gcaatggcgt gatcttgcct gactgcaacc tctgcctcct gggttcaagc aattctcctg  19620
cctcagcctc ccaagtagct gggactacag gcgcacatca cgcccagcta atttttgtat  19680
ttttagtaga gacggggttt caccatgtta gccaggctgg tctcgatctc ttgacctcgt  19740
gaccctcccg cctcggcctc ccaaagtact gagattacag gcgtgagcca ccgcgcctgg  19800
ccttcgcaat attaattctt cctatccgtg agcatgggat gtgtttcctt ttgtttatgt  19860
catctgtgat ttctttcagc agtgttctgt agttttcctt gtagaagtgt ttcacctcct  19920
tggttaggta tattcctaag tattttgttt tacttttttt gcagctattg tagaaggggt  19980
tgagttcttg atttgattct cagcttggtt gctgttggtg tatagaagag ctactgattt  20040
gtttacatta attttgcatc tggaaactgc tgaattcttt tatcagttct gggagctttc  20100
tggaggagtc tttagggttt tctaggtaaa cagtcttatc atcagcaaac aacaacagtt  20160
tgacttcctc tttactgatt tggatgccct ttatttcttt ctcttgtctg atttctcggg  20220
ctaggacttc caatactttg ttgaagagaa gtggtaagag tgggcatctt tgtcctattc  20280
cagttctcag agggactgct ttcaactttt ccctattcat tattatgttg gctgtgggtt  20340
tgtcatagat ggcttttatt acattgaggt atgtaatgga caggcattct aagcccttta  20400
caaatattaa ctcatttcat tcttgtaata actctttgaa gtcggtacta ttagaataaa  20460
cttaaaagta tgagaaactg aggcatggag ggctttttgc acaaggtccc acatcactct  20520
ttcttgtctc gggtaaccct gtgattcaca tagttgcaga ccacatagtc acaccggaag  20580
tttttcagga aacctttcta gacatcttgt taaaaactta caaaggggac aacttttgat  20640
```

-continued gtgtaaaaca attaggaagc atgtccagag tctaagtgtt ctttaaaaac caaaaaaagg 20700
ccgggcacag tggctcatgc ctgtaatccc agcactttgg gaggccaaga cgggtggatc 20760
acctgaggtc aggagtttga gaccagcctg gccaacatgg caaacccctg tctctactaa 20820
aaatacaaaa attagtgggc catggtcgtg tgcgtctata atcccagcta cttgggaggc 20880
tgaggcagga gaaacacttg aacccggggg tcagaggttg cagtgagccg agatcgcacc 20940
acttcactcc agcctgggcg aaagagcgaa actcagtctc aaaaaaaaaa aaaaaaagaa 21000
cctccaaata gcagtttgcc cattttctcc ttccaagttc acatatagac cttaataaaa 21060
gttatagact ccaacaacta gtaaatattt ttttccactt gtttcgttaa atttatttcc 21120
attaaattgg gagtaagatc aaaacagaat aatgtttact gtcatcagtt taagaataaa 21180
tgttgtgctt actccgcaga ggcggatgga tccactactt ctccccccac tgcaaaattt 21240
ggttaagatg tggaaactga tgataccata tgtgcaccag gacggtacga aaagggttta 21300
tgactcactt actgaggctt tttggggaga gcagggcagg cttcccatgc aggtacaaga 21360
atggcttgag aaagcaggaa aaggatactg gctctccttt tatggtgata agttgctgag 21420
tctggagtga aggtccttat atgccccttc agccaggtct tggtttgaac ttcccacctg 21480
ttccaaagga tggctcactt gggctttctt attagcttgc cctgaggaaa ggggtacagc 21540
ttgaaagctc ttggcagtca aatatcaaaa atgatgtcag actctttatt acaaatatat 21600
ttttaagtgc ttgtcattgt ttatgttatg gggcaaaaat cttgcattgt actaaacacc 21660
atgtcactaa tagtgtgaat agaagattca gcagactaat gtcaagaatg tttttggaac 21720
cttgaacaca gggaatatcc tgtgtgtctt ttaaaaacac ggaaaatact taacatctct 21780
attttgtttg ggttaacact gatgatgctg aaatgttggg tattgattgc ctgggtcact 21840
atgggcaaag aagctttttt tgtttttgtt tagttttatg atattactga tttctgtgtt 21900
ttgtcatatt ctttttgtat tttattaaac atgtttttaa taaatgggca ctcttatttt 21960
caaacttaat aaataggact cattttacta tgcatatcct gggttttaaa ttctgagcta 22020
agaaacaaga gatagaagaa ccaaatttgg gtaaaattca gagtcttaga tgccagaagc 22080
cagggagacg ctggaaaaca attattgaga tgtgttatag gttaactgat agttggaaga 22140
caacatgcct ttcaggtttg tggtttactg cctttcatta attctgacac agtttttaat 22200
attttaatat ctctgatatt gggatatgcc ttacaattgt tggcgagtca tagccagcat 22260
ttttatttct tggggacaca gaaaataatg tgtcttaccc tcagtggtgt cttcaattac 22320
atgaactatg acaattttta cacctttata agtcttttaa aataaaaaat tcatttatac 22380
ttcagaaaaa atacctatga ttagaccacg agttagggga gactttgcag tggtgattgc 22440
cttggagttg ccttgaagga agagtgggag ttggcccaac gggagtgggt tggtggagaa 22500
ggcattcaga ctgagagata gcatatacag catattataa agagtgtgct gtgttgggga 22560
aagggctaga agtttgatgt ggcaaaaatg taggctctgg gatgagatga gaatgataaa 22620
ctggctggaa tggtaacctg gagccagcct ttgaaaggct ctgtgtgccg tgcgagggag 22680
ttgaggctgt cttggcatgt taggcagcat tgtaaagcag ctctccctcc ctgtttgcat 22740
cagcaaaggg gtgggcagca ttggcaccaa taacagaaga gtgaagacaa tacatatgtc 22800
gaataagatc tctagcacag agttctccaa aatggaaagg gctgcaccct ggaatcagat 22860
ggaagggaga actttaccaa gggggtgcta tttccttctg ctctgttgtg aatggagttg 22920
gggttcagtg gcctgtttta gaagcctgtt tgtgggcaag ctgtgtgaca aagttgttga 22980

-continued aaaatgagga atggctttca gagggcagta ttaatccatt tggatggaaa tttaggagtg 23040
gaacatgtgt ttctaagctg tttttggctt tttcctaagg gctatatatt cttaaattaa 23100
aggtgattta tcattcttag tttcctctaa aatataactt tttgtagagg gaggctttat 23160
cacaaaattt aagaaaaaat aagtttgtta ttcttgctgt ggttttattt ttataagaaa 23220
tttgggaatt tgatccttca tagcagaaat ttgttcagtt tgggtctcca aacaagagac 23280
acagaaaatt tgttcatcag agagccactg agatatatag agagttagaa gatcagtcag 23340
gaaacattaa tggaaccgga attatacaat agaggaagaa aactgcaaat atttctgttg 23400
tttcagccta attttaacac tcattaccat ttgcagccca taagcgaatt gttttgcata 23460
gagcctgcat tgctaagcca gtagaaggaa ctagtctttt aaaaacattt tctaatttca 23520
ttccctttta tttttgagac agggcctcac tctgtcgtct aggccggagt gcagtggtgc 23580
gatctcagct cacagcagcc tcaactatcc aggctcaggc agtcttccca tctcagtctc 23640
tcaaataact gggatttaca gcatgagcca ccatgcctgg caaattttta aaaaatgttt 23700
tgtagaaaca ggggtctcac tatgttgccc aggctggtct agaactccta ggctcaagtg 23760
atcctcctgc ctcagcctcc cgaagtgctg aatgaaccac cacaccaggt cttttatttc 23820
acgtttaaat aaaaatgtta gatagtagta tgttgacata gttcaaaagt taaaaaagaa 23880
tacatgataa aaagtcttcc tcctagtccc ctgtcccttt gctgaggaac tcagtgttag 23940
tatcctgtgt atggttccag agatatttta tggagatgtg agcaaatcta taagtgatag 24000
catctcatac acatggttct acagctgctt tttttttaa cagaagtttt actgtgatat 24060
aattcacata ctgtggaatt cacccatttc agttgggatt cagtggtttt tcagtgtatt 24120
cacagtgtgt tgcagccgtc attacttata taatattaga acactttcat caccccataa 24180
agaaacctta tatccattag ggcttagtcc ctcttcccct agcaactact aatctacttt 24240
ctgtattaga aattttatat ggatagaatc agataatatg gggccttttc tgtctggcat 24300
ctttcactta gcataacatt ttcagttttc attcatgatg tagcatgtat caatatttca 24360
tttcttttta tagccataat attccattgt atgaatatac cacattttgt ttatctgttc 24420
ataagatgag ggacatgttt ttctcttgtg tatatactta ggattgctat tgctgagtca 24480
tcataactct gtgtttaacc atttgaggac ctgccaaact gtttttcaaa aggctgtatc 24540
atttctattc ccatcaacaa tgtagagagt tctaatttct ctacatcctc tccagctact 24600
ggttagtgcc atctttttga tatagccatc ctagcgagtg tgaagtggta tctcattgtg 24660
gttctaatat gcctttttgc taatgactta gtgatccttg agcaccatta agtgcttatt 24720
ggctatgtat gtctttggag aaatgatatt catgtacatt acccattttt aaattgttta 24780
atctttgcaa tgttgatggt aagtgttctt tatatatttg aatacaagtc tcatatatga 24840
tttgcaaata ttttctctca ttctgtggat gtcttcttgc tttcttggta gtttaaagca 24900
aaaaatttta aattttgggt aagtccaatt tacctattat ttcttttgtt actcatgctt 24960
ttggtgtgtt atctaagaaa ccattgccta atacaagatc acagagctta ctcctatgtt 25020
tttttctaag ggttttatag ttttagctct tacctttaag tctatgtttt atttgagtta 25080
atttttgtat atgatgtgct ttacattttg tacttttcat ttaataatat cttgggagat 25140
cattctattc cagcactaaa gaacttcctc agtttttctt atgatactat agtattctct 25200
tatgttgata tatcatagct actttaaaca gtctctcatt gatggagatt tacacaaaca 25260
tttgggtttg gaaattatct caaaatgaca ttgtggcttg aaagttgttt catatcaccc 25320
ttctcaaaaa tacaatttca tccatttcac agatttggtt gttccaggca actcatgcta 25380

-continued

```
ttcagaagcc ctggaataaa tcccagtcct ttgggtagaa tgaccccaag gaattcaaga  25440
tatttcattc cattaaatgt ttacagtaag tcaggaagca aaagtttctt tcaattatct  25500
gaaaatatat ggaaaaatac ttttggaggg acaaggtgct ctaaaatttt gttgtaccat  25560
ctaagctaca gtcagtttca gatgacttaa tggcatgtgt tcttttactc ttttgttgaa  25620
ttgttgtctg tgtgtataaa tcaaagtgag tagtaatcta aacttcaggc aatacaggca  25680
gccaactcag taagatataa aatatccaga gattatgaaa catataggtt tctttgttaa  25740
agaggaggct taggggaaaa tcttgaaata catcaacact ttcctaatct gcagaggcat  25800
atttggccac tggaaagtaa acaaaaaaag gctaatagga agctaagatt agtatggcaa  25860
aacccattcc ttcaacttct tgatctttac ctgtaacaca gttcttcact aagagactat  25920
tcttatttta tacactgatc aagtcagtgt gatatcacaa aaaaagaact tcagaattgt  25980
ttaaattctg tttctgttct ctatgatctg gataccttca ataagttact ttcctttttt  26040
gggctagagt attttcatct ataaaatgaa cgtgaactag atgagttttc aagcctatag  26100
tagaacaatt aattagaggt gaaatagagg ctactactgg aggcaagctg caatcagcag  26160
tggccacagc tggcctgatc tgcatggagt agacagtaag aatgttaaaa gcatttacaa  26220
aagttcaaaa ataatcatgg ctggagacat ctggctagga gcaaatagtc cgacatacct  26280
gagtggcccc agagggcaca ctaagttaca ttatgttcct aatgtccaca caagttctga  26340
gctaccaaat aaaggttaaa tggaatactg tagttctttc ttttgcagtt ttattttgat  26400
ataatttctc atttacagaa agtttcagat agaacacaaa gaataccatc tatccttcac  26460
ccaggttttt cttttctttt ctttttcctt ttcttttctt ttcttttctt ttttgagacg  26520
gagttttgct ctcgttgccc aggctggagt gcaatgccgc gatctcagct cattgcaacc  26580
tccgcctcca gggttcaagc aattctcctg tctcagcctc ccaagtagct gggattacag  26640
gtgcatgcta ccaacgccca gctaattttt gtatttttag tagagacagg gtttcatcat  26700
attggttagg ctggtctcta actcctgacc tcaggtaatc cgcctgcctc agcctcccaa  26760
aatgctggga ttaaaggcgt gagccaccgt gcctggccca cccaggtttt tcagatgtta  26820
acattttatt acatttgctt aaatctttct ctccccttcc tccccctccc accttgtata  26880
tgtgtttctg taccacatgg aagcagtaaa aatgccgttc ctttatttat aaataattta  26940
acatgtattt cctgaagact aaggacatca tgttatataa ccacagtgta attatcaaaa  27000
ttaggaaatg aatattgaaa cagtaacagt actgttatct aatatataga gtttatttgg  27060
atgatgcccg ttgatccaat aatgtccatt agagcagaag aaaatccaga atcatgtgat  27120
tcacttagcc atcatgtctc tttcatcacc tttagtctgc agcatttcct gagtcatttt  27180
ctttaaagtt ttacattaat atttttaatg tatattatat aagccagtta catagtagat  27240
tgcccctcat tcaagtgtgt ctgatgattt aggctatcca tatttggcag gaacaccacg  27300
gaagtaatgt tctgttcttc tcagtacctg atctaaggag aaaggtgctg cttatttgtt  27360
ccactgctgg tgatgttgac tttgatcctt ggttaaggtg ttgtctgcca tgtttctcca  27420
ctctaaagta actatttttt tccccttttgt aattaataac tatcttatgg gtaattcttt  27480
gaaactaggc aactatcatg tttctcctta aactttcact caccatatta tctttttatg  27540
aagacagaag gaaaataata cattttagta agagtcccat caaaatggtt gtgatgttta  27600
aaaaaataac ttcaaggaac atggagtagt catttgacag atataatcat gtagaattac  27660
ttactatcag aaattaaatg tatgcgccgg gcgcggtggc tcacgtctgt aatcccagca  27720
```

-continued

```
ctttgggagg ctgaggtggg cggatcactt gaggtcagga gttcgagacc atcctggcca  27780
acatggtgaa accccatctc tactaaagat acaaaaaatt agccgggcgt ggtggctcgc  27840
gcctgtaatc ccagctactc aggaggctga ggcaggagaa tcgcttgaac ctaggaggca  27900
gaggttgcag tgagccgaga tggcaccatt gcactccagc ctgggcgaca ggacgagact  27960
ccatctcaaa aaaaaaaaaa aaagaaaaga aattaaatgt atgcaatact tagtttttaa  28020
aaatatccct cacatatcta aagtcaattt gcaggtttat acatgtaaaa ataatttcat  28080
ttgttagtag tattgttttt gaaagattta gagatgagtc actcatggaa atttttctat  28140
ttttccagta ttggaggcag aatgaaacta acaaaaatcc tttggggaaa aaattattcc  28200
aataaatttt ccagtaatta ttccaaatgt ctcttctttt cctccctttt ttgtgtatct  28260
ttacaactca accaaaaagt ccactgttac tatatcaagc ctgcttaaga atcctccgtg  28320
atgcccactt cctacaggat caagttccag ctcatctgaa ttcagactac cttttcatct  28380
taaaactttt cctctattcc agccaaattc atcttcataa ttcatcttta aacatcatct  28440
catgtttttc tgtctctgca aaatgccctt tcaatctatt ttgagtcttc tcagtatacc  28500
agataaaatt caagtgcatc tttcataaaa tattccctga cctcttcatt tttcaaattt  28560
tgactttaat tagctacata tagtctattt gctacttcag ggggatggtt tagtaggaac  28620
ttaccttagg gaagataagg tggcataaat aacaataaga tacagaccag gcagtgctga  28680
ctccctgctt ggagggccat tttcccatgc cctgcactgt gccataccct gcacactgta  28740
ggacacaaag tttgttgtac acattcttgt gtatatttcc atgtacagta tctaatgaga  28800
ctcatcccac tcagaactta ggacttatta tatattcaat aaatgaattg ttcagttgat  28860
actgtctttt aaaaattctg ataaagccag catctcaata ggaagcaggg gcagatgttt  28920
ccattcctcc ctcatatttt actttctgtt caagggtgag tgtttacact ttgaactctt  28980
tctggcagtg atgaatcagt gctgattaat caatactctt ttgccagatt tttctaggag  29040
ccagagagag cttgactggg gtcaggcatc catttaaggg caggttggtt tccttatttt  29100
aggaaaaaaa atagtgctta tatgtttcat taatcataac ttcactttac aggaatccaa  29160
aaaatttagt gttatctgtt cactcctttt gaagtgttct ttgagagctc tctgaccacc  29220
aggaagtgta gtaggtgcta ggcacactga agccaagtaa ggtgtagttc catggctcaa  29280
ggagttgtga gtctaacagg ggagctgaag ttaattgcaa gggagattgt gcttttcact  29340
gaaaggtgtg tcttcggtag actacagcca tagagtcgtg tgagaattac tgaagagtgt  29400
ggcagaagaa aaggtggtaa gatcagggag ggctttacca aagtcacgtt caggtggagt  29460
cttgaaattc tgtaagcttt cagaggtggg ccttgttcca agctgtgtga gtatagccct  29520
gaggtaagct ggctgcgtgg catgttgaag gaagtgagag caagctgata ccagctcgcc  29580
accaacagcc tttgccaaat gtaaagcagg aaaaggaggg ttactttgaa aagcctagtg  29640
tgccatgctg agaatgatgg actttatgaa gcaatggagg agcttttaaa tgtgttttca  29700
ataagaaatt gtcatggaca aatcagcatt gaattcagat ctcattaaaa acgtgtccaa  29760
aggataactc gacagtaaac atatctcgaa agtacccatg gctgtaaaaa aggcgaagta  29820
tttctttctc catttaattt accctcccct gggtgattgg tttgtggtta ggccgtttgt  29880
ccagctgcag cagactggtt ttacaccctg aagtaaactt gaatttcttt tttttttttt  29940
gagacggagt ctcgctctgt cacccaggct ggatggagtg cagcggtgcg atctcggctc  30000
actgcaacct ccgcctccca ggtttaagcg attctcctac ctcagtctcc caggtagctg  30060
ggattacagg tgcccgccat cacgccgggc taattttcgt atttttagta gagatgggat  30120
```

-continued

```
ttcaccatgt tggccaggtt ggtctcgaac tcctgacctc aggtgatcca cctgcctcag  30180
cttcccaaag tgttgggatt acaggtgtga gccactgcgc ctggcctttg aatttcttaa  30240
aaccaagcag aacagtgatt ttcaagctct cttcattaga ttctagcagc tggagtttat  30300
ttatttattt atttgagaca gtctcactct gttgcccagg ctggagtgca gtggcgtgat  30360
ctccgttcgc tgcaacctct gcctcctggg ctcaagcaat cctccccgct cagcctccca  30420
agtagctgag attacaggtg tgcgccatga ggctcagcta atttttttta tttttggtag  30480
agatggggtt tcaccatgtt gcccaggctg gtcttgaact cctgagctca agcgatccac  30540
ccacctcagc ctcccaaagt gctgggatta taggcgtgag ccactgcacc tggcacagct  30600
gcattttaga gcttccaaat gcttagtgcg tatttcattt gtttccaaag tacattttaa  30660
accattaaaa tcacaataaa aaatagcaca cacacttgtg ggtggttata tgaataattc  30720
gtggactttg gacaccaatg tcctgttaac tcaggctgcc agtgcagtct tcagaataaa  30780
gtagattttt gtaatttctc tgccgacatg taaacttata caagtgtgtt attgattaag  30840
aagctgagta gagcactgcc ctggtatttt gaaaagttca ggttcatgca tgtgcactaa  30900
taatgtattt tacaagtgaa catacctata cctacagtca atcaaatgcc aggcaaggtg  30960
tggctcgtct gcttcaggca tggtcttatt gtataatagc atcgtaagtg aagtcccaac  31020
atctcatttg tatgctgggt agtaattaca tgtttcaaat cacctggggg ccttttaaaa  31080
atcctgatac ccaggccata ccccttacca attaaatcag aattcctgga ggtaggggtg  31140
ggacccaggc attagtattc ttttaagagt tagactgttt agagcagtta tggtttacag  31200
caaaatagag cagaaggtac agatttccca tctgtctcct ccatggcctc tcctattatt  31260
ggtatccccc accagagtga tacattgtta cagttggtga acctacagta acacatcatt  31320
atcacccaaa gaccattata tttacgttag ggttccttct ttctgttgta cgttgtatgg  31380
gtttcaacag atgtacaatg acatatatct attattataa tatcatatag agtaatttag  31440
tatttttcag tagtttcagt aggcatcagt atttttaaat ttttaaaaat tttttgctgt  31500
attttggagg agaggaatat attcttattg ccatcgaccg taggcgtatt ctttccaatc  31560
tcttgttctg tccttctagt aataattgta ttggcttttc tggtttcagt taaattttgg  31620
ttcacatatc ttcaaacata ctataaacct gataagattt gagagcccag aaagataagt  31680
ttaaggtaca gtggtctttt tcctgaagag caattttaat atgccatttc agcacctggg  31740
aagtgtaaaa tatgtgagag tgttattttc ttatctatca gatatgcctc cagagctttc  31800
aacatgttct ttatgttaag cattttagtc ccctgtactc tagcagaagt aaaatctgat  31860
ttttcctacc aaaagttcct tattttcatc tgcttgctaa gaaccaagaa atgtttggat  31920
gctttatgca gatgatacaa ttcaaactaa ctgcaactgg ggcatttgtg ttgcctgctt  31980
catgttttga gcctttagta tttaatggaa gccctgcgct gtggaaagtc tcctaatagc  32040
actttgtgca tcccaggggc cagccacggt gcttctgcag ccgcactgta gatgtttgtt  32100
tatttgtctc cactaggctg tccagtacat ttagaggctg agtctcagtg tgtgtttgaa  32160
agaatgaatg gttgattgaa gaaaggagac catttgcagg agagagagag agatgaacag  32220
tacatatata gaggagggca agaagaaatc ccagggcttt agagtcaagt gattagttca  32280
gtgactggcc tgattcagga ccctttgagc atttctcatt tgagaaacag aaagatcttt  32340
gttggtacaa aaaaggttaa ggatagatat gtggccagct ggacatcgat catgagcgga  32400
aggaattgac tccgagaggg atttggtaat cttgtgtgtt agtaaaagta catggatttt  32460
```

-continued

```
ttttttttac agtctcactc tgtcacacag gctggagtgt agtggcacaa tcacagttca  32520
ctgcagcctc aacctcccag gcccaggcag tcctcctatc tcagcccccct gagtagctga  32580
gatcacaggt ttgagccact atgcccagct aatatttttt tgtcaagacg agggctggtc  32640
ttgaaactcc agggctcaag ccatcctcct gcctcagcct cccaaaatgc tgggattaca  32700
ggcatgagcc accttgtctg gccagatttt tttttttttt tttttttttt tggtaatcaa  32760
atatttcaaa aggtgagtct cctttggggt gattctctca cacagaaaga tgattcttgg  32820
aggaaacata tctaagcatc ctccaaggta gtgtcagcat tcaaagttga tcctgaatta  32880
tctctgcaga cactttttgt gttgggcatt atgctgaagc catttgttgt agagcaagtt  32940
gatttttatg gctgagctta tctgaattta gtttgatata ttgtattctt tatttattca  33000
ttcattgatt cactgattca ttcatttttc ctgacattca aacaaatgtt tcttgaacac  33060
attgtgaaag ggccaggcat ttgtcaggta atgagggtat aatggtaaac aaggtagaca  33120
cagccctttg ccctcttggg ggtgcagaca gccggtcatt taagtggggt gtgaggagag  33180
catttacaag gaaaggacag gatgtcgggg agcacagggt ggggagtgtg gggcagacgc  33240
taggaggaag tcccttgaga ttaaggcctg aagcataact ttagacaaag agtgcagaag  33300
agtgtgttcc tgactaatga aaagcttagt ttattaatac ttagggcttg ttgaatggag  33360
gatacttttg cagccttccc ctactttgtg ccatccagcc aagagaggtc cacaatagca  33420
gccctgattc gcgggaggaa agagcccact tcagctgcag ggtggccctg ttcccaggag  33480
agatttgagt ctgaccccac agtggcagca aggcagctct gtgcctgtgt tatctccacc  33540
agcacacgtc attgagtcag ctttacttta tccagcctga ttgtagaagt catagtagac  33600
actgtgaggg aatcgtgtgg aattttcact ggagcattct gaaacttaaa aagtaaatct  33660
tttattgctt tactaatgtc ttcctgtgtc tgtcttttta aaaattttta ttgtaaaaag  33720
taaaatatat accaaagagt gtatgtgtgt acagtttaca ctatcagtat taaaatgggc  33780
acccatgtac tcatgaccag cctaggaaat aaaacattac caatagtgtg tacctttcac  33840
atcctgcctc ctccaccctg tcccagttgt aactactacc ctgaatttgt atttagtgtt  33900
ctcttttgtt cctctcttct agtatgtttt aaaaggtcat atttatgctt attaggagat  33960
attacagtat cagactcttg ctgtgtacca acaaagaaca agagataggt cagaacgctg  34020
tttaaataaa ttgcttgatt gtactctttt aagcaggagt ttatagtggt aacatcaaag  34080
tgcttaaaaa aattcaaaac aaaagccttt ttcagtttca aggaaaacct taacaaggtg  34140
tgttaaaaag ataaggtttt tagaggttgg gtgaggtggc tcacaccttt agtcccagca  34200
```

<210> SEQ ID NO 11
<211> LENGTH: 43320
<212> TYPE: DNA
<213> ORGANISM: Homo sapiens

<400> SEQUENCE: 11

```
ctttgggagg ccaaggcagg tggatcactt gaggtcagga gttcaagacc agcctgacca     60
acatggtaaa accctgtctc tacttaaaaa aaatagaaaa attatctagg catggtggca    120
cgcccctgtg gtcccagcta ttcaggaggc tgaggccaga gaatcacttg aacccagaag    180
gtggaggttg cagtgagttg agatcgctcc actgcactcc agcctgggca acagagcaag    240
attcttgtct caaaaaaaaa aaaaaaagat aaggttttta caaaccagta tgctataaat    300
ggacccagta gtaacatgac attgaattgc ttcaaccagt aacagcttca agatccctgc    360
ctatgttccc tgctgtgaac gtgtttattt gttcctaata atactgccac agtgtatttc    420
```

-continued

```
aaattatttt atggtatgag agtttgaatt tacttggagt aagatcatct cggcatgtag    480

ttgggagaca ttatttactc tattgtttca gtaattcaga atattgaaat aggtcagtca    540

tgtcaggaaa tagactctta ggtgaaccat tcttgaattt gcctttttct ttgtgattgt    600

gatggatatt gttttgtttt ctatctttgc tttttttttt ctttctgaaa tgttctggtt    660

gtccatccaa attgtaagaa tattacattt tgaatatcct ttgattattg taaaaatgac    720

ccctagtcag atgattccac agactttttg attacttgtc aaatgacttt gcgggctttt    780

ttcatttgaa ttgatttcct attttaaggg tcagtgtcac ttcattgcta aatgatacct    840

ttgagcaaca tggtacattt tagaaacctt attctccaga gtactctaag agaagggttg    900

tttggatttt atttgtttat attcttgccc tttaaactct agcataactc agcaggattc    960

ggtactcctt atagaaccgt tccccagaga gaaagtaagc tcagctctca tttccatgtt   1020

gaagtttgta tgcaagttta catggagctc agaatccaaa gttggcagga tatgaaaatg   1080

tttgtatatc atttaatcta ttttatttca tttcatttct gtgtttttat tcccaaagca   1140

attggtttta ttcaggaatc aacagacttt tttaaatcca tctataagtt tttgaaccaa   1200

agctttacta catttcacag ccatttttgc cactatgcca taattataaa tccttggcct   1260

caaagaaacc tatttaatat cttattcaga ttgagattct agtcttcagt gacatggaat   1320

gtagattaga acaatagttt ctgtatatct caatggtctt tacatttgca tttttagcca   1380

ttttaactag cccctaaaaa ctctctttta tgactctgtg gatgagctat ctgaattcaa   1440

caataatttt actatgtatt cccataatac tcctagtcat ttaaaaaaag gcaggggaat   1500

ggacaaagca aatcattccc aattgtttaa gaaaccagtg aactcatccc ttgcttggac   1560

tgcatagaat acagcctgag agggaaacct gtgatttagt ttctctcttt acccacacag   1620

gagaacactt ctgacaagat gccattcgtg ctcaccgtag ttggtcagaa actgcggctc   1680

tgtgcttggc aaaagttaat ttggatttta gatgctgtgt gcaaggaaac catgtgcagt   1740

tttaagcaag gatcttcact gaaatttctc gctgcaatca actacgcaga gtgcccagct   1800

ctcagcattt gacacagttg gccactcttc ccttgtctct catggcatcg tgatttcctg   1860

ggataccttt ggtctctttg tccatagcat tctctatctg ggtacactc acaataggca    1920

gaggaaaaac atggtaacca gggtggctgc tgcaacatat ttgagggggt cagggtaggc   1980

aatgaggtcc gagaggtagc caggagttag ctcatgtagg actttgtagg ccacttgagg   2040

actggcctga tctggctgat gggaaaccca tagaggattt tgagtagaag agtgatatga   2100

tccaacctga attttaatga gatctctttg gcctctctgt ggactagttg ctgtgaagtg   2160

gggaaggctg aaggaggcag acaccaatta ggaagctatc aatacttaat ccaggtgaaa   2220

gatgacagtg gcttggacca agatggtgac accaaatgag gcagagagag atcaatttct   2280

agataggttt cttttgtttt gttttgtttt gtttttttgag acagagtctc gctctgtcac  2340

cccgcccaga gtgtagtggt gtgatctcag ctcactgcaa gctccgcctc ccgggttcac   2400

gccattctcc tgcctcagcc ttccgattag ctggtactac aggcgcccgc caccacacca   2460

gctaattctt ttgtattttt agtagagacg gggtttcacc atgttagcca ggatggtctt   2520

gatctcctga cctcggtgtt ccgcccactt tggcctccca aagtgctggg attacaaacg   2580

tgagccaccg cacccggccc ctctagatag gtttctaagt agagatgaca tgtgtagctg   2640

acagcttgga ggaaagttgt gcaaaagaga ggagtcacaa aacagtccag ggttttggtc   2700

tcagccacta gaaaactggt gttaccattt actgatttgg agaagaccat ggaaaggaag   2760
```

-continued

```
tttgggggt gggaatcagg agtttaattt ggacatatta aatttgagat gatgccaatt   2820
acatccaagc aaagttgaat aggctgtgtg tgtgtgtgtg tgtgtgtgtg tgtgtgtgtg   2880
tgtgtgtgtg tacaggtgtc atcagcattt gaaactgagt gaggtcacca agagaaggaa   2940
tgttaaatag atacgcagtc agagaaatga tctgggctct taatcatata gaggtcagga   3000
gaaccaggga aggagcagtc aatgagataa gagaatcaag agggagaggc attccaaaag   3060
ccaaactgtt aaaaaacaaa aaaaaaggtt ttagcaggga gtaactttca aaggttttag   3120
atagggcaat aagacaagat ttgagaatta accatggagg tcattgcatt ccttaacaaa   3180
aacagtttct atggagtaac ggagatgaaa gcctaaattg gatttatcca agagaacaga   3240
agaggagaga aattggacac agtgtgtaca gacagttctt tcaagattga taaaataaag   3300
gaggacaaag gggccagagc tgcagggaga tgcagggtca aggtttttt tctctaaacc    3360
tgggatataa atataaatat gtatgtttat attgctgctg gtggtaattc agtagtgagt   3420
gaaaaattca gaagagggag aattgctgga tcaataaatg tccttaggta ggcaagagat   3480
gagatgcaat gtgcagtgga gaggttcatc ctggagaggg atgcagacag acactttcta   3540
cataggagtg cagggaaagc agaatgggca cagatgcagg gaggtgggta gctatggtgt   3600
ctggacatag ggaggttctc ttctcattgc ttctgttttc tcggtgaaat aagcagctca   3660
gtcattagct gggagtgaga aaccagagga agtggaaatt tgaggttaga gaggaaggtt   3720
taaactagtc ctctagggaa atggaaagca gatggattag ggcaatgtgg gtggattgct   3780
agacagcatt aagagtccct ttaaggttag tgaccataca tttaaggcga aaatagtcag   3840
tgggattgtg tgcttttgtc cagctgtggt cagccaccct ggtggagatg catagtggat   3900
agagaattga atttaaccag gatagaggtt ccaggtgaag gccctgaagg gagaggcaag   3960
agagctgatt gtgtatgcaa gggggtgagt ataatggtgg cctatggggt ttagtctgag   4020
taaggcaaat gaagacatgc tgggatttta gtttctgatg cagcttaggg atcagtgaac   4080
tcagggtttt ggaggatatt ggaaagctaa gaggtggtca attagggagt agagaagcct   4140
gaaactacga ttctggagtg ggtgcaggta ctgatgattg ggtctagagc tagtgattct   4200
caactggggg gatttcacct ctgaggaggc atttgcaatg tctggagaca tttttggttg   4260
tcacaactgg aggcagagga gatactgctg tcatctagta gaggccaggg gtgctgctca   4320
acatcctaca aggtatagca cagtttccca caacaaagga ttgtctgtgg cagttgtcag   4380
tagtgctgag gttgagaagc cctggtttag ggtataaaag aaaaacttca gctgaattaa   4440
atttaaagga gtttaactga acaaagaatg aactgcgaat tgggcagcct tctgagccaa   4500
ggtaggctca gagacgccag cgcagccacg tggcggaaga agatttatgg acagaaaaag   4560
gaaagtgatg tacagaaaac gggagtgagg tacagaaaca gctgcattga ttatagctca   4620
gcatttgcct tacttgaaca caatttgaac agttggctac atttgattgg ccaaaactcg   4680
gtgcttggcc caaggtgatt ggctacggcc tgtttacacc tacacttgtt atagttcaca   4740
gtgtacagaa aaacccttag gctgaactta aaatatgtaa ggaggcagct ttaggctaaa   4800
cttgattgaa caggtatgac catagaaatg agtggctggg gtaggcctga tcttacccag   4860
attattggag aagataaaca gactagggtt ttagaaggtt tatcttacaa ctgatgaaat   4920
ctccaaaaat gatgacaaga gtagtattag agaaaagtgt agatagccag ggatgggagg   4980
aagttaattt ctcagtgtgt ggcatcattt tctttttctt gagctagctg atgggctagc   5040
tttggatttc ataatcctgg ctaagagcta cacgttcaga ttagccaaag agtgttgtgt   5100
gtttttaaa aagccacctg tttattacct aactttggta taatgaaatc tgtgtcttaa    5160
```

-continued atagatgcct aaaagccatt tgggaatttg gttagtcttt ttgctcaaaa ttctgtgact 5220
gtaaacttgg acacttggtc taattccatc tttaaataat gtctcgggat gacaagtctt 5280
gcagctaggc ctcgaggaag ggatctggtt taagaaaatc cttgaagaag gctgggtgcg 5340
gtggctcacg cctgtaatcc cagcactttg ggggggccgg ggctggtgaa tcacctgagg 5400
tcaggagttc gagaccagcc tgggcaacat ggtgaaaccc cgtctctact aaaaatacaa 5460
aaattagctg ggcgtcgtgg tgggtgtctg taatcccagc tactcgggag gctgaggcag 5520
gagaattgct tgaacccagg aggcggaggt tgcaacactg cactccagcc tgagtgacaa 5580
gattgagact cggtctcaaa aaaaaaaaaa agaaagaaag aaaagaaaat ccttgagaaa 5640
ctttatttat agacttttag agactgtggc tttccagtac tcatcaccat ggagaaaact 5700
agtcaaaatc acacagagtg aataagggtt gcaagccagt gctgcttcct ggaataagct 5760
ggtccactag tctagtcttg tgctttgtcc ttcattttga actcaagtgc cctggggctg 5820
cttttctgcg tacccacaat agcaaggaac tcttttgttt gcatctcctc tgaaagaaat 5880
gcttgttttg aggtttggac cgcaaataat aatctattgt tccctgtaat aataatccac 5940
cctctttcgc agaaaaaaaa atctgcttga tgcagtatgg ctatcagttt atttaaaaga 6000
atagccaaaa gtgcccatta tgtcctgaga ataaacattt gcaagatggt tgggaggaat 6060
gggggagtac tcttgttctc cttggctgag agtcagttaa gtcttcaagg agaaaaaatt 6120
ctgaaaatga ccatcagtcc tggctgacaa tactcttcct tattctgccc gtctgttaca 6180
ttctaagaat tattgcaaca ctgcagatat ttattccaaa cgatttcttt aaaaaatatg 6240
gaagatgggt atttttaagt taccaatttt gggccaaata agtttttttt ttctgacttt 6300
cattttgtct gtgaaagcat ttcttttata gcagtatgtt caaattagca atctttaaga 6360
atttggcaaa tacttttaac agcaatcctt aacaattcct gcagttgcct actattgcag 6420
atcttgaaaa aagagccatt tttatattct aagtggtaga cacatttcaa ttactatttc 6480
ctgggcttag gctaactgac aaaacttgat gggtgaaatg aaaatgtgat atacggtgta 6540
atcagctgtt tacttaccta gcacagtgaa atcttatggt aggtatgatt gcactaacaa 6600
aaccaaaaca tgcatttttc ttccttaagt tctttataag aaaaggatca gttaaataat 6660
aaatgtggct ttaaaatgaa gttatatctt aggatagttt taattgcatt acatatggat 6720
gatgagaaaa gttcagtgtg ataacaattg cgtaacagat aagcatgaga actacttaaa 6780
gaaataaaaa tatgcccatc acctcattaa aaatagacca tcagggaagc caccaagaag 6840
tccttcagta ggtgaatgaa taaactgtgg tacatccata caatttgtat attattcagc 6900
aataaaaaga aatgagatat tatgccacaa aaagacacgg aagaaagtta agtgcatatt 6960
actaagtgaa agaaggcaac cttaaaaggc tacatgctgt ataattttaa ctagataaca 7020
ttctagaaaa ggcaaaccta tagagacagt ataaggtcag tgtttgccag gggtgtgggg 7080
ggaaggacgg caggaataaa ttggtgtagc acaggggatg cttagggagt gaaactattc 7140
tgtatgatac tgtaatggtg gagacgtcac tattcacctt tgtcaaaatc cataagatct 7200
acaacactaa cacaaatcct aatgtaaact atggactgtg gttaacaatg atgtaaccat 7260
attggctcat caattaaaac aaacgtataa cactaatgcc agatgttaat aataggagaa 7320
acaggttggc catgggagag tgagggaata tgagaattct accttctatt caatgtttct 7380
gtaaacctga aactgctctt taaaaagtct attagtttaa aaaaaaaatt caatataacc 7440
agactaataa aaatatctta actaaaaagc aatacaaacc taaactgtca gcaattattc 7500

-continued

```
tgtttatagt gctattctga ttgaacttag ctgtagaata ttctgccaga aatatgtaat   7560
ggcagtgaat tactgtatat atctagtaac tttgctgtat cttttcttgt ctggcaaaaa   7620
tgcacagtgg tattcatgtt aagtcctact ttcaactacc cttattcctt tctcttcagt   7680
gacagctgga gtatcagcct tggaagtata tacgccaaaa gaaatcttcg tggcaaatgg   7740
tacacaaggg aagctgacct gcaagttcaa gtctactagt acgactggcg ggttgacctc   7800
agtctcctgg agcttccagc cagagggggc cgacactact gtgtcggtaa gaatgcttga   7860
cttctcttgg ctagtcctgc ctcacaggtt tctttactgc tgtataattg gtgatccatt   7920
tttctgatgg ttcatttcca aaatgagtgt attttttatc tgttatagac ttcaaggccc   7980
ttcttttgct tcaggataaa ataagttcag catctcttaa atgcgtctgg tttccttgtc   8040
tttgatcagt tcctctccac catcaaatcc cattctgaaa ttgatcttaa ttgaccacac   8100
tgactctaat caggatttat cctgcatctt ttcatctttt attgccccat atttattgat   8160
atttgtttta tgtattatca aattttatat atatatgtat gcatcttctg atttgattat   8220
ctttttttaa tttagcgtat agtccatctg atttagcaat attgatttgg gagcttacta   8280
tgtagtgggt tatgtagggc cttcaaaaat gtctaaaaca gaatccttgc tctcacctag   8340
agatgattag gaggaaggct gatatataga tgactttgga gtaagataaa ggatgtaaca   8400
gaaatacagc accagagcat tgaaaaaagg ttatttagta actagtggag tgctggttat   8460
taaacatgaa ctgactatct tggttctggt ctgtaaaatg gagacgataa aacctcccac   8520
acaagggtgt taggaggata aagtaagatt attcaagata agtgctcagg agagtgtcta   8580
gctcttgagt tactaaaata caccatttgt tgttactgtt gctctcccag catgtggaat   8640
gcccttcata tattggcaca tattttagta ctgttgcatg tttcaggttg tcagtgttta   8700
gcaaggacag tctgtcatct atctttaaga atgcccaatt cttcttctga atggtgagtt   8760
acattgttga tcaccaccta gatgttgggc ccatcatatg cctatgccat ttaatcttca   8820
cagctctatg aggaagacag ggtggggagg atgggagaca ctgactcaag agttattcac   8880
ctgtggccat accacacagg ttagaattgt ttaaacttca atacggtatg atttccctta   8940
tgtattattt ctctctcagg tagaaaaatc tgctaataat atttacggcc tcataggttt   9000
tagggattac ctaaggcagt gcttctcagt atttttaaa atttattttt aaaaggagcc    9060
ttttcacatt tttcttaatc tctgcccccct tccatgaaat tttaatattg tagatatcct   9120
ctgcaactgt tttacatata aaagagaaag attttctcaa agcttcccac ccaagagcca   9180
gtgtttgctc ccttggggga gaatctcccc tatggagaat gcatagtcta gaggtcttta   9240
taagagaggc cttcccttac agtagccata agggtgagca caggaatcca tacagatacc   9300
atggaaagac ataaagaggc attctctgct tcacgtaaat atggcatcag catagaacat   9360
acactaatgt tcccatagag gcaagattaa acacataagt ttactcaaga gagtccaaag   9420
aactatttaa acatttaaag atttcccact gaagtcttct gcaagagtgg gtgtgagagc   9480
cacccagagg taataacttt cttttaaaga gcggttccat ttatgctgga aacagtcttg   9540
tcgtgtaggt ccatgaaggt ttacataact caaaacttaa tattaagaac atgctgtaat   9600
tctgattaat atttttagct aatcaattta tacttacaca cgagtctgat tgcagttaat   9660
cccagcatgt tcagttattg acataggatc ctttaattcc aaaatgtcgg gacacattta   9720
ataagatgag tgggttgctt ttttgttttt ataggtttta caggaaaagt atattcaaac   9780
ccagtatatt caaaagccat actgtggatg gctttttttgg cccatggcct tgggatccac  9840
atgtctgaaa ctgaactcat tttttctccc ttctgtttcc cttttctgct ttttttttt    9900
```

-continued

```
tttttttttt ttaggttaat tgtgttcatc tgcagatgag ttttgtaatc attttgtttt   9960
gttttgtttt gttttgtttt gttttgtttt gtgttttctg tcctttcctt ccctgtccct  10020
taccacttcc cttctgcccc caagaaataa gaacctttgc tggttcttcc tactttgttt  10080
ctggtgtcta gctttttgtc agccttcctg tgtctctgct gtctattgag caatgttaac  10140
tgtgtgcctg gtcttgtgca gtagcccctt gttattcttc tgcttctgtt tttctcatct  10200
ttcaatccaa ccctcatatg ccagcaggtg catagtctta gaacagctct ttcaccttgc  10260
cactgcaggt tatcaggaac ctagattccc attgtggaca acatttgtct agaattaaaa  10320
gctcattaca atttggccca gcctaccact ttagcctcac ttctgttctc ttatggcatc  10380
acttccagtt tagtaaaaat gctttgtgct ttgttttcct acttctgaac acttgtcatt  10440
taagctgtac cccattttta ccctctgtct cctccataat gcctcttttt ttttttttaa  10500
ccttttagcc cttaaaactc actaccctta tctgggccat tcctataata cagatccctt  10560
aatatgacag ttttcctctt cttcctgaat atgggtgttt taagaggact tgcctgtctt  10620
acatctttag tatacctcat agctttagca ccatggcttg tactttaaaa atattgattg  10680
ataatgattc tagtcttttc tgtgaatttt tcactgtttt atttccatct ctcactggtt  10740
tgaccaagac gttattcctc agtttgattc agcaaactat gtagttcctg ctgtgtccaa  10800
agtgctaagg agtacagaga taaatacatc ttatcctctg ccttcaaatg gcccccattc  10860
aatgagggag cctgactgag ggagctgtct cagacccagt gctgagaaac agcatcatgt  10920
agctcatccc cgctggttca gaaatgcaag gcagggaata tgtggagatg ttgtgggaag  10980
ggaaggcaga gagcaggtga tggaaggatt catttgcaaa gctgagagtt tatggttcat  11040
tttctagtga agaagagaga gtgaagaact ttgaacagat aagacatgat ctcacctgag  11100
aggccttaaa cattggaaat agcataagct ttgaaatcag agctgagttt gaattccatc  11160
tctaaaacct gtgactttgg gaaagtcacc aaggtttcct gagcctcaca ttccctattt  11220
atgaaatatc aggtaggcga atctcacctt gcagggtggt tgtgagggct agagagttgt  11280
tgggagacag ttttctatgg gtctttcacg tttttgcaca ccttgctagc aaaggcactg  11340
gctgcctttg ttctggactt tttttataca gtaactagct ttggaaggca gagatgatgt  11400
taccctctgg agcaaaggac aaatttgtgt attcttgagt atagtaaagg tagtgtctcc  11460
tttcagggct gaagtcagac atgtcttctg ccccttgtaa gagaatagtg ttccctgagc  11520
ttggggttcc tcggctgtga tgcaacgcct ctgcctgcac aacatccatg tgagcccctc  11580
catgtcatgg ctatgggact tgcggggcaa gagaaacaaa cacatgcttt ctgctcataa  11640
ggttctttgt ttctgagtct tcttcatggg agtgaagatt tcacaggagt ccgtgtcttc  11700
tgtcagcacc tatgaacctg tggccaacta actttgttag cttgtaagta gggtaaaatc  11760
tcagaccctt cacggttctt aacaagcatt taggtcatat gaaatgcagg gtaaatattt  11820
gataaatgtt ataataataa ccattattct ttatcagtga tcatttaggc attgtggaag  11880
atgatgagtt agacatacca gttaagaggc catagtccaa gatgatgaaa acataaaaac  11940
agatattgtc agtgggaacc gaatagagag aagagagaac tgagagaaac taatgagaca  12000
ttgacaatat tgggggatta actggatagg aagaaagaga atcaaggatg acttcaagat  12060
ttatggtttt ggaaagaaac agtagccatc agtgaagaca cgatacatga agaggggaag  12120
atgaagtttg taagagaggg tgacaagctt gggggagagg ggcagccagg tggtaaagtg  12180
agtaggcaag gagtctagag cttaggggac gctattgatg gagagagagg tttgggagtt  12240
```

-continued

```
aagaaaatct agatgatcat taaatcatag gaatggatga gtctgcactg gggttttcac  12300
cgtgctcaaa gggttctgaa aatgttctgt ttgaattgct aatagagctg gtttctatcc  12360
ccagctccac catcaccccg tccattaacc agaacaaaga catcaggcct ccagcatagc  12420
tgcttggatt agagccaagt gtgaggatag atcccctccc actgggcctt aaccctgctt  12480
ccaggtgctg agtttgacaa ggtttacttt gagaagacag ttcctttgct gaaagcagga  12540
ctgaggagag actgaggagt ggaaagagaa aggggctaaa ggctgaactt tcaaaagccg  12600
gcaagagtat cttgtgttat ctgggctttg ttcctttcac acacccatga cttttccata  12660
ggaaaccaga aggaagaggg cgaaactcag attagctgat ctgagatatt taggattctt  12720
ctcctttgtg cttctgtgta tcttagtggt aagctaactc aacactaagc tttctgaagc  12780
cttgggaatc actgggctca atcatggtgt tactggaaga acattggctt tgaagactca  12840
gatgggccta aattttactc tgggtcccca atttactatc attggtacct tgggaaaatg  12900
gcttctctta agtctccatt ttgtctttta taaaattatg ggtggtaata attatatcaa  12960
tgaaatattg agaggattag aggtgatata tgagtctgat tcttccattg aaacctggca  13020
gggttgagtg ccgtgatctc taaacttctg tctggcttag attccataac ttgtgatttg  13080
taatatgatg ttgcatttct tttttttttt ttttttaatt gatcattctt gggtgtttct  13140
cggagagggg gatgtggcag ggtcatagga taatagtgga gagaaggtca acacgtgaac  13200
aaaggtctct ggttttccta ggcagaggtc cctgcggcct tccgcagtgt ttgtgtccct  13260
gggtacttga gattagggag tggtgatgac tcttaacgag tatgctgcct tcaagcatct  13320
gtttaacaaa gcacatcttg caccgccctt aatccatttc accctgagtt gacacagcac  13380
atgtttcaga gagcatgggg ttgggggtaa ggtttataga ttaacagcat cccaaggcag  13440
aagaattttt cttagtacag aacaaaatgg agtctcctat gtctacttct ttctacacag  13500
acacagtaac aatctgatct ctctttcttt tccccacatt tccccctttt ctttttgaca  13560
aaaccgccat cgtcatcatg gcccgttctc aatggtcgct gtctcttcgg agctgttggg  13620
tacacgtgca gaaaggctgt cacttcacac ttggaagatt gcacagcggc caggcagagg  13680
cgctcctcac ttcccagacg gggtggtggc cgggcagagg cgctcctcac ttcccagaca  13740
gggtggccgg gcagaggggc tcctcacatc ccagaggatg ggcggccagg cagagacgct  13800
cctcacttcc tagatggggt ggcagctggg cagaggctgt aatcttagta ctttgggaga  13860
ccaaggcagg tggctgggag gtggaggttg cagcgagccg agatcacacc actgcactcc  13920
agcctgggca gcattgagca ttgagtgagc aagactccat ctgcaaaccc agcaccttgg  13980
gaggctgagg caggcagaac actccaggtc aggagctgga ggccagcccg gtcaacacgg  14040
caaaacccct ctccaccaaa aatacaaaaa ccagtcaggc gtggccgcac gtgcctgcaa  14100
tcccaggcag tcggcagccc gaggcaggag aatcacagga gcccgaggca gggaggttgc  14160
agcgagccaa gatcacggca gtacagtcca gcctcagcaa cagagggaga ccgaaaaaag  14220
gaggagagag agggggagag ggagagggag agagatgttg catttctttc cgtatgaagt  14280
ctttaaaaga acctttcata gcatgcacat tacagagttt aggaattctg cctttgagaa  14340
tagttcatgt gttccttttt tctaattgca gtttttccac tactcccaag ggcaagtgta  14400
ccttgggaat tatccaccat ttaaagacag aatcagctgg gctggagacc ttgacaagaa  14460
agatgcatca atcaacatag aaaatatgca gtttatacac aatggcacct atatctgtga  14520
tgtcaaaaac cctcctgaca tcgttgtcca gcctggacac attaggctct atgtcgtaga  14580
aaaaggtact tccttgagta ttttggcagt aataatgcag tctcctttat ctcatgtttg  14640
```

-continued

```
gttggaaaac atgagttgca tttcatggtg ggtttggagg gaggattttt gccatacagt  14700
tgtgctccct gttgccacga acctgtggct ctaccaaaca cacttggagc tgggaaactt  14760
gttgctcatt ctgacccaga gtggctgatt tctccatttt tattcctacc gtctggtgcc  14820
tattggtcta atttcaggag tatgaatttt tcagtgttaa ttagaagaaa gaccaaattc  14880
attatgtttg gatgtgatgg gcagtgggaa agaaggagat tcatactgtt ttatattctc  14940
caggagaaag ctttcaacaa cagcacagtt atttcttcct tttgattttg agaacaaaca  15000
ggaaatgcag gttctggtgt ctcatttttg agacaaagtc tgttttgttg gagagtagat  15060
ccaggtaaat tcacacctcc ggtttttctt tagagcactg agagggattg taggtgtaga  15120
aatgcttagt tccatagttc attctttctc atctaatatt cacatgtcat gaattacata  15180
gtaataggat agatagtagg atctcatagt ttggataata aaagagggta cggtaactgc  15240
taaatgaaga tacttgctcg ttaatttaat aaaattccat gttttctctc tgtagcaatg  15300
taccttaaaa ctattttgtt ctttctctct agagaatttg cctgtgtttc cagtttgggt  15360
agtggtgggc atagttactg ctgtggtcct aggtctcact ctgctcatca gcatgattct  15420
ggctgtcctc tatagaagga aaaactctaa acgggattac actgggtaag aaacactgtt  15480
tttttagggc aggggtggag ggagggaatc agggtttata gaaacttctg tatttaatga  15540
aaaaaggatt ttaaagaatt aactactatt ttctttcatg tcagaatcag gcagtctcct  15600
taggaggtgt tctaacatgg gcaagtggaa atcagtgggc ctgctattaa atgtggaata  15660
tgattctaat ctctgttcca gtttccttct taggtttggt gagatgagct gctcagcagt  15720
ctgtgctctg tgtttcaata ccatccacta tgcaattagt attcttaaga catcacttac  15780
ccaatttaag agtttaattt caatttcttg ctaataaact cacaaggtgg ttctttccag  15840
ttaggaaata taaaacccta attaagaagt tgtgagctgg aattagtggc atgtgcctgt  15900
aagtcccagc tacttaggct gtggcaggag gattgcttga gccgaggcgt ttgaatctag  15960
cctaggcaac atagcaagat cctgtctctt taaaaaaaaa aaaaaagaaa gaaagaaaga  16020
agaagaaaaa gcagtggttt taataaacta cctcccccag cccagtgtga tgatggtgca  16080
gggcttttcc tttttgtagt tcccctaccc cactccaagc ttaagtagct ttattgcttt  16140
gatcattctt agctagattc acccaaaatg ggataataag aattgatgac aaaatatatc  16200
agcaataaag aaaaatagac tttctttttg tttatggctt ctcagatgga acacgtttaa  16260
gcatagggtg tgtatctaat taaaggacct tctcttttcc ccactccagc tggaaagcta  16320
acccatataa gctatgtaga actcatgtgg taagactggg agcagaggct ggattcaagt  16380
tgatatagca tgagcagtgt tgcagatgca cagatctaac tttagccatc ctgaagggac  16440
tctgatgtga aaggattgca tgtcctgaac tctcttgctg gtggatggtg ggaacctcta  16500
tctatgggct ctgctgatct agagttttta ggagtgctgt gttttaacaa gtttgagtgt  16560
tcaaattcag atattacttg cttggaatgc ttctattctg ctgactgtat ctgcccccct  16620
tgcatggtga gtgttttatg attaaatata gttggactat tggtttcaac atgagactaa  16680
tccagggtgg tgacatgccg gtctttgtag ttcttgcttc ggggttaatg aggggcagga  16740
aagagttcct tagactcctg catggcatca tgaatgctgc tgttcttctt accttggttt  16800
ttttcctcct cctctacctt ttctaccttg gtgtgctggg atcagatcct gcttatcttc  16860
cacttcttaa gaaaagctga catagaagac acattgggac tataacaggg ctgggtctcc  16920
tcttccactc ccactagaca catggtaact aatcacattg cccattactg ttaatattcc  16980
```

-continued

```
tgtgtatgta ttcagcccct ctcccttgtt gatgactaac cagctagctc tgagctaacc  17040
caacagctat tatgatttgt ccatgaatat gtcacatgtt tgtattggaa acatgttgag  17100
catactatct ggatgaaatt ggattgtgaa gttacataga gtttttatgc acatctgaat  17160
atttgtgctc ttcatgtaaa atgccattgt gtatgtgtgt gtgtgcatta gttttctttt  17220
ttcatatatg tattatgtta tcaatattta agatcctgac tgattatgta ttagaataat  17280
taaaccattt tggttcagag catgtagcct cccatttcac agaaggaaca gtttgcagaa  17340
tgcatggtat gctttggtct tagtaatgac actttaaatg tgattctccc caaactccta  17400
agttttaaaa gtatatatca aaaggcttta agctgtactg atgacacatc tcattggaaa  17460
atccctacgc tgtaccccag ctttcttact tcctggcatt cactttccct gattcattta  17520
tgagatagtg cttgttgtta aagactactg tcaccgtgaa aaggttcagc ctgtgtgacc  17580
tggcattccc taatttctca ttcatgactt cctgagtttt tggggggatt tgattgtggt  17640
attggtaggg aataaaaata tggagagaac aagataagcc aagacttgcc tggatatata  17700
tctgtaattt aaaacataca ttcagaagag gtttgccttt gattataaca aaagtgaatt  17760
gccattaagc taataaaagg taccatagag cttgttccct taaaccttta tcccaaagga  17820
gggttgatgg caggggggaaa agacaaacag caaaaggata aatgtgtatt gtaactagaa  17880
ttccaatatg atttttgtaa actgggttga agaggttgta ccatatttgt ttctgtgcct  17940
cccccagtga tgagttcatt gacttagaag aatgagtgag tgtcaggtat agaaaatagt  18000
ttaaaaacat gtgatcattt tgacacccat tgttatgttg tcttttgttt ttatatatct  18060
gttgcttcat cttgccgtca gttgcatttc tatatttttg tttctattta tttattatta  18120
ttatttttta catttgttct tcaaattgcc aattcatcag ctgcagtaca tcagagagtt  18180
tgtcaccagt taagcaggct cctcggaagt ccccctccga cactgagggt cttgtaaaga  18240
gtctgccttc tggatctcac caggtaatgg ctgattgcga ttctgcccac tgcactgttc  18300
cctacagctt ggtgctctgt cacttccttg ggtgtggaaa agaatactga gctatgagag  18360
acagagacag agacagacag acagagacaa agagagagtg ggagtgagga attaaagggc  18420
tggcctagga agaccacagg aaaatatgtg gtgaagaatc tgcttgagta aagatttcca  18480
tgaaaccacc aataacataa attgtttact aaccatgtag cttccttgcc tcaagcagaa  18540
ttaggaaatg gctttgtcag taaaagattc tttaattgcc caaggaaatg aatctaatga  18600
aggagattct ttctgtattg aggtactcta agataagaaa ttagcaagga aaagttggta  18660
ttcttagtat tgataataaa accaaaatta ttttctgtgg attctttaga aaaaatggaa  18720
agtaagcatt tatctgaata attaataggc ttgatgaaca aggaatggtt ttggtttcta  18780
cttgtagaaa gtacagaaga gaaacaggtt ttatttggaa gttagcatat aatctagctt  18840
tgtgtgtttt ggctgtagta ttttaattat aactgtggct tggcaaaaat tccatagctt  18900
agttcagttt gatttttctg gggtagaaag catgctaaag aatttggcca gttatagctt  18960
tgtcctaaaa aggtgttagc tggtgggaat ggatttaaga ggaaataaag agagtaacag  19020
tgttttgtgg gaaaagtacc catagtctta ttccatagtt gttatatgtg gtgaggaaac  19080
taaggcattg tgatgttaaa ttactaaaag cacacaccca gttagtgaca gaactggggc  19140
tagaacccag gtgtctagat agcatgttct ctaccacagc atcaggctca ttacttgttc  19200
ctgttctatc tgtctgtctc tctctcacat tacataaatat atgtcagata cctcagtcta  19260
ctaatttggg ttgtgaacag gaatatggtt gtaaatgaag acatgaaagt tacatacaca  19320
taggcatagc atctaaaaaa gcattggaac atttttattc cgcccttgaa gcactatgga  19380
```

-continued

```
agttgctttt ttgctgaaaa caaaccagaa aaaagaaaaa gaaactgtgg ttttcaagac  19440
agtggaacac aaattatgca gcactgtcat ccccaaaaga aaggaaacag acaatgtgag  19500
ccgtgttatt gccccagtgt actgccttga agcagtttcc acactgcagt gtaggtgggg  19560
aaaatggaaa ctgggcccag ctgtctcact caattgagaa ggcggaaatc agaatttggg  19620
gaggtcaagg aggctaagat ttatgaggct gagtaccaaa gaaggaacca tagagagagc  19680
gtgctaggat gagcacgagc acttcagaga tttggagcgg ggtccccttg agtctttgtc  19740
tgattacaga gttgtataca cataggagaa cactctctga aaccagggga agaactacct  19800
gaaatgcagt aggttgcaca atgcctggtg ctcacacagg tgagggacta gtttgtgttc  19860
ctaagagcca gagtagagag acttataata cacagggtat tggttggggt tctcaaaatg  19920
gtcataccta aatgggttaa attagtacca gaataaagga tgctatggac ccaccataac  19980
aaagcttaaa aggaagcctt taaagaatca aactaatcca aaagtaattt agttgcattt  20040
tacaacaaaa tccaacacgc tttatgctac aacaaaattc atcacccaac aatgtacaat  20100
ttacaatgtc tggcaccaat caaaaactac caggcatggc ctggtgcggt ggctcacgcc  20160
tgtaatccca gcacttaggg aggccaaggc gggtggatca cgaggtcagg agttcgagac  20220
caacttgacc aacatggtga aaccctatct ctactaaaaa tacaaaaatt agccaggtgt  20280
ggtggtgcac acctgtaatc ccagctactc aggaggctga ggcaggagaa tcacttgaac  20340
ctgggaggca gaggttgcag taagccgaga tcacaccact ggcactccag cctgggtgac  20400
agagtgagac tccatctcaa aaaaaaaaaa acaactatca ggcataaaaa gaaaccaaaa  20460
aataaaacac ataagccaga tatagtggtg tgtacctgta gtcccagcta cttgaaagcc  20520
taagtgggag gattgcttga gcccaagagt gtaagaccag cctgggcaat atagtgagac  20580
cctatctcaa ataaatagat gggtggaaag aaggaaggaa ggatggatgg atggatggat  20640
ggatggatgg atggatggat ggatagattt aaaaaaataa taatttaata attaattaca  20700
ataaaaaatc aggagaaatc aatcagaaac aaattcagaa tggatggaaa tgatgggatt  20760
cataaacaaa gaccttaaaa tgagtattat caatcttatt agtaaactta aagatgtaaa  20820
ggaaagcttg aacccaatga ggaaagaaat agatatctaa aacagaccaa aatggaactt  20880
ctggaaataa aaaaaaattg gatggtgtta acaacagatt agatactgca aaaaaaaaag  20940
gtcaatcaac ttgaagacat agcaatagaa actatccaaa atgaagctca aagagaaaga  21000
cagatggcgg ggtgaaagtg aacagagcct aacacggtga aaacccatct ctactaaaaa  21060
tacaaaaaat tagttgggca tggtggcacg tgcctgtagt cccagttact caggaggctg  21120
aggcaagaaa atcacttgaa cctgggaggc agaggttgca gtgagctgag atcatgccac  21180
tgtactccag cctgggcaac agagcgagac tctgtctcaa aaaagaaaaa aagaaaaaaa  21240
agaaagtgaa cagagcttca gtgagccacc ggacaatatc aagcaatcta attagaatcc  21300
gagaagaaaa agggagagaa aaaaatatgt aaagaaatag tgaaattttt agtaaattta  21360
atgaaaaaca taaacacaca gaaagcaata gcgaaaattg ctgggcgcag tgactcaacg  21420
cctgtaatcc tagcactttg ggaggctgag gtgggtggat cacctgaggt caggagttcg  21480
aaaccagcct ggccaacgtg gcaaaacccc atctctccta aaaatacaaa gattagttgg  21540
gcatggtggc aggcgcctgt aatcccagct acttgggagg ccaagacagg agaattgctt  21600
aaaccacaga agcggacatt gcagtgagcc aagatcgcgc cactgcactc cagcctgggc  21660
aacagagtga gactccatct caaaaaaaaa aaaattgact ctttacagca aaaataatga  21720
```

-continued

```
cagcatttta tgaggctata acatgtggaa gtaaaatgta tgacaacagt agtacaaagg  21780
atggggtgga aggatggaag aatactgttg taaggtcctt atattatcca tgaaattata  21840
atttgaaggt agactgtggt aagttaaaga tatatgctgc aaattctaga gcaaacactg  21900
aaaaaaataa aagagataga tacagctaac aagctctatc tccgaatggc aatactgata  21960
agaacaaaat tctgacatat gctacaacat ggaaaatggt aaatgcggat ggtaataata  22020
tcaacgttgg catcagaaca agaaatagaa ccagagatag agggactttt tatgatgata  22080
aagcgatcta cttacaaaga agacataatc ctaaatgttt atacttgtaa tagtagagct  22140
tgaaaataag taaaactgag agaattggaa ggaaaaattg acgtatttac aatcatagtt  22200
ggaggtttca acaagaaact ttaatgtaat catttcaaaa tactcagtta atccaaaagt  22260
gagcaggaaa ggaggggaaa atgagcaaag ggtagatggg gcaaatagaa cacaaataat  22320
gaagtggtag atttaaactc aaccagactg atgattgtat tactataaat gggctgagtg  22380
tgccaataaa aggtggagat ggacaaattg gatagaaaag caagaaccaa tcatatgctg  22440
tctgcaataa accactttaa ataaaaagat ccaggtaggt taaaaatatt aatacaagga  22500
tgaaattgaa agcagagtct tgaagagata tttgtacatc catgttcata gcagtattat  22560
tcacaagagc caaaatacag aagcaaccca agagtccatc agtatacaag tggataaata  22620
gaatgtggta tatatataca caatggaata ttattctgtc tttaaaagga aagaaattct  22680
gacacatgct acaacatgga tgaatcttga agatatgcca agtgaaataa gccagcccaca  22740
gaaagacata ctatgtgatt ctactaatat cccataccct acagtggtcc agttcataga  22800
gacagaaagt agagtggtag ttgttgggga aggaagaata gggagttgtt taattggtac  22860
agtttcagtt tttgcaggat gaaaatatcg tagagattgg ttgcacaagg atgtaaatgc  22920
acttaacact actaagctgt acactttaaa atggtaaaga tgctaatttt tatgttatat  22980
atattttacc acatttttta aacagtaaaa ggatggaaat gatatgctac attaacacta  23040
atcaagagaa atctgggtgg taataatatc agaataggct tcagaacaag aaatagaacc  23100
agggataaag acagactttt tatgatgaca aagtgatcta ctcatgaaga agacataatc  23160
ctaaatattt atacttctaa taatagagct tgaaagtaag tgaagtaaaa ctaagagaat  23220
tgaaaggaga aattgacata ttcacaatca tagttggagg tttcaacact cctttctcag  23280
cagttggtag aacaggttta cagaaaatca aaaaagatgc ggaagactta acagtgaaac  23340
cagtttgagc taatagacat ttataaaaca ctccttccat caagcgcaga attcttactc  23400
tttttaagta cacatgaaaa ttaaccaaat atagaccata ttctggttca taaaacaatt  23460
ctcattaaat ttaaaagggt tggaatcata tagagtacgt tctctggcca caatggaatt  23520
aaacagaaat caacagaaag atacctggaa agtctcaaat atttcaaaat tgaacaaccc  23580
atgagtaaaa caagaagtca caagaaaaat tagaaaatat tttgaactga gtgaaaataa  23640
catatcaaaa tttgtgagat atagctaaag aagtgctttg aagatttgta gcattaactg  23700
tttatattag aaaaaaataa agctctaaaa ttgatgatct aggcttctgt ctgaagaaac  23760
tagaaaaaga agagcaaatt aaacccaaca taaacagata gaattaataa agagaagagc  23820
tgtggaaaaa tcagctgaca ttctcattgt ttccctgtag gtaatctgtc gcttctctct  23880
ggctgctttt cggatcttct ttatgccttt ggtgtttggc attttatata ctatttaatt  23940
atagattatc ccttgttgca tctgcttgta atttcattgg acctcctgag tcttaaggtt  24000
gatgtcttta ataaattcta aaaaatttct agtcacaatc tctttgaatt tttcctttct  24060
gcattttatc tatttatctt tttatggaac tctgattata tgtgtattat actttctcta  24120
```

-continued tgctctaagt ctcttaacct ctcttgcaga tctttcattg tattgtcttt ctgccatttt 24180
ctgcataatt tcttcatctg ccttcattca ctaattcctt agctgtgact agtctactgt 24240
ttagcccctt ttaaaagttt ttaaacttca atttcatatt acaggtttat tttctagaaa 24300
ttttatttgg ttctttttta aatatacctg gttaattttg atagttcctt ataacttcat 24360
attttcaact atcttattta agcatgttaa atattcttat tttatacctc aaaactgata 24420
attccagtgt ctgtagtctt tattgatctg actacggttt ttgtttctat atttcttgct 24480
aatggtggct attttctcat ctcatgggtg ttttataatt tgaagactgt acttacgttc 24540
ttggcacttt gtacaaattg attgagtctt catttaaaat atatttactc atgagaagat 24600
ttgtatttct tctgcctgtg tcttggatac taccaaccca gtgagaagaa atgcacagga 24660
ggtaaaaaaa ttttgagaac ttgaatggta gactataatg gccccacaaa gaggtccaca 24720
ttctaatctc tggattcttt aggatatgtt accttacgta tcaaaaagga cttggcagat 24780
gtgattaaat tgccttgaga tagggagatt gtcttgggtt atctgggtgg ctccattgta 24840
accataaagg tccttagaag agggaggcag aagggtaagc atcggggaga gactggaaga 24900
tgctatactg ctgactttaa agatgaagaa ctcatagcca agaaatacag gcagcttcca 24960
gaagctggaa aaagcaagga gacagattct ctcctagaac ctgtggaagg cacgcagtcc 25020
tattgacacc ttgatcttag cacagtgaaa cacatttcag acttctgacc tgtaaaactg 25080
tgagataatt aatatgtttt taacaccttt aaaattgtct ttattctcct ccctcaaact 25140
tgattgcgaa tctggtgggg taggattccc agttggaaat cattttcctt cagcattttg 25200
agtcattgct gattgttctg gcttccagca ttgtggctta gaagctgatg ccattctgat 25260
tcactcttag ggcagaggaa ggtagggtca tctacctgag caaagggaga gtaaagacca 25320
gaaccaaact ggggctcttc cagccaagtg gagtgggagg ctgggttggg aaggtgttag 25380
ataggcacta cctagagttt agagtgttaa ggcactgtgg aaaaaaataa gaaaattttt 25440
tttctttgtg aagcttagtt ttgaatgaga ttggtataaa gtaattttttg tatatgtatt 25500
tgaggagtag ttggttttct agatcctttt ctggatatcg ttgatgctct gtatgcaaaa 25560
ggtaggtttt tgggttatgt tgttaaacag tgattgaatg gaatatttat gtatttgtca 25620
actatagtgc atagcataga cagggtaatg tttcaagaag tagttatgtg cgtttttcct 25680
ttagtcctca caacagtcct ccagggtaag ttcttctgtt gtctctattt tacacatgaa 25740
gaaactgagg cttagttagg caagtcactt gctcaaggtc agtagttagt ggctgagcca 25800
gatctgtctg gttctaaggc acatgtatat tttatcctgt ccaatttttt tcacctctgc 25860
tttgataatc agtatttgtc tcatttatct caaagaaagt cataatacat agctgtgttt 25920
catatttata ttttacttaa aaaacagtgg aataaatact aaaaaaaaag gtgttctgtc 25980
agtagtcaat gagcacatgg taaaaataga tgttctttct tagtgattcg tgctaggctt 26040
ttggggatga ctcctctaac acctgaagga ctagaatcaa attaaatagg gctacaggct 26100
acagagactg tgaaaggtgt actacaggac acaacataat gactcctgag cagttaattt 26160
gtagttagaa gcaggtctct ttgcttttct agaatccttt cttcctggac cttctccccc 26220
aaccttcacc agttatggtt tttttattgg aataaataat taattttggt acaagtaaac 26280
ttcagaggta attttatctc tagttgtaac taaaataata ggcctatatt aagcaatgtg 26340
tttcttgaaa cattttcaat agctaaggcc tattcatgca gaaagtagct gaaaacatac 26400
tcagaccaat ttttcacttt attgttgtaa ttctttgtgt aaaagcaaag ataaataaat 26460

-continued aaatgaaatg gagggtgggg agggtgagta ccaagagata gagtaaaaca gctaggttaa 26520
tgtaggtttt gttgttgttt tccttcttta ttatacccaa aagtgaatgt cttaacaatg 26580
gtaggttcat ttcaaagttg atcgtggttc tgtggatcct cttgaagtcc tgagcagcct 26640
catttgccct caaaatcgag gtgctgaggc atgttccata gagactcagg gctccttcca 26700
cctctaaata gcactcagaa tcaaacttca tagaggtgtt ctagattgag ctagatctgt 26760
cagcagaccc caatctcaac ctacatctgc agtttctctg catcctttct ttcatccatc 26820
ccttcatcca gcacctgtgt tctgccaagt tctaggaagt taacaaagtc cctgacttaa 26880
gaccttatta tattctaagg gggaagagga atgaggataa catcaggcag tggtaaacag 26940
tttgaagaat accaagtcca tcagcaggaa gggatttctt cagtgttttc ccatttactt 27000
tcatgagata gttgtattct tttgacatga aagacagtac tgtctcacat gaaagacctc 27060
attgatattt taacatttac agactaaaag ataattctgt gttctttttc ctctttactt 27120
tctctgttct cattcttttc tactcacata atatatcaat tatctactgc tacgtaacaa 27180
accccccaaa atatagtggc ttaaaacacg cactatttat ttggctcccc attctgtgga 27240
ttggtcgagc agattctggt ctggatgagc tcagctgatc tctgctggct cacttgtgca 27300
tctgcagttg gctagaaggt tgactggtag ctggacagtc tacagtggtc tcacttacag 27360
tctaaccatt ggcaggctgt tggccaggca gacagaggac agctgggcca tgcatctctc 27420
atcagccatc aggctgactt tggcttcttc acatggtagt ggtggctgtg tgggtcccaa 27480
gatcagtgag agtggaagtg gcaaggtctg ttgaggtctg ggtgtggaaa ctgcacagca 27540
tcactgctgc ctcattctgt tagtcagagc tgatcacaag atcagcccag attcaagggg 27600
tagagaaaca gatttctact cttgattgga aggacctaca gcattatgtt gcaaagagta 27660
agatgcagag aaggaaagag tttgtagcca tttgtgcagt cagtcacaca ttgtaaaccc 27720
cttctcccat gaacataccc taaaactctt agtgagtttt taggaattat gatatggggt 27780
tttattatct aagaatttat ataatttaat gttgggagtt ccgtcctatt cttggaaata 27840
gctgttacca gggaacagtt agtttaattc tgttcctagt agaaaacagt cttttttttg 27900
tttttttgag acggagtctc gctttgtcac ccgggctgaa gtgcagtggc gctatcttgg 27960
ctcactgtaa gctccgcctc ctgggttcac accattctcc tgcctcagcc tcctgagtag 28020
ctgggactcc aggcgcccac caccatgccc ggcgaatttt tttgtatttt tagtagagac 28080
ggggtttcac cgtgttagca aggatggtct cgatctcctg acctcatgat ccgcccgcct 28140
cggcctccca aagtgctggg attacaggcg tgagccacca cacccggccg aaaacagtct 28200
ttttaacttc cttttgtttt ttggtggggt tagcatttaa cttgtagctt tctgagatga 28260
atatagaggg tctgtatgat tattaaccat gtgatctgtt aatatttcct atgacagcca 28320
ttatagacta aagataaaca cacagagttt gactatttaa tttacttgac cagttacctc 28380
agtgcatttt aaagtatgtt tgtgtaacaa gacgttcata ataataacta acatgtatta 28440
agtactgtct gtgagacact gcctaagtta taggtatcat cttatttaat tttcataaca 28500
acaaaaaaca aaaatgtaga tattattagt agtaccattt tagagatgaa gaaacttgtg 28560
cttagaaatt tacaaatgtg cccagggcca cgtgaccagt gctcttctct aaggttcaac 28620
aaagacgata tcataattca gactgcagat ctgccaacat tcaaatggct ctagtcctcg 28680
agtgttattt tctaactccg cttttagatg caccattgta tagcccttac aactgggcct 28740
gtcccttctg tagatgtggg agtagctgaa ctccacagaa ccccaggtta cacactaagg 28800
acacaggttg ttagggctcc tggatgaggg taagtgtgtt tattttaaac cacgtgcttt 28860

-continued tggctattga gcttatgatt tcaaaggtga aagcttaagc acgttattag acttctcaag 28920
gagagttccc ctagattggg agaaaagttg acattgggta atattaaatc tttcttttaa 28980
aaccagggct attttgttgt tgtttacaat tttaagagtc tagactgaaa gagtcatgaa 29040
atgcagccac ctatctgacc tcttccccca acagttaggg aattcgctct gcccccaggc 29100
cacccaacct tcccttgctc tcctgaatgg gaccctgaca attccctgga attgtaacct 29160
cttccttact gctgaggctg agaagaggat cttttctact ttactccatt tagggttttt 29220
ctttatatct gtgtagattg tggctttttg tttttttcttt ttaattttat tttaaaacag 29280
gaagaacagt tatctgatat taaaaatcaa ggaagcaata tttgtattgg tcacaatacg 29340
ctcagactaa aagaattatg ctgtaagtag ttgtattgaa gaatatttga agtgctttta 29400
aactatttgt ttaaaactat acctatttgt ataacgtgac cagatcaaat tgattgtatc 29460
tttgggtggc accaaatatg ttggtttctt gcatggattg attattctga agctcatgat 29520
ttctgtgggt ctcaggtgcg tggaagttcc catcttagtc cttaagactc ttaccccaat 29580
tgtaagagct gaggaattct gtgatagcta ttaagataag agatattcct aagaaggaat 29640
atattattac agaaattttc aaacatcaaa aaggtttgaa agaataatgt aacaaagccc 29700
catgtacttg ctttaactat tgtcaacgta tgtccaatct tgtttcaaag tcagtcctgg 29760
atgtatcatc cataagaagt cttcctgaag acattcaaga gggaagtctt tgctttggaa 29820
ccctgatgtg atcacgttaa tcattgcttc tatgcctgta gctgaaggaa ccgccagcgt 29880
tttcagtcct ctaatccttc tgcttccctt ttccagggcc cagtcatata tgcacagtta 29940
gaccactccg gcggacatca cagtgacaag attaacaagt cagagtctgt ggtgtatgcg 30000
gatatccgaa agaattaaga gaatacctag aacatatcct cagcaagaaa caaaaccaaa 30060
ctggactctc gtgcagaaaa tgtagcccat taccacatgt agccttggag acccaggcaa 30120
ggacaagtac acgtgtactc acagagggag agaaagatgt gtacaaagga tatgtataaa 30180
tattctattt agtcatcctg atatgaggag ccagtgttgc atgatgaaaa gatggtatga 30240
ttctacatat gtacccattg tcttgctgtt tttgtacttt cttttcaggt catttacaat 30300
tgggagattt cagaaacatt cctttcacca tcatttagaa atggtttgcc ttaatggaga 30360
caatagcaga tcctgtagta tttccagtag acatggcctt ttaatctaag ggcttaagac 30420
tgattagtct tagcatttac tgtagttgga ggatggagat gctatgatgg aagcataccc 30480
agggtggcct ttagcacagt atcagtacca tttatttgtc tgccgctttt aaaaaatacc 30540
cattggctat gccacttgaa aacaatttga gaagtttttt tgaagttttt ctcactaaaa 30600
tatggggcaa ttgttagcct tacatgttgt gtagacttac tttaagtttg caccccttgaa 30660
atgtgtcata tcaatttctg gattcataat agcaagatta gcaaaggata aatgccgaag 30720
gtcacttcat tctggacaca gttggatcaa tactgattaa gtagaaaatc caagctttgc 30780
ttgagaactt ttgtaacgtg gagagtaaaa agtatcggtt ttattctttg ctgatgtcct 30840
ttctgcttga aataacagtc accatacagc taaaggagag gagtttcttt ccttctaagt 30900
aggcagaaat ggtatcatta tgttgccgct ctccaatctc ccagagctcg ctctctagag 30960
aatcaccttc tttcgctttt tttttttttt ttgaggtaga gtctcactat gttgcccaga 31020
ctagccttga actcttgggc tcaagtgatt ctccctcctc agcctcccga gtagctggaa 31080
cgaactatag ttgcaccact gcagctggca agaatcacct tctttataaa gcgtcagtca 31140
tgcttccagc aagaggcagc atcagtcatg gctttataac agcttcatgg tgcctcaaag 31200

-continued actgttgagg ttaatgagag cctagattag acagtttggc tgtccttccc taaaacttgt 31260
tttctcctat tcactactcc ccaccgcact taaaatctat gagtttttac tttttactgg 31320
gaatggaaag tgtggtgaag atcattcaac acttatgttg tcatttctcc cattttctga 31380
attttttttt aaatttcccc ccttttaaaa ttgttcgaaa gcccacagtt atggaaagaa 31440
ttactgtcta gatggtctgc agaacgtgtt tggggtgagt gggagtgagg ggcaatgtta 31500
ctttttctcc ctgtagtttg gagtccatta tgagctgctg ctttttcttc tcatcttgtc 31560
atcttctggg gatgtttgaa ggctgagttc caacagaatt cacaaaggga ataaaacagg 31620
attgagattt tgaggtgtgc acaaggtggt aagataaagg gcatatgagc ttcaaaacta 31680
atgctgttgc atacatgaag ccttttgttt tttgaggagc tatttttgtt attcttgtaa 31740
cgctccacct tacatgccac atctgtgtga gtcaacaggg atcaggtttg gtcaccacac 31800
atgtctgaag ctgggcagcg tctgctctgt gttctgtgtg gaatggagaa aaaaacgcct 31860
gccctgctgc cttccatgtt cataggccca gcccaagaga gtgacacaca gtgctggccc 31920
tgagacattt ccacaaagtg gtcaactctg ccttgcatcc taaaactttt tgggcatcta 31980
ttttgaaaac tataggagcc tttggaaggc ctcttatgtt tggaggggaa gggtgttgag 32040
attgtcacca tccttcaagc tgagactcct ggtgagcctt tgccaccatg aaaaccacat 32100
agctgaccag ggctgtgctt gaggtacaga ggacacacat tgtagacagg cctgtgtcat 32160
gtttccttac agtcgttttt tacagagaaa aggggcattg ttttttcact gctttctcaa 32220
cagttcctgt gaataaatga aacatttcgg agctccctga gagcaagagc cttcacttct 32280
tcttgcggtg ccgggaccat gtgttggtga agctggtgct gtgggggcca ctcactcgaa 32340
tgacacctgg aggcctgttc ctcccttacc actcccttcc ccagcccgac ttcttggcct 32400
cctgcccaac cagacacctc aaactctgtc agtgccctgg cattctggca gagaatcctc 32460
accagttctc accaaccttc cccccaggca agggcagctg ccagcatggt gctctgccag 32520
gacaggtttc cctgaaggaa gctgctcaca ctgagatgag cctctcaggg caggacctct 32580
tcccaagccc tgcacaccca cccctgcagc ccttttggct ccccttttcc ctgtgcctca 32640
gcactccttt cctggttgca gataacgaac taaggttgcc taaagggcag atctgccctc 32700
tccatgtctt cgtcctggca aacagggtcg tcttaaaatt atgcgctaat tctgtatggg 32760
agcactcaaa aggcattact tagagattga aatttcaaac tatctctagt ttttcaatgg 32820
aaatatatca gctagggaaa aaccatcaag ctcattatta ttttttgatc ttcagttgta 32880
tttttgtgaa tattttaata catctttttc aatttctgaa ttgtgttgtg tgctcatttt 32940
gaccagaata gaaaaagaga tatgcctttc actcatatca ttccagctac acctgccttc 33000
ttttcttcaa aaatgccgtc cgtgtgcctg cttctgggcc tttgcacatg ctgttccctg 33060
ggcctgaagc atgccttctg ccaatattcc tgtggtttgc tctctgactt cctttaagcc 33120
tctgctcaaa tgttacctcc tcagggagac cttctgtgat atataaaaga gcaagccccc 33180
caccccaccg cctcagcctt cctggccccc tcagttctgc tctagttact ctatttctct 33240
ccctctttcc cagtacacac ttgtctgttc tcccgcatta gaacatagtt aacaagagac 33300
cagaaccttg ctgttttgtt cactgctccg tctgcagtaa agggaacagc acctggcact 33360
tagctgctca atacatgtta cgtggatgga tgagtaggtg gaagcattca tccattcagc 33420
aacctacact gagaacaatc ctgtgccaag cactgtgcta agcataagga aacaaaacaa 33480
gacaaagctc ctcaaggagc ttgccacagg gtggaggtga caggtgacat gaatggaagt 33540
aactagtagt taccaaatac ttggtgtgag ccaggcactt tgcatttctt tctctattat 33600

-continued

```
ttctgtgagt taacagtaat tgtactaatc ttaatcccat tgtttgaaag attatatggc  33660
ttacccaggg ccacttagct aataaaggaa cagagaagag gggctgggcc tggggccgct  33720
gtttgatcca cagccttgtt cctaaccact atgccctgtg gcctctcaca ccaaaaggaa  33780
gtaccaaact gcttccttac tcaaataaat gtgctgaaat gcagttgcag ttttctccca  33840
gtcccttagg agctggttag agagtccctt aggaacttga gagggtagtg tagtctaggt  33900
ggtaggcaca gatgtctgag agctttaacc tcagtctgga agacaatgtg gtgacttaat  33960
ttgttgagaa ctatgttaca aataatgtgt tactaataaa acattgaggc ttcgcagtga  34020
cttagtaatt ttataaatta ccatggattc acaatgagcc cctgccttgc ataactttgg  34080
gcttgcaaaa cctaatgcgt tcttgagtgg gagaagatga gttacagctg gcaggaactc  34140
ccctgggagt aattctcaca tgtgaacagc atccatcttg cgtgatgtga caaaaagaaa  34200
agggatgctt ccttcaccac acaagggcag cagtgagtga tggaatcaca tttttgtcat  34260
ctctgcaatt ccttccaagt cagcactaag tgtcggaggg catccacctg ctggggctct  34320
ggtttccaag ctacataggg gccttgccaa ccaaagatgg actttttatt tatgagagca  34380
gcttccaccc ctgagggagc tgagttgagc agtgtttaga ggaaactcag atactctctc  34440
accccagttg gctcccttct gacccctctg ggtagttcct gtgctaactg gactggggaa  34500
ccactgactt catcctccca ctgtgcagga aaggcgaggg agcagccacg gggaggaaag  34560
tggcatctgt ggtattggta gagctggtgg taggagccaa ccatctgctt ttatggcggg  34620
ttctcccctg cactttcctc ttgcatagtc aagatattgt atgaacaatt tcaatatatt  34680
ttgttttttt gtagaattac tttaatgaaa ttaccctttg atataatttg aaaaaaattt  34740
ttttttgaga cagtcttgct ctgtcatcca ggctggagtg cagtggcatg atcttgcctc  34800
actgcaacct ccacctccta ggttccagcg attctcccac ctcagcctcc ccagtagctg  34860
gcattacagg cacgcgccac cacacccggc taattttttg tatttttagt agagatgccc  34920
gcctcagtct cccaaaatgc tgggattacc ggtgtgagcc actaggccca gcccctttga  34980
cataattcta tcagcctaca ttgaagtatg tcataaaaaa gagtcctagg aaactagcta  35040
cttattgtac tttactgcca gcatggcttt gagaacgtta ttccctgtca tacatttttc  35100
aatgttataa agacccacag cacaaatatc tctctggatt taataccaga tgatatggtt  35160
gagatctgtg tcgcagccta aatctgtcga attgtgatac ccagcattgg aggtgaggcc  35220
tggtgggagg tgattggatc acagtgggta gatttctaat gaatggttta gcaccgtcct  35280
ccttggtact gttctcgtga ttgtgagttc tcatgggacc tgtttgttta aaagtatgca  35340
gcaccctccc actctgctct ctcgctcctc ctcccgccac gtgagacgcc tcatgagaag  35400
cctcactacc cctttgcctt ccgccatatt tggaagcttt ctggggcctc accagaagcc  35460
aaagacgcta tgcttcctgt gtaacctgca gaacggtgag ccaattaaac ctcttttctt  35520
cataaattac ccagtcttgg ggttttgttt ttgtttgttt tttgtttgtt tgtttgtttt  35580
ttgagatgga gtctcactct gtcgcccagg ctggagtgta gtagcacgat ctcggctcac  35640
tgcaacctcc acctcctggg ttcaagcgat tcccctgcct cagcctcctg ggtagctggg  35700
attacaggca tgcgccacca ttcccggcta attttttttt gtattgtagc ggagataggg  35760
tttcaccatg ttggccaggc tggtctcgaa ctcctgacct caggtgatct gcccgccttg  35820
gcctcccaaa gtgctgggat tacaggcgtg agccaccaca cctggccttc agtcccaggt  35880
atcttttata gcagcgtgaa aacaagtaat acaccaggaa aactgtttct tatgaatatt  35940
```

-continued ttgtttcaaa ctagtcatgt gcactgactt gtcactgatt gtatttgtct ctttgctttt 36000
gctattctct aggtcctagc caaatttgtg ggtcactttc taccactgta cacagattgt 36060
acactccata tacactttgt acattaactt tactcatagc tttatgtgta tcttggatta 36120
tgttcagctc tatgatctgt ctcagttttt tccagtgata caataataga tgtgtcctga 36180
tttagataga gaaagtaggt aggcagagat tctggccatg gcatcagaga ttcataatgc 36240
caaccacaga cttactcttg actccacaaa aaccatttca caaattccta ttgttgccca 36300
aaagaggtga aaataaaagt atatgactgg ctgagtgtaa caaaactaca tgacaggaat 36360
tacgactcac atacagcctg gagtcacctt tctgttacac cctgttcatc agtgatggaa 36420
aggcagcttc ctatgtgctg aaagttcatc tctcttattg caggtatgat ttccactggt 36480
attaatgagc ttgaaatatg aaggccactt aaatttccca gaggtgtcaa gtgatgtggg 36540
gatttcagag catgtatcaa ctcacttcag caatattagc atttttgttt gaaataccca 36600
gttagacagg aaacttgaaa gataattgtt tcaattattt gtatcatcat actgaaaatt 36660
gcttaaaacg ttctggttgt tccttgaaga cattaaaaga atagatccta ttaatgcccc 36720
ataggttatt tgatcctttt ggaaatgaaa agattgactg atgattgatt gaattttctg 36780
ctttttatta aattggtgag atggcaaaaa aagaaaaatg taaacatata caaaagaaga 36840
gagaatagta aaatcaacct gcatacactt attatcttca atacttattt tatccagccc 36900 ctttttttctt ttttcctctt ttctgaatta ttttaaaaca aatcccaaaa tcatgtaagt 36960
gcacccctac attcttcact gtgcatcttt taaaaatgtg gacattttct tacataatca 37020
caatatcttg tcacatttaa caaaaacctg tcctaaaaca catttttttac aaacaaaatc 37080 cttggtttta tatattatta cccagttaat attcaagttt cccttgtctt aaaaaatggc 37140
attttacaag tggtttcttc cagtcaggat ccaaacatag ttctggtaaa gttttttttt 37200 ttttttttt tttgcctatt tttaaaccca aaatgggatc atggtgctct gcagtttgct 37260
ttcttccctt agcattatgg cagagaagtt tcagcatgaa gaactaggtc attagataat 37320
agcacctgca ggactttgtc ttttgtagat gcgccggaat attttaaacc atttcttttt 37380
ttctttctat tttaaacaga gtttcactct tgttgcccag gctggagtgc aatggcgtga 37440
tctcagctca ccacaacctc cacctcccaa gttcaagcga ttctcctgcc tcagcctccc 37500
aagctgggat tacaggcatg cgtcaccatg ccctgctaat ttggtatttt tagtagagac 37560
agggtttctc catgttggtc aggctggtct caaactccca acttaaggtg atccgcccac 37620
ctcggtctcc caaagtgctg ggattacagg cataagccac cgcagccagc ctttgcattt 37680
taaaccattt ctgatcttct ggataggttg tttccagttg ttttgttatt ggctattaca 37740
agtagtgctg taattgtcat ttgccttcat gagctattaa ggaagaaaag ccaaataatt 37800
tgcaggctca gagaagcaac acagaatcag tcacgtcctt ggccttggaa atgggatcta 37860
atatctgaga gcgatgaaag tggctcacaa gctcccctgc cctcctcaca tccttcctaa 37920
agccatcagg agctggccac agagcacact ggctgctctc aagtttgact gagtcttggg 37980
ttgttagaaa aacaactggg agtggaaggc aggagggagc tctagaatcc acgggagacc 38040
tggctgtgtt tgcaaagaag aaaacataga cgtaaagccc aaaggggtcc gtagggaact 38100
gctgcttcca gcttccattt cctcctgcaa acaggatgtg aagctattgt cccttcttgg 38160
ctcaggcttt tggatttgtt tgtccatcca tttcttcact gtggcctttg tggagctggc 38220
ctttagtgtt gcagaatata aggaagggct gggtttgttt gtttgtttgt cttttaaaat 38280
ctccctacct ctgtgaagag gatgtggtgc agatttgctt tcaagccttg ccctccgtgc 38340

-continued

```
tgtggggctg acaaaattct ggttactttg cccttcaggg cattaaatga tttcaggtat  38400
ttatacctga gtcactgctc tgctatggga gcgggggata gaacagctaa aaaccatctt  38460
aaggcctgag gtttctcatt ctgtgataag gactccaagg aaactgaatt tcaatactag  38520
agtacattgt tggttctttc tctgcctttg aatagaatta ttttttaaat tacaaagttt  38580
cttttaaaag aaagaacttt taaatatatt ttgtagggaa tctcttagaa ggtacaatag  38640
attcatagga atgtggaaca tttggccggg tgcagtggct catgcctgta atcccaacaa  38700
tttgggaggc cgaggcaggc ggatcacttg aggtcaggag ttaaagacca gcctggtcaa  38760
catggtgaaa ccccatctct actaaaaata caaaaaatta gccgggggcg gtggcatgct  38820
cctgtagtcc cagctactcg ggaggctgag cggggagaag gggagaatca cttgaaccca  38880
ggaggtggag gttgcagtga gctgagatcg tgccattgta ctccagcctg ggcaacaagc  38940
gagactccgt ctcaaaaaaa aaaaaaaaaa aaaaaaaaag aatgtggaac attttacaaa  39000
atctcgtcca tgatcttgcc ggcccagcag aatcccagat gtttgtctat aacgcgtctg  39060
gatgttccta tctgagaaaa agccttagtc ttttacttgt aagctattcc tgaagaaggt  39120
tgcctcagca ggggaaaact ttctgaaaag cttgatcaag tacctgggtc ccaagaatgt  39180
caagcatctg tggaacacac agttcccagc agccagcaag tcccacactg ctcagtgtcc  39240
tgcagccaag gaagctgaac tgagctcatg gggttacagg aagatgaaac aacactgcct  39300
cactggcaag gagatcacac tgctgagtgc tgcctgagtc cctctgacac accaggctct  39360
tggagaggag gtcgtggtaa tcatttaatg ctgactaatt gaggttgagc aagagagaaa  39420
aatacccgag ggagatacat gaaataaact taggaggaga gcttgtactt ggctggaaat  39480
aactggcctt cttccatatc ctctctaaaa aataccataa gagaaagtaa aaaatttgtg  39540
gtttctattg taaattgtgt tgattcaaat taatttcaag cttttagatt gtagttctat  39600
ggctacccat cacacctcct cctcccatca gtaggcatgc cattaaagtc acggcaaaat  39660
gcaggttctt ctggtagagg cagagaggtc atatgaagga ggatagagaa ataggagcag  39720
cttagccaat gtagtacctg tgcattagac taatatctaa tctgttacta agcactaaat  39780
tgatatcctg gaatcacaag aattggataa ctacatattg ataaaagggt ttgcctctcc  39840
agcctgatat attttctctt atatattagt acctctcttc tcatccaagt tgatatcatt  39900
ctgtgctata gaaacatctc agttcaacct tcggtggctt tgttttggca tgttaaggtt  39960
aatggagata ggcacagacc tacactgtac tacatggcag ccactggcta catgtggcca  40020
tttaattttg tttgtttgtt tgtttgtttt agacagggga ttctgctggg ccggcaagat  40080
cttggacaag gttttgtaaa atgttccaca ttcttttttt tttttttga gatggagtct  40140
cgctctgtca cccaggctgg agtacaatgg cacgatctcg gctcactgca acctccacct  40200
cctgggttca agtgattctc ccctctcagc ctcccgagta gctgggacta caggtgtgtg  40260
ccgccacgcc cggctaattt tttgtatttt tagtagagat ggggtttcac cacgttgacc  40320
aggctggtct tgaactcctg acctcaagtg atccacctgc ctcggcctcc caaagtactg  40380
ggattacagg catgagccac cacacccgac cctacttttt ttttttaatg aaagagatgg  40440
ggcctcactc tgttgcccag gcttgagtgc aatggtgcaa tcacagctca ctacagcctc  40500
aaactcctgg gttcgagcag tcctcccgcc tcagcctcct gagagctggg actacagatg  40560
catgccacca cacctgacta attttttttt aattaatttt ttgtagagac tggatcttgc  40620
tctgttgccc aggctggtct tgagcttctg ggctcaatca gtcctcctgc ctcaatgtcc  40680
```

-continued

```
taaagtgctg ggattagcct tggcaacatg gtgatgttct caaaccaaac tgagggtcag  40740
gctgctatgt ctcgcagccc aataatgaga tgcagatgaa ctggggagga agagagtttt  40800
tatttctgta accagttaca gggagaaggc ctggaaatta ttgccagaac aactcaaaat  40860
tacgaagttt ttcagagtgt atataccttc aagctatatg tctgtgtgta agtgtgcatt  40920
aatctaaaga cataagtgat taacttcttt taatctatga ctaaggtctg agtcctgaag  40980
accttcttct ggagcctcag taaatttact taatgtaaat aggtgtaggt gctggggtga  41040
ttacccttat cttgtctcct gttaaatcat aaaggtttgg ggagttcctt tagatcccag  41100
taaacttgtt tgtggaggcc tggggagttt cttcagaccc ccaataaaac ttgtttaatc  41160
gtaaaagggt cctgttaaga attccttcat tatcttgtca tgcttcaagg cccaggaaaa  41220
gcctaggcac aactcttggt gggctctttg ttacattccg ccctttgtat aagggcactg  41280
gctcaatcag ctttaatgtt taacctagct actcagtcag agctgggaca gttgtaatgg  41340
aggcctgcgt tagtgagacc tggcttgcca cagtgatacc ctgtctctac aaaaaaaaat  41400
acataaaaaa atagccgggt gtggtggcac atgcctgtag tcccaactgc tcaggatgct  41460
caggtggggg ggctgcttca gcccaggaag cggaggctat agtgagccgt gattgtgcca  41520
ctgcactgaa gcctgggtga ctgagagaga ccccatctca aaaaaaaaaa aaaaaaaaaa  41580
aagtgctggg attacaggca tgagccaccg cacccagcta aacttaatta aaattaataa  41640
catttaaaat ttatatctct agtcacatta ccatactgca agtgttcagt ggctacatgt  41700
gtgtcttgtg actaccatat tgatcagtgc agatacagaa catttccttc attgcagaaa  41760
gttctattgg atgacactgg tgcagaccac acaggggttg gcaacgtttt agatagttgt  41820
gtcaggttat atgcacacaa gctcagaatc ctccatagcc tttttttttt catggtgggg  41880
atgggggtac cccccacagc agtggtctgg tggctgacac tttctcgtgg atagacagca  41940
tacactcttt actcactcaa tataatttat agcctatgat gtcccacaca ttgcaaagtg  42000
ctacaatgca tctgagaaca agatagagct tgctgaaggt cttctaagct ttgaccttat  42060
gccaagttct gggatataaa gatgagggct ggctgggcgt gatggctcac gcctgtaatc  42120
ccagcacttt gagaagccga agtgggagga ttgcttgagc ccaggagttt gagaccaacc  42180
tgggctacat aatgaggcct ctatctctag aaagaattta aaaattagcc ccagctactc  42240
agggatagtg ggtggtgggg gctgggggca agggcgggag ggtaagatgg gaggatcact  42300
tgagcctggg aggtcaaggc tgcagtaagc tataatcatt gtgccgctgc acttcagaca  42360
aaacgagacc ctgtctccaa aaactaaaaa taaattagaa ataaagataa gagcaacaga  42420
atccctgcca ttgatgagct caaagaggag acagccccaa acagcagcag tcctggaaga  42480
gcctggggga aaaacaggga ccaactgata aacccaaccc atagcagtca gaagcaggcg  42540
ctttgaggca gaagcatgtg aaagactctg gcacagacat tccagctgga gcaacgagtc  42600
acaagggttc agggtaggag agtggggcca atgtggttgc agtatgggga tttgggttga  42660
gccagacctt aaaagcccac cttccaggct aagaaatcag tatgtatcct gaaggccaga  42720
tttgaagtag agtgataaat ggggattggt attttagcaa gcttatccta ccaatggctg  42780
aaaatctgaa atcagatgga aatttgaaat caggaggcca cttaattatg tggccattcc  42840
agagctcagt cagagatgaa ggaaatggtt tttcagcagc aatgggaata agaggatagg  42900
aggggtgtaa gaaatatgta ggaagatgtt caagagcatt ggcaaaatat gactggctct  42960
gggattggag gagtcttgac cgcaggggct ggtaccatta acagatagga aacgtcatga  43020
gcggacaacc ggggaaaggt tggggttcgg agtgcagcag gagggacaaa cataacagtc  43080
```

-continued catttagcaa gtaacgagaa ccatgcaaat gcttgaaatt gttcagtcct tagtttactt 43140
agcctctctg aatgtgtttg ttaattttga gcatcctcct taaaaagtcc acctctgatt 43200
tcaatatgtt cttcctccat tatctgtcaa atcaacgcct tcatctctgt ctccactgat 43260
acttctttct tgcaggccac cctaattcca agcttgcaac agcaactatc tcccagtctt 43320

<210> SEQ ID NO 12
<211> LENGTH: 21900
<212> TYPE: DNA
<213> ORGANISM: Homo sapiens

<400> SEQUENCE: 12
catcttgact cagctgtctt ctaacccatt ctggataaag aatggtggtc cttctacttt 60
tctttttttt tttttttttg acaaagtctc gctccgtcgc ccaggcagga gggcagtggc 120
acaatctcag ctcactgcaa cctcggcctc ccgggttcaa gtaattctgg ctcccaagta 180
gctgggataa caggtgtgtg tcaccacagc cggctaattt tttttttttg tatttttagt 240
agagacggtt tcacaatgta ggccaggctg gtcttgaact cctgacctca agtgatccac 300
ctgcctcggc tcccaaagta ctgggattac aggcgtaagc caccacaccc gaccctactt 360
ttttttttta atgaaagaga tggggcctca ctatgttgtc cacactggtc actaactcct 420
ggactcaagc aatccttctg cctcagcctc ccaaatgctg ggttataca tgtgagtcac 480 catgcctggc caagagtgat ggtctttcta aaacggaaat atggtccatg cacttccttg 540
ggaaagtcat tcagtgcctc ctactgctgg caggataagg tctcaaactc taccacctgc 600
cccataaggc ctgagggcat gcagctcctg cccgccctct agtcatcaca cacatgtcac 660
cctgctgagg agaactccag ccagaccaag tgggaggacc caggctccaa aactcctcca 720
gcaccaaacg ctgtgtccca aatctgtaaa gctcttcacc tggctgagtc ctgtttcctc 780
tctcaggaag ctttctccag ccttctaaag ccaggatagg gtgcatgccg ggccccttca 840
tagctatgcg ttttaatgat ctgttccccc agcggaattc tgagtgcttt acctgttgta 900
ttaatccatt ctcacactgc tattaaaaac tacctgagac gaggtaattt cagaacaaaa 960
gaggtttaat tgactcacaa ttccacaggg ttaataggaa gcgtgactgg gaggcctcag 1020
gaaacttaca atggtcgaag gagaagcaag taccttctta ccatggaaga ccaggagaga 1080
gagagtgagg gtggaagtgc caaacatttt taaaccatca gatctcgtga gaactcacta 1140
ccatgagaac agcatggggg aaacctgccc ccatgatcca atcacctctc accggcctct 1200
tctccaacac tgaggatcac aactcgagat gagagttggg tggggacaca gagccaaacc 1260
ttatcaccct taacccacaa caaccttatg aggtggatac tgttattatc cccattttac 1320
aaacaaggga aagaaagcac aaacaggtta aataacttac ccaaggacac aaagaagtag 1380
caactggatc cagtccagtg tggtcccagg cccacatcgg taaccaccat gcagagtgtt 1440
tcttacttct cattgtaacc ctagtgcaga gcctgattag tatagttgat gttaagtaat 1500
ttttgtttac ctccatattg tttactcatt caataaatat taggtttcta cttctaaggt 1560
agtctgtaag aattagcttg aaatgatcaa atgaaaatat tattggccag gtgcagtggc 1620
ttatgcctgt aatcctaaca ctttgggagg ccaaggcggg cggattacct gcggtcagga 1680
gttggagacc agcctggcca acacggtgaa acactgtctc tactaaaaat acaaaaatta 1740
actgggcgtg gtggcacacg cctgtaatcc cagctactca ggaggctaag gcaggagaat 1800
catttgaacc tgggatgcag aggttgtggt gagccgagat cacaccattg cactccagcc 1860

-continued

```
tgggcaaaaa gagcgaaact ccatctcaaa aagaaaagaa aatattattt aatgaactta   1920
ttaatttaca ctttctgaag acttactgtt tgtgcaggca cactggtctt agtgcgagaa   1980
atagagaatg agaacaatac ctttaccctt gagttgacag gcatgggggt tgtgacagaa   2040
ataaatattt taaaaagatc atcacttttt cattcctgtt cctgaagcct tcgtggatta   2100
tttatgtctg ccttctccta aaaataattc tatccaggat gccccgagga tgtcatgctg   2160
gaagcttcct gtaggtaacg aggggcgccg cagtggtgct aagtgctgag gctgcaggtc   2220
tgaagacaaa agcctccaga gcgtgaccag gaatggttcg tttggctgca gccacagtaa   2280
ggagccagtg ctgccacctg ctggccaaga gcaggttcgc ccacacccat tctgttgtta   2340
ggaggctgaa tcacagccag atggaggagg gaagggattt tatcacaact cgcttagttt   2400
agagatgagg aaactgatga aaaagggact tgcccaaggt cacgtaactg gtttgtggca   2460
tagtcagaac cggaaccaag tacagggttc ctgcaaaacc tgatgcacgc tcctctggat   2520
tcaggcacat ggaacttaac cttcaaattg cagtatggtc ttttctcgct ttttcctttc   2580
tctcttccct ccccccttc cctcccctcc tctcctttct cctccccctc cctcctctct   2640
ccttccttcc ccctcccccc atccctcccc tctcctcccc ttcccatctc tcctcccctc   2700
tcctcttttt tttttttttt gaaaccagtt ctcatcactg cacttccagg acaggggaag   2760
cactggggaa tgaggcatcc tagctctgtg gagggaaagg gagctggtca acatatgctt   2820
taggtatttg tgggtttgtt tttaattaat aaactttatt tatagagcag ttttagactc   2880
atagcaaaat tgaatgaaag gtagagaatt cccatatagc ccctgatcct acatactcac   2940
aacctcacct gctaacagca ttccccacta cagcagttca tgtgatacaa ttgatgaacc   3000
cacactgaca cggcattttg acccaaagtc catagtttac attaagagtc actctgctgt   3060
tacacattct atgggtttga acagatgtat aatgatgtga atcctccttc agagtaatgt   3120
acagaatagt ttcattgccc taaaactccc ctaggttcct cctgttcatc tctcctcctc   3180
ccaccccact ggcaaccact gtctccatag ttttgccttt tccagaaggt cacatagttg   3240
gaaccataga gcatgtggcc ttttcagact ggctttcact cagtaatgtg catttaaggt   3300
tcttctctgt ttttttcatg gcttgatagc taatttcttt ttagtgctga ataacattcc   3360
attgtctaga tttaccacag tttatccatt cacttactga gggacatctt ggtggcttcc   3420
acgtttgggt aattatacag ttgctataaa tgtccatgtg cagggttttg tatggatatg   3480
agttttcagt tcatttgggt acatgccaaa aagcacaatt gctgaattgt atggtaagaa   3540
tatgtctggt tttgtaagaa actataaact gtcttccaaa atggctgtac aacttcacat   3600
tccctccagc aacgagtgag agttcccgtc actccacgcc cttgccagca tttggtgtct   3660
tagattttgg ccattctcgt aggtgtgtgg tatgctttag ttttttagta atttgggaga   3720
tgaactatta gtttcagaaa tcctcacact cattagcact atctacccat agaatcaaaa   3780
tcacagggaa gcctggtggt gttgacttac agaaaacatg aatacttgcc tgcagttcac   3840
aaagggcaca ggggtgagac tcatgctttt ggcagctgtt gggcagctga gtataaacca   3900
gactaaggtg gttggggcag aaccccagag tactgtcccc tgagcctatg ttcaagcaat   3960
gcagagtggc aaccagagga tgctaaactc gaaggagatg acttgacttt atcatgatca   4020
ctgcctgcag ttaccaccag gaaggcctaa cacagggtgc aggatattta aagagaagga   4080
acgagtataa cccaataagg aaggcatagg ctagagataa aggccaccat ccagagagag   4140
tgcccaaagg cctaccttcc tttgcccatc agcatttaga catatgtttt agtttacttc   4200
tctctcactg gctaaaagca gaccacagtc ggtttctttg tttcctgtct gtaccgtctg   4260
```

-continued ttctctttaa agtaaaaaaa aacaaactgt ctaaatacag gatggggaga acttgttaga 4320
atacatgtga cagtattaaa ggctaatgct tatggatctc cttctgtata ctaggcagca 4380
ggttttttta agttaaaaaa attgtttttt tggtttttgt ttttgttttt tttttagtat 4440
ttattgatcg ttcttgggtg tttcttggag agggggatgt ggcagggtca taggataata 4500
gtggagagaa ggtcagcaga taaacacgtg aacaaaggtc tctggttttc ctaggcagag 4560
gtccctgcgg ccttccacag tgtttgtgtc cctgggtact tgagattagg gagtggtgat 4620
gactcttaag gagcatgctg ccttcaagca tctgtttaac aaagcacatc ttgcaccgcc 4680
cttaatccat ttaaccctga gttgacacag cacatgtttc agagagcacg gggttggggg 4740
taaggttata gattaacagc atcccaaggc agaagaattt ttcttagtac agaacaaaat 4800
ggagtctcct atgtctactt ctttctacac agacacaata acaatctgat ctctctttct 4860
tttccccaca tttccccctt ttctattcga caaaaaccacc atcgtcatca tggcccgttc 4920
tcgatggtcg ttgtctcttc ggagctgttg ggtacacgtg cagaaaggct gtcacttcac 4980
acttggaaga ttgcacagcg gccaggcaga ggcgctcctc acttcccaga cgaggcggct 5040
gggcagaggt gctcctcact tcccagacag ggtggtggcc gggcagaggc gctccccact 5100
tcccagacgg ggcagccggg cagaggcgct cctcacttcc cagacagggt ggcggccggg 5160
cagaggcgct ccccacttcc cagacggggc agccgggcag aagcgctcct cacttcccag 5220
acagggtggc ggccgggcag aggcgctcct cacctcccag acggggctgc tgggcagagg 5280
cgctcctcac ttcccagatg ggatggccag gcagtggggc tcctcacatc ccagacgatg 5340
ggcggccatg cagagatgct cctcacttcc tagacggggt ggcggccagg cagaggctat 5400
aatcttagca ctttgggagg ccaaggcagg cggctgggag gtggaggttg tagtgagccg 5460
agatcatgcc actgcactcc agcctgggca acattgagca ttgagtgagc gagactctgt 5520
ctgcaatccc agcacctcag gaggccaagg caggcagatc actccaggtc aggagctgga 5580
gaccagcccg gtcaacatgg caaaacccca tctccaccaa aaatacaaaa accagtcagg 5640
catggcagcg cgtgcctgca accccaggca ctcagcaggc ctaggcagaa gaatcacggg 5700
agcccgaggc ggggaggttg cagcgagctg agatcacggc agtacagtcc agccttggca 5760
acagagggag accgaagaaa gaagggagag ggagaggggg agagggggag agggggaggg 5820
agaaggagac ggagagggag agggaaaaat tgtttttga gatggtctga ctcttgtctg 5880
ttgcccaggc tggagtgcac tggcatgatc tctgatcact gcaacctccg tctcccaggt 5940
tcaagcaatc ctcccacctc cacctcccaa gtagctggga ctataggcgc ttgccaccac 6000
acccagttaa cttttgcatt tttttttttt ttggtcgaga cagggtttag tcgtgttgcc 6060
cagcctggcc ttgaactcct gagctcaagc aatccacctg cctcagcctc ccaaagtgct 6120
gaaattattg ttgtgagcca ctgcgcccag ccctaggcag tgtttttcat gtaattctca 6180
aaaaaaagaa ccccacacaa ctccatgcag tatgtacaac tattatttcc acttacagat 6240
gaggaaacta aggcacagag agtaagtagc caacttggga ttatcttcca gataattgga 6300
atatgtccac agtgactcca aaactggctt ccaaaaaagt gaaggcgcat aagtggtttt 6360
aataggactc ttctaggtag aacaaaagaa gtaagagtcc tctcctattc cagattggcc 6420
aatctatagc tcatatataa gagaaatgga gataaatttg aatatattcg gagacaagtg 6480
atcaggatac tgagggaacc gaaaacaagg agctggtagg agaagcagaa gcaaccggag 6540
atatttagct tgtagaaggc tcaagagaac catgagaggt gtgttcaaga gtttgaaggg 6600

-continued

```
gtcagtgagg aacaagttta aatttattct gtatgattcc aaagagtaga actaggtcca   6660
ttttttggaa gctaaaggga acttgaatct ttagatggtc aaagcgattt ttaagacaga   6720
aaacactgtt tcctgatggt ttgcacagac agagagccag aaaaagtgga cttgaatatg   6780
cttcgacaag ggcacacaat ttctggactt aggctccagt tcagccactt actggccaga   6840
tgatctcagg caagccaaag catctgccat tctcaccatt cagggtttac agggagaaga   6900
taagagcagg tcccagaact ctctgtatct ataaagagtt gtacaaatgt aaggaattgt   6960
tatgattaag gcattagctt attatgacaa tgcagtcgaa atgaatcaga ggctgttccg   7020
ctgagtcttc aagatgtcca ggttttgtat gtgtcactcc ttccaccatg aaggatttga   7080
acacagctct attatattac agtagaatgg gctcagtgag gtttacacgt gcatctgttt   7140
tttctattgg acatgtgagc ttgctgaggt caagaattgt gcccttcatg tttttatatc   7200
ttaacctcca gtacttagtc agggattagt atacagtaat gagttggaaa attgtagtgg   7260
ggtgaataag tgagagaatg aataaagtac aaaataaggc aactagaaag caagggattt   7320
ctatattgca gcatggggca agcatgcagc ttccaggatg acagttttga aggggacaat   7380
acttaattga agtttagtat ttgatgtgtt tattttaaaa tcagtcatct aatattagtt   7440
tgtttttatt tgtatggcac attgtaattt tcaacacttt ttaactttca ctatcttatt   7500
cagtattcac aaatgtacac taacatagtg aagttatgtg gatcaggcag ggtgtatgta   7560
tcagacagga ataaagtgtg cttatggcag agctcatgtt agaacctaat gttctgattt   7620
cttagcttgg agctcttccc tccatgccag gccatcaggc ctctgtggtt aacctcgtgg   7680
tatcatctgg gtctgtccaa cctcgtttgt ggaactcagt tatgtgatca ggagaaaaaa   7740
tgcacagcct tgcttttgca tctgggaaat gatgaagaat gaatgttatt tcttaaatat   7800
aaaaaaacat gtaaactcta aatatgtaaa agatacccgt gtaaaaatta ttaatatttt   7860
aatttttaaa acttgatctt tattttatat taaacatatt tatctgatat taaaatttta   7920
tttgatattt gatgcatgtg gttagagggg ctaagacatc accctggctt tggaagctgc   7980
agtcaggccc tacaaacatg tatcttttct aattctgtct ttgtagacca tgacaaatgt   8040
ttgctatttg taatattgtg ctacctccaa aagacttaac aattggacat ttaaaaataa   8100
gtattttcag ttaacatact aactagaaac atgtcttttg caacacacga tgtcatacca   8160
tcttgagatt aataatttgt aatatgatac agttttgcat gggctgaaat aaacaggtca   8220
agctaaaaca acatgaatgg taaaagcaat tttttgtaac attaggaaga agtaaaccat   8280
gacactcctg acccttgtag gccctccaga aagagaagaa atcaacatgt ctgtttctgt   8340
gtctggaaca gaagagatta tgtaggaacc tggagtgggc cagccacgga gaaaggtcaa   8400
taatagataa tcacaaggac atagtgctta ttaaaatctt ttttctttga catgttagaa   8460
atgattgtcc acggtattag ctctcatcag gaatttgttt ttttgaagat cctgaatgtt   8520
taccctgcct gctacaattt tttcccatga tgggagactc aagatcgtct gaagccattg   8580
gtcttctttt aactcagagg ttgagtacca tgattcctga gaggaaagaa acagaacaaa   8640
gaaatcatta gtgcttcttg acttttgtaa tcaaggttag tccaatatca aacaaggcaa   8700
aacatctttg gtaaaaacca tgtgaaccca tagacaaaaa cgaatcttgc tgtccaaact   8760
aggatactga cacagccctc tttaaataca cacatatact catacattca ttcacttatt   8820
caacaaaact gagtataggg ctctgtgcta ggcactaagt gtggtttttg ctttcaaaga   8880
gttcacattc tcaaggagag gaaagacacg cagacagatg taacacaaag tggaaagtgg   8940
ccacaaagaa gggcagagag agggcatgct aagggggatt tggatgaggg agagagacca   9000
```

-continued

```
tgagaactta aaggggaaga ggaagctcac aatcctgaac tatggacatg tcaccctttc   9060
tggtaagaat ccagaaaggc ctatggtgac tgctatggtc tgaatgttgg catctcctga   9120
aattcatatg ttgaaaatta acccccaagg taatggtatt aagagttggg cctttggaag   9180
gtaattaggt catgagggct ctgccctcat aaaagggctg gagggagcaa attttctttt   9240
tccatccttt tgacatgtga ggacacagca aaaggcacca tctgtgagga acggaccctc   9300
accagacagc gaatctccag agccttgatc ttggacttcc agcttccaaa actgagcagt   9360
aggtttctat tgttcatcaa tgacccagtc taagatattt tgttaatggc agcctggtga   9420
aacctaacca ggcagtaggc ttctgggctt ctttatatgg gtgagcatcg ccaccccggt   9480
ttgctagctg atgatacata ctttgttcat gttcagccag catttctcca gtatattccc   9540
ctgtgtttca gagagccgca aggctgtgtt caggaagagg ccacatttct gcccatctcc   9600
cattaatata cagacgtaag ccatcaggtg gtagagcctt gggcaaaaga cagggccagt   9660
ggtattttga gccaccagat tctccaagtt ctaaagaaaa aaaacccaca acagtatatt   9720
agaattaaac aggggtcctt gactgtaagt tatttccttc acagatgatt tgggaacatt   9780
tcaaggattt aagcaatcaa gtgagaaaat acattataga gacatacaca gtaggtattg   9840
gagataagac aataaatgtc aggcagagta gccaccatgg tccactgaga tcaggaattg   9900
acctgagaga tcccatcatt acttctctgc aataactttt tttaaaaaat tattttgatt   9960
attatgatta ttaaggcagt acaagttaat tgttgaaaaa ttaggaaaaa aaattggcca  10020
tttctgcatg taaggagctt ggaaataacc acttggtcct agaaacaagt aaaaagctga  10080
acaggctggg cgcagtggct catgcctata atcccagcac tttgggaggc cgaggtgggt  10140
ggatcacaag gtcaagagat caagaccatc ctggccaaca tggtgaaact ccgtctctac  10200
taaaaataca aaaattagcc aggcatggtc gtgcacgcct gtagtcccag ctactcagga  10260
ggctgaggca ggagaatcgc ttgaaccagg gaggcagagg ttgcagtgag ccgagatcgt  10320
gccactgcac tccagccttg tgacagagtg agactccatc tcaaaaataa ataaataaat  10380
aaagctgaac agactggaag atcaacaact attcttggat ccataagaga agtgagaaca  10440
cagggcaaac tgctgcccct aagactggag agacaaacag atggagactc acaagtggaa  10500
accactgtgg gaaccagtgc caggctagaa aaacctgaac tgtaattgat gaattgctag  10560
aaactcagac tggaccggtc tgggagttaa aaactctagg gagaagagga ttctggagag  10620
acggcagagt aggaagtacc aactatctgt agccccacct agactatcat tacactggca  10680
gaatctgtca gaatgtaact attttagaac tctggagtct actgaaggct tgtaaatacc  10740
agaggaaggc ttggatggta aactgaggtt aatttcagtt tcagctctta gcacagctgc  10800
ctgtccccca gcctcaaaac ctgtggcaga cagttgttgt gcacatgctc ctgaagaacc  10860
tgcgtacaac ttgtgggaac aagggtgggc aaaaaggacc ctgtctgaga tatcagggat  10920
ctgtgctctg atcaccaatt gctgcttctg atggaagagg taggcagtca ttgttgcacc  10980
tctccccgtc attgcaagcc cctcccactc cagttgaagt gacttccagt ggatttaaag  11040
ggctattgcc ctttcctccc ccaactttat ttttttctcc acccaccctc caccaccttg  11100
acagccagac attaaatact aggacattca aaagcaactg cctataaaag gaaaattaga  11160
aagtgactgt gcatgcctta gggaaaggca caggctcaga aaagatctgg gaagacctta  11220
agtttgcacc tcaggctgat ccttggcata gagacagcct acaacaataa aaaacaaaaa  11280
caacaacaaa acccagaaaa ccctggggaa gagggagaat ttgatatcca gagctgtgat  11340
```

-continued attattagat tcaaaggtct agtttccaat aataacaaca aaaaggcata ccaagaaaca 11400
ggaaagcatg gctcatccca agggggaaaa aatatcaaga gaaactgtcc ctgaaaaaga 11460
cctaatggca gatatcctac acaaagattt ttaaacaact ctaaagataa tcaaagaact 11520
aaaggaaaat gtggataaag tcaagtaatt gatgtatgaa aataatggaa ataacagtaa 11580
agtgacagaa aacctaaaaa tataccaaaa agaaattctg gaggtgaaaa ctgcaataac 11640
taaaatttaa aaaaatcact agagggattc aaaggcagaa ttaaacaggg agcagacttg 11700
aagataagac aatggaaatt attgagtctg atgaacagaa agaaaaaaga ttgaagaaaa 11760
gttaacagag cctaagggac ttgtggaaca ccaagaagtg aaccaataaa tgcattgtgg 11820
aagtccctga agaagaagag agagagaaag gactagaaag aatatttgaa gaaataatgg 11880
ttaaaaactt tccaaatttg ataaaagaca tgaatataaa catccaagaa gctcaacaaa 11940
ctccaagtaa gataaactta aagagataca cactgagaca aatataatca cttttgaaaa 12000
gtgaaagaca caaaacttga aagcagtgag agaagcaact aatcacatac aagacatctt 12060
caataagatc atgagcagat ttctcatctg aaaatttaga ggtcagaagg cagtgggcca 12120
atacattcaa aatattaaaa aaacaaaaaa aaacccgtca accaagagtc ttctattcag 12180
caaaagcgtc cttcgaagat aagggagaaa ttaagacatt cccagacaat caaaaacaaa 12240
gttaattacc accaggactt tcttccaaaa aatgcccacg ccttaaaaaa aagaaagaaa 12300
agaaaagaaa gaaagacaag aaatacctaa aggagccctg tagggtaaaa tgaaaggaca 12360
gtcaaagctc taagaagaaa taaagatctc aacaaaggta aatacatgga caattaagtg 12420
ttattgtaat aacagtttgt aacttgtttt gttttctacg tttttaagag attaatacgt 12480
ttttaaaatt tagtagccca aaagctagta gtattgtaac tttgggttgt aactccacag 12540
tttgttttct acataattga agagactgat catttaaaat aattattcat ttatgttttg 12600
gggcatataa tgtacaaaaa tgtaattctg tgacatcaac aactgaaagg ggtgggaagc 12660
tattaaagga gtggagttct ttgtgcatta ctgaagttaa ctttaggatg ctaaatgtaa 12720
tcctcatggt aaccataagg aaaatagcta tagaatatat acaaaagaaa atggggaaag 12780
aacttaaatg ttccactatg aaaaattaaa tgcaaaataa gacactagtt caggaaatga 12840
ggaatgaaaa agctgtaagg catattgaaa acaaatagca aaatgataca cacaagtccc 12900
tctttatcag taattacttt aaattgaatt aaactctcaa caaaaaaaca agttggcaga 12960
atggattttt taaaaacatg atctaattac atactaaaag agactcactt tagatccaaa 13020
gacacaaata aatggaaagt gaagatagaa aaagatactt tatacaaata gtaacccaaa 13080
gagaataaag gtggctatac taatgtcaga caaaataaac tttaaatcag aaagaaactt 13140
acaagaggca aagaataata tattaataaa aatttaaata cagcaaaata tatataacaa 13200
ttataaacat ttgttttata attatatttt taaaataaaa atataacaat tataaacatt 13260
tatgcatcca ataagatcgt caatatatat gaagcaaaaa ctgacaaaat taaaggtaga 13320
aatagacagt tctataatag tagttggaga cttcactaac agtcaataat ggatagaaca 13380
attatacaaa agataagaca cagaggactt agacaacaca ataaaccaac taaatataac 13440
aaacatacac ttaatgggta tagagttgtt gtttgacaag atgaagagag ttatggagat 13500
ggagggcaga catggataca caacattaga aatgtatttc ataccactga actgcatact 13560
taaacatgat taaaatgtta agttttatgc tatgtgtatt tggatcacaa taaaaaaaaa 13620
ttaggccaca cgtgggctca tgcctgtaat cccagcactt tgggaggccg aggtggtcgg 13680
atcacctgag gtcaggagtt caggaccagc ctggccaaca tggtgaaacc ccatctctac 13740

-continued aaaaatacaa aaattagcca ggcatgatgg cgggtgcctg taatcccagc tactcgggag 13800
gctgaggcac gagaatcact tgaacctagg agacggaggt tgcagtgagc cgagatcacg 13860
ccattgcact ccagcctggg cgacagagtg agactctgtc tccaacaaca acaacaacaa 13920
aaattagaca aaaaaaaacc ccaaacacct tcaggtgagc ccccacagtt ttgtgtgttt 13980
tacctccaga agctcaacca ggatctctca gtaaatattg gaggaaaaaa aatctctcat 14040
tctttcagca gaggaagagg aaaaggaacc attttgaaat atgccagagt actccgtttt 14100
tctaaacaag gtgtgccctc aggagaaact atgtaaccag agcctaacct ccaggggttt 14160
tactagagtc taactgatct tggggaagag gaatacccaa ctaaacccag ttctagccat 14220
tatgtcccac ctaaggaaga ggggactgaa aagcacttgt gaagttctta gtccagagga 14280
ataggctcac taaaagactg agacctaatc ataggactgt agaatgcttt ccctctcctc 14340
acaccttacc atcacattac taaagactta tttagacaaa gtctttttac ctgatacatc 14400
atatctggct atcaagaaaa attacaaggc atactaaaag gcaaaaacat agtttgaaaa 14460
cacaagtcag aagcagacat gacagggatg ttgaaattat cagactggga atttaaaata 14520
actatgatta atatgctaaa agctctaatg aataaagtag agagcatgta agagcaatat 14580
aagcagagag atggaaatcc taagaacaaa aaataaatgc tagagatcaa aaacactgtg 14640
agagaaatga agaatgcctt tgacaggctt attagtagac aggaccccgc tgaggaaaga 14700
atctctgagt tcaagagcat atcaatagaa acctacaaaa ctgacaagct aagagagcaa 14760
agactagaaa agaaaaacca taacagaata tccaaggatt gtgggataag tacaaaaggt 14820
atactagatg cataatagaa atatcagaag gagaagaaag aggaaagtaa catcagaaat 14880
acttgaagca agaaagactg aaatgttttc caaattaagg tcaaacacca aaccacagat 14940
ccaggaagct cgcagaacac catgtaggat atatgcccca aaaccccaac acataggcat 15000
ataatttgta aactacagaa aatcaaagat aaaaaatttt aggtcaggca cggtggttca 15060
cacctgtaat cccagcactt tgggaggcag aggtgggcag gtcacttgag gtcaggagtt 15120
caagaccaga ctggccaaca tggtgaaacc ctgtctttac taaaaataca aaaattagtc 15180
aggcatgttg gcgggcacct gtaatcccag ctactcagga gtctgtggca ggagaattgc 15240
ttgaacccag gaggtggagg ttgcagtgag tcaagatcac gccactgcac tccagcctgg 15300
gtgacagagt gagactccat ttcaaaaaaa agagaaaaac aaaaagtttt aaagaagccc 15360
aagggacttc tataaaggaa caacaacaaa aaaagaattg cctttcactt ttcctcagaa 15420
accatgcaag caagaagaca gtgccatgac ctgttgacag gaaaaaaatc cctagaattc 15480
tttacccagt gaaattatcc ttcaaaattg aagacaaaat aaagacttct caaactaaaa 15540
ttgaaggaag ttgttgctaa tagctctgac ttgcaagaaa tgttaaagaa attctttaga 15600
gagaaggaaa atatgtagtt cagaaactta gatctacata aagaaagaaa gcattgaaga 15660
aggagtaagt ggaggtaaaa taaaaatttt ccttttctta ttctaaaaga tgacagtttg 15720
ttcaaaataa cagcaacaat gtgttcaatt attcaattat gtctacttat gtaaatacat 15780
ctcctaagca gagatcccag accagaccac ccaggctttg gacccgccaa actgtgagtt 15840
aagaagtggt gttgttttgg ccttggcatg gtggcttaca cctgtaatcc cagcactttg 15900
gaaggctgag gtgggtggat cacttgaggt caagagttca agaccagcct ggctaatgtg 15960
gtgaaatccc catctctact aaaaatacaa aaattagcca ggcatggtgg cacgtgcctg 16020
taatcccagc tacttgggag gctgaggtac gagaattgtt tgaacccggg aggcggaggt 16080

-continued

```
tgcagtgagt cgagattgcg ccactgcact ccagcctggg tgacaaaggg aggctctgtt  16140
aagaagtggg tgttgtttta agctgtttac tttgtggtaa tgagtgacag agcaatagaa  16200
aactagtaca cctgtgctca gtgtttacaa gaacaaggca aacgtgtcaa cccaacacca  16260
gagatttagc cctttattct cttgggggct tgcccatgcc aggttgtaaa ctcttggagg  16320
tgtttaattt gctcactctt gcgccccagc actcttgtat taatatgctt aatacatatt  16380
tgaatttttt aaattgtcgt gtggaatgat ttgtctacca ggatgcttta tcacagcaat  16440
agcaataaaa tcatacagaa aagttctatc caataataat taggccatac aatcatatat  16500
ctgtaagata aagtaccatg cttcctttta aatcgtgatg tgaaaaacaa tttaatgaca  16560
ggaaattatt cataatatat ttaatagcaa attacaaaat agagaaatgt gcatgcacac  16620
acacagaaaa atacttgaaa agtgggatct caatatacaa aaagtactta tctctgagta  16680
gtaaggttat gggcaattta tattttcttt cttactttgg ggaagtgcct tcaaaaactt  16740
ctattataaa aatatatgaa ttctataatg agaaaataat tagcacagga agtagacaga  16800
gatccattta aggcatattt tatactggaa actggagaat aggcctcacc ttgagtagct  16860
cctccccact ggcttgggca ttctctgact gttctttgat ttgtttttga aggtgaagaa  16920
cttgcccctc catgtaccta gatattccgt catagtaagt aagtgtcatg gttcttcttg  16980
gcaaaagatt tttagctcta ttggaaaatt tgtaaaagtt gtcccattcc tgaagtctgg  17040
catacctgca ttaccacaag agaataagaa aaatcagtat cacccattag gaataggctg  17100
gctttctgaa atgtctctct ggatgtgcag cttcctttac ctgggtctct ggaagtgtgt  17160
agtctcctgc ctacccctgc ttcacactcc ctaaaaaagc aggaaattat gtgatacaga  17220
gcaaggaaat aataaatttt tttgatgact tgagatgaat agaatccttg gaaacactca  17280
ggtaatatta gccaccattg aactctttgg ctttggcttt ttttcttttt ttgagacgaa  17340
gtcttgctct tgtcccccag tctggagtgc aatggcacaa tcttggctta ctgcaacctc  17400
tgcctcctgg gttcaagtga ttctcctgcc tcagcctccc gagtagctgg gactacaggt  17460
gtgtaccacc acgcccagct aattttttgt attttaagta gatacggggt ttcaccatgt  17520
tggctaggct ggtctcgaac tcctgacctc aggtgatcca cccgccttgg cctcccaaag  17580
tgctgggatt acaggctgtg ccaccatgcc cggccacttt ggctttttaa attaaaaagt  17640
gagggagatc agacacttgg agctgtggat tctggggctt gaagaaattg ttccaatacc  17700
aaagagagat gatttaggcc agtactgctc aaaatgtagt ccacagactg gcatcatcag  17760
tatcacctgg attctcatta atgcaggttc tctggttcag tccaggtcta ctgaatcaga  17820
caggctctgg gggtgtggca tctctgagtt aacaagctct ccaggtgatt ttttttttaa  17880
cccttcaaag taattaaaaa taagacattt attccaacaa ttcttacatt gcatgaaata  17940
cctctttaat attctacctg catttggaac taccttcaga gtatatggta caatcctttg  18000
aatattttct gtgtagaaaa tccgattttt tttttttttt ttttttagat ggagtttcac  18060
ccttgttgac caggctggag tacaatggca cgatctcagc ccactgcaac ctctgcttcc  18120
ctggttgaag caattctcct gcctcgctgg gattacaggc gcctgccatc acgcctgcct  18180
aattttttat atttttagta gagacacggt ttcaccatat tggccaggct ggtctcgaac  18240
tcctgacctc aggtgatcca cccacctcag cctcccaaag tgctgcgatt acaggcgtga  18300
gccactgctc ctggcctgct tatgattttt ttattttttta ttttttttta ttttttgaga  18360
cccaagtttt gctcttgttg cccaggctgg agtgcaatgg cgcgatcttg gctcaccgca  18420
accttcgcct cctgggttca aacaattctc ctgcctcagc ctcccaggta gctgggttta  18480
```

-continued

```
caggcatgcg ccaccatgcc tggctaattt ttttgtattt ttagtagaga tggggtttct  18540
ccatgttggt caggctggtc ttgaactccc gacctcaggt gatctgccgg cctcggcctc  18600
ccaaagtgct gggattacag gtgtcagcca ccgcgcccgg catgattttc taatagccaa  18660
atatttaaag ccaaatcgga tcaacagtag gcaaaacatc ttctccaggc catcaacttc  18720
atcttcatct gtgctgtatt cttccattgt tttgccacta acaaagtgga tgactctcct  18780
tgggactttc ttcttttttc ctatgactcc cagttctacg tttcaaagcc tctttcgtta  18840
ctcatccttg agataaaatt tggctatggt tgtcctgaca tcaacgtttc cttttggacc  18900
atgactcagc tttttggatc ccttaatttc ctgccccgca gattccccga atgccgcggc  18960
ggccgcagct cccgaggctg cgacggcttc tcctcgttcc acagggccca ctgggtcctg  19020
gtccatcgtc gtcgccacca cagggctgct ggcgccgcag cgccggccgc ctagccaagt  19080
ctctgggaag gggactagcc ggccttgagg ggcggggccg gccagagggg cggggccagc  19140
ccgcgcctcg cctagcccgc ctggctcagc accccgagag ctggccgact gccctccagg  19200
tgatttttat gcccactaaa gtctgagcag cattggccta ggacacagct gtttaaaaaa  19260
ttctcctgct gagatagaca agaaaaataa atttggatga tttctggact ttagattcct  19320
taacctttaa ctcacattgg taagttattt gattttgaac tttaattggc aagagtaatc  19380
aatttttgga ttttaatttc tcctcattaa ttttaataat aagaggggat ttcttgccag  19440
gtgcagtggc tcatgcctgt aatcccagca tttgggaagg ctgaggtaga cgggacctga  19500
gcccaggagt tggagaccag cctgggcaac atcacgacat cccatctcta caaaagatta  19560
aaattagcca ggcgtggtgg tatgtgcctg caactccagc tactcaggaa gctgaggtgt  19620
ttgggaggat cacttgagcc tgggaaggcg aggctgcagt gatccgcgat cgcaccacgg  19680
gactccaacc tgggtgacac agcaagactg tctcagaaag aaggaagggg tggatttcta  19740
ttccaatttg gagctgttct aacttgtagc attttatata ggaatgtctt catattgtca  19800
tttagtctca tcacaaacct ctgatagacc atacggttgc atataattaa gataggaaat  19860
aaaataatag ggggcgattt tcagtcttgg ggatagtcat ggaaataatt taatgaatgt  19920
tctgttctga cccattttag aaccttagca ttcatctcct tccttaaggg tatgaccata  19980
atagctacat gcttaactga gttaaaaacg tagtaggtta aaggaattga gccttaggct  20040
taatgagtta atggggtgcg gggagaatgc tgcttcctca ctcctgaaat ttccttccat  20100
gtaaggggcc tctatttggt gcaaagcacc agaactcttt ccccgcttta cttgcccttt  20160
caatgataag gagagatctt gctggtgatt tgggagatga attgggcaag tataactcag  20220
tccgtgtctc tctctatctt gagagccagt gaagccaaca gggagtgtga tactgatctc  20280
tctgctacaa gaggcctgcc tccatgtgag tagacctaca gttttccaga actgcctgct  20340
gctgaatggg ttaagtctaa ttccagtgct caatattacg aagcccgctt tcgtgaagat  20400
ataagccatg tcttccaaca ttggctttgt caatccatgt gattagatat gggcaggtgc  20460
cgggtgggca agtggtgcta ttcattagtc ttcctcaaac cccagcaccc ctctgaagaa  20520
agcaatcttt tcttatttat ccctgtatca ccacaacatg atatgtttgc gataaatgtt  20580
tattgcatgg atgtaattga gataaattta cttttctgtc cttggccaag ggggatgaac  20640
tagttgatcc ctaacatgtc tctctgtgta aatatcctct gacaccctta agctgtctca  20700
ggtataaatt atgaatactt tctaaaagat ttttcaagaa ctcttccttg ggattcaaca  20760
ttttcacttt gggaatttag tgatatgcca cacattgtta ccagatagct acagaggaat  20820
```

-continued

```
aaagtcccag gaggagtcca ctgtggaact tgaggattct gttgttttcg tattggtgta  20880
tgaattccaa acattcttca aatgttctat aaacaaaacc taagagagag aggaatgggt  20940
gagagttatt agtaggtgtg ggtgatcatc tttctagcct agtcactctc agttgaattt  21000
cccactgcag ggagagttgc ctctgattat tgtatgaatc cagagggtcc cgtggattgc  21060
aacaacctca tgactggatt gccctgtgtt tgctgagtcc tacctattgg ggagtgttat  21120
ggatatatac tacagttcca cagtaccgac caggcaggtg tggggtttaa actaatcctt  21180
cctggcctta gtgcagccta ggacttctct gtctctccac acatgcttcc tttgttgatg  21240
gcaatgtctg catccccttt caagatcaca tgtggggaaa acaattcagg ttggttcctg  21300
tggtttagtg tgtacacttc aagtgaccta cttggtgtca cttgaaggtt atcaggaagt  21360
aacttatttt ccaaatcacc aatagctacc agcctggaac tctcacctca agcaatctag  21420
tccttcattc taaagcgtga agtctctaag tacatcctgc taaaagttaa aaacccctgg  21480
taaaaggcac atagtaagac agtcagccac tatcacttag gtgcaaattg atctgacagt  21540
ttaactggca gctcatatcc atcaggttcc ttcagactta attctccttc ttgccgtgcc  21600
tttacaatct cggcacctgc tagacagtgc ttcagctcac acaaccagcc tctctccatc  21660
cctgccctgt aagtccacca gccagaaacc tagtggtccc aaagccccaa cctgagagct  21720
gccacaccac accagcacag gtatcaacac ccccaagttc ttttacatcc caaacccaca  21780
cttaccagaa taaagcagga tgtccaagca gacaaaatag aaaaatgcct tgctgaagat  21840
gtgttcctgt gttacagaaa gctcccacag ccgccccagc acctggatca attgcgggta  21900
```

<210> SEQ ID NO 13
<211> LENGTH: 28810
<212> TYPE: DNA
<213> ORGANISM: Homo sapiens

<400> SEQUENCE: 13

```
tctatggaaa agaaaaggta gtggccatta aaaagtggtg gatattgtaa tcccagcact     60
ttgggaggct gaggtgggtg gatcacgagg tcaggagttc gagaccagcc tggccaacat    120
ggtgaaaccc catctccact aaaaatacaa aaattagctg ggcatggtgg cgggcgcctg    180
taatcccagc tacttgggag gctgaggcag gagaatcgct tgaaaccaga aggcggaggt    240
tgtggtgagc caataacgca ccactgcact ccagcctggg caaaagagcg aaactccatc    300
tcaaaaaaaa aaaaaaaaaa aagcagtgga tataatggac tttggggcct cggaggggag    360
gggaggaggg aagtgaggaa taaaagacta catgttgggt atgtgtacac tgctcgggtg    420
acaggtgcac taaaatctca gaattcacct ctataaaatt catctatgtg accgaaaacc    480
atttataccc ccaaagctat tgaataaaaa aagcagtgga taggatgagg ttcagtaaag    540
tcccttcctg gtctagtctt ggtccttctc agtaattcgg aaccaaatat acctcttaaa    600
cagatttcaa acacacccct atccaggact aaaacctcaa tctcaaattg gctctttttt    660
caaattgttc tttcctgggt cctctatatc agggtgacca gagtcagagc aaattggcct    720
tgacctctag tcctggttgc tattctctgg ccatttgcct ccctggaaga cttttccctt    780
tgtctccacc tgacagaagt ggaggcctga ttcccacagc tgggatgact gtctgactac    840
cctctgatca ctggccagag caaccagatt agagatgatg caaggcaaag aattctgttt    900
aaaataaaaa agacaaggcc tggcgcagtg gctcatgcct gtaatcccaa cactttggga    960
ggctgaggtg ggtgggtcac ttgaggtcag gagttcaaga ccagcctggc caacagggtg   1020
aaaccccctc tcttctaaaa aatacaaaaa ttagctgggt gtggtggcac gttgcctgta   1080
```

-continued

```
atcccagcta cgtgggaggt tgaggcagga gaattgtcta aacccggaag gcagaggttg   1140
cagtgagcca agattgcact actgcactcc agcctgggag acagagcaag actctgtctg   1200
aaaaaagaaa aaagggtgac tactatcagt tacattttct tactgcaaac tctactccct   1260
tccccaccct aggactaggc taaagttgaa cccagaatac tcaataatac ggcctcctcc   1320
ccctaatttt ggaaaatgct ttaagataaa tacctgctgt tcagaaggag acatctgcta   1380
agtctgcaga gggactgata atgtcggttg ggattctgga gcagtgccca catctgaagg   1440
gctcgggagc ctgggaagaa aacaattcca gtatattgtg gggcattcct tgtatcctca   1500
tgtcccatct tgcccagcca gcccttacct aactcaatgg ccaaatccag gtgtcccatt   1560
atgagcttgt tgaagaccag tgtctcagcc acgtatgcca cgatttcaat gccctcgcct   1620
ttcaggggga ggttgaagat gtgctccatg gccatgactt catatttgaa ccacacacct   1680
ttgtagccag ccaggtggtg gtatagcgaa tagtctaggt aagccttaat gatctgaaat   1740
ggcagagtgg aggaagagtg aggcagaacg caaagcagaa agctcaggaa catcactcaa   1800
tgtctgccag taaatgtttg tttattaagt ttgggaatag agctggacat ttggccgaag   1860
ccatgggctt agaaatagaa atcaaattgg gtttctgcta cctgtttact gagtcattca   1920
ggataagctt gatggcccct tgcccatgta gtccttaaat gaaatataaa aattttaatt   1980
tctgtgaaaa ataaaagcaa tagcttacat attagatgta taattgcaga gcaaaaaggc   2040
tgcaaggata cactccaaag tgtaaacagt agttatatat ttgttggggg tgggaggaga   2100
gattttactt tatgcacctc tgtgatgttt gttataacaa gcatgtataa tttttgtaat   2160
ttaacaaaaa agaaagaaag gttggttttg tttgtttggc tttttttttt tttttaaata   2220
aggactagtt ttaaacctaa tttggaggtc aggtgcagtg gctcacatct ataatcccag   2280
cacttctgga ggccgaggca ggaggattgc ttgagctcag gagttccaga tgagcctggg   2340
cacaatagtg agaccctgtt tcaacaacaa caaaaactag ccaggcatgg tggcatatgc   2400
ctgtagtcct acctactcag gaggctgaga cgagaggtca cttgagcaca ggagtttgag   2460
cccagcctgg gcaatatagt gagacctgat ctctacaaaa gattttaaaa aaaagtagcc   2520
agcatgatga cacaagcctg taatcctagc tactcaggaa gctgaggtgt ttgggaggat   2580
cacttgagca ggggaggttg aggctgcagt gagccatgat cacgccactg cactccagcc   2640
tgggtgactg agtgagaccc ttctcaaaaa cgaacaaaca aataaatcta atttgcagat   2700
ttaagagaaa ctggttactc taaacaactc tttaaaaaga taaagttgct tcagagtata   2760
catgcttaga gaatagtgag gagaaaaggg ttccttctaa agaagcagtt ttattatata   2820
tacaaaaaca aaataataca tgtaaactac tttgaaaaat acaaacagga aaaataaagt   2880
atctctagtg gtgggagtat tggggtcggg gaagtgtttt agagtagagg ctttttttctt   2940
ggaattcctc agatgggaca aaataagcag cctacaaatt ctgtgttata ggcaggtccc   3000
tggatactta aaccacatca gtcttagaga attcctttct ttctggtttg gaacatgttc   3060
cagataatgc taccagaagg taaggatagc cagaaatggt ggtgggggaa gagagaagtg   3120
ttgggcacga gaaatccaag gctgtaataa agcctaggac ctcttggatt tggaccaaga   3180
gaatggaggt ccaactgctt cactttacag agaaaatata aagctccttg tttatgcggc   3240
ttttcagtgg tcacactgca gataggcgga gtcctggaaa ccaccctctg gctctcagtc   3300
tggttctttc cattctccca tgctgagtcc ctcacctgcc tttgagcact gaggggagcg   3360
cttctttgct ttcaatccca gccaccttga tgacaaatgt cttggttcac attctatcct   3420
```

-continued gactttttat tttccccacc ccaactctac cacaattctt aggatatagc tccaagtgtg 3480
gagaagtatt tcagtccata taaatttctt gagcaactgc aaatgttcta gaaacttagg 3540
atgtgaacaa gacagctgaa gaggtccttg cttccaaggg atttacacac tggtaaggga 3600
gagagaccaa gaaccaatgc aggagcaaac aagaaattgt caaatggtaa taatacctat 3660
taaaacagag tgacaagtta gaaagtgaat gggtggccat gaccagttcc ctccaagcag 3720
aggaaacatc cagtgacaga tgggattaaa cttctgtgtt tgaggaacca aaagaggacc 3780
aatatggctg ggcttgtggc tacttcatgg cctacagagc tagaagagga tgggaaatag 3840
gcaggggtca atcttgatgg gctttataaa tacttctgta ttctaggaga gccagcctaa 3900
attcaccaaa aggaactaat gtagaggaca gactccaggt taggaatcta agctcctcca 3960
acagtagctc cttggtgcta cttgacccct tcccttaatt cttgacaact aatgactcca 4020
ggaggaagaa acccagactt aatgtacttt tttttttttt cctgagatgg agtcttgctc 4080
tgtcgcccag gctggagtgc agtggagtga tctctgctca ctgcaagctc cacctcctgg 4140
gttcacacca ttctcctgcc tcagcctccc gagtagctgg gactacaggc gcccgccacc 4200
acgcccggct aatttttttt tttttttttg tattttcagt agagacaggg tttcaccgtg 4260
gtcttgatct ccttaccttg tgatccgccc acctcggcct cccaaagtgc taggattaca 4320
ggcataagcc accatgcccg gcctgctgat ttaatgtact tttataaagg agcaaggtca 4380
ctctcattag atgagtttga tttagcttaa taatttcttg atcatgtctc ctgatatctt 4440
cttcatccag tcaaaggctt ctttggttat gacctagact agtggttctc ccaattcatc 4500
ctgggagccc tagggatccg tggcaccttt tcagagacca catgaggtca aagctagttc 4560
cataatatct aggcatttta aatttaaaaa aaaaaaattt ttttttttga gttggagtct 4620
cgctcttgtc atccaggctg gagtgcaatg gtgtgatctc atctcactgc aacctctgcc 4680
tcctgggttc aagcaattct cctgcctcgg cctcctgagt agctgggatt acaggcaccc 4740
accaccacac tcagctaatt tttgtatttt tagtaaagat aggttttccc catgttggcc 4800
aggctagtct cgaactcctg acctcacgtg atccgcccac ctcagcctcc caaagtgctg 4860
ggattacagg cgtgagccac catgccccgc taatatccag gcattatttg tgacaggaaa 4920
aatagtgaaa gaccttaaaa tgggcaaaaa cacaacttag tggggatcct atctagctta 4980
ctaatcaaag ttatctctat ttttctttgg actatcttac aactatgttg cagaaaactg 5040
atattaatat aagtgatatg atttgttttt catagaaatg taaatattca gtggaataca 5100
agtgattatt atgctgttac tagacaagtt ttgtatccat tggtaaacag attctccttg 5160
gaaccacttg gttccaatct tactaatttt gattgagtca actcagtgag ttaaataaaa 5220
tctttgatgt gtactttcca tatttgttat cagttataat tctatctttt taaaaaagaa 5280
ttatccttta acatttttct ctttcaccct cattctctca tgaatataca ctggagtctt 5340
ccagaggcaa catatgtgat actgcaacag tgaaagcaga agcagatgtg agaatctagt 5400
tgtcttctaa gaagccagat gttaaaatat tggcaaaaat ttaatacaat gccacatttc 5460 ccatttttttg tttgcggaac agagttttaa aaaatgaaaa tggtaattat gttaatatgt 5520
aataggcttg ttatctttat tttaaaataa tattttaggc caggtgcagt gcctcacgcc 5580
tgtaatccca gcactttgga aggccagtgt gggcagatca cttgaggtca ggagttcaag 5640
accagcctgg ccaacatggt gaaaccccgt ctctactaaa aatacaaaaa ttagctgggt 5700
gtggtggcgc atgcctgtag tcccagctac tcaggaggat gaggcaagag aatctcttga 5760
acccgggaag tggaggttgc agtgagccga tattgtgcca ctgcactcca gcctgggtga 5820

-continued

```
cagagcaaga ctccatctca aaaaaaacca gcaaaaataa taataataat attttagaat   5880
tttctcgact tttgtttctt atatgctatc aatagattca acccatatga ataaaagcta   5940
ttcgggatct tcaataattt ttaagagtgt gaagtgatcc tggagccaaa gtgtttgaga   6000
actgctggcc ttgtcaaaac aagccaatca gaaagccttc tattattata tcctcagaat   6060
tttgaatcct aattggcttt cactaggctt ttcttcccaa atgaaattca gaaacttaaa   6120
ggagcagcta caaaaatccc ctacctggaa acaattttga gtttccagtg cagtattcat   6180
ttgcatcata actgccaggt gggcataata cttgcagtga aaaagataac tgtagctata   6240
gatgcgccac agcaaggaaa ggcagacagt ttgccggtaa agttgtgcca gcctcttctt   6300
cctattggat aaggtaaaca caaatggaac atgaaaggta tcatcattac catgatttag   6360
gggagcacag gtacatggtg tcctcactat gggcctggga atcaaaactg acttgaattt   6420
gaggcctgtc tccatgactg acaaacaagc acattaattt ttatggagca cattttcttc   6480
attgtaaaat gggaatcata atacctactt tataatgatt aagataattt atgtaaagca   6540
tctgtcctga gtcaggtaat tgctaaatga agctatttaa aaagcacatt gatattattc   6600
atcacatttg attctgatga caatcctgta agaaaagagt ggaataactg actccatttt   6660
acatttgagg aaggtgagac tcaggttaag taattaaggc aaagacacac agctggaatg   6720
tggtggtgcc aggattcaaa ctccatctac ctccagccca aaagcccaat gtattatttt   6780
ctccattgca cactgctttc aggaactact tctcagctca acaaaggtgt gaaaggaaaa   6840
taaaaactca ggatcccaat tcactatgcc aaaaggaaaa aattaagctg aaagctgagt   6900
catgcaagaa gttgcctttc cttttgttcc ttagcagaca gctacagata aaaagttaag   6960
tatctgcacg ggtagctact ctatgtctgc cttatcctac cttaagtgcc tatttactga   7020
gtgtgagaca atacataatt gactattccc ctagctgctc ctattctctt gcaacatgtg   7080
gattattatc acgccctccc tcattttcct ccagcccact tttccccttt aaatactgca   7140
gtctcaaaca gggactgttt ctgtggtttt gtgttttttt ttcttctggg catgtcctta   7200
accttggcaa aataaactta cagattgatt gatacctgtc ttgggtactt tttagtttac   7260
aaaaaaaaaa aaaaagagga ttttttgttt tttgagcctc gctctgttgt ccaggttgga   7320
gtgcagtggc atgatctcag ctcactgcaa cctctgcttc ccaggttcaa gcgattctct   7380
ttcctcagcc tccccagtag ctgggattac aggcacacac caccatgtct ggctaattat   7440
tttgtgtttt tggtagagat ggggtttcgc catgttggcc aggctggtcc tgaacccctg   7500
acctcaggtg atccgcctgc ctcagcctcc cgaagtgctg ggattgcaag cgtgagccac   7560
tgcgcctggc caaaaaatga gcatttttaa ctattgcatt ttgaaaggaa aatatcttgg   7620
gcccccaaaa tcactaagga aaactcaagc tggaaactgc ttagggcaaa cctgcctccc   7680
attctattca aagtcactcc tctgcccttt gacatagatg catatctgat ttgcctcctt   7740
tggaaaggcg aatcagaaac tcaaaagaat gcaacttttg tctcacctat ctgtgacctg   7800
gaagctccct cccaacttcc tgcctttgct tcaagttgtc ccacctttcc agaccaatgt   7860
acttcttaca tatgttgatt gatgtctcct gtctccccaa atgtataaaa ttaagctgtg   7920
ccccgaccac cttgggcaca tgtcgttagg acttactgag gctgtgttac aggcgtgtcc   7980
tcaaccttgg caaaataaac tttctaaatt atgatgtgga aatgattttt tttaaaggtt   8040
cttaggaaac atggacaggg taaaatctct ctctcttttt tttttgagac ggagtctcgc   8100
tttatcgccc aggctagagt gcagtggcgc gatcttggct cactttaacc tccacctccc   8160
```

-continued

```
tggttcaagc aattcccctg cctcaacctt ccgagtagct gggattacag gtgcacgcca   8220
ccacgcctgg ctaaattttt tctgtatttt tagtagagac gggatttcac catgttggcc   8280
agactggtct cgaactccca acttcaggca atccgccccc ctcagcctcc ctaagcgttg   8340
gtattacagg cgtgagccac aacacccagc cctgggtaaa atctcttata gggcattcgt   8400
gagggtcatg gacactctga cattaaatgt tgttccatgt catactcatt tttgagatga   8460
gaaccttttg acctgtggat attttaagcc aacagctcct cagtttttc ttcttcaaca   8520
cttttctacc ttttcccttt gtgcaggtac ttcttactcc ttttacaaaa tgtgaaatgt   8580
gtaaattacc tgttttagca gatgaaaata caggatgccc aattaagttt gaattttaaa   8640
cctaataatt tttatggaat gcatatgtcc taaatatttc atatgataga tgtatactaa   8700
aaaaagtatt cactgtttat ctgaaattca aattgaggca tcctgcaacc ctatgtgtaa   8760
tgcaaagacc actgccttct cagagagatc tctgctgaac atctcccagc ccttcctctt   8820
ggggtttcca gaaacagcca ggttttccca ggagcccacc tccaacgtgc acaggagctc   8880
agctccatta catttccttt tcacctcagg attccctaca tttaaaggaa catgtttgga   8940
agctggggaa ggcagtttct gatggggttg caaaagagtt gtagtagctt gctcgtagga   9000
atagatgttt gtatcttagg cagaacctat agtaatatag ctacagagct cccccaagat   9060
ggaagaggtg tcctctgtca gctctccagg tacccaacaa ggaggcatct cctttgccat   9120
gaattgctag ataggtggaa tatttttgaa aacatttatt atagaataat tcaagcatac   9180
acacagcaaa caagagtatg atgagcaaaa tgcactcaac acctaccttc aacaactagc   9240
aacatgctta tttcatctac ctctccactc actatttctt cccactcatt attattatag   9300
ttatcttata ggtagaattt atatatattg aaatgcccaa atcttaacag tacaattttg   9360
accaacggat auccccccatg taacccatat ccctattgag attcctagat gggtgggagt   9420
tttgtccttt ggcaaatgtc ttcagggctt gctatttttc tttggggcgg ggcaaaaccc   9480
agtgtcttag cacctaatgg aagagggctt gtgactgagg tcccaggagc agtggtgcag   9540
gttccatcca atgagaacac ggatggccat gggggttaaa gggctagatg agttaggacg   9600
gaccctagaa cttaccttac aacgaggtcc cttatgtttg agtcatcaaa attccctttg   9660
gcaaaaactg cctgtaaagt actttgtggc aaccctggta tgggagcacc tcccacactc   9720
gccccctccc cagtgaatgg tcagagccaa acaggagtcc ttgtgccccc tggaggccag   9780
gctttgggggg ctgacttgga ttatgtgtag gcctctctgg ggagtgagac taaacagtct   9840
gctctcccca gctccttccc ttaccctgga ggtgggctct cttgggcctg ccgattcaca   9900
taatgaaagt gtctgttttt ctcgacatgg atatggagaa acaaggagat taagttgtaa   9960
ggaaagattc ggttgaggag cttcagtgcc ttcctcagca ttttcttggc aagcactatc  10020
tggcccatat tgaaacagac ctacagggag gtgggaggga agagaggaaa agaggaaaac  10080
gatgattcta acttaattag taggtcccaa caatccatat tttggggatt cttatcaaaa  10140
aaggtaattt atggaccaga aacaaaatct tcctgtgcct ggcataatag aaaatgtcta  10200
ttggatatat gcatgaaggg tggttgaatg actaggattt agcatcttag ttgtgcattg  10260
tctacctctg agacaatgtt tacccattca ggtccatttt tagagattgt aacaaaaata  10320
tttcataaag gtgtcaacct gggccgggca cggtggctaa cgcctgtaat cccagcactt  10380
tgggaggtca gggcgggcgg atcacttgag gtcaggagtt tgagaccagc ctggccaaca  10440
tggtgaaacc ccatctctac taaaatacaa aaattagctg ggcgtggtgg cgcatgcctg  10500
taatcccagc tactttggag gctgaggcag gagaatcact tgaacccagg agacggaatt  10560
```

-continued

```
tgcagagagc cgatatcacg ccactgtatt ccaggctggg caacacagca agactccctc  10620
tcaaaaaaaa aaaaaaaaaa agatgtaaac ctggaagaca gggaagatct tgctggtaag  10680
ccatggtgag gaggttggag cccagggatt tgagtttcta gagtcttggc tagaagtctg  10740
tggcaagaga tgggaggagg gtgtagaaag tatagggatg acttctactt ctatggaaag  10800
gcctaagata tataacagat aaattcaagt ctttaatggt ttcttacctc acctttgagg  10860
ctgtaaaagg tggcagactc aaatgtctgg ctccaagatt tgtccttctt gagagttttt  10920
agcaacttct gtccttcatt caaatacatg tatgcctgta accagcccaa ggagtagaaa  10980
agtgttgatt cagcagggat tgagcccaca gaagggccat tgccccagac tctactgaag  11040
taagagatgc aggagccatt tcagttacca cctccacttc catccccagc tccactgatt  11100
aaaatgggct tccaaattcc agacaggagc tgatgggtaa agatctcacc ttcatgctta  11160
cctttgtctg ctggatcact ccatcaagag aatgaatctg gaaatctcca cctttcttca  11220
cactatcatc taggttgcct tacccgaagt ttccctcaag ccagtttctt cctctcaata  11280
attctatccc caacctccct attcccaaca acacatccac ttcccttgaa cagcatcccc  11340
acatctgtga gaagttggtc ttcagttttt aaatgaatta tgaatcaccc ccacttcctt  11400
tgccagggtc attttgggag gtggatgagg aagtaagtcc ctgcacaact ctcatcactt  11460
cagcttcacc tcccaacatc attaggcaaa tcttagcacg tgtgcacacc aaggtaagat  11520
cagacttgaa gaatataata aggtgaggca gtatctccca gtctcatgca tcctgttggg  11580
tatgtgtggg aggcaaaaaa agagggagac atgatgagtt ggccaccagc cccagtccca  11640
ctggagtttg atgggagagg gggtacaaat gtcacattct gggaccttgc actgaggctg  11700
tgcttctaat cattgtcttc ttgtcaagtg aaacggggta tgcataggtt ttagaaagtt  11760
ggcccccagg gctacctaag cctcctcctc ctgggactca ttggctacat ccccatcatc  11820
acctcgaata tgtgcatgaa atatgcagga gactttcatt cttaacataa atgtttcaag  11880
gacaggaact tagtgacatt tttaacagtt taattttata attttatata aatctaaggt  11940
aggagggttg attaggctgc tgtgaccagt agcaactgta aattatggaa ggtctatgaa  12000
gctcttcctg aagctggctg aagtcagatg aagcaagggc ccagaaagac atttcctcaa  12060
gtgagttcat ggaaggttag cccagccagc tgctccatga aaagagatct aagggcaaat  12120
aagtttgaga aacacagtat gcttcagcct agcctggcct ttacccttct gtgtcctctg  12180
aacagattta tatatatatc tcagcatatc aaaggccctg aagtatctaa aggcatctat  12240
ttacctgtat tcagctcagt gatttccaac ttacttaaca atgaattctg tttatttcat  12300
catgtgtatc aaatcccctc atttctatgg gcatagtgcc ctggaacctt atttataatt  12360
accctagaga aacattcact agtgctttgg tggtctaatg gtatgtgtaa taatctagca  12420
cacattgcat gatgacaaag gcagggagag cctctttggg gatcacaata ttaaaaccag  12480
aattggctgg gcacagtggc tcacacttgt aatcctagca ctttggaagg ccaaggaggg  12540
cagatccctt gagctcaggt gttcaagacc agcctgggca acatagtgta accccatctc  12600
taccaagaac acaaaaaatt agctgggcat ggtggcatac gtctgcagtc ccagctactc  12660
aggaggctga agtgggagga tggcttgatc ccgggaggca gacgttgcag tgagcagaga  12720
tcgcgccact acactccagc ctgggtgaca aagacttcat ctcaaaaaca aaacaaaaaa  12780
ccagaattgc acttatccaa agacctacag gtattttgtg ctcacaggta ttttaggctt  12840
aacagagggt aaatgccact tgaggaagac tatgctgaga gtcctctctg catcattttg  12900
```

-continued

```
ggaatgagat gtgcccctt acctcccata caggtagaca attcatggca agtttctaaa  12960
ggtggcaata ttttaaataa tttacaatgc tagttgcaat gtattccaat tctcttttct  13020
caatcttaga tcatttccct tctaagcaat gtgattttca gtggaaaggg gtgctgtcgg  13080
gaatatacaa cgtgaagtaa tcagaaagca tgctggagct tccttctggc tctatgttct  13140
atgaattgtc tctagggtgg aggtggtctg ggtagaaaca gcttaccatg tagttatcac  13200
aaaagatgag ataagcagat gcaatttcta agaagtaata taaggctttg tcattttctc  13260
ccaaagccag aaaatggtgg gccagaggca agatgacaat ctctaggatt tcttcacact  13320
ggcaagattc cagagggata atgtcttcgt cagatgtctt catttttgtt aaaacgtggt  13380
caaagaaatt caagatcttt tctcttattt cttcaggact gtccatatgc agaaataaat  13440
aatagtaact tatacagtat cacttttgat attaaaatat ctttaggcca gacgcggtgg  13500
ctcacgcctg taattccagc agtttgggag gccgaagctg gtggatcatc tgagatcagg  13560
agttcaagac cagcctggcc aacctggtga aaccccatct ctactaaaaa tataaaaatt  13620
aggccgggtg cggtggctca tgcctgtaat cccagcactt tgggaggcca aggcaagtgg  13680
atcacgaggt caggagatca agaccatcct ggctaacacg gtgaaatccc gtctctacta  13740
aaaatacaaa aaattagccg ggtgtggtgg caggcgcctg tagtcccagt tattcaggag  13800
gctgaggcag gagaatcact tgaacccaga aggcggaggt tgcagtgagc tgagattgtg  13860
gcattgcact ccagcctggg tgacagagcg agactccatc ttgaaaaaat aaataaataa  13920
aataaaatat ctttaaaaac aaaagagcag gataataaaa cctagtgtgg atactactga  13980
ctaaactcac catgcatacc ccccaaagtt tcccacttgc atctaagagg tcaaaagtac  14040
tggccagaca aatgattcta atagtgttct gaatttaatg acaattattt atgctctact  14100
tcctaaacaa tgatatatgc ctctacctgc gattttcagg aaaaaatgca gatgtctcag  14160
gaatctctga gttggacaag ataagctttt cttcagctag aaaataaaca aatgagttgt  14220
atgggtcatt gaaatgttct ctgcagtgga gatatctgct gtctacccaa gactcttgtt  14280
cccttttcgg agttgttgct gcccagccag aaaccacatt gcctagtccc cattgtatct  14340
taggtgaagc cacgtgatga gttctcacaa tagaattaga tcagaagtaa tatatgtcac  14400
ctctaggcta agatggttat gtgtcttctc tgccttctct ttccacaaga aagcaagtaa  14460
ttctaagaac ctgaaggata gcaaacccac aagttgggag gagcctgggt cccttgctaa  14520
ctgcatgcaa agccattggt caacacttgc attggattat ttcataaggg ggaaataatc  14580
actctcttgt gttaatccac agaaatgctg gggtttgtga tagctaataa cattatccta  14640
actcatttat tctgcaataa aaactatgaa ttaaacctga agaaagtgac atcaatttcc  14700
agtggagaaa tatagataat taaatgaaat accccaaaag gttaactgaa gggcagagaa  14760
tcttaaatta aaaacctcag tctaagcaga cttgaacagg ttagaaaatt ccataatgat  14820
cttaaaacag aaaacaaatg aggcttgtct agtccagcca tttctccctt caggcagaag  14880
aaagaatccc agagagggga atgaacttgt ctcaggtcat acatctgtta gtggtggagg  14940
caggactaga acttaggttt tctggctccc aggctaatgc attactccat acatcttata  15000
gatgcagttt gaacatctaa gaagttacca ccttcttctg aaagccctct gtgctcttgc  15060
ctccatagat aagtacccca actcctgtgt gcccgtcaac cctgtgcaga cctgtatcat  15120
agtccttatt gtactgcaca gagatcaatt tggccacctc ttctcctaga ttactattta  15180
ttgattcctt agtgactagc agctgaatat attgaattat gaccctgtcc ccctacttct  15240
ctaaaactgc tgttgttaaa gttacctgtg gccaccatgt tgccacatcc aaaggctaca  15300
```

-continued

```
tctttgtctg cacttgatta cctctcagca gcatttaata caagtgacca ctctcccttt  15360
tcactgattc ttttagcaca cattgttttg tgtgttataa gggaattggt tgcctactta  15420
attggctact attcgtctac caacattcta aatgttggta aacctcagtt tggtcctggg  15480
ctccgttctc ctttcacaat ttctccctag gcagtttcat ctgcccatga cttttaatta  15540
cattcatatg ctaatggatt tccattttat atatctaagc ctcgacatct actttaacta  15600
cagacccata tattcaaata ccaccttggc aactgccatt tgaatgtgta ataggcattt  15660
caaaattaac atgattcaaa cagaaactct cgaatctctc ctccagaaac ttatacccac  15720
ttacaacttt tcctaacata gtaagcatca ctgtcatata tccattttct caagacaaaa  15780
acctgcgcaa gatccttgat tattttcttt ttcttacccc cttccctatt cagtccatca  15840
gaaagtcccg ttgaccatac ccaaaaacat atctgaattc atcgtcttct gtccatcttc  15900
actacagcac cacctcagtc cattaccaaa attttacctg gacaactgca aaaaactaat  15960
ctcccttcta ttcctatcct tttcaatctc tttctgtaga gaaggcagta ccatttaaaa  16020
agcatgattc agatctctgt ggcaggaact gccggtttcc caactcaatc tccattgtcc  16080
cttttctcat tagtaataga cagcgacatt cttcagcttc ccttgcaact ggatatagtc  16140
atgtgagtag gttctgatca atgggatgta agaggaaata ctgggtagga cttttagaag  16200
atcctttaaa agggagggga tatcctttca tgttttggct tcttttctcc ttctggcatt  16260
aaacatgctg gctggagcct cagcagctgt tttggaccaa ggaccctgat gatcatgaag  16320
cctccatact agtcccagtg atgaggcaag ccttttacat gagaaataca taaatacaat  16380
acatttaata ataaataaat ttaagccaca ctagctaggt ccttattata tgcagccaat  16440
actcattcta attgatatat ttccaatgtg ttccaattca cttagactga aatttagact  16500
atttatcaaa gtctacaagg ccccttgaag attttattac ttaatctgtt cattgtctgt  16560
cagttgccat taaaattcaa atttataaga agagacatgt ctatcttaat aataaaataa  16620
aaattgataa taaatgtcta ccatttttca ctactatggt ccgaatatct aggtcacttc  16680
ctggcacatg gtagacgctt aataaatgtt tgttgcataa acgcacgttt gttgaaaata  16740
aatcaatcag taaaatgaaa atgctattcc ttcttcaaca ttctatgtat tttttatgtt  16800
taaagttgta atggtggcca ggcacagtgg ctcatcccta taatcccaac actttgggag  16860
gctgaggtgg gaggatcgtt tgagtccagg agtttgagac tagcttgggc aacatggcaa  16920
gacctgtcta taaaaaaaaa aaaaagaaaa gaaaaaaaaa ttagcagcac atggtggcat  16980
gtgcctgtag tcccacctac ttgggagtct gaggtgggag gatggcttga gcctggaagt  17040
ttgaggctgc actaagccca gatcatgcca ctacattcca gcctgggcaa cagagcaaga  17100
ccctgtctca aaaaaaaaaa atggtaatgg tgatagaatg ggatgcaaag attggataga  17160
taaagcaaat agaatcaggg catatgaggt atgctctttg tcattatgtc atttattgct  17220
tgggtgaatc atattattat tactattttt tttggatgga gtttcactct gttgcctagg  17280
ctggagcgca gtggtgcaat cttagctcac tgcaacctct gcctcctgga ttcaagcgat  17340
tctcctgcct cagcctccca agtagctggg actataggcg tgtcccacca tgcctggcta  17400
attttttgta tttttagtgg agatggggtt tcactgtgtt agctaggatg gtctcaatct  17460
cctgaccttg tgatctgcct gcctcggcct cacaaagtgc tgcaattaca ggcatgagca  17520
accgtgccca accagaatca tattattttt gattctcatt tttttcattt acaaaggaga  17580
tattatatta agagtttcct actacaagga gaatctgtaa aaatcaaaag aaaaaaacat  17640
```

-continued acaaatgcct ataggttctc aaatgaaaag agaaaagcaa agatatcacc tgcccacctt 17700
atggtttcaa agaactaaaa ctaagacttt aggttcaaga tgtcagacta cctcttgggt 17760
ttatcttctg tctccccagg ttcaggacat tttacctaac taaatgagaa taaaatgatt 17820
tttttttttt ttttttgaga cagggccttg ttctgtcgct caggctggag tgcagtggcg 17880
ccatcatagc tcactgcagc ctcaacctcc ctggctcaaa tgatcttccc acctcagcct 17940
cctgagtagc tggggctaca ggcacctgcc accacaccca gctaattttt ttgtattttt 18000
tgtagaggga gagttcatca tgcttctctg gtttgtcttg aactcttgag ctcaagcaat 18060
ccacctgtct cagcctccca aagtgctggg attacaggtg agccactgtg cctggcaaga 18120
ataaaatgat ctctaaaagt ataaattcaa catgtataga atggaagggc cacgctcctg 18180
tcttagggtc actgcattct ctacccctct gcctagaaca gtcttcccca gccactcaca 18240
cagcaaaatc cctcacttcc tctgtcttta catgaatctt gctttgcagt gaagtcaccc 18300
aaatggctct gcgctcctcc tacccaacat tcttttctgt ttttccccat gggatttatc 18360
gcttatacta tatgctttcc tttttttttt tttttttttt taagagttgg ggtcttgctt 18420
tgtcacccag gctggagtat agtagggtga acatggctta ctgcagtctc aaactttcgg 18480
gctcaagcaa tactcttgag tagctgggac tacaggcaca agccatcgca cctggctaat 18540
tcttttttta agagatgggg tcttgctatc ctgcccaggc tggtcttgaa cccttggcct 18600
caagcctcca aagccactgg gattataggc atgagtcact gcacccagat atttacttct 18660
ttattatgtt tttgttctcc actgtctact tttctccaac agaatgctgt tttgttcacc 18720
gatgcatttc agatgcctag agcagtaagc aatgcctggc acataaataa ataattgtgg 18780
aatgagtaaa tgaaatgctg aatgaaagtt caacatatct gtagaagata aaggagtgag 18840
aagagtagtc actgatgaaa taggtggaag aagctgaagg acagccccca ggagggtaaa 18900
ccgttggaat gaatcaagac ttagaaaata acagttctta agaaggacat gaggatcaaa 18960
agagaattga aagggaccag ctaccagctt cctccctatc tgattcacac ataatgcagt 19020
agccctgaat ctcctccaat tatgtctttt ttttcccctt ttggggagag cagtggccat 19080
gatcacggct cactgcatcc ttgaactcct gggctcaaga gatcctccca cctcaacttc 19140
ctgagaaact gggactatag atgtgtgcca tcatacctgg ctaattttct tatttttagt 19200
tttttgtaga gacagagtct cagtttgttg tccaggctgg tcttgaacca gccctggctt 19260
gaacctggct tcaagtgatc cttccacctc agcttcccaa agtgctggga ttacaagcgt 19320
gagccaccac acttggtccc aattatgtcc ttgaccagta ttgcctaaag gttatactcc 19380
acactttggg aggttcaggg ataaaggata gacagagtat ctatctgtct aggatagatt 19440
aaagcaggat attttaagga agacactgca aaaaaaaaaa cgtttcctag taaccctagg 19500
gaaaataaac atttgttaag aaatctattc acagtatatt acttggtttg taatggacaa 19560
catttacata gtcttaataa tgtaaacact tcattggctt atctaatgcc agttatatga 19620
caatataggg gagaggggcc gaggagtggt gtaacagagt taaatcctca tctgccatag 19680
ccagaaaaca gatgtcagaa tttgattttc ttaaaaatca gtaaaagcaa tgttaatata 19740
ccatttagta tatggaggta atgactagaa agaacagcta aattaaaaat gtttgcccct 19800
gactggaatt actgaaggtg tgtgggacgg tcggccatgg gattactgtt ttgtgatacg 19860
acatttaggg aatttacaaa gtctctaaag tttgtcgagt cgatagcctt ctgaacaggt 19920
gaaaaattct gataagagaa atagtagagc tgtggcctca ctcaggtgga ggtgctgatg 19980
gaagggatac cagcagacat tattcagaga catttggtca tatatgttcc agagctgaac 20040

-continued

```
tgccagttga ttggaaaatc tgcaaataac tgaaattgtt tgctttgatg acactagtca  20100
acctgctcaa ggccagctgc tcaaactgac ctatattcta gctgtcagtg tattttagct  20160
tattttatcc cccaaaataa aacatcaatc taccaaaaaa tgcatctatg tatatgtatg  20220
tgtgtgtaca tgtgtatgtg tgtgtgtata tgtatgactc actgaccccg cacagtcaaa  20280
tattcttctt tcccctttcc ctcatctctt tccatcattt catctcctac tgatactttc  20340
attggttctt tgaatagggc cctgtgtggg atccttcact aaagcttcct taattcaggc  20400
agcgcatctt ctcggtgctc cagtctgtcc cccttatccc tgtctcattc tagcagtcca  20460
cacccaaggg tcttgttacc ctcccaaggg caccctggga agaacttaaa atggttccag  20520
actggctgtt tctcccaggt gggttttatc tgatccatga gaaaccctca cacatccttt  20580
cccacagtct gggatggcag cttgatccca atgcagccac aggccacttc agccttctta  20640
ggcatgaggc aggccccagt gttctatgtc ctctgattct aaggaagaca cctcaccagg  20700
cttgaggtga tgaagtaaac aacccacttg aggagggcac acagcacctc atcagttctc  20760
accaaagaga tctcttcaca aatcctgacc ctctacatcc tcttcctcat ttctatgtct  20820
taggtctggg cgaaggatcc aagattataa ttgattctca gctatttctt ttgtaattct  20880
gtatatccac tgcctcagtt tgaattgcag cattagttgt atcttggtgc tctggcacaa  20940
atttcaattt caacataata ttacacacat accacttttg tgataataat attaccaatt  21000
ttgtaaaaat ataacaaaca agagagaatt taataaatgc tagtaataga actagactca  21060
ggtaggtgta cattcccctg acatcttccc tgcccagtgc agatgagact attgctgaag  21120
tcttatcctc tttgtactca agctctcaga ggactaaaaa tcttcatggt ccagatccta  21180
aggctctgaa cctacagcct gattcctgtt ttccaaaaag ggagatggac tagtgttagt  21240
gcagtttcaa caacatgctc gtcccactgt gcaaagctgc aactttctca ttctcttgat  21300
ttctacttca tgctgtgtct acgaacttcc tatcttctgg caagtattac ctaaaatcca  21360
accccacatt tgggggagct caggtataat gagcagagga tgaacttagg aattagactg  21420
atggcagatt gaataaagcc tgtcactcat tctgtggtat tgggtaagtt acttaagctt  21480
ccagaaccac aatttaaaaa atctatacaa tgaaaacaac cctcatcaac cttaaagggt  21540
taatatgagg atccactgag aaggcacatg aaatggagaa cgaatgagaa aaaaaagttt  21600
attttgcacc tgctatgtac taggcagttt agatacattt cttcctgatt tttaatatcc  21660
ttataatata ggagtcctct acttgtagcc tctgatttcc caaccagatt tagccataat  21720
caccaaggtc ctctgactag agtaggcagc ccattaggag ctccctggcc accatgaatg  21780
ggggctagaa ttggtggtgt tgctctgtgt ctgacaccca tcatgcccat agtgactgag  21840
tctttgggtc cttacacccc ctgaatcctc tgctatgttt tctcagatca catggctggt  21900
tggtattatt ggcttgtaac tttttaactt ttgcttctcc gatggtcttg aattcttgcc  21960
ctgaaaccaa gccctgtttt ctggagccct gacctgctta gccctggcta attctctctc  22020
agtcatgttc tttacccact ggaacctgtt tcaaactaga ccaacaaagc aataatattc  22080
ttatctgcca agaaacacca tgtcatcatg tcagattgta cccccctttg gattccatcc  22140
tttggtgtga attaagtggg atattttagt ttgagttctg gtcacatccc attttgccag  22200
agcccctatc cccaaaccct ccctgacagt tatagtgaga ttggttcgct agactcaata  22260
caggtacatt cccttacttt tctcttcccc attggcctag gctgctgaag tctcatcatt  22320
ctttgtgccc aagccgctta tgagacttga agccctcaag atccacaccc actccttcta  22380
```

-continued gatcttagtc tctagatttc ccaagaacag ttaggataat tttaaaatga agtaggttac 22440
ttttaaatcc atgagacata gccatctttt taatggcatc catgtctaaa gcgttgagcc 22500
gaatattcac tgtgaagtga tgatagggaa tgaagtccct gcctcggcag tggtcacatc 22560
tgtgggcatc ttcttctaaa aagcgggcac atttcaagtg catggctttt ctctggtcct 22620
tgagccacag ctcgtaggct gttttctgca tcatagggtt acagaatcga atcctgtggc 22680
actcgatcac ctcattctcc agttcacgaa gctgttcctc ttcaccgtga tctggagaga 22740
gcaaaaaggg tttttcagcc aggcagtggg caacagatca gccccttcta cctaacatag 22800
gtcaattctt tgatctagat gggtccttaa gaggaaattg ggtcactcca ggtgctactc 22860
acccatccct tcactgggct tcagagacaa ggaacgatag tgcacctcaa atgagggatc 22920
attctgtttc agggcctttt gaagctcctt gccattccgg aaacaataaa aaatgttaga 22980
ttccactagg gttgccaggg tcttgatcat catcttcata ttccaacagg ggagaatctc 23040
aaacaacaac tcagtggtga aggtcaggcc aatgatggca gcacatctca ccagcatttg 23100
gtgggaaagt ctcatgctat ccagctggat cagagagatt tctgcaggta gaaggccaca 23160
cagtagaaaa ctagttattt atctttatct aatatgctgt atttaatata gagcaggtgg 23220
acaaccatcc tgctctacag ttcttgttgc aagaaactca gccaagctaa gtcaaaagaa 23280
gtatttgttt agtacctaat ttgtggatag cacttgtgct gggagtacta aagatgcagg 23340
cttatggcct agaaagacac acagcacaat gacctgacaa aattaagatc tatttcatgg 23400
tgttctgatt ttgtgctaaa gtgtgacaag tgtgtgtgag gagaggagag gacattgtaa 23460
tcactattgt cagaaggagc aggccctgcc attcctgtgc tttgttgact tcctcagctg 23520
gtccttttgt atcttcttct ctgcctcccc tttctcctag aaactcctgg tttctctcta 23580
tctgccctag aaatttatgt attctcatga catacattat catctctgtg tcatgaccaa 23640
gtgtcagaga gttcacagct cctatcccaa cttttcatct aagcttgaat atcggtagct 23700
catgtgactt tctggacatt ttgaccagga tgtccttctg ttagggacaa aattagaatt 23760
tctcaacttg cccaaaaaac acagtagaaa ctaagctagt ccatcctctt tttttttttt 23820
tgagatggag tctcactctt gttgcccaag ctggagtgca atggctgatc tcggctcact 23880
gcaacctccg cctcctgggt tcaagagatt ctcctgcctc agcctcttga gtagctggga 23940
ttataggcac ccaccaccat gcccggctaa ttttttgtgt ttgtaggaga gatgggattt 24000
caccatgttg accaggctgg tctcgaactc ctgacctcag gtgatccacc tgcctcggcc 24060
tcccaaagtg ctgggattac aggtgtgagc tactgccttc tcacattagt agacacagct 24120
aacgaaacat aaatggcact cttttgaaga ctgaggacct tgagatgtcc ctaggccacc 24180
tttctaaaca ttgaaagttg cttatggatg gcatgaattg gagctgagtt catactaaaa 24240
cattccttga aagtcatttt tctttaaaag aataataata catctttctt tctttctttc 24300
tttctttttt gagacagagt ttttctcttg ttgcccaggc tggagtgcaa tggcgtgatc 24360
tcggctcact gcaacctccg cctcctgggt tcaagcaatt ctcctgcctc agtctcctca 24420
gtagctggga ttacatgcat gcgccaccat gcccggctaa tttttttttg tatttttagt 24480
agagacgggg tttctccatg ttggtcaggc tggtctctag aacttctgac ctcaagtgat 24540
ccacccgact tggcctccca aaatgctggg attacaggag taagccactg tgcctggcca 24600
ataatatgtc tttcatataa actcgtttgt catttctttc tcataaaagt ggatgacagg 24660
aagtatctca gtattagatt ttctccctca ttatttggtt tctgtttaat tgaaaatgta 24720
caatatttca ttcttttatg cagatcccag aatatacaca gggggaaaga tggctcttag 24780

-continued

```
gagcaaagcc aagcctaccc tgagccttct cactgcttca ggcagtacag agcaaacaga  24840
caaacaacca atgttgctgt ttttcttttt ccttttaaaa acagacatcc tagagaaagc  24900
caaagtggag tttagggact agaaaataaa taccaggtca gattttcttt tctttttttt  24960
tttgagatgg agtctcactc tgtcacccag gctggagtgc agtggctcac tgcaacctcc  25020
gcctcccagg ttcaagcaat tctcctgcct cagcttcccg agtagctggg attacaggtg  25080
tgtgcctggc taattttttt gtatttttag tagatacggg gtttcaccat attggccagg  25140
ctggtctcaa actcctgacc ttgtgatccg cccgcctcgg cctcccaaag tgctgggatt  25200
acaggcgtga gccactgcgc ccggccagat tttcttacct tttaatgacg ttggaggtga  25260
caggtttttc agtctgacac cacttgtgag gtgacagact tcttcacttt ccttatcact  25320
atggagagta accatgttta acttctctgt tagcttaatg gaatactcta caggggtata  25380
aaagggaaga aaagttgagt cattatcctg tcttataagg tctgattttc caatgaactt  25440
tgagatggat ctcatatgag gaagactggg cagagatgta tattggctca ccaaatattc  25500
tggaaacctt tttttgttt tgttttgttt tgtttttgt ttttttgagg tggagtctct  25560
cactgtcgcc caggctggag tgcagtggcg tgatctttgc tcactgcaac ctccgcctcc  25620
caggttcaag cgattcctgc ctcagcctcc caagtagctg ggattacagc cgcccactac  25680
catgcctggc taatttctgt agagatgagg tttcaccatg ttggccaggc tgttctcaaa  25740
ctcctgacct caagtgatct gcctgcctcg gcctcccaaa gtgctgggat tacaggtatg  25800
agccacactg caccaggccg ctggaaacct tattctaagt aaaactgatt catgaaaatc  25860
tagatgtact caaaaatgtt ttgtctccct ctgccaaccc tgcccaacca aaagaattgg  25920
cactattgat gtcttccata ggatataagg ctttacaaac gtttgattca cagtcagatt  25980
atcagaatgt attatatatg tattatgtat atacataatg tatatcagaa tgtattatta  26040
tatatataca taaacatata tttgtatgta tacatttaca tacccacact cagttacaaa  26100
cacattctgt gaggcactgt actctaatta ggacatagct actatcagag atattttaaa  26160
tggtgaagtt tgaatagtaa atgtgcctag taatttggtt tcctagtact ccaaaatgca  26220
ttatttttct atcccttcag ccattcatgt agtccttggt agcggcaaga ctgtgctagg  26280
tgaggtggaa ataggaaggt gaataaaacc aagttcctta tttcctggag ctctaagtca  26340
tgtacactaa gagctggact gccaggcagt agatgagtgc catgtgattg ggcacataca  26400
gtaagcacca gagttcacat caatacagga catatttatt aaggactttc tgtgcatcat  26460
atccagtgaa ggctatcaat gtgaataaca catgcttcca gccctcaaga ggcttaaaaa  26520
tctgtggaga cagatacata agtaactaat tataacatca ggatgggtga cttaagagct  26580
aaagagcaaa gagtaacatg ttgtgggaac agaaaataac aattaaatca gacttggtgg  26640
attcagaaag gcttgatagg ggaggaagta ctttgatcct tgaaggatga agagatattc  26700
taagcggcaa gtggaggaga ggccaacgcg aaggcacagg aacctcagag tacttagcga  26760
gttaggggaa tggagcggcc cagcgtgact aaagtgcagg gcctggagtg ctcaggtgct  26820
atgtgggaga cgtgtttgga gagctagttt gggagcagag catggagggc attaaacacc  26880
ataatatgaa gactggactt tatagacaag agggaaaggt cacagatttc tgaagaggag  26940
atagtagtaa tccaactagt cgtatttagg aaggtaccac tggaagcagc atatggaaaa  27000
ggcgagagac taggacaggg aagactatgt aaggagctat aacaatggaa tgtcaagaag  27060
tgaggatgga tagaaccagg caagtggttc agcaaggaga aagcaaatac taaagatatg  27120
```

-continued

```
gaggaaatgg ggcctaagca agacagtgat agaagtgaca gagacacgaa gtacagaagg  27180

aggggtggtt gagcgggagg ataatgcatg aagttttaga tttattaagt ttaagggaat  27240

ctgtggaata gttcaatggg caattggaaa tatgggtgtg gaattaaggg tgaggttagg  27300

gttcgacaca cacgaaggct gagaaataga tgagtaaatg aaaacaactg gggagagagt  27360

tgtttccaat tctggcaagc tagcaagagg aaagggttaa ggatagaact tgaagaatgt  27420

cccaggagga gtagacccag gtagagagcc aaggattatc tgaggactgg tcagagaggg  27480

gaacaggagg agtgtggggt caggaaagcc aagggaggat agcataccaa aaagggggcc  27540

gtgtgtgtgt gtgtgtgtgt gtgtgtgtgt gtgtgtgtgt gtgttgggag taggagagtg  27600

gggctcaagg atatgacgtg gtccatgcta ttttatgctt atttcccctt ccaggaccta  27660

gcattgagac aaccattctt tccatcactc aaccagtatt aactgattgc ctctaggtgc  27720

taggaatttt cctaggattg gggattcagg agagcacaaa actccatgcc tcatgaagct  27780

cacattctag tgggaaacaa acattaaaca atagataaat acattaaaag gataatctcg  27840

taattcaatt atgtgaaaga aataaaaggg tgatagacag aatgtactcc ctactcaggt  27900

tcgcctgttg tcagcctttg ccctatttac tatatcctag gttccttcta tgtgtacata  27960

tttttctgaa gcatttgaat ataagtcaca tacatcacac cctatactcc caaatacttt  28020

actctgtatt ttctaaaaat attgacactc ttttgtttgt ttgtttgttt tgtttttttg  28080

agacagggtc tcactcctgt tgcccaggct ggagtggaga gttgtgatca tagcttgctg  28140

cagcctcaac ctccctggct caagcaatcc tcccacctca gcctcccagg tagctgggac  28200

tacaggcgtg cgacaccaca cccggctaat ttttgtattt ttagtagaga tggggttttg  28260

tcatgttgcc caggaaggtc tcaaactcct gggctcaagc aatccgcccg cctcagactc  28320

ccaaagtact gggattatag gtgtgggcca ctgcacctgg ccaacactct ctcatataac  28380

tagaatatag ttatcacctt caagaaactt aacattggtc gggcacagtg gctcacgcct  28440

gtaatcccag cattttggga ggccgaggtg ggtggatcac aagttcagga gttcaagacc  28500

agcctggcca aggtggtgaa accccgtctc tactaaaaat gcaaaaaaaa ttagtcaggc  28560

atggtggcag ttgcctgtaa tcccagatac tcgggaggct gaggcagaga attgcttgaa  28620

cccaggaggc ggaggctgca gtgagccaag atcgtgccac tgcactccag cctgggcgac  28680

agagtgtctc aaaaaaaaaa aaaaagaaat ttaacattga tacaatactt tagtctactg  28740

tccatatccc aattttgtga attgatcaaa taatatcctt taacattctc ttttcttcca  28800

gtataggatc                                                         28810
```

<210> SEQ ID NO 14
<211> LENGTH: 34500
<212> TYPE: DNA
<213> ORGANISM: Homo sapiens

<400> SEQUENCE: 14

```
acaagcttgt tctattaggt tttacagagc aaagcagcta ggctcctggc atggcaggga     60

agactgttgg gtgttcagcc tgcagaggtt tgctgatggc cagccctctc tcttccaccc    120

accctttcct ctggatgctc cctttgggcc ttgggctgat tcacagttac tgtcccctcc    180

cagggctgac ggaaagcatt ccagggcttt ccgtcatggt cccatgagaa ttcagacctg    240

tgtgtgggga gtggcaagtc ccctctgtaa ctagcatcat ccgcatactc aggaattctc    300

tctacacttc cttcctgctc actgtctctc tttagaaact ggttttgaat gagtagtagt    360

aggctttcat aatgtatttt tcaacagtaa taaaacagct aatttactga atgattattg    420
```

-continued

```
tgccaggtac tgtgctaaga tgatctcatt gaatccccat gacacctctg tgacatggat    480
tcataattat ctccttttta ctgatgagag aattgagact caggagccca agtaactgaa    540
ttatgggttg tggagctact gatgggagat ctggaaccca tgctcagttg gtttattaaa    600
gcctgtgctc ccaaccacaa ctccacactg cctccagcag gaaaagcata gagagtttac    660
gttttgggat taaaaagtgc tcatttggct aggcatggtg gcttacgcct gtaatcccag    720
cactttggga ggctgaggca ggcctatcac ttaaggccag gagtttgaga acagcctggc    780
aaacatggcc aaaccccgtc tcgactaaaa atacaaaaat tagccgggtg tggtggcaca    840
cgcctgtaat ctcagctact caggaggctg aggcacgaga atctctggaa cctgggaggc    900
agaggttgca gtgagtggag atcatgccac cgcactccag actgggcaac ggagtgagac    960
tctgtctcaa aaaaaaaaaa ggtgctcatc aaatttatta ataatgagac aatagtaaaa   1020
atgggcaaag gatttaaaca gacacttcac caaaaaatac atatgaatca ctaataagca   1080
cattagtcat taggtaaaca caaattaaga ctgtaaagag ataccactac acacccacaa   1140
gaatggctaa attaaaatga actgacaata ccaaatgacg gtgaagctgc agaacaactg   1200
gatcactcct atattgttgg tgggaatgtg aaacagtata gtcactttga aaaatatttt   1260
ggtagctgct cgtgaagtta agcatacacc tacactacac ctaccaacaa tcttacttgt   1320
atttgcccaa gagaaatgaa agcttatgtt cacataaata cttgtataca aatcttcaaa   1380
gaaattttat tattaatatc tgagacctag aaataactca aatgtccatc aatgggtaag   1440
tagacagaca aattgtgtta tacgtacatt atggaatact attcagcaat aaaaaggaac   1500
aaactactga tacacacagc aacatgcatg aatctgaaaa gcattgtgtt aagtgaaaga   1560
ggtcagacag aaatgacttc ccgtatggtt ctatttacat aacattcttt aaaaggcaaa   1620
actataataa cagaaagaag atcactgatt gcgtgggacc agtggtgggg gcagggaatt   1680
gactgtaaag agtgtgaagg gtcttttggg gtgatagaaa tgctctatat cttcttcttc   1740
tttttttttt tttttttggt gacacagagt ctcacttcat cacccacgct ggagtgcagt   1800
ggcacgatct cggctcactg caaccttcac ctcctgagtt caagagattc tcgtgcctca   1860
gtcttctgag tagctcggat tacaggcatg cgccaccacg cctggctaat ttgtattttt   1920
agtagagaca aggtttctcc aggttggtcc ggctggtctt gaactcttga cctcagttga   1980
tccacccgcc ttggcctccc aaagtgctgg gattctaggc gcgagccact gcactgggcc   2040
aatttttgta tttgtagtag agacagggtt ttgccatgtt ggccaggctg gtctcaaact   2100
cctgacctca agtgatctgc cagcctcagc ctcccaaagc acaaggatta caggcgtgag   2160
ccataacagc cagccagaaa tgctctatac cttgatcatg gtctacatct cgtggtggtg   2220
gctatatgac tgtatacatt tgtcaacact catcaatgta tacacttaaa aggggtgaat   2280
tttattgtag atatatttta cctcaaaaag gtgattaaaa cattttaaag tgctcatgat   2340
agttcaaata caaaagttga ggtgcactca ggctgcagga ggtctttcat ttgccctagg   2400
gctaggaacc tggcttggtc tcaggatgcc agctctgtgt gcctcagggc gtgagcagga   2460
atgcgctgtg gctgcaggag gctggcagcc tctggtagct gctgggagta ggccacatcc   2520
agccactcct gtccagccca gggcagctgc caggactcat gcagcaagat agtggagaca   2580
gcacagaatt tggagcttgg caagaccagg tttggatccc actctgtaat tgacgggttg   2640
tgggatccta ggcaattgac ttaactgttc agactctcat ctgtaaaatg aggataataa   2700
cacccccctac aaggtcatgg ggatactagg agatggtgtt tgattagaca gtttgggttc   2760
```

-continued

```
acatccagac cttgcctttt actagatgtg tgatcttagg caagacactt gaccttattg   2820
agccttagtt tccccacttg taaaataaac atttataata gcacttattt tttagaattg   2880
tgataaagcc caaatgagat attgcatata aagccccagc acagtgcctg gcacataata   2940
agctctcccc tcattttagc tattgttgtt gtcacctaag ataccaactg gcacacagta   3000
ggtgttagtc aaaatgtggg ctcccttgca ctcttcgtag agataccagg ctgttgccag   3060
tttggccctg aagaattcta agggggtggc agggatctgc tgttgccaag tcattttcat   3120
tcccatcttg cagaataggt tggcagagca gatgggctgg cattgcatct tcatgtcgga   3180
ggaatttaca aatgggagtc tttggaacca caagagcaag ctggagtgtg attctggcct   3240
ccagccatga ggacactctc tcagagaagg gccatttgtg tgctggggtc atttggatgt   3300
ctccaggctg tggggtaggg taatgggtca ggatcagcct tcagagggaa gactgcttgt   3360
ggcttctgca ggttggggag ggtcttgccg ttacccaggc gtatggtatg aaggggccat   3420
aaagggcaag tccagtgcag ctggctagtg cagctggcct caggggtgtg gccacagttt   3480
gagggctgtg cctgcccctg caggtctagg cctgatgggg ataatttctc aagtgagggc   3540
aggggctctc aaaggcttct gtgggtgaat ggcctgagta gttctccagg gaacacaatg   3600
gtctagggag tgggactacg gggttaagtc tctgagcaga caagccctgt cctgcaaagt   3660
tagaagggaa gatccagatg agtcatttca agagctgagc agctgggagg caggcgaggc   3720
cactgaccca gcagtcagag gagcggcgtg aactcactgg ccctgatgac cttctgcttc   3780
atctgtgaga tgaggggctt gcaaaggacg cttcctaaga cccacgctgc tggcttgctc   3840
ttcattttta acataacgta agaagaaaat tgggaaaact tgggttatct ttcttatgta   3900
gatgaaaata gaggtggata atggataacc taaataagtt caggcagaat cgcaagaaac   3960
tcggccaggg aactcaggga tgccaagcaa acccagcgct tgctacagcc ccaacatctt   4020
cacactcagc tcttccaagt aaagaatccc atccctcctc ctcctcttcc ttcctaagaa   4080
gattttagga gtggaactcc ctgcctttct taaatcagga ataaaatgcc caatatgata   4140
cggtcctttt attccaaatt agcaagctga ggccagccgt tctttcgaaa aggagagttt   4200
ctggaaagca gatggcatgg ctcaaatagc ctaggaggtg tccacaagca attatagagg   4260
aaagtggatg aaaaactggt aatgaagaac agtgaccaag atgatcaagg gacacaaggc   4320
cagaagaagt ataattgtga acggggagaa gaaaaaaaga aatgaggagg cagaaagaga   4380
aagagagaaa gagagagaca gcaagatcaa gacagcctgc atataccaca tacacacacg   4440
agtgtgctgc ctgcacaccc caatccccca gcaccccagg ggattgctgc tacccagcta   4500
gggaaaaaat aaccttcact ttggtttcat cagaaaagtc ataaaagatg gaatgaagat   4560
tttgttttct ttcctgttac ttttttgcca tctgctacag caagggcaca ggcccagccc   4620
cttggccagc ttgaaagcct catggttctg aagcaggaag ggtcaaggca ggaagcaggg   4680
gctctaagaa tagaatgggt catctaggga agcttttgga atagatacag acagggcttt   4740
tcactaatcc cctagggtga gtgactgggg cactcctcac tccctcaggg ggctcccaga   4800
ctctaagcag aggttaacat acaaggttgc tgcacagatc aatctgtgca ttatattcct   4860
catgggaaac ccaagaaggg tcctccttat agtgagcaca gaaatataat ggcccctcag   4920
cccaagaagc aatgaatgca agatctaaga tacaaataag ccaatcttct cttgctacac   4980
tcccatcagc atctgtacta tcctccacca aaggcatgag gaatctcttt ttggatactg   5040
gccaatctgc tccttgtgta gttatttggg cagatgactc acaagatttt atatatatta   5100
atcgacagcg gaactgtgga cagcccaggc agtactttat cccaccacct cagcacatcc   5160
```

-continued

```
acatccactt cctagtggcc tccaggagcc caggatggtg gctgctgtgg cttttgcagg   5220
agaggtggct ccactcttag tggcttccag ccactacacc cagagaggat ccaggattgc   5280
aaaaggacct tctagatccc tacagaaagc agagagcaga aatggtgttc atttccaccc   5340
cagggtcagc acagtgctgg cagtgaggcc agactggccc atgcttgtct gtctgcgatc   5400
agcctaacgt ccaagcacag gctggcatgg aagatccaga actaggccct caaccaggga   5460
ctccaccagg ggaggatgtg gagttagaag tgcagggtct agtcccagac ctgcacttca   5520
cggcagggac cctggacaag ctacctatct tttctcgact tcattttctt cctctgtaaa   5580
atggggatga tatctactac ataggattat aatgaagata agtcacaatg tgtatggtaa   5640
gtgccttata aaccaatgtt tatttaaaaa taaggaaatc ccaatatgta ttattcctat   5700
tttcaactga ttttacttaa tgtggttagg ggcaggccca tgttggggat agaacatgct   5760
tgatagtcaa gatcaagcag ggacttcttt aggcccctag ttgaaagcaa tgagatttaa   5820
gaagattcag tgtccctaca gaattcttag ctaaacctca ttttggtgga ggccaaagga   5880
agttcctgaa aaataaaaaa caatcaacca acaatttggt ggtggggagg agtttataga   5940
gaaattaagt tcctctgtat tgaagttgac agaccagtta gggaaatatg aaaccagggt   6000
atatcaaatg caagagtgaa ttaaagctgg gcacggcggc tcacacctga aatcccagca   6060
ctttgggagg ccaagtcaga aggattgctt gaagccagga cttcaagaac accctggaca   6120
acaaaatgag actccattgc tacacaaaaa tagagaaatt agcccagcat gctggcatgc   6180
acctatagtc ctacatattc aagaggtatt caagaggctg aggtgggaag atcacttgag   6240
cccaagactt caaggcttca gagagctatg actgcactcc agcctgcaac agagtaagac   6300
cctgtttcta aaaaaaaaaa aacaaaacag tgaattaagg agccaatggt atagaggttg   6360
taactctagg gggcatgatt cacagcccaa ggagcagcac aggttgttaa gtgtggctgt   6420
ggctatgggc ccaggaagga gaagtgatgg ggtaaggatg gggatcagat gtgatcaaaa   6480
cgtgattata gacagtgttc tggagatgga gtgtctgact gacatctcca ctctgttcct   6540
tatgtgaccc tgggcaagta acaacctctg taagcatcag gggcctcatc taaaagtgag   6600
gataggaacg cttaacatca taggcgtcaa acaagagagc acatgtaaaa tgcttaacac   6660
agagcttggc acacagacaa gtgttcaaca aatgcaagct attaagcatg gagccaaggt   6720
atttggaatc tatcctgaag ggtaaatat gacgaggagt ttaagagaaa acacttgtcc   6780
tgaattctta cgtgcaaacc aagattgcaa aaaagaggca cgtgggcagc cctcacagtg   6840
atgcagacat ccttttggag agagcgttca atgtccaggg aagggtgagt gacctggcta   6900
agatggcagg aaaagaccct gtaaccctgg gaggccctgg agcagaggca tggcgagttc   6960
agggacattc cacatctatc ccaccagaga gaagggcaaa atatagaaga gagctgagaa   7020
aatggaagga aaacttccat ttaaggagca aatgggggag ggggctgaca agggaggaaa   7080
gagatgacag aagctaaaag ctggagctag aaaaattcca gactggtatc agctgtaaga   7140
tctggccagg gaatggacac gtggtccaag gggagcctgt gatcacagtt cccagcatgc   7200
tttgctggat tcccacgcct ggctctgcag ttcatggcat tctgaaggca aattgagatt   7260
acttagttga aacataggat gcagtggcag agtgtagagt gtgcccaaaa aggtgttaaa   7320
ataaatgttt ccctttttta actaagggaa aactcccaga aactattaaa attttaaaac   7380
cccaggaaac aaaacctcct gactataaag gaaaatgtaa aacttattta catatagaaa   7440
tactatcaaa gaagtaaaga gaaaactaga gacctggaaa agtattctaa cacagatgaa   7500
```

-continued

```
aatgaggtaa tgtctgttat ataaagcact ctcgcataat gacaggaaca atacataaca   7560
aaggatataa ataggcaatt catagaaaag caaattcaaa acgccaatca acataaaaag   7620
atgctcaaac ttacgatagt acttgtcagg gaaatgcaag ttaaattaac actaagattt   7680
ctttttatgc ttatcagatg atgggcggtg ggaaggagag ggagagagag aggagggaaa   7740
atagcaattg cggttgggga aatggagata aggaaccctc atatattgat atattgctgg   7800
agtaaatgtg acttgttaca gccttttggg aaagtaatct ggcaacatcg attaaattag   7860
attacacaaa cccttcagct caccctacac tcctgagaat ctaccccata gacataaatg   7920
ctagcgtaca cagccatggg ggctaactgc agtactgttt acagcagcaa aacactagag   7980
acaaaaaaaa aataccataa aaagggaaat ggtttatggc ccatccacat aacaggttat   8040
taggaaacca ttaaaaagaa tgaactaggc caggcatggt gactcatgct tgtaatccca   8100
gcactttggg aggccgagga gggtggatca tttgaggtca ggagttctag gccagcctgg   8160
ccaatatggt ggaactccgt ctctccaaaa aaaagaaaaa aaaaattaac caggcgtggt   8220
ggcacgtgcc tgtaatccca gttactcagg aggctgaggc aggagaattg cttgaaccca   8280
ggaggcggag gttgcagaga gccaagattg caccattgca ctccagtctg ggcaacagag   8340
cgagacttca tctcaaaaaa caaacaaaca aacaacaaca acaaaaaaac tccaacttcc   8400
aggaaaaatt gtaaagtgag aattgtaaga tgcagataag tttatataac actagtttta   8460
taaatcaaca accagaaaac ttaccccttg tgtgtgtatc tctatgtaca catatgctca   8520
caatgtatat gtaatttttt atatagttat gtgaatgtaa agtatcctac agaaaggtat   8580
atgtgaagtt tctggaggct ggacacaggg aggggggctg atctggtgga agcaaaccaa   8640
aagaaaagca ctgctgcata aacccagtgt gtctcatacc atctcagtta tgtaaaagtg   8700
tgtgtagcca ggtgtggtgg tgcacacctg tagtcccagt tactcgagag actgaggcag   8760
gaggatcact tgagctcagg agcttgaggc tgcagtgagc taggatcgca ccactgcact   8820
ccagcctggg tgacagagtg agaccctgtc tctaaaaaat taaaacaaaa ataaaacgtg   8880
catgtgtgtg tgtgtgtgtg tgtgtgcatg agtaaactag aactgatttt gtagggctgt   8940
ccacgatata ttttcaagga aaaggaagca agttgtcaag atatataata tggaaaacat   9000
caaataaaga aaaaaaattt taatgctgaa atgagaattt taagctctgc tctccaggac   9060
gtctgatttg agcaggggaa caaatacctg gaaaacaacg ctgcagtgag cagtccatct   9120
gctcagcata tcaaaaccaa gtcctgggtg tctggggact gggcacagat gcccagaggg   9180
gaggggagga aggaggtgaa attactaata atcccataag gatatttcat tactaaattt   9240
aaatgtatgc accttgaagc tgtttttagg aagtatgagg cttaccaaaa tttaggtcaa   9300
tttgccccat ttgcagccag ccctaaacat atttttaaaa atgctgtccc tttgctattg   9360
gcaactgctt tctgctcaag caaatgatca atctgaagcc aaaatgggcc ctgtcatctc   9420
agcatatact cttaaaaatc caaatcacag gacaaaagaa agagaatggg aacataggtg   9480
attttcttta ggccccacac ccctgatttt ctgtaggtct tggacaaaca agcatagatc   9540
catctatatc cctggtgata aacagattgt atctccaaag gagtcatgta ttcaccagtt   9600
tcgaaaaaaa ccagcaggac aggaatcaac atctatagat tgagtgctta ctatgtgcaa   9660
ggcacatcat ggacactggc tcacttaatc ctcttacttg ccctatgaag tagatattat   9720
tgtattatca gtcccatcta acagggaagc atagagataa agtggctttc ccaaccaggg   9780
tcacatgctg gcatagtgaa ggtgggttca aaatgtgtcc cagtctgact cttaccaaga   9840
cacagctatc ctcccttcta tgaactctct ttctactctg tgtcagtgat gtaaattctg   9900
```

-continued aacagcagct cctattttga gactgcagct tgactcttgg gagcaatgac cccctttaga 9960
gcagatggaa aagggagagc ttcccaatgt gcaagaccca ttttcatcca ggcccagctt 10020
tgtagcttgt ttccatgcct ccctctccca tcatttagag gaggcgttgc taactccagt 10080
gcctttagat ggtgggcagg caatgtaaat gactatgtgg aaggcgtcct gtcctgtccc 10140
catccaaatg aatggagctg ctgttcctca gctctagccc actgtctacc tgtgttacat 10200
tgggtcattt ttcaaaagat cattcaaggc ccagtgtcac caaatgatct gatttttcaa 10260
aacaagatta aaattcagat aaaatgcaat ctattgattt taaaaatttg ctcaattaaa 10320
aaaggaaaac aaagaagaac ctcaatagtg gagaaaatgt ttgcctgctg cattttattc 10380
cagtaaaagc attccatttg cccgacaagg aggtgtctct tggtttaata tattaatttc 10440
tttttaatta ttatatgcat atcattatac cattgttctt actatgaaat aatatcaaag 10500
gtatcattac ctcctcactg aattctaggg aggattatgt catagaactc gagacaggtt 10560
gaaaagacct gggttcaagt cctccgcttg cgcctcagca gctactcaac cccttaacca 10620
tcctgagccg tagtttctta aatgagtcca caatacccac ctcacagaat gtctgtgagg 10680
gttttaaaag ataggctgta taattaaaat attcaataaa tatttgttct gttgcttcta 10740
aaagacagat gtgaggctcc ataaatccat gtatattgta aacagataca tttagagaga 10800
ttatgttgtt taactaatag tttcttcact ttgtaagagg atttcccata atgggcttct 10860
ctggtgcaag tagaacatgg tgtttttccc aaagttttag tttatgtata acattttttc 10920
ttgcctaaat gaacaagtat tctgcctttt caatagcgaa ggcatcctca cgggttctac 10980
agggctgtca tctctggttg ggatgggaga gttgtcttat gtatgagaag caaagattct 11040
attggagctg cctagcagta gctaggaact caacaaccac agagtattgt tggagaccaa 11100
gggcttcctg ctctcctaat ctccactttt gtacctctta tcagctggta ttaagagaga 11160
gccctgcctt gccccccagg gtgactggtg gagggcacag agcaggttat gcagcagtgg 11220
tgtgttccct tcaccttgcc cagagggggt ttgggatggc acacgcaggt catagcaggg 11280
agacttttttg ataatctcag gaacaaagct gattatgtga cgagctctgt cctttctgac 11340
agcaacacca taggaaacac ctgtagacag caggaaacta gaggaattaa aaatatctcc 11400
ctgatcccta aaaaataaaa gaggagagaa aaaaatggtc tcttttcttc acagggaaaa 11460
caaacaaagc gatatctggt ttgagccatt tcctctctgc aaagcacctc tctcctgtgg 11520
gccaaccctc cccaggcaga gatgggcctg gaccagacgc tttaacaagc tatccggatg 11580
cctaagggtg atgtcagtga gggtcttggg gcaggttcca agtgtctaaa cttaagattt 11640
cttttgcagg agggaggttt ggggaagctg agctcatttc cttcgggaga ggtgcagcct 11700
ccatccagct tcggaaacaa gaggcccttg tactcttcct ccacagcctt ctcaacctca 11760
ggaagtcagt ccctgggagc catgaagtgc agcaatgaca ggcccatctg gagaagacat 11820
gacggctggg tctgcaggac ccagctgaac tcaggagcag atttggggat ggcaatcagg 11880
taatgtcgga ttctgtctcc cctgccttct cacatccagt aggtcactaa gcctagtcct 11940
gtcttctata tatatatttc tggtctagac tcttcatcct cactgtagtt actgaacttc 12000
aggctgccat cacctctctc tcgactgtgg gaagagatta tggttaccta actgatttct 12060
ttctgctctc cttcctcttg tctattctgc cctctcctgc ccacataacc tttctcaaat 12120
ataagtctca tcatgacttt tcttggttta tatactacct actaaataat caaaacatct 12180
tagtagagaa tataaggccc ctgtcaatct ctccttccag aaaggtaact atggaggcta 12240

-continued acacagcact atgttgactt ctgcttaacc ctggctacag gaatgcctct gaaatttcca 12300
gtttaagtat tgttccttgt gtaagagcac aaacttactg taaatcctgc ccttacataa 12360
aatcatcctt gataaacttg tactgactta aatcctgccc ttagatcaaa ttcctaccca 12420
ttccctctga agcacgtgta ccctttccct atggtatata atccctggtc tgaggggtaa 12480
tggtgcagcc acccaagacc atacttctgt ccataagttc cccagtaaaa tcaccctcca 12540
atggcacact ggacttcttt gtcgctcagc tccttctgca tttgggagcc actttgtgta 12600
catggccctt tcaccaaaca gtaacacttc ctcaataatg gccaacactt attaaacatt 12660
taccatgtgc ccaataccat gcttagtgct taacgaagat gatctcattt gatcctgaaa 12720
actacctttt gaaccagcca agcattatga tccgtatgct gtagaaggtg gaattggagc 12780
tcagagaagc aaaatgacaa aggtgacaaa gctgcagcag agctggggtt tcaaccctgg 12840
cagtccaatt ccaggcccct gctcttccca ccagggactt cctgcagcct tctgaaccta 12900
ttacgcattt tcctgcctct gtgtctgcag atgctgttct tctacctcaa atgccttgat 12960
ccttattctc ttcacctgga cagttcttct tcatcatcca agatccagct ccttcctgcc 13020
ttctttaaga agccttcatg gacctctccc ctgggttatg ccatcatagc cactccatgc 13080
aattctctct catagcactt atcttgctac attgaactgt ctgtctctct aacagagtgt 13140
gagcccgcct tgaaggtagg taccctagcc tttaccttga catccccata ttcctagcag 13200
agtggccaac acgtaatagg tgtgcaatat ttgtgggttt aaagacatca gccgctggat 13260
aaagactgag gctctgtctt ccggatcaag taactgggct acaatgccta ggcagatctc 13320
catctgttaa atcagattag cagtctgccc agttcctcag gtgttgaaat tttagaaact 13380
ctccccccag gactctaaca ggaatccaga gttgagaacc actgctttca taaaagcaga 13440
ttttgtggag gcaagggctg ccagggtaga agcttgctaa ggaaaattac acaacatgtt 13500
tatacctgcg aaatctgtgt aaaataaaca ccagaaagca actaaaggag ataaacttcc 13560
aaagcatggg agaaaatacc aacccaaagt tatagtttag gaagacacat gacattgaca 13620
gtcattaata aaatgcaaag taactctaag gtatcgttgc acaactgtga gatgggcaga 13680
aatatgtaat aatgataaaa ggctgccagg attatggcga aaattgttcc cttaaaaact 13740
gctgttagca ttacactttg attaattcta ctctgttttg agacaataat ctgcaactgt 13800
gtaaccaaag ctcgagaagt ctttgttcta tttttagaat atactataag aaaataaaga 13860
agaatgcagt ttattcaaaa ttgcctgtag cagtggcatg acataaaagt gaaaaattag 13920
aagccatcta aatactgaat tttgaagact agttgaagta aattatggat cacaaagtaa 13980
attctggagc ataataaaac actatgctac cattacaaat gacgaatatc caacatttct 14040
cacacatgga gatgtgtatg aaacaagaaa aaggctaaaa aaaaatcccc catgctttgt 14100
gccctgcgat gagtcacata acagcaaatc aatacaaatt cacaaagact ggaggtgcat 14160
tcgatgggca aaaaaggtac tgttcattag ctttaaagtt gtttgacttt cttgtaatta 14220
gaaaataata tttagaaaat gtgtgtcctc tgctggggca gcaactgttg gtctgtctcg 14280
agggagcagc aggcctgttt ccagcctgac aactgcttgt atctttacct aggcctctgg 14340
ctgaaaatac actcaagtat ctgggcccgg tgaggtttca tctttaaagg gcccagttcc 14400
ttttaaactt aaatcctctc caggctagat gctaagaggg gaatcatggc tccaggagga 14460
atgaaaagtg aacagaggcc aagcgtggtg gctcacgcct gtaatcccag cactttggga 14520
ggctgagcct ggcagatcac ctgaggccag gagtttgaga ccactctggc caacatggtg 14580
aaaccccgtc tctactaaaa atacaaaaat tagccgggca tggtggtgca tgcctgtaat 14640

-continued

```
cccagctact caggaggctg aggcaggaga atcgcttgaa cccgggtggc agagattgca  14700
gtgagctgag atcgtgccac tgcactccag cctgggtgac agagcaagac tctatctcaa  14760
aaaaaaaaaa aaaaaaaaag atgaacagag gcaggagcct gggctggggg aacctcctcc  14820
catctcaggc ctggaaatag ggcttctgcc cttctgtggg aaaaggcact gttaactgtt  14880
tgggtgagaa aaaacacctg gacccaaccc ccagataaga gtggaggtca gggaggaacg  14940
cagcccccct caagaacagc ggggagaagg cctatcagag gctcatccca ccctgttccc  15000
tgccatgctt tccctgtatc tataccctct tctcctctgt cttggctggg aagacctagc  15060
accccaaatg gaataatcct gggagggtaa gagctcaaca ggaacaaaat tacttgcagg  15120
atggcaggga acaggcaggg aggtgttgca ggtagaggga ccagcaggag caacaggcca  15180
agaagataga agggcaggaa gacacctggt cacagtccac agcattgcac tctgtgttag  15240
aaaggcgtga catgagttta tcgacccaga aggaggtgac ataagggaag ctgggcccag  15300
gtcggcgtgc gaggagagtt gcatagcaac agtgccagcg cagaatgcag tgtgccctgg  15360
tgcctgggac actctttcta ggatgtggcc cagggcaggc atgacagaag gagccaggca  15420
tgaagggaaa ggtgggaccc agaactccag tacagatcgg gtgttcagag cctgtggcat  15480
tctgtggtta ggtgtggtga cttctgctgt gacttttcca ttctcaccca cagctggaag  15540
tgaggctcca ggctggtggc attgtcctgg gctgaactgt ctcctgaaat tcccatgttg  15600
aagccctaac ccctagtacc acagaatgag actgtatttg gaggtagggt cttcacagag  15660
gaaattaagt taaaacaagg tcattacgat ggcccttggt cccacctggc tggtgtcctt  15720
atgagaagag atgaggacac agacacgcac agagagaaga ccacgtgaag acacagggag  15780
aagatggaga gaggcatcag agggagccag cactgctgac acctccgtct cacatttcta  15840
gcctctcgaa ttgcaaggaa ataaagtttt gctgtctaag ccatccagtc catggcactt  15900
tgttacagca gcgctaccga actaataaag gcattgaact tggcctcggg gaagctgctt  15960
ctggggctgc ccccctcctt atcccctcct taccccatcg taccacgcac actccgctca  16020
cccctctccc tactccattg ctaacctcac acgagcagag ccattggctc cactccctgc  16080
tttgtgctta attggtgctt ttgtttctaa aactcaaaat gcttaaccag agagagggca  16140
gtccctacag ctcctggact ttggctttgg ctgtggctgg aacagagatc ttggctgaag  16200
ggatgggcgg cggtccttct ggttagagag cacaggcctc ctggtaggcc tctggggtac  16260
caggccagag ctggacccaa acactcgaga gtcaggaaat cctgcctacc ccctggctgg  16320
tggcttcaaa cacagcctct gcttctgagt gagtggtctg ggcctggccc agcctggcct  16380
ctcatctgta acagctgctc agagcttcaa agggaagcca caagaagagg aggaagcaga  16440
ggccagaggg gaggtgaacg cctcacagct tgaccctgcc cccaccccaa cacacacaca  16500
tccaggctcc agagcacctg cttctctttg agggaccaag ctgtttgcag acatttcccc  16560
gtgttttcca aaacacagtg gagacaacac cttgcatctg tggagtcttt tatattcttt  16620
ccaaatcctt aactctgaat tcattatctc atttaatcct cccaataagc caggcaggga  16680
tgagatgatc attccggtga ggcccccaaa tcttgtgcca ctgattcaag atcccacagc  16740
aatttagtga tgggatttgg tccagagcct tgaactcctg ttggccactc tgcctagctt  16800
cctcctgcaa cgtgttaaca cttgcttggt tcccctctgg cacacacatg gacacacaca  16860
gtgcatcttt acagctgccc cagaggcaca ggtgagctgt ttattattat ggacacaaga  16920
cacccaggcc ctggtctgtc tgtcctttaa atgttatgcc tacacccagg catccccatt  16980
```

-continued

```
aacacacagg tcccttggaa caatgctgtc ctctccctta gtcgtcagct aggccttaga  17040
tagaaaattc ttgtccctgt gaggaaggat cctcctctca aactcctttt ctctttctct  17100
gccctcacag tcccttctga agcccagctt tcctggtctc tagtccatat gaatgaccag  17160
cctcctaaag gcctcatacc atgctctctc caatccattc cttgaaccac ggccagagcc  17220
aacttcctga aattcaagtc tggttatgta actttctgcc cccccatcac tctgggaata  17280
aaacaagtgg tgaggccaag ctgtggtttt tgagagctgt aacaccccat aatatcatca  17340
gccacaccaa atacatattc cgttttaggc gaaaagtatg cttgttatac aaataacagt  17400
gtcaaggcta gccccttgga ctctcccctt gcaattagac tgtagcccca agcgccttct  17460
gtgtagaaat cccggcacct cccggatcaa gccctgaaga ggttctcgag gtcttgcctg  17520
gcttaccaac tcaatctggt tggatcctgc acactgtcct ctttcacgct acttcctcca  17580
gctagaacac cctcctcctc acccttcaac tatccattcc ctctttgtcc tcctggattg  17640
agctcaggtt tcactgcctt taagaagtct ttctttcccc cagcccctcc ccactctggg  17700
caagatacct aggtcatact cagatctgtg ttctgagcac agatctctta gaatacttaa  17760
ccaaactgtt tcaatcactt gttatcattc tgactgtctt accagactgc aacctccctg  17820
agggcaggat ccaagtttta ttaccttttg tgtccagaat tcccagcaca gaatctgaca  17880
cagtgggcac ttattaaata tttattaagc aagcgagtga ctgattgctt ctcctcccaa  17940
actcaggcca ctcttgctca ggacttcaag ggatttccta gaggaccagc ccatcattct  18000
ctagagttca gcccaaaccc tctggtgttc tgcctccatc cctgactggt gggtgagatt  18060
cttggtgtcc tggtgtcccc gggctcactg ttgcccgcac cccatcactg gtatgtaact  18120
tccccctatc tgcagctgct ccagcgggaa ctaccatatg attgcttcat ttccaggggg  18180
tccacacccc tttcctgtgc tcccctccta tccactccct gctggtggag ggggaaccac  18240
aggacttgct ggaagaccct gggaggaaag ggctctttgc taaaccggct tagtggaggg  18300
ctctcacctc atgtctccta cctggcacat ctcgctgagc ctgcaattgt acacaccagg  18360
tacatacagt gagtctttgc aaaaggaagg aaggccaggg ctgatttggc aatgcttgtc  18420
aagagacact catatccttt gacctaataa ttccactcct gggaattgct tccagagaaa  18480
taattcaaaa gaaggaaaaa gatacatgta ctgtttatag ctatgttatt tgtaataagg  18540
agaaagtaaa agcaaatgct gtgttccaaa atagaaaaat gattaaataa ttatgatata  18600
tttgtataac agagtgtcgt gaagacattt acaatgaaaa tatgactatg aggaacaaga  18660
atactgacct ggaaataatg ttaagagaaa agatagagta cagagttgta tatacactga  18720
ttaaaattat gtaagaatta tgcatttggc taaaactaat aaagatgtgg aaaattcgaa  18780
gtagttatat tatacaggat tgtcttttta ttccaacttt aaaaaataat aaaagggata  18840
taattgagga tttcaaggaa caaaaaaaag aaaaagaaaa tagttgtgtt aagatgatga  18900
atttcaaatc ttaaaatatt taagattagc ttaattttag caaattagta ttttaaaaca  18960
aagtgactag aaactagaga aaatgtcctg aacagtccta gggttttcta gaaagaattt  19020
ttattggttg tggtcttatc gttgttttgt tttatttttg atatagggtc ttactctgtc  19080
acccaggctg gagtgcagtg gtatgatcac agctcactgc agcctccatc tcccaggctc  19140
aagcaatcct cctgcctcag cctcctgaat agctgggact acaggtgcac caccatgcac  19200
tgcttttatt ttatttattt aattaattta gttagttatt ttagagatga ggtctcacta  19260
tgttgcccag gctggtcttg aacttctagg ctcaagcaat tctcctgcct tagcctcctg  19320
aataactggg actacaggta gaccaccatg cactgctatt tttttttttt ttgtagcgat  19380
```

-continued

```
ggggtctcac tatgttgccc gggctgatct tgaactcctg ggctcaagta gtccaccctg  19440
cctcagcctt caaagtgctg agattacagg tgtgagccac tgtgcttggc cccttgtttt  19500
aaaaataaga acatgcctca tgcaggcctt cccaatgcat ggctgtgggt tataaattgc  19560
ttgctgtgga acctgcagcc tgattaacac taaaagcact taaagacatg tgcctaatgg  19620
acaagtaatt ctgttgcctc taccccttc tctctctctt tttttttgag atggagtttc  19680
actcttttttg cccaggctgg aatgcaatgg tatgatctcg gctcactgca acctctgcct  19740
cccaggttca agcgattctc ctgccacagc ctcccaagta gctgggatta caggcatgca  19800
ccaccatgcc aggctaactt ttgtattttt agtagagatg gggtttcacc atgttggtca  19860
ggctggcctt gaactcctgg cctcaggtga tccaccctcc ttgtcctccc aaagtgctgg  19920
gattacaggc atgagccacc gcagtggcct ctacctgctt ctctacctgg ctaacactac  19980
cccaggtttt gggcgatgcc ccagaagttc cgaggatcct atttctcttg aggcatctac  20040
tccctgagct tgagaaagag ctctggaaag gagggggtca cacaaaggag agtcctgggg  20100
atgacgccta ggcaggatta gaaactcgag catcaggaca atagctaatg catgtggggc  20160
ttaaaaccta gatgatgggt tgatagatgc agcaaaccac catggcacat gtatatctat  20220
gtaacaaacc tgcacgcatg tatcccggaa cttaaagtaa tataaaaaga aaaagaaaaa  20280
gaaaaagaaa aaaaactcta agtctcacac aaaattgagt ctttctactt cttttttttt  20340
tttttttttt tagaaaagtg ttagcttatg gtcggctata actcccaagc cctctttcac  20400
tgtccttagt cttcctggca ttcctcaaat gtgagggctg tcccgagctg tctttggcct  20460
gcttctctcc ttatagccgc tgctcaccac ccaggcctgt ggtgaaccac tgctgcgcga  20520
atgaccaccc agctgcgcct tggcccaaag ccctccaaac tccacttctg aatttccaac  20580
agggtgtcct gtcaatgcct caaccaaaac tcagcctctt ccgcaccccc aacgagtaaa  20640
attctccatg ctcctagatg gaaaacacag tcattctgat cactttctct ctaactctgc  20700
ccctgtgaca gtctccaacc aaataccaaa tctgcactgt ggattcttcc cgcagttggt  20760
ttcgcagctt cattgccttt ccattctcaa ggccacctct caccggtgcc ttggcctctc  20820
aactggtatt tcggcttcta gattaattaa tggccctcca gtgctccttc catcccttcc  20880
atcccgtgag ccccactctg caaggaccct catgacagac tgagggaagc aggcagcatc  20940
agtgctgtct ccctaacgtg tgcaccacct cactgcatcc agtccttcca acagtgttta  21000
cccaccctct ccccatctgc tgtgcacaca catgtgcacc cacacccaca catgtgggtt  21060
aagaggtctt ccactctagt cgcttagggc actcacagtt ccccgtgggc atccttcatt  21120
tcttctcatc acactagctt ctcaccacca tccccttctt tgccccttca ttattaccat  21180
ctgtttaaaa aaaattcttc ctagtttttg gtggccactc tgatgtcacc ctctcccaat  21240
aagccttctt cagttgaata agttgagaat gttctttctc tgtgaaattc cccagcctcg  21300
tggtcttgtt gcttatataa cactttagca tatcctgtgt cctgctttat ctggggacat  21360
atcttatctc ttggcaccac caccactaaa cctccagctt attgagatac tgtctttata  21420
ttttactccc tccaggaatc cagacagcat ctgtcataca gtaggcccaa taaatatttg  21480
tggaacaaat gcatgcgtat ttccaagcca ggtctgtcct atgctagtgc atgaaatttt  21540
cctaaagtta agcagaggat tttacattca tccctgttta attttattat gttggttttg  21600
gcccagcatc ccatcctata taaatcattt tgaacttgaa tatgtcacgt agcatattaa  21660
ctatcccagc tgtgggtcat ctggattctt tctatttttc atccaagtca ttaacaaaaa  21720
```

-continued tgtttaataa tcagggccaa ggatagagcc ccgtggcctg ccactggaga ctttcttcag 21780
gaaagacctg gggtccttaa tcaaaatact ttgggcaagg tagttcaacc tgcactgaat 21840
acatcttgtc aaaaaatcct ttgtaataca agtaatgtga ccacgtgaga aatcagaata 21900
cccttattgg cataggaaag cactcagttg gaaagatcag gactgatgtc agcttagaca 21960
gggagagggg ctctggtctg aatgcttagc ctcttactgt ccaatccccg cagctgtttt 22020
agcagtctcc gaatcccacc ctgttcagct ccctaggcag gggcctcccc acagaggtgt 22080
gaaaggtaag gaattgtcag ggtacaggca acccaggtat gtggggggag gaagtggaag 22140
gggagctcta ctccagactg ctctccttcc catttcctac ctcctcgttt cattgatcta 22200
cctgggtgaa ctcaaaaaat acacttgcca tctgctctcc ttccctccct ttctttgaaa 22260
tgtatgtatg tatgtatgta tgtatgtatg tatgtatgta tgtatgtatt tattttttga 22320
gacagagttt cactcttgtt gcccaggctg gagtgcaatg gtgcgatctt ggcttactgc 22380
aacttctgcc tcctgggttc aagcaattct cctgtctcag cctcctgagt aggtgggatt 22440
ataggcgcac accaccacac ccagctaatt ttgtattttc agtagagaaa gggtttctcc 22500
atgttggtca ggctggtctc aaactcctga tctcaggtga tcggcctgcc tcggcctccc 22560
aaagtgctga aattacagac gtgagccacc gtgcccagcc aaaacatatt tcttgagcca 22620
aggagactga ctcccttttt cttgcaggtt ttggctgccc atgagcctga cacttggatt 22680
tgctattcta tgcccaagcc tcccctagtc tcccaggttc tagtatggat ttatgtggga 22740
tactgttcca gcattgcccc caagacccag cctcctacag aagcccagag agatttaccg 22800
gcagttttgc aggcaggatg caataaccac ccctctgtca aactctcagg ctggaggaga 22860
acttcagatg tcctcttgtc catcccgtgt cccagtcaga gctgcaccaa aagcgcagga 22920
ggctgttctc ttctaaatga ttataaaagc ctctttcctt aatcaataaa caattacatc 22980
acacctaata tgtgcaacgc actaagcact ttacacaacc accgactcat ttacacctca 23040
caacaaccct agcaggtagg tgttatcatt atttccattt tacaaatgga aaaaccaagc 23100
catggagagg tcacaagcta gtaaatggca aagtcaaact caaacccagc catatggctc 23160
tctgtgtgtg ctcttagccc ttaagccatt gcactgcctc cccatgaggc atatgaagcc 23220
tgcattcctg catctactca caggatgtgt tgaatataca ttatgctcat cattggatgt 23280
tagaacctat gatggggatt tgcagagctt acagtttagc tgaacagata cgggaaagta 23340
ctttgacaat aaagtgtggt agaagtgtaa agtatttttc ctattactgt tgcacagctt 23400
aaaacctcct ttatgctata aaaagcctct ttgtcctata ttggaaaggt tcactttgct 23460
catgtgcacc aatgtcaccc tctttgcctt cccttctgcc accttccact aggcacagag 23520
agcgccagtg ctttcttaca gaagacacgc tcagggttgt tacaattttt cacaatatca 23580
gtttaataaa tactaataac accaccacca tgcatttgtg aaataattga acgcttcaag 23640
gtactttcat aagatattta ttacatgcat aatcttactt ccttttcaaa ataaccttgg 23700
aaggtaggta aagcaggtat cggttttaca gagcacggaa ctgaccggga tcctgaggct 23760
ggtaactgac cctgaaccta aaacccagga ttgatggtct ttctctgcat ggcatccccc 23820
ttgatctact acaaaatcaa taatcaggca aagaaagcct taagggagca gagggctgtc 23880
tgttgctacc atttcttcaa attctactgc ctaattccaa tgttactcac aggccgactt 23940
tcaccaactc cttccttagg gacaaaaggt agggcttatg tacaagcctt atgggaaaga 24000
atggtgattc taagtgttat ataactgcat gtagaaaaaa gacatagatt ccctttcacc 24060
aagggggagt gcattccaat caaaaggcgt agacaattcc atgctgctca catagccaca 24120

-continued

```
aagacgttca cctcccaaga gccacctagg ctataagttg caactcctgg tggcatgctc  24180
catggaattg gctgttccag gactaagaaa cttgagaaac agtctaaaca gatgccctta  24240
acgcttatgt ttatatttct ctgatatatt ttcctgcata tctgcacccc tagcttctcg  24300
ttcaaaccta cttgcctctc tcaatcaccc ccaaagcatg aagaacagct gacatcattg  24360
aaaacattat ttgtgcttat gaagcagttt tcatttcaat ctgcaagaac atctccgacc  24420
acaaaagccg tgtaagactc aagcgaatga gccctgagtg gtgcagataa acactttctc  24480
cctcggcttt cccctcttg tcagcctgaa agacacagtc ttacttccag acacagctca  24540
aagatcgtct gctttgtgaa ggcttctaag actctatcag gccactaaca atgtttgtga  24600
agtacttcta gctctcatca tttggaggcc atgagaggat ggtacttcct gcccctatgg  24660
ttaattggag ccatgtggat agttaggaac cttccaaaag agagcattta atggccagcg  24720
tgagtcttcc agaactttcc ttccttctgc catgacaaca agcaaagggg tagctgctcc  24780
cacagcttag gtctcagagg gaggacaaga aatgagccag agcagagccc ccagccaacc  24840
ctcaatggac ttgcagcagg ggtgaaaagt aaacctttgt tgttttcagc cactaagatt  24900
gtggcatggt tacagcaaca ctagcctgtc ctgttattta tgcaacagga ctgtttactc  24960
actgcctttt cagaaccaat cacactgttt tgtaatcact tctttcattt atgtcccctc  25020
tttaccttca gactgtatga atcttgaggg caaggattgt gtcttattct tattttttg  25080
agacagagtt tcactcttgt tgaccaggct ggagtgcaat ggcgcgatct cggctcaccg  25140
caaacttcac ctcccaggtt caagcgattc tcctgcctca gcctcctgag tatctgggat  25200
tacaggcatg caccaccatg cccggctaat tttgtatttt tagtagagac ggggtttctt  25260
catgttggtc agggtggtct caaactcccg accttctgtg atccacctgc ctcggcctcc  25320
caaagtgctg agattacagg agtgagccat tgcacccagc caggattggt cttattaatt  25380
tgcatttggt agcgtcttgg tgcatctcta aataaatgaa tgaagggatt aatgaaagaa  25440
taagatattt aagaatagga ttttataatc ttgctaggca tgatccttta caatggtggt  25500
ggtgatccta gataatctcg agtggctctt cccagcctgc ttacaccata gttatctccc  25560
tgaaaagtga ccagatgagt tgggggtgat cctcatggct tcatggaaat gctccatagc  25620
ggcctggaga cagacttccc ctcccaactg cagctctctg aacagagaat tatagctgag  25680
acccaggcac taggggtatg gatgacacag ctgtatatac gggctaccta agaggcagga  25740
aattagtcac acaacaggtg tcaataaata ttccttggta atttgcaccc aaggcactag  25800
tgggggctcg gggggtggtt ataatatagc ttaacaataa cccaggattc actcctccaa  25860
tccccaagtt ctttaccttt atatggatag caggttgact gcgatagtgg ggtgaatggt  25920
gaccccctaa aagttatgat aacttcctag acaggcacag tgtttaatgc ctgtaatccc  25980
agcgcttcag gaggctgtgg tgggaggatc acttgagccc aagagttcaa gaccagtctg  26040
ggcaacatag tgagacctcg tctctactaa aaatacaaac attacctggg tgtggtggtg  26100
cacgcctata gtccagctac tcaggaggat gaggtgagag gatcacttaa gccctggaag  26160
gttgaggctg cagtgagcca tgattgtgcc actgcattcc agcctgggca acagagcaag  26220
accctgtctt gaggaggaaa aaaaaagata tgctcacttc ctaatccctg gaacctgtga  26280
atgttacctt atgtgcaaaa acagtcttag cagaggtagt taccaatttt gagatgaaga  26340
gatcatcctg gattatcaac gtaggtcctg atccaatgac acaggtcctt ataagagaca  26400
cacagaggag aaggtgtggc aaagatgagg cagactggag tgatgtggcc acaagtcaag  26460
```

-continued gaagctggca accaccagga gccaaaagaa acatggaatg gagccgcccc tcgagcctta 26520
gtggggaatg aggtcctgct gacactctgc ttttagacat ccggcctcca gaaccatgaa 26580
aggagacgtt tctgttgttt tgagccaccc agtttgtggt aatctgttac ggcagcagcc 26640
ctcgcaaact catacacctg ccaactccac tggcatcaga ttctccacct gggcagcact 26700
tccgcactgt atagcagcct ggagtgccag gcatctcttt gagtctccca tttgtttccc 26760
caaggaaaac aagcatttgg aatcatcctt gttcttctcc tctccagtac ttaaattcag 26820
gcctttgtga ggggattcag gcatgactgg acaacagggg ccaaggggct cccccagaaa 26880
gaccccttga gggcatcgga gaaagtaagc ctagtagaac aaggcgtggc gctgcagcta 26940
gggtagctgg gccctcctag cctcagctct gggtctcttg gcatttgtta aaacaatgag 27000
aatgggccgg gcatcatggc tcatgcctgt aatcccagca ctttgggagg ccaaggcagg 27060
tggatcacct gaggtcagga gttcaagacc agcctggcca acatggtgaa accccgtctc 27120
tattaaaaaa tacaaaaatt agctgagcac agtggcaggc gcctgtaata ccagctactt 27180
gggaggctga ggcaggagaa tcgtttgaac cagggaggtg gaggttgcag tgagccgaga 27240
ttgcaccatt gcgctccagc ctgggagaca gagcaagact ccacctcaaa acaaacaaac 27300
aaagaaaaaa aaaacaatga gaatgaaaat ggttcttctc cctacccacc ctatccccac 27360
agatagtagt gcttgctagg gaagacctag agagctgagc accactgtgt ggaggacttc 27420
agagagccaa gaagacaata cacaaaaatg caaaatcaat aaagtcatta tatatgagtt 27480
catttgaaca tgcgggtcaa aggcgtccta gtgtgctggg agtcagagga cctttttgtt 27540
tgtttgtttt tgtttttgct ttttgtttgt ttgtttgttt tgagacggag tctccctgtg 27600
tcacccaggc tggagtgcag tggcgtgatc tctgctcact gcaacctccg cttcccgggt 27660
tcacgccatt ctcctgcctc agcctcccaa gtagctggga ctacaggtgc ctgccaccat 27720
gcctggctaa tttttttgtat ttttagtaga gatggggttt tatcgtgtta gccaggatgg 27780
tctcaatctc ctgacctcgt gatccgccct ccttgccctc ccaaagagct gggattacag 27840
gcataagcca ccgcccccga ccaggacctt ggttttaact cttgacttgg ctactaactg 27900
actttaagta cgaccattgg taaattgctt atgttcaatt tcgtcatctt taaaatgaag 27960
gggatggaag aaattgctat ggttctttct tgctctcaaa actccaaagc cctaaaaatg 28020
aatttggaaa agtcttcctg ttttgcttta ggtgtgggca ccagtttcac ccagagacac 28080
aactggggcc tttcagaagt cttttagctg tgcagaggag ggctcggagt aaacctgtgc 28140
caggccttac aagcaccaag ccttgagctg gctggcctcc accacagcct ggcctgagct 28200
ggaggaagac tggccaggct gaggagcctg ttgtctcccc gagagcccac acaggtgctg 28260
tgggggaagc cagagtttct ccagagcaag aggaagaaca gggacaggat cccaccggat 28320
agggtaggtt caaatgttag aaggttggta attaccttct agaccctggg cacatcattt 28380
aagcatctca aagcctcagc atcctttcct agaagacata atatgacttt atgaagatta 28440
aaagaaataa atctgtgcac agcatctata tatagtaggc attcaacaag tggtagtaat 28500
taccatgaca acaagcttta ggtctctccc acactgacat cggtgtggct gctcagaaat 28560
gaatttccca ttattcatca aaacatatct gtaaaggatg acaagccagg aacctgaatc 28620
ctgggaatgt gcttcagaga tggaggtcgt ggtgggcagc ccagcagggt gggaaaagcg 28680
tacatttagc tcacgcattg ggaatgaact attgaaggtg gagggtctag cggggaggct 28740
cagaggaggc ccaaagcctg ctgcggcaca ttgtgagatg caaattctct gtgacctgtg 28800
gcgtgggtgc tggattgtgc aatagcagcc acaaggccca gcggcactgc ttactgggtt 28860

-continued

```
tgggctgatg catgtggttg gctgctgctc tacagtccac cctggtgcat cccttgtctg  28920
cctctgggca agcaggagaa acgctgactt ttcagggagt gtacaggaag tgtggccata  28980
gtggaaggaa tgagcggggc tgcaggtgga agtgtgagtg ggaacagaag gggtgtgtgt  29040
gtgtgtgtgt gtgtgtgtgt gtgtgtggtc tattcctaga gccctctttc tgtcagagaa  29100
ggtaggagga cttggggtgg ctttttggtg agcttgaaca aaggcattcc ctcgggacct  29160
ggagcctatt tcaaatcaac ttctctagca ggagcctttg gggcaggccc caggcaggca  29220
tgtgctgcca ttagattgag gtctcctgtg tgttctgcac cctagggctg ccaggaggtg  29280
ggggaagagc agcacttgtg gaggaatccc cagcacagga agctagtttt ctctaccttg  29340
tattagagga gcttttgaac gcccacatac cttagaactt atcaagattc tatcttgcat  29400
gtttttatgt catgtcattt gggtatatct tgtttcccca aatagaatga gttcctttta  29460
gggcaggaac tgcaacttac atttcctgta ctccccatct agtcctcaaa tatctttatc  29520
ttgctttatc ctccaggaat gaactactta ttatttccca tgcacaccgt gctgtttctt  29580
gcaccagtag ctttgctctt gtcactcttt ctgattggaa tgctcttccc aattttctgc  29640
ccttggttaa ctcttactca cccctcaaga ttcaactcag aaattatttt tagcaggaag  29700
ccctccctga gccccaggct gatgctcctc ctctgtgggt gtaagctctc atccctgctc  29760
tgcaataatc tgtttaggtg tttgtctccc ctcttagact gcaagttctt caagggtcag  29820
caagctggta gatacgtacc cctttagatc cgcagtgcct ggcaggcagt aagggctcag  29880
tgtgtgctta ctgaatctaa ctaaaaacct agtgcatggg ccaggcgtgg tggcctgtaa  29940
tcccagcact ttgggaggct gaggtgggtg gattacctga ggtcaggagt tcaagaccag  30000
cctgaccaac atggtgaaac ctcatctcta ctaaaaacac aaaattagcc gagtgtggtg  30060
gtgcatgcct gtaatcccag ctacttggga ggctgaggca ggagaattgc ctgaacccgg  30120
gaggaggttg cagtgagctg agatagtgcc attgtactct agcctgggca acaagagcaa  30180
aactccgtct aaaaacaaac aaacaaacaa aaaaaaacaa aaagaagcta gtgcatggca  30240
tgccgtgaat cattaatgat taattataaa agattcagcc tgggaaagag tagtgattgc  30300
tacctcgagg ccaggaggtt ggccctgaca tggtacaaac aggttcaaaa caaagggctg  30360
gagacatcta tgatgctgac tcaaattttt ggctggagat aatgtctgtt ccaatgtcca  30420
gaatttctca gtgcccccac ctgactgctc tagcttggag gcttctaata ctattcatta  30480
aggataggct ctaatggcat ctcagagggg tctcttacag aggtaagggc cctgcacctc  30540
tcttagggac tcattgggat ttggaattgc actggctgga ggcccttccc atggaatagg  30600
atttgatcca ttcaaataaa tggctctaca gggtgagcct catgggctta gccagctgtt  30660
tccacaattc ccaggagatg ggtattcagg aagctccaaa ggaaaaaaac gggaggctga  30720
ctgcccagaa gaccaaagaa ccaggacagt gttcattcgg gtctggctct ggtgatgagc  30780
ttcaggagat tcctagggca atcctgttga tagtggcaac tcagtgttca tcctgtgtcc  30840
gaagcattac tgaaactttg ctgctacaag aaccatcctt ctgtcttact tctgaaggct  30900
tgggttgaac tactccccag gtaagagaaa aattgcaagc tgttggcttt ccaaaagtcc  30960
aatagtgcct aaatcctcaa gatacctctt ggtgagttgg tttatccctt taccatatgg  31020
cagagggcag ttaaagattg ttttatttca cccagagctc tgagattttt agattctaat  31080
gagttgaata gggttggtca ggctggctcc acagacttaa atattattac tggagaaaag  31140
cggagctgcc ttcagatttc tctggaacca aaatgctttc tcttgcggcc ctgataagat  31200
```

-continued

```
taccgggctg ctgagccgcc agtgttcaga tttcccacgg aaccgcgcgc gccaagctct  31260
ggctcgcagt gctgtgagga gccacgctgc ggatcaggct ctgaaacccg actcctttcc  31320
aggaatgcac attcaccccc tcctgtgata gggcctgggc tgggccctta gagtctcact  31380
ccccaaattc cccctgtcgt cgcagtccaa caaatggaag atgtctgctg agtgggggcc  31440
agtgtgaggg tgagggtccc acagaacacg cgggagccag agaggaatgt ggggtatttg  31500
ggcatgccac aagtccaccg agccaaactc tagcttcaga ggctgtgcaa ttcctaatta  31560
cggcccatca gctccaacca gcagccaaca tatggctcag tgagagggtg ggtgggtcaa  31620
aaaacagcga ggctgtgggt gtttctccta gtgtttcacg gtgaaatatc aaaataatct  31680
ttttaagatt tggattcgtt acatgtttct cttctatctc ctagtcccat aattttaaaa  31740
aatgtggtag aaaatgttta ctgaagtaaa aagatatgga tgaaaaagta ggtcacaaaa  31800
caaacacatt atatacacca atatgtacac acacacacac acacacacac acacactctc  31860
atcatagtaa tactgacagt ctgtgagaat gtaaagacat gagagctcca taatttttaa  31920
gtaacattta aaatacaaga tctggtatgt aataagggcc caataaatac tgagtaggtc  31980
catgaatgac aaataatatc tgggaatgat ttgcagttac cccagagaaa aggattcatt  32040
tattgtctcc acctaagtta gaaatttatg actttttttc agtgccatga tgtgcctaca  32100
atttagttga acaaacaaag gatttagtca gcgaaaatta tacttttttt caagtgccct  32160
caggctattg gcagtgcaca caatttatat ttaagtgact aacagtatta acttaaatgt  32220
gacatcatac gcctccagct ccttctttac acacctctgt cctctgggtt cctatccaca  32280
atagcattac ctattatctc ttctagagga gaatcacatt tgtatcataa caggtttgta  32340
tttcttaggg agtggtggac attctgctta gaacaatcaa aaccaacata tctaaacact  32400
gcttgttaaa aaaaaaaacc ctgatcttcc ttccctcttc aatatttgct catgcaacaa  32460
gcctttcttg gtgcccatta ggctctaaat atataagaca tggcccctgc cctcaaggag  32520
ccttccgggg tgacagttag ggaggctgac agttccagtt ctgcctagtg ttctaatagt  32580
ggcttgaaca aagtgctctg agagtgctgt agagtctggg ggcttcacag aagccttcca  32640
gaggtggaga cgtttgagct acagaccgag aggggaagga gttccctatt tatgctaatc  32700
atttatcaag caaactttta ttgagaaatt atatgactat atgccaggca ccgtgctcat  32760
tctggagact caaagaccaa tgagaaaatc tgcctgcaaa aggctttgta tggagctgta  32820
aaagttggta ctgccatttt ccctggcacc atagagaact tcactcttct gggcagcttg  32880
gtgatttctg acttcccttc cagcgcatgg tctttactct tttccatctt ctccattctt  32940
attgtatcct gaagtcagaa tatacctgta ctggaaaaga tgctttctca cctggttccc  33000
ttgctcactc catgaagtgg catttttgct gtatcatccc ggctacatca ctgctgccag  33060
ctgcctcaac acctctcaga gtttcctact gtccatggag cagaatccag ggccatacaa  33120
ctctggcctt caagagttgc agatggcctc tgcatgaatt agaaaaagcc acccgtttga  33180
ggctcaacta ggcaaggaga ttttgtatga acaaaaagta accttttcct ccaagtgact  33240
tggatttcag ctcccactca cccacttagc tgggcatcta ctatactcag tgaccttgga  33300
tttatcttat tactttcatt tttttctgtt actgctttcc taccttcctt cccagccagc  33360
tggacaaagc tggcatgttc tccctgtgcc catcccttat accttctcca ccttacccac  33420
atctttcttc caaggcttct tctgaaccta atctagtctg aactcctgca gaactcatga  33480
tctgcagcag tattcaactg gcatttatgc atttgaagat tatatatgtg acaggatata  33540
gtccctttat tggggttgtga gcttttaaaa ggcagggatc agatggcatc tatactttgt  33600
```

-continued

```
ttattccaca gggctttatg agggatgaag attgatgttg ttgataatgg taacagtgac  33660
tttaaaaaaa gatctctcaa agacttccaa taatacgtga gctttagaga atgaatattg  33720
agtaaccctc tttggtctgg tttggattcc tagtactgag aagtaatata acttaatttc  33780
tttccagata cagtagccct ttcatgtccc aaaactgagt ttcacctctc aaaagagggt  33840
tttactctga gattttcaga aacccccaaa tccaactcct gcatatcatg cttcaccatg  33900
aaaagtttac ttcctggcta agaatggtca cttccctggc ccctagattt cctctttact  33960
ttcttcacta gcagttgcat gttgtttttt tgtttgtttg tttcattttt gttgtttttt  34020
gttttccagg catttggaca aagaaacttc aaaagcagcc actgtccaac cagcaaattg  34080
atggactagg cttagtgacc tactggatgt gagacgcagg gtgatttgtc aggcttctgg  34140
ctggctgagc tattccctcc ctgcgtccct cccaaaccct agcacgggag tgattttggt  34200
atcttggtgg aatcctgcat aagttactac acatctcaat aagggagggc cttctctttt  34260
actgcaatcc cctccacccc ccaagccaca caggaagttg ctcagctgat agtttcaggg  34320
cctctgccat acactattcc ttcctcatct gagggggggag aaactgcctc tgtggaagga  34380
gaccctcctt gttttcctag aacaaagttg acacttgcat ttggccctcc agcagcaacc  34440
tgcttgaagt ctaagagttg cttttctctt atctccaatc cttttcttca agaggttaga  34500
```

<210> SEQ ID NO 15
<211> LENGTH: 30480
<212> TYPE: DNA
<213> ORGANISM: Homo sapiens

<400> SEQUENCE: 15

```
caggccatac atcatagtga atctgcagcc tggggcctaa ggcagtttgt acacttccag     60
aagagggaag ccacttctaa aacaatttct taaggagact tcacccaacc caagaagctg    120
ggtgttgcct gggccatttc cctcctctgc cctgaagcag tggccagctc agagagaacc    180
ctgttgtttt gtgtttgtgt gatctttggg tggatgtgtg cacaccacct gctgagcttc    240
gctgtgtgcg tgcctcaccg ccagccctaa tctgccagag cttcctggcc ttgcaaatgt    300
ttctgtggag ggtccatatt agactccagt ggttcttgca gtctataaag tctccttgaa    360
ggtgattccc tgttccttga agacaactgg ctgggctgga tgcctgaata tagctccctg    420
acttctctaa aggacaaact tattgcccct ttagagaagt catgaagctt tgccggcaag    480
cacagagtct agcttagaaa acacaaccag ggccaggagt ggtgtggctc atgcctgcaa    540
atccagcact ttgggaggcc aaggcttaga ggatcacttg agcccaggag ttcaagacca    600
gcatgggtaa tatagtgaga acttgtctct acaaaaaatt ttaaaactag ccaggcatgg    660
tggtacacac tggtagtccc agccacttgg gaggctgagg tgggaggatc ctttgagcct    720
gggaggcaga ggttgcagtg agctgagatt gtgccactgc actccagcct gggtaacaga    780
atgagaccct gtctcaaaag aaaaaaataa aaagaccacc agggcccagg cacagagcct    840
ggagcgggga agagatagcg gagttaactg tgaatcctga ttgcactgac cacagtctag    900
tgagcaacac atgtttcctt ttgaatatga gtgggaatca cctttaaaac tatataacat    960
ttgcatcttc tcaaaagccc caggtcctac taagattgac ttagggctac atatcaggtc   1020
tcattttcaa ggaggaaaca cagggaagcc tcaagatgtg cagaagagag ggatgtgggg   1080
aatacaccca accactcctc tgctgaggtt ggaacagaac aaggaaagtc cccggacctc   1140
ctctcagcag gcagagaagt gcggggcctc cctctggcaa agcctgcaga tgtggccagc   1200
```

-continued

```
atacctccat acacacagct tcagaggcaa gggtgtccaa gggagtctta agttttatca   1260
gaaataatgt cattcgactg accagtaagg ggagctttca gaaagttatg gaagaagatg   1320
cgacagacac aggaaggact tcagaagcaa gaagacaact ggactctcta aaatgccact   1380
ccgaaagcga aaagggaagc ccacagaccc acgaagacgt gctggcctcg tgttgccagt   1440
tctgtttctc tttcaatacc catctcttca gattgaaggg cttctgcctt cttgcagttt   1500
ttgctgacac gtttacccat ttacaaacct tggctgcacc taactttttt tttttttttt   1560
tttttttttt ttttttagca tttaagttcc tagccaaaat acccgggcct ctaggaaagc   1620
ccttttctct ccctctgaga tctttcctta ccaaccccag cctcccaacc cgggtgtcct   1680
aggtgggacc agggacgatc cttcggagtt ggtcaaggag gcgtcggaac agcaggcatt   1740
tgcccttcta gttggcagca gcgatgagcc gcgtgctcca tgctcagggc aggggcagcc   1800
gcccggggaa ggggcgcccg atacaccgct caccgctcag ccccgcgtct ccctccgggg   1860
tcctttacct ccatgtcctt caggtgccga ctctgcggca gacgcacccg ctcgcccggg   1920
ccggagctca cgatccccgc tgtcccctcc gctcccggcc gtggccagtt tcgggctgcg   1980
gcgggcacag ggcgagtggg cggtggcgcg cgcccggctg cgctcggctg cgggactgcc   2040
ccggccgcgg gggccctgcg cgagagaacg aggaaggagg aggagggagg gagggaggaa   2100
ggggagggga ggggagggtg gggagcgggg agggaggccg acgatcaggg tttaaattta   2160
gacgcaaatc taaacagata ctgtccctcc cagggcagga ctcaagagcg ggagccacga   2220
ctccatgtgc ccaaacatgg ggatgggcag ccaccgggcc cctctgtctc gcgaagtttc   2280
tcaggaccct gggctttgcc acggtctcag tccttctcaa cgtctccctc ccttaatgcg   2340
ccttctttct ttttcctgtc ccttcaagaa ttagagtggt cctttaattc tttttgtttc   2400
ctctcttttc gatttccttc ttttgtgtcc atccttcctg ctttccttct tcctctccct   2460
ctttttaaaa ttgcattact gtcatacctg gtttccctgc agttcttggg tggagttcga   2520
ggaccctccc tggtggaagg cgtttgtgtt ctaccaaaag aggagccctt ctgaccgagg   2580
cttcagagct cagcgtggcg ccgacgggac cacctttccc ttctcacctc ttttcctctc   2640
caccttccag gaaaccacta tctatccatc tatccatcta tcttctgtat acgagtagaa   2700
ggaggaggag gaggaggaaa atcaggaatc cacgcaaagt tttccaagct ccctgaagtg   2760
gtaaatcttt tcttcaaacc ttgctttgac tgatgcattc ggttttgtgg gaattttggc   2820
tcccacaagc tgcttgctaa aggcctcgt ctccattcct gttaaatata gcaaagggca   2880
agatgctcaa catctgattc ccatagggcc cagcatagca accttccttt agggccatcc   2940
cggctgggca gcagagaccg catgggaggg attcggggac tggaatctgc accagggtca   3000
ctccctgcta cccggatccc ggcccccttc agacccttcg gcagagagaa acaggaaaat   3060
gccttgagag acctgtgagt gccagggtat tggctgggta tatgacgcct ctgggttatc   3120
ccacagcatt ctcacccgcc caaccccagc tcaaccaggg gaggggagcc ccatcagagg   3180
tgggcaatgg gacaggtgat ggtgagcact gtgaagagac atgtggagaa acagtagaga   3240
aaaaaggctg agagtctgct cctgctacaa agactaccct gattctggtt atcccggcac   3300
catctttgca ctttcaggca cttagattgc tgctttgggt accagtctta gaaatatggc   3360
ctccttcctg tcctagaact ttctaaggcc caactttcta aaacactggc agccctaatg   3420
ccagagtggc ttctagttct ttagcttagc taagcataga ggaagacgcc tggttttagg   3480
aacagacaga ttgagggctg aattccagct ctgctacttt ctagttgtat tttttagaca   3540
agtcacttaa ctgctctgat tctcattttc ctcacctata caatgtagta ggcactctgc   3600
```

-continued

```
aaaaagtggc tgtttttatc atgcttagcc ccatgtacaa gcttcagatg aataagagcc   3660
tgatatttct tttatttaga gacaggcact cggggaccca gtgaaaagag ccctcactcc   3720
caggaattaa tagtgaggcc cctcccagtc cagccacatg gctgctcagg tgaagactcg   3780
agagcagagt cggcagtaag gaagggtatt tactggtaac ctgcaaggca cacttttgct   3840
cgtgcttctt tcctttcttt ttaaaggtgc aggacgtagt gatgactgca tagtctacta   3900
tcaggtcttc taactctgct ccacagggcc ttttcctttc tccctctacc tagtcctcct   3960
ttgtgctcag aatggggctg ccccagcaca ggtttctggc ttcacaaaca ggagggcgga   4020
agtgcttacc cagaggaaac cgttaggcct agataacatc agtcacccaa ggtgacttgc   4080
agctgctccc cacgccctgc ttaggcctct cttggctgag aacagatgac cacaaagcaa   4140
acaagcttgg cctccaccat gctcctgggt ccccagtgca gagtttaatg ctgctccaga   4200
gctatttggg ccccagactg ggacttctcc tgagggaggg ggtggaaaac ggggagggag   4260
ggaccaagag gtagccccga gctgtgttta ggcagccatg agtaggtgtg gtgtgtgtac   4320
tccccttatc ttcttcttct gtccctacag aagatctcca ggagccagaa tagcagtaac   4380
tctgctgata aacacccagg tttgctgggt tatctgggat tgtaactggc tgctctgggg   4440
gctgggagga aacaacagcc caaggggaag ggaaagtgac tttccgagga gttggttccc   4500
ctctctctct ggaggtctgg ctggctaaca cggaaccact tccttcagtc taccctgggc   4560
cttccccttc atatatcctg atagccagaa ccagccacgc aataagtaga ggtcatcagg   4620
taactaacaa taaaaacacc aggctgggct catgcctgta atcccagaac tttgggaggt   4680
gaggcaggtg gatcacaagg tcaggagtta gggaccagcc tggccaacat agtgaaaccc   4740
catctctact aaaaaaatac aaaaattagc tgggcatggt ggcgtgtgcc tgtaatctca   4800
gctacgcggg aggctgaggc agaagaattg cttgaacctg gggggcagag gttgcagtga   4860
gccaaattct tgccactgca ctccagcctg ggtgacagag ccaagactcc gacaaaaaaa   4920
aaaaaaaagg ccaggtgcag tagctcacgc ctataatccc agcactttgg gaggccgagg   4980
caggcggatc acgaggtcag gagtttgaga ccagcctggc caacatggca aaccccgtc   5040
tctactaaaa atacaaaaat tagctgggcg tggtggcatg tgcctgtaat cccagctact   5100
taggaggctc aggcaagtga attgcttgaa ccccacaaggc agaggttgca gtgagccgag   5160
atcgtgcagc tgcactccag cctgggcaac agagtgagac tccatctaaa aaaaaaaaaa   5220
aaaacaaaaa ataaaaaaac aagaacacca gagatacagc tcagccaagg gaggggcgta   5280
tggggaggta tggggaggag ccaggcatat agaaggccct caataaatat ttagtgaatg   5340
aggccaggtg gtagctcaca cctgtaatcc cagtgctttg ggaggtggag gatggtttga   5400
gcccaggagt tcaaggctgc agtgagcact ctatccttgg caacagaaca agaccttgtc   5460
tctaaaaaaa taaagtaaaa taaaaataat ttggcgaata tgtgcgtgaa tgaatgaaca   5520
agtgaagcaa attaggatct ttccctttaa gtcagagaca gagtctttca gagatgggtc   5580
tcccatggaa ataaggaccc agtgggagaa aagatcatga aaggccacaa taagtagtaa   5640
cttaattagc tttcaagcag aattgcaaag aggtctaatc aatcagctgt ttatagtgga   5700
cacactgtac tgctgatcat ctattttaaa aatgaagagc aagaagcaaa tattctttta   5760
cgactacaaa tactacctac tatggtatag gtaaatgcat atataggtaa aaattacctc   5820
atatggtatt acatgaaata tcatctatat aatatagtta tattaatata atatataaat   5880
atatacaata taaatatata aaataatata aacataatat atataacatt ttacataata   5940
```

-continued

```
ccattcattc ctaaattctg ggaatctggc aaaacaaaat ataatgaaac acacacacac   6000
acacacacaa atcccaattc attttgccgt aactgtcatt gaggaataaa tttgaattac   6060
attgaaatga aagcacaaag tctgaagtgt ttttatgtct ttaagaacct gcaatggaaa   6120
gtttcccaaa ggcagatgag gaaattgagg agaaagacag cacagcagca gtgggactgc   6180
agcgggagga tattggagtg gtggagaagg cagtcagcat aggctgggga cttcatgagg   6240
agagcttttg actaggcctg tggggtagca gccctgcaga gatcaggaaa ttggctacac   6300
agagaaattg agcaaataga tatttagata ccttgaggac aacgggagcc agattcctca   6360
ctgatgggga agggatgtac aaatatgcaa aggaaaaggg ctagaatgaa ccctgggatg   6420
ttgcattgga ataggaggta ttggtgtgag gtcatggttt tcagtataca tagatagata   6480
tggaagtaaa tgtagatata aatgtgtgta catgcataca tatatttcct ggtttgatgc   6540
actgagaaag cctgggagcg atgacactcc agtaacaata ggtgcacata aagcccagat   6600
cttggtttct aactactgtg cttcattaat agaaccagga cttcttggag taaatggcta   6660
attacagggc cagggcaggt aggacaagat aagcctggaa catcttattg tagcagaaaa   6720
taaggaagta ctcaaagagt gatgagggag atgttaaaat gatacaaaaa tcagtttaca   6780
ggtgctcctg ccagtaatat tgagattgtg taaaaatcaa aataaataat gaaagcaatg   6840
gattagaact cttcaaataa aatgggagct catgaatcta caatgatata aataactaag   6900
tgaataagta gaagagaaag ttctttctta cagtataatg ctgtcttagt ccattttatg   6960
ctgctgtaac agaataccac tgactgggta atttataatg aaatttttat ttggcaaata   7020
gtcctggagg ctgtgaagtc caagagcata gcattaacat ctggtggggg ccttcttgct   7080
acatcatgtt gaaaagtgtt gcatgggctg ggtatggtgg cgcctgtaat ctcagaattt   7140
tgggaggctg aggttggagg atcacttgag cctagaagtt catgaccagc ctggtaaata   7200
tcttgagact ctgtctctac attaaagaaa gaaagaaaga aagaaaggca tgcattggtg   7260
tgagggagca tgagagagag agagagagag agagagaggg agagggagga ggggaggaaa   7320
ggagctgaac tcatcctttt atcaggaacc cactcttttg ataactaact cactcctgag   7380
acaacagcat taattcattc atgagaggag agccctcata atcatctctt aaaggtccta   7440
tctcaaaata ttgttgcatt gggaattaag ttcccaacaa ataaactttg gaggacacat   7500
tcaagacata gaaaatggga tgggtgcggt ggcttacacc tgtaatccca gcattttggg   7560
aggttgaggc aggtgggttg cagaccagcc tgaccaacat ggtgaaaccc tgtctctact   7620
aaaaatacaa aagctagcca ggtgtggtgg tgtgtgccta ttatcccacc tactcgggag   7680
tctgaggcag aaaaatagct tgaacctggg aggtgggggt ttcagtgagc caagatcacc   7740
ccactgtact tcattcagcc tgggagacag actaagactc catctcaaaa aaaaaaaaaa   7800
aaaaaagaaa aagaaaacat agaaaatgcc aactaacgtg taaaaaaagt tagaaaattt   7860
ccatctaaca accatcatag ttaaattaat tttaggaaag aaacaaagtt gtgtgctaaa   7920
tctattgggt agaagtgggg taaggaatga ggttttacat aatttaaact agctccctca   7980
agtcactgat taattacaat aaggagaaaa gcaaccttac agagaagaag ctttaataga   8040
catcatatta atcaagtgac caaagtcgac atcaccagta atgaaacaaa ttgacgtcac   8100
atgatgagat gcaataagaa tgcaccatca cttctgtaat attctggcca aaaggacata   8160
acttgaatct aatcatgagg aaacaccgga gaaaccaaat aggaagacat tcctcaaaat   8220
gactggtctg tagtttttat aagtgtcaat gtcaggaaag tcaaggaaag gctgaggaag   8280
ggttctggtt aaaggaggct agagagacat gataactggg ttaaatgagt ggtttgggtt   8340
```

-continued

```
ggcttgtttg agccaagcat attaaaggaa ttattaggat aattggcaaa actgaaagga   8400
attctgggtg ggaggctata tgggagttct ttgtgttaac tttataactt ttctcaaagt   8460
ttaaaattat ttcaggctgg gcacagtggc tcatgcctgt aatctcagca ctttgggagg   8520
ccaaggtggg aggattgcct gagctcagga gtttgagacc agcctgggca acatggcaag   8580
accctgtctc tataaaaaat aaaaaaattg gctgggcacg gtggtatact ataaattgta   8640
gtcccagcaa cttgggaggc tgaggtggga ggattgcttg agcctgggag gtcaaggctg   8700
cagtgaactg tgatcgtgcc actgcactcc agcctgggtg acagagtgag accctgtctc   8760
aataaataaa taaataaaat tgtttcaatt ttaaaaatta agaaaaaagg tagttagggg   8820
gaagaattga gccctcacac tgctttgatt ctggactgac tcctgtgcca gctttttgtc   8880
accccctcct ccttaccccc accacagaga tccacagaca agctggggcc tgagggcact   8940
ggccatggag agagacaggc ccagagagag cctcatcttc tcgagtaata gagaatggat   9000
acgggaagag gaagattatt caaatatttc ttggtagaaa taactttgtg ctgtttcaat   9060
ggttatagta aacacatgta ttttcgtaat ttggggggag agatctaatt tttaaaaaag   9120
aagaaaacaa aagagttaca gactggactg aggaaagggt ggctgtgagg atagagactg   9180
cactcagctc aggtactcta agaaaagggc tgggtggtct ccagctgaga gaagggccaa   9240
tgagggatgg ggctaggaga agacactggt ctaataactg aggctaaaaa acagtgttga   9300
tggaaaaccc aaggggatga ctgagaggtc ccaaaagatc acaaccttct ccttctaaca   9360
cattatccca ggttttagga atgacattag gtaaatctac caaggaagct cgaaccttct   9420
taaacctaag aagtatatca tgcagggcgc ctgcacaaca gtttcaagtc aggctgtaaa   9480
ttagaatgac ccagggagct ttggaaaaaa tctttcttgg ctggattcag tggctcatgc   9540
ctgtaattcc aacactttgg gaggctgagg caggaagatc acttgaggta gagaccggtc   9600
tgggtagtgt agtgagaccc catctcttaa aaaaaaaaaa aaaaatctgt cctagctact   9660
caggaggatg aggtgggagg atctcttgag ccaggaattc aaggctgcag tgagatacga   9720
tcatgccact gcactccagt gtgggcaaca gagtgagacc ctgtttaaaa gaaaaaatct   9780
gggcctgggc cccatgctag aacaataggg agtggggcct ggtgttagtg ggttttttaa   9840
ggttcaataa aaagatattt cctgcatcgt ctaagccagt tttagaaata tcattcccct   9900
tgccagaaat tgttttattt tttagggagg gataagtgag gaaattttga ctaatgagac   9960
aaaaggggga aagcattacc ctttctgata aagaagcaca caggaagaga tgccctgtaa  10020
atattggatg ttatcttacc ttataatgat gcctggaact gcaacagcta ttttgctacc  10080
atgaggcaaa gctgcgaaaa gccagaatgt aaactccatg aacacagata tctttgtttc  10140
ttttttttca gtgtgtttcc tgtgtgccca aatcaaggcc aggcgcaaat aggcgcttag  10200
tgaatgttca ttgaataaaa aacccgataa ctctgttgag gtgctgaatc aagcaaccct  10260
gagatgactt ccccctctgg acttcttgtt aggtgaagca atacatttct ttctttcttt  10320
cttttctttc tttctttctt tctttcttgc ttgcttgctt gcttgcttgc tttctctctc  10380
tttctttctt tcctttcttt ctttctcccc tcccctcccc tccccttccc ttcccttctt  10440
tctttctctt tttcctgaga cagagtcttg ctctgttgcc caggctggag tgcaatgtct  10500
tgatcttggc tcaatgcaat ctctacctcc tgggttcaag caattctcct gcctcagcct  10560
cccgagtggc tgggattaca ggcgcaagcc accacgcctg gctatttttta gtgtattttt  10620
agtagagaca gggtttcacc atgttggcca ggctggtctc aaactcctga ccttgtgatc  10680
```

-continued

```
tgcctgcctc agcctcccaa agtggtggga ttacaggcat gagccactgc tcccagcaga  10740
gcaatacatt tccttatggc ttaagccatt caagttatga tcttccctct ccccgccccc  10800
tgagatggag tctcgctctg tcacccaggc tggagtgcag tgtcgcgatc ttggctcact  10860
gcaacctcca cctcccgggt ccaagtgatt ctcttgcccc agcctccgag tagctgggat  10920
tacaggcgcc cactaccatg cctggctaat ttttgtattt ttagtagaga cggggtttca  10980
ctatgttagc cagactggtc tcgaattcct tacctcaagt gatcctcctg ccttggcctc  11040
tcaaagtgct gggattacag gcatgagcca ctgtgcctgg ctgagttatg atttttttgtt  11100
atagctgaag gtattcaact gattcagata gatacaaact tataagaaga caaaatcaga  11160
cacatatatc agtacaaaga aagaggttga ccctcagaaa aatgtggagc agagatggag  11220
agaaagagac tggcagggaa gggcagagag agaaacatat gcacacatac acacacacac  11280
acacacacac acacacacac acacagagag agaaagagag agaaacagaa agatgggaca  11340
atgcgatgca gaaaaaggga gtgagaagcc taacatcatt cgtggaggaa aaacaattgt  11400
aaattgaaaa aaataagagt aaccattgtc agaatttaaa gtgttttaat tcctatctga  11460
attttaaaga gcagttggta ttgataatcc tttttctcat tcttaacaaa gaactaattt  11520
ctccgagaaa atgcggtgat gtttactgaa atgaaggttt tttttgatat aatttcttta  11580
ggatattgtt gataaggtta agtgatgttg cagttttacc tctaagggca ttcactaatt  11640
caaatcagta tcttgaagtg ggcaggagct tgcccaagct cgaggttacc cgcttggtct  11700
taaaacaatt atctccaaca attctataca aataaagtta aacagattat aagaaataat  11760
agtatccaaa tcccacctat gactcatctc cctttgtctt tttacatgga taacaggcag  11820
agaagtatgt caaaagtttt ctgcacaacg tgttcttgtt tttgactttg gcaaagtgct  11880
catttgcaaa aacatactga aaacctgtgt ccccgcctga tagtttctct ttccctcttg  11940
cagtggcctc agtatccatc catttgctca tgacagaaac ctgggagtca ctctcgattt  12000
atccttcatc tttagcaatc aggtgctgcc gttctagctc tgaagctccc tgacatcatc  12060
ccccctccct ccatcactgt cactgccctc ttaacgtcag gattatgaaa acagtgtcct  12120
agttaatctc tgcatcttct agttgttctc cttacctcca gccttgactc atactccccc  12180
catcccatct attttccgct ccacaggcaa taatctttca agaacatgta actggctccc  12240
agaagcattc aggataaagg ctaacttctt agatggctca ctcacatccc ttcctgacat  12300
ggctgcactt atctgtctgg cctcttctca acagagaaca gccagtattc cagactccag  12360
gcatcctgag ctgctttcag gtccctgaat tggctcttcc ctctgcctgg aatacatttc  12420
ctgatttgcg caaagtgaat tttattcatt tttgagtaag agttcttggt tcaggctttc  12480
tctaggaaaa tggtcctgac caccaccacc cctttcccca ctctcccacc acctgggaga  12540
gagatatttc ctatgtgcca ttcaacacct gtactattac tgccattgaa agaattatta  12600
tataattgcc catttacttt ctattttttt gtttttttgag acggagtctt gctctgttac  12660
caaggctgga ctgcaatggt atgatctcgg ctcactgcaa cctctgcctc ccaggttcaa  12720
gcgattctcc tgcttcagcc tccccagtag ctgggattac aggcacccac ctccacgcct  12780
ggctaacttt tgtattttta gtagagacgg cgtttcacca tgttggttag gctggtctcg  12840
aactcctgac ctcaagtggt ccatccacct cagcctccca aattgctagg attacaggcg  12900
tgagccacca tgcccggccc catctacttt ctttatattc ttatgaaact ttaagcttaa  12960
ttaaggcaca ttccacccta tctcagtcaa agttctatga tcagtgccac cttcaaatct  13020
ggtgaatcaa tacatgttgg atgaatgagt gcacactagc cccgtgcaaa aaagtagata  13080
```

-continued

```
attcattttg tcatccactt ctcacatgcc cacttaaaaa tgcagtaata acatagggag  13140
ttgtaatata cagtatacca tagcgcagtt aaagacctga cctttttttcc taattaccac  13200
atatcaacta gtttacatac tatcatctcc ttgtataaag tcacaactcc tggtgctgaa  13260
gtctcttccg tatttttatg gtttgggagt atgttataat tacactgcct gcttcctgct  13320
gtgtgataat ctttgagact tttaaagact tttctcatct tggtgtacct aataccactc  13380
taggacccat gaggcaaaca tagagttcat accttgtgag tgtcatttat ctgaaaaggc  13440
agtaatagat ccttgagtct tcgaatcaga atacaagcta aatactaaat gtgctaaagc  13500
agtgtaagac tggatgttgc tgggtactga ggaaggccgg aaggactagg atggagcgtc  13560
aaggaaggcc tcgggggcaa gaggaagaag acgttgactt aggtgtgctc ggtgcagggg  13620
ctgatggcag agctttatgt ggaaggatcc tgtgagcaaa cagccccagg agcccgcgga  13680
gggggtagaa gagaacgtga gctattgcca gagccagctt cagtcctcag gtttgcgggg  13740
cccgctccaa cagggtgcac atccgtcctt tgagtgggca caaagtttgg aatccatttc  13800
agcctcctta tggagatcct gctgcactca gaatgttgtt ctgggagagt tttgcgcttg  13860
gtgtttgcat ctgcgaaaat gggtgatatc tgtattttga agataattga acttgagcag  13920
tggcttctga tttgtatttt ctgcttctgt ttccttcatt gcacgtggaa gggcttttag  13980
gtggcaacaa agagaaagag atgggatgag actaaccaag ggaaagaaag atttgacaac  14040
caattaccta tagataacct gtaggcaaag gggccaaagt gaggcctggg gattcgaaga  14100
tcctaccaga taggtgattt gcagagagca aagtgacttt accgttctcc ttttctaatt  14160
tgatgagagt tctcatcagt cacccaggaa tgtggtaagg aactcctaat caaaatgacc  14220
ataaatctga aaccataatg aaatgggtta agcactaatc tgacccctta cagccaggcg  14280
gcaatgaagc aaaggaagca gacagcccct gatggaagtc acacagggag atgaatgctt  14340
tgccgcagaa aggggaatgg tgtgggtggc agccgttggg gagaggggtg ggggtggggt  14400
ggaaaaggaa tttgcatctc atggctcaat cagatctgaa acctaacatc ctgtttttct  14460
gtaggttggg cacatcagta gctgagagac tcctctgacc atggccagcc tcaggaagtg  14520
agtgtcaaca gccttgcaga tggaactca actcctgggt acccatgcct gaaaagacgt  14580
aagtcctgct cccaccggca ccagaccccc tgccctccct ctaccccaat actagaactc  14640
cagacctcac ccctcctccc cagagacata tcagcaggaa gttaagtcag ctggaacact  14700
ttgttccctt gacatttctg ttttaattct gcagctgtgt ttaaggcttc atgaattatc  14760
tgtccagcac ggtctgtttg tctgcctagt gcctcttctc ccacttccct gcaccaggtc  14820
atgattaccc taaggctggt agagcagaac tggaactagg gttggtaaga aggaagtggg  14880
atggtaagaa agggcattag ggactgtaat attagctgtt gatgagctaa ggatgatgat  14940
ctgattgctt gctcaaggag gaggaattcc taaatcatta acagtgtgcg ttgccgatag  15000
ctctctttcc tcaccctctc atggtattta tctctacatc acatcatagt gatgaatagg  15060
tgtgtctttt ctcctcagta ttctatagtg cctacttaca tgccttattc atgcttattc  15120
atgttcagga agcagttggt aattgaagga atgagccttc tcgccttcct tttatctcaa  15180
gtcagcttat cacttaaaaa caaaaacaaa aacaagccat agcttccaaa ttcaacttgg  15240
tcctgctcag ggtggtattt cttaatttct tatagctgca attcacaggt ctgtatcctt  15300
gcttgccaat gtctgttttg gtattcatgg tagttggctc tgagacatat cagagcacta  15360
tattgttctt tcctggttgc tttttcttct gcttctcatc aaagtctaga gagaaactca  15420
```

-continued

```
gtttctaaag ccattaagaa cctagtagga aaatggtgat tagtctctcc aagttcttct  15480
tcctcagcag acccacgaag agtgttctcc attcactggt caatcaggct cacatgtgtg  15540
aaacgtcaag gttggcctta aaggaccacc cgggcaaatg acttatcgtt agttacgtga  15600
gctgggtatg ttttgtcaac caccccgctt gaaacctaag catgagagaa cgtagctcac  15660
aagacaggta tggccccata tgtctccata agcccacatc tagaaaatac gtatgcagat  15720
ttttctgttg ccagttggtc atcctgagct atcatttcta atgtgtgact agtttcaacc  15780
aaatttaata ttttaaaacc agtctcaaag ccctatattt taaaaagtaa aactataagt  15840
gggcctggca tggtggctca cgcctgtaat cccagcactt tgggaggttg aggagggcag  15900
atcacaagat caggagttca agaccagcct gattaatatt gtgaaacccc atctctacta  15960
aaaatacaaa aataagccgg gcgtggtggc acgcacctgt agtcccagtt gctcgggagg  16020
ctgaggcagg agaatcactc gaacccggga ggcagaggtt gcaatgagcc gatatcatgc  16080
cattgcactc cagcctgggc aacagagtga gattccatct caaaaaacaa aaacaaaaca  16140
aaacaaaaca aaacaaaact gtataaagcc cacaattaac attatactca acagtgaaaa  16200
actgaaagct ttcttttttt tttttttctt tctttttttg agatatagtc tcactctgtc  16260
acccaggcca gaatgcagtg gcacgatctt ggctcactgc aacatccacc tcccgggttc  16320
aagtgattct cttgcctcag cctcccaagt agctgggatt acaggtgtgc accaccatac  16380
ctggctaatt tttgtatttt tagtagaggt ggggtttcac catgttggcc aggctggtct  16440
caaactcctg acctctaatg atccacccac ttcggcctcc cagagtgttg ggattatagg  16500
cgtgagccac tgcacccagc caactgaaag ctttctaaga ccaggaagaa ggcaagcttg  16560
cttcctctta ccacttctat tcaacttggt actggaagtc ctagccagag caattaggca  16620
ggaaaaagaa ataaaaggca tacaaatcag aaaggaagaa gtaaaatgat ctctgttcac  16680
aaatgacatg atcttatatg tagaaagccc tgaaaattgt acaccaaaac acagttagag  16740
ttattacatg aattcagcaa agttatatga tacaaaatta gcatgaaaaa agttgtgctt  16800
ttatgtacta acaatgaaca atccaagaaa aaattaagaa aacaatccca tttacaatag  16860
caacaaaaat agtaaaatac ttaggagtaa acttaatcaa ggaggtaagc tgaaaactac  16920
acctatacac tgaaaactac aaatcattcc tgaaagaaat taaagacaca aataaacaaa  16980
aacacactct atgttcatgg atcagaagac ttaatgttgt taaaatggcc ataccccaa  17040
agctatctac aaattcaatg taatacctat caaaatttca atagcttttt ttttgcagaa  17100
atagaaaaaa aattcaaaat tcgtatggaa tctcaaggga ccccaaattt ccaaaacaat  17160
cttgaaaaag aacaaaattg gaggcttcac acttcctgaa ttcaaaacat aatataaagc  17220
tacaataatc aaaacaatgt ggcatgagca taatgacaga catatagacc aatgaaacag  17280
aatagagagc ccagaaataa accctcatgc atatggacaa atgatcttca aaaaggttac  17340
caagaccaca tgatggggaa aggacaatct cttcaacaaa tggtgttggg aaagctggga  17400
tatccacatg tgaaagaatg aagttggacc cttaccttac actatataca aaaattaaca  17460
caaaacggat taaagaccta aacctaagac ctgaaactat aaaactccta gaagaaaaca  17520
taggaggaaa gctttatgac attggatttg acaataattt cttgaatatg acactgacag  17580
tgtaggaaac aaaagcaaaa atggacaaat gagactatat caaacttaaa aattcctcca  17640
cattaaagga accaacagtg aaaatacaat ctatgtaata ggagaaaata attgcaaatc  17700
acatatctca taaggggtta atatctagaa tataaagaac tcctacaatt caacagtaga  17760
aaaacaagta actggccagg catggtggct catgcctgtt atcccaacac tttgggaggc  17820
```

-continued caaggcagga gaacagcttg agcctaggag ttcgagatca gcctgggcag catagcagga 17880
ccctgtctct aaaaaaaata aaaataaaaa aattagccag gcatggtggc atgtacctgt 17940
agtcctagct actcaggagg ctgaggtggg aggatcactt gagcccaaga ggttgaggct 18000
gcagtgaact atgattgcac cactgcactc caacctgagt aacagagcaa gaccccatct 18060
caacaacaac aacaacaaca acaaaccaca aaaaaaaaac aacaaaggaa ggaaggaggg 18120
aaggagggcg ggagagaggg aagaaggagg gaagaaggaa ggaagaaggg aggaaggaag 18180
ggaggaagga aggaaggaag gtccgttaaa aaaataacaa aaaataggca aaggacttca 18240
aaggacattt ctgcaaagaa gttacatgaa taaccaacaa gcatatgaaa ggatgctcaa 18300
catcactaat cactggagaa atgcaaatca aaaccacaat gagatagttg agtgtacccc 18360
atactcatta gggtggccac tatctgaaaa aaaacccaga attctctaat tttttatgga 18420
gaaattagaa cactgtgcac tgctggtagg aatataaaat ggtgcagtcc cagtgaaaaa 18480
cagtatgaag tttcctttaa aaacaaaaat agggttgggc atggtggctc acacctgtaa 18540
tcccagcact ttgggaggct gaggcaggtg gatcacgagg acaggagatc gagaccatcc 18600
cggctaaaac ggtgaaaccc cgtctctact aaaaatacaa aaaattagcc gggcgtagtg 18660
gcgggcgcct gtagtcccag ctacttggga ggctgaggca ggagaatggc gtgaacccgg 18720
gaggcggagc ttgcagtgag ccgagatccc gccactgcac tccagcccgg gcgacagaga 18780
gagactccgt ctcaaaaaaa aaaaaaataa ataaaaataa aaataaaaaa taaaaaaaca 18840
aaaacaacaa caacaaaaaa acaaactaaa aatagaatta ccatatgatc ctgtaatctc 18900
actttagggt atatattcaa aagaattgaa agcaagatct tgaagagatt atttgcacac 18960
ccatgttcat ggaagcatta ttcacaatag cctggaggtg gaagcaactt acatgtccat 19020
tgacagatga atggataaag aaaatgtgtt tggctgggtg cggtggctta tgcctgtaat 19080
cccagccctc tgggaggcca agttgggcag actgcttgag cctaggagtt tgagaccagc 19140
ctgggcaata tagtgagacc ccatctttac aaaaaaatac aaaaattagc cagcccatga 19200
ttgcaccact gcactccagt ctgggtgaca aacaagaccc tgtctcagaa aaaaagaaaa 19260
gaaaaagaac aaaaaagaaa atgtgttata tgcattcaat gggatattat gcagccttta 19320
aaaaaagaga attttgtcac atgctataac atgaataaac cttgtggatg acattatgct 19380
gaatgaaata agccaggcac aaaggactgc atggttctac ttatgtgata tgtctagagt 19440
agtcaaaatc atgggaaaca aaagaatact ggttgtcaga gacttgggga aggaggaaaa 19500
gaggaattgc ttgatagata taaagtttca gttttgcaag atgaagaagt tctagagatc 19560
tgttacacaa caatgtaaat acggttaaca ttactgaact gtacactgta cattactgaa 19620
ctgtaaaaaa tgattgagag ggtaaatttt ataatatgtg attttttttac cacaattaaa 19680
aaatttttaa gaataaaaca ataaacacct gaatatgcct gaccataaat tgccaccatc 19740
agtgtcactc ctctgggtta acttctaagt ccaggtatat gactaactgg gtaaaaattc 19800
taagaaagca gatttggcat caataaagac aacactttta taagccttct agctgtggtc 19860
tcttttctaa agatgtgtgt tctccagcac tgaacatcac aaaccaatct cagacaatca 19920
cttttggttt gttatgtcca tgttctgata gagtctaatg acttgacttt caaagtagtt 19980
tccaatgtgg ggattctgag gttggaaacc atacatttgg gctgagaagt ggtgatagga 20040
caggtagaag gccctttggc tttgtgcatt atctctcttt ctgtgattag tcatgatatt 20100
aactgttgaa gccacaaact aacatcacac ttgagtggat gaaatgtagg acagctatga 20160

-continued caatgtgtgt ctggtggatt ggccgggggt ggcaatatgg tatgtgggca ttgagagatg 20220
ggcaggaata gagcagaaaa caagcaaagc cctgggggag tgaaagggag gagggcaggt 20280
gaaaggtggg cagcatcttt caaaatgagg caagaagaca ttatgcccat cctgatatga 20340
tgcagtaagt gccacctatg atgatgggat atttgcaaaa gtaaaaaaat ataaaatgaa 20400
accagagact aatcaagcct ccagctctaa ctttcagttt acaggaaaca tggcagatgg 20460
cccatgtaca tcccatgagg atttaatcag caaaaactag aatgtgggaa atttctatag 20520
atcaaatgaa ctggtttctt taacaaataa acaacatttt aaaaaaagaa agagggagaa 20580
agaattgtta tatatttaaa gagacttaag agaagtatca gcaaaatgca atgtgtgtac 20640
cttcattggg tcctgattca aacacaccaa taattttgag acaattggga aaatttgaac 20700
acagatggta ttagatgatg tcaagaaatc catgttactt ttcctaggtg tgaatgtgat 20760
atagtgattg tgttaaaaat aaaagatttt atctgccaga gatacatact gaagtaccat 20820
ggctaaagtt acatgaggtg tgagattttc tttaaaatct tccaggggtg aaaaatcgtt 20880
aaagagatag atgaggcaga attgggaatg cattgatagt tgttgaaact gggtgcacgc 20940
atgtgggaat tcatagcact attctctctg gacttgtata ccctcataaa tttccaaaat 21000
aacaacaaaa ataataacaa caacaagaac aaaaacagtg agtagactca gggtgatcgg 21060
atacccagga taggctcttg gtgatggaga gagaaaggtc actgaaaact ttgagatcag 21120
taaatacatc tttatctact ttaaaggttt gcttaagggc agcattcttc atatggctgt 21180
tggaaaagtt tagtttattc atttcctgaa aaatttgtga ctctgctcca tgaaccagga 21240
atttcaaact taggcatgct cccaagagaa ataggtagat atacctatca aaagacacat 21300
acaagcctat catattggta caaatcagtt ttatccatga tagtacaaaa ctacgaacaa 21360
tccaaatgtc caagaacaga tcaacaaatt gtggaatatt aatgcaataa aatattacca 21420
cactcggcaa taaaaagaaa caaaatactg acacacgtga cagaggtgaa tttcaaaaac 21480
ataatgctga gcagaagaca gacacagaag agtatgtgct atgacgctca agaataggca 21540
caactaattc agggtgatag atgttagaat aatagctacc cctgagctgg gatattgact 21600
gggaaggtgc atgagggacc cttctgaggt gatggaaatg ttttacatct tggtccaggt 21660
gctggtgtat acaaatgcaa gaactcatta agcaggacat ttaagatcag tgcccttgtg 21720
cactctatgc tatttgtatt ataactcaaa aatagtaatc ataatgaata aacaataaaa 21780
aaggaaaaga aaaaaaacct ggaaatgttt tgaatttcca aaagaaatct aatggtagaa 21840
aaatttaaga caatattttt agggtctaaa gaaaattgag ttcctgactc agaaagctaa 21900
agtcttatgc taggaaaatg ttgtctggaa tgttctataa tccaggggtc agggaaaggg 21960
ttccagttct attccagact tctatcctgc cttttccctt ttgcaaaatg catcagccct 22020
gtttagtcag ctctttgccc cagtagcaat gaaagaatcc agtctttttt tatattttgt 22080 tttttttttct gaaaacattc atgagaaaat cctaataatc accagttcaa cacattaagc 22140
caaaggaagt tgtcatgtac agaataatga gcatgcagcc tgcaaagaag aaatggtttg 22200
tttcccagga cctcttcctg gggtacaagg tctgaggcag aaggggatat ggggtaggat 22260
gaggtggggt agggtggtgg agttcagtaa atggtactag gctggtcttc ctactaaaag 22320
acttgggttc taaatatagc tatttcttga atgtgtttgg gggcaaatca tgccaacttc 22380
tcttgtcatc agttcttcct ataaaaattc agggtgatga aattgcaggg atatcgtgag 22440
gattaaatca gatcatgtgc acacagtcgc acaatcaaca gagacttaaa tagaaaagaa 22500
gtaggaggaa ccaacatttt ccagtttttt cttttcatct ttgtactagt tccttttctt 22560

-continued

```
ttcctcttac ctcctggtgc ctcaaaggac ctcaggccct cctgctatgg tcaataccgc  22620
actctggcac ctcacctcaa gtactccact acaaacctga gatagagtct tagatgtagc  22680
cagtgctctt agcctggggc agagatgcga cagcagtgag agctaaggtg ctgaggaggt  22740
gtcactgagg actgagcact ggggttaata acgaagaccc aagtcagatt tttcaaggct  22800
gtgaagctat caggagcaaa ctggaggata cacaaagggg tgcactgtac agagggaaaa  22860
gcaaagtcca ttgtggcggg gatgacagag aggaacaggg gctggaattg gacatgcaaa  22920
ggaatttgga ctttgtcagt aggagaaagg gcaacatctt aagagctgtt ttgcaggggt  22980
cagatttaca ttttaggaag atgattccga cagcagaagg aatcagaggc aattttgcag  23040
acaggaaaac aagtcaggag agttgaagac ctaagctgga gaggaaaaaa gagggttgaa  23100
agacactaca agtttgattt tccagggatt aagtacatat taggatgtgg gagtaagtag  23160
gaggagccga gattaactta aactttcaga gtaaggctgt caggtttatc aaataaaaat  23220
acaagccatc cggttaaatt tgaacatcaa actattgata agtaattttt agtataaata  23280
tctcccatgt gtattagtct gttctcacat tgctataaag aaataactga gactgagtaa  23340
tttataagga aaagaggttt aattggctca cagttctgca ggctgtatag gaagcataat  23400
gacatctgct tctggggagt ccttggggag cttttactta tggtggaaag caaaacagga  23460
gcaggtgtct tacatggcag gaacaggact gacagacagg aggaggtgcc atggactttt  23520
aaacaaccag attttgtgag aactccatca ctctcatgac aatagcactg aggggatagt  23580
gctaaatcat tcgtgagaac tctgccctca tgatccaatc acctcccatc aggccccacc  23640
tccaacactg ggaattacaa tttaacataa gatttgggtg gggatccaaa ccatatcatt  23700
ccacccttgg cccctccaaa tttcatgtcc ttctcatgtt gcaaaagtac aatcgtgaca  23760
tcccaataat cccccaaatc ttaactcatt ttggcattaa ctcaaaagtc cagagcctgt  23820
aaaatcaaaa tcaagttagt tactcccaag atacaatgga ggcataggga ttgggtaaaa  23880
accccctttc caaaagggag aaatcagcca aaaggaaggg actacaggcc ccatgcaagt  23940
ctgaaaccca acaggacagt ctaaatctta cagctccaaa acaatctcct ttgcttccat  24000
gtctcacatc cagggcacac tagtatgagg ggtaggctcc caaagccttg agcagctcca  24060
cccagtggct ttccaggatt cagccccctc aagagctggc attgagtgtc tgcagctttt  24120
ccaggtgcag ggtgcaagct gttggtggat ctacaatttt gggatctgga agatggtaac  24180
ccccttctca tagctccttt aggcagtgct ccaggggggga ctctgtatgg aagttccaac  24240
cccacatttc ctctttggac ttccctagta aaggttcttc atgagggccc cacacttctg  24300
tagcacactt ctgcttggac gtccaggctt ttcattctct gaaatttagg tggaggctcc  24360
caagcttcaa ctcttgcact ctgcacatta gccggcttaa cacaatgtgt aagctgccaa  24420
ggttcatggt ttgtaccctc tgaagcagtg tcctgagttg tacctgggcc tctttgggcc  24480
acaactggag ccagagtggc ttaggatgca gggaggagtg tccccaggct gcaaagggca  24540
gggggccct aggcctggcc catgaaacta ctcttccctc ctaggcctcc aggcctctga  24600
tgagaggagt gccacaaagg ttcagccttt tccccattat cttggctatc agcacttgct  24660
ttccttttag ttatgcaaat ttctgtagtt ggcttgagtt gctcccctga aaatgggctt  24720
ttcttttctc ccacatggcc agccttcaaa ttttccaagc ttttatgctc tgcttccctt  24780
ttaaatataa gttacagttt cagatcattt ctttgctcat catatgagca taggttacta  24840
gaagcagcca ggtcacatct tgaatgcttt actgcttaga aatttctttc accaggtacc  24900
```

-continued

```
ctaaaatcat cattctcaag ttcaaagttc cacagatact tagggcaggg gcataatgcc  24960
tatgagttct ttgctaatgc atgacaaaag tgacctttgc tccagttccc agtaagttcc  25020
ccatctccat ctgagacctc ctcagcctgg ccttcattgt tcatatcacc atcagcgttt  25080
tggtcacaat tcaagcagtc tctaggaagt tccaaatttt cccccatctt ccaatcttct  25140
gagccctcca tactcctcca acctctgcct gctacccaat tccaaagtca cttccatttt  25200
caggtattct tatagcaatg ccctacttct cagtaccaat tttctgtatt agttcattct  25260
ggtattgctg taaataaata cctgagactg ggtcatttat aaggaaaaga ggtttaattt  25320
gctcacagtt ccacaggctg tccaggaagc ataacagcat ctgcttctgg ggacgcctca  25380
gggagctttt actcatggca aaaggcaaag ccagagcaga catcttacat ggcaggaaca  25440
ggaccaaggg cagtggctgg tgccaaacac atgtaagcaa caagatcttg tgagaactca  25500
atcactagca tgaggacagc accaagtgga tggcgctaaa ccattcatga aaaccctgac  25560
cccatgatcc aatcacctcc tatcaggccc cactttcttt ctttcttttt ttttttttga  25620
gacggagtct tgctctgtca cccaggctgg agtgcagtgt cgatctcggc tcactgcaag  25680
ctccacctcc tgggttcaca ccattctcct gcctcagcct cccaagtagc tgggactaca  25740
ggcacctgcc accatgcctg gctaattttt tttttttttt ttttttgtat ctttagtaga  25800
gacagggttt caccgtgttg gccaggatgg tctcgatctc ctgaccttgc ctcagccttc  25860
caaagtgctg ggattacagg cgtgagccac cgcgcccggc caggccccac tttcaacact  25920
ggggattaca attcaacatg agatttgagt ggggacagat tcaaaccata tcaccatgca  25980
ataatcaatc tgaagttcaa attgaattgg gtattctgta ttttatctgg caactctatt  26040
tcagaatcac ctctctaaaa tgcaaatctg atctgtttaa tctattgcta tcttaatgtg  26100
acttcacagg taaataatct tcctcaaaag agactgtatt tatcagctgg aaggagtatt  26160
tgggtcaatt gaaaaatcat atttctcatt tttgaccaga gaatcagcat agtgaagagc  26220
attttcccag caccattttt tttttggtgt catgggccat ccataccatg actttttca  26280
gtaagtttga gatctatatt aaattaattt actttttaaa ttttgcatta cactaagtaa  26340
tgatatccat gaaatcacca ctccaatgag ctactgattt tttataccta ttacaataaa  26400
cacagggcta caataaattt ttattcctat gttatctaaa acttgcacgt acactctggg  26460
aaataccaat agaggaagga gagctgtgct ggcgctggtc tgatctgact catactctac  26520
catcccggag cctcaatcac tgtctggttg gagaggagaa ggccctggtg tgctggcaaa  26580
ccctgaactt gactggatta gattaggatg agagggacag gacagtcagg cttctgataa  26640
ggatggaaaa gtgggaattg gagttcagcc tccaggaatc ctgcaggccc cctggtagtg  26700
gagccatata tgtatttggg gtcccactac cagagaggag atacatgggg accggtgagg  26760
gccaagaacg tggccagagg ttgtggttga ggagtttagg accccagatg aaaaactcct  26820
gtctccaggg gctgaaagca gatacttaag aattcttctt gtgggatttg gacacagact  26880
gtgatctacc tgcctgcaca atgtctcatt gttcctgact tgttaagaaa gcttctcctg  26940
atacttggta gcagttcagg ttgatgtcag cccctgggct gtccagcaga aagattttcc  27000
caggtttctc agtggagact ggagccacca gaactgtgac accctgaact tgaaccaacc  27060
agccagtctt gtcaggtacc tctgacccga aaggtcatgc caagagccca gaggctctga  27120
tcatgatctc agcacttcat ccacataaag gagcccactg ttgtgtttcc caaatgctgc  27180
aaggctcttt tgctccgggt ttcactgatc cgcccctcct tttaaaaaga ctcttggatt  27240
ctgccaacat tactctaggc ctccactctc tgctcaccaa agcctaagcc ctgtggcctt  27300
```

-continued

```
agggccgata agtccttgga tacatttccc agtgtgtttt tccttggtgg gccggtgaga  27360
caagagacga tgggggtctt tactgtactc atgtgacaca tggctgttct gcatgcggca  27420
aggcagaggg gctgggaagg agggagagta tgaagtgtct gttttgtgcc aagcattgag  27480
ctaagccaat tgtcacaata atcctggagg cagataccat catcttcagt ttatagatga  27540
ggaaagctaa gctcagagag attaaataac tgtgaacggc agaaaaaacc gagccggaat  27600
tagacttcag atcttctgac cttaagtctg gtgctctttg agtcatgcca cctgaaatca  27660
atttgagaga aagggcaatt gttggctcaa ttttgatgaa ataagaattt gaggggacac  27720
cctctgtgtg cctaaggatg aggcccaaca cagggaacag aattcaggag actctgcaag  27780
ggcagaacat actggtaaca tgtcctgcag gctttaactc ctattctttt ttcatgattg  27840
ttccacagtc ttctttccta aggactatta tcagatccat atacccatgt tagttagagt  27900
aaatgttagg cttctgtaac aaataaaccc aaaatataat ggcttaaact taagtttatc  27960
tctctcacat aaaattccag gtgagtggtt cagagctggt acaccacaaa atgtcttgct  28020
cagctcctat catcacatct tgcatcccta ccatcaagat ggaggagaac atgcaacttc  28080
tttttaagag tctggccttg aggattgcac atatcacctc tacttatatc tcatgttgtc  28140
ccaaacaatg acatgaacaa ttgtagctgc aagggaagtt gggaaataga gtctttatct  28200
gagtttccat gtacacagta aaaaaacttc tgttgctata gaaaagagaa aaaaattggg  28260
gagaacatag aggagccact actataataa ttttggaaca ctcttacatg aattgatagg  28320
ccatttatgt tttctttaag aagtctgggc caggcgtggt ggctcatacc tgtaatccca  28380
gcactttggg aggccaaggc aggcggatca cctgaggtca ggagttcaag accagcctgg  28440
ccaacatggt gaaaccttgt ctctactaaa actacaaaaa ttagccgggc atgatggcag  28500
gtgcctgtaa tcccagctac ttgggaggct gagatgggag aattgcttga acccgggagg  28560
cggagcttgc agtgagctga gattgtacca ctgcactaaa gcctgggcga cagagcgaga  28620
cttcatctca aaaaaaaaaa aaaaaaaaaa aaagtctgga ttatgtggct tagagccaca  28680
actctgctac ttagatgtga tcttggcaag ttgtgtaact tctctgaatc tcagattttt  28740
cctctgtaca atgaagtgat gaaattagcc tacctaccaa gctcggatat tggaaggccc  28800
aaataaactc atgtctttga atgctgcatg taagctgcaa ggtcccatga aaagtgaagt  28860
gctacagcat tgggccaccc agagggggt ttttgttttt gtttgtgtgt ttgttaagca  28920
tttggtgctg gttcctcagc ttggtttagg gtgaaaacca catatccaag tcttctgtat  28980
ggtatttcca ctctcaaggg aatactttag cacatcctat tcacttctac tggttagcct  29040
gcctctctcc ccagagccct gccactcttg tgggctccca tccttccctt gggtgcaagt  29100
cactgccaac ccaccccgac tggccacttc tgatccctaa tcacaagtgg gtaataaagg  29160
ccccgaaact tactcctccc ggagtggatt tgggtggagg gccccgaaac aggccctgca  29220
ggaaggagcc caggaaacgg cccccggcaa tgctaatctg agcgtttttc cccaagcata  29280
tgcaacaaac ctcaaaaggc cacctcggca tgctttcaca cccctagttg agattgtatg  29340
acagtcagca gtgtgtgtta gttacagcag gaccagttgt tatctattag cctctaagct  29400
ccttaaggaa agaaggaaat aaaccttttc tcagcatcta ttatgcctta ggctcataaa  29460
caatgtgcca gcatttattc ctcacccaac ctcactgcca ggaggaatta tgacctcctt  29520
cttggtagat gaggagtaag aggttgaaag agtaccttgt tcagtaccag acagtcatca  29580
agtgaaggtg gcaagatttg aatccaggat ctgatgccaa gtctggctcc ctcctatgac  29640
```

-continued

```
accgtgatta atctgtactg tagttgagtg tgaaaaggtg gaaactatgt gttcagccat  29700
tgtaccttcc cttgagcact aacacgattt catgccagca gggcctcaaa aggattaaag  29760
agaatggcat ttttcaccat tttatctctg acagtgcaca gcacagttcc tgatacgtga  29820
aacaggtcat tatgatattt attggacata ccgaaattgt tggactgata ttttttaaaa  29880
aatcatagct gtatttattc attccaagag ctgaaggtga aagtgccttg caaagccttc  29940
ctgggagtaa ggttgtcagg cagataaaac aagctagtga aatcagggaa aagatttcct  30000
ggacacaact gttcatgcca ggcttcctgg cggaaccaca gcaggagtta accaagggtc  30060
tactgtggtt attgcctgag ccacactcac agccatgaat ctgtggcaaa agcagatggc  30120
acttccggca gacatccccc agaggagaga attttccatg aggcctgtgt atggcagcca  30180
gccatcctgg gtttcctggc atggtccaat ttcccatctt ttgtctcaaa gtccttagaa  30240
ggacatatgt atggggtggg taaagtcctg ctcttagtta tttaatttat ttatttttac  30300
aggcagcctc tcaaaccaga gtaggctcag agagactcct gagtcctgct tttgaatttg  30360
gaaaatatgg ttatagcagg cacgtggaaa gtgcctttta ttgcctccca cctgcagatc  30420
aaaggcagag gggccggcct gcccaggtca gcctgtttca cccgggaaag ggagggccat  30480
```

<210> SEQ ID NO 16
<211> LENGTH: 32580
<212> TYPE: DNA
<213> ORGANISM: Homo sapiens

<400> SEQUENCE: 16

```
ctgctccagt caggaagccc tggggagcct tctaatagag gaagcccacc agggccagag     60
cagggctgtg tcctaagaat tcaacagtcc ccgaaaagtc caagaaagtg gtaacaggaa    120
agaagcaaca gcagaagcag aaactgctct tttgatctca ttgcgcaaag gaaggaggtg    180
acccaaggcc tcttgtgaca cacacagaag cacatagaag tatatttggg gaagtgtgtg    240
agagctctcc ccaaagatgt cttcagatta gaggtcaacc ctgggtggct gccctggggc    300
aagctgggat gctcttgtgg ttcagctctt tccacactca gacggggtca ctgctgggta    360
acaatatgcc tagcaagcac aggtaaacca agccaaaagc ctatttgttt tctaggatca    420
gtctgttaac ccctcaactc ccagcccagc caggcaggtc cctatgggtt aagctttgtg    480
ctaggcctca ggagaccttg ggtctcatcc cgatccccta aacagctctg aagcctgggg    540
cacatcactt ttttcctctg acctcagcat tctcaccggt tcagttaagg aatcaagaag    600
gctaacagaa gtttagaggg cttaccgcac actggctgat cactttgccc tgaagtgatt    660
caacactaaa aaagctcgaa agtgttagtt ttcttcagtt tggtaaaatc tgtgtgattc    720
tacacatcct attcattcat tcgcttgctt aaacttgtcc tgagcatcac tatacatcag    780
cactgctaag taacaaacac tattagtgtc tccttattga gttccaacta agtgtcaggc    840
gctttagata gattaccccc acttaatctt cctcacagat ctgtgaggca atacctccat    900
ttttatttat ttacttttct tttttgagac agggctttac tctgtcaccc agactagagt    960
acagtaatgc agtcatagct cactgcagcc ttgacctccc aggctcagtt gaccctcccg   1020
tctcagcctc ccaagtagct gggagtacag gtatgtgcca ccatgcccag ctaattttta   1080
tatttttttg tagagatggt gtttcaccat gttacccagg ttggtctcaa ctcctgagct   1140
caagcagtct gcccaccttg gcctctcaaa gtgctgggat tacaggcgtg agccactgtg   1200
ctcagcaata cctccatcat tagagcaaga aaaggttaag cagcttgctc taggtcattc   1260
atctttcatt ctcagtcagt ctccaaagct ggtgttttaa tacactagtt ctatccctgc   1320
```

-continued

```
agagctaaat gagatgaggt catcctcatt tcaaggaagt tccagctagc aaccctgtgg   1380
tcagaaggcc aggttgcagc cccgagagtc ctggcattgt tcatagggta cattaggaca   1440
tgtcacactt ggaaaacctg gcgagcctag aacacatagc aaaccatttt tctctgcatg   1500
ttcctagcca cggttctgca gacctagctt cccacatgaa tattctttct gtaccatgaa   1560
tattacaaac tacagaaata gtgccctcat gtgtcaggag cacaacgcac ctttgaactc   1620
tggagaaagg cacattttaa acaatcttaa aactatgaaa cacttttgtt tttgcttctt   1680
ttgtttgttt tcgcttttgc tttctatgtc tttgaagcat gctgggaaga aatgatgaaa   1740
aattgctaaa tctgcagaac tccacccaga ggcaaattac taagtaccag gacctgcagg   1800
agaaactaaa gggaagtaat cttggaatag ttggtattct atgaattgtg catctgtgga   1860
ttcaaccaac tgcggatcaa aattgtgtga gaaaaaaatt ccacaaagtt tcaaaaagca   1920
aaacttgaat ttgcatgcac tgagtactac attgaatcca ggcaaatgaa gtgatgtgta   1980
agcattgcat taggtagtcc agatgtgatt taaagtattt gggaggatat gtgtacatta   2040
tatgcaaata cgatgccatt tttttttttt tttttttttg agacggagtt tcgctctgtc   2100
gcacaggctg gagtgcagtg gcgcgatctc gactcactgc aagctccgcc tcccgggttc   2160
acgccattct cctgcctcag cctcccgtgt agctgggact acaggcacac gccaccatgc   2220
ccggctaatt tttgtatttt tagtagagac ggggtttcac cgtgttagcc aggatggtct   2280
cgatctcctg acctcgtgat ccgcccgtct cggcctccca aagtgctggg attacaggcg   2340
tgagccaccg tgcccggccg atgccatttt atataaggga cttgggcatt gatacggttt   2400
ggctgtgtcc ccacccaaat ctcaacttga attctatctc ccagaattcc tacatgttgt   2460
gggagggaac caggaggagg taattgaatc atgggggctg gtctttctca tgctattctc   2520
gtgatagtga ataagtttca caagatctga tgggtttatt aggggtttct gcttttgctt   2580
cttcttcttc tctcttgctg ccgccatgta aaaggcgact tttgccctct gccatgattc   2640
tgaggcctcc ccagccatgt ggaactgtaa atccattaaa cctctttttc ttcctagttt   2700
tgggtatgtc ttcatcagca gcatgaaaat ggactaatac agtaaattgg taccagtaga   2760
gtggggcgtt gctgaaaaga tactcagcaa atgtggaaaa tgtggaagca actttggaac   2820
tgggtaacag gcagaggttg aaacagtttg gagggctcag aagaagccag gaaaatgtgg   2880
gaaggcttga aacttcctgg agacttgttg aatggctttg cccaaaatac tgatagcaat   2940
atgaaaaata aaatccaggc tgaggtggcc tcagatggag atgaggaact ttttgggaac   3000
tggagcaaag gtgactcttg tatgtcttag caaacagact ggtggcattt tgcctctgcc   3060
ctagagattt gtggaacttt gaacttgaga gagatgattt agggtatctg gtggaagaaa   3120
tttctaagca gcaaagcatt taagaggtga cttgggtgct gttaaaggca ttcagtttta   3180
aaagggaaac agagcataaa agttcagaaa atttggagcc tgactatgga atagaaaaga   3240
aaaacccatt ttctgaggag aaatttaagc cagctgcaga aatttgcata agtagcaaga   3300
gcctaacgtt aatccccacg accatgggga aaatgtctcc aaggcatgtc agaggtcttc   3360
actgcagccc ctcccatcac aggtccggag gcccaggaga gaaagtggtt ttgtgggcca   3420
agcccagggt ccccgtgctg tgtgcagcct agggacttgg ttccctgtgt cccagctgct   3480
ccagccatgg ctgaaaggga ccaacataga gttcaggctg tggcttcaga gggtgaaagc   3540
cctaagcctt ggcagcttcc atgtggtatt gagtttgcag gtacacagaa gtcaagaatt   3600
gaggtttggg aaccttcgcc tagatttcag aagatgtacg gaaatgcctg gatgcccagg   3660
```

-continued

```
aaaaagtttg ctgcaggggc agggccctca tggagagcct ctgctagagc agcgcagaag   3720
ggaaatgtgg ggctggagcc cccaaataga gtccctactg gggcactgct tagtggagct   3780
gtgagaagag ggccactgtc ctccagaccc cagaatggta gatcactgac agcttgcacc   3840
atgtgtgtgg aaaaactgca gatactcaac gccagcctgt gaaagcagcc agaagggagg   3900
ctgttacaga ggcaaagctg cccaagacca tgggaaccca cctcttgcat cagcatgacc   3960
tggttgtgag acgtggagtc aaagcagagc attttggagc tttagaattt gactgcccca   4020
ctgggtttca gacttgcatg ggccctgtaa cccctttgtt ttgcccaatt tctcccattt   4080
ggaatggctg tatttaccta atacctgtac cccgattgta tctaggaagt aactagcttg   4140
cttttgattt tacaggctca taggtggaag ggacttgcct tgtctcaaat gatactttcg   4200
actgtggaat tttgggttaa tgctgaaagg agttaagact ttcggagact gttgggaagg   4260
catgattggt tttgaaatgt gaggacatga gatttggagg ggccaggtgc agaatgatat   4320
ggtttggctg tgtccccacc caaatctcaa tttgaattgt gtctcccaga attcccccat   4380
gttgtgggag ggaaccaggg ggaggtaatt gaatcgtgga ggctggtctt tcccttgctg   4440
ttctcgtgat agtgaataag tctcatggat ctgatgggtt tatcagcggt ttctgctttt   4500
gcttcttcct ctcctctctt gccgccatca tgtaagaaat gtctttcacc ctccgccatg   4560
atttcaacct cccagccatg tggaactgta agtccaatta aacatctttt tcttcccagt   4620
ctcaagtatg tctttatcag cagagtggaa tcggactaat acaggcatcc atggattttg   4680
gtatctgctg ggaatcctgg aatcaatccc ccatggatac ccagggatga ctatactctc   4740
atgcatgctg aggggagctg atgtcctgtg ctagcctgga aagtctagaa attttgtttc   4800
aagggatatg atgaggaaaa tatatgtaat aacaataata atcagaaaat ggtccttact   4860
tctttaccat gtttgttttt tcttttatac tttcttttcc atgtctttta ttattttccc   4920
ttcatttgct tttttccctt cctctctcta cgcttcctat caacttttag aaatagttat   4980
gttggccggg cacggtggct cacgcttgta atcccaatac tttgggaggc cgaggggggc   5040
ggatcatgac gtcgggagat tgagaccatc ctggctaaca tggactccgt ctctactaaa   5100
aaaatacaaa aaaaattagc caggcgtggt ggtgggcgcc tgtagtccca gctacttggg   5160
aggctgaggc aggagaatgg cgtgaactca ggaggtggag cttgcagtga gccaagattg   5220
cgccactaca ctccagcccg ggcgacagag tgagactccg tctcaaaaaa aaaaaaaaaa   5280
aaaaaaatag ttatgtttac ttagaaatca tggcattttt attttgctca tttatgtggt   5340
tttaaaattt tgcctcttct tttttgagtg tgtgttgggg tgagtgtaga tgtgcagaga   5400
ttgaagcgct atgatataac caagagaaaa ccagacttgg atttaaaaga tctaggttcc   5460
tctccatcta tcctcccctc cctgctctct ccacaaagaa ttagcaatca ttcattaaaa   5520
cacatacagt aaataatcat acaatatact cttaagggat atgatgaagg aaaataataa   5580
aaagtaatgt ataacataga gtcctgtata tttgctcaag gtaggtcaca agacatttca   5640
ttgtgaaaac tctcagaaac caaagcgaaa gggaaaaata attaataatt gtttttatca   5700
tctccattag attaaaagaa accagttgct ctttggaagt attatgcttt ctgatattga   5760
gacttgacac attctcttat gggtgctcat aaggaaagta ctgttttata gagggagaca   5820
tctcaacata gccctacaag agcgatagta acacatttcc tcctgttctt tcttataact   5880
gtgtttgaag taagctgata ttgtaactct ggggtacaat tcaataaaaa caaaaccaaa   5940
caaaaggaca aatagtacaa ttccagtagg caattctttg atactcagat gcatttcaag   6000
ggtacaattt agaatagctt aaaaaaaaac cccaatatga atggactgca tgttcttagg   6060
```

-continued aaatccacca cagatattat ttctcctaac tgggcatttg ataaaactga acatggcaga 6120
gtgtgaagtt gtaacatctc aaaagaagca gcagaaggta gattaagtgg gtaccccaaa 6180
aacagaagcc aaagtctctt tcgaagaaca gtttggctcc tttagcttat gagagaaaga 6240
gagaggcatc taaaaattct cgaatgttat agtgcatagg ctgtactagg atatttgtta 6300
aaaatgcaga gtcccaggaa tctctctatg gatttttgat tctagtgttc tagagtaggc 6360
caatgaatct gcattttaaa caattactca agaaacaact gggacaggac actaccttaa 6420
gcaggtctat gataactcta gctggggaaa aaattcaaag cagatgctca agattgctca 6480
cttggacaaa catctctcag taaaacacct taacttaatt ttaaaatata gagttaaaat 6540
gagtttagcc taaagctgcc tccttacata taaatatctt aagttcgacc taaaggtttc 6600
tctatatatc atgaactata acctaaatgg acttgtaaac agactgtagc ttactcttgt 6660
gccaatcacc aagttttagc cagtcaaagg tggccaacag ttccaaccgt gttcaaataa 6720
ggcgaacact gagctgtaac ccatctggct gttttgtccc tcacttcagt tttttataga 6780
gcactttcct ttttctgtct ataaatcttc catcacatgt cagtgctgga gtctcggagc 6840
ctactctggc ttgggaggct gcccgattca caaatcgttc tttgctgaat taaactctgt 6900
taaatttaat ttgcctaagg attttatttt aacagtagtt tcctggtaaa ccctctagga 6960
caaattagtt tggaattgcg gtccctgagt aaatgaatgt tttgacctgc tgtatagaat 7020
tgctgctaaa gctaatttat gttaaaggat gtctgccaaa ttttttgact ttagagtagg 7080
taaactaaag ccattagatc aatttggatt aggtttggct gcatatgaca gaaaaaatac 7140
agtggcctaa acatcataga tgttctttct catagaaatg ggtttcttat ttcatcctgt 7200
aattccagca ctttgggagg ctgagtcagg cggatcactt gagcctggga gtttgagacc 7260
accccaggca acttggtgaa actgcatctc tacaaaaaat acaaaaatta gccaggcatg 7320
gtggcacaaa cctgtagtct cagctacttg ggagggtgag gtgggaggat tgcttgagcc 7380
cgggaggcag gggttgcagt aagccaagat aataccactg cactccagcc tgggtgacag 7440
agcaagaccc tgtctcaaaa aaaaaaagaa aaaaaaagaa aataaatggg tttcagaggc 7500
tggcagcgct gagtgctgag caggtatcat gctctccaat ggaagggacc taggctccct 7560
ccattgctct gatcttcagc gtgtggcttc tacatgctga agacatcaca cccaagacgg 7620
ctgctggagc tcctgctacg gttccacatt gcagattgca ggaaataaga agggcaaagg 7680
tggatgtact ccctcccttt aaggacattt tccggttttg tagtcaggat gtgtgcatac 7740
atgtcattga ccaggacttc gtctcatggc catacctagc tctgaggagt caggggtaag 7800
agggtgttgg gaaatgtaat ctttattttg gatggccaca tgcccagcta aatatggagg 7860
ttgattacaa aagaaaaagg ggggaaatgg gtctaccagt ctctgccata gccatttgtg 7920
gacatagatt aggagacaaa agcaattgtc tgttgaagct agacatgata ctatgataaa 7980
acttagttgg caatgtcaaa gccatgtcac ctttcttaga aaaagtcttt ctgatttcaa 8040
taacaaatgc acatgcttcc tccttacctg aaagcaaaag caattcatga gatacacact 8100
gaaaaggtgt ggggtcaaaa tccctctgct tttttccatt tctactgtta tgaaattttt 8160
acatgtgtaa cgtaccctta ttgtaacaaa cccaagcagc acagaagagt aaaaagtgaa 8220
gcgtcctcct gttgaaacgc ctccttcctc caatcctacc tcaagtgctg ccttggttaa 8280
cattttgagt gtttctttcc aaacaagatt tatgtctcct actccaaatt gttacctaat 8340
ctatcaggac tccatgctta tcctgacttc tattctgctt tgttccatat tagtgtggca 8400

-continued

```
ttttacagtc attgcaagaa gggatgcagt gggggtcaaa gattacaaac gttaaaaagt   8460
gaaaggggct tgagatatca caaagcattc tcacaaataa ttccttggtt tatgttggaa   8520
tgtaaatatg actacacttg ctttttttccc acatgactta aggaattttc ttcatgttgt   8580
aatgtttgat ggatgcaaag caaatgtgta gcttatatgt ttatgaagca taataacata   8640
atcaaatctg tgcacccacc gcccagttta taaaccaatt tatgtccagt accatctaaa   8700
ccacctgcgt gcttctcctt tcagccctcc acctccccat gagaagtcat actatcctac   8760
ttttacattt taattaattt ggccttttaa aaaatagttt tactacagat gtatatgtgt   8820
acaaactata tattaatctt acttcttttt tgagcttcaa aaaagggatt atatggtgga   8880
ttgccttctg caacttgact ttctttttcc cactacatta tatttccaag atgcattcat   8940
gttgatacag gtagctggtg aagacatttt tttttcttt ccttttcttt ttattttttt   9000
gagacagggt cttgctctgt cacccaggtt ggagtccagt ggtgtgatca cagctcactg   9060
cagcctcaaa ctcctggact caagtgatcc tcccacctca gcctcctgag ttgctgagac   9120
tacaggcaca tgcaactgtg cccagctaga gagatagttt ttcattgttg tataatattc   9180
cactgggtaa gcatttcaca agttatttat ctattctcct gttgatggaa tttgggtagg   9240
ttctgttctg ttttgttttg gtcatataaa aattactgcc ctcaacatgt ttcttggtgg   9300
gcatacatga gcaacagttt ctctagggta ttatgtccat gatgaatgga gaggcgggtg   9360
gaggatatgt gtctaactat agaagacaat gacaaattgt ttttcttttt tttcttttct   9420
ttttgttttt cttgagacag agtctcacac tgttgcccgg gctgaagtgc agtggcacaa   9480
tctcggctca ctgcaacctc cacctccggg gtccaagtga ttctcctgcc tcaaccttct   9540
gagtagctgg gattacaggc acctgccacc acacccggct aattttttgt atttttagta   9600
gagagagggc ttcagcatgt tggccaggct ggtcttgaac tcctgacctc aagtgatccg   9660
ccctcctcgg ccttccaaag tgctgggatt acaggcgtga gccactgagc ccggcccgac   9720
aaattgtttt tcacagtggc taaaccaatt tacattccca cagtcatgta taatacgtta   9780
ttgacatttg gtttagccag actttgtcat ttctgtccat ctactgtata taaatagtgc   9840
tgtcatttgt ataattcata gtgtggcttg ggatcttttc atagtgacct tatcctaaac   9900
tttaaggtga taccaggatt ttattttatt tttatttttt taagtatata tacagacaag   9960
gcctacaaac ttactttttc ctgaatccac tcacagtaca gccatggcag ccagtggtct  10020
tggcatgctg gcctcagaca caaaggtccc agaagtggca tagccttcta tcgacctgaa  10080
tcttcttcag tcgctccagg tcttcacaga gcttgttttc cagaccagga cctagctata  10140
gtttccatcc tttacatcct tctgtctgtt caggaactag tctgggttct tgtactggcg  10200
tggattctgc atcatggtga tcctcagggc attccacctc atcctcagtg aattctcctg  10260
ccctcttggg gaagccgatg tctgcttttt caactccaca cgagcataag ttcagctcac  10320
acccttaatg gcagtgatgg caagggctat tttctgctac acattgatgt tggggttgag  10380
tactcacaaa acatggcttg aacttctcag tgatcactca agacacggtg gcagcatgag  10440
tggcagtgcg caggcctcct gtggaagagc tttgtcagcg ctttgaatga ccaagcatca  10500
agattaagtc tgcacagctc cgactgataa cctgtcctat ctacaggctc aaaggcaaag  10560
gctgaggaaa aaatattttt aaataaagga cacatctttt tttttttttt tttttttgag  10620
atggacactc actctgttgc tcaggctgga atgcagtggc gcaacctcgg ctcactgcaa  10680
cctctgcttc ccgggttcaa gcaattttcc tacctcagcc tcctgagtag tgattattac  10740
agcacctgcc accacacctg gctaattttt gtatttttag tagagatggg gtttcagcat  10800
```

-continued gttggccagc ctggtcttga attcctgacc tcaggtaatc tgcctgtctt ggcctcccaa 10860
agtgctggga ttacaggcat gagccactcc acccggacaa ggacacattc ttatgttgat 10920
tcttacagac ttccccacaa ggtgtttcac atataagtca tgaactgggg ctgggttcaa 10980
aacccacatg cttctggtag ggaatattga tccaaaaaac cagatctgtc acgtatgaaa 11040
gcaacctgga gtttataaac tgtttattat ataaactgac ctattattta tgggaataga 11100
gaattgtcct cctaactatg aatcagcttt atatttagga tagacttaag ataaatctga 11160
ttgtagaaaa cctttagcct tatattagtc cgttttcatg ctgctgataa aaacataccc 11220
gagactgggc agggtgcggt ggctcacacc tgtaatccca gtgctttggg aggctgaggc 11280
gggcggatca tgaggtcagg agatcaagac catcctggct aacacagtga aactccatct 11340
ctactaaaaa tacaaaaaat tagccgggtg tggtggaggg cacctgtagt cccagctact 11400
tgggaggctg aggcaggaga aaggtgtgaa cccaagaggc ggagcttgca gtgagcggag 11460
atggcaccac tgcactccag ccagggtgac agagcaagcc tctgtctcaa agaaaaaaaa 11520
aaaaataccc gagactgggc aatttacaaa acaaaagagg tttaatgtac ttacagttct 11580
acatggctgc agaggcctca taatcatggt ggaaggcaag gaggagcaag ttacatctta 11640
catggatggt agcagataaa gagagagctt gtgcagtgaa actccccatt tttaaaacta 11700
tcagatcttg tgagactcat tcactatcat gagaacagtg caggaaagac ctgcccccat 11760
aattcaatca cctcccacca ggttcttccc aagacacaag ggaattgtgg gagctacaat 11820
tcaagatgag atttggatgg ggacacagcc aaactgtatc aagcctgtta tttgagggtt 11880
ctgatctcct gtacctgatc acagaggggc ctgggatcag caaagatcag agtggtttct 11940
cctggatcac aaggccaaac aatctttctg cgtgagatac tgaccacacc ttttgggagc 12000
aaatgcaccc gaaagtacat tgcttgattc tacgtcgaca gcttggttgg tagcggggag 12060
ctcatgagcc tgactcagta agcaggctta gttgttggag agggaagatt ttgactaaga 12120
ttgctttctt ctgttagtct gccccaggaa cagtccccag gaacttacag cttggtccta 12180
tagagaaggg gggtgtacat taaaactctt tgaggagtgg aggcacaagc agtccttctt 12240
tgtttgtggc caatctgcgg ccaatatttc tttgtttatc tcccagcatc ctctcccttg 12300
gtgcagcaac actccctgac ttccccgccc tctcctagtc atgttgttgg ggtgcaacac 12360
atgactcagc cttgggcagt gggcatagtt cattccctgg cttaggagtg ggctccttgc 12420
ctgagctggt ctgatgagaa gaaacccaag actcctctgc agaactccca gaagagaggc 12480
tttccttgta ctgccttgga ggccgttagg ttatgatggt ttgcccctgc ctagagccta 12540
agaatgctgg caacacaggg aagggcagag caaagagtta gaaagaaccc agaagacaac 12600
actcgagctc tgagcccagc cacatctgaa cgtaaagctc ctcttgggat tttttttttg 12660
aacactatac ttttttattt ttaattatat tagttgtaca tattttgggg tacataagat 12720
attttgatac atgtatacaa tgtgtaagga tcaaatcagg gtaactggat atccatcaca 12780
tcaaacattt ttcttttctt tgtgttggga acattaaaat tcttctcttc tagctatttt 12840
gaaatacaca ataagttatt aactataggc caggcatggt ggctcatgtc tgtaatccca 12900
gccctttggg aggccaagga gggcagatca cctgaggtca ggagttcgag accagcctgg 12960
ccaacatggt gaaacccccct ttctactaaa aatacaaaaa ttagtagtcc cagctacttg 13020
ggaggctgag gtgggagaat cacttgaacc caggaggcag aggttgcagt gagctgagat 13080
cacgccactg cactccagcc tgggtgacaa agcaagactc tgtctcaaaa aaaaaaaaat 13140

-continued

```
tttaactata acttcccatt acactataaa atactagaac ttattccttc tatctaactg  13200
tatctctgta cccattaacc aacttctctt gatcttcctc ccacttcctt tcccagcttc  13260
tggtagccac cattctactt tccatgtcca tgaggttcac ttttttagtt cccacatatg  13320
catgagaaca tgtgatattt gtctttctgt gcctggctta ttttacttaa cataatgatc  13380
tccggttcca tccatgttgc tgtaaatgac aggatttcat tattttccat ggccaaatag  13440
tattccactg tgtatatatg ccatatttgc tttatccatt ctcccgctga tggacaatta  13500
ggttgattct acatctttga tattatgaat agtgctccaa taaacatggg agtgcagatg  13560
tctctttgat atattaattt cctttctttc aaagatatac ccagcagggg gattgctgga  13620
tcatatggta attctatttt tagcttttta aggaacctcc atattgtttc ctgtaataga  13680
tgtactaatt tacattccca ccaacagtgt gtgttcccct ttctccatat tctcagcagc  13740
attttttttt ttttactttt tgataatagc tattctaacc ggggtcatat gatatctcat  13800
tgtggttttg atttgcattt tcctgatgat tagtgatgtt gagcatttct caaataccca  13860
ttggccattt gtatgtcatc ttctaagaaa tgtcttcagt aacataaata gtatcttcct  13920
tttggttgct tacttatttt ttgccatggt cggtttgagt gtgattttgc tgacacttga  13980
ttcggaaaat gtccccaaag gtaaccacct aaaatagtat gaaacaaatt caggaaaaga  14040
gaggccatct tccttttcta ccatagcatt taggggctcc agtggcacag aaggtggcag  14100
aagccccctg ccaggaattg tggggtctgc cacagtggcc ccttcagatg catgtgaaga  14160
ggccagaaga agtagtgata tcttgcaagg gcagtagtgt ctgcaggaga tccccagcag  14220
aggaagctct agcaggagga ggtgagaaca tggtccatgt gatgcgtaca ccagtctcct  14280
cgccccaggg ctgtggctgc cagtgtgctt gctgctgtgg tcatcatcac ttcatctcct  14340
catactgcca gcagcttcag cctccccctg gagacagcct gcttctacat ggcttctata  14400
atgcttatgg ggacagcaca ggtgtccaaa tttttcctga ctagacccac agctgctgtg  14460
gctcctctca cacttctggg ctcaggtgaa gaccacattg gaggacatgg gatctggcct  14520
ccctattaac tgcatagagt agccacataa ctcaaccaga agagtagggg aaccaacacc  14580
ctgtatagtg aatcttaaca atgacagaag gtgaaagacc tggcagatat agccctctcc  14640
tttttcacta agagggacat ttccagggca tgggtttcta cagggcctgt ctagacaaca  14700
ttctgcacag ctgagcagct gctctctttc cttggaagct gtgggctgct aatccaagtg  14760
ccaccttgca tttgctttcc ttccttccct gccttgcccc cgccctggga tttacattga  14820
gctgtagcat gtgaggcttg cctctgctct gtttttctag aaaacatggg ctgagggagt  14880
aactgatagt atttgtcatg aacacatgtg agctgctccc taaagggagc attgcaagat  14940
ttaacaaata aaaacagagg gccaggcacg gtggctcagg cctgtaatcc cagcacattg  15000
ggaggttgag gtgagcggat cacctgacgt caggagttca agaccagcct ggctaacatg  15060
gtgaaacccc atttctactg aaaatataaa aaaattagct gggcatggtg gcgcacacct  15120
gtagtcccag ctacttggga gggtgaggaa agggtaccgc ttgaacccag taggcagaag  15180
tttcagtgag tcgagatcca ctactgcact ccagcctagg caacagagtg agattccatc  15240
tcaaaaaaag aaacaaagca aaaaaacaaa acaaaacaaa acaacccagg acacttagtt  15300
aatattgaat tccagatgaa tataaaaaaa atgtttagta tacatatatc ccaaatattg  15360
catgggatat agtcatgcta agaggaatta tttgttattt acctgaaact caaatttaac  15420
tgcgtgtcct gtattttatt ttaactgtgt gtcctgtatt ttatctggca accttatctg  15480
atgactccca atgactccca gaaatacctg ggggaaaagg aggacctagg tctttgatga  15540
```

-continued

```
tgtcattaag gcactacact atctctggac tatatttctc cagacttctt agagtttaag  15600
aaaatgaaac cccaattatt taggactaca aatgtcaggt tttatttcac ttgcaaaaaa  15660
ttgattaacc tgtcgaattc atctttgttt ctttctttgg aacttagcac agtgtttaag  15720
cccagagtaa gtgctacata aatgactgtt aaatcattta tatttagagg aaataaattt  15780
ctttcaatgt atagactagg catcatgtat ttataggaaa acaagggaga ccgggcacag  15840
tggcccatgc ctctaatccc aacactttgg gaggccaagg caggagattg cttgagcccg  15900
ggagttcacg atccgcctgg gcaacatagt gagaccctat ctctttaaaa caaacaaaca  15960
agggctaaat aattttgtca agtttttatt aaggaaaaat ttaaacatat aaaattgcat  16020
gtaaaataac acaataagcc ctaaagtccc atgtacatat cacccagctt aacaattgag  16080
gataaataat ttaatgcttt atgactatta cataaaatga tactttatat ccatcactga  16140
taactttctt tttttcaga cggcatcttg ctctgtcacc caggctggag agcagtggca  16200
caatctcggc tcactgcaac ctccgcctcc tgagttcaag caattatcct gcctcagtct  16260
ctcaagtagc tgagactaca ggcacatgcc gccatgccca gctaattttt tttattttag  16320
tagagacggg tttccactgt gttgcccagg ctggtcgcga actcctgagc tcaggcaatc  16380
ctcccgcctt ggcctcccaa agtgctggga ttacaggcgt gagccaccct gcccagacca  16440
tcactgataa ctttcttttg tggaggtgat cactgttcaa tcgccattcc atctcttgca  16500
tcctgagata ataacaaaga tgtaattggt tttttgccaa attaagtatc accatttaga  16560
ctccttcagc agatagaaag agaaagattt tcagaatttt ataaagtcaa aaccagaaag  16620
ccatagcaga aagagcaata ctggaagtca aaagctctgt ttgggtcaaa ctgtgtctaa  16680
atttctcatc catgacgagt ggggtctgaa acggaatatc ctctaagggc tttccaactc  16740
caacaataca tgagttttga aagaatccta catgtttact gagtggcatt tgaaccacac  16800
actcaaggta tgagttctgc tttgggtctg cacttggatc ctgctttagg tcaagaatga  16860
ctctctcaga gaggatgctg tggtgtgccc ctcagatacc cacttccaac ccctttcggg  16920
actgggtcac ttatttcctc attcgctcag agtgttgaca actcacagct ggtagctgag  16980
gccctctctg gagattgccc tcagctgttg aacacaacta gtaaagacag ggtgtataaa  17040
tatctagccc ccttgcccca gtgtgggatg gctatgagcc atctcagctc cacaggacca  17100
gtgggattgg ttcaggcttt tgatgtgact acatcacagc ttaacttctc ctgttgcccc  17160
atcatgctcc cttcccttcc cctgggagtt aattttaaaa gcactccccg ataaacctct  17220
tttttgttgt tgttgttgtt gttgtttttt ttttgagaca gaatttcgct cttgatgccc  17280
aggctggagt gtaatggcat gatctcagct cactgcaacc tccgcctccc agattcaagc  17340
aattcttctg cctcagcctc ccaagctggg attacaggca tgtgtcacca tgcacctctt  17400
gcacccggtc tccttctcag agtctgatgc ccaggaaatc tgatctgtgg cagtgtgggg  17460
attcatccaa gaatgaagac tgtttgtaaa ttgagatttg agggtggaat catccactgg  17520
ccagccagct gtgaggacca gccgctggtg gttgggggtg cacaaatggc ctcaggcccg  17580
ctgtactgct gcaactatta aaactccacc atggtgtaca tggaaggatg gctggtagaa  17640
taggacttac tggcaagtag tgtatcaggc atttgagaga tacagggcaa tagtcattat  17700
aaagacaata gaactagata gttgttgtta ggaaataatc tattctttgg ggcaagaccg  17760
taaaaggctg agggtaatta atcacctctt acaggctaag tcagaattcc agaggacatc  17820
ctcagaagca taaaaagata ccctcatctc ctatcattgg agtgcagaaa aacctgagga  17880
```

-continued atgaatttag gatttaatta tggaagcaca gagtttcaga gaaggttgag ttctgagttc 17940
cacagaccag ctctgccaag gtcagagccc taattatgaa ggaatggaac tgcaatacat 18000
gggatgtgga caactgatgt aggatttttt cttcttggtc actttgcaag cctgggacct 18060
ccagccagtg atgtccgccc agggcttgct tggctatgct ggtgtgcctc agcttgtctg 18120
tgttatagct tgtacccaca tttggtgatt ctcaagctct tgtaccacac ccaagaagat 18180
tgaggatatg ctgcacattg aagggtgagg agggcagaga agaattttac tgagcgaccg 18240
aacagctctc agtggagagg ggacacaggg gatggtccct cacccccaca gtcaggtggt 18300
tctctcctcc ttgcgtaggt gggtctgggg atttttatgg actcagaatg gggaggggca 18360
ggccataggt agtattggaa aaggcaacac tcaattggtt aaaaagtatt attcagaaag 18420
aatcaatagg gaaagggtga gcaaacagga acagaagttc tcattctggg tcaccggttt 18480
catctgggac cagcaatcta gtttttcagc cttcaagctg tttttgactt gaaggtgggg 18540
tttcaccagg gacccacccc tatctgcctc agcatttggc tgactcctat cgctatcaaa 18600
actgtgttaa tgtattagaa actcttgaat ccccagattc tcctgtatcc tctgggtctg 18660
cagaagcaac ccactccttc ctgttaaaag atggtactct gatgtgcacc accaccccca 18720
aggaacaccc cttggtttaa gccaatgcaa agtcctttgc cttgcgagac agcatgcaca 18780
ctcctcaagg atatgttctc aactcccctc ctgaccaata atcagaaata tgtcacaacg 18840
taacccaact gtgctgggcc tgctaagaga ggaaagggat tacagccagc aggagccacc 18900
ggacatatat gcatatgcat acattccaat atgcgctggc aggagctggg agaatacata 18960
aatgactaga ttctaagggt actggatcaa ggggcatggg acataaagtt ggttagggga 19020
cagtttatca atatggcagc actcttctgc aatacagatt taatacccta tttaaggagg 19080
tgaagctaac atatttctag gatggccctt agaagcttgg acaaagtgaa gtagaagtgc 19140
cagaattgct gtggcagatg gtggaagagg gatagaaacc ttgagcagta ggcctactac 19200
agtggatata attagcaaaa ctgggaaact cactctatga ctatgtttgg tgggaagccc 19260
tggaggacac actgttgata aaatcaataa gaaatgcact gacaagaagg caccagaatc 19320
tctgagaagc ttagtggttg gtgatagtct tctgcaaggt gggagatcct gttgcagaac 19380
tgggctctct gatagtagaa ggaaatgaca gaattccaaa ataatagagt caggtgacac 19440
ttaaatacca gaagaaaagt gggtgcaatt attgtcatga aaagcaaagc tgaagtggaa 19500
gcccaggagg cctgacctga gagctattga agcagcaact agaacgtgat gtccctggag 19560
gtaagacaaa cagacagtca acagggtctt gcccaatcta tacaagcaaa agaaatcaag 19620
agtagatgat taggagacta aaagtagcca ccacagtaaa aacttaaaat ctcttttta 19680 gtttccagac ctgagccagt tttctgacct agcacccatt gattgaagga gaatctaaat 19740
ccctgggaag gccttataaa accatagcaa gtataaatgg caatgattcc cctagtcttc 19800
cccccaaaat actaagaact atttacttag gtaattatgt actgggaaag cgtggtaccc 19860
atatagtttg aggacacaga gcccaagtta atattggtac ctggaaacct aagacattag 19920
gagagccatc tattagagga ggggtgaatg ggcaccaggt aataaatggt cgaggcctag 19980
gtcgagctca cacttggtcc cctggggtcc acagactcac ccagtgatca tggtcctaat 20040
ccccaaatgt gtaatttgaa atggacatac ttgagggttg gcagaaacct tacattggtt 20100
cattggcctg cagaatgaga agtatcacag tagagaaggc tcagtgcaaa ccttgaacta 20160
tccctctagc ccatgcaaga taaggcagaa caggaacccc ttttaggagc ctgtaccctt 20220
cttcccctga gcatgaaaat aaaggaaaat cttccttcaa aggaaatttg aggcaactag 20280

-continued

```
ctagcctaaa taagggaaca acttaataag caagaaggta atagtaactt aaaacaatag  20340
ccaaggaagt tagagtcagc agataatttg tttcctatag aaactaaagg taacatccta  20400
acatatgtca ctgagttgtt tttcaaaaac ccggatcccc accaaatgga tccattggca  20460
cttaggccca gataaggagg aaatgaggac tgaaccctga ccgctgttct ttgttctaaa  20520
tttcttccta aggggcctgg aggaggtcac acccacgagc cagagctgac gttctttttt  20580
agagacaaaa ctttgcctcc ttaaccaatt gcaaatgaga aaatctttga gtctgccacc  20640
aacctatggg ctcctgcttt gagatagccc acttttttag gtcaaaccaa tgtatagcct  20700
ccgtgttttg ctttatgact ttgcctgtaa cctctgcctc ttcaccttta gaaactgtta  20760
cccgtaagtc atctgggagt tccggtctta agcatgagct gcccgattct tcttgcttgg  20820
tgccctgcaa taaatgcctc actttctctt gatgctatgc caatgtcagc atgtggcttt  20880
gctgccccag gcaagtggac cccagttcag tttgataaca aagataagta aatcaaaacc  20940
aatatcatat cctgggggaa aacagcagct gaaaacatct gcctcctccg tggtcatgtt  21000
cccacatcca gtggcaggcc aatccttgag gatcaggaca attctgaaag gccatccttc  21060
atctggagtc ttccatgaga ttgactgaga ccactggtgc gaccgtgtca caccccaatt  21120
ccccttctgc ccagtctggc tttctccacc cccgacaggt gttgattccc aagagtctct  21180
cccaataacc ttattgcatg tgaatatata ttttagaatc tgcttcctgg gaaatctgac  21240
aggacagaat gaatccacaa cattcactac cagaagatgc tctgcctttg aactggcctg  21300
cccatgggct tttccctgga ccttgggagc acctctaatc aaaagttaat acccagagcc  21360
tcagaggttt cactgaaaca ctgcccagga aggagtcact gaaaatccta tgaggaaggg  21420
aagtggggga acctgggagg aaggaaacta cacaatctga aagatgtata aatacaaagt  21480
ttccataagt ttggggcttg aatcatatac ctgagagaga gagatttcta ggaatgaaaa  21540
gaagcaagcc acagcctttc atcaactacc taagccaagc agtgggcaga tctaccagct  21600
ggccaggcag gggtgctga atggctgtca gtcttgtgga caggacgtcc caactattct  21660
gacctgtcac cgctattttg ggcacagaag ggaggaccgt ggggtcgtca gcctcaaggc  21720
atttagtctt ctattccttt tctcttcctt tccagttctt tgaaatgaga atcagggttt  21780
atgtccagtc ccagagtgac accttagaca ccttaattac accactttgt tctctctctc  21840
tctctctttc tttttttttt ttttttgaga tggaattttg ctcttgttgc ccaggctgga  21900
gtgcaatggt gcaatctcgg ctcaccgcaa cctccccctc ctgggttaaa gtcattctcc  21960
tgccttagcc tcctgagtag ctgagattac atgcatgtgc caccacaccc tgctaatttt  22020
tgtattttta gtagagacag ggtttctcca ttttggtcag gctggtctcg aactcccagc  22080
ctcaggtgat ccacctgccc aaagtgctgg gattacaggc gtgagactac aacatggtcc  22140
agccctgatg cctccctttt cctccacccc catctaagtt gagaagattc ttagctgtaa  22200
aactgtcatg agctgactgg agaggtctat attttgagct ttaaatgcac ctggaaagca  22260
tatttttgct ctgaaagtgc ccagacatgg aagaattaaa acaattttta atttccactt  22320
tctacaggac tcagaggaag aaaaccccac ctgagaggca tttttttttt ctctttctcg  22380
gtgtctcagt ttcctagggc tgctgtaaca aagcaccaca aactgggtac ttaacagaaa  22440
tgtctcattc cacagtgctg gaggctagat gtctgcagtc aagctgtggg cagggccaac  22500
ctgcctcgga aagctgtggg gatcctttct agcctcactg ctagcttctg ctgatttgct  22560
ggcaatctgt gatgatttga tttttggctt gcatctgtgt gactccactc taccctcatt  22620
```

-continued

```
gtcacatggt gagggagaac aaggaggcca tgttctcatg gccatcttaa aggacatcag  22680
acagattagg ggcccactct agtccagcat gacctcatct taactaattg catctgcaag  22740
agccctattt ccaaatgagg tcacattctg aggtactgga ggttagaact ttagaatatg  22800
aatttggaga gcacacaatt caacccataa tactcagtgg ggattgcatt gccacccttt  22860
ctctgaaccc ctggtaaaaa gaaaagaaag aaattgtgct tgggatgaaa tgaagggtca  22920
gaatgattgg aaatctcaag ctctttcagg cactcctggg tggtagttga ttgggagtca  22980
gtgaaaaaga agagctcagc tgggcgcggt ggctcacacc tgtaatccca gcactttggg  23040
aggccgaggt gggtagatca cctggggtca ggagttcaag accagcctgg gcagtgtggt  23100
gaaaccctgt ctctactaaa aatacaaaaa ttagctgggc gtggtagcgc gtgcctgtaa  23160
tcccagctac tcgggaggct gaggtaggag aattgcttga gcccaggaga cagaggttgc  23220
agtgagctga gtttgcacca ctgcactcca gcctgggtga cagagcgaga ctccatctca  23280
aaaaaaaaaa aagaagagct caaatatgtt attaaataca aattagccag tagagttgtt  23340
ggatgattac aagacatctg ataaaaaatc acattttcag aagacattat tctctaagta  23400
agtaccaaac gctggcaccg tatctgggct tgtggaaata acgtatttga tttcaatgct  23460
ggtctaatcc agaagaatgt aacctgctta acgttcacta gaatttttat ctgtgctctt  23520
cctttgacat ccatttttgt cacagaatgt tatccagggc acactggcct agaagtaaat  23580
gtagtatagt atactaacat ttatcaagtg ctgattttgc accaggtact tttctaagaa  23640
ctttatctgt gtatttaatc ctcacaacaa ttctattatt gccatttggt aaattaggag  23700
attgaggtac agagagatta cacagttagg aagtggcagc atgaacaaca aaagaaaaaa  23760
ttagataaac tggacttcct caaagttaaa aacttttgtg catcaaagga cattatcaag  23820
aaagtgaaaa ggagacgtgt agaatggaag aaaatatttg caaatcatat acctgataag  23880
ggtctaatat ccagaatata taaagaactc ttgtagccta gcctaacatg aagaggacta  23940
cccaatttta aaaatgggca aaggacctga atagacattt tcccaaagat acacaaatag  24000
ccatcaagca cctgaaaagg cactcaacat cattagtcat tagggaaatg caaagcaaaa  24060
cctcaaccag ctaccactta acacccacta ggatggcaat aatcaaaaaa atagtcaatt  24120
acaagtgctg gcgaggatgt ggagaaattg gaaccgttgt tcgtggctga tggaaacata  24180
aaatggtgaa tccactgtac aaaagagttt ggtagtacct caaagagtta aacatagaac  24240
tttcatttga cccagcaatt ccagtcctag gtgtatactc aaaagaattg aatacaggta  24300
ctgaaatcct tgtacatgaa tgttcacagt agcactattc agaatagcca aaaggtggaa  24360
acaacccaaa tctgcatcac tggatgagtg gatgaacaaa tggtgattat atatatatct  24420
atatatatct atatatctat atctatctat ccatatatct atatatatct atatagatat  24480
acaatggaat attattcagt gataaaaagg aatgaagtac tgacacatgc tgtgacatag  24540
ataaatcaca aaaactttat gctcaatgaa agaagcccat cacagaacag cacatatata  24600
ttgtatggtt tcatttatat gaagtattta gaataggaaa atccatggaa acagaaagca  24660
ggtgagtggt ctcctgggga tgaaagtaaa gggaatgggc acaaccgctt aatgggtaca  24720
gggttttatt tggcagtgat taaaaggtct tgggattaga tagatgtgat tgtacaactg  24780
aattgttctg ttttaaatga tttatgttat gtgaatttca cctccattga gaaaaaactt  24840
tattctacaa gcaatgggac atagtaaaaa ggtttaaaag caggagaatg ccccaagttc  24900
ttgtatttgt aaagtcattt agctcctttg tggagaatgg actcttggca agggtggaaa  24960
gactagggac aaggaggcac tcaggaggct actacaacca tccaagtgag aaaagggtgc  25020
```

-continued caagaagggg atagggagaa ggcatgggag gaagaatcaa cacggttaag ggttagatga 25080
aggaggagtc aaagatgtct caggttttca ggtgacaaac cagcagtgta cccttttatt 25140
cagttaaaaa atacaagaat aagattgggt gggaagttca tttttagact taaggttgag 25200
agtcctgtga cacattcaag tggagctgct aattaggaag ctggaaatac agagtcaaga 25260
gctgttatcc ttctgatggc taatgaagcc acaggagagg atgagagtgc ttagggaaag 25320
agtgtagaat aagaaggaaa gacggcttac aacagagcct caaggagctg caaattttat 25380
ggctaagtag aaaatgagga ggaggcagag gagattaaga tgtgccaaaa aatagcagaa 25440
gaacaggaga agaaaatcag gggtcaaag gaagagaatg ttttgagaag aatgaagttg 25500
gcagttatgt tgaatgcttc tgagaagtga agtgtccact ggcgttagta acatgggagt 25560
aattgtcacc tttgtatgga aggatgggga ggaaagccag agtcattaag tcaaagagtg 25620
ggaactgtta tttcttcacc ctcttgactt ccaggtcact gcagggttgt cttagattct 25680
gtcctctgac ttctcactgc tcattcctca ttcttcattt ttcctctgtg atgcacaatt 25740
ttttgctcct tagttcagct aaaatccagg tccttatctc atgaccgaga aaaattaggc 25800
atgcagacac attgaaaagt gaggagggtg gaaaggaaaa ctctcaacaa gaggggtcct 25860
gcactcaggt tttccacctc aaaaattgaa taccaggcca ccacgcacga gttgaagaga 25920
cccggctccc gcctgcataa ggcacgaatt cctggtggct ccaccccatt ctttcagtgc 25980
gcatacaggc tcttagtctg agccactcca cgttgattta gtttccttac tgcgcgtgtg 26040
ttaagggatg aaattttcca ctgtgggcat gttttttttt ttttttttatt ctattttatt 26100
tttttgagac agagtcttac tctgccaccc gggctggagt gcaatggcac gatctcggct 26160
cactgcaacc tccacctcca gattcaagca attctcctgc ctcagcctcc tgaatagctg 26220
ggattacagg tgcacaccac cacgactggc taagtttttg tattttagta gagacagggt 26280
ttcaccatgt tgcccaggct ggtctcaaac tcctgaactc aggcaatcca cctgcctcgg 26340
cctcccaaag tgctagaatt acaggtgtga gccactgcac ctggcccact gtgggcatgt 26400
taggcaagcc ccctgtgcac aatgacctgg atggcatttg gctgtctcct gcctctatca 26460
ttccccacct aaagaagtac atctaactgc tattagaata aggataaata taaggatgaa 26520
gactaatctt aactgcttcc tgctgacagg atatgctgtt ttgggaaaat ggtagtcaga 26580
tctcccttgg agacctatct aagggtcctg gtaaaagggg ccatcatccg agtctccagt 26640
tgcatgacca cttggagttt aatggcctga aggtgagaag agataaacca ggttattaga 26700
agacatgtat caaaacaaaa caagagggca aggatggctc aaaaatcctg aggctgctga 26760
catgcccaga taactggtgg ctacagttat gcttgctaag atttggatgc acagggcttg 26820
gctttggtta gctcccttgc tcttattttc tcaaaaaagg aaaccttcgg gtgatgggca 26880
ccctatttac tcttatcaac tggaaggatt tgtaggatag ttgcccagaa ctagaatatt 26940
gatccaagca cttatccttc tttaagccaa ttaattagag ctttcttata gacatcacac 27000
acaacacata tataactaaa cagagaaaga agatctgata gctataagat tttttatttg 27060
ccaatctcct aattggatta ttgccctcca ggtggggccc tttaagagca aggctaggaa 27120
agcatgctgt ttccagggcc cgacaaacag gtatagctgg aagacaaaaa caaattttga 27180
gagggaccta tctgttttta attcctgggg ttccatgagg aaaacagagg tttctcccca 27240
aatggaatct gtggcacctt ttctgttttt cccaaggagt cctaggccat cagaaattat 27300
cttagggtct ctcatgcatg cattaagagt ggcaacgcaa aatggagaaa agtaattcag 27360

-continued ttgacttttt ctagcaaaac aagatccaag aagagaaaaa cataaagtcc ttttaaatac 27420
acctataact tggatatcca cttttaatta agctgagtgc tctttaagaa agtcctggct 27480
gggcatggtg gctcaaacct gtaatcccag cactttggga ggtgaaggca ggtggatcac 27540
ttgaggtcag gaactcaaga ccagcctggc caacatggtg aaagcctgtc tctactaaaa 27600
atataaaaat taggctgggc atggtggctc acacctgtaa tcccagcact ttgggaggcc 27660
aagatggctg gatcacctga ggtcaggagt tcaaggccag tttgactaat atggtgaaac 27720
cttgtctcta ctaaaaatac aaaaattagc tggacgtggt ggcatgcacc tgtagtccca 27780
gctactcggg aggctgaggc aggagaattg ctcgaacctg ggaggtggag gttgcagtga 27840
gctgagatcg caccactgta ctccagcctg ggccacagag tgagactcca tctcaaaaaa 27900
taaataaaat aaataaatat atatacaaaa attagtcagg tgtgatggtg cgtgcctgta 27960
gtcccagcta ctcaggaggc tgagacagga gacttgcttg aacctgggag gcggaggttg 28020
cagtgagctg agattgggcc actgcactcc agcctgggtg accagggctg acattcctga 28080
cccctgagag tgtcagggtt gggggatagg gtgcagtttc ctctccctta agtctgagga 28140
caagaaggct cagaaacaaa agggaaagag atttttgagt ctgcatttta ctcacccttt 28200
ttcaggtccc catacaggca ccaaaataat gcaggatatt ttgctcctta gttcagctaa 28260
aatccagcta aaatcttgtc tcacaaccaa gaaaaattag gcctgtggac tcattgaaaa 28320
gtgaggaggt tgtaatttat taagtgaaaa gaaaaactgt caacaaaaag aggggtcctg 28380
cacacaggtt ttccacctca caaaattgaa taccaggcca ccacacacga gctgaagagg 28440
ccccctcctg ccctccataa ggtgtgaatt cctggtgcct ccaccccatt cttccagtgc 28500
acatgtgggc ccttactctg agccactcca cattgattta tttcccttac tgtgcatgtg 28560
ttaaggaacg gaatttccta ctgtaggcat gtttaggcaa gctccctgtg cacaatgacc 28620
tggacagcat ttggctgtct cctgcctcta tcacctggat ggctttctct atgtctctcc 28680
ctcttcttaa caggtaacag accctcctcc cagattgtgc atagaagttt gaggcaaatt 28740
tgtctctggt gcaagggcat ggtggcctag gaagcacatt caatattatt ttccactttc 28800
tagtactagg gcaagggcca ccattcacac aaagccctag taatcaatgg tgtgctagta 28860
agtgtttaac agccagctct ccaggtagaa aaaaaagggc cctaattttc agcatttgcc 28920
aatatctgtg gtgtaaatgc tgtcaacatg gccaatttca agccactgta aggtaactga 28980
acttggagat aggaagctac atgtggaatc ggctacttag agctggtaca tgctggctcc 29040
agcacacggc tgcctctgca cctaccttca aacttctgtc tggaaaccac ttgtactttt 29100
ttcttcaaat ctacttcctc cagaatgtat caacagattt ggcttaagaa gcatacttga 29160
cacataggag ctattaaatt gtatttgttg aaagactgaa ggaatgtatg aaatcgtttc 29220
atgctctacc aactgtgtgt atatagcatg agccgaatgg tactcattga agaaaatata 29280
gtttatttga aagacaccct ggacatagaa agtgccctga acttgaagtc agaaaactta 29340
ggtttaagac ctagctctgt cacacattat gaatctcact tagggtatgt ctgttaatgg 29400
ctctggactt tatttggatt gtctgtaaaa tgaggctact aggaatctgc cagaggctgc 29460
tggcaagatg gccgaatgga acagctccgg tctgcagctc ccagcaagac cagcacagaa 29520
ggcgggtgat ttctgcattt ccaactgagg taccctgttc atctcactgg gactggttag 29580
gcagtgggtg cagcccacgg agggtgagca gaagcagggt ggggtgtcac ctcacccaag 29640
aagtgcaagg agtgggagag cctcttcttc ccagccaagg gaagccataa gggactgtgc 29700
tatctggccc agatactatg cttctcccac agtttttgca acccacagac caggagattc 29760

-continued

```
cctcaggtgc ctacaccacc agggccctgg gtttcaagga caaaactggg tggctgtttg  29820
ggcagacact gagctagctg caggagtttt tcttttcata ccccagtggc gcctggaacc  29880
ccagtgagac agaaccattc actcccctgg aaaaggggct gaaaccgggg atccaagtgg  29940
tctcgctcag cagttcccac tcccacgcag tccagcaagc taagaactac tggcttgaaa  30000
ttctcgctgt cagcacagca gtctgaagcc aatctgggat gattgagctt ggtgggggga  30060
aggcatcagc cattactgag gcttgagtag gcggttttcc cctgaccgtg ctaaaaaagc  30120
ctggaggttt ggaacgggca gaactcaaca cagagcggca aattggctgt ggccagactg  30180
cctccctaga ttcctcttgc ctgggcaggg catctctgaa aaaaaggcag cagccctagt  30240
caggggctta tagataaaac tcccatctca ctgggacaga gcatctggag gaaggggcgg  30300
ctgtgggcgt agcttcagca gatttaaatg tttctgcctg ccagctctga aaagagcagc  30360
ggatcctgac aaagagggtt ctaccagcgc agtagagctt gagctctgct aagaggcagg  30420
ctgccacctc aagagggtcc ctgatccccg tgactcctga ctgggagaga catcccaaca  30480
ggggttgaca gacaccttat acaggagagc tccagcaggc atcaggccag tggccctctg  30540
ggacaaagat tccagaggaa gtagcaggca gcaatcagag ggtgcagaga aataggaaca  30600
cttttacact gttggtggga gtgtaaatta gttcaaccat tgtggaagac agcatggtga  30660
ttcctcaagg atatagaacc agaaatacca tttgacccag caatcccatg actggggtat  30720
atacccaaag gactataaat cattctgttg taaagacacg tgcaaacgta tgtttattgc  30780
agcacttttt acgatagcaa agacttggaa ccaacccaaa tgcccatcaa tgatagactg  30840
tataaagaaa atgtggcaca tatacaccat ggaatactat gcagccataa aaaagaatga  30900
gttcatgttc tttgccggga catcgatgaa gctggaaacc atcatcctca gcaaactaac  30960
acaggaacag aaaaccaaac actgcatgtt cttcctcata agtgagagct aaacaatggg  31020
aacacatgga cacagggagg ggaacaacac acactggggc ctgtcggggg atgggaggca  31080
aggggaggga gagcattagg acaaatacct aatgcatgca gagcttaaaa cctagatgac  31140
gagtgatagg tgcagcaaac caccgtggca catgtacacc tatgtaacaa acctgcacgt  31200
tcagcacatg tatcccagaa cttaaagtaa aatacaaaat aaaaaaaaaa agctacaagg  31260
atctagaacc agaaatacca tttgacccag cattcccatt actgggtata tacccaaaga  31320
attataaatc attctactat aaagacacat gcacacgtat gtttattgca gcacttttta  31380
caacagcaaa gacttggaac caagccaaat gcccatcaat gagggactca ataaagaaaa  31440
tgtggcacat atacatcatg gaatactatg cagctataaa aaagaatgag atcatgtcct  31500
ttgcagggac atagatgaag ccatcattct cagcaaacta acacaggaac agaaaaccaa  31560
acaccgcatg ttatcactca aagtgggagt tgaacagtga gaacatatgg acatagagag  31620
gggaacatca cacactgggt cctgtggggg gatgggggc aaggtgaggg agggcattag  31680
gacgaataca taatgcacgc agggcttaaa acctagataa cgggttgatg ggtgcagcaa  31740
accatcatgg cacatgtata cctatgtaac aaacctgcat gttttgtaca tgtatcctgg  31800
aacttaaagt aaaataaaca attaaaacca aaacaaacaa ataaaaaaga atgtgcctga  31860
cataacagga gtgttgtggg gatcacatga aattacactg agtaaaaatt ctatggtgct  31920
gttttattgg gatcactgga attggattgg aatttcaaaa ctggaagttc caattcagca  31980
aaattggaaa ttcaaaaaag ctatgaacct gtttgtaaga atattcatca aaaagtaaag  32040
ttcataaatg taagtataaa ttcagcgtag tgagcacagg cactgggtca gatggaggtg  32100
```

-continued gatttgaaaa tagtctccac catgtatttg ctctgtggcc tgagaaaatc acatcaataa 32160
catggagata ataatacctg tttcagaggg tgattgcaag aattacaatt agatagtata 32220
tcaaagtagg ctaggctata ctatggtaac gaatagtcct taaatctcag tgacttcaaa 32280
taacaggttt attgtttatt tcccactcat aatacgtgtt tactgtggtc cctgcagacc 32340
agctttggtg ggagagggat ctactctaca ctgatccaag atacaagtgg acagagcacc 32400
cacaatctgg aacacagcaa cctagggtaa gggaaagagc cttctggagg gtctgaatgg 32460
aagtgataca tgtcatttcc atttagatct cagtggccag aactagtcat atggccccac 32520
taaccctaag ttggcccccc ttgtgcccag aaggcagaga gccagaaata ttgggtggac 32580

<210> SEQ ID NO 17
<211> LENGTH: 34200
<212> TYPE: DNA
<213> ORGANISM: Homo sapiens

<400> SEQUENCE: 17
agtataatgc ctaccacaga tagcacacat gattaccttt ggcacaaaat gcccactcag 60
atgttcctcc cacacacaca aacacaaatg ttatacacac acacacacac acacacacac 120
acacacacac accctttttt tttttttttt gaaacagtct catactgtca cccaggctgg 180
agagcagtgg catgctcaca gctccctgca gccttgatct tctgggctca agtgatcctc 240
ccacctcagt ctccctagta actgggacta caggtgtgtg ccaccatgtc cagctaattt 300
tttttttttt tgtatttgtt gtagagatgg ggtttctcct tgttgcccag gctggtctca 360
aactcccggg ctcaagtgac ccacctacct tggcctccca aagtgctggg attacaggcg 420
tgagccactg tccccaggct ttcctccctt tctatggagg aataagatga atttaagcag 480
tatgcttgaa atttatttga tcagcatata ctgagtaact acttaaagtt tccctttgaa 540
attttgtaaa tgtgaaagag ggagttttaa aatgggccct agaatttatt taaaagaaga 600
aatatatttc atttaacaaa atgctcagaa agccatttta ttgtggaaaa atactgccat 660
gcctcgttgg ctgtgctaag agaagacatt gagcaaaatt attgtacata ttaaagggaa 720
aagaatttca agtttcttaa ggcagcctgg gaagctttct agaatagaga ctgaaacatt 780
caattttaaa taatctgccg tggtacatgg caatgtaacg cctcccctaa atcttcaaca 840
aaaacctgct atgctttggg tgagcagtgt ttgttgcagg gaaattaagg caaagtagtg 900
tttgttgggt taattcagga caagaagcag agaaagcttc cagcaagata aaaaatcttg 960
cagaaaacta ttgtgaacag catatacccc tgggaatcct cagttattct gtggggaaat 1020
gctgagtttc caagcccagc atatgaaata tttccattta aatgttaaag gaaaaagtga 1080
cacaactaaa ctaaaggaaa cggggctctc taggctgcta agttttaaat aactagtata 1140
gccctccgat atttgtgggt tactttgtag ttggttagca tttaaaaaat catagttgaa 1200
actgatttct ttgagaaatg ctagcctctt attaagcaag ttcagtatat aaagtattga 1260
aatgagttcc ctgcagagac gttgctatta taatacagca agtcaggcat ccatttccct 1320
gtgcggctga gacaggagct gctccagcct ttcttcccga gcatccctct gttctcctga 1380
tgaagtcact ccgtaaccca cagccctcca gggcagctaa gccagcaata agaaaggagg 1440
ttaatttacc tctacctgcc tcctcccaaa gagaaaatca catttttgaa atccacatga 1500
aacttagggt cataataagc ttatgtgtga agaatgtagg tggtttgcgt tgtttgtaga 1560
acaaaactag gctctgcgaa gaggttgcag tgaaataaac attttatgga gcccttcctg 1620
cagtgttttt ttttttgttt gctttttgga ggtggggcct actaaaaatt tctgtaacat 1680

-continued

```
gtctgctttt aaaaacattt gcccatcttt acccatgaag tattgagagc gcttattgag   1740
ggttaaagtg cttattagtg ggagttgacc tcatggctgc atggccagag aagccctgca   1800
gtgggaaggg gctgcccttg tcttcctgtc agatcttgaa ggcctggcca gagcatgtta   1860
ccctctttag gcatttttct ttttactttc aataaggggt caggctttta aaaacattct   1920
atgtcatcct taaggaaaaa ataaaaacaa attattgtga atggccaaga aagtctatca   1980
ggaaggaaat aaagtggaga gaaaaacaac cacaggctct ttcaccaact cttggagaag   2040
caggaaacat ggcaacatca gggcgaattt ttactcatcc ttgacctctg tctggagagg   2100
ggcagtgact ctacctccca cccaggacag gatgctgtgg tcgtgaggag ggcacctctg   2160
ggcacagcac ctacctgggg ctatgcattc cttctgaccc agcctctctg gcacctggga   2220
gtgacttgtg gaaaacagga tgtctgttag tctactcact aaatgctaga tcttgagcaa   2280
ggtctgtaac ccccaggggc ttcagtttcc tcagctgtaa gatggggctg agaaaaagag   2340
ctcgtaatcc cttacccaag acccttgggc caaacgtgtc tcagaattca ggattttcag   2400
atctgagaaa ggtaagaagc tgcccagaag tatctatttt atgtactaca cagaaaagaa   2460
aagaatttca catttcttga ggcagcctgg gaaacttcct agaatagaga aagtggtgtc   2520
tggagcagta cctgcaatcg aatacactga gagacaccga aggaccaaga agtttccact   2580
gaggctgtgg catgtcctcg tcctccacag ctgttcttcc acccactcta acacgtgacc   2640
ttagccccta actgctcctc ctcatccctc ttaatgaaat ccaaattgcc tgaacaatgg   2700
tggctgatgt gcaagaattc ctctctcttc taaaatccat ccctcaccta ctattcctga   2760
acttcctgaa ttaaggctga cccccctgct aaggccctat aacagcaata aaaacaacaa   2820
caacaaacaa caaacccaaa aaccctccct cctcccccaa ggtatttgag aacactcctt   2880
tcagggactg cttctgcctg gcagtctgga ttaaagtcta cggtcatggt gttccggttg   2940
cttttcctcc acaacattca tagttctgca gtgaaacata ggaacacctg cggagcacag   3000
gatggataaa aaacatgaag agtctcaccg agggaaggtg tgctggcaaa tgactgtttt   3060
cagagctttt tgaattttgg aaatgaggat gtgaaattga ggacctgtgg tattatgtcg   3120
tagagttgat gtgaaaatga agtgagatag tacatgaaag tatttggaat agtactgggc   3180
acacagagct tgataaatat ttgccatggt gattatgctg agagttttat gtaaccaagg   3240
agctgtcaca ttggggttca gactcacagg tgcacagagg gaccacagct taggacaaca   3300
ccatgggaga gggtatcctc tcatccctgc accctgaaaa actttgcaat ggcaagtttc   3360
cagccatacc tgcatctggc tctaggctgc ctgtttctgg aagagatcct gtgcatcctc   3420
aacagctcca catacaggct ctgaatgcag cctctctgca gaagactcca gtttcccagt   3480
tatcaaatga tttatttttg tacaaggcaa tcgtaactga ccccatggct tgaagagcag   3540
cccagaattc ttgggcttct tactggggca catagataga aagaatatat tcttttgata   3600
gaagtaaaag aatgtagagt gatatcatct taaattgtac ttcaagttat agaaactatg   3660
gaaggaaaca tagctaaaaa catttaaaac aagcttgtgc aacctgtggc ctgtgggctg   3720
catgcagccc aacacaaatt cgtaaacttt cttaaaacat tatgagaatt ttttgcgatt   3780
ttttttttta gctcatcagc tatcattagt attagtgtat tttacaagcg gcccaagaca   3840
atttttcttc caatgcagcc tagggaagcc aaaaaagtgg acaccccgat ttaaaacatg   3900
gctcataatt taatcatcca catattaatt catttaacaa tcagtgcctg tgcacctgtg   3960
tggcccaggc actgttctat gcccagggga ttccgagctg aacaaaacag acaagtttct   4020
```

-continued

```
cctcccatgg agtttccatc ctagtgaaga cggtggacaa ataactaagt aatataatga   4080
ttaatcgtgg tgggtgctag gaaaaaaaca aaactgggta atggagctgg gagtgtctgg   4140
aagtgggtat tttggatggg gtaagtcagg gaaggtctct atgaaattat cttcaacagt   4200
tgagaagggg tttggaaaga agctggctca tgaagagctc agagaagaaa gttcttagca   4260
gaaagaggaa caagtgtaaa gcccctgagg cagaagggat tggagatgtt tggggagcag   4320
ccaggagagg catgtggctg gagctgggga ctgagaacag gaggtgtggt tggagaggta   4380
tgcagaggcc cgctctacca ggtcagaccc tgcaggccat gccaagcagt gtagctagta   4440
agtgtaagga gtagccactg gagggtttaa gcaaagacat gatgcaatct cgtttatcat   4500
tgcttgagga gcaggagaat tgttttctat agtgccttct ggtcttttat ttttcacaca   4560
cccttcatgg aatttgctag gcatagcttt taaagggctc tgaattcatt cttgtgactg   4620
tatctggtat tctagtggtc atctaggtca ctaacagtgc cttgggtcac cacctccaaa   4680
attaagccat ccccacatgt aaaaacctgt gactatcagt cttaatgcat atgatgttgt   4740
gtgacttttt ctactgtaca aaaaacccct tccattaaat ataaatgcac attaaatatt   4800
tagcaaacac ttgtttaagg aatgatgcat gtggaacaag aagtaaatgg cataagctcc   4860
caatatacaa gccacatatt atcgtgacaa ttcaacctta cctgtcatta ttaagctttc   4920
attttccttc ttgcttttag gaaaaacagc cccagcattc cctatctcct gacgcctccc   4980
tgcatcacac atccacattt taggtagaag gagactttca cacccagctc aagactctcg   5040
gaggttgtag acaagcaaca aggagaatgt aagggccagc cagtctggat tcagtccagc   5100
agctgcccag ttgagacctg gaccaaagcc aacttctcac tcacctccag catagtcact   5160
atctatctag ctgatgattt ctccttcctt tcaatgaaag ctttaagtgg cttctgtttg   5220
cctgggagac aaagtgagtc acattcacag tagctcttta tattgatgac ccttgtctcc   5280
actcatgatg gtggggcctc tacttctcct ccaagtcgct cctatcacca gaggcgtctc   5340
acttatgagc tcaacctcct ttgcctgctc gggccacctc tgcctgcaca gctgcatcag   5400
ggcccttctt ctgttgtcac agccttcaga tgagccactt tcatggggaa ctgttgcacc   5460
ggatactgca gctctgcact ggcctacaac caccgggcat catcgaaact ggacctccac   5520
tattgccaaa cattactgcc aacatatgca ctttcagttc atgttgttga ggtttttttt   5580
agcccctcct tcccctatcc atcatgttcc acttctagac taaggcatga gaccagggga   5640
ggttataaag ctggactgga ggataaatat aagttgtagg tgttcttcca tcttctttgt   5700
taccccctcc tctctgaata ctggagtagt ataacagcac caatcccata tgcttgcctt   5760
cctcaccccc tggtatcatg tcctgtgtta atctcctctc cttgaatgac ggaatgtcat   5820
tctgagatta tgaaaaaatt gtaagactcc agtggagccc tgagatgact gcggctcctg   5880
tcaacagctt gactgcgact gtcatgacag accttaagcc agaactactt agtcaaccca   5940
cacctcaatt cctgacccaa agaaataatg gaataataca tattcattat ttaagtcact   6000
aagtttaggg ataatttgtt aaggagcaac acaaacatag acacataaaa gtataaaaat   6060
caagtgtaga gctcaatgat tgtttcataa ggtgagcaca cctctgtaag cactgcccag   6120
ctccagaaac gaacattgcc aacagcctcg aagctcccct catgctctct tccagtcatt   6180
atctcccaaa aggaactgtt gttttcatat ttagacctta gaattatttg tctacttttg   6240
aattttatat aagcagaatc atacatgtgt tttgtggctg gcttctcttg ctcaagatca   6300
tctttatgtg attcatccat gttgcttcat gtagcagcac tcattgctga actattccac   6360
tgtgggaata aaccacagtt tattttccat cccactgtca atggacattt gggggctatt   6420
```

-continued

```
acaagtaatg ctgctatgaa cattcttgta cacatctttt ggtcaacata tgtcagtatt   6480
tcaggctggc tatggtggct caggcctgta atcccagcac tttgggaggc caaggtgggt   6540
ggatcacttg agtctaggag ttcaagacca cctgggcaac atggcgaaac cttgtatcta   6600
ccaaaaaata cagaaaatta gccaggaagg atggtgtgca tctgtagtcc cagctacctg   6660
ggaggctgag gtggaagaat cacctgagcc agggaagtcg aggctgcagt gagctgagat   6720
cgtgccactg cgctccagcc tgggcaacca gagtgagacc ctgtctcaaa aacaaacaaa   6780
acaaaacaaa aaatatatac aagtatttca gctgggtata tactggggag tggaatttct   6840
gggccatatg tttaatagac actgctggcc gggcacggtg gctcatacct gtaatcccag   6900
cactttggga agctgaggcg gggggatcat gaggtcagga gattgagacc atcttggcca   6960
acatggtgaa accccatctc tactaaaaat ataaaaaatt agctggatgt ggtggtgtgt   7020
gcctgtaatc ccagctactc gggaggctga ggcaggagaa ttgcttgaac cagggagtcg   7080
gaggttgcag tgagctgaga tcacgccact gcactccagc ctggtgacag agtgagactc   7140
catctcaaaa aaaatagata ctgccaatca gtttccaacc tggctgcagc agttcacatt   7200
tccaccagcg gtatgtgaaa gtccccactg tttcacattc tcaccaacac ttggatttta   7260
gctattccgg tgggtatgta gtcacatcac attgcgattt taatctgcat ctcatgagtc   7320
attatgccat tgccccactt ccgatggacc atatacactc cagaactcct taggaagagg   7380
ggctttgtca ggcctgcact gcaggttcgc ttctctctct gcccaatcct gctgccaccc   7440
tttttttccc ccacagatat tgatccttaa taagtacaga tgctcctcaa cttacgaggg   7500
ggctatgtcc caacaagacc atcgtaagct tgaaatacta taagtcaaaa tgcatttaac   7560
ttaaacttgc ctaccttaaa cgtgctcaga acacttacat tagtctacag tcgggcaaaa   7620
ccatctaaca caaagccaat actataataa aggattgaat atctcatgta atttattgaa   7680
tactgtactg aaagtgaaaa cagaattgtt gtgtgggtga tcaaagtatg gtttctactg   7740
aatgcccatc acttttgcat catcttaaag tcaagcaatc attaagtcga agtattgtta   7800
agtcagggac catctgtgct ctgcaggcca aactctgtca gtgtctgctt ctgaggaatc   7860
caatctgtaa caatttgcct attcctacca tagttcctac agctgcctca attactgtca   7920
tgtacagtgt gttttaacct atgagctttt gtcaatgaac acatatatat ttgtttttca   7980
tgacactgta aggtagcaaa aatcaatcta aatcctataa atggtattgt tatatgtttg   8040
ttaaaattat gctttaaagc tttaagttat actgttacat acacatttct tggagagatt   8100
acagtatgat tgatatttat agggcaattt ccccccttact gcttttcttt tgcaaaaata   8160
tcttagttac ccacatggat tacaattcca aataaattcc aaaatgagtt catcagtttc   8220
ccttaaaaaa ttctgtggag attttggttg gaagtcactg aattaatagg ataacttggg   8280
gagaacagat atcttcataa aattatattt ctttctttct ttctttttct ttctttcttt   8340
ctttctttct ttctttcttt ctttctttct ttcttccttc cttccttcct ttctctttct   8400
ttctcttttt ctgtctttct ttctttcttt ctttctttgt ttctttttct ttctttcttc   8460
ctttcttttt cttttttgtt gagacaaggt ctaactctgt cacctaggct ggagtacagt   8520
ggtacaatct tggctcactg caacctccgc cttctgagct caagggatcc tcccacctca   8580
gcctccccag tagctgatac tacaggcatg caccaccatg cccagctaat ttttttttgt   8640
attttttggt agagacggga tttcaccatt ttgtctaggc tggtcttgaa cccctgagct   8700
caagtgatac acctgccttg gcctcccagt gctgggatta caggcatgag ccatcatgcc   8760
```

-continued

```
tgaattgatc tttctaacat atgaattttc tatggcttcc caaaatcaaa atctcttctt   8820
ggcatgatat atttccccta cccagctgaa catgctcatc tgcctgcatt ggttcttcac   8880
attcttttca acttaaaatg gctttttctg acacatcatg tcttcttgcc tctgtaccta   8940
ctatttcctc tgtgtaaaac tcttcctctc cttctctcta gtcccacctt ctcactgtct   9000
gccacgcttc tatttgttct tcaagtttca actcaagaat tacctctgat atgaaccttc   9060
cctcgagaca ggcctatgct ccttcttccc tggcgccttt gcctgtggat agccctccac   9120
gttgcactaa tgacatcgaa ttatactttg tctctttgct tatttgtgaa ttaattaagc   9180
agaaattttt cttaaaatta aggacaatgt ctattaataa ttttaattct catcacccat   9240
cacagcaccc agggcttgtt tggcactcaa tgcatacttg ttaaatgcat acatctaatg   9300
tacaaatgca taagtagtgg aattatgggc atctggcagg caaagaggac agatattttg   9360
ttacaggcac tctttcattt gtgcttttaa aattactatg atgatgatgt gaaaggctgg   9420
ccttatttta gtgcaaattc taatctaatt attttcttct gactcgcagg taactttctt   9480
ctcctgttta atattgctga tatattgata caccatggaa taatatgtag ccataaaaaa   9540
gaatgagttc acgtcctttg cagcaggaag ccatcattct cagcaaacta acacaggaca   9600
gaaaaccaaa cactgcatgt tatcactcgt aagtaggagt tgaacaatga gaacacatgg   9660
acacagggag gggaacatca cacaccaaag tctgttgcgg gttgggggta aaggggaggg   9720
agagcgtaaa acaaatacct aatgcatgtg gagcttaaaa cctagatggc aggttgatag   9780
gtgcagcaaa ccaccatggc ccatgtatac ctatgtaaca aacctgcaca ttcggcatat   9840
gtatcccgga acttaaagta aaattaaaaa aataaatttt acagatatat tgaaatactg   9900
ggatgactac tcttctaaag cttagttaat gtgtttttga ttaaacaaat gcaatccaaa   9960
agatacatat taacatgtct ttctatgtag caagcactat taggcatttg gaaaacatgt  10020
cctctagatt gaaaggagtc aagaattgtt ccccaaatgt ctggaaaata attgttatcc  10080
aaatgtaaac gtgcatgaaa gagaaacatg taaaactcaa ggcagtcagc aaaagggcag  10140
gttttcattg ctacctttta aattcggaac atttgactaa agtgaaggga tgtgagaaga  10200
accatgggga aaggctatct gcttaatgaa aaataatagg catcggcatt ttctccctca  10260
aagctggggt gggctatgaa agtacttcct caatagctgc ctggggactt tcaagacatt  10320
ttataaagtt atttttttca agaggctttt tttttttcct gcagaggcca cagtgaaaag  10380
tgtgaaaaat ctatagagaa attaaatgaa gcaatctaca gatttttaga gtagaaagtg  10440
ggaacagaaa tagtgggaaa aggcctggta tggtggctca cacctgtaat cccagcagtt  10500
caggaggccg agacgggcgg atcacctgag ttcgagttcg agaccagcct ggccaatata  10560
gtgaaacccc atctctactg aaaatacaaa aatcagctgg gcgtggtggc atgcctgtaa  10620
tcccagctac ttgggaggct gaggcaggag aatcacttga acccaggagg tggaggttgc  10680
agtgagccaa gattgcacca ctgcactcca gcctgggtga caaagcaagg ctccgtctca  10740
aaaaaaaaaa aaagaaatag tgagaaaaaa gctaacaatt actaacacat agctaacaac  10800
tactgagcat ctattctgtt ccaggcacta taatggatat tttaaatgca ttctctcatt  10860
taatccccat aaaaatccag tgaaggagga gctatgattt taatgacagg gaaattgtgg  10920
ttcagtatca tcctatgtaa gctcatgctt aagtggctaa ctccagagct aactctcttc  10980
actgtttcac tagctatcta ctatttgaag catgcatacc acaaaagaga agttttctat  11040
tctttaaaga ctaaagcctg agctatggca gacagcctga gaaccctctg cccttggtgt  11100
gactgttctg atacaattct tttgtcaata acatgtaatg ggtacctgct agatgcctgg  11160
```

-continued

```
atctgtgctc ggtgctggga gacggaaagg acaaagccac tgcttctaac ctagaaggaa  11220
ccggtggtga cctagacaaa taagcaaggg caacaccatg taaaagaagg agtttgcagg  11280
gtgggttctt cataaggatc aaacctagac ataaggaaaa gataactatt ccacagtggg  11340
cctgtgggga tggggaccag tgtaggttgt tcacataaaa acataaagtc aggatgagaa  11400
gcagcaggat ctgggatgat tatttcagcc actcctggct aagggcttcc cctaatatcc  11460
caatgaggag gatttgctaa acaaaagctg gagcgcctgg ttgttagctt atgctgattt  11520
actcatcctc actttttaat cattttatac agctctatgt gcaaagaatt ttgccagata  11580
ttattcactg tcaggtagtc tttcaataaa tatttatgta gtgcccactc tgagcattgg  11640
gaatacgaag gcggacagga tagacaacat tcctgctctc ccggagctcg cgttctacca  11700
gtggagacaa taaacacgta gctaaaaaaa taaatactgt tattatagta tttatttttg  11760
ttgtgatgaa ttaatgattg ctatgaaaga aatagagttg gctgagggag agtaactggg  11820
gaaggcctct cggaaagagt gctctaggag tcactgctga ggagtgacat ctaagtggag  11880
gtcccaatgg gagtgaggta gccatgccag cagctgaggg aagagcattt tgagcatagg  11940
gaacagcaaa cacaaagata gatactgagg tggcgtgctt aaagccagag ggtttgtaga  12000
cctcattctc ctgctctgat gcctgagacc aagctctagg cacctgtttt gtaatggagc  12060
tgtaataggg tctattgcta ttttgtatgc cagcaataaa tgatgtagca ataaataaat  12120
ttttttcatc tttttgcaaa aaaattcaca ttgtgaaact tacaaaaggc tcatactttg  12180
catgttaata gaaaaataag gccaggcaca gtggctcatg cctataatcc cagcactttg  12240
ggagaatgag gtgggaggac caattgaggc cagaagttca agaccagcct gggcagcata  12300
tgagacccca tctctacaaa aaattaaaaa ttagccaggt gtggtggcat acacctttag  12360
tcccagctac atgggagtct gaggtgggag gatcacttga gggaggatca cttgagccca  12420
ggattttgag gctcacagct cgtgagccac cactgcagtg tagcctggat gacagagcaa  12480
gaccttgttt caaaaaaaaa aaaagagaaa aagaaaaaca aacaaccaca aagaaaaaga  12540
agatataggg ctggaagagg catcagatat taatatcatc taatccaact cctcatttta  12600
gatgagaaaa ttgaggccca aaggtaagat aaaatcccat ggtcacatgg cacgatagtg  12660
gcagacctga gattagaact ccaaatgtga gagtattctt tccttaacag gtaagggatg  12720
aaatgtttat aaccggcagg tactcaaact atttgtatta atcatttgtt tttaaaatga  12780
tgaacccaat tttcctcctt ttgaatttct cccacttagt tttccatcta ttttgaagtt  12840
cttccaaatt cagttgttat aaagcaaacc aactttgatt aaggatcctt cttaccccaa  12900
tgtcgaaatc agggtgtgtg acatcatttg gccaccagag ggcactgaag tctcctgttc  12960
agagtagatg atcttgcttc ttctgataca caattcctac tgtgtagcct gagaagttgg  13020
ctgaatatta ggaggctggt tttgagaagg gaagtagcgg tgggactttg gctcacacac  13080
ctgttgccca cggctgctca catgactggc caacagcagc tgagtgaaat tacctcacct  13140
ctgttacaca actcagcctc acagggccag gtgtctgcca gagccagctt tacaagatga  13200
caaactcttg cactaacacc accatacagt ctttataaca acaattacag tggaaatttg  13260
aggccaggcc aaaaagatta agacttgctc caaaaagacg tgaccaaagc ttaaagtcat  13320
aaagaatgga ggccaggtgc tatgagctta ttgaccagtt tccagaatag cagaatcagg  13380
agcacccgtg agagaatgag acaggccatc ttagaagaag caaaaggaat gtcccttaca  13440
tggagcaggg aagggcagcg gggcaataa attcatgaaa ccgccgaccc caagcttaat  13500
```

-continued

```
gtcttaacag gtcctgaact ggtaagttca aatttgtaca tgggatattg atagtagact  13560
aacaatccct ttgtgcgtct atatgaggga ctcctgggcc agtagtttaa aaggtcttga  13620
cgggcaataa caaatgttgg tgaggatgtg ggaaaaagga aacccttgta cactgttggt  13680
gggaatgtaa attagaataa ccgctttgga aaaaaatttg gagttcctca aaaaattaaa  13740
aatagaggta ccatatgatc cagcaatccc acagctaggt atatccctaa aagaaagaaa  13800
atcagtatat tgagagatgt ctgcactcct gtgtttactg cagcactatt cacaacagct  13860
aagatttgga agcaacctaa gtgtccatca tcagatgaat ggataaagaa aatgtggtat  13920
atatacacaa tggagtacta ttcagccata aaaaatgaat gggatcctgt ctgtctttgc  13980
aacaacatag ttggaactgg aggttattac gtgaagtgaa ataagccagg cacagaaaga  14040
caaacttcac acatcctcac ttatttgtgg gagcctaaat ggaaacaatt gaactcatgg  14100
agacagagag tagagggatg gttaccagag gccaggaagg gtagtggggg gacttgcagg  14160
ggaggagtgg ggatggttaa tgggtacaaa aaatagttag aataagacct agtatttcat  14220
agcacaacag ggtgactata gccaataata atttaagtgt acatttaaaa taactaaaag  14280
tataattgga ttgtttgtaa cacaaaggat aaatgcttga ggcaatggat accccattta  14340
ccctgatatg actattatgc attgtatgcc tgtagcaaaa tatctcatgt accccataaa  14400
tgtatacacc tactatgtac ccacaaaaat taaaaatttt aaaataagta aataaaaagt  14460
tttttaaagg tcttgaactt tcgggcttct gcctaacttt actactagtg taagtgggcc  14520
ccttgagatt tcagcacccc agcatttgtt agtgactgaa ataatgaaaa ttctgatcag  14580
gcccttgctt gcacatgttg acaactctct ttttgcccaa tatcccttgt tcctacaaca  14640
taatcataaa ctgctgatgt actgtttctt tatcaagcag gaggagataa taacttcagg  14700
gttacgaaaa agtttgcagg aggaataagt cctttgaagt actttgaggc cagcttctgt  14760
cgcccagaag tctgattgtt caaggaatta tctgagactg aagaaacaca gactttttcc  14820
ctcgattccc tgaaactccc cctccctgac tcgctggccg cataaacact ctctgcttct  14880
tctttttgtt agggcggatt tgagagatct tgccctcccg ccttctcgct ttggccaaat  14940
cgaataaact tttatctcca agcacctata tgtcagtgtt tggcatcagc tacacatggg  15000
gtacacgagc ctgagtctgg gcttctacaa cgctgggacc ctcgctgttc tttggagctg  15060
atggtaaatt caacagaaaa gaggcgcatg ggtagaaaat gcagcatttc ctctcagatg  15120
ccagatattc atctccaaag gtattaaaag gagggggtgt gtgcctgtgt aaagaggctg  15180
gtcttttcct agcagtacga tttgggcaag ttgcttgatt tcttcaagcc tttctttttc  15240
cgcctgtcaa acaaaacaaa acaaatatcc cgtttaggac aaattcacaa tccttaaaga  15300
gggcaggcag agcgattgga atgcagatga accaatccct tctcctgcag gttgcggagc  15360
tgcagaggga ccccgccccc tgcattgtgc ttagctctga ttggcgcctc gcggaggggg  15420
cggggcctgg gcgcgccgag ctccggctgg gtccctgcag gtcttggggc ccgggactct  15480
tcctggagac accgccatgg ccgggctatc ccgcgggtcc gcgcgcgcac tgctcgccgc  15540
cctgctggcg tcgacgctgt tggcgctgct cgtgtcgccc gcgcggggtc gcggcggccg  15600
ggaccacggg gactgggacg aggcctcccg gctgccgccg ctaccacccc gcgaggacgc  15660
ggcgcgcgtg gcccgcttcg tgacgcacgt ctccgactgg ggcgctctgg ccaccatctc  15720
cacgctggag gcggtgcgcg gccggccctt cgccgacgtc ctctcgctca gcgacgggcc  15780
cccgggcgcg ggcagcggcg tgccctattt ctacctgagc ccgctgcagc tctccgtgag  15840
caacctgcag gtgagctggg gcccgcggct tccccaggcg ggctgtgggc ggggcggcca  15900
```

-continued cagagcgagc cttcactctc cccagaattc ttcccgggaa gtggagcgtg gctcgaacgg 15960
ctgttgcttc tctgccgcgc aggcaggtag gtgggcgttg cagcgtccca gatgttgggc 16020
agctgggtac caggaatttc ccacaagcct ccgccactgg gccacgcacc tggggtaaat 16080
tctctgccag cagcccgagg acttctcatc cgtgagtggt tctcagtcgt cttggggccc 16140
agtgtctcta ttaactgtgc tcctattctc tttttttttt tttttccctt tgagacagaa 16200
tctcactttg tggcccaggc tggagtgcag tggcgctatc tcagcttact gcaacctctg 16260
cctcccaggt tcaagcgatt ctcgtgcctc agcctaccga gtagctggga ttacaggtgc 16320
gtgccaccac acccggctaa tttttgtatt tttagtagag gcggggtttc accatgttgg 16380
ccaggctggt ctcaaactcc tgacctcacg tgatccaccc atctcagcct cccaaagtgc 16440
tgggattaca ggcgtgaacc accgcgccct gcctgggctc ctattcttaa aggttttaca 16500
gggcatagag attgttaggt acttaagcac tttaatatgt gacttcaggg tttctcactc 16560
tcttaccctt cctgaattaa gcttttccct cctgcagcaa gacgctaacg tacaatatca 16620
tggacgatta caatgattac tgcagtcttt aggcctccac aggcatagtg gctcctcagt 16680
aagatgcaga gctgattgaa ggtgtatctc ttcctcgccc tttgcccacc ttctggtgca 16740
gggccacact tacaactctg atggatctct gctgtctcag ggatggggtc acagacaccc 16800
agcttgggag gccggagaca cacagagtcc aggaatggag cctgatttga tggagggtct 16860
ttttgacaaa gctctcacat ttgagttcaa ctctgaaagt acaacattgt tgataaagac 16920
aggatgcaag aaactgatgc ttgattaatc acttttccat ttgccttcca ttcgttgtct 16980
cttctattaa ttctttgaag taggtattat ataccccatt ctgcagatga agaacttgag 17040
gcctacctag gttaagtaac ttgtttaaag ccagcgggca aacccctagt ttcatctcag 17100
gttcatcttt cttcaaacca cctatcacag gctggtggcc catcagctga atatgtccca 17160
cagaccggtt tggcctacac aaagttctgt tttgttttta ataaatttga atttgttacc 17220
aacattttaa aatttagatt ttactttaaa atgtaaatct ctaactttc ttgaaaaatg 17280
ggaagatcca gtgacactgt gggcctgcac tctttgagca aaaacagaag cagtgccctc 17340
ttttagctaa ggcagataca ccccagttca ccattttctt attcccagcc cattccacac 17400
ctttaggcgt ttgctcaaaa caaactcact ccactccatc agtggtgctc aactttgact 17460
gcaaatcata gtcacctaag aaggctttaa aaatgggatg ccaaggtatt ttattgaaag 17520
cacattttat tttaagacaa cacccccttcc cgcctcccca caaaccactc cctgatgatt 17580
ctaatggggg aggagggaga ttgaccaata cataatcata tttaaatttg tgaggtgact 17640
agggagttgc tggtattatt gtccccattt aggaagtgag gaaacacaga ctcagaggtg 17700
cagggactta ccctgtgacc agtcagctaa tggctgtcag gtaggacatt agcccaggtc 17760
tttcatgttt ctagaaatag acagggcagt ggcaaggaac ctacccaggg ctttaggttt 17820
ccatgatggc agtgaaaaga agtggccaca ttagaatttg tctgacttga ttccatcaat 17880
tagcaggtca aagtttctgc ttttttcttt tcctcctcct gacctccagg gtgctctgca 17940
tttcttctca ttgacagggg gtgaaatcgt tcagaaggaa caaaaagacc taggtttggg 18000
accatttctc atgtgtaaaa tacctgtcct ctgtaactta gagatatgtt gtgagcttca 18060
aacgtactta ccactgggct gtttcttttg tatgtctctt tctttgtggc atttttgtat 18120
agtaaatgtc tgtaggacag tgttgctgat gttagcttat agtgggaccg tgtttggctg 18180
cagagccagt gagtctgaag ggaaatcttg ggtttgatt atttgcacca agacctctta 18240

-continued ctattagcct cccttccatt ttggcattct tttcttgtga tgtgcccctt tctgttctgg 18300
tcactcttgg ttttttttct ctgacccact aaaataagta tccctcaaag tcagtttcct 18360
actcttttgt tccctgcagc gatcctcaga agattgtata cactctcgtt gtatacattc 18420
tcttctagtc cttactagga ctcacttcca gatgtgtgtc catttctgac ctcttcaaag 18480
ttctctatat ttctgcttgc tgttcatttt tgcttcgtta ctttgccacc acttcaaatt 18540
caacatgttt aaatccagtc cttcttcctc ctgaaacaag ctgcttttga tcttctgcat 18600
ttctgttagt ggaattattg ttttctcagt aaacccagtt ggttctcact gcctccccaa 18660
atccctcagt tcccaagtcc tgacagtttt ttgttgcctt ctttacctct gtccttgccc 18720
cttcctcttc attcctgcca cctcatcctt aagcttatca tctcatgcct aaaagtacta 18780
gaacagctct tacatagtct tcctgtctgc cccatccacc ttgcctaccc aaatagatta 18840
acaaaaatac ctgtcacagc attgccctct ggccagaaac ctttaacaat acccagctgc 18900
ctatagctgc gtaagagcta cctgggatgt ttgtttaaaa tgcatataga ggcgggtgcg 18960
gaggctccag cctgtaatcc cagcactttg ggaggtcgag gtgagcggat cacctgaggt 19020
caggagtttg agaccagcct ggccaatatg gtgaaaccca cctctactaa aaatacaaaa 19080
attaactggg tatggtggtg tacgaccgta gtcccagcta tttgggaggc tgagttgaga 19140
gcatcagttg agcctgggag gcagaggttg cagtgagctg agatcacgcc attgcactcc 19200
agcctgggtg acagagcttg attctgtttc taaataataa aatgcagata gaggacagct 19260
tggtggctca tgcctgtaat cccaacactt tggaaggccg aggtgggagg atcacttgag 19320
tctaggattt tgagaccagc cagggcaaca cagtgaaact ccatgtctac aaaaaataaa 19380
aaaatattag ccgggtgtgg tgatgcacat ctatagttcc agctactcag gaggatgaga 19440
tgggaggatc acatgagccc tggaggttga ggccacaatg agccatgatt gtgccactgc 19500
actgggtggc tgcctgggtg acagagtgag acactgtctt aaaaaaaata ttgcaggcca 19560
ggtgcggtgt ctcacgcctg taatcccagc actttgggag gccgaggtgg gtggatcaca 19620
aggtcaggag ttcaagacca gcttggccaa catgatgaaa cccagtctct actaaaaata 19680
caaaaatcag ctgggcgtgg tggcacacac cagtaatccc agctactcgg gaggctgagg 19740
caagagaatc gcttgaactt gggagttgga ggttgcagtg agctgagatc gcaccactgc 19800
actccagcct gggtgacaga gcaagactcc gtctcaaaaa aaaaaaacaa aaaaaaattg 19860
cagttatttg ggttgggagt gaagcctgtt tcaacatttt aacccaaatc agcattttat 19920
caagctctcc aggcaggtgg ttcttagaaa acagtgccta aggttggccc acaaattaca 19980
atctagactc cttaacttag gttggagccc tctccactcc caaccccagg ctcctcccgt 20040
aggaaagccc ttctttccag caaatcaggt ttcttggtac tgttcatcaa gtcttaggct 20100
cacccagttc tgtgtttttt gcagtcagtg tctcctctcc ctttaatatg tcctcccacc 20160
ttctatcctg gttttgaata tattataaag ctccttacag ttcctctatc actctggtct 20220
atgctggaca tacacatttg tttatgtctg ccttttcaac cagattataa actcacggag 20280
ggagagagtt tacctgagtg tccccctccc cttctttggt ctcctgtggt gccttgccta 20340
atagtttcta gacagtgact atttggctaa atgatttcaa agaaatctct ttatgactct 20400
ttgttttgat gggtcagtgt gaaatggcaa aattctccac acaaggcact tagagcttaa 20460
agagctaaat agtctaaaat gcgatgtgtg aattttgcta taatctgtca acagtgcctt 20520
ttatgaagtt gatttctgaa taagaaagca ttaagaattt tacttgtgtt actttttgaa 20580
tgtgggataa aactcattgt tactaaagca ggaatgaaca acttctccag ttttgaaatc 20640

-continued

```
acatgacagt ttctgctaat gtaagataac caagtagcat gattcagcta ctttcttgct  20700
taaatcgcgt agttagccaa ttgagcaact gtggtgtttt tagcaatggt tttgtataga  20760
gtttaaccct ttaaatcttt cagtgaagcc tatagaacag ccttgaattt gggtgtcact  20820
ataattataa ttcttctgat gaatatggaa taaattcagg gtttcagaaa aagaatattg  20880
aaataatttt taccaagtca gttcatttta aatatgaacc cccgcacccc ctttggggag  20940
tggtcaggat actttccaag tattattttc ccctgagtgg aaggtgatgt tttatgattc  21000
attgtttcgt ggaagaccag tcaagctcta gggacatcat gtatgcaact tttgaaattt  21060
attacctctc cagaaaccat atttcacatg agaggatctt cattttctct ctataggaga  21120
atccatatgc tacactgacc atgactttgg cacagaccaa cttctgcaag aaacatggat  21180
ttgatccaca aagtcccctt tgtgttcaca taatgctgtc aggaactgtg accaaggtaa  21240
gtagttatcc tacaggaagg gagatggttt cagaacacca tcgtattcac aatgaaagaa  21300
tagatcattt ttcttttgag acagagtctc actctgtctc ccaggctgga gtgcagtggt  21360
gtgatctcgg cttactgcaa cctctgcctc ctgggttcaa gcgagtcttg tgcctcagcc  21420
tccctagtag ctgggattac aggcacgcac caccacaccc agctaatttt tgtattttta  21480
gtagagatgg ggtttcacca tgttggccag gctggtcttg aactcctgac ctcaagtgat  21540
ccacccacct cgacctccca aagtgctgag attacaggcg tgagccacta tgcctggcag  21600
aatagatctt ttcagaatga aatgcagttg atttgtgatt gccatgccca gtcagaacat  21660
gttctattct aataggtgaa gtaattccat gaaaaccaaa cgttttaata agttgctttc  21720
atataggtgt taaataagat atgacaaaaa tgaatgattt tctgaagcca agcagatgta  21780
acaactatga agctcctgta tataaagtta ttcttactaa agagcatctg gttgaccaaa  21840
gccctctact ctccattaca ttttacattg gtataatgtt tttccatgtc tgggctcctt  21900
gtctccatat tttaacagtg gcttaaagca gagaaaacat attaagtagg ccaaccagag  21960
gactatccat tactgaaaac tggaagtgaa tttagtttgg atcacctgct gaagggaaga  22020
ggtcaaatac aatctcagga agagcagtgg gcatggtgtc aggagtgctg atctgattac  22080
ccagccagca gatttgcttt ttgaccgtgt caatcattaa tgcctcagac aagtgttatt  22140
tatggtctgt aaattctttg tggatgcatc tctgtagttg agtgtccttc actggcagga  22200
aaaagatgga ggagcagcac atgcttttga gttctgttat gtggtttcta aacattttta  22260
tccttcagta cattcatctg tatgtttaac atgtccatgt tatgggataa atatgctaaa  22320
cattacatgt cttaggcacc agtaatgtta cagtacttag tgctagttat tctaatagct  22380
caaaatgcct ttttaccaat gaaagttggt attatactta cagtggtttc ccacttcgtg  22440
gtatctgtta ttaccaacaa ttgaaatctt tattctctgc attctttaca tttcctttat  22500
tttctcttga ttccttaagg ttaagatcaa gatttacaag taagtaaact cttaggattt  22560
atagaatgct agagtcacac attctttttt ttttttgaga tggagtcttg ctctgtcatg  22620
caggctggag tgcagtggca cgatctcggc tcaccgcaag ctccgcctcc cgggttcatg  22680
ccattttcct gcctcagcct cctgagtagc tgggactaca ggtgcccacc accacatctg  22740
gctaattttt tttttttag tagagatggg gtttcaccgt gttagccaag atggtctgag  22800
tctcctgacc tcgtgatccg cccgccttgg ccttccaaag tgctgggatt acaggcgtga  22860
accactgcac ccggcctaat cacacattct taacaaatga gaagataaag tgttactgcc  22920
ataagaatgt ttatttcata tatgtccttt aggtgaatga aacagaaatg gatattgcaa  22980
```

-continued

```
agcattcgtt attcattcga caccctgaga tgaaaacctg gccttccagc cataattggt  23040
tctttgctaa gttgaatata accaatatct gggtcctgga ctactttggt ggaccaaaaa  23100
tcgtgacacc agaagaatat tataatgtca cagttcagta agtacttaca catctttcac  23160
ctaagattgc cgcccttaca gccatcctca gccttctaag gcaagggggg tttaaccgtt  23220
tcatgtgccc tggacaccct gggcagtctg gtaaagccgc tgaccccttc tcagaataat  23280
gttttaaaca cataaaatac agaggattaa gaagaaaatc aactataatg aaatacattt  23340
atgaaaatat ttgtaaatgt gtggtataat cgttttatta atatattaaa tataagatct  23400
agtaataagt ctattacttt ttcttttttt ttcaagacag agtcttactc tgtcacccag  23460
gctgagtgca gtggcaccat ctcagctcat tgcagcctcc acctactggg ttcaaacgat  23520
tcttatgcct caagcctccc aagcagctgg gaatacaggc atagaccacc acacccagct  23580
gatttttgt attttcataa agagggtggt gtcgaactcc tgagctcagg cagtctgcct  23640
gcctcagcct cccaaagtgc taggattaca ggcatgagcg accatgcctg gccttttctg  23700
tgcttttaaa gtagtgagga ttgaagacaa tattttaaga catctgcaac acctgtgaca  23760
tgatatgaac gtatctgtga tttctctatt tctgttggag acagtcacag ataggctgtc  23820
accctgtggt ttattcccta cattcattat tgaaggaaat gatacattca gttagagcct  23880
aatgaaaatg aaaaaaaaat ttttttgagc caagttcgca gacccctgaa ctctgtctac  23940
aggcctggac accaggttga gactccattt taaggctgtg cttattgggc cctgaacaga  24000
gcccagttat gacccacgat ggcattttct catgaggctt agactcaggt gctcctggac  24060
tgtgaatgcc cttcatctga gtctgagcaa gtaaccccat cccatcagcc ccagtactac  24120
aaatgcctat ggggatgtgt ggtttatccc actaagaagt gcatggaagg gaggaggctg  24180
agataaaaga ggccatggga gaaaataaag cccaggacct gaagacagaa agggaaagga  24240
aagaagagtg taactggagt ctttggagtt agctaagggt tcaaatgagg gaatacaagg  24300
gactggtgct tctcccaggt gacacaggga attctggcat atctggggag gtgataagaa  24360
cagtaacaat aacagctagt gtccattgtt tattactggc tgggtgctat actggctact  24420
tttcatgtat taactcattc agttctcacc acatcccttt cttgcgcaac cttccaccgc  24480
aacaggtagg tgctgttttt ccacatgtgt gaaatggaaa gctgatgcac agagaacaaa  24540
ctggcctaaa ctgtttgttc ttgcagccag gaagtggtgg tgctgggact caaacccagg  24600
cattcttgct ccagagccat cacctgactt ctatccatga tgctgtactt ctcctctggc  24660
tgcctcactg gtagctggcc aggctcctag ctcagtgtaa tttataatgc actttctgct  24720
tgtaatgatt gactgctgtt tcaggagatt acggtgatga taactaaggt agacttgtag  24780
gttgtaggtc atttgagggc ttaaattctt agcatttatt taatctctgt ctttttcaat  24840
tgtagaacaa ttccgtgttg aactattgac tccctaccat gattggaaat ctcagttttg  24900
ttttgtttct aattttttt aattccaagc agggcctagg acagtgtgtg tcatagagca  24960
ggtgtttagg aatgattgtc tggctcatta cttgagacaa acactctcac actctgttgg  25020
aataaagaat cccacagtcc tggcgcttgt tttgctgctg tgcatgcagg agaggcacgg  25080
gccactggtc gtcttctggg ctggcaaagc catctgactt cataggaata tagaggtagc  25140
aattacaact ttattccctg gcaacaaatt atcaggatga ctgttaagaa gggcctgctc  25200
ttcgaagtta aagtttactt tcacaggaca taatctctaa agcgcagtta tctttatata  25260
aataacatgc ccaaaggcag tgcctggttt aataacaaaa taaaactgtt ttcccataag  25320
tctccacact gaataagtga gtaaaacaga tacttttgag gttcccactt tattatgctg  25380
```

-continued

```
acaaaggagc acttctctgc agcacagaga tagaacattt ttcccttgtc ctgagaggcg  25440
gcccaaaggc tagagcagat gtgactcttc tgaggcagtg caccagaacc cgagggatgg  25500
gcagggcctg aaagctgccc gctctgaccg ggtgcctctg gctaggaatt gtccatctcc  25560
gagtctagga gtgcccccac taatcccacc cgccaggttt gccaccagag ctgtttaata  25620
gtccggggag tgtacagtga tatctgtgag gaccagggcc cccatcttct tggagaacca  25680
cccacagggg cctcacaggc gttctggagc ttccccacat tggcagccac cttgcttggc  25740
ttgcccagat cggttttgga aggtattatt cctccaaata ccacgaagcc ctctgcatct  25800
gaaatctgtt tcacacagat ggagactgcc acttgtgaga gctgatacgg agcttaactg  25860
aatgtggttt gcctcattgg actgttgggt gaagccccca tgagcatgtt tgcatgatca  25920
gtggaaggct taaatgtcta cacgaagcat ttgctggcac cctggaataa gcagttcttt  25980
tttttttttt tgagatggag tctcactctg ttgctcaggc tggagtgtgg tggtgcgatc  26040
tcagctcact gtaagctctg cctcctgggt tcatgccatt ctcctgcctc agcctcctga  26100
gcagctggga ccacaggcac ctgccaccac gcctggctaa ttttttgtat ttttagtaga  26160
ggcagggttt catcatgtca gccaggatgg tctcaatctc ctgacctcgt gatctgcccg  26220
cctcggcctc ccaaaatgct gggattatag gtgtgagcca ccgcgcccgc ccaacaagca  26280
gttcttataa gcataagcat tgcttttgac cactgttaag tctgggcagc agcatgtttg  26340
tgctaagcct cattttatct cctctggcgc acatccggat atttcctagc aaacacacag  26400
gtaacaaaag gtcatggatt acagacttgc ccagtcttga tacctagaga tggattccct  26460
ggttggtggc agcagaaagg gggaaagttc acctcccagc tgtggtcact atcactgggc  26520
aatggctaat cactgctctt ctgccctgat gttcaggacc ccttctgttc tcaactattt  26580
ttgtctttta agccttcaga tactcttaaa tgagataaca acagcagcca cggcagtggc  26640
ctgcttcttg ctacatccta gtagcgttta tcagtgtgtc agaatcatac ttggagagga  26700
gggttattgc taaaatgagg attcctaggc cccaccctca acctattgaa accgaaactc  26760
aggagtctgc attttaacaa acccaagtgg ttatttagta tattctagtg gttgaaatga  26820
actgaaaatc ttaatttaga tcagaaattt tatctagtcc ttccctagaa tgaattaatt  26880
tttaagattt gttaacccag tttaacaaaa taattcttct ctgttcccct ttctaggtga  26940
agcagactgt ggtgaattta gcaacactta tgaagtttct taaagtggct catacacact  27000
taaaaggctt aatgtttctc tggaaagcgt cccagaatat tagccagttt tctgtcacat  27060
gctggtttgt ttgcttgctt gtttacttgc ttgtttacca atagagttga cctgttattg  27120
gatttcctgg aagatgtggt agctactttt ttcctatttt gaagccattt tcgtagagaa  27180
atatccttca ctataatcaa ataagttttg tcccatcaat tccaaagatg tttccagtgg  27240
tgctcttgaa gaggaatgag taccagtttt aaattgccca ttggcatttg aaggtagttg  27300
agtatgtgtt ctttattcct agaagccact gtgcttggta gagtgcatca ctcaccacag  27360
ctgcctcctg agctgcctga gcctggtgca aaaggattgg cccccattat ggtgcttctg  27420
aataaatctt gccaagatag acaaacaatg atgaaactca gatggagctt cctactcacg  27480
ttgatttatg tctcacaatc ctgggtattg ttaattcaac atagggtgaa actatttctg  27540
ataaagaact tttgaaaaac tttttatact ctaaagtgat actcagaaca aaagaaagtc  27600
ataaaactcc tgaatttaat ttccccacct aagtcgaaac agtattatca aaacacatgt  27660
gcacacagat tattttttgg ctccaaaact ggattgcaaa agaaagagga gaagaatatt  27720
```

-continued

```
ttgtgtgttc ctggtattct tttataagta aagtttaccc aggcatggac cagcttcagc  27780
cagggacaaa atcccctccc aaaccactct ccacagcttt ttaaaaatac ttctactctt  27840
aacaattacc taaggcttcc tcaactgccc caaatctctt aatagcttct agtgctgcta  27900
caatctaagt caggtcacca gagggaagag aacatggcat taaaagaatc acatcttcag  27960
aagagaagac actaatatta ttacccatat acatgatttc agaagatgac ataagattcc  28020
tcttaaagag gaaatgtcag gaatcaagcc actgaatcct taaagagaaa agttgaatat  28080
gagtcattgt gtctgaaaac tgcaaagtga acttaactga gatccagcaa acaggttctg  28140
tttaagaaaa ataatttata ctaaatttag taaaatggac ttcttattca aagcatcaat  28200
aattaaaaga attattttaa tgaaatgtgt tggattcgtt ttcttaaaca tagacattaa  28260
tatttattac actttgtttt attgtctact gtcgaaatag catgttccta aatcagtcac  28320
tggctgtttc aaaacttgaa gtgaataata ccactctttc taattggcaa aaagctcatt  28380
gtgtcctaaa attctgggca tggccagatc tagcctttgt cacaggttct gcctcaggga  28440
tttggttgcc agtgtacctt gtgatagaat taggttgagg gcagctattt ggttttctcc  28500
ctttacccac ttagtgagtt ttttctccag catttggaac cacataaata catatcgaca  28560
ttcaggtaag atctagttat catacagagt aaagtcaacc agtgtttcac agcaggcaga  28620
ttcttttata attgaatgtg ccagaatatg tcactgttaa tattccagtt agccactagg  28680
gggcactgga ctactctttg tgcaagtttg ggtttcttac acagccaaat caagccccta  28740
ggaataatgc tctgggttag gagctggagt aaatgcagct cagcaggggc aagaggagaa  28800
gcagaggcct gatttgctgc tgctgctgct gctgctgctg ctgctgctgc taggttttcc  28860
tgggtttatc attccctcca caccatgtgc ttctacatca ggcttctggt ctccttgcac  28920
cccacctgct gcagaaggag aacagatccc tgggctcaaa cagctaggag atgagtatct  28980
tagactgggg tggggagggg gagtcagcct tggtgcagag agcaggacag gccctgatag  29040
agaaagataa aagtgtaaag aggggccggg cgcggtggct cacacctgta atcccagcac  29100
cttgggaggc tgaggcaggt ggatcacgag attaggagat cgagaccatc ctggctaaca  29160
cggtgaaacc ccatctctac taaaaataca aaaaattagc cgggcgtggt ggcaggcgcc  29220
tatagtccca gctactcgga aggctgaggc aggagaatgg cgtgaacccg ggaggcggag  29280
cttgcagtga gctgagaccg cgccactgca ctccagcctg ggcgatggag cgagactccg  29340
tctcaaaaaa aaaaaaaaaa aaaaaaaaaa aagtggaaag agggagtagc tcaggatcct  29400
gaagctacag agtccagaca gctgcgtttg gcagatgcta tcttgaccat ccttctgcac  29460
tcagctggtc aaggccattt gtctttacca accatggcca ataatcatag tttattctgt  29520
gttctagtcc aggttcaaag tccttgacag gtatgtgggg gagtggagaa aaatctttat  29580
gaaatgtgac gaagttcaat gaaataaatg catcagatat tctgaggagg ttgctagtgt  29640
gatgttccct tcttagtagt atttagactg aagatcacaa agtaattgaa aaggagacta  29700
ctttctttta agggagcatg tttttcagtt ttagtactga ggaaataatg ctctaatttg  29760
tgtaatgctg gttggtcagt gtttcctagg ggaattccaa actgtcactt caaaaccaag  29820
tgttctataa atattattag agaagataat tataatttaa ttataattcc ttttggaatt  29880
aaggggggta caaatcagta aaatgtaaat ttttcagttt tttctttaag atttattgta  29940
agacatttgt ataggaaatg tggagaataa aaagtttgac atttataacc tcaccaacca  30000
gcatggttgc taatattttg ggtgtgtttt cttgggagtg atgtttaaac atagtcaaga  30060
tcttgctgtt taatgaatgt gtatcatgct tctttcactt tatcataaac aaccgtgttc  30120
```

-continued

```
ctagaagcca ttcacgagga tggctgagaa tggctgcaga atatttcatc agatcaatat  30180
aagcaggcca ccaaataatg gtctgcattg ggactctgtt gctagtgaca agaaacctaa  30240
gtcaaagttg tttaaacaaa aagagttcat tgatcttata ttattcagaa cttggctttc  30300
atttcctggc tcctctttct gccgtgttag ttttcattgc agccagcaat cttaccacca  30360
agaggatgtg tccttcctag ctgggcccta gccattcccg aataatcact gtgtctggga  30420
atggggtgcc ctctttggcc gaacttgagt agtgtggctt ctcctggagt tgcgggttca  30480
ctcagcacca tcagaatcac agagactggg agaatgtaga agggggactc ctgcaatgaa  30540
aagagtgctt atgcgaactg aaggaacact gagcaggcaa aaaccaaagg ctattagcat  30600
tttctccagt ttttgcatat ttaggttact ttcagttttt tcctcttaga aaagtcttac  30660
acataaaata ttttctacat ttctgtttat ttccttagat tcccagcagt ggaatttcca  30720
agccaaaagc ttttggtaca tgttataaat tgcttttaag aatgtgtatc aattataatg  30780
tccagtgttt gctttaaaac attctagcaa agaaaaaagt atagggggatt agatgaggag  30840
aaactggcaa aatggtaaca gttgaagcta ggtgaggtgc ctggagattc attttgctat  30900
tattctcttt tgtgtatgtc tgaaaattac aaagatttct aaattgaatt gaaaaaaaat  30960
aaagaattga ggatctagag aggttaagtg actttcccaa gcccacccag ttctggtctc  31020
caggctttaa atcctggcca tttcttctac tccacactaa attggcatgt ggtcatattg  31080
tctgagacac agattatgcc agcgtaaggc ttcctgactc ttcttcaccc cgcaacacac  31140
caaggcagga atgcagagct aatctatgtt tgtgggtggg gagggggcat gagtagtggg  31200
tgctagggag ctagataaca agtttggctt ggtgattcag gagttcaata gagatttctt  31260
gaaaggatgt tttcagtaaa attttggaaa atacataata atgggggagg ggagagaatt  31320
tatatcaatg aacagccctg caagcagtgt atgaaagtgc ttactctgcg atgggttaaa  31380
atagtgtgtt attttaattg gcaattctta aggttactaa taacattgaa cattaaaatt  31440
tattttggtt tatttttcct cattgaaaac tgtcaattta tattctttgt ccacttatgt  31500
ttgggggatc attttaaaaa attgatcttg ctgaattctg tatattcagt ctatgaaatc  31560
atttagttag taaatttgtt gctaatactc agttttcctt ttaagttatt ttgtttaaaa  31620
cctatagatt ttccatttct atagaagaaa ttaacataat atttttccct tgacttcttt  31680
aagtttaatt tcctttaaac ttggtatgtt tgtttccttt gagaaatttg ataaatgtca  31740
attcagattt tcaaattgtt atgtttaatt tttatacttt ttaatccttt agaatgcatt  31800
ttgtgtataa tattcttcac ttttttggat gacaaaccca aattatgctt agcttttgta  31860
gtctagatgt gaacccaaat ctaagcatag ctttctcaga agtgaggatg taagtgagtt  31920
agggccatcg gcctagcctg ctggacagtc tgtctgagag acactctgta tcccttagct  31980
tgaacttgag ggattggaat tggcaaagaa gcatggttct gataatattc tcataacctt  32040
tggaggttgt ctaacacaca cacacacact ccttagctag attctcaagt cccaccacaa  32100
taaaacttca gctggctctc ccaacattat ctgccattcc tcagtgtatc ctatgccatg  32160
accagccaat ctgatctggt tataccccaa acttttccct ttggactttt ccacatgctc  32220
ctcccttagc caggcatctc ctacctcctc atctccctca cttttcagga gtaggtagtc  32280
ctttgaaggc cgagtctgca tctgatatat ttatcactgt agccccaaaa caccaagtgt  32340
caatattcca ttacgtggag taacccctca atgaaatttt aacaaacgtt ttgcttacag  32400
actttgtact ttagtgaata tagtggaaga tggaggttgg acctccaact tgctgtgtga  32460
```

-continued

```
cttagaatga agtgatttgt ttcagtgaag gcacatttaa tcccaagcac ttggcaaatc  32520

tcaaggagac tttgcttggc accccagaca tcagcctcca ttaaggaatg gcattccaca  32580

ttacaggctt ggatggagac atctgtcttg tgggcacgct gagcaactct gccacaaacg  32640

ttccatgagg aagcaaggga tttcgaagtg agttaattat catgtctttg atttttcaga  32700

tttggcggac tatgtctcat tgttctgttc ccaaagcctg atgtatagac gctgctcaaa  32760

tacgcttttg agcatggaat gagggcagag cagcttaacc aagacacagt ctcctctctc  32820

tctttacggc tgctctgaga aggggaattc agcacattat atgcatgccc agagtcggtc  32880

aacacaaact ctcctatttg gttgccaaga gtcatctgtg accctgggat ttatctttgt  32940

cttagtttgc ccaggctgcc agaacaaaat accatagact gggtggctta aactgcaggt  33000

atttatttcc cgcagttcta gaggctggac atctgcgatc agggtgtcag caagagtggg  33060

ttctggggag ggctttcttc ctggcttgca gacggccgcc ttcttgctgt ttcctcacat  33120

ggcagagaga gatctctttc tgtcttcctc tttttttttt tttttttttt tttttgagac  33180

ggagtctcgc tctgtcgccc agactggagt gcagtggtgc tatctcggct cactgcaagc  33240

tccgtctccc gggttcacgc cattctcctg cttcagcctc ccaagtagct gggactacag  33300

gcgcccgcca ccacgcctgg ctaatttttt gtatttttag tagagatgag gtttcactgt  33360

gtttgccagg atggtctcga tctcctgacc tcttgatcca cctgcctcgg cctcccaagg  33420

tgctgagatt acaggcgtga gccaccacgc ctggcctctc tcttcctctt cttctaagac  33480

cacagtcctg tcagatcagg gccccaacct tccaacctca cctaacctta actacctcct  33540

aaagactcta cctcccgata caatcatagg gtgggttatg gcttcaacat atgaatttgg  33600

gggaaaacaa ttcagcttat agtaattgtg tttggaagag aataaatgat aaggctgctt  33660

tgttcatccc aaacctttcc tcctttgata actcccaggc ccacccacgc aagaagattt  33720

atcctcaatg gtttctagtc cattcctgct ctggactgtg gttttacgac acgcttttgc  33780

aggttgtatc ctgcacaaag gccccagctg acagggaagc aggggctgaa acccagcctg  33840

agctcatgcc tttgtcctgg tgtgagcagc atcaccccaa agggcatctt tcctaaaaat  33900

gacactttat gggttggtgg cacctggctt tcgggccatt tcttacttta gaagtttttg  33960

cttcctatgc atggaatccc agagagggca aaaagagtgt gaacagagcc caagggagcc  34020

ctgggctgtg gggggcccca ccggtggatg gatgggggga gcagccaagc aggagcagta  34080

tagcggaggt taggagcggt tcggctgcga gagcactggg ttctgagcta gttgtgcact  34140

tgctgcacgt ggccctgggc aaatcattct acttctcaga gccttagacc ccatctgtaa  34200
```

<210> SEQ ID NO 18
<211> LENGTH: 6840
<212> TYPE: DNA
<213> ORGANISM: Homo sapiens

<400> SEQUENCE: 18

```
agcaagggca atacttcaca ggtgggagta cagattagca aaaatgtcca caaatcactt     60

agcacagtgc ctgacacagc agtgatcctt gttagggcca gtagaagagg catcctcaag    120

ctctgggggt cctcattgca tcctctctgg gagactggaa tgtatccttg aagaacagca    180

gagtaagtgt caaaatcaag cacagtggct ctgcagtggg gctgcatagg aacacatcct    240

cgttccatca ctatttcatc atggacaagg tgcctcccct gtgtgggctg cagggttttc    300

atcagtaaaa tggagaataa aaataggacc tgcctccctg gtttgtagga aaaagttcga    360

gctaatacgt aaaaagtaca cagaacacta tccaatatat caaacattcc ataaatactg    420
```

-continued

```
gttgcatttt ttttctttag cttcaaatat cggttggtaa ctacaggttg ttttcacaaa    480
aataaaagtt ataatcgtca aattacttaa ttttataaaa tatgttcaat cgtggcgttt    540
cagctaactc ttgcaacaag ccctagagat aggcaggaca ctctttattt ttatttcgtg    600
gaggaggttg gattcgcaaa tggttacctt gggcaagttt acacgtgtca gacccatccc    660
ttcaacctag ctctgtctcc aagaatccgg tgacccctca actgctggtg gcacatgggt    720
cctttgaaga gatgtcttct cacttgtttt agaggtgcat cgtatagaat tggcaagtgc    780
catgtgctgg aaaacaccag gttttcatga ggagcacact cacatctttg agggcaggca    840
gtatgaactc tgaagtcaag cggcagcgtt caaattcctg ctcaaccact tagccaggtg    900
gccttaggca agtgctcctc aagaggttcc cctctgtgaa tcagggacgc tgcctaggat    960
agatgttggt tattggtatt acttagtatc catccaggtg tggaatgtcc tgaggctggg   1020
aaggctggag accgcagttc gacaaaacag ccgctagagg tccccatgga gccgcattga   1080
acatccaaga attctgttta atcctcctgt cttgggccag accagctggc cctgctggaa   1140
ctgagggccc ctctttgtcc tgataagcac tcttccttcc cttaaagctg gtgacccttc   1200
taaggggctg tcaagggcta atgctgagac tcacaggttc ctgaccttca gtccccagaa   1260
gtgggccctc aggtttaatc ctgaggcgag ggttgcaggg cctgttccag tggattccca   1320
ggggccagga tgggctctgt gaggactcca ggtcaggctg tctccaccct gggcaaactc   1380
aggcaacctt ttcgtctttc acttttagaa aagacaaaaa tgtaatctgc atgaagtcag   1440
ggtgtcttgg cagaccctgc aggccaggag ccagaccctc atagggaagg aaccctggac   1500
atgggccatc actgcatgcc tgggatgtgg cccagaggca gcacacagca caaccctgtg   1560
gggaggtaac agctagtgga gctgaaagag aaaggggcac tggagaagca ggaatcatta   1620
tacgaaaatt taatttccag ctggaagaca tcttgtggag accatctagt tcagcttctt   1680
cattgtatag ctgaggacac ccaggcccag agaggggaag tgatttggtc aaagtcacac   1740
agcaagtaaa ggacaaagct gagagcagat cccaggtttg tgcattccca tagcagctgc   1800
tttccacaca ccccactgag ggaagaccat ttggtcaagt cagagcacgg ggggtggggg   1860
gttttaaaaa gcagagctga ggaacttagg aatacacact gcttagcaca tggttattag   1920
ctggtccttc agatgcccca gggtctcagc gttcgaagct tgctcattcc acaggataat   1980
tttgtgtttg ctcaggtgcc cagaaaatgc ctttttaaga tttctgagaa taaacccatc   2040
acctccaaca gtcccaggaa ttgcaactgt ctattcataa cgaatgagag gcaggtgcat   2100
taaattctga cctagtgctc aagaactttg gagggataaa aagaggaagc acacaggtcc   2160
ctattctggg aatgtggggc ctccctcacc tccccatagg agggcttgtc cacaccacct   2220
cctctttcct cctcttcatc tcccaccctt tccaccaaga cagtgacccc attccccatg   2280
ctgggttcca atcattcctg gaaggatttt tcccagagca gttgccagca aacattttac   2340
agtcctctcc tcctctctgt gatgtaacat ttcccaacac cttctatata ctaggcacat   2400
aacctacatc atcttactca ttcctccaac aagacagtac agtaggcatt gttagccaat   2460
gtgggacaaa agatttcaga tatttattaa cttgttcaaa acatacagcc agctagtaga   2520
tggaatttgg aatttgaacc taggtctaac ctgttctaaa gctcatgttc ttccactact   2580
gtgaaccagc acccagaaaa cttgagtttt agttttgatt ctaccagctt tgtgacctta   2640
gaaaaataac ttaattttaa gtttcctaaa ctacaaaatg gaaactggct gggcatggtg   2700
gctaactctt gtaatcccag cactttggga agctggggca gccggagttt gagaccagcc   2760
```

-continued

```
tggccaacat ggtgaaaccc catctctact aaaaatacaa aaaattagcc ggttgtggtg   2820
tggggggcct gtaattccgg ctacttagga ggctgaggca ggagaatcgc ttggacctgg   2880
gaggcggagg ttgcagtgag ccgagatcgc ggcattgcac tccagcctgg gcaacaagag   2940
caaaactcca tctcaaaaat tttttttttt taatttaaat aaataaataa ataaaatgga   3000
aacggtacac caatattgac aaccttactg agtcatcaag attaaaaaga caatatggct   3060
gggcatggtg gctcatatct gtaatctcag cactttggaa ggccgaggtg ggaggatccg   3120
tgaaggccag gagttcaaga ccagcctggg caacacaggg agacccctat ctctactaaa   3180
aaaaaattaa aacattggcc gggcattgtg gtgtgtgcac ccgtagtccc agctactcaa   3240
gtggctgaga cgacagggta gcttggcccc aggaatttaa ggctgcagtg agctatgact   3300
gcaccactgc actctagcct gagtgacagt aaaaccctgt ctcaaaaata aatttaaaaa   3360
atacaatata ttaatatgtg aaaatgacac acaaatgtaa gacacccccca ttaaagcaaa   3420
aaaggttctt tttccaatta aaggggcttg gctatcaata gcaatattta gtaggttata   3480
tataactata gttgaccctt gagcaacatg agtttgaact gcatgggtcc acttatgcat   3540
ggattttctt ctacctgtgc cacccctgag atggcaagag caaccctcct cttccttctc   3600
ctcagcctac tcaatgtgaa gacaatgagg atgaagacct ttgtgatggc caggcacagt   3660
ggctcatgcc tataatccca gcactttggg aggctgaggc aggaggatga cctgaattca   3720
ggagtttgag accaacctgg ccaacatggt gaaacctccg tctctactac aaatacaaaa   3780
aattagcggg gcatggtcgt gggcacctgt aatcccagct actcaggagg ctgaggcagg   3840
agaattgctt gaaccaggga ggaggaggtt gcagtgaact gagatcactc cactgcattc   3900
cagcctgggc aacagagtga gactatgtct caaaaaaaaa aaaaaaaaaa agagaaagac   3960
cttcatgatg atccacttcc acttaataaa tagtaaatgc attttctcgt acttatgata   4020
ttcttaataa cattctcctt gctttagctt actctcctgt tagaacacag tatataatac   4080
atacagcata caaaataggt gttagttgac tatgttgtta gtaaggcttc tggtcaacag   4140
taggctatta gtagttaagt ttttggagaa tcaaaagtta tacgcagatt ttttttactt   4200
catggggttc agcagcccta actcctgagt cattcaaggg tcaactgcaa ttcatcttat   4260
ccattcatag tatctctcta atcttaccca tgtccccagc ttattttttt tgccatcttt   4320
cacagtggct tttgatagaa aatctttgtg cagcctttta ctttcatttt ttttttctg   4380
gagtgtttgg acattaggtg tgtttttcct ccttagtgtc tcactaaaaa aaagccccaa   4440
aattgtgcgg ttaatttttt aaagggcaat tagtcttttg aggggtaggg cgcactaggt   4500
aaatctccca tcaaagtgga tttgtgccag ctgtgaagtt tgcaaacatg tctttaatag   4560
ccatgcaatt tcagcatctg taatactcaa gaccatttca attccaagtt gcagaatcaa   4620
agtcaaataa cttaagaaaa aagctattgg ctcgtgagat ggaaaagccc ctgggacagg   4680
cagctaggca tggcacgatc caggttctca acaatgcagc aaatgctctg cctgtcttta   4740
tgtctcttgc tcagctgttc tctgtgttgg cttcattccc aggcaagctt cttccatctg   4800
gtgaaaaaga tgaacaccag gcgtgtctga tcttcccaga ggaagaaggg agcatctttt   4860
tgaacagcat ttctgtgaga aatgggatcc taaggtggcc tccaagattg acacgccatg   4920
gtacaatctt cgtgatcgta agaagaacct gtgaatacga tgagctatca ctcctgtgct   4980
tttgcggttt tatgtggcaa agggagagtg ttctgggtgg gcctgacctg atcaggcata   5040
tcctctaaaa tcagagtttt ctccagctgg ttccagaaga ctaagtcaga gagatgctct   5100
gtgtttgggc cagaagcaag caaacatcca cattgtgaac tgcctatggg ggccacctgg   5160
```

-continued

```
caaggaactg caggtgtttt ctgggacctg agagcattcc ctggccaatc attagcagga   5220

aaacaggaac tcactcctat aactgagagg aaataaaatt taccaacaac caatgagcct   5280

ggaagaagac cctgagcctc aaatgagaac tgcagcccca gccaacactg atttcagcct   5340

tgtaagtacc tgagcagaga actcagccat gctatatcag gacttctgac ctacattact   5400

gtaagatcat aaatgtgttg ttttaagcca ctacatttgt gatagtttgt tatgcagcaa   5460

tagaaagcta atacaacttc caaaaattct actgtgtaag tcaggatcct ttggttgcaa   5520

gcaacaaaaa tcagctctgg atagcttaag caaaaaagga aattggctgg aacagtgttc   5580

gtgtagccac agaatatgag caacttctgg gatggatcca agaaggagaa acaaacaagg   5640

gttatgtcca ggtcttgttt cattctgtta agatttaaag tccggggaga aagcagctga   5700

ttgacattac ctgatagcct catcaagcga ttataatcgg ccggcacggt ggctcacgcc   5760

tgtaatccca gcactttggg aggccaaggc aggcagatca cctgaagtca ggagttcgag   5820

accagcctga ccaatatgat gaaaccccgt ctctactaaa aatataaaaa ttagctggga   5880

gtggtggcag gcacctgtaa tcccagctac tcaggaggct gaggcagaga attgcttgaa   5940

cctgggaggt ggagattgca gtgagccgag attgcaccac tgcactccag cctgggcgac   6000

agagagagat tccattaaaa aaaaaaaaaa agagattata atcgtggaga atagttgact   6060

cttcaaagca aaattgatac tattgctaga agatgggggt cttgatgcca ggcctacaaa   6120

aacatccctg cattaatatg ttcttcccct aatcagttac aatggcgagg aagacagaat   6180

actctaatgg agcaggttta gtcatgtgac catccctgag cgcagacagg ctaggggtta   6240

gctccacttg tactgcatgg tctggccagg gttaatatgg gggttggggg gaggaaggga   6300

tgctgggtgt aaatataagc atataatgtc tattatggca tcccgtttac tgagaatcag   6360

agcacttcag ttgcagtctg gactctgaaa ctagctaatt ctatatcttc agtaagtcat   6420

gttaccttc tgggtctcaa ttctctcatt tactaaataa aggttagatt aatgatttcc   6480

agtccccatc taactgggac aatggtctgt gactcagtat ttaacacaaa ggtataaata   6540

actgataagg ctttatatat ctctcaaggg catttgcttc tgaatggaag aaaagtgttt   6600

agtcagtggt gtgctggggc atacagaatg aactttcatg tataatgtct gcccccacca   6660

cagccaattt caagttacca atgatttaac aaccaactgg gaaaattcct gaaaatttaa   6720

cagttggctc tcatgtgctg atatcagcca gctcccacac accattatta taattttagc   6780

caaaagagtg actctctaag catgtatttt tgggtggata ttagtaggtg agtggagagg   6840
```